(12) United States Patent
Nomura et al.

(10) Patent No.: US 11,666,661 B2
(45) Date of Patent: Jun. 6, 2023

(54) METHODS AND COMPOUNDS FOR TARGETED AUTOPHAGY

(71) Applicants: THE REGENTS OF THE UNIVERSITY OF CALIFORNIA, Oakland, CA (US); FRONTIER MEDICINES CORPORATION, Portola Valley, CA (US)

(72) Inventors: Daniel K. Nomura, Walnut Creek, CA (US); Roberto Zoncu, San Francisco, CA (US); Carl Ward, Berkeley, CA (US); Sin Ki Fung, Berkeley, CA (US); Chris Kumar Varma, Portola Valley, CA (US); Benjamin Fontaine, Berkeley, CA (US)

(73) Assignees: The Regents of the University of California, Oakland, CA (US); Frontier Medicines Corporation, Portola Valley, CA (US)

( * ) Notice: Subject to any disclaimer, the term of this patent is extended or adjusted under 35 U.S.C. 154(b) by 376 days.

(21) Appl. No.: 16/362,573

(22) Filed: Mar. 22, 2019

(65) Prior Publication Data

US 2019/0290778 A1 Sep. 26, 2019

Related U.S. Application Data

(60) Provisional application No. 62/647,569, filed on Mar. 23, 2018.

(51) Int. Cl.
| | | |
|---|---|---|
| *A61K 47/68* | (2017.01) | |
| *C07K 16/28* | (2006.01) | |
| *A61K 45/06* | (2006.01) | |
| *A61P 35/00* | (2006.01) | |
| *A61P 25/14* | (2006.01) | |
| *A61P 37/06* | (2006.01) | |
| *A61P 3/10* | (2006.01) | |
| *A61P 25/28* | (2006.01) | |
| *C07D 495/04* | (2006.01) | |
| *C07D 417/12* | (2006.01) | |

(52) U.S. Cl.
CPC ...... *A61K 47/6889* (2017.08); *A61K 47/6803* (2017.08); *A61P 3/10* (2018.01); *A61P 25/14* (2018.01); *A61P 25/28* (2018.01); *A61P 35/00* (2018.01); *A61P 37/06* (2018.01); *C07D 495/04* (2013.01); *C07K 16/28* (2013.01); *A61K 45/06* (2013.01); *C07D 417/12* (2013.01)

(58) Field of Classification Search
CPC ............ A61K 47/6889; A61K 47/6803; A61K 45/06; A61K 47/545; A61K 47/555; C07D 495/04; C07D 417/12; C07K 16/28; A61P 35/00; A61P 25/14; A61P 37/06; A61P 3/10; A61P 25/28
See application file for complete search history.

(56) References Cited

U.S. PATENT DOCUMENTS

| | | |
|---|---|---|
| 2003/0032584 A1 | 2/2003 | Ts'o et al. |
| 2013/0190340 A1 | 7/2013 | Hedstrom et al. |
| 2014/0127210 A1 | 5/2014 | Kim et al. |
| 2015/0250808 A1 | 9/2015 | Deretic et al. |
| 2016/0015796 A1 | 1/2016 | Savelyeva et al. |
| 2016/0032005 A1 | 2/2016 | Borg et al. |
| 2016/0272639 A1 | 9/2016 | Crew et al. |
| 2017/0253673 A1 | 9/2017 | Kent et al. |
| 2018/0243244 A1 | 8/2018 | Kwon et al. |
| 2019/0112268 A1 | 4/2019 | Nomura et al. |
| 2020/0163970 A1 | 5/2020 | Arimoto et al. |
| 2020/0223848 A1 | 7/2020 | Arimoto et al. |

FOREIGN PATENT DOCUMENTS

| | | |
|---|---|---|
| EP | 3 578 549 A1 | 12/2019 |
| EP | 3 679 935 A1 | 7/2020 |
| KR | 10-1569966 B1 | 11/2015 |
| KR | 10-2017-0023045 A | 3/2017 |
| KR | 10-1734931 B1 | 5/2017 |
| KR | 10-2019-0112673 A | 10/2019 |
| WO | WO-2005/035504 A2 | 4/2005 |
| WO | WO-2005/035504 A3 | 4/2005 |
| WO | WO-2011/009624 A1 | 1/2011 |
| WO | WO-2013/106643 A2 | 7/2013 |
| WO | WO-2013/106643 A3 | 7/2013 |
| WO | WO-2013/192224 A1 | 12/2013 |
| WO | WO-2015/050383 A1 | 4/2015 |
| WO | WO-2016/207730 A1 | 12/2016 |
| WO | WO-2017/047846 A1 | 3/2017 |
| WO | WO-2017/079723 A1 | 5/2017 |
| WO | WO-2018/023108 A1 | 2/2018 |
| WO | WO-2018/045348 A2 | 3/2018 |
| WO | WO-2018/045348 A3 | 3/2018 |
| WO | WO-2018/143403 A1 | 8/2018 |
| WO | WO-2019/013181 A1 | 1/2019 |
| WO | WO-2019113711 A1 * | 6/2019 ................ A61P 9/10 |
| WO | WO-2019/183600 A1 | 9/2019 |

(Continued)

OTHER PUBLICATIONS

Cook, C., "TDP-43 in neurodegenerative disorders." Expert opinion on biological therapy 8.7 (2008): 969-978.*
Green, D.R., "To be or not to be? How selective autophagy and cell death govern cell fate." Cell 157.1 (2014): 65-75.*
Ying, H., "Optineurin: The autophagy connection." Experimental eye research 144 (2016): 73-80.*
Adams, G.P. et al. (Sep. 1993). "Highly Specific in Vivo Tumor Targeting by Monovalent and Divalent Forms of 741F8 Anti-c-erbB-2 Single-Chain Fv," *Cancer Res* 53:4026-4034.
Bersuker, K. et al. (Apr. 25, 2016). "Protein misfolding specifies recruitment to cytoplasmic inclusion bodies," *J Cell Biol* 213(2):229-241.

(Continued)

*Primary Examiner* — John M Mauro
(74) *Attorney, Agent, or Firm* — Mintz, Levin, Cohn, Ferris, Glovsky and Popeo, P.C.

(57) ABSTRACT

Provided herein, inter alia, are methods and compounds for targeted autophagy.

79 Claims, 31 Drawing Sheets

Specification includes a Sequence Listing.

(56) References Cited

FOREIGN PATENT DOCUMENTS

| WO | WO-2019/190172 A1 | 10/2019 |
|---|---|---|
| WO | WO-2020/022783 A1 | 1/2020 |
| WO | WO-2020/022783 A9 | 1/2020 |
| WO | WO-2020/022784 A1 | 1/2020 |
| WO | WO-2020/022785 A1 | 1/2020 |
| WO | WO-2020/076996 A1 | 4/2020 |

OTHER PUBLICATIONS

Gruber, M. et al. (Jun. 1, 1994). "Efficient tumor cell lysis mediated by a bispecific single chain antibody expressed in *Escherichia coli*," *J Immunol* 152(11):15368-5374.

Holliger, P. et al. (Jul. 15, 1993). ""Diabodies": small bivalent and bispecific antibody fragments," *PNAS USA* 90(14):6444-6448.

Hu, S. et al. (Jul. 1, 1996). "Minibody: A novel engineered anti-carcinoembryonic antigen antibody fragment (single-chain Fv-CH3) which exhibits rapid, high-level targeting of xenografts," *Cancer Res* 56(13):3055-3061.

International Search Report dated Aug. 6, 2019, for PCT Application No. PCT/US2019/23753, filed Mar. 22, 2019, 7 pages.

Johansen, T. et al. (Mar. 2011). "Selective autophagy mediated by autophagic adapter proteins," *Autophagy* 7(3):279-296.

Kostelny, S.A. et al. (Mar. 1, 1992). "Formation of a bispecific antibody by the use of leucine zippers," *J. Immunol.* 148(5):1547-1553.

Li, Z. et al. (Nov. 2019, e-published Oct. 30, 2019). "Allele-selective lowering of mutant HTT protein by HTT-LC3 linker compounds," *Nature* 575(7781):203-209.

Lin, S. et al. (Feb. 10, 2017). "Redox-based reagents for chemoselective methionine bioconjugation," *Science* 355(6325):597-602.

Lovrinovic, M. et al. (Sep. 30, 2005). "Rapid synthesis of DNA-cysteine conjugates for expressed protein ligation," *Biochem Biophys Res Commun* 335(3):943-948.

Marcus-Sekura, C.J. (Aug. 1, 1988). "Techniques for using antisense oligodeoxyribonucleotides to study gene expression," *Anal Biochem* 172(2):289-295.

McCafferty, J. et al. (Dec. 6, 1990). "Phage antibodies: filamentous phage displaying antibody variable domains," *Nature* 348(6301):552-554.

McCartney, J.E. et al. (Mar. 1995). "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides," *Protein Eng* 8(3):301-314.

Pack, P. et al. (Feb. 18, 1992). "Miniantibodies: use of amphipathic helices to produce functional, flexibly linked dimeric FV fragments with high avidity in *Escherichia coli*," *Biochemistry* 31(6):1579-1584.

Takahashi, D. et al. (Dec. 5, 2019, e-published Oct. 9, 2019). "AUTACs: Cargo-Specific Degraders Using Selective Autophagy," *Mol Cell* 76(5):797-810.

Tanaka, K. (2009). "The proteasome: overview of structure and functions," *Proceedings of the Japan Academy Series B, Physical and Biological Sciences* 85(1):12-36.

Tomoshige, S. et al. (Sep. 11, 2017, e-published Aug. 9, 2017). "Discovery of Small Molecules that Induce the Degradation of Huntingtin," *Angew Chem Int Ed Engl* 56(38):11530-11533.

Tomoshige, S. et al. (Feb. 15, 2018, e-published Jan. 12, 2018). "Degradation of huntingtin mediated by a hybrid molecule composed of IAP antagonist linked to phenyldiazenyl benzothiazole derivative," *Bioorg Med Chem Lett* 28(4):707-710.

Weintraub, H.M. (Jan. 1990). "Antisense RNA and DNA," *Scientific American* 262(1):40-46.

Written Opinion dated Aug. 6, 2019, for PCT Application No. PCT/US2019/23753, filed Mar. 22, 2019, 11 pages.

Zhu, Z. et al. (Apr. 1997). "Remodeling domain interfaces to enhance heterodimer formation," *Protein Sci.* 6(4):781-788.

Bauer, P.O. et al. (Mar. 2010). "Harnessing chaperone-mediated autophagy for the selective degradation of mutant huntingtin protein," *Nature Biotechnology* 28(3):256-263.

Extended European Search Report dated Jun. 30, 2022, for EP Patent Application No. 19772486.7, 15 pages.

Fan, X. et al. (Mar. 2014). "Rapid and reversible knockdown of endogenous proteins by peptide-directed lysosomal degradation," *Nature Neuroscience* 17(3):471-480.

Gao, N. et al. (Jun. 1, 2017). "Chemical Methods to Knock Down the Amyloid Proteins," *Molecules* 22(6):916.

Ottis, P. et al. (Apr. 21, 2017). "Proteolysis-Targeting Chimeras: Induced Protein Degradation as a Therapeutic Strategy," *ACS Chemical Biology* 12(4):892-898.

Tsuboi, K. et al. (Oct. 19, 2011). "Potent and selective inhibitors of glutathione S-transferase omega 1 that impair cancer drug resistance," *Journal of the American Chemical Society* 133(41):16605-16616.

\* cited by examiner

EN7

IA-alkyne labeling

METHODS AND COMPOUNDS FOR TARGETED AUTOPHAGY

CROSS-REFERENCES TO RELATED APPLICATIONS

This application claims the benefit of U.S. Provisional Application No. 62/647,569, filed Mar. 23, 2018, which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 052103-514001US_Sequence_Listing_ST25.txt, created Mar. 22, 2019, 74,034 bytes, machine format IBM-PC, MS Windows operating system, is hereby incorporated by reference.

STATEMENT AS TO RIGHTS TO INVENTIONS MADE UNDER FEDERALLY SPONSORED RESEARCH AND DEVELOPMENT

This invention was made with government support under CA172667 awarded by the National Institutes of Health. The government has certain rights in the invention.

BACKGROUND

Even with the identification of many novel protein targets to treat human diseases, these potential therapy targets have remained largely untranslated, because the majority of the proteome is "undruggable" or difficult to target with small-molecules. These undruggable proteins do not necessarily possess known functional binding pockets or "druggable hotspots" that conventional small-molecules may bind to affect their function. This represents a major challenge in developing next-generation disease cures. Disclosed herein, inter alia, are solutions to these and other problems in the art.

BRIEF SUMMARY

In an aspect is provided a compound including a monovalent cellular component binder covalently bound to a monovalent targeted autophagy protein binder. In embodiments, the monovalent targeted autophagy protein binder is a monovalent autophagy adapter protein binder (e.g., a monovalent compound described herein). In embodiments, the targeted autophagy protein binder (e.g., autophagy adapter protein binder) has the formula:

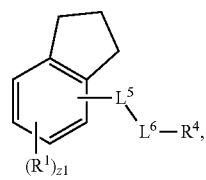

(I)

wherein z1 is an integer from 0 to 9;

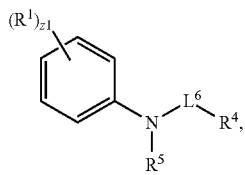

(II)

wherein z1 is an integer from 0 to 5;

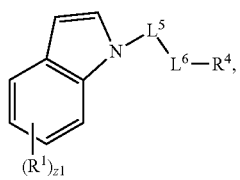

(III)

wherein z1 is an integer from 0 to 6;

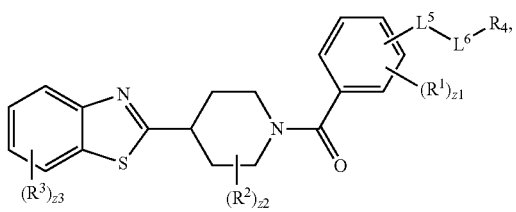

(IV)

wherein z1 is an integer from 0 to 4, z2 is an integer from 0 to 8, and z3 is an integer from 0 to 4;

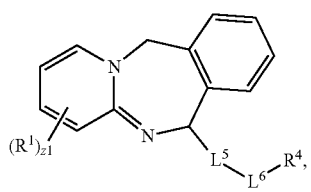

(V)

wherein z1 is an integer from 0 to 11;

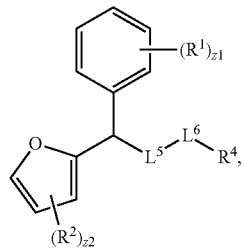

(VI)

wherein z1 is an integer from 0 to 5 and z2 is an integer from 0 to 3;

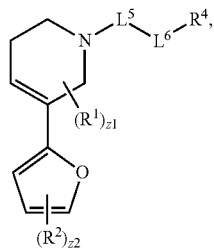
(VII)

wherein z1 is an integer from 0 to 7 and z2 is an integer from 0 to 3;

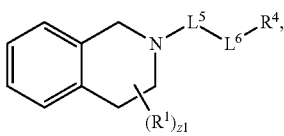
(VIII)

wherein z1 is an integer from 0 to 10;

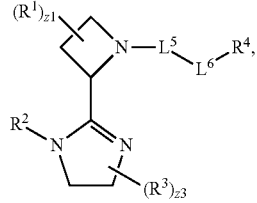
(IX)

wherein z1 is an integer from 0 to 5 and z3 is an integer from 0 to 4;

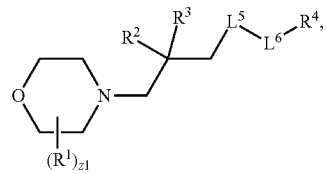
(X)

wherein z1 is an integer from 0 to 8;

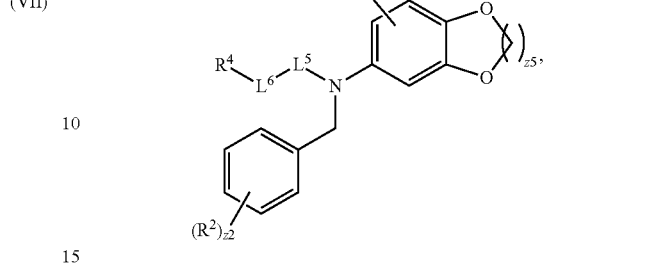
(XI)

wherein z1 is an integer from 0 to 7, z2 is an integer from 0 to 5, and z5 is 1 or 2;

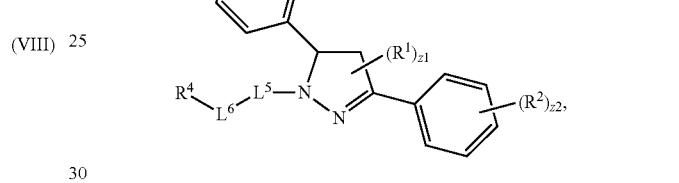
(XII)

wherein z1 is an integer from 0 to 2, z2 is an integer from 0 to 5, and z3 is an integer from 0 to 5;

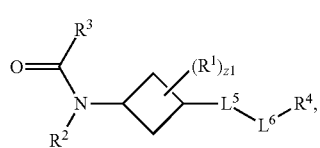
(XIII)

wherein z1 is an integer from 0 to 6;

(XIV)

wherein z1 is an integer from 0 to 6;

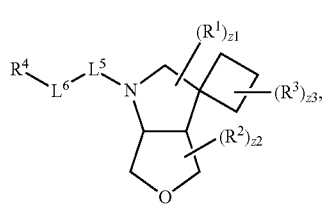
(XV)

wherein z1 is an integer from 0 to 4, z2 is an integer from 0 to 6, and z3 is an integer from 0 to 6;

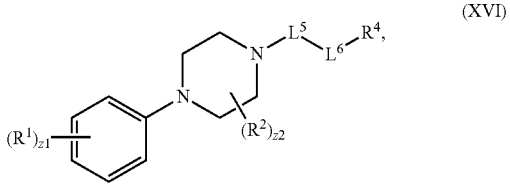

(XVI)

wherein z1 is an integer from 0 to 5 and z2 is an integer from 0 to 8; or

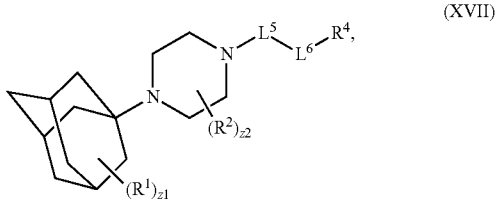

(XVII)

wherein z1 is an integer from 0 to 15 and z2 is an integer from 0 to 8. $R^1$, z1, $R^2$, z2, $R^3$, z3, $L^5$, $L^6$, and $R^4$ are as described herein.

In an aspect is provided an autophagy adapter protein (e.g., LC3, p62, NBR1, NDP52, Optineurin, NUFIP1, WDFY3, RETREG1, Nix, TOLLIP, or TAX1BP1) covalently bonded to a compound described herein.

In an aspect is provided a method for treating a disease associated with a cellular component (e.g., aberrant level of a cellular component), the method including contacting the cellular component with a targeted autophagy degrader (e.g., as described herein). In an aspect is provided a method for treating a disease associated with a cellular component (e.g., aberrant level of a cellular component), the method including administering to a subject in need thereof a therapeutically effective amount of a compound described herein.

In an aspect is provided a method for treating cancer, the method including contacting a cellular component associated with cancer with a targeted autophagy degrader (e.g., as described herein).

In an aspect is provided a method for treating neurodegenerative disease, the method including contacting a cellular component associated with the neurodegenerative disease with a targeted autophagy degrader (e.g., as described herein).

In an aspect is provided a method for treating a metabolic disease, the method including contacting a cellular component associated with the metabolic disease with a targeted autophagy degrader (e.g., as described herein).

In an aspect is provided a method for treating a metabolic disease, the method including administering to a subject in need thereof a therapeutically effective amount of a compound described herein. In an aspect is provided a method for treating a metabolic disease, the method including administering to a subject in need thereof a therapeutically effective amount of a targeted autophagy degrader (e.g., as described herein).

In an aspect is provided a method for treating an infectious disease, the method including contacting a cellular component associated with the infectious disease with a targeted autophagy degrader (e.g., as described herein).

In an aspect is provided a method for treating an autoimmune disease, the method including contacting a cellular component associated with the autoimmune disease with a targeted autophagy degrader (e.g., as described herein).

In an aspect is provided a method for treating an inflammatory disease, the method including contacting a cellular component associated with the inflammatory disease with a targeted autophagy degrader (e.g., as described herein).

In an aspect is provided a pharmaceutical composition including a compound described herein (e.g., a targeted autophagy degrader) and a pharmaceutically acceptable excipient.

BRIEF DESCRIPTION OF THE DRAWINGS

FIG. 1A: Reactivity-based probes consist of a reactive warhead that can covalently modify nucleophilic hotspots in proteins and an alkyne handle which can be conjugated to analytical handles (e.g., fluorescent tags or biotin handles) by CuAAC for subsequent analysis of reactive protein hotspots. Shown are examples of reactivity-based probes. FIG. 1B: Isotopic tandem orthogonal proteolysis-enabled activity-based protein profiling (isoTOP-ABPP) for mapping druggable hotspots in complex proteomes. Proteomes can be labeled with reactivity-based probes, followed by conjugation of probe-labeled proteins with a biotin-azide tag with a TEV protease cleavage site, followed by avidin-enrichment, tryptic digest, enrichment of probe-labeled tryptic peptides, elution of modified peptides by TEV protease, and LC-LC/MS/MS analysis of probe-modified peptides. The sites of modification represent potential druggable hotspots. The sequences shown in FIG. 1B are as follows: protein 1: YWKDAC*SHR (SEQ ID NO:1) and protein 2: SYC*WHIL (SEQ ID NO:2).

FIG. 2A: Examples of scaffolds in our covalent ligand library. FIG. 2B: Gel-based or fluorescence polarization-based ABPP. Pure protein is incubated with vehicle or covalent ligand, followed by labeling of protein with the corresponding reactivity-based probe. Rhodamine-azide can be conjugated to probe-labeled proteins using CuAAC and read-out by SDS/PAGE and in-gel fluorescence or fluorescence polarization in a 96 or 384-well plate. FIG. 2C: Competitive isoTOP-ABPP platform for mapping druggable hotspots targeted by covalent ligand or natural product leads. Complex proteomes can be treated with vehicle or compound, followed by labeling with reactivity-based probe, and appendage of a biotin-azide tag bearing a TEV protease recognition sequence and an isotopically light (control) or heavy (treated) tag. Probe labeled proteomes can then be combined in a 1:1 ratio, avidin enriched, tryptically digested, and probe-modified tryptic peptides can be released by TEV protease. Light/heavy peptides can then be analyzed by quantitative proteomics to identify all sites of probe labeling and sites where the covalent ligand displaced probe labeling, enabling the identification of targets and druggable hotspots targeted by covalent ligands. The sequences shown in FIG. 2C are as follows: protein 1: YWKDAC*SHR (SEQ ID NO:1) and protein 2: SYC*WHIL (SEQ ID NO:2).

FIGS. 9A-9G. Compounds used in the gel-based ABPP screen of LC3A depicted in FIG. 4. It is understood that when a compound as shown anywhere in the specification (e.g., in FIGS. 9A-9G) is connected (e.g., bonded) to another moiety through a linker, it is understood the compound is intended to be a monovalent form of the standalone compound at any attachment point following the replacement of a substituent (e.g., hydrogen or halogen), for example, a monovalent form of

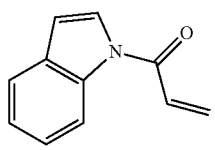

may be understood as

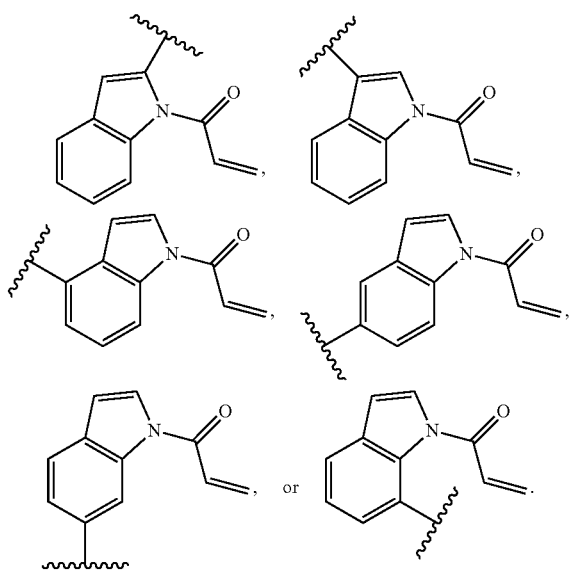

Figure 10A:
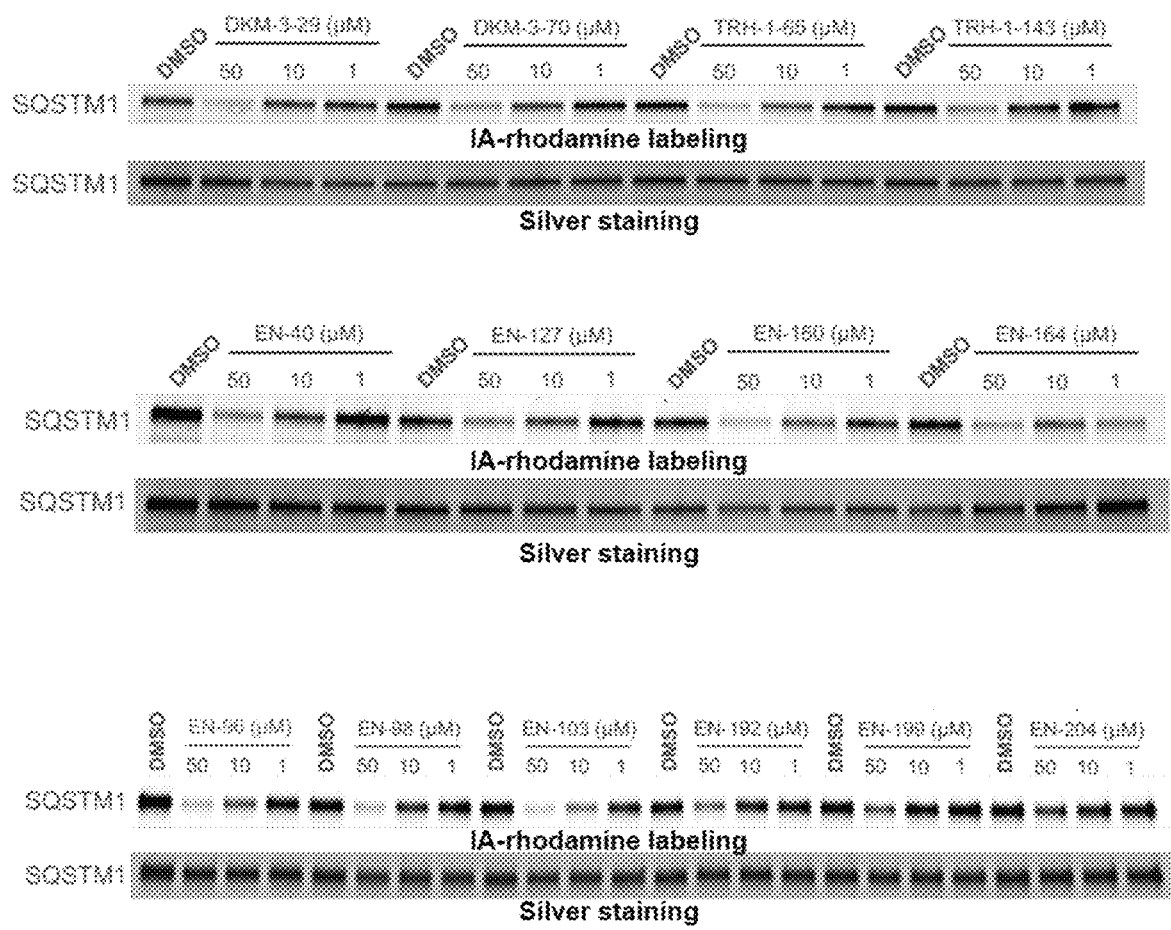
Figure 10B:
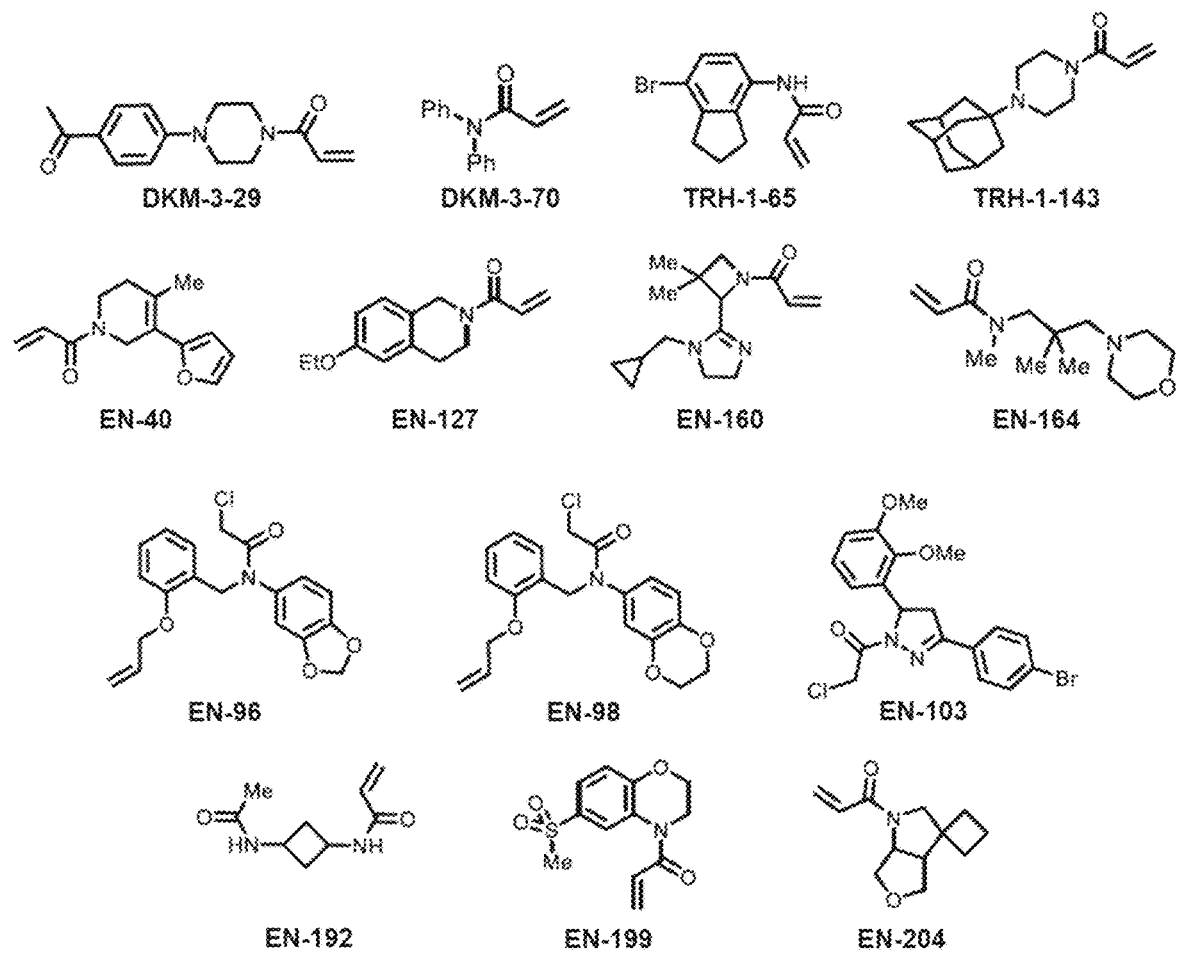

FIGS. 10A-10B. FIG. 10A: Dose-response of hits from a cysteine-reactive screen against autophagy adapter protein SQSTM1 (p62) using gel-based ABPP. In this screen, we have pre-incubated vehicle or cysteine-reactive covalent ligands (50 microM) against a cysteine-reactive probe (rhodamine-functionalized iodoacetamide probe (IA-rhodamine)), followed by SDS/PAGE, and analysis by in-gel fluorescence. Silver staining of the protein is also shown as a protein loading control. FIG. 10B: Structures of ligands tested.

Figure 11:
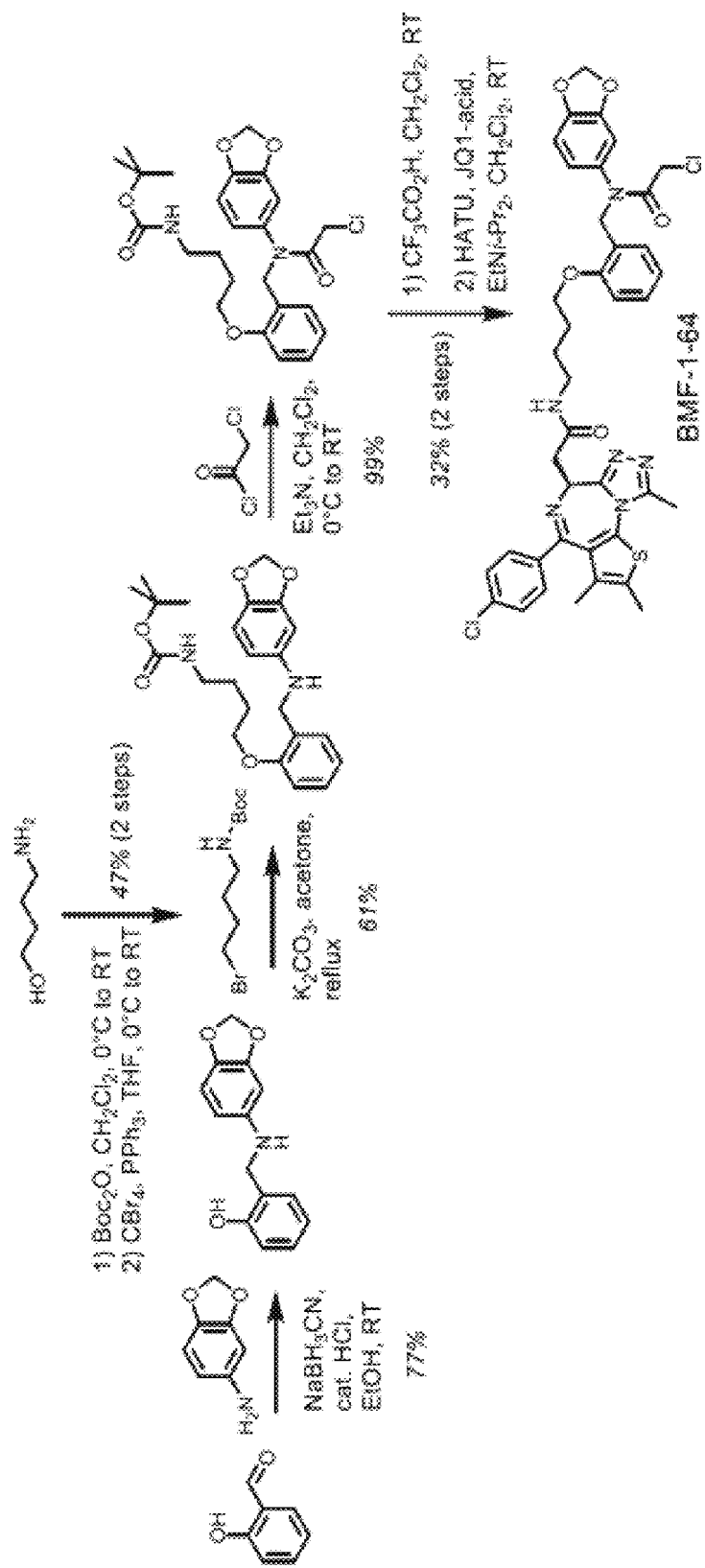

FIG. 11. Synthesis of p62-based BRD4 degrader. Described is the synthetic route for linking EN96 to the BRD4 inhibitor JQ1.

Figure 12:
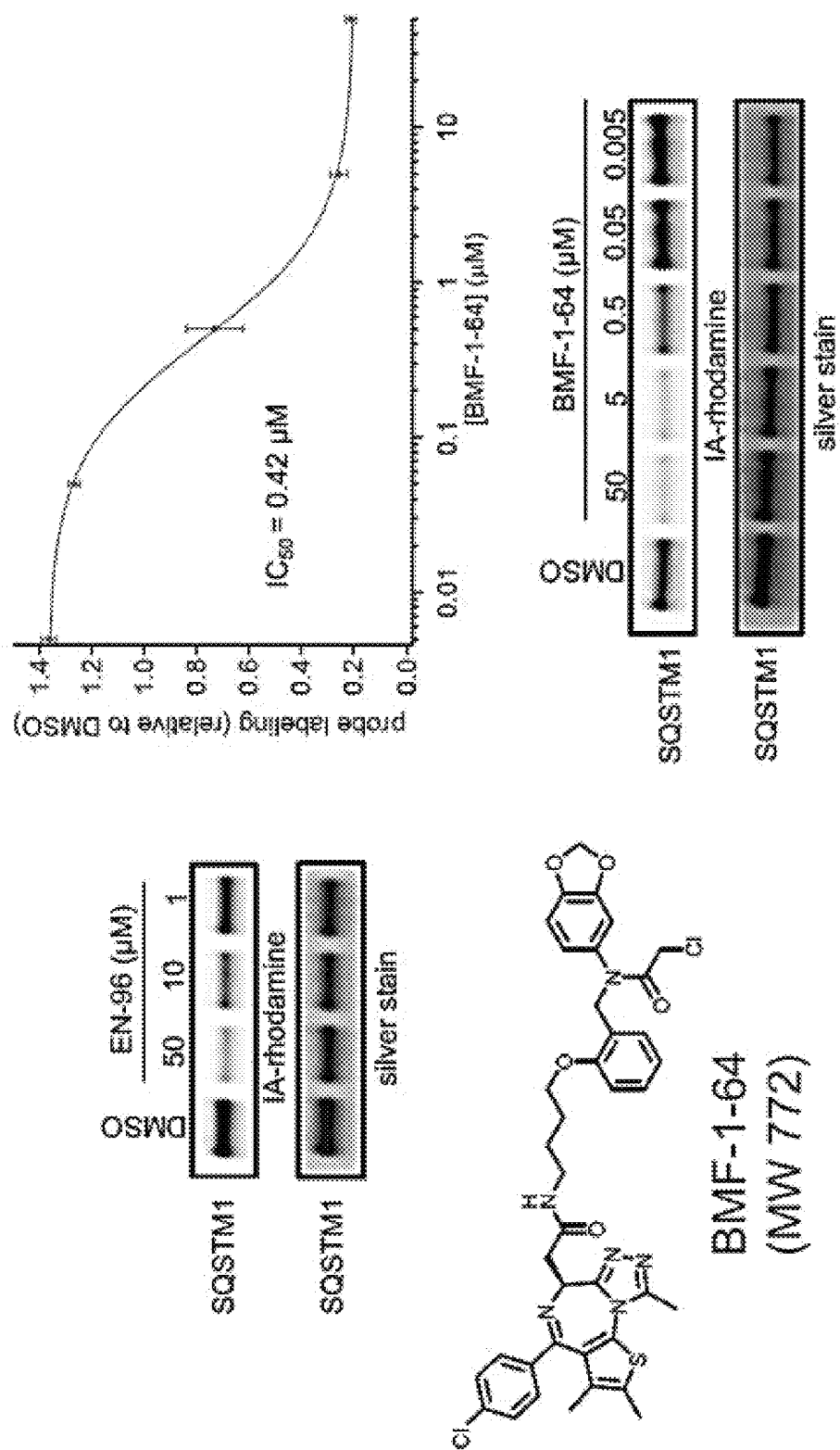

FIG. 12. BMF-1-64 still interacts with SQSTM1. Gel-based ABPP of EN96 and BMF-1-64 against pure SQSTM1 human protein. DMSO vehicle or EN96 or BMF-1-64 were pre-incubated with SQSTM1 protein before incubation with IA-rhodamine. BMF-1-64 still interacts with SQSTM1 with an $IC_{50}$ of 0.42 microM.

Figure 13:
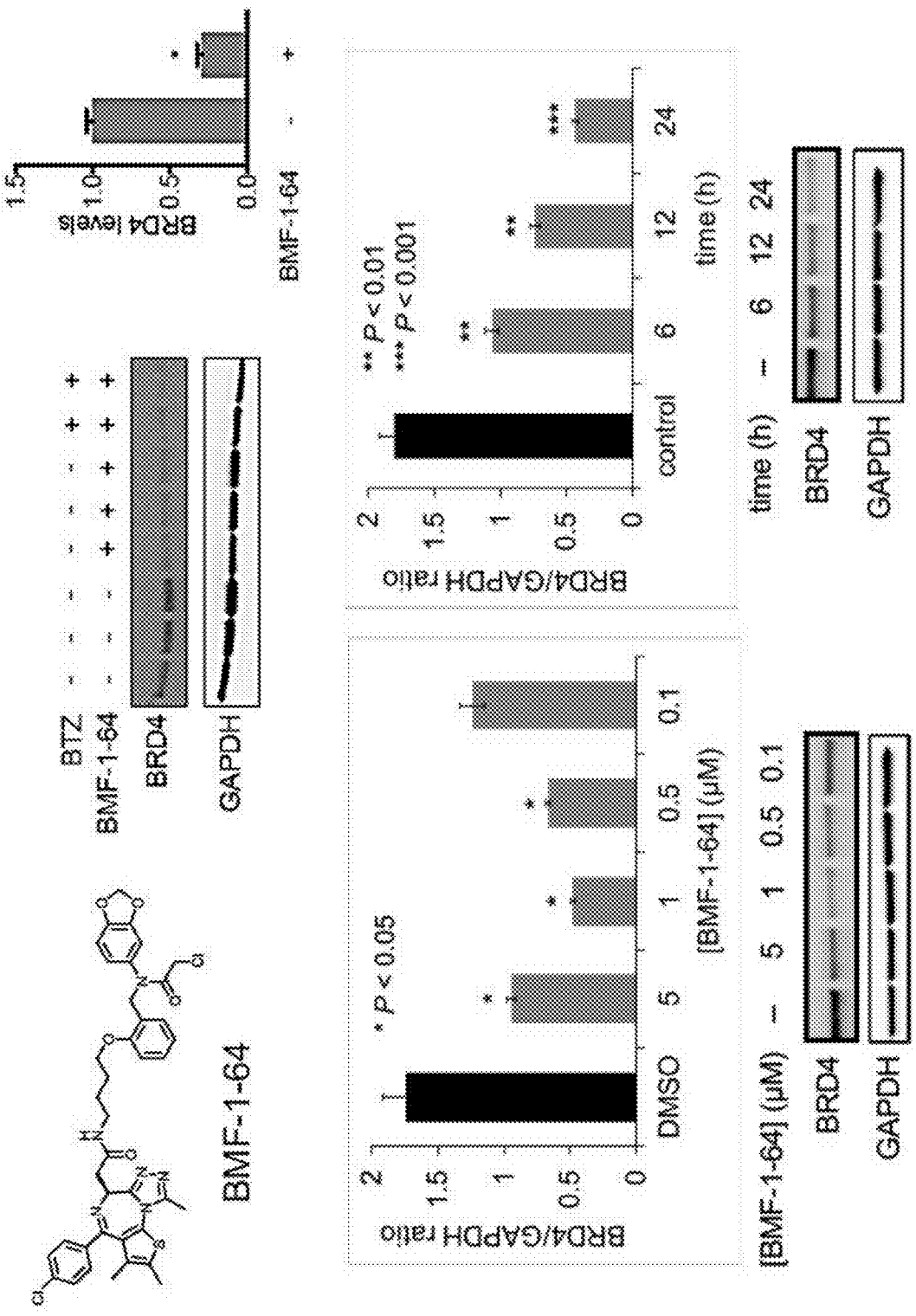

FIG. 13. BMF-1-64 degrades BRD4 in a proteasome-independent, dose-responsive, and time-dependent manner. U2OS cells were treated with vehicle or BMF-1-64 in the upper panel at 1 microM for 12 hours and BRD4 levels were monitored by Western blotting. Cells were pre-treated with vehicle or BTZ for 1 h prior to vehicle or BMF-1-64. In the bottom left panel, U2OS cells were treated with BMF-1-64 at various concentrations for 12 h. In the bottom right panel, U2OS cells were treated with BMF-1-64 at 1 microM for various time points.

Figure 14:
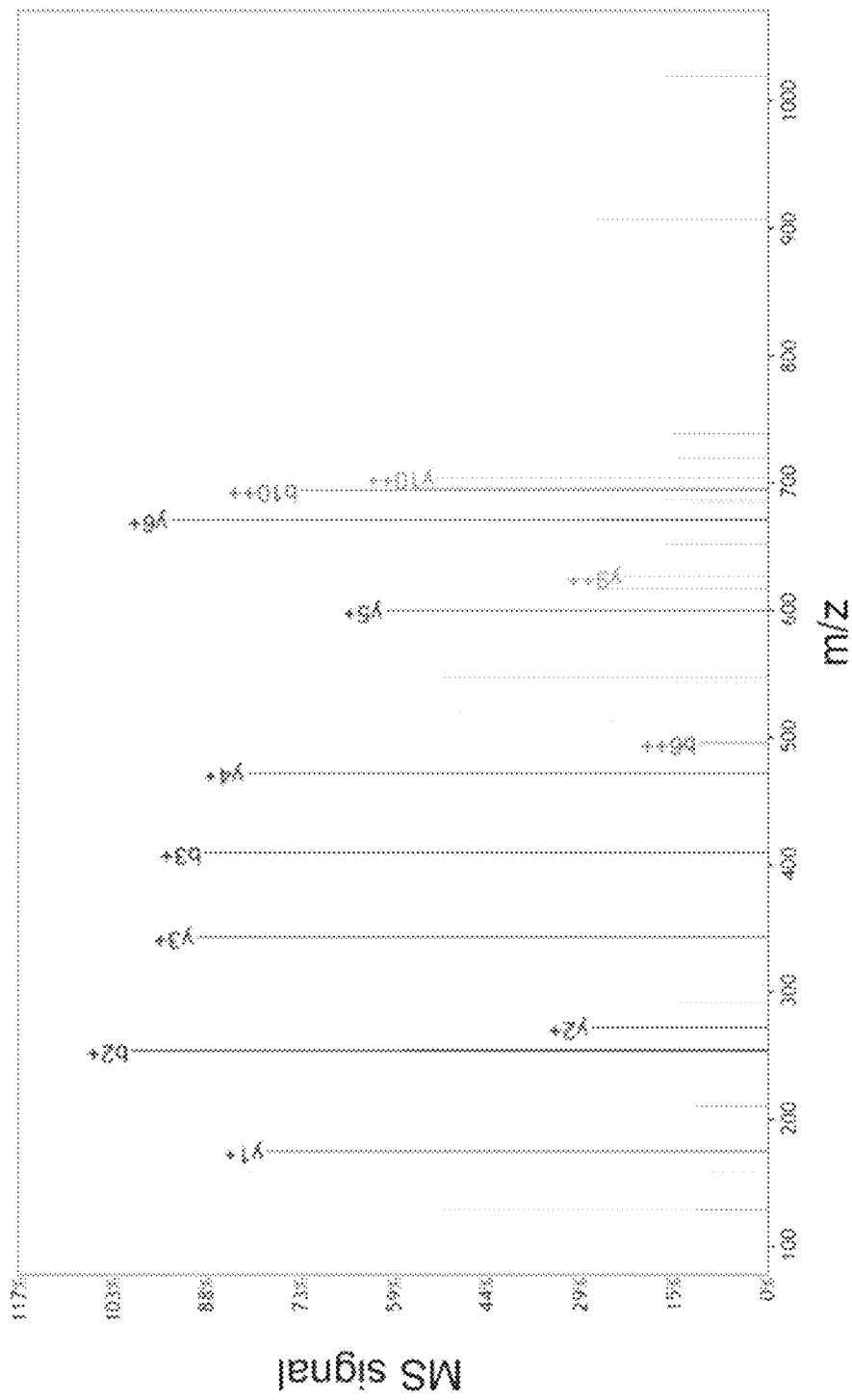

FIG. 14. MS/MS data corresponding to the direct adduct of EN96 on a peptide derived from p62/SQSTM1. The p62/SQSTM1 protein binder EN96 reacts with C113 of the p62/SQSTM1 protein.

Figure 15:
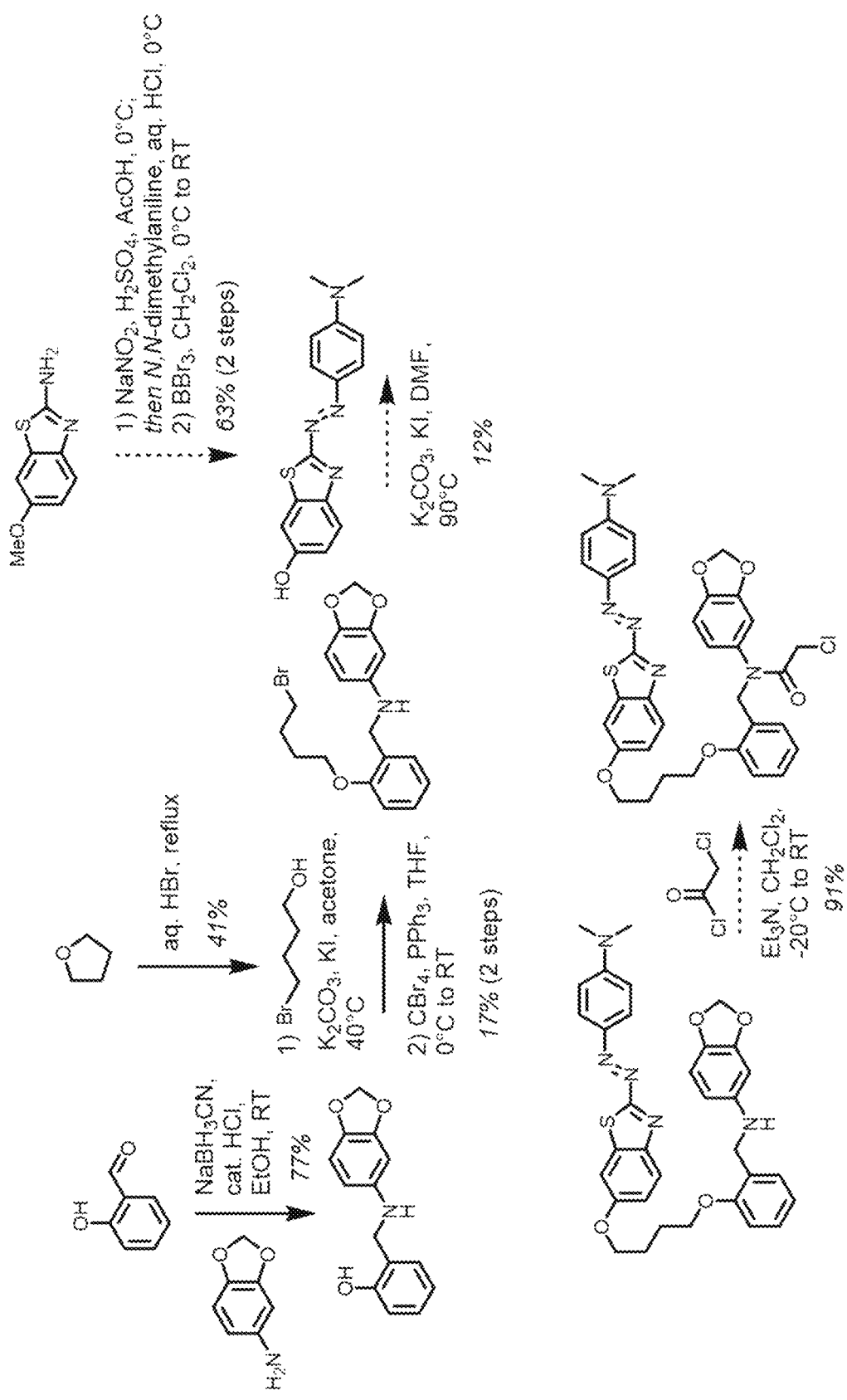

FIG. 15. Synthetic route for making BMF-1-141 linking a Thioflavin T derivative that recognizes Huntingtin (HTT) aggregates to the p62/SQSTM1 covalent ligand EN96.

Figure 16:
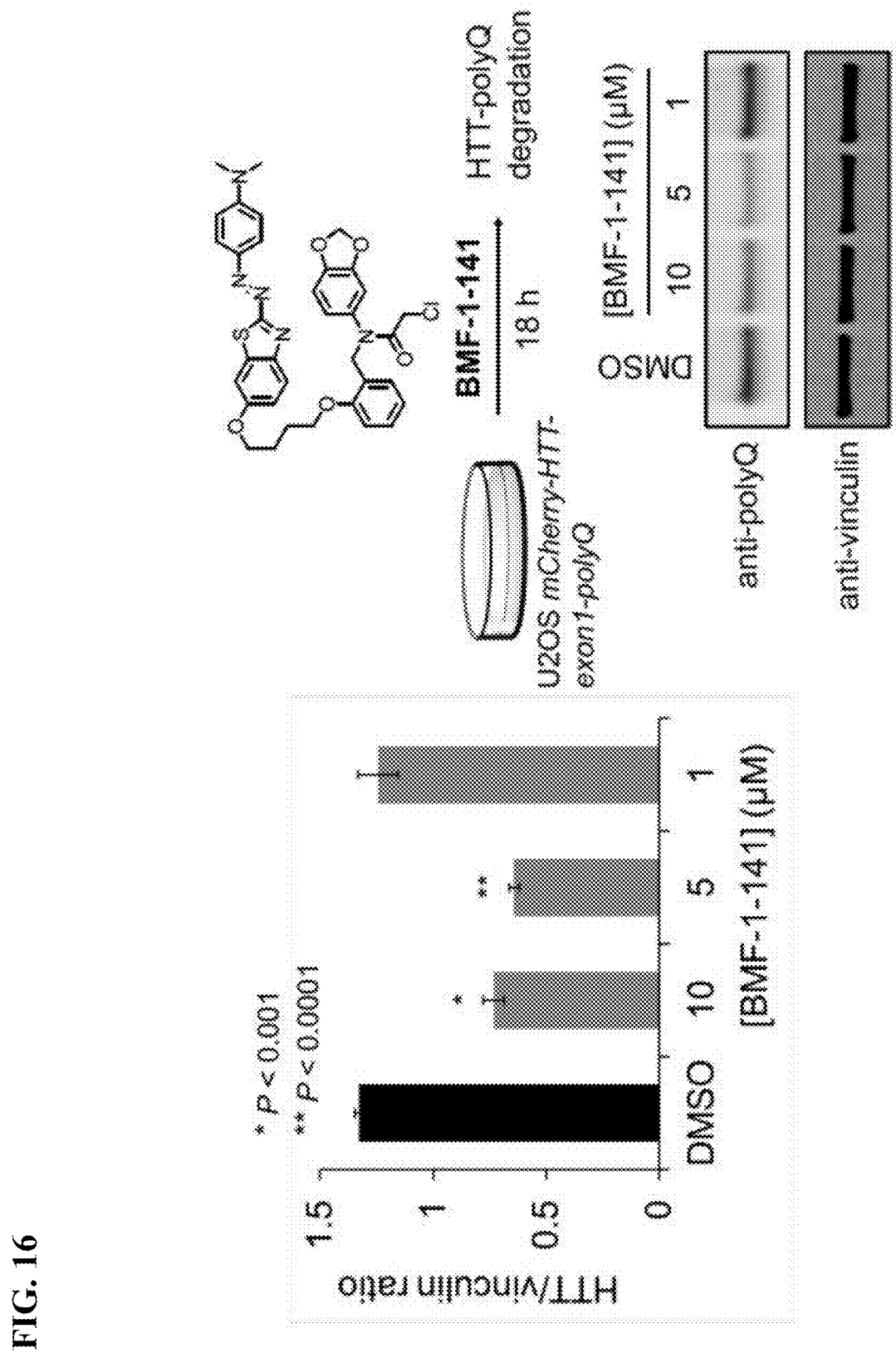

FIG. 16. BMF-1-141 treatment leads to reduction in HTT levels. U2OS mCherry-HTT-exon1-polyQ cells were treated with DMSO vehicle or BMF-1-141 at 10, 5, and 1 microM for 18 h and polyQ-HTT levels were assessed by Western blotting and quantified against loading control vinculin levels by densitometry. Values shown in bar graph are average +/− sem from n=3 biological replicates. Significance is expressed as *p<0.001 and **p<0.0001 compared to DMSO vehicle-treated controls.

DETAILED DESCRIPTION

Disclosed herein are methods which use bifunctional small-molecule degraders that consist of a protein-targeting ligand, a linker, and a recruiter for autophagy adapter proteins to target specific substances, for example proteins, misfolded proteins, protein aggregates, organelles, or microorganisms to autophagosomes for lysosomal degradation.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. In embodiments, alkyl refers to an aliphatic hydrocarbyl.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —S—$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R$^1$, —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〜" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

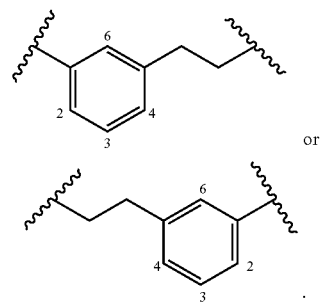

or

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —Cl$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'") =NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R""—CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R$^1$, —NR'—C(O)NR"R'", —NR"C(O)$_2$R', —NR—C(NR'R"R'")=NR""—NR—C(NR'R")=NR'", —S(O)R', —S(O)$_2$R', —S(O)$_2$NR'R", —NRSO$_2$R', NR'NR"R'", ONR'R", NR'C(O)NR"NR'"R""—CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
  (i) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —N$_{112}$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —Cl$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —Cl$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkyl ene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate linker" refers to the resulting association between atoms or molecules of bioconjugate reactive groups. The association can be direct or indirect. For example, a conjugate between a first bioconjugate reactive group (e.g., —NH$_2$, —COOH, —N-hydroxysuccinimide, or maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g. ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., sulfo-N-hydroxysuccinimide moiety) is covalently attached to the second bioconjugate reactive group (e.g., an amine).

Useful bioconjugate reactive moieties used for bioconjugate chemistries herein include, for example:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.;
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido or maleimide groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold, or react with maleimides;
(h) amine or sulfhydryl groups (e.g., present in cysteine), which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding;
(m) metal bonding to reactive phosphorus groups (e.g., phosphines) to form, for example, phosphate diester bonds;
(n) azides coupled to alkynes using copper catalyzed cycloaddition click chemistry; and
(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound. A "derivative" is a compound derived from a chemical compound via a chemical reaction. A derivative of a compound described herein may refer to the compound described herein with the addition or removal of a substituent.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The terms "polypeptide," "peptide," and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild-type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease. In embodiments, treating is preventing. In embodiments, treating does not include preventing. In embodiments, the treating or treatment is no prophylactic treatment.

An "effective amount" is an amount sufficient for a compound to accomplish a stated purpose relative to the absence of the compound (e.g., achieve the effect for which it is administered, treat a disease, reduce enzyme activity, increase enzyme activity, reduce signaling pathway, reduce one or more symptoms of a disease or condition (e.g., reduce signaling pathway stimulated by an autophagy adapter protein, reduce the signaling pathway activity of an autophagy protein). An example of an "effective amount" is an amount sufficient to contribute to the treatment, prevention, or reduction of a symptom or symptoms of a disease, which could also be referred to as a "therapeutically effective amount" when referred to in this context. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g., signaling pathway) of a protein in the absence of a compound as described herein (including embodiments, examples, figures, or Tables).

"Contacting" is used in accordance with its plain ordinary meaning and refers to the process of allowing at least two distinct species (e.g., chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a cellular component (e.g., protein, ion, lipid, nucleic acid, nucleotide, amino acid, protein, particle, organelle, cellular compartment, microorganism, virus, lipid droplet, vesicle, small molecule, protein complex, protein aggregate, or macromolecule). In some embodiments contacting includes allowing a compound described herein to interact with a cellular component (e.g., protein, ion, lipid, nucleic acid, nucleotide, amino acid, protein, particle, virus, lipid droplet, organelle, cellular compartment, microorganism, vesicle, small molecule, protein complex, protein aggregate, or macromolecule) that is involved in a signaling pathway.

As defined herein, the term "inhibition," "inhibit," "inhibiting" and the like in reference to a cellular component-inhibitor interaction means negatively affecting (e.g., decreasing) the activity or function of the cellular component (e.g., decreasing the signaling pathway stimulated by a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)), relative to the activity or function of the cellular component in the absence of the inhibitor. In some embodiments inhibition refers to reduction of a disease or symptoms of disease. In some embodiments, inhibition refers to a reduction in the activity of a signal transduction pathway or signaling pathway (e.g., reduction of a pathway involving the cellular component). Thus, inhibition includes, at least in part, partially or totally blocking stimulation, decreasing, preventing, or delaying activation, or inactivating, desensitizing, or down-regulating the signaling pathway or enzymatic activity or the amount of a cellular component.

The term "modulator" refers to a composition that increases or decreases the level of a target molecule or the function of a target molecule or the physical state of the target of the molecule (e.g., a target may be a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)) relative to the absence of the composition.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g., caused by) a cellular component (e.g., protein, ion, lipid, nucleic acid, nucleotide, amino acid, protein, particle, organelle, cellular compartment, microorganism, vesicle, small molecule, protein complex, protein aggregate, or macromolecule).

As used herein, the term "cancer" refers to all types of cancer, neoplasm or malignant tumors found in mammals (e.g., humans), including leukemia, lymphoma, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Strussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

Neurodegenerative diseases may be caused by (i.e., associated with) the accumulation of (e.g., insoluble) protein aggregates in and around neurons. In Huntington's disease, the huntingtin protein may form protein aggregates, also known as "huntingtin aggregates".

The term "polyglutamine diseases" or "polyQ diseases" refers to a group of neurodegenerative diseases caused by expanded cytosine-adenine-guanine (CAG) repeats encoding a long polyQ tract in the respective proteins. The protein including the polyQ tract may form a protein aggregate ("polyQ protein aggregate"). In Huntington's disease, the huntingtin protein may include a polyQ tract and may form a protein aggregate or "polyQ huntingtin aggregate".

As used herein, the term "metabolic disease" or "metabolic disorder" refers to a disease or condition in which a subject's metabolism or metabolic system (e.g., function of storing or utilizing energy) becomes impaired. Examples of metabolic diseases that may be treated with a compound, pharmaceutical composition, or method described herein include diabetes (e.g., type I or type II), obesity, metabolic syndrome, or a mitochondrial disease (e.g., dysfunction of mitochondria or aberrant mitochondrial function).

The term "cellular component associated disease" (e.g., the cellular component may be a protein, ion, lipid, nucleic acid, nucleotide, amino acid, protein, particle, organelle, cellular compartment, microorganism, virus, vesicle, small molecule, protein complex, protein aggregate, or macromolecule; the disease may be a neurodegenerative disease, cancer, a metabolic disease, autoimmune disease, inflammatory disease, or infectious disease) (also referred to herein as "cellular component related disease") refers to a disease caused by the cellular component. Other diseases that are associated with aberrant activity or level of the cellular component are well known in the art and determining such diseases are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a targeted autophagy degrader" means administering a compound that inhibits the activity or level (e.g., amount) or level of a signaling pathway of a cellular component targeted by the targeted autophagy degrader to a subject. Administration may include, without being limited by mechanism, allowing sufficient time for the targeted autophagy degrader to reduce the level or activity of the cellular component or for the targeted autophagy degrader to reduce one or more symptoms of a disease.

The compounds described herein can be used in combination with one another, with other active agents known to be useful in treating a disease associated with cells expressing a disease associated cellular component, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., Bacillus Calmette-Gurin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y or $^{131}$I, etc.).

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At and $^{212}$Bi, optionally conjugated to antibodies directed against tumor antigens.

In therapeutic use for the treatment of cancer, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent.

The term "associated" or "associated with" in the context of a substance or substance activity or function associated with a disease (e.g., a protein associated disease, disease associated with a cellular component) means that the disease (e.g., neurodegenerative disease, cancer) is caused by (in whole or in part), or a symptom of the disease is caused by (in whole or in part) the substance or substance activity or function or the disease or a symptom of the disease may be treated by modulating (e.g., inhibiting or activating) the substance (e.g., cellular component). For example, a neurodegenerative disease associated with a protein aggregate may be a neurodegenerative disease that results (entirely or partially) from aberrant protein aggregation or a neurodegenerative disease wherein a particular symptom of the disease is caused (entirely or partially) by aberrant protein aggregation. As used herein, what is described as being associated with a disease, if a causative agent, could be a target for treatment of the disease. For example, a neurodegenerative disease associated with aberrant protein aggregation or a protein aggregate associated neurodegenerative disease, may be treated with a protein aggregate modulator or protein aggregate targeted autophagy degrader, in the instance where increased protein aggregation causes the neurodegenerative disease.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

"Anti-cancer agent" is used in accordance with its plain ordinary meaning and refers to a composition (e.g., compound, drug, antagonist, inhibitor, modulator) having anti-neoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "electrophilic" as used herein refers to a chemical group that is capable of accepting electron density. An "electrophilic substituent," "electrophilic chemical moiety," or "electrophic moiety" refers to an electron-poor chemical group, substitutent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue (e.g., LC3, p62, NBR1, NDP52, or Optineurin cysteine residue) and may be referred to as a "covalent cysteine modifier" or "covalent cysteine modifier moiety" or "covalent cysteine modifier substituent." The covalent bond formed between the electrophilic substituent and the sulfhydryl group of the cysteine may be a reversible or irreversible bond. In some embodiments, the electrophilic substituent of the compound is capable of reacting with a lysine residue. In some embodiments, the electrophilic substituent of the compound is capable of reacting with a serine residue. In some embodiments, the electrophilic substituent of the compound is capable of reacting with a methionine residue.

"Nucleophilic" as used herein refers to a chemical group that is capable of donating electron density.

An amino acid residue in a protein "corresponds" to a given residue when it occupies the same essential structural position within the protein as the given residue. For example, a selected residue in a selected protein corresponds to C17 of human LC3A protein when the selected residue occupies the same essential spatial or other structural relationship as C17 in human LC3A protein. In some embodiments, where a selected protein is aligned for maximum homology with the human LC3A protein, the position in the aligned selected protein aligning with C17 is said to correspond to C17. Instead of a primary sequence alignment, a three dimensional structural alignment can also be used, e.g., where the structure of the selected protein is aligned for maximum correspondence with the human LC3A protein and the overall structures compared. In this case, an amino acid that occupies the same essential position as C17 in the structural model is said to correspond to the C17 residue.

An amino acid residue in a protein "corresponds" to a given residue when it occupies the same essential structural position within the protein as the given residue. For example, a selected residue in a selected protein corresponds to C26 of human p62/SQSTM1 protein when the selected residue occupies the same essential spatial or other structural relationship as C26 in human p62/SQSTM1 protein. In some embodiments, where a selected protein is aligned for maximum homology with the human p62/SQSTM1 protein, the position in the aligned selected protein aligning with C26 is said to correspond to C26. Instead of a primary sequence alignment, a three dimensional structural alignment can also be used, e.g., where the structure of the selected protein is aligned for maximum correspondence with the human p62/SQSTM1 protein and the overall structures compared. In this case, an amino acid that occupies the same essential position as C26 in the structural model is said to correspond to the C26 residue.

An amino acid residue in a protein "corresponds" to a given residue when it occupies the same essential structural position within the protein as the given residue. For example, a selected residue in a selected protein corresponds to C27 of human p62/SQSTM1 protein when the selected residue occupies the same essential spatial or other structural relationship as C27 in human p62/SQSTM1 protein. In some embodiments, where a selected protein is aligned for maximum homology with the human p62/SQSTM1 protein, the position in the aligned selected protein aligning with C27 is said to correspond to C27. Instead of a primary sequence alignment, a three dimensional structural alignment can also be used, e.g., where the structure of the selected protein is aligned for maximum correspondence with the human p62/SQSTM1 protein and the overall structures compared. In this case, an amino acid that occupies the same essential position as C27 in the structural model is said to correspond to the C27 residue.

An amino acid residue in a protein "corresponds" to a given residue when it occupies the same essential structural position within the protein as the given residue. For example, a selected residue in a selected protein corresponds to C120 of human NBR1 protein when the selected residue occupies the same essential spatial or other structural relationship as C120 in human NBR1 protein. In some embodiments, where a selected protein is aligned for maximum homology with the human NBR1 protein, the position in the aligned selected protein aligning with C120 is said to correspond to C120. Instead of a primary sequence alignment, a three dimensional structural alignment can also be used, e.g., where the structure of the selected protein is aligned for maximum correspondence with the human NBR1 protein and the overall structures compared. In this case, an amino acid that occupies the same essential position as C120 in the structural model is said to correspond to the C120 residue.

An amino acid residue in a protein "corresponds" to a given residue when it occupies the same essential structural position within the protein as the given residue. For example, a selected residue in a selected protein corresponds to C321 of human NDP52/CALCOCO2 protein when the selected residue occupies the same essential spatial or other structural relationship as C321 in human NDP52/CAL- COCO2 protein. In some embodiments, where a selected protein is aligned for maximum homology with the human NDP52/CALCOCO2 protein, the position in the aligned selected protein aligning with C321 is said to correspond to C321. Instead of a primary sequence alignment, a three dimensional structural alignment can also be used, e.g., where the structure of the selected protein is aligned for maximum correspondence with the human NDP52/CAL-COCO2 protein and the overall structures compared. In this case, an amino acid that occupies the same essential position as C321 in the structural model is said to correspond to the C321 residue.

An amino acid residue in a protein "corresponds" to a given residue when it occupies the same essential structural position within the protein as the given residue. For example, a selected residue in a selected protein corresponds to C558 of human OPTN protein when the selected residue occupies the same essential spatial or other structural relationship as C558 in human OPTN protein. In some embodiments, where a selected protein is aligned for maximum homology with the human OPTN protein, the position in the aligned selected protein aligning with C558 is said to correspond to C558. Instead of a primary sequence alignment, a three dimensional structural alignment can also be used, e.g., where the structure of the selected protein is aligned for maximum correspondence with the human OPTN protein and the overall structures compared. In this case, an amino acid that occupies the same essential position as C558 in the structural model is said to correspond to the C558 residue.

The term "isolated," when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide," and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, "biomolecule" is used in its customary sense and refers to a molecule found in nature or derivatives thereof, including macromolecules such as proteins, carbohydrates, lipids, and nucleic acids, as well as small molecules such as primary metabolites, secondary metabolites, and natural products. A biomolecule may be present as a moiety attached to the remainder of a compound. A biomolecule includes but is not limited to nucleic acids (e.g., DNA and RNA), peptide nucleic acids, sugars, peptides, proteins, antibodies, aptamers, lipids, small molecule affinity ligands (e.g., inhibitors, biotin, and haptens).

The term "targeted autophagy degrader" refers to a first substance (e.g., compound, biomolecule) capable of binding a targeted second substance (e.g., protein, protein aggregate, cellular component) and also binding a third substance, wherein the third substance is a component of an autophagy pathway or is associated with an autophagosome or with autophagy and wherein the targeted autophagy degrader binding to both the targeted second substance and third substance results in encapsulation of the targeted second substance in an autophagosome and subsequent degradation by autophagy. In embodiments, a targeted autophagy binder is a compound described herein.

The term "autophagy adapter protein binder" as used herein refers to a substance (e.g., a biomolecule, macromolecule, or compound) which is capable of binding (e.g., covalently binding) an autophagy adapter protein. In embodiments, autophagy adapter protein binder is a targeted autophagy binder. In embodiments, autophagy adapter protein binder is a part of a targeted autophagy binder. The term "targeted autophagy binder" refers to a substance (e.g., a biomolecule, macromolecule, or compound) which is capable of contacting a component of an autophagy pathway or component (e.g., protein) of a complex involved in the autophagy and/or formation of the autophagosome. In embodiments, the targeted autophagy binder is capable of binding (e.g., covalently binding) an autophagy adapter protein.

The term "autophagy adapter protein" as used herein refers to a protein which act as cargo receptor for degradation by autophagy. In embodiments, the autophagy adapter protein is LC3, p62, NBR1, NDP52, Optineurin, or a derivative, fragment, or homolog thereof. Additional information and characterization of the mechanisms involved with autophagy adapter proteins may be found in Johansen and Lamark (Johansen T, Lamark T. Selective autophagy mediated by autophagic adapter proteins. Autophagy. 2011; 7(3): 279-296. doi:10.4161/auto.7.3.14487), which is incorporated herein by reference in its entirety.

The term "cellular component binder" as used herein refers to a substance (e.g., a biomolecule, macromolecule, or compound) which is capable of binding a cellular component. In embodiments, the cellular component binder is a compound (e.g., a compound described herein). In embodiments, the cellular component binder is capable of binding a protein (e.g., BRD4). In embodiments, the cellular component binder is capable of binding a protein aggregate. In embodiments, the cellular component binder is a protein (e.g., antibody, antibody fragment, or receptor), nucleic acid (e.g., siRNA, antisense nucleic acid), aptamer, or compound).

The term "cellular component" as used herein refers to matter contained inside a cell (i.e., intracellular). Cellular components include matter naturally inside the cell (i.e., on the interior of the cell's lipid bilayer) as well as originally foreign agents (e.g., microorganisms, viruses, asbestos, or compounds or extracellular origin) that exist inside the cell. Non-limiting examples of a cellular component includes a protein (e.g., LC3, p62, NBR1, NDP52, Optineurin, or a derivative, fragment, or homolog thereof), ion (e.g., $Na^+$, $Mg^+$, $Cu^+$, $Cu^{2+}$, $Zn^{2+}$, $Mn^{2+}$, $Fe^{2+}$, and $Co^{2+}$), polysaccharides, lipid (e.g., fats, waxes, sterols, fat-soluble vitamins such as vitamins A, D, E, and K, monoglycerides, diglycerides, triglycerides, or phospholipids), nucleic acid (e.g., DNA or RNA), nucleotide, amino acid, particle (e.g., nanoparticle), fibers (e.g., asbestos fibers), organelle (e.g., mitochondria, peroxisome, plastid, endoplasmic reticulum, flagellum, or Golgi apparatus), cellular compartment, microorganism (e.g., bacterium, virus, or fungus), virus, vesicle (e.g., lysosome, peroxisome), small molecule, protein complex, protein aggregate, or a macromolecule). In embodiments, the cellular component is a biomolecule. In embodiments, the cellular component is a protein aggregate, soluble protein, midbody ring, damaged mitochodria, peroxisomes, intracellular bacteria, phagocytic membrane remnants, or viral capsid proteins. Non-limiting examples of intracellular proteins include BRD4, KRAS, MYC, YAP, TAZ, CTNNB1, APP, HTT, SNCA, NRF2, and MAPT. In embodiments, the cellular component is a protein aggregate (e.g., HTT, APP, SNCA, or MAPT). In embodiments, the cellular component is PINK1, ATG32, ESYT, PI3KC3, RAB10, or ATGL. In embodiments, the cellular component is a microorganism. In embodiments, the cellular component is a bacterial cell-surface glycan or bacterial cell surface protein.

The term "microorganism" is used in accordance with its plain ordinary meaning and refers to a single-cell organism, or multi-cellular organism (e.g., bacteria, fungi, protozoa) that is not visible to the naked eye. In embodiments, the microorganism is a bacterium.

The terms "virus" or "virus particle" are used according to their plain ordinary meanings within Virology and refer to a virion including the viral genome (e.g., DNA, RNA, single strand, double strand), viral capsid and associated proteins, and in the case of enveloped viruses (e.g., herpesvirus), an envelope including lipids and optionally components of host cell membranes, and/or viral proteins.

The term "small molecule" is used in accordance with its plain ordinary meaning and refers to a low molecular weight (e.g., with a molecular weight equal to or less than 900 Daltons) compound. In embodiments, the molecular weight of the small molecule is less than 500 Daltons. In embodiments, metabolites (e.g., secondary metabolites) are considered small molecules.

The term "protein complex" is used in accordance with its plain ordinary meaning and refers to a protein which is associated with an additional substance (e.g., another protein, protein subunit, or a compound). Protein complexes typically have defined quaternary structure. The association between the protein and the additional substance may be a covalent bond. In embodiments, the association between the protein and the additional substance (e.g., compound) is via non-covalent interactions. In embodiments, a protein complex refers to a group of two or more polypeptide chains. Proteins in a protein complex are linked by non-covalent protein-protein interactions. A non-limiting example of a protein complex is the proteasome.

The term "proteasome" is used in accordance with its plain ordinary meaning and refers to a protein complex which degrade proteins by proteolysis. The proteasome is made up of two subcomplexes: a catalytic core particle (also known as the 20S proteasome) and one or two terminal 19S regulatory particle(s) (RP) that serves as a proteasome activator with a molecular mass of approximately 700 kDa (called PA700). In embodiments, the proteasome degrades proteins thereby generating oligopeptides ranging in length from 3 to 15 amino-acid residues. Further information regarding the proteasome may be found in Tanaka (Tanaka K. The proteasome: Overview of structure and functions. Proceedings of the Japan Academy Series B, Physical and Biological Sciences. 2009; 85(1):12-36. doi:10.2183/pjab.85.12), which is incorporated herein by reference in its entirety for all purposes.

The term "protein aggregate" is used in accordance with its plain ordinary meaning and refers to an aberrant collection or accumulation of proteins (e.g., misfolded proteins). Protein aggregates are often associated with diseases (e.g., amyloidosis). Typically, when a protein misfolds as a result of a change in the amino acid sequence or a change in the native environment which disrupts normal non-covalent interactions, and the misfolded protein is not corrected or degraded, the unfolded/misfolded protein may aggregate. There are three main types of protein aggregates that may form: amorphous aggregates, oligomers, and amyloid fibrils. In embodiments, protein aggregates are termed aggresomes. In embodiments, the protein aggregate is HTT, APP, SNCA, or MAPT. In embodiments, the protein aggregate includes the protein Beta amyloid, Amyloid precursor protein, IAPP (Amylin), Alpha-synuclein, PrPSc, PrPSc, Huntingtin, Calcitonin, Atrial natriuretic factor, Apolipoprotein AI, Serum amyloid A, Medin, Prolactin, Transthyretin, Lysozyme, Beta-2 microglobulin, Gelsolin, Keratoepithelin, Beta amyloid, Cystatin, Immunoglobulin light chain AL, or S-IBM.

The term "amyloid" is used in accordance with its plain ordinary meaning and refers to a protein aggregate wherein the protein is folded into a shape that allows multiple copies of that protein to stick together. In embodiments, amyloids form fibrils. In embodiments, the compound described herein binds an amyloid, and is therefore an "amyloid binder".

The term "macromolecule" is used in accordance with its plain ordinary meaning and refers to a substance (e.g., compound, protein, nucleic acid, carbohydrate, lipid, or macrocycle) of high relative molecular mass, the structure of which may be derived from molecules of low relative molecular mass. In embodiments, a macromolecule has a molecular weight of greater than 900 Da. In embodiments, a macromolecule has a molecular weight of greater than 1500 Da. In embodiments, a macromolecule has a molecular weight of greater than 3000 Da.

A "nanoparticle," as used herein, is a particle wherein the longest diameter is from 1 to 1000 nanometers. The longest dimension of the nanoparticle may be referred to herein as the length of the nanoparticle. The shortest dimension of the nanoparticle may be referred to herein refer as the width of the nanoparticle. Nanoparticles may be composed of any appropriate material.

The term "vesicle" is used in accordance with its plain ordinary meaning and refers to a small membrane enclosed compartment within a cell. Vesicles are typically involved in transport, buoyancy control, or enzyme storage within a cell. Some vesicles, for example a lysosome, may include enzymes, proteins, polysaccharides, lipids, nucleic acids, or organelles within the compartment. Vesicles are typically formed within cells as a result of exocytosis or phagocytosis, however some vesicles are formed at the Golgi complex and transported to the cell membrane. Vesicles may be unilamellar or multilamellar.

The term "Sequestosome-1" or "SQSTM1" or "p62/SQSTM1" or "ubiquitin-binding protein p62" or "p62" refers to an autophagosome cargo protein (including homologs, isoforms, and functional fragments thereof) that targets other proteins that bind to it for selective autophagy. p62 harbors active nuclear import and export signals and shuttles between the nucleus and cytoplasm. The term "p62" refers to the nucleotide sequences or proteins of human p62. The term "p62" includes both the wild-type form of the nucleotide sequences or proteins as well as any mutants thereof. In some embodiments, "p62" is wild-type p62. In some embodiments, "p62" is one or more mutant forms. The term "p62" XYZ refers to a nucleotide sequence or protein of a mutant p62 wherein the Y numbered amino acid of p62 that has an X amino acid in the wildtype instead has a Z amino acid in the mutant. In embodiments, p62 is a functional fragment thereof. In some embodiments p62 refers to UniProt C9J6J8, having the sequence:

(SEQ ID NO: 3)
MASLTVKAYLLGKEDAAREIRRFSFCCSPEPEAEAEAAAGPGPCERLL

SRVAALFPALRPGGFQAHYRGGGFR.

In some embodiments p62 refers to UniProt Q13501, having the sequence:

(SEQ ID NO: 4)
MASLTVKAYLLGKEDAAREIRRFSFCCSPEPEAEAEAAAGPGPCERLL

SRVAALFPALRPGGFQAHYRDEDGDLVAFSSDEELTMAMSYVKDDIFR

IYIKEKKECRRDHRPPCAQEAPRNMVHPNVICDGCNGPVVGTRYKCSV

CPDYDLCSVCEGKGLHRGHTKLAFPSPFGHLSEGFSHSRWLRKVKHGH

FGWPGWEMGPPGNWSPRPPRAGEARPGPTAESASGPSEDPSVNFLKNV

GESVAAALSPLGIEVDIDVEHGGKRSRLTPVSPESSSTEEKSSSQPSS

CCSDPSKPGGNVEGATQSLAEQMRKIALESEGRPEEQMESDNCSGGDD

DWTHLSSKEVDPSTGELQSLQMPESEGPSSLDPSQEGPTGLKEAALYP

HLPPEADPRLIESLSQMLSMGFSDEGGWLTRLLQTKNYDIGAALDTIQ

YSKHPPPL.

In some embodiments p62 refers to the sequence:

(SEQ ID NO: 5)
RFSFCCSPEPEAEAEAAAGPGPCERL.

The term "Next to BRCA1 gene 1 protein" or "NBR1" refers to a protein (including homologs, isoforms, and functional fragments thereof) which acts as a cargo receptor in selective autophagy. The term "NBR1" refers to the nucleotide sequences or proteins of human NBR1. The term "NBR1" includes both the wildtype form of the nucleotide sequences or proteins as well as any mutants thereof. In some embodiments, "NBR1" is wild-type NBR1. In some embodiments, "NBR1" is one or more mutant forms. The term "NBR1" XYZ refers to a nucleotide sequence or protein of a mutant NBR1 wherein the Y numbered amino acid of NBR1 that has an X amino acid in the wildtype instead has a Z amino acid in the mutant. In embodiments, NBR1 is a functional fragment thereof. In some embodiments NBR1 refers to UniProt B7Z5R6, having the sequence:

(SEQ ID NO: 6)
MEPQVTLNVTFKNEIQSFLVSDPENTTWADIEAMVSINSQGEYEEALK

MAVKQGNQLQMQVHEGHHVVDEAPPPVVGAKRLAARAGKKPLAHYSSL

VRVLGSDMKTPEDPAVQSFPLVPCDTDQPQDKPPDWFTSYLETFREQV

VNETVEKLEQKLHEKLVLQNPSLGSCPSEVSMPTSEETLFLPENQFSW

HIACNNCQRRIVGVRYQCSLCPSYNICEDCEAGPYGHDTNHVLLKLRR

PVVGSSEPFCHSKYSTPRLPAALEQVRLQKQVDKNFLKAEKQRLRAEK

KQRKAEVKELKKQLKLHRKIHLWNSIHGLQSPKSPLGRPESLLQSNTL

MLPLQPCTSVMPMLSAAFVDENLPDGTHLQPGTKFIKHWRMKNTGNVK

WSADTKLKFMWGNLTLASTEKKDVLVPCLKAGHVGVVSVEFIAPALEG

TYTSHWRLSHKGQQFGPRVWCSIIVDPFPSEESPDNIEKGMISSSKTD

DLTCQQEETFLLAKEERQLGEVTEQTEGTAACIPQKAKNVASERELYI

PSVDLLTAQDLLSFELLDINIVQELERVPHNTPVDVTPCMSPLPHDSP

LIEKPGLGQIEEENEGAGFKALPDSMVSVKRKAENIASVEEAEEDLSG

TQFVCETVIRSLTLDAAPDHNPPCRQKSLQMTFALPEGPLGNEKEEII

HIAEEEAVMEEEEDEEDEEEEDELKDEVQSQSSASSEDYIIILPECFD

TSRPLGDSMYSSALSQPGLERGAEGKPGVEAGQEPAEAGERLPGGENQ

PQEHSISDILTTSQTLETVPLIPEVVELPPSLPRSSPCVMHGSPGVDL

PVTIPEVSSVPDQIRGANNF.

In some embodiments NBR1 refers to the sequence:

(SEQ ID NO: 7)
KTPEDPAVQSFPLVPCDTDQPQDKPPDWFTSYLETFRE.

The term "Calcium-binding and coiled-coil domain-containing protein 2" or "CALCOCO2" or "NDP52" or "NDP52/CALCOCO2" refers to a protein (including homologs, isoforms, and functional fragments thereof) that in humans is encoded by the CALCOCO2 gene. NDP52 proteins are believed to be associated with the nuclear matrix on the basis of their resistance to nuclease digestion and salt extraction. The term "NDP52" refers to the nucleotide sequences or proteins of human NDP52. The term "NDP52" includes both the wild-type form of the nucleotide sequences or proteins as well as any mutants thereof. In some embodiments, "NDP52" is wildtype NDP52. In some embodiments, "NDP52" is one or more mutant forms. The term "NDP52" XYZ refers to a nucleotide sequence or protein of a mutant NDP52 wherein the Y numbered amino acid of NDP52 that has an X amino acid in the wildtype instead has a Z amino acid in the mutant. In embodiments, NDP52 is a functional fragment thereof. In some embodiments NDP52 refers to UniProt Q13137, having the sequence:

(SEQ ID NO: 8)
MEETIKDPPTSAVLLDHCHFSQVIFNSVEKFYIPGGDVTCHYTFTQHFIP

RRKDWIGIFRVGWKTTREYYTFMWVTLPIDLNNKSAKQQEVQFKAYYLPK

DDEYYQFCYVDEDGVVRGASIPFQFRPENEEDILVVTTQGEVEEIEQHNK

ELCKENQELKDSCISLQKQNSDMQAELQKKQEELETLQSINKKLELKVKE

QKDYWETELLQLKEQNQKMSSENEKMGIRVDQLQAQLSTQEKEMEKLVQG

DQDKTEQLEQLKKENDHLFLSLTEQRKDQKKLEQTVEQMKQNETTAMKKQ

QELMDENFDLSKRLSENEIICNALQRQKERLEGENDLLKRENSRLLSYMG

LDFNSLPYQVPTSDEGGARQNPGLAYGNPYSGIQESSSPSPLSIKKCPIC

KADDICDHTLEQQQMQPLCFNCPICDKIFPATEKQIFEDHVFCHSL.

In some embodiments NDP52 refers to the sequence:

(SEQ ID NO: 9)
RLSENEIICNALQRQ.

The term "Optineurin" or "OPTN" refers to a protein (including homologs, isoforms, and functional fragments thereof) that in humans is encoded by the OPTN gene. Optineurin may function in cellular morphogenesis and membrane trafficking, vesicle trafficking, and transcription activation through its interactions with the RAB8, huntingtin, and transcription factor IIIA proteins The term "OPTN" refers to the nucleotide sequences or proteins of human OPTN. The term "OPTN" includes both the wild-type form of the nucleotide sequences or proteins as well as any mutants thereof. In some embodiments, "OPTN" is wildtype OPTN. In some embodiments, "OPTN" is one or more mutant forms. The term "OPTN" XYZ refers to a nucleotide sequence or protein of a mutant OPTN wherein the Y numbered amino acid of OPTN that has an X amino acid in the wildtype instead has a Z amino acid in the mutant. In embodiments, OPTN is a functional fragment thereof. In some embodiments OPTN refers to UniProt Q96CV9, having the sequence:

(SEQ ID NO: 10)
MSHQPLSCLTEKEDSPSESTGNGPPHLAHPNLDTFTPEELLQQMKELLTE

NHQLKEAMKLNNQAMKGRFEELSAWTEKQKEERQFFEIQSKEAKERLMAL

SHENEKLKEELGKLKGKSERSSEDPTDDSRLPRAEAEQEKDQLRTQVVRL

QAEKADLLGIVSELQLKLNSSGSSEDSFVEIRMAEGEAEGSVKEIKHSPG

PTRTVSTGTALSKYRSRSADGAKNYFEHEELTVSQLLLCLREGNQKVERL

EVALKEAKERVSDFEKKTSNRSEIETQTEGSTEKENDEEKGPETVGSEVE

ALNLQVTSLFKELQEAHTKLSKAELMKKRLQEKCQALERKNSAIPSELNE

-continued

```
KQELVYTNKKLELQVESMLSEIKMEQAKTEDEKSKLTVLQMTHNKLLQEH

NNALKTIEELTRKESEKVDRAVLKELSEKLELAEKALASKQLQMDEMKQT

IAKQEEDLETMTILRAQMEVYCSDFHAERAAREKIHEEKEQLALQLAVLL

KENDAFEDGGRQSLMEMQSRHGARTSDSDQQAYLVQRGAEDRDWRQQRNI

PIHSCPKCGEVLPDIDTLQIHVMDCII.
```

In some embodiments OPTN refers to the sequence:

```
                                        (SEQ ID NO: 11)
KCGEVLPDIDTLQIHVMDCII.
```

The term "Nuclear fragile X mental retardation-interacting protein 1" or "NUFIP1" refers to a protein (including homologs, isoforms, and functional fragments thereof) that in humans is encoded by the NUFIP1 gene. This protein is associated with the nuclear matrix in perichromatin fibrils and, in neurons, localizes to the cytoplasm in association with endoplasmic reticulum ribosomes. This protein interacts with the fragile X mental retardation protein (FMRP), the tumor suppressor protein BRCA1, upregulates RNA polymerase II transcription, and is involved in box C/D snoRNP biogenesis. The term "NUFIP1" refers to the nucleotide sequences or proteins of human NUFIP1. The term "NUFIP1" includes both the wild-type form of the nucleotide sequences or proteins as well as any mutants thereof. In some embodiments, "NUFIP1" is wild-type NUFIP1. In some embodiments, "NUFIP1" is one or more mutant forms. The term "NUFIP1" XYZ refers to a nucleotide sequence or protein of a mutant NUFIP1 wherein the Y numbered amino acid of NUFIP1 that has an X amino acid in the wild-type instead has a Z amino acid in the mutant. In embodiments, NUFIP1 is a functional fragment thereof. In some embodiments NUFIP1 refers to UniProt Q9UHK0, having the sequence:

```
                                        (SEQ ID NO: 12)
MAEPTSDFETPIGWHASPELTPTLGPLSDTAPPRDSWMFWAMLPPPPPPL

TSSLPAAGSKPSSESQPPMEAQSLPGAPPPFDAQILPGAQPPFDAQSPLD

SQPQPSGQPWNFHASTSWYWRQSSDRFPRHQKSFNPAVKNSYYPRKYDAK

FTDFSLPPSRKQKKKKRKEPVFHFFCDTCDRGFKNQEKYDKHMSEHTKCP

ELDCSFTAHEKIVQFHWRNMHAPGMKKIKLDTPEEIARWREERRKNYPTL

ANIERKKKLKLEKEKRGAVLTTTQYGKMKGMSRHSQMAKIRSPGKNHKWK

NDNSRQRAVTGSGSHLCDLKLEGPPEANADPLGVLINSDSESDKEEKPQH

SVIPKEVTPALCSLMSSYGSLSGSESEPEETPIKTEADVLAENQVLDSSA

PKSPSQDVKATVRNFSEAKSENRKKSFEKTNPKRKKDYHNYQTLFEPRTH

HPYLLEMLLAPDIRHERNVILQCVRYIIKKDFFGLDTNSAKSKDV.
```

The term "WD repeat and FYVE domain-containing protein 3" or "WDFY3" refers to a protein (including homologs, isoforms, and functional fragments thereof) that in humans is encoded by the WDFY3 gene. This protein is required for selective macroautophagy. WDFY3 acts as an adapter protein by linking specific proteins destined for degradation to the core autophagic machinery members, such as SQSTM1 and LC3. The term "WDFY3" refers to the nucleotide sequences or proteins of human WDFY3. The term "WDFY3" includes both the wild-type form of the nucleotide sequences or proteins as well as any mutants thereof. In some embodiments, "WDFY3" is wild-type WDFY3. In some embodiments, "WDFY3" is one or more mutant forms. The term "WDFY3" XYZ refers to a nucleotide sequence or protein of a mutant WDFY3 wherein the Y numbered amino acid of WDFY3 has an X amino acid in the wild-type instead has a Z amino acid in the mutant. In embodiments, WDFY3 is a functional fragment thereof. In some embodiments WDFY3 refers to UniProt Q8IZQ1, having the sequence:

```
                                        (SEQ ID NO: 13)
MNMVKRIMGRPRQEECSPQDNALGLMHLRRLFTELCHPPRHMTQKEQEEK

LYMMLPVFNRVFGNAPPNTMTEKFSDLLQFTTQVSRLMVTEIRRRASNKS

TEAASRAIVQFLEINQSEEASRGWMLLTTINLLASSGQKTVDCMTTMSVP

STLVKCLYLFFDLPHVPEAVGGAQNELPLAERRGLLQKVFVQILVKLCSF

VSPAEELAQKDDLQLLFSAITSWCPPYNLPWRKSAGEVLMTISRHGLSVN

VVKYIHEKECLSTCVQNMQQSDDLSPLEIVEMFAGLSCFLKDSSDVSQTL

LDDFRIWQGYNFLCDLLLRLEQAKEAESKDALKDLVNLITSLTTYGVSEL

KPAGITTGAPFLLPGFAVPQPAGKGHSVRNVQAFAVLQNAFLKAKTSFLA

QIILDAITNIYMADNANYFILESQHTLSQFAEKISKLPEVQNKYFEMLEF

VVFSLNYIPCKELISVSILLKSSSSYHCSIIAMKTLLKFTRHDYIFKDVF

REVGLLEVMVNLLHKYAALLKDPTQALNEQGDSRNNSSVEDQKHLALLVM

ETLTVLLQGSNTNAGIFREFGGARCAHNIVKYPQCRQHALMTIQQLVLSP

NGDDDMGTLLGLMHSAPPTELQLKTDILRALLSVLRESHRSRTVFRKVGG

FVYITSLLVAMERSLSCPPKNGWEKVNQNQVFELLHTVFCTLTAAMRYEP

ANSHFFKTEIQYEKLADAVRFLGCFSDLRKISAMNVFPSNTQPFQRLLEE

DVISIESVSPTLRHCSKLFIYLYKVATDSFDSRAEQIPPCLTSESSLPSP

WGTPALSRKRHAYHSVSTPPVYPPKNVADLKLHVTTSSLQSSDAVIIHPG

AMLAMLDLLASVGSVTQPEHALDLQLAVANILQSLVHTERNQQVMCEAGL

HARLLQRCSAALADEDHSLHPPLQRMFERLASQALEPMVLREFLRLASPL

NCGAWDKKLLKQYRVHKPSSLSYEPEMRSSMITSLEGLGTDNVFSLHEDN

HYRISKSLVKSAEGSTVPLTRVKCLVSMTTPHDIRLHGSSVTPAFVEFDT

SLEGFGCLFLPSLAPHNAPTNNTVTTGLIDGAVVSGIGSGERFFPPPSGL

SYSSWFCIEHFSSPPNNHPVRLLTVVRRANSSEQHYVCLAIVLSAKDRSL

IVSTKEELLQNYVDDFSEESSFYEILPCCARFRCGELIIEGQWHHLVLVM

SKGMLKNSTAALYIDGQLVNTVKLHYVHSTPGGSGSANPPVVSTVYAYIG

TPPAQRQIASLVWRLGPTHFLEEVLPSSNVTTIYELGPNYVGSFQAVCMP

CKDAKSEGVVPSPVSLVPEEKVSFGLYALSVSSLTVARIRKVYNKLDSKA

IAKQLGISSHENATPVKLIHNSAGHLNGSARTIGAALIGYLGVRTFVPKP

VATTLQYVGGAAAILGLVAMASDVEGLYAAVKALVCVVKSNPLASKEMER

IKGYQLLAMLLKKKRSLLNSHILHLTFSLVGTVDSGHETSIIPNSTAFQD

LLCDFEVWLHAPYELHLSLFEHFIELLTESSEASKNAKLMREFQLIPKLL

LTLRDMSLSQPTIAAISNVLSFLLQGFPSSNDLLRFGQFISSTLPTFAVC

EKFVVMEINNEEKLDTGTEEEFGGLVSANLILLRNRLLDILLKLIYTSKE
```

```
KTSINLQACEELVKTLGFDWIMMFMEEHLHSTTVTAAMRILVVLLSNQSI

LIKFKEGLSGGGWLEQTDSVLTNKIGTVLGFNVGRSAGGRSTVREINRDA

CHFPGFPVLQSFLPKHTNVPALYFLLMALFLQQPVSELPENLQVSVPVIS

CRSKQGCQFDLDSIWTFIFGVPASSGTVVSSIHNVCTEAVFLLLGMLRSM

LTSPWQSEEEGSWLREYPVTLMQFFRYLYHNVPDLASMWMSPDFLCALAA

TVFPFNIRPYSEMVTDLDDEVGSPAEEFKAFAADTGMNRSQSEYCNVGTK

TYLTNHPAKKFVFDFMRVLIIDNLCLTPASKQTPLIDLLLEASPERSTRT

QQKEFQTYILDSVMDHLLAADVLLGEDASLPITSGGSYQVLVNNVFYFTQ

RVVDKLWQGMFNKESKLLIDFIIQLIAQSKRRSQGLSLDAVYHCLNRTIL

YQFSRAHKTVPQQVALLDSLRVLTVNRNLILGPGNHDQEFISCLAHCLIN

LHVGSNVDGFGLEAEARMTTWHIMIPSDIEPDGSYSQDISEGRQLLIKAV

NRVWTELIHSKKQVLEELFKVTLPVNERGHVDIATARPLIEEAALKCWQN

HLAHEKKCISRGEALAPTTQSKLSRVSSGFGLSKLTGSRRNRKESGLNKH

SLSTQEISQWMFTHIAVVRDLVDTQYKEYQERQQNALKYVTEEWCQIECE

LLRERGLWGPPIGSHLDKWMLEMTEGPCRMRKKMVRNDMFYNHYPYVPET

EQETNVASEIPSKQPETPDDIPQKKPARYRRAVSYDSKEYYMRLASGNPA

IVQDAIVESSEGEAAQQEPEHGEDTIAKVKGLVKPPLKRSRSAPDGGDEE

NQEQLQDQIAEGSSIEEEEKTDNATLLRLLEEGEKIQHMYRCARVQGLDT

SEGLLLFGKEHFYVIDGFTMTATREIRDIETLPPNMHEPIIPRGARQGPS

QLKRTCSIFAYEDIKEVHKRRYLLQPIAVEVFSGDGRNYLLAFQKGIRNK

VYQRFLAVVPSLTDSSESVSGQRPNTSVEQGSGLLSTLVGEKSVTQRWER

GEISNFQYLMHLNTLAGRSYNDLMQYPVFPWILADYDSEEVDLTNPKTFR

NLAKPMGAQTDERLAQYKKRYKDWEDPNGETPAYHYGTHYSSAMIVASYL

VRMEPFTQIFLRLQGGHFDLADRMFHSVREAWYSASKHNMADVKELIPEF

FYLPEFLFNSNNFDLGCKQNGTKLGDVILPPWAKGDPREFIRVHREALEC

DYVSAHLHEWIDLIFGYKQQGPAAVEAVNVFHHLFYEGQVDIYNINDPLK

ETATIGFINNFGQIPKQLFKKPHPPKRVRSRLNGDNAGISVLPGSTSDKI

FFHHLDNLRPSLTPVKELKEPVGQIVCTDKGILAVEQNKVLIPPTWNKTF

AWGYADLSCRLGTYESDKAMTVYECLSEWGQILCAICPNPKLVITGGTST

VVCVWEMGTSKEKAKTVTLKQALLGHTDTVTCATASLAYHIIVSGSRDRT

CIIWDLNKLSFLTQLRGHRAPVSALCINELTGDIVSCAGTYIHVWSINGN

PIVSVNTFTGRSQQIICCCMSEMNEWDTQNVIVTGHSDGVVRFWRMEFLQ

VPETPAPEPAEVLEMQEDCPEAQIGQEAQDEDSSDSEADEQSISQDPKDT

PSQPSSTSHRPRAASCRATAAWCTDSGSDDSRRWSDQLSLDEKDGFIFVN

YSEGQTRAHLQGPLSHPHPNPIEVRNYSRLKPGYRWERQLVFRSKLTMHT

AFDRKDNAHPAEVTALGISKDHSRILVGDSRGRVFSWSVSDQPGRSAADH

WVKDEGGDSCSGCSVRFSLTERRHHCRNCGQLFCQKCSRFQSEIKRLKIS

SPVRVCQNCYYNLQHERGSEDGPRNC.
```

The term "Reticulophagy regulator 1" or "RETREG1" or "FAM134B" refers to a protein (including homologs, isoforms, and functional fragments thereof) that mediates endoplasmic reticulum delivery into lysosomes through sequestration into autophagosomes. The term "RETREG1" refers to the nucleotide sequences or proteins of human RETREG1. The term "RETREG1" includes both the wild-type form of the nucleotide sequences or proteins as well as any mutants thereof. In some embodiments, "RETREG1" is wild-type RETREG1. In some embodiments, "RETREG1" is one or more mutant forms. The term "RETREG1" XYZ refers to a nucleotide sequence or protein of a mutant RETREG1 wherein the Y numbered amino acid of RETREG1 has an X amino acid in the wild-type instead has a Z amino acid in the mutant. In embodiments, RETREG1 is a functional fragment thereof. In some embodiments RETREG1 refers to UniProt Q9H6L5, having the sequence:

```
                                             (SEQ ID NO: 14)
MASPAPPEHAEEGCPAPAAEEQAPPSPPPPQASPAERQQQEEEAQEAGAA

EGAGLQVEEAAGRAAAAVTWLLGEPVLWLGCRADELLSWKRPLRSLLGFV

AANLLFWFLALTPWRVYHLISVMILGRVIMQIIKDMVLSRTRGAQLWRSL

SESWEVINSKPDERPRLSHCIAESWMNFSIFLQEMSLFKQQSPGKFCLLV

CSVCTFFTILGSYIPGVILSYLLLLCAFLCPLFKCNDIGQKIYSKIKSVL

LKLDFGIGEYINQKKRERSEADKEKSHKDDSELDFSALCPKISLTVAAKE

LSVSDTDVSEVSWTDNGTFNLSEGYTPQTDTSDDLDRPSEEVFSRDLSDF

PSLENGMGTNDEDELSLGLPTELKRKKEQLDSGHRPSKETQSAAGLTLPL

NSDQTFHLMSNLAGDVITAAVTAAIKDQLEGVQQALSQAAPIPEEDTDTE

EGDDFELLDQSELDQIESELGLTQDQEAEAQQNKKSSGFLSNLLGGH.
```

The term "BNIP3L" or "NIP3-like protein X" or "Nix" refers to a protein (including homologs, isoforms, and functional fragments thereof) that in humans is encoded by the Nix gene. Nix is a protein that induces autophagy. The protein directly targets mitochondria and causes apoptotic changes. The term "Nix" refers to the nucleotide sequences or proteins of human Nix. The term "Nix" includes both the wild-type form of the nucleotide sequences or proteins as well as any mutants thereof. In some embodiments, "Nix" is wild-type Nix. In some embodiments, "Nix" is one or more mutant forms. The term "Nix" XYZ refers to a nucleotide sequence or protein of a mutant Nix wherein the Y numbered amino acid of Nix has an X amino acid in the wild-type instead has a Z amino acid in the mutant. In embodiments, Nix is a functional fragment thereof. In some embodiments Nix refers to UniProt O60238, having the sequence:

```
                                             (SEQ ID NO: 15)
MSSHLVEPPPPLHNNNNNCEENEQSLPPPAGLNSSWVELPMNSSNGNDNG

NGKNGGLEHVPSSSSIHNGDMEKILLDAQHESGQSSSRGSSHCDSPSPQE

DGQIMFDVEMHTSRDHSSQSEEEVVEGEKEVEALKKSADWVSDWSSRPEN

IPPKEFHFRHPKRSVSLSMRKSGAMKKGGIFSAEFLKVFIPSLFLSHVLA

LGLGIYIGKRLSTPSASTY.
```

The term "Toll interacting protein" or "TOLLIP" refers to a protein (including homologs, isoforms, and functional fragments thereof) that in humans is encoded by the TOLLIP gene. TOLLIP is a protein that connects the ubiquitin pathway to autophagy by functioning as a uniquitin-ATG8 family adapter. The term "TOLLIP" refers to the nucleotide sequences or proteins of human TOLLIP. The term "TOLLIP" includes both the wild-type form of the nucleotide sequences or proteins as well as any mutants thereof. In some embodiments, "TOLLIP" is wild-type TOLLIP. In some embodiments, "TOLLIP" is one or more mutant forms. The term "TOLLIP" XYZ refers to a nucleotide sequence or protein of a mutant TOLLIP wherein the Y numbered amino acid of TOLLIP has an X amino acid in the wild-type instead has a Z amino acid in the mutant. In embodiments, TOLLIP is a functional fragment thereof. In some embodiments TOLLIP refers to UniProt Q9H0E2, having the sequence:

(SEQ ID NO: 16)
MATTVSTQRGPVYIGELPQDFLRITPTQQQRQVQLDAQAAQQLQYGGAVGT

VGRLNITVVQAKLAKNYGMTRMDPYCRLRLGYAVYETPTAHNGAKNPRWNK

VIHCTVPPGVDSFYLEIFDERAFSMDDRIAWTHITIPESLRQGKVEDKWYS

LSGRQGDDKEGMINLVMSYALLPAAMVMPPQPVVLMPTVYQQGVGYVPITG

MPAVCSPGMVPVALPPAAVNAQPRCSEEDLKAIQDMFPNMDQEVIRSVLEA

QRGNKDAAINSLLQMGEEP.

The term "Taxi-binding protein 1" or "TAX1BP1" refers to a protein (including homologs, isoforms, and functional fragments thereof) that in humans is encoded by the TAX1BP1 gene. TAX1BP1 is a protein that inhibits TNF-induced apoptosis by mediating the TNPAIP3 anti-apoptotic activity. The term "TAX1BP1" refers to the nucleotide sequences or proteins of human TAX1BP1. The term "TAX1BP1" includes both the wild-type form of the nucleotide sequences or proteins as well as any mutants thereof. In some embodiments, "TAX1BP1" is wild-type TAX1BP1. In some embodiments, "TAX1BP1" is one or more mutant forms. The term "TAX1BP1" XYZ refers to a nucleotide sequence or protein of a mutant TAX1BP1 wherein the Y numbered amino acid of TAX1BP1 has an X amino acid in the wild-type instead has a Z amino acid in the mutant. In embodiments, TAX1BP1 is a functional fragment thereof. In some embodiments TAX1BP1 refers to UniProt Q86VP1, having the sequence:

(SEQ ID NO: 17)
MTSFQEVPLQTSNFAHVIFQNVAKSYLPNAHLECHYTLTPYIHPHPKDWVG

IFKVGWSTARDYYTFLWSPMPEHYVEGSTVNCVLAFQGYYLPNDDGEFYQF

CYVTHKGEIRGASTPFQFRASSPVEELLTMEDEGNSDMLVVTTKAGLLELK

IEKTMKEKEELLKLIAVLEKETAQLREQVGRMERELNHEKERCDQLQAEQK

GLTEVTQSLKMENEEFKKRFSDATSKAHQLEEDIVSVTHKAIEKETELDSL

KDKLKKAQHEREQLECQLKTEKDEKELYKVHLKNTEIENTKLMSEVQTLKN

LDGNKESVITHFKEEIGRLQLCLAEKENLQRTFLLTTSSKEDTCFLKEQLR

KAEEQVQATRQEVVFLAKELSDAVNVRDRTMADLHTARLENEKVKKQLADA

VAELKLNAMKKDQDKTDTLEHELRREVEDLKLRLQMAADHYKEKFKECQRL

QKQINKLSDQSANNNNVFTKKTGNQQKVNDASVNTDPATSASTVDVKPSPS

AAEADFDIVTKGQVCEMTKEIADKTEKYNKCKQLLQDEKAKCNKYADELAK

MELKWKEQVKIAENVKLELAEVQDNYKELKRSLENPAERKMEGQNSQSPQC

FKTCSEQNGYVLTLSNAQPVLQYGNPYASQETRDGADGAFYPDEIQRPPVR

VPSWGLEDNVVCSQPARNFSRPDGLEDSEDSKEDENVPTAPDPPSQHLRGH

GTGFCFDSSFDVHKKCPLCELMFPPNYDQSKFEEHVESHWKVCPMCSEQFP

PDYDQQVFERHVQTHFDQNVLNFD.

The term "autophagosome" is used in accordance with its plain ordinary meaning and refers to a vesicle that contains a cellular component slated to be degraded by autophagy. In embodiments, autophagosome formation is a multistep process that includes the biogenesis of the phagophore, followed by its elongation and closure. In embodiments, more than 15 autophagy-related ATG proteins, as well as class III PI3 kinases, may be required to construct the autophagosome, including the transmembrane ATG protein ATG9, along with membranes from multiple sources cellular sources.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including, e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein) and is capable of reducing transcription of the target nucleic acid (e.g., mRNA from DNA), reducing the translation of the target nucleic acid (e.g. mRNA), altering transcript splicing (e.g., single stranded morpholino oligo), or interfering with the endogenous activity of the target nucleic acid. See, e.g., Weintraub, *Scientific American*, 262:40 (1990). Typically, synthetic antisense nucleic acids (e.g., oligonucleotides) are generally between 15 and 25 bases in length. Thus, antisense nucleic acids are capable of hybridizing to (e.g., selectively hybridizing to) a target nucleic acid (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein). In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein) in vitro. In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein) in a cell. In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein) in an organism. In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein) under physiological conditions. Antisense nucleic acids may comprise naturally occurring nucleotides or modified nucleotides such as, e.g., phosphorothioate, methylphosphonate, and -anomeric sugar-phosphate, backbone-modified nucleotides.

In the cell, the antisense nucleic acids hybridize to the corresponding RNA (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein) forming a double-stranded molecule. The antisense nucleic acids interfere with the endogenous behavior of the RNA (e.g., a nucleic acid coding for one or more amino acids corresponding to C17 of human LC3A protein; C26 of human p62/SQSTM1 protein; C27 of human p62/SQSTM1protein; C120 of human NBR1 protein; C321 of human NDP52/CALCOCO2 protein; or C558 of human OPTN protein) and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or precursors, such as nucleotide analogs), short hairpin RNAs (shRNA), micro RNAs (miRNA), saRNAs (small activating RNAs) and small nucleolar RNAs (snoRNA) or certain of their derivatives or precursors.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$," or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J. Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

The term "irreversible covalent bond" is used in accordance with its plain ordinary meaning in the art and refers to the resulting association between atoms or molecules of (e.g., electrophilic chemical moiety and nucleophilic moiety) wherein the probability of dissociation is low. In embodiments, the irreversible covalent bond does not easily dissociate under normal biological conditions. In embodiments, the irreversible covalent bond is formed through a chemical reaction between two species (e.g., electrophilic chemical moiety and cysteine).

II. Compounds and Compositions

In an aspect is provided a compound including a monovalent cellular component binder covalently bound to a monovalent targeted autophagy protein binder. In embodiments, the monovalent targeted autophagy protein binder is a monovalent autophagy adapter protein binder (e.g., a monovalent compound described herein).

In embodiments, the cellular component binder is a compound described herein. In embodiments, the cellular component binder is an oligonucleotide (e.g., DNA, RNA, or siRNA), protein (e.g., antibody or antibody fragment), or compound (e.g., compound described herein).

In embodiments, the targeted autophagy protein binder is a compound described herein. In embodiments, the targeted autophagy protein binder is an oligonucleotide (e.g., DNA, RNA, or siRNA), protein (e.g., antibody, anti-LC3 antibody, anti-p62 antibody, anti-NBR1 antibody, anti-NDP52 antibody, anti-Optineurin antibody, anti-NUFIP1 antibody, anti-WDFY3 antibody, anti-RETREG1 antibody, anti-Nix antibody, anti-TOLLIP antibody, anti-TAX1BP1 antibody, anti-LC3 binding antibody fragment, anti-p62 binding antibody fragment, anti-NBR1 binding antibody fragment, anti-NDP52 binding antibody fragment, anti-Optineurin binding antibody fragment, anti-NUFIP1 binding antibody fragment, anti-WDFY3 binding antibody fragment, anti-RETREG1 binding antibody fragment, anti-Nix binding antibody fragment, anti-TOLLIP binding antibody fragment, or anti-TAX1BP1 binding antibody fragment), or compound (e.g., compound described herein).

In embodiments, the oligonucleotide is an antisense nucleic acid. In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C113 of human p62/SQSTM1 protein; C120 of human NBR1 protein; C321 of human NDP52/CALCOCO2 protein; or C558 of human OPTN protein) in vitro. In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C113 of human p62/SQSTM1 protein; C120 of human NBR1 protein; C321 of human NDP52/CALCOCO2 protein; or C558 of human OPTN protein) in a cell. In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C113 of human p62/SQSTM1 protein; C120 of human NBR1 protein; C321 of human NDP52/CALCOCO2 protein; or C558 of human OPTN protein) in an organism. In embodiments, the antisense nucleic acid hybridizes to the target nucleic acid (e.g., a nucleic acid coding for one or more amino acids corresponding to C17 of human LC3A protein; C26 of human p62/SQSTM1 protein; C27 of human p62/SQSTM1protein; C113 of human p62/

SQSTM1 protein; C120 of human NBR1 protein; C321 of human NDP52/CALCOCO2 protein; or C558 of human OPTN protein) under physiological conditions.

In embodiments, the compound is a targeted autophagy degrader. In embodiments, the targeted autophagy binder is capable of contacting an autophagy adapter protein. In embodiments, the targeted autophagy binder is capable of binding (e.g., covalently binding) an autophagy adapter protein. In embodiments, the monovalent targeted autophagy binder is capable of contacting an autophagy adapter protein. In embodiments, the monovalent targeted autophagy binder is capable of binding (e.g., covalently binding) an autophagy adapter protein.

In embodiments, a divalent linker binds the monovalent cellular component binder to the monovalent targeted autophagy protein binder (e.g., monovalent autophagy adapter protein binder).

In embodiments, the divalent linker has the formula -$L^1$-$L^2$-$L^3$-$L^4$-.

$L^1$ is connected directly to the monovalent targeted autophagy protein binder (e.g., monovalent autophagy adapter protein binder). $L^1$ is —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconugate linker. In embodiments, $L^1$ is —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is a bioconjugate linker.

$L^2$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker. In embodiments, $L^2$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is a bioconjugate linker.

$L^3$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconugate linker. In embodiments, $L^3$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^3$ is a bioconjugate linker.

$L^4$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconugate linker. In embodiments, $L^4$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bioconjugate linker.

In embodiments, the divalent linker -$L^1$-$L^2$-$L^3$-$L^4$- has the formula —O-$L^2$-$L^3$-$L^4$— and $L^2$, $L^3$, and $L^4$ are as described herein. In embodiments, the divalent linker has the formula —O-$L^2$-$L^3$-O— and $L^2$ and $L^3$ are as described herein. In embodiments, the divalent linker -$L^1$-$L^2$-$L^3$-$L^4$- has the formula -$L^1$-$L^2$-$L^3$-O— and $L^1$, $L^2$, and $L^3$ are as described herein. In embodiments, the divalent linker -$L^1$-$L^2$-$L^3$-$L^4$- has the formula —O-$L^2$-$L^3$-O—, $L^2$ is $R^{44}$-substituted or unsubstituted alkylene (e.g., $C_1$-$C_8$ alkylene, $C_1$-$C_6$ alkylene, or $C_1$-$C_4$ alkylene), $L^3$ is $R^{45}$-substituted or unsubstituted alkylene (e.g., $C_1$-$C_8$ alkylene, $C_1$-$C_6$ alkylene, or $C_1$-$C_4$ alkylene), and $R^{44}$ and $R^{45}$ are as described herein. In embodiments, the divalent linker -$L^1$-$L^2$-$L^3$-$L^4$- has the formula —O-$L^2$-$L^3$-O—, $L^2$ is unsubstituted alkylene (e.g., $C_1$-$C_8$ alkylene, $C_1$-$C_6$ alkylene, or $C_1$-$C_4$ alkylene), and $L^3$ is unsubstituted alkylene (e.g., $C_1$-$C_8$ alkylene, $C_1$-$C_6$ alkylene, or $C_1$-$C_4$ alkylene). In embodiments, the divalent linker -$L^1$-$L^2$-$L^3$-$L^4$- has the formula —O-$L^2$-O—, $L^2$ is $R^{44}$-substituted or unsubstituted alkylene (e.g., $C_1$-$C_8$ alkylene, $C_1$-$C_6$ alkylene, or $C_1$-$C_4$ alkylene), and $R^{44}$ is as described herein. In embodiments, the divalent linker -$L^1$-$L^2$-$L^3$-$L^4$- has the formula —O-$L^2$-$L^3$-O—, $L^3$ is a bond, $L^2$ is unsubstituted alkylene (e.g., $C_1$-$C_8$ alkylene, $C_1$-$C_6$ alkylene, or $C_1$-$C_4$ alkylene). In embodiments, of the divalent linker of formula -$L^1$-$L^2$-$L^3$-$L^4$-; $L^1$, $L^3$, and $L^4$ are a bond; $L^2$ is $R^{44}$-substituted or unsubstituted heteroalkylene (e.g., 2 to 8 membered heteroalkylene, 2 to 6 membered heteroalkylene, or 2 to 4 membered heteroalkylene); and $R^{44}$ is as described herein. In embodiments, of the divalent linker of formula -$L^1$-$L^2$-$L^3$-$L^4$-; $L^1$, $L^3$, and $L^4$ are a bond; $L^2$ is $R^{44}$-substituted heteroalkylene (e.g., 2 to 8 membered heteroalkylene, 2 to 6 membered heteroalkylene, or 2 to 4 membered heteroalkylene); and $R^{44}$ is as described herein. In embodiments, of the divalent linker of formula -$L^1$-$L^2$-$L^3$-$L^4$-; $L^1$, $L^3$, and $L^4$ are a bond; $L^2$ is $R^{44}$-substituted heteroalkylene (e.g., 2 to 8 membered heteroalkylene, 2 to 6 membered heteroalkylene, or 2 to 4 membered heteroalkylene); and $R^{44}$ is oxo. In embodiments, of the divalent linker of formula -$L^1$-$L^2$-$L^3$-$L^4$-; $L^1$, $L^3$, and $L^4$ are a bond; $L^2$ is unsubstituted heteroalkylene (e.g., 2 to 8 membered heteroalkylene, 2 to 6 membered heteroalkylene, or 2 to 4 membered heteroalkylene). In embodiments, of the divalent linker of formula -$L^1$-$L^2$-$L^3$-$L^4$-; $L^1$, $L^3$, and $L^4$ are a bond; $L^2$ is unsubstituted 2 to 8 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 2 to 6 membered heteroalkylene. In embodiments, of the divalent linker of formula -$L^1$-$L^2$-$L^3$-$L^4$-; $L^1$, $L^3$, and $L^4$ are a bond;

$L^2$ is unsubstituted 2 to 4 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 2 to 12 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 2 to 10 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 2 to 8 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 4 to 12 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 4 to 10 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 6 to 12 membered heteroalkylene. In embodiments, of the divalent linker of formula -$L^1$-$L^2$-$L^3$-$L^4$-; $L^1$, $L^3$, and $L^4$ are a bond; $L^2$ is unsubstituted 8 to 12 membered heteroalkylene.

In embodiments, the linker is a linker described in US20160272639A1, WO2017079723A1, US20130190340A1, or WO2013106643A2 which are incorporated herein by reference in their entirety for all purposes. In embodiments, the linker is

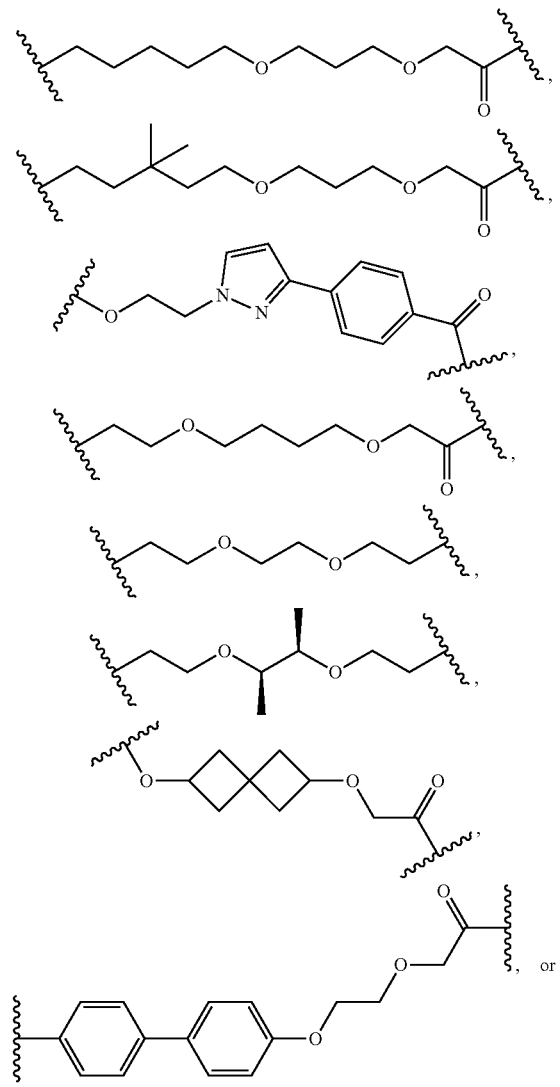

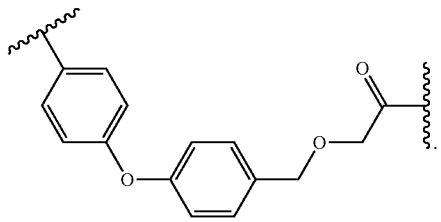

In embodiments, the linker is:

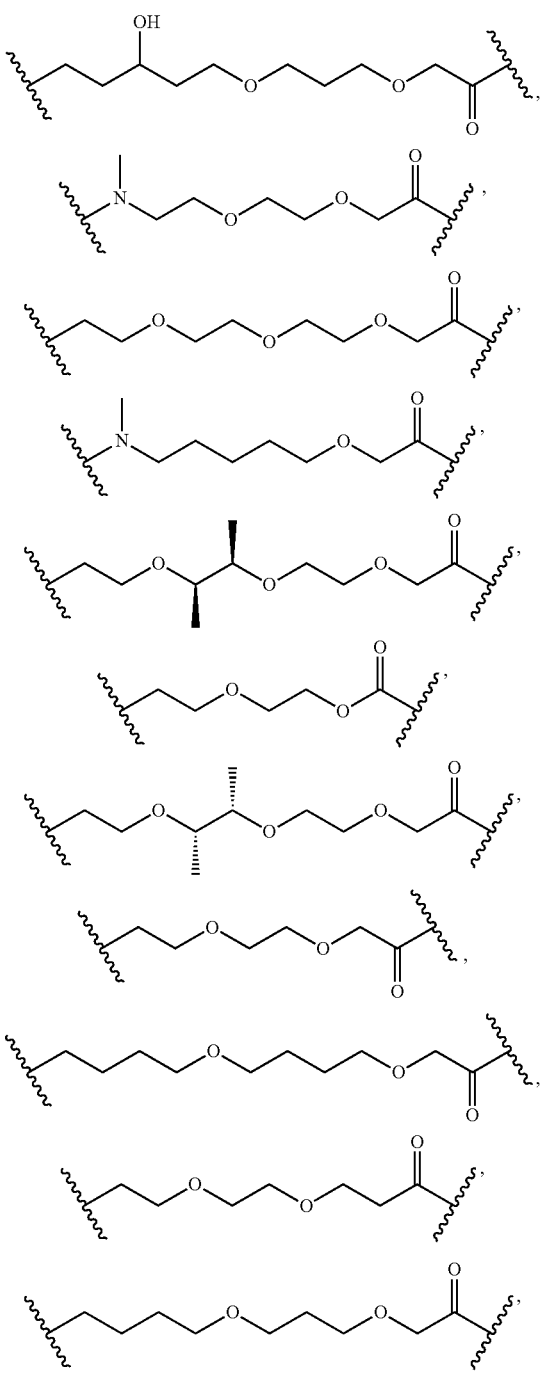

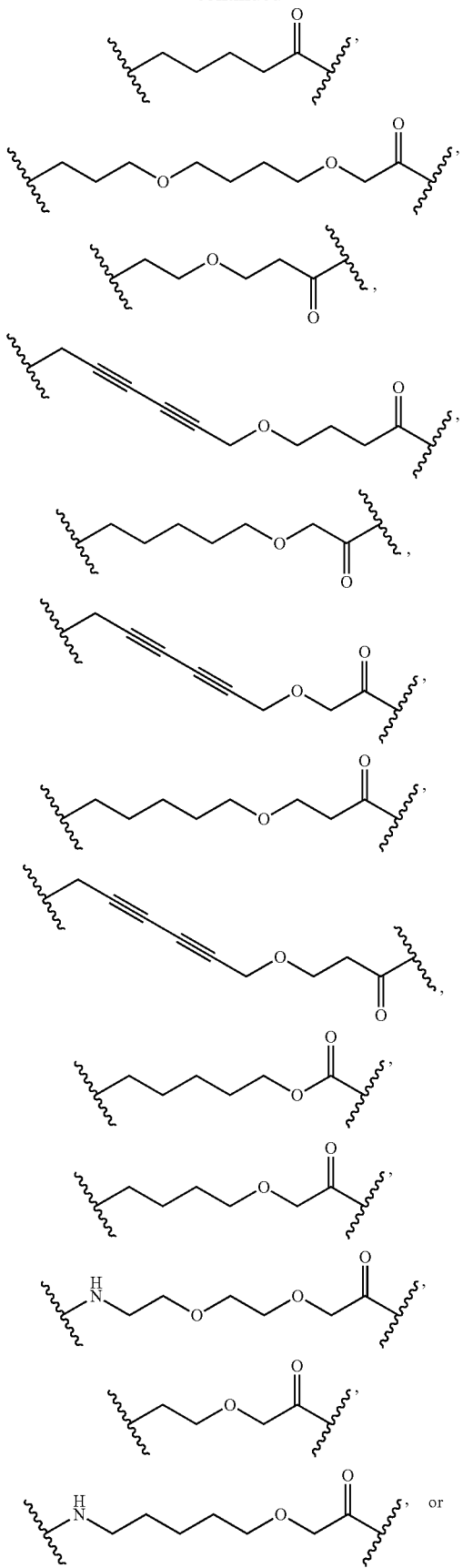

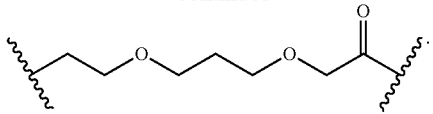

In embodiments, the linker is

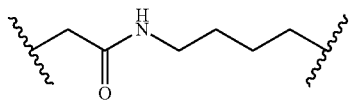

In embodiments, the cellular component is a protein, ion, lipid, nucleic acid, nucleotide, amino acid, protein, particle, organelle, cellular compartment, microorganism, virus, lipid droplet, vesicle, small molecule, protein complex, protein aggregate, or macromolecule. In embodiments, the cellular component is a protein. In embodiments, the cellular component is an ion. In embodiments, the cellular component is a lipid. In embodiments, the cellular component is a nucleic acid. In embodiments, the cellular component is a nucleotide. In embodiments, the cellular component is an amino acid. In embodiments, the cellular component is a protein. In embodiments, the cellular component is a particle. In embodiments, the cellular component is an organelle. In embodiments, the cellular component is a cellular compartment. In embodiments, the cellular component is a microorganism. In embodiments, the cellular component is a vesicle. In embodiments, the cellular component is a small molecule. In embodiments, the cellular component is a protein complex. In embodiments, the cellular component is a protein aggregate. In embodiments, the cellular component is a macromolecule. In embodiments, the cellular component is a lipid droplet. In embodiments, the cellular component is a virus.

In embodiments, the compound including a monovalent cellular component binder covalently bound to a monovalent targeted autophagy protein binder, includes a plurality of optionally different monovalent targeted autophagy protein binders.

In embodiments, the cellular component is a ion (e.g., $Na^+$, $Mg^+$, $Cu^+$, $Zn^{2+}$, $Mn^{2+}$, $Fe^{2+}$, and $Co^{2+}$). In embodiments, the cellular component is a polysaccharide. In embodiments, the cellular component is a lipid (e.g., fats, waxes, sterols, fat-soluble vitamins such as vitamins A, D, E, and K, monoglycerides, diglycerides, triglycerides, or phospholipids). In embodiments, the cellular component is a nucleic acid (e.g., DNA or RNA). In embodiments, the cellular component is a nucleotide. In embodiments, the cellular component is an amino acid. In embodiments, the cellular component is a particle (e.g., nanoparticle). In embodiments, the cellular component is a plurality of fiber (e.g., asbestos fibers). In embodiments, the cellular component is an organelle (e.g., mitochondria, peroxisome, plastid, endoplasmic reticulum, flagellum, or Golgi apparatus). In embodiments, the cellular component is a cellular compartment. In embodiments, the cellular component is a microorganism (e.g., bacterium, virus, or fungus). In embodiments, the cellular component is a virus. In embodiments, the cellular component is a vesicle (e.g., lysosome, peroxisome). In embodiments, the cellular component is a small molecule. In embodiments, the cellular component is a protein complex. In embodiments, the cellular component is a protein aggregate. In embodiments, the cellular component is a macromolecule. In embodiments, the cellular component is a biomolecule. In embodiments, the cellular component is a protein aggregate, soluble protein, midbody ring, damaged mitochodria, peroxisomes, intracellular bacteria, phagocytic membrane remnants, or viral capsid proteins. In embodiments, the cellular component is a misfolded protein.

In embodiments, the monovalent cellular component binder is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the monovalent cellular component binder is a substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the monovalent cellular component binder is a substituted or unsubstituted alkyl (e.g., $C_1$-$C_8$ alkyl, $C_1$-$C_6$ alkyl, or $C_1$-$C_4$ alkyl). In embodiments, the monovalent cellular component binder is a substituted alkyl (e.g., $C_1$-$C_8$ alkyl, $C_1$-$C_6$ alkyl, or $C_1$-$C_4$ alkyl). In embodiments, the monovalent cellular component binder is an unsubstituted alkyl (e.g., $C_1$-$C_8$ alkyl, $C_1$-$C_6$ alkyl, or $C_1$-$C_4$ alkyl). In embodiments, the monovalent cellular component binder is a substituted or unsubstituted heteroalkyl (e.g., 2 to 8 membered heteroalkyl, 2 to 6 membered heteroalkyl, or 2 to 4 membered heteroalkyl). In embodiments, the monovalent cellular component binder is a substituted heteroalkyl (e.g., 2 to 8 membered heteroalkyl, 2 to 6 membered heteroalkyl, or 2 to 4 membered heteroalkyl). In embodiments, the monovalent cellular component binder is an unsubstituted heteroalkyl (e.g., 2 to 8 membered heteroalkyl, 2 to 6 membered heteroalkyl, or 2 to 4 membered heteroalkyl). In embodiments, the monovalent cellular component binder is a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, the monovalent cellular component binder is a substituted cycloalkyl (e.g., $C_3$-$C_8$ cycloalkyl, $C_3$-$C_6$ cycloalkyl, or $C_5$-$C_6$ cycloalkyl). In embodiments, the monovalent cellular component binder is an unsubstituted cycloalkyl (e.g., $C_3$-$C_8$ cycloalkyl, $C_3$-$C_6$ cycloalkyl, or $C_5$-$C_6$ cycloalkyl). In embodiments, the monovalent cellular component binder is a substituted or unsubstituted heterocycloalkyl (e.g., 3 to 8 membered heterocycloalkyl, 3 to 6 membered heterocycloalkyl, or 5 to 6 membered heterocycloalkyl). In embodiments, the monovalent cellular component binder is a substituted heterocycloalkyl (e.g., 3 to 8 membered heterocycloalkyl, 3 to 6 membered heterocycloalkyl, or 5 to 6 membered heterocycloalkyl). In embodiments, the monovalent cellular component binder is an unsubstituted heterocycloalkyl (e.g., 3 to 8 membered heterocycloalkyl, 3 to 6 membered heterocycloalkyl, or 5 to 6 membered heterocycloalkyl). In embodiments, the monovalent cellular component binder is a substituted or unsubstituted aryl (e.g., $C_6$-$C_{10}$ aryl, $C_{10}$ aryl, or phenyl). In embodiments, the monovalent cellular component binder is a substituted aryl (e.g., $C_6$-$C_{10}$ aryl, $C_{10}$ aryl, or phenyl). In embodiments, the monovalent cellular component binder is an unsubstituted aryl (e.g., $C_6$-$C_{10}$ aryl, $C_{10}$ aryl, or phenyl). In embodiments, the monovalent cellular component binder is a substituted or unsubstituted heteroaryl (e.g., 5 to 10 membered heteroaryl, 5 to 9 membered heteroaryl, or 5 to 6 membered heteroaryl). In embodiments, the monovalent cellular component binder is a substituted heteroaryl (e.g., 5 to 10 membered heteroaryl, 5 to 9 membered heteroaryl, or 5 to 6 membered heteroaryl). In embodiments, the monovalent cellular component binder is an unsubstituted heteroaryl (e.g., 5 to 10 membered heteroaryl, 5 to 9 membered heteroaryl, or 5 to 6 membered heteroaryl).

In embodiments, the monovalent cellular component binder is a $R^{49}$-substituted or unsubstituted alkyl (e.g., $C_1$-$C_8$ alkyl, $C_1$-$C_6$ alkyl, or $C_1$-$C_4$ alkyl), $R^{49}$-substituted or unsubstituted heteroalkyl (e.g., 2 to 8 membered heteroalkyl, 2 to 6 membered heteroalkyl, or 2 to 4 membered heteroalkyl), $R^{49}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{49}$-substituted or unsubstituted heterocycloalkyl (e.g., 3 to 8 membered heterocycloalkyl, 3 to 6 membered heterocycloalkyl, or 5 to 6 membered heterocycloalkyl), $R^{49}$-substituted or unsubstituted aryl (e.g., $C_6$-$C_{10}$ aryl, $C_{10}$ aryl, or phenyl), or $R^{49}$-substituted or unsubstituted heteroaryl (e.g., 5 to 10 membered heteroaryl, 5 to 9 membered heteroaryl, or 5 to 6 membered heteroaryl). In embodiments, the monovalent cellular component binder is an unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, the monovalent cellular component binder is a $R^{49}$-substituted or unsubstituted alkyl (e.g., $C_1$-$C_8$ alkyl, $C_1$-$C_6$ alkyl, or $C_1$-$C_4$ alkyl). In embodiments, the monovalent cellular component binder is a $R^{49}$-substituted alkyl (e.g., $C_1$-$C_8$ alkyl, $C_1$-$C_6$ alkyl, or $C_1$-$C_4$ alkyl). In embodiments, the monovalent cellular component binder is an unsubstituted alkyl (e.g., $C_1$-$C_8$ alkyl, $C_1$-$C_6$ alkyl, or $C_1$-$C_4$ alkyl). In embodiments, the monovalent cellular component binder is a $R^{49}$-substituted or unsubstituted heteroalkyl (e.g., 2 to 8 membered heteroalkyl, 2 to 6 membered heteroalkyl, or 2 to 4 membered heteroalkyl). In embodiments, the monovalent cellular component binder is a $R^{49}$-substituted heteroalkyl (e.g., 2 to 8 membered heteroalkyl, 2 to 6 membered heteroalkyl, or 2 to 4 membered heteroalkyl). In embodiments, the monovalent cellular component binder is an unsubstituted heteroalkyl (e.g., 2 to 8 membered heteroalkyl, 2 to 6 membered heteroalkyl, or 2 to 4 membered heteroalkyl). In embodiments, the monovalent cellular component binder is a $R^{49}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, the monovalent cellular component binder is a $R^{49}$-substituted cycloalkyl (e.g., $C_3$-$C_8$ cycloalkyl, $C_3$-$C_6$ cycloalkyl, or $C_5$-$C_6$ cycloalkyl). In embodiments, the monovalent cellular component binder is an unsubstituted cycloalkyl (e.g., $C_3$-$C_8$ cycloalkyl, $C_3$-$C_6$ cycloalkyl, or $C_5$-$C_6$ cycloalkyl). In embodiments, the monovalent cellular component binder is a $R^{49}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, the monovalent cellular component binder is a $R^{49}$-substituted heterocycloalkyl (e.g., 3 to 8 membered heterocycloalkyl, 3 to 6 membered heterocycloalkyl, or 5 to 6 membered heterocycloalkyl). In embodiments, the monovalent cellular component binder is an unsubstituted heterocycloalkyl (e.g., 3 to 8 membered heterocycloalkyl, 3 to 6 membered heterocycloalkyl, or 5 to 6 membered heterocycloalkyl). In embodiments, the monovalent cellular component binder is a $R^{49}$-substituted or unsubstituted aryl (e.g., $C_6$-$C_{10}$ aryl, $C_{10}$ aryl, or phenyl). In embodiments, the monovalent cellular component binder is a $R^{49}$-substituted aryl (e.g., $C_6$-$C_{10}$ aryl, $C_{10}$ aryl, or phenyl). In embodiments, the monovalent cellular component binder is an unsubstituted aryl (e.g., $C_6$-$C_{10}$ aryl, $C_{10}$ aryl, or phenyl). In embodiments, the monovalent cellular component binder is a $R^{49}$-substituted or unsubstituted heteroaryl (e.g., 5 to 10 membered heteroaryl, 5 to 9 membered heteroaryl, or 5 to 6 membered heteroaryl). In embodiments, the monovalent cellular component binder is a $R^{49}$-substituted heteroaryl (e.g., 5 to 10 membered heteroaryl, 5 to 9 membered heteroaryl, or 5 to 6 membered heteroaryl). In embodiments, the monovalent cellular component binder is an unsubstituted heteroaryl (e.g., 5 to 10 membered heteroaryl, 5 to 9 membered heteroaryl, or 5 to 6 membered heteroaryl).

$R^{49}$ is independently oxo, halogen, —CCl$_3$, —CBr$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHF$_2$, —OCH$_2$Cl, —OCH$_2$Br, —OCH$_2$F, —N$_3$, $R^{50}$-substituted or unsubstituted alkyl (e.g., $C_1$-$C_8$ alkyl, $C_1$-$C_6$ alkyl, or $C_1$-$C_4$ alkyl), $R^{50}$-substituted or unsubstituted heteroalkyl (e.g., 2 to 8 membered heteroalkyl, 2 to 6 membered heteroalkyl, or 2 to 4 membered heteroalkyl), $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{50}$-substituted or unsubstituted heterocycloalkyl (e.g., 3 to 8 membered heterocycloalkyl, 3 to 6 membered heterocycloalkyl, or 5 to 6 membered heterocycloalkyl), $R^{50}$-substituted or unsubstituted aryl (e.g., $C_6$-$C_{10}$ aryl, $C_{10}$ aryl, or phenyl), or $R^{50}$-substituted or unsubstituted heteroaryl (e.g., 5 to 10 membered heteroaryl, 5 to 9 membered heteroaryl, or 5 to 6 membered heteroaryl). In embodiments, $R^{49}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{49}$ is independently oxo. In embodiments, $R^{49}$ is independently halogen. In embodiments, $R^{49}$ is independently —CCl$_3$. In embodiments, $R^{49}$ is independently —CBr$_3$. In embodiments, $R^{49}$ is independently —CF$_3$. In embodiments, $R^{49}$ is independently —CI$_3$. In embodiments, $R^{49}$ is independently —CHCl$_2$. In embodiments, $R^{49}$ is independently —CHBr$_2$. In embodiments, $R^{49}$ is independently —CHF$_2$. In embodiments, $R^{49}$ is independently —CHI$_2$. In embodiments, $R^{49}$ is independently —CH$_2$Cl. In embodiments, $R^{49}$ is independently —CH$_2$Br. In embodiments, $R^{49}$ is independently —CH$_2$F. In embodiments, $R^{49}$ is independently —CH$_2$I. In embodiments, $R^{49}$ is independently —CN. In embodiments, $R^{49}$ is independently —OH. In embodiments, $R^{49}$ is independently —NH$_2$. In embodiments, $R^{49}$ is independently —COOH. In embodiments, $R^{49}$ is independently —CONH$_2$. In embodiments, $R^{49}$ is independently —NO$_2$. In embodiments, $R^{49}$ is independently —SH. In embodiments, $R^{49}$ is independently —SO$_3$H. In embodiments, $R^{49}$ is independently —SO$_4$H. In embodiments, $R^{49}$ is independently —SO$_2$NH$_2$. In embodiments, $R^{49}$ is independently —NHNH$_2$. In embodiments, $R^{49}$ is independently —ONH$_2$. In embodiments, $R^{49}$ is independently —NHC(O)NHNH$_2$. In embodiments, $R^{49}$ is independently —NHC(O)NH$_2$. In embodiments, $R^{49}$ is independently —NHSO$_2$H. In embodiments, $R^{49}$ is independently —NHC(O)H. In embodiments, $R^{49}$ is independently —NHC(O)OH. In embodiments, $R^{49}$ is independently —NHOH. In embodiments, $R^{49}$ is independently —OCCl$_3$. In embodiments, $R^{49}$ is independently —OCF$_3$. In embodiments, $R^{49}$ is independently —OCBr$_3$. In embodiments, $R^{49}$ is independently —OCl$_3$. In embodiments, $R^{49}$ is independently —OCHCl$_2$. In embodiments, $R^{49}$ is independently —OCHBr$_2$. In embodiments, $R^{49}$ is independently —OCHI$_2$. In embodiments, $R^{49}$ is independently —OCHF$_2$. In embodiments, $R^{49}$ is independently —OCH$_2$Cl. In embodiments, $R^{49}$ is independently —OCH$_2$Br. In embodiments, $R^{49}$ is independently —OCH$_2$I. In embodiments, $R^{49}$ is independently —OCH$_2$F. In embodiments, $R^{49}$ is independently —N$_3$. In embodiments, $R^{49}$ is independently —OCH$_3$. In embodiments, $R^{49}$ is independently —CH$_3$. In embodiments, $R^{49}$ is independently —CH$_2$CH$_3$. In embodiments, $R^{49}$ is independently unsubstituted propyl. In embodiments, $R^{49}$ is independently unsubstituted isopropyl. In embodiments, $R^{49}$ is independently unsubstituted butyl. In embodiments, $R^{49}$ is independently unsubstituted tert-butyl. In embodiments, $R^{49}$ is independently —F. In embodiments, $R^{49}$ is independently —Cl. In embodiments, $R^{49}$ is independently —Br. In embodiments, $R^{49}$ is independently —I.

In embodiments, $R^{49}$ is independently $R^{50}$-substituted or unsubstituted alkyl (e.g., $C_1$-$C_8$ alkyl, $C_1$-$C_6$ alkyl, or $C_1$-$C_4$ alkyl). In embodiments, $R^{49}$ is independently $R^{50}$-substituted alkyl (e.g., $C_1$-$C_8$ alkyl, $C_1$-$C_6$ alkyl, or $C_1$-$C_4$ alkyl). In embodiments, $R^{49}$ is independently an unsubstituted alkyl (e.g., $C_1$-$C_8$ alkyl, $C_1$-$C_6$ alkyl, or $C_1$-$C_4$ alkyl). In embodiments, $R^{49}$ is independently $R^{50}$-substituted or unsubstituted heteroalkyl (e.g., 2 to 8 membered heteroalkyl, 2 to 6 membered heteroalkyl, or 2 to 4 membered heteroalkyl). In embodiments, $R^{49}$ is independently $R^{50}$-substituted heteroalkyl (e.g., 2 to 8 membered heteroalkyl, 2 to 6 membered heteroalkyl, or 2 to 4 membered heteroalkyl). In embodiments, $R^{49}$ is independently an unsubstituted heteroalkyl (e.g., 2 to 8 membered heteroalkyl, 2 to 6 membered heteroalkyl, or 2 to 4 membered heteroalkyl). In embodiments, $R^{49}$ is independently $R^{50}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{49}$ is independently $R^{50}$-substituted cycloalkyl (e.g., $C_3$-$C_8$ cycloalkyl, $C_3$-$C_6$ cycloalkyl, or $C_5$-$C_6$ cycloalkyl). In embodiments, $R^{49}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{49}$ is independently $R^{50}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{49}$ is independently $R^{50}$-substituted heterocycloalkyl (e.g., 3 to 8 membered heterocycloalkyl, 3 to 6 membered heterocycloalkyl, or 5 to 6 membered heterocycloalkyl). In embodiments, $R^{49}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{49}$ is independently $R^{50}$-substituted or unsubstituted aryl (e.g., $C_6$-$C_{10}$ aryl, $C_{10}$ aryl, or phenyl). In embodiments, $R^{49}$ is independently $R^{50}$-substituted aryl (e.g., $C_6$-$C_{10}$ aryl, $C_{10}$ aryl, or phenyl). In embodiments, $R^{49}$ is independently an unsubstituted aryl (e.g., $C_6$-$C_{10}$ aryl, $C_{10}$ aryl, or phenyl). In embodiments, $R^{49}$ is independently $R^{50}$-substituted or unsubstituted heteroaryl (e.g., 5 to 10 membered heteroaryl, 5 to 9 membered heteroaryl, or 5 to 6 membered heteroaryl). In embodiments, $R^{49}$ is independently $R^{50}$-substituted heteroaryl (e.g., 5 to 10 membered heteroaryl, 5 to 9 membered heteroaryl, or 5 to 6 membered heteroaryl). In embodiments, $R^{49}$ is independently an unsubstituted heteroaryl (e.g., 5 to 10 membered heteroaryl, 5 to 9 membered heteroaryl, or 5 to 6 membered heteroaryl).

$R^{50}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{51}$-substituted or unsubstituted alkyl (e.g., $C_1$-$C_8$ alkyl, $C_1$-$C_6$ alkyl, or $C_1$-$C_4$ alkyl), $R^{51}$-substituted or unsubstituted heteroalkyl (e.g., 2 to 8 membered heteroalkyl, 2 to 6 membered heteroalkyl, or 2 to 4 membered heteroalkyl), $R^{51}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{51}$-substituted or unsubstituted heterocycloalkyl (e.g., 3 to 8 membered heterocycloalkyl, 3 to 6 membered heterocycloalkyl, or 5 to 6 membered heterocycloalkyl), $R^{51}$-substituted or unsubstituted aryl (e.g., $C_6$-$C_{10}$ aryl, $C_{10}$ aryl, or phenyl), or $R^{51}$-substituted or unsubstituted heteroaryl (e.g., 5 to 10 membered heteroaryl, 5 to 9 membered heteroaryl, or 5 to 6 membered heteroaryl). In embodiments, $R^{50}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{50}$ is independently $R^{51}$-substituted or unsubstituted alkyl (e.g., $C_1$-$C_8$ alkyl, $C_1$-$C_6$ alkyl, or $C_1$-$C_4$ alkyl). In embodiments, $R^{50}$ is independently $R^{51}$-substituted alkyl (e.g., $C_1$-$C_8$ alkyl, $C_1$-$C_6$ alkyl, or $C_1$-$C_4$ alkyl). In embodiments, $R^{50}$ is independently an unsubstituted alkyl (e.g., $C_1$-$C_8$ alkyl, $C_1$-$C_6$ alkyl, or $C_1$-$C_4$ alkyl). In embodiments, $R^{50}$ is independently $R^{51}$-substituted or unsubstituted heteroalkyl (e.g., 2 to 8 membered heteroalkyl, 2 to 6 membered heteroalkyl, or 2 to 4 membered heteroalkyl). In embodiments, $R^{50}$ is independently $R^{51}$-substituted heteroalkyl (e.g., 2 to 8 membered heteroalkyl, 2 to 6 membered heteroalkyl, or 2 to 4 membered heteroalkyl). In embodiments, $R^{50}$ is independently an unsubstituted heteroalkyl (e.g., 2 to 8 membered heteroalkyl, 2 to 6 membered heteroalkyl, or 2 to 4 membered heteroalkyl). In embodiments, $R^{50}$ is independently $R^{51}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{50}$ is independently $R^{51}$-substituted cycloalkyl (e.g., $C_3$-$C_8$ cycloalkyl, $C_3$-$C_6$ cycloalkyl, or $C_5$-$C_6$ cycloalkyl). In embodiments, $R^{50}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R_{50}$ is independently $R^{51}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{50}$ is independently $R^{51}$-substituted heterocycloalkyl (e.g., 3 to 8 membered heterocycloalkyl, 3 to 6 membered heterocycloalkyl, or 5 to 6 membered heterocycloalkyl). In embodiments, $R^{50}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{50}$ is independently $R^{51}$-substituted or unsubstituted aryl (e.g., $C_6$-$C_{10}$ aryl, $C_{10}$ aryl, or phenyl). In embodiments, $R^{50}$ is independently $R^{51}$-substituted aryl (e.g., $C_6$-$C_{10}$ aryl, $C_{10}$ aryl, or phenyl). In embodiments, $R^{50}$ is independently an unsubstituted aryl (e.g., $C_6$-$C_{10}$ aryl, $C_{10}$ aryl, or phenyl). In embodiments, $R^{50}$ is independently $R^{51}$-substituted or unsubstituted heteroaryl (e.g., 5 to 10 membered heteroaryl, 5 to 9 membered heteroaryl, or 5 to 6 membered heteroaryl). In embodiments, $R^{50}$ is independently $R^{51}$-substituted heteroaryl (e.g., 5 to 10 membered heteroaryl, 5 to 9 membered heteroaryl, or 5 to 6 membered heteroaryl). In embodiments, $R^{50}$ is independently an unsubstituted heteroaryl (e.g., 5 to 10 membered heteroaryl, 5 to 9 membered heteroaryl, or 5 to 6 membered heteroaryl).

In embodiments, $R^{50}$ is independently oxo. In embodiments, $R^{50}$ is independently halogen. In embodiments, $R^{50}$ is independently —CCl$_3$. In embodiments, $R^{50}$ is independently —CBr$_3$. In embodiments, $R^{50}$ is independently —CF$_3$. In embodiments, $R^{50}$ is independently —CI$_3$. In embodiments, $R^{50}$ is independently —CHCl$_2$. In embodiments, $R^{50}$ is independently —CHBr$_2$. In embodiments, $R^{50}$ is independently —CHF$_2$. In embodiments, $R^{50}$ is independently —CHI$_2$. In embodiments, $R^{50}$ is independently —CH$_2$Cl. In embodiments, $R^{50}$ is independently —CH$_2$Br. In embodiments, $R^{50}$ is independently —CH$_2$F. In embodiments, $R^{50}$ is independently —CH$_2$I. In embodiments, $R^{50}$ is independently —CN. In embodiments, $R^{50}$ is independently —OH. In embodiments, $R^{50}$ is independently —NH$_2$. In embodiments, $R^{50}$ is independently —COOH. In embodiments, $R^{50}$ is independently —CONH$_2$. In embodiments, $R^{50}$ is independently —NO$_2$. In embodiments, $R^{50}$ is independently —SH. In embodiments, $R^{50}$ is independently —SO$_3$H. In embodiments, $R^{50}$ is independently —SO$_4$H. In embodiments, $R^{50}$ is independently —SO$_2$NH$_2$. In embodiments, $R^{50}$ is independently —NHNH$_2$. In embodiments, $R_{50}$ is independently —ONH$_2$. In embodiments, $R^{50}$ is independently —NHC(O)NHNH$_2$. In embodiments, R$^{50}$ is independently —NHC(O)NH$_2$. In embodiments, R$^{50}$ is independently —NHSO$_2$H. In embodiments, R$^{50}$ is independently —NHC(O)H. In embodiments, R$^{50}$ is independently —NHC(O)OH. In embodiments, R$^{50}$ is independently —NHOH. In embodiments, R$^{50}$ is independently —OCCl$_3$. In embodiments, R$^{50}$ is independently —OCF$_3$. In embodiments, R$^{50}$ is independently —OCBr$_3$. In embodiments, R$^{50}$ is independently —OCI$_3$. In embodiments, R$^{50}$ is independently —OCHCl$_2$. In embodiments, R$^{50}$ is independently —OCHBr$_2$. In embodiments, R$^{50}$ is independently —OCHI$_2$. In embodiments, R$^{50}$ is independently —OCHF$_2$. In embodiments, R$^{50}$ is independently —OCH$_2$Cl. In embodiments, R$^{50}$ is independently —OCH$_2$Br. In embodiments, R$^{50}$ is independently —OCH$_2$I. In embodiments, R$^{50}$ is independently —OCH$_2$F. In embodiments, R$^{50}$ is independently —N$_3$. In embodiments, R$^{50}$ is independently —OCH$_3$. In embodiments, R$^{50}$ is independently —CH$_3$. In embodiments, R$^{50}$ is independently —CH$_2$CH$_3$. In embodiments, R$^{50}$ is independently unsubstituted propyl. In embodiments, R$^{50}$ is independently unsubstituted isopropyl. In embodiments, R$^{50}$ is independently unsubstituted butyl. In embodiments, R$^{50}$ is independently unsubstituted tert-butyl. In embodiments, R$^{50}$ is independently —F. In embodiments, R$^{50}$ is independently -Cl. In embodiments, R$^{50}$ is independently —Br. In embodiments, R$^{50}$ is independently —I.

R$^{51}$ is independently oxo, halogen, —CF$_3$, —CBr$_3$, —CCl$_3$, —CI$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCI$_3$, —OCHF$_2$, —OCHBr$_2$, —OCHCl$_2$, —OCH$_2$F, —OCH$_2$Br, —OCH$_2$Cl, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{51}$ is independently an unsubstituted alkyl (e.g., C$_1$-C$_8$ alkyl, C$_1$-C$_6$ alkyl, or C$_1$-C$_4$ alkyl). In embodiments, R$^{51}$ is independently an unsubstituted heteroalkyl (e.g., 2 to 8 membered heteroalkyl, 2 to 6 membered heteroalkyl, or 2 to 4 membered heteroalkyl). In embodiments, R$^{51}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{51}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{51}$ is independently an unsubstituted aryl (e.g., C$_6$-C$_{10}$ aryl, C$_{10}$ aryl, or phenyl). In embodiments, R$^{51}$ is independently an unsubstituted heteroaryl (e.g., 5 to 10 membered heteroaryl, 5 to 9 membered heteroaryl, or 5 to 6 membered heteroaryl).

In embodiments, R$^{51}$ is independently oxo. In embodiments, R$^{51}$ is independently halogen. In embodiments, R$^{51}$ is independently —CCl$_3$. In embodiments, R$^{51}$ is independently —CBr$_3$. In embodiments, R$^{51}$ is independently —CF$_3$. In embodiments, R$^{51}$ is independently —CI$_3$. In embodiments, R$^{51}$ is independently —CHCl$_2$. In embodiments, R$^{51}$ is independently —CHBr$_2$. In embodiments, R$^{51}$ is independently —CHF$_2$. In embodiments, R$^{51}$ is independently —CHI$_2$. In embodiments, R$^{51}$ is independently —CH$_2$Cl. In embodiments, R$^{51}$ is independently —CH$_2$Br. In embodiments, R$^{51}$ is independently —CH$_2$F. In embodiments, R$^{51}$ is independently —CH$_2$I. In embodiments, R$^{51}$ is independently —CN. In embodiments, R$^{51}$ is independently —OH. In embodiments, R$^{51}$ is independently —NH$_2$. In embodiments, R$^{51}$ is independently —COOH. In embodiments, R$^{51}$ is independently —CONH$_2$. In embodiments, R$^{51}$ is independently —NO$_2$. In embodiments, R$^{51}$ is independently —SH. In embodiments, R$^{51}$ is independently —SO$_3$H. In embodiments, R$^{51}$ is independently —SO$_4$H. In embodiments, R$^{51}$ is independently —SO$_2$NH$_2$. In embodiments, R$^{51}$ is independently —NHNH$_2$. In embodiments, R$^{51}$ is independently —ONH$_2$. In embodiments, R$^{51}$ is independently —NHC(O)NHNH$_2$. In embodiments, R$^{51}$ is independently —NHC(O)NH$_2$. In embodiments, R$^{51}$ is independently —NHSO$_2$H. In embodiments, R$^{51}$ is independently —NHC(O)H. In embodiments, R$^{51}$ is independently —NHC(O)OH. In embodiments, R$^{51}$ is independently —NHOH. In embodiments, R$^{51}$ is independently —OCCl$_3$. In embodiments, R$^{51}$ is independently —OCF$_3$. In embodiments, R$^{51}$ is independently —OCBr$_3$. In embodiments, R$^{51}$ is independently —OCI$_3$. In embodiments, R$^{51}$ is independently —OCHCl$_2$. In embodiments, R$^{51}$ is independently —OCHBr$_2$. In embodiments, R$^{51}$ is independently —OCHI$_2$. In embodiments, R$^{51}$ is independently —OCHF$_2$. In embodiments, R$^{51}$ is independently —OCH$_2$Cl. In embodiments, R$^{51}$ is independently —OCH$_2$Br. In embodiments, R$^{51}$ is independently —OCH$_2$I. In embodiments, R$^{51}$ is independently —OCH$_2$F. In embodiments, R$^{51}$ is independently —N$_3$. In embodiments, R$^{51}$ is independently —OCH$_3$. In embodiments, R$^{51}$ is independently —CH$_3$. In embodiments, R$^{51}$ is independently —CH$_2$CH$_3$. In embodiments, R$^{51}$ is independently unsubstituted propyl. In embodiments, R$^{51}$ is independently unsubstituted isopropyl. In embodiments, R$^{51}$ is independently unsubstituted butyl. In embodiments, R$^{51}$ is independently unsubstituted tert-butyl. In embodiments, R$^{51}$ is independently —F. In embodiments, R$^{51}$ is independently —Cl. In embodiments, R$^{51}$ is independently —Br. In embodiments, R$^{51}$ is independently —I.

In embodiments, the monovalent cellular component binder is capable of binding the protein BRD4. In embodiments, the monovalent cellular component binder is capable of binding the protein thioflavin T. In embodiments, the monovalent cellular component binder is capable of binding the protein amyloid beta plaques. In embodiments, the monovalent cellular component binder is capable of binding Bromodomain-containing protein 4 (BRD4), KRAS, Myc proto-oncogene protein (MYC), yes-associated protein 1 (YAP), tafazzin (TAZ), Catenin beta-1 (CTNNB1), Amyloid precursor protein (APP), huntingtin protein (HTT), Alpha-synuclein (SNCA), Nuclear factor (erythroid-derived 2)-like 2 (NRF2), or microtubule-associated protein tau (MAPT). In embodiments, the monovalent cellular component binder is capable of binding a protein aggregate (e.g., HTT, APP, SNCA, or MAPT). In embodiments, the monovalent cellular component binder is capable of binding PTEN-induced putative kinase 1 (PINK1), Autophagy-related protein 32 (ATG32); Extended synaptotagmin-1 (ESYT1), Extended synaptotagmin-2 (ESYT2), Phosphatidylinositol 3-kinase catalytic subunit type 3 (PI3KC3), Ras-related protein Rab-10 (RAB10), or Adipose triglyceride lipase (ATGL). In embodiments, the monovalent cellular component binder is capable of binding a microorganism. In embodiments, the monovalent cellular component binder is capable of binding a virus. In embodiments, the monovalent cellular component binder is capable of binding a lipid droplet. In embodiments, the monovalent cellular component binder is capable of binding a bacterial cell-surface glycan or bacterial cell surface protein.

In embodiments, the protein aggregate is Beta amyloid, Amyloid precursor protein, IAPP (Amylin), Alpha-synuclein, PrPSc, PrPSc, Huntingtin, Calcitonin, Atrial natriuretic factor, Apolipoprotein AI, Serum amyloid A, Medin, Prolactin, Transthyretin, Lysozyme, Beta-2 microglobulin, Gelsolin, Keratoepithelin, Beta amyloid, Cystatin, Immunoglobulin light chain AL, or S-IBM.

In embodiments, the protein aggregate includes Beta amyloid, Amyloid precursor protein, IAPP (Amylin), Alpha-synuclein, PrPSc, PrPSc, Huntingtin, Calcitonin, Atrial natriuretic factor, Apolipoprotein AI, Serum amyloid A, Medin, Prolactin, Transthyretin, Lysozyme, Beta-2 microglobulin, Gelsolin, Keratoepithelin, Beta amyloid, Cystatin, Immunoglobulin light chain AL, or S-IBM.

In embodiments, the protein aggregate includes Beta amyloid. In embodiments, the protein aggregate includes Amyloid precursor protein. In embodiments, the protein aggregate includes IAPP (Amylin). In embodiments, the protein aggregate includes Alpha-synuclein. In embodiments, the protein aggregate includes PrPSc. In embodiments, the protein aggregate includes PrPSc. In embodiments, the protein aggregate includes Huntingtin. In embodiments, the protein aggregate includes Calcitonin. In embodiments, the protein aggregate includes Atrial natriuretic factor. In embodiments, the protein aggregate includes Apolipoprotein AI. In embodiments, the protein aggregate includes Serum amyloid A. In embodiments, the protein aggregate includes Medin. In embodiments, the protein aggregate includes Prolactin. In embodiments, the protein aggregate includes Transthyretin. In embodiments, the protein aggregate includes Lysozyme. In embodiments, the protein aggregate includes Beta-2 microglobulin. In embodiments, the protein aggregate includes Gelsolin. In embodiments, the protein aggregate includes Keratoepithelin. In embodiments, the protein aggregate includes Beta amyloid. In embodiments, the protein aggregate includes Cystatin. In embodiments, the protein aggregate includes Immunoglobulin light chain AL. In embodiments, the protein aggregate includes S-IBM.

In embodiments, the protein aggregate is Beta amyloid. In embodiments, the protein aggregate is Amyloid precursor protein. In embodiments, the protein aggregate is IAPP (Amylin). In embodiments, the protein aggregate is Alpha-synuclein. In embodiments, the protein aggregate is PrPSc. In embodiments, the protein aggregate is PrPSc. In embodiments, the protein aggregate is Huntingtin. In embodiments, the protein aggregate is Calcitonin. In embodiments, the protein aggregate is Atrial natriuretic factor. In embodiments, the protein aggregate is Apolipoprotein AI. In embodiments, the protein aggregate is Serum amyloid A. In embodiments, the protein aggregate is Medin. In embodiments, the protein aggregate is Prolactin. In embodiments, the protein aggregate is Transthyretin. In embodiments, the protein aggregate is Lysozyme. In embodiments, the protein aggregate is Beta-2 microglobulin. In embodiments, the protein aggregate is Gelsolin. In embodiments, the protein aggregate is Keratoepithelin. In embodiments, the protein aggregate is Beta amyloid. In embodiments, the protein aggregate is Cystatin. In embodiments, the protein aggregate is Immunoglobulin light chain AL. In embodiments, the protein aggregate is S-IBM.

In embodiments, the protein aggregate is a huntingtin aggregate. In embodiments, the protein aggregate is a polyQ huntingtin aggregate.

In embodiments, the monovalent cellular component binder is capable of binding a protein aggregate. In embodiments, the monovalent cellular component binder is capable of binding a huntingtin aggregate. In embodiments, the monovalent cellular component binder is capable of binding a polyQ huntingtin aggregate.

In embodiments, the monovalent cellular component binder is capable of binding BRD4. In embodiments, the monovalent cellular component binder is capable of binding KRAS. In embodiments, the monovalent cellular component binder is capable of binding MYC. In embodiments, the monovalent cellular component binder is capable of binding YAP. In embodiments, the monovalent cellular component binder is capable of binding TAZ. In embodiments, the monovalent cellular component binder is capable of binding CTNNB1. In embodiments, the monovalent cellular component binder is capable of binding APP. In embodiments, the monovalent cellular component binder is capable of binding HTT. In embodiments, the monovalent cellular component binder is capable of binding SNCA. In embodiments, the monovalent cellular component binder is capable of binding NRF2. In embodiments, the monovalent cellular component binder is capable of binding or MAPT.

In embodiments, the monovalent cellular component binder is capable of binding HTT. In embodiments, the monovalent cellular component binder is capable of binding APP. In embodiments, the monovalent cellular component binder is capable of binding SNCA. In embodiments, the monovalent cellular component binder is capable of binding MAPT. In embodiments, the monovalent cellular component binder is capable of binding PINK1. In embodiments, the monovalent cellular component binder is capable of binding ATG32. In embodiments, the monovalent cellular component binder is capable of binding ESYT. In embodiments, the monovalent cellular component binder is capable of binding PI3KC3. In embodiments, the monovalent cellular component binder is capable of binding RAB10. In embodiments, the monovalent cellular component binder is capable of binding or ATGL.

In embodiments, the monovalent cellular component binder has the formula:

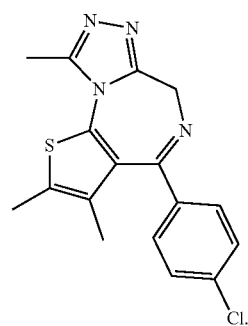 [SMILES: Cc1sc2c(c1C)C(c1ccc(Cl)cc1)=NCc1nnc(C)n1-2]

In embodiments, the monovalent cellular component binder is capable of binding a protein aggregate. In embodiments, the monovalent cellular component binder has the formula:

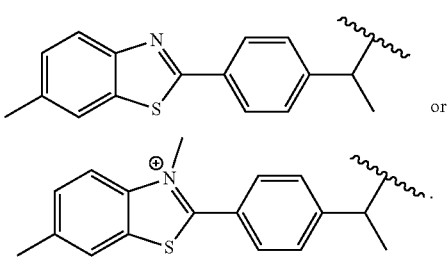

or

In embodiments, the monovalent cellular component binder is capable of binding a protein aggregate. In embodiments, the monovalent cellular component binder is a monovalent form of thioflavin or a derivative thereof. In embodiments, the monovalent cellular component binder has the formula:

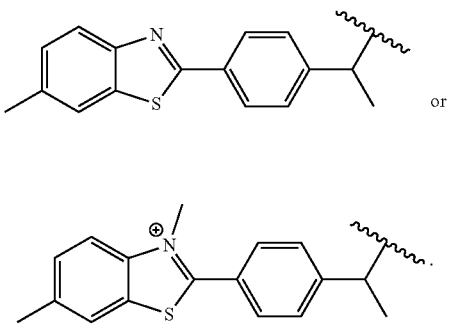

or

In embodiments, the monovalent cellular component binder is capable of binding a protein aggregate. In embodiments, the monovalent cellular component binder is a monovalent form of thioflavin or a derivative thereof. In embodiments, the monovalent cellular component binder is a monovalent form of the formula:

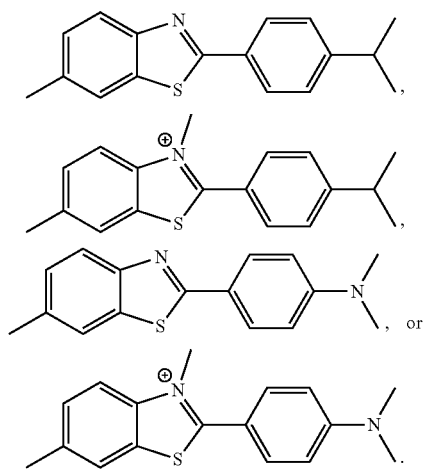

In embodiments, the monovalent cellular component binder is capable of binding a protein aggregate. In embodiments, the monovalent cellular component binder has the formula:

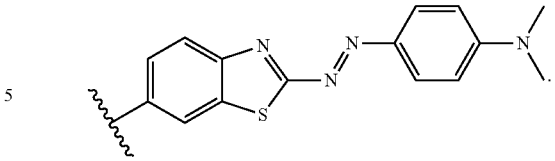

In embodiments, the targeted autophagy protein binder (e.g., autophagy adapter protein binder) is capable of contacting an autophagy adapter protein. In embodiments, the monovalent targeted autophagy protein binder (e.g., monovalent autophagy adapter protein binder) is capable of contacting an autophagy adapter protein. In embodiments, the autophagy adapter protein is LC3, p62/SQSTM1, NBR1, NDP52, Optineurin (OPTN), NUFIP1, WDFY3, RETREG1 (or FAM134B), Nix, TOLLIP, or TAX1BP1 (CALCOCO3), or an analog, derivative, fragment, or homolog thereof. In embodiments, the autophagy adapter protein is human LC3. In embodiments, the autophagy adapter protein is human p62/SQSTM1. In embodiments, the autophagy adapter protein is human NBR1. In embodiments, the autophagy adapter protein is human NDP52. In embodiments, the autophagy adapter protein is human Optineurin/OPTN. In embodiments, the autophagy adapter protein is human NUFIP1. In embodiments, the autophagy adapter protein is human WDFY3. In embodiments, the autophagy adapter protein is human RETREG1/FAM134B. In embodiments, the autophagy adapter protein is human Nix. In embodiments, the autophagy adapter protein is human TOLLIP. In embodiments, the autophagy adapter protein is human TAX1BP1/CALCOCO3.

In embodiments, the targeted autophagy protein binder (e.g., autophagy adapter protein binder) is capable of contacting an amino acid corresponding to C17 of human LC3A protein. In embodiments, the targeted autophagy protein binder (e.g., autophagy adapter protein binder) is capable of contacting an amino acid corresponding to C26 of human p62/SQSTM1 protein. In embodiments, the targeted autophagy protein binder (e.g., autophagy adapter protein binder) is capable of contacting an amino acid corresponding to C27 of human p62/SQSTM1 protein. In embodiments, the targeted autophagy protein binder (e.g., autophagy adapter protein binder) is capable of contacting an amino acid corresponding to C113 of human p62/SQSTM1 protein. In embodiments, the targeted autophagy protein binder (e.g., autophagy adapter protein binder) is capable of contacting an amino acid corresponding to C120 of human NBR1 protein. In embodiments, the targeted autophagy protein binder (e.g., autophagy adapter protein binder) is capable of contacting an amino acid corresponding to C321 of human NDP52/CALCOCO2 protein. In embodiments, the targeted autophagy protein binder (e.g., autophagy adapter protein binder) is capable of contacting an amino acid corresponding to C558 of human OPTN protein. In embodiments, the targeted autophagy protein binder (e.g., autophagy adapter protein binder) is capable of forming a covalent bond to the cysteine. In embodiments, the monovalent targeted autophagy protein binder (e.g., monovalent autophagy adapter protein binder) is capable of contacting an amino acid corresponding to C17 of human LC3A protein. In embodiments, the monovalent targeted autophagy protein binder (e.g., monovalent autophagy adapter protein binder) is capable of contacting an amino acid corresponding to C26 of human p62/SQSTM1 protein. In embodiments, the monovalent targeted autophagy protein binder (e.g., monovalent autophagy adapter protein binder) is capable of contacting an amino acid corresponding to C27 of human p62/SQSTM1protein. In embodiments, the monovalent targeted autophagy protein binder (e.g., monovalent autophagy adapter protein binder) is capable of contacting an amino acid corresponding to C120 of human NBR1 protein. In embodiments, the monovalent targeted autophagy protein binder (e.g., monovalent autophagy adapter protein binder) is capable of contacting an amino acid corresponding to C321 of human NDP52/CALCOCO2 protein. In embodiments, the monovalent targeted autophagy protein binder (e.g., monovalent autophagy adapter protein binder) is capable of contacting an amino acid corresponding to C558 of human OPTN protein. In embodiments, the monovalent targeted autophagy protein binder (e.g., monovalent autophagy adapter protein binder) is capable of forming a covalent bond to the cysteine.

In embodiments, the targeted autophagy protein binder (e.g., autophagy adapter protein binder) is capable of forming a covalent bond with an amino acid corresponding to C17 of human LC3A protein. In embodiments, the targeted autophagy protein binder (e.g., autophagy adapter protein binder) is capable of forming a covalent bond with an amino acid corresponding to C26 of human p62/SQSTM1 protein. In embodiments, the targeted autophagy protein binder (e.g., autophagy adapter protein binder) is capable of forming a covalent bond with an amino acid corresponding to C27 of human p62/SQSTM1protein. In embodiments, the targeted autophagy protein binder (e.g., autophagy adapter protein binder) is capable of forming a covalent bond with an amino acid corresponding to C113 of human p62/SQSTM1 protein. In embodiments, the targeted autophagy protein binder (e.g., autophagy adapter protein binder) is capable of forming a covalent bond with an amino acid corresponding to C120 of human NBR1 protein. In embodiments, the targeted autophagy protein binder (e.g., autophagy adapter protein binder) is capable of forming a covalent bond with an amino acid corresponding to C321 of human NDP52/CALCOCO2 protein. In embodiments, the targeted autophagy protein binder (e.g., autophagy adapter protein binder) is capable of forming a covalent bond with an amino acid corresponding to C558 of human OPTN protein. In embodiments, the monovalent targeted autophagy protein binder (e.g., monovalent autophagy adapter protein binder) is capable of forming a covalent bond with an amino acid corresponding to C17 of human LC3A protein. In embodiments, the monovalent targeted autophagy protein binder (e.g., monovalent autophagy adapter protein binder) is capable of forming a covalent bond with an amino acid corresponding to C26 of human p62/SQSTM1 protein. In embodiments, the monovalent targeted autophagy protein binder (e.g., monovalent autophagy adapter protein binder) is capable of forming a covalent bond with an amino acid corresponding to C27 of human p62/SQSTM1protein. In embodiments, the monovalent targeted autophagy protein binder (e.g., monovalent autophagy adapter protein binder) is capable of forming a covalent bond with an amino acid corresponding to C113 of human p62/SQSTM1protein. In embodiments, the monovalent targeted autophagy protein binder (e.g., monovalent autophagy adapter protein binder) is capable of forming a covalent bond with an amino acid corresponding to C120 of human NBR1 protein. In embodiments, the monovalent targeted autophagy protein binder (e.g., monovalent autophagy adapter protein binder) is capable of forming a covalent bond with an amino acid corresponding to C321 of human NDP52/CALCOCO2 protein. In embodiments, the monovalent targeted autophagy protein binder (e.g., monovalent autophagy adapter protein binder) is capable of forming a covalent bond with an amino acid corresponding to C558 of human OPTN protein.

In embodiments, the targeted autophagy protein binder (e.g., autophagy adapter protein binder) has the formula:

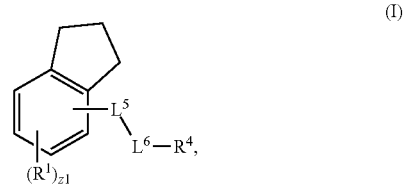

(I)

wherein z1 is an integer from 0 to 9;

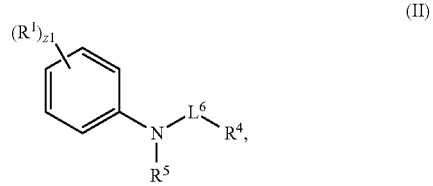

(II)

wherein z1 is an integer from 0 to 5;

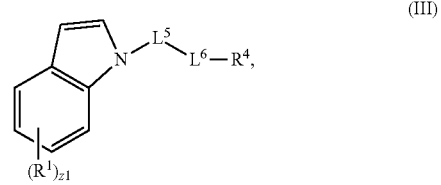

(III)

wherein z1 is an integer from 0 to 6;

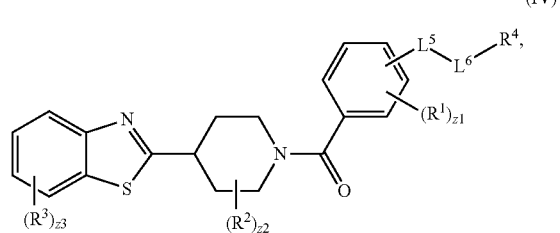

(IV)

wherein z1 is an integer from 0 to 4, z2 is an integer from 0 to 8, and z3 is an integer from 0 to 4;

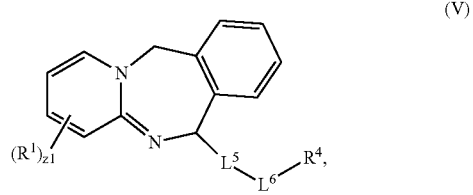

(V)

wherein z1 is an integer from 0 to 11;

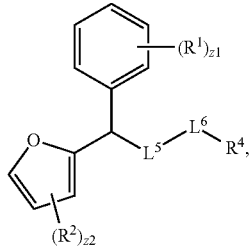
(VI)

wherein z1 is an integer from 0 to 5 and z2 is an integer from 0 to 3;

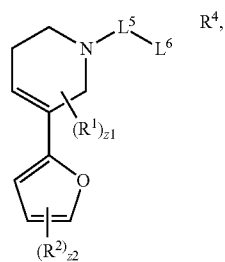
(VII)

wherein z1 is an integer from 0 to 7 and z2 is an integer from 0 to 3;

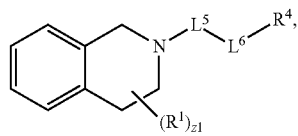
(VIII)

wherein z1 is an integer from 0 to 10;

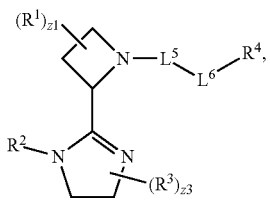
(IX)

wherein z1 is an integer from 0 to 5 and z3 is an integer from 0 to 4;

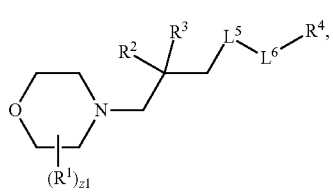
(X)

wherein z1 is an integer from 0 to 8;

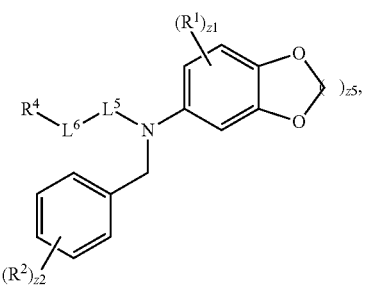
(XI)

wherein z1 is an integer from 0 to 7, z2 is an integer from 0 to 5, and z5 is 1 or 2;

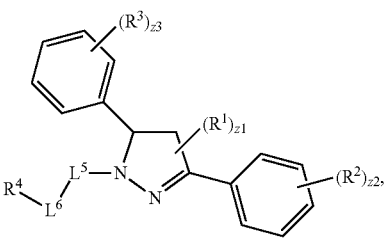
(XII)

wherein z1 is an integer from 0 to 2; z2 is an integer from 0 to 5, and z3 is an integer from 0 to 5;

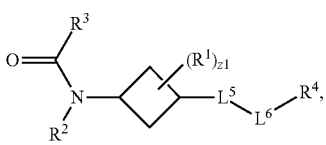
(XIII)

wherein z1 is an integer from 0 to 6;

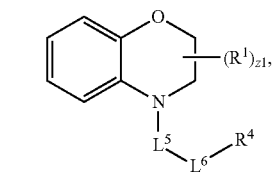
(XIV)

(XIV), wherein z1 is an integer from 0 to 6;

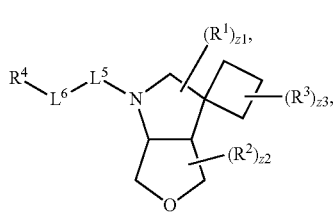
(XV)

wherein z1 is an integer from 0 to 4, z2 is an integer from 0 to 6, and z3 is an integer from 0 to 6;

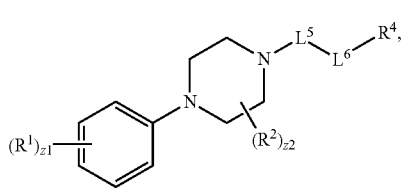
(XVI)

wherein z1 is an integer from 0 to 5 and z2 is an integer from 0 to 8; or

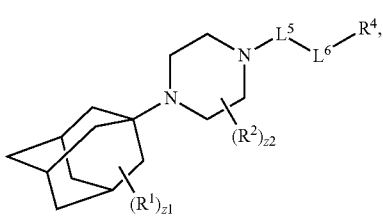
(XVII)

wherein z1 is an integer from 0 to 15 and z2 is an integer from 0 to 8. $R^1$, z1, $R^2$, z2, $R^3$, z3, $L^5$, $L^6$, and $R^4$ are as described herein. It will be understood that floating R-substituents in the formulae described herein may be position on any ring in a fused ring system even though the formula may show the floating R-substituent on a single ring.

In embodiments, the targeted autophagy protein binder (e.g., autophagy adapter protein binder) has the formula:

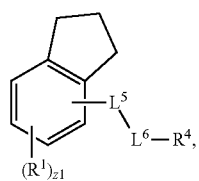
(I)

wherein z1 is an integer from 0 to 9;

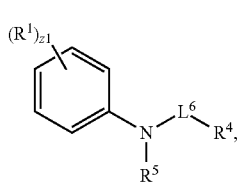
(II)

wherein z1 is an integer from 0 to 5;

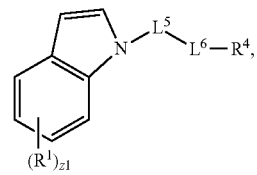
(III)

wherein z1 is an integer from 0 to 6;

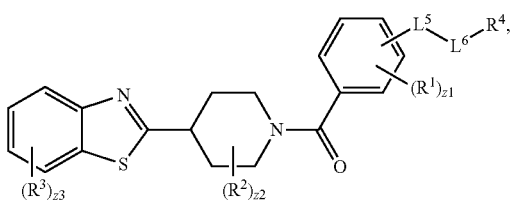
(IV)

wherein z1 is an integer from 0 to 4, z2 is an integer from 0 to 8, and z3 is an integer from 0 to 4;

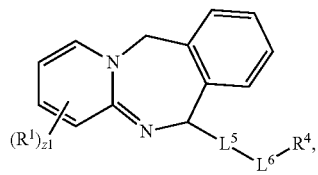
(V)

wherein z1 is an integer from 0 to 11;

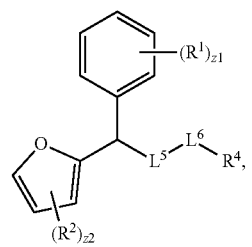
(VI)

wherein z1 is an integer from 0 to 5 and z2 is an integer from 0 to 3; or

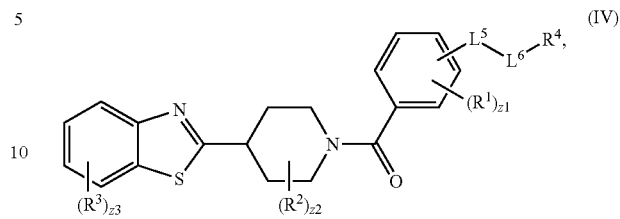

(VII)

In embodiments, the targeted autophagy protein binder (e.g., autophagy adapter protein binder) has the formula:

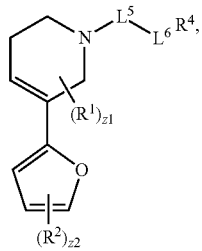

(IV)

wherein z1 is an integer from 0 to 7 and z2 is an integer from 0 to 3. $R^1$, z1, $R^2$, z2, $R^3$, z3, $L^5$, $L^6$, and $R^4$ are as described herein. It will be understood that floating R-substituents in the formulae described herein may be at any position on any ring in a fused or bridged ring system even though the formula may show the floating R-substituent on a single ring of the fused or bridged ring system.

The symbol $=\!\!=\!\!=$ represents either a single bond or a double bond. In embodiments, $=\!\!=\!\!=$ is a single bond. In embodiments, $=\!\!=\!\!=$ is a double bond.

In embodiments, the targeted autophagy protein binder (e.g., autophagy adapter protein binder) has the formula:

wherein z1 is an integer from 0 to 4, z2 is an integer from 0 to 8, and z3 is an integer from 0 to 4. $R^1$, z1, $R^2$, z2, $R^3$, z3, $L^5$, $L^6$, and $R^4$ are as described herein.

In embodiments, the targeted autophagy protein binder (e.g., autophagy adapter protein binder) has the formula:

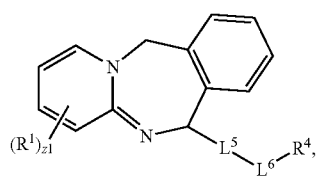

(V)

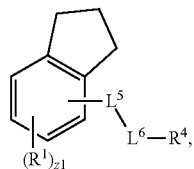

(I)

wherein z1 is an integer from 0 to 11. $R^1$, z1, $L^5$, $L^6$, and $R^4$ are as described herein.

In embodiments, the targeted autophagy protein binder (e.g., autophagy adapter protein binder) has the formula:

wherein z1 is an integer from 0 to 9. $R^1$, z1, $L^5$, $L^6$, and $R^4$ are as described herein.

In embodiments, the targeted autophagy protein binder (e.g., autophagy adapter protein binder) has the formula:

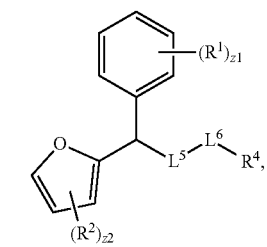

(VI)

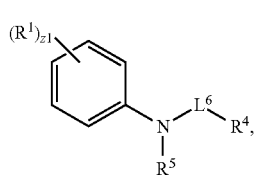

(II)

wherein z1 is an integer from 0 to 5. $R^1$, z1, $R^5$, $L^6$, and $R^4$ are as described herein.

In embodiments, the targeted autophagy protein binder (e.g., autophagy adapter protein binder) has the formula:

wherein z1 is an integer from 0 to 5 and z2 is an integer from 0 to 3. $R^1$, z1, $R^2$, z2, $L^5$, $L^6$, and $R^4$ are as described herein.

In embodiments, the targeted autophagy protein binder (e.g., autophagy adapter protein binder) has the formula:

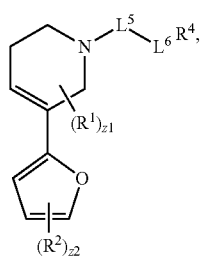

(VII)

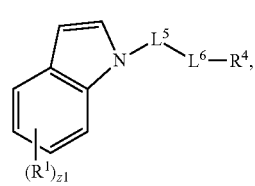

(III)

wherein z1 is an integer from 0 to 6. $R^1$, z1, $L^5$, $L^6$, and $R^4$ are as described herein.

wherein z1 is an integer from 0 to 7 and z2 is an integer from 0 to 3. $R^1$, z1, $R^2$, z2, $L^5$, $L^6$, and $R^4$ are as described herein.

In embodiments, the targeted autophagy protein binder (e.g., autophagy adapter protein binder) has the formula:

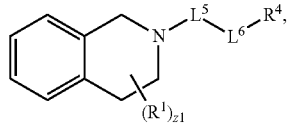
(VIII)

wherein z1 is an integer from 0 to 10. $R^1$, z1, $L^5$, $L^6$, and $R^4$ are as described herein.

In embodiments, the targeted autophagy protein binder (e.g., autophagy adapter protein binder) has the formula:

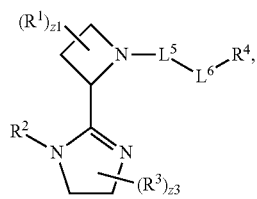
(IX)

wherein z1 is an integer from 0 to 5 and z3 is an integer from 0 to 4. $R^1$, z1, $R^2$, $R^3$, z3, $L^5$, $L^6$, and $R^4$ are as described herein.

In embodiments, the targeted autophagy protein binder (e.g., autophagy adapter protein binder) has the formula:

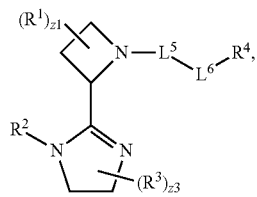
(X)

wherein z1 is an integer from 0 to 8. $R^1$, z1, $R^2$, $R^3$, $L^5$, $L^6$, and $R^4$ are as described herein.

In embodiments, the targeted autophagy protein binder (e.g., autophagy adapter protein binder) has the formula:

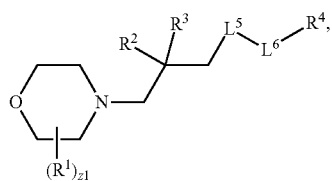
(XI)

wherein z1 is an integer from 0 to 7, z2 is an integer from 0 to 5, and z5 is 1 or 2. $R^1$, z1, $R^2$, z2, z5, $L^5$, $L^6$, and $R^4$ are as described herein.

In embodiments, the targeted autophagy protein binder (e.g., autophagy adapter protein binder) has the formula:

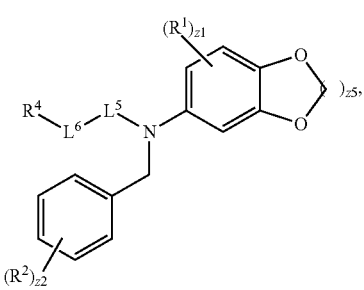
(XII)

wherein z1 is an integer from 0 to 2, z2 is an integer from 0 to 5, and z3 is an integer from 0 to 5. $R^1$, z1, $R^2$, z2, $R^3$, z3, $L^5$, $L^6$, and $R^4$ are as described herein.

In embodiments, the targeted autophagy protein binder (e.g., autophagy adapter protein binder) has the formula:

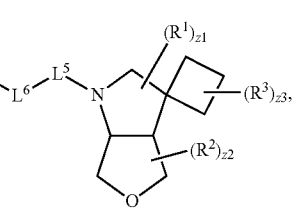
(XIII)

wherein z1 is an integer from 0 to 6. $R^1$, z1, $R^2$, $R^3$, $L^5$, $L^6$, and $R^4$ are as described herein.

In embodiments, the targeted autophagy protein binder (e.g., autophagy adapter protein binder) has the formula:

(XIV)

wherein z1 is an integer from 0 to 6. $R^1$, z1, $L^5$, $L^6$, and $R^4$ are as described herein.

In embodiments, the targeted autophagy protein binder (e.g., autophagy adapter protein binder) has the formula:

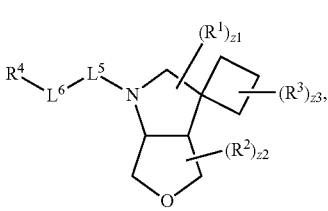
(XV)

wherein z1 is an integer from 0 to 4, z2 is an integer from 0 to 6, and z3 is an integer from 0 to 6. $R^1$, z1, $R^2$, z2, $R^3$, z3, $L^5$, $L^6$, and $R^4$ are as described herein.

In embodiments, the targeted autophagy protein binder (e.g., autophagy adapter protein binder) has the formula:

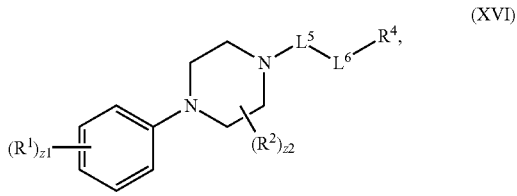

(XVI)

wherein z1 is an integer from 0 to 5 and z2 is an integer from 0 to 8. $R^1$, z1, $R^2$, z2, $L^5$, $L^6$, and $R^4$ are as described herein.

In embodiments, the targeted autophagy protein binder (e.g., autophagy adapter protein binder) has the formula:

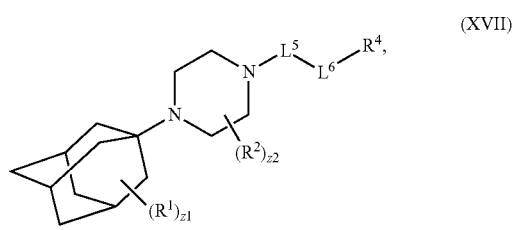

(XVII)

wherein z1 is an integer from 0 to 15 and z2 is an integer from 0 to 8. $R^1$, z1, $R^2$, z2, $L^5$, $L^6$, and $R^4$ are as described herein.

$R^1$ is independently oxo, halogen, —$CX^1{}_3$, —$CHX^1{}_2$, —$CH_2X^1$, —$OCX^1{}_3$, —$OCH_2X^1$, —$OCHX^1{}_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)_R{}^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

$R^2$ is independently oxo, halogen, —$CX^2{}_3$, —$CHX^2{}_2$, —$CH_2X^2$, —$OCX^2{}_3$, —$OCH_2X^2$, —$OCHX^2{}_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl.

$R^3$ is independently oxo, halogen, —$CX^3{}_3$, —$CHX^3{}_2$, —$CH_2X^3$, —$OCX^3{}_3$, —$OCH_2X^3$, —$OCHX^3{}_2$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl.

$R^4$ is hydrogen, halogen, —$CX^4{}_3$, —$CHX^4{}_2$, —$CH_2X^4$, —$OCX^4{}_3$, —$OCH_2X^4$, —$OCHX^4{}_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, —$N_3$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

E is an electrophilic moiety.

$L^5$ is a bond, —$S(O)_2$—, —$S(O)$—, —$NR^5$—, =N—, —O—, —S—, —$C(O)$—, —$C(O)NR^5$—, —$NR^5C(O)$—, —$NR^5C(O)NH$—, —$NHC(O)NR^5$—, —$C(O)O$—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. It will be understood that when $L^5$- is =N—, one of the two direct covalent connections to $L^5$ shown in "-$L^5$-" is a double bond and $L^5$ may equivalently be shown as "=$L^5$-" and the atom to which the double bond is directly attached must obey standard rules of chemical valency known in the chemical arts and be capable of forming such a double bond. For example, it will be understood that the formula:

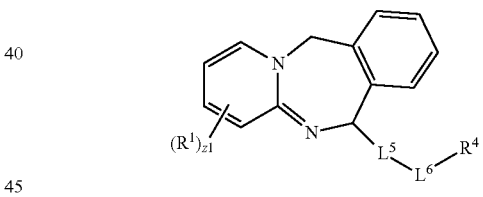

may include $L^5$ linkers that are connected to the seven membered ring of the fused ring by a single or double bond and when $L^5$ is connected to the seven membered ring by a single bond, the carbon of the seven membered ring bonded to $L^5$ is bonded to a hydrogen or an $L^1$ as well. When $L^5$ is connected to the seven membered ring by a double bond, the carbon of the seven membered ring bonded to $L^5$ is not directly bonded to a hydrogen or $L^1$, for example, when $L^5$ is =N—, the formula

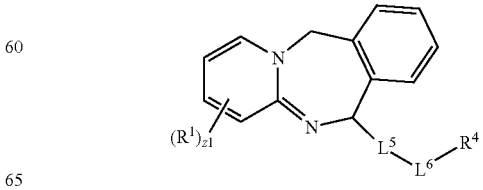

may be

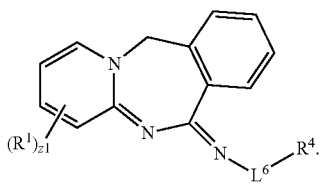

It will be understood that the floating substituent $R^1$ may be attached to any one or more of the fused rings and may be optionally different.

$R^5$ is hydrogen, $-CX^5_3$, $-CHX^5_2$, $-CH_2X^5$, $-OCX^5_3$, $-OCH_2X^5$, $-OCHX^5_2$, $-CN$, $-C(O)R^{5C}$, $-C(O)OR^{5C}$, $-C(O)NR^{5A}R^{5B}$, $-OR^{5D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^6$ is a bond, $-S(O)_2-$, $-S(O)-$, $-NR^6-$, $=N-$, $-O-$, $-S-$, $-C(O)-$, $-C(O)NR^6-$, $-NR^6C(O)-$, $-NR^6C(O)NH-$, $-NHC(O)NR^6-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. It will be understood that when $L^6-$ is $=N-$, one of the two direct covalent connections to $L^6$ shown in "-$L^6$-" is a double bond and $L^6$ may equivalently be shown as "=$L^6$-" and the atom to which the double bond is directly attached must obey standard rules of chemical valency known in the chemical arts and be capable of forming such a double bond.

$R^6$ is hydrogen, $-CX^6_3$, $-CHX^6_2$, $-CH_2X^6$, $-OCX^6_3$, $-OCH_2X^6$, $-OCHX^6_2$, $-CN$, $-C(O)R^{6C}$, $-C(O)OR^{6C}$, $-C(O)NR^{6A}R^{6B}$, $-OR^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{1C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, and $R^{6D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl.

$X$, $X^1$, $X^2$, $X^3$, $X^4$, $X^5$, and $X^6$ are independently $-F$, $-Cl$, $-Br$, or $-I$.

n1, n2, n3, n4, n5, and n6 are independently an integer from 0 to 4.

m1, m2, m3, m4, m5, m6, v1, v2, v3, v4, v5, and v6 are independently 1 or 2.

In embodiments, the targeted autophagy protein binder (e.g., autophagy adapter protein binder) has the formula:

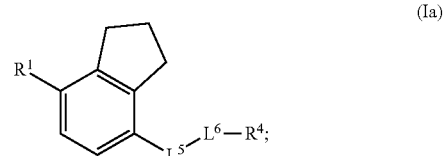

(Ia)

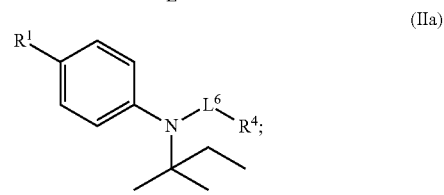

(IIa)

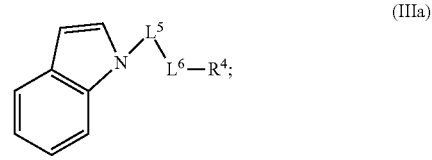

(IIIa)

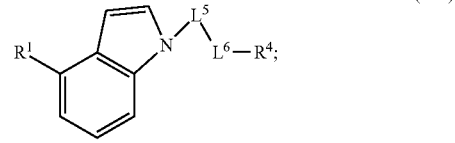

(IIIb)

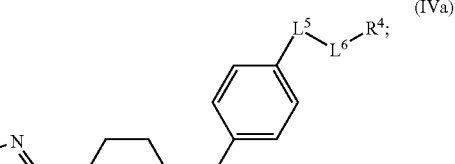

(IVa)

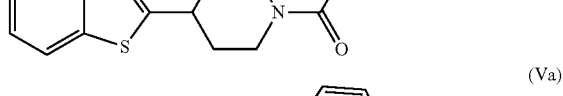

(Va)

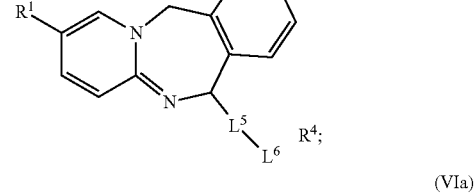

(VIa)

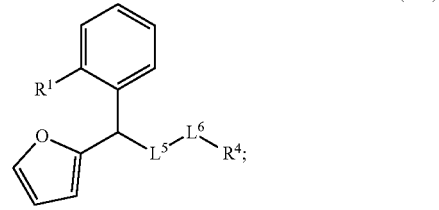

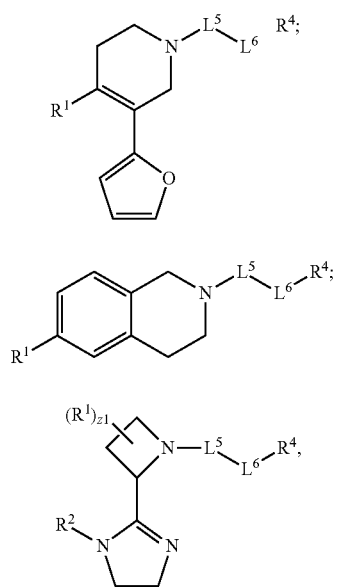
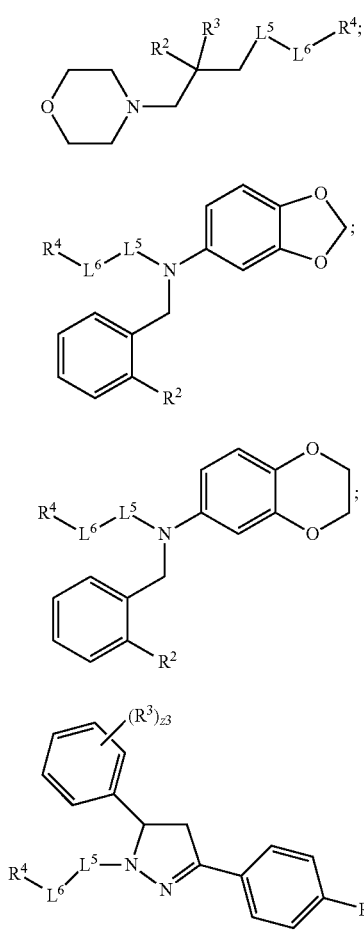
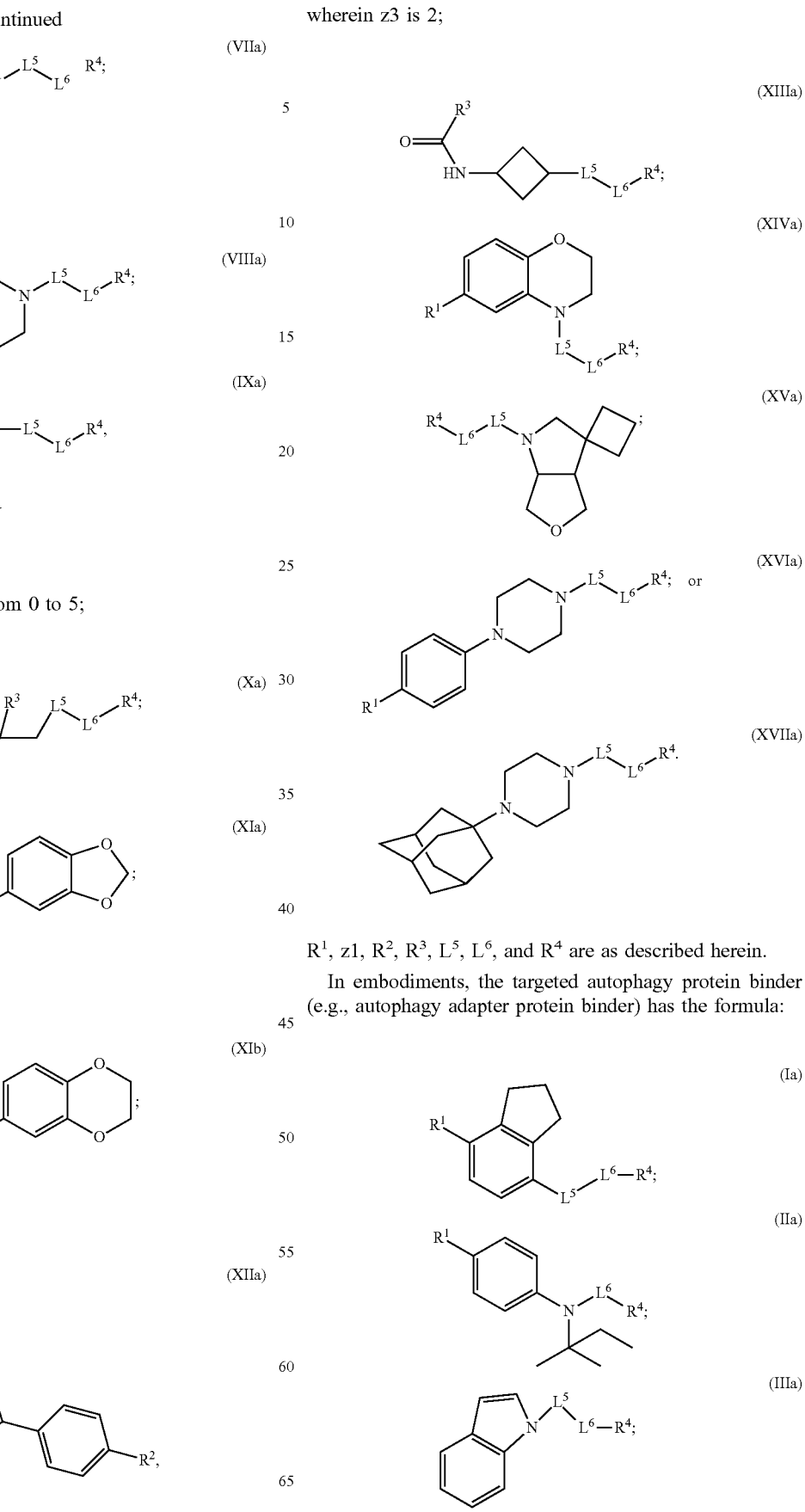
wherein z1 is an integer from 0 to 5;
wherein z3 is 2;
$R^1$, z1, $R^2$, $R^3$, $L^5$, $L^6$, and $R^4$ are as described herein.
In embodiments, the targeted autophagy protein binder (e.g., autophagy adapter protein binder) has the formula:

-continued

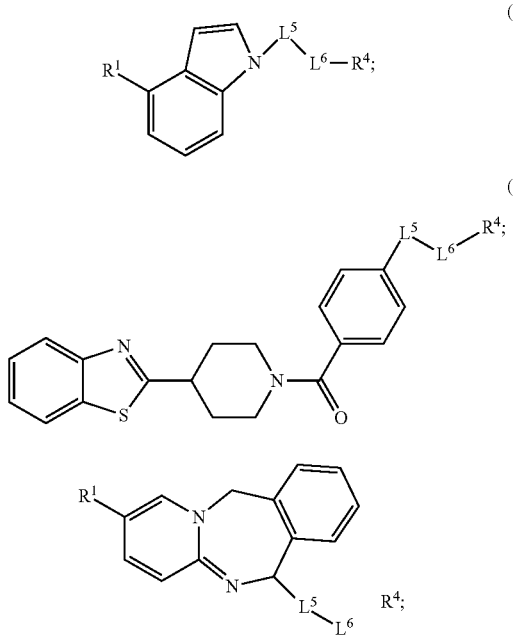

$L^5$, $L^6$, $R^1$, and $R^4$ are as described herein.

In embodiments, the targeted autophagy protein binder (e.g., autophagy adapter protein binder) has the formula

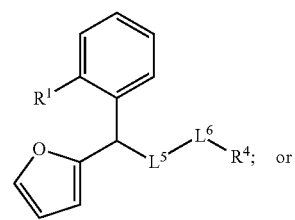

(Ia)

$L^5$, $L^6$, $R^1$, and $R^4$ are as described herein.

In embodiments, the targeted autophagy protein binder (e.g., autophagy adapter protein binder) has the formula:

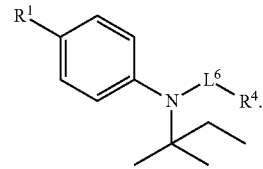

(IIa)

$L^5$, $L^6$, $R^1$, and $R^4$ are as described herein.

In embodiments, the targeted autophagy protein binder (e.g., autophagy adapter protein binder) has the formula:

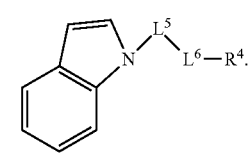

(IIIa)

$L^5$, $L^6$, and $R^4$ are as described herein.

In embodiments, the targeted autophagy protein binder (e.g., autophagy adapter protein binder) has the formula:

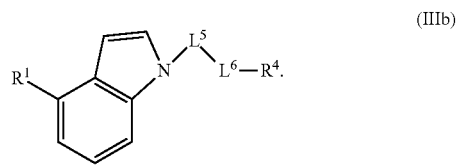

(IIIb)

$L^5$, $L^6$, $R^1$, and $R^4$ are as described herein.

In embodiments, the targeted autophagy protein binder (e.g., autophagy adapter protein binder) has the formula:

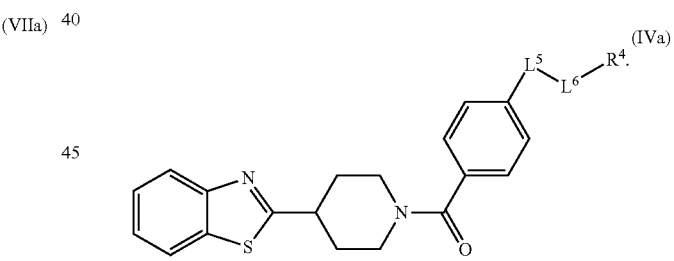

(IVa)

$L^5$, $L^6$, and $R^4$ are as described herein.

In embodiments, the targeted autophagy protein binder (e.g., autophagy adapter protein binder) has the formula:

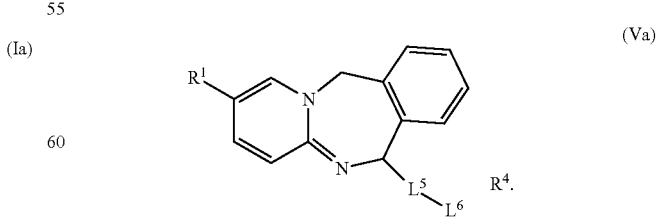

(Va)

$L^5$, $L^6$, $R^1$, and $R^4$ are as described herein.

In embodiments, the targeted autophagy protein binder (e.g., autophagy adapter protein binder) has the formula:

(VIa)

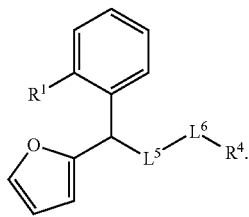

$L^5$, $L^6$, $R^1$, and $R^4$ are as described herein.

In embodiments, the targeted autophagy protein binder (e.g., autophagy adapter protein binder) has the formula:

(VIIa)

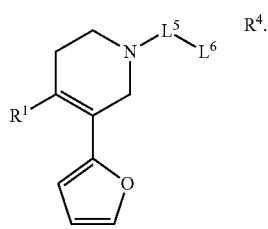

$L^5$, $L^6$, $R^1$, and $R^4$ are as described herein.

In embodiments, the targeted autophagy protein binder (e.g., autophagy adapter protein binder) has the formula:

(VIIIa)

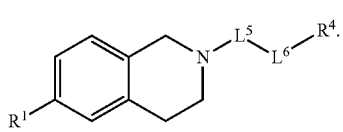

$L^5$, $L^6$, $R^1$, and $R^4$ are as described herein.

In embodiments, the targeted autophagy protein binder (e.g., autophagy adapter protein binder) has the formula:

(IXa)

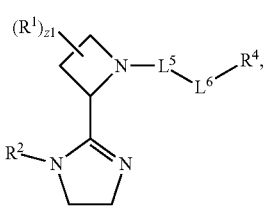

wherein z1 is an integer from 0 to 5. $L^5$, $L^6$, $R^1$, z1, $R^2$, and $R^4$ are as described herein.

In embodiments, the targeted autophagy protein binder (e.g., autophagy adapter protein binder) has the formula:

(Xa)

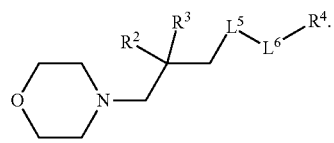

$L^5$, $L^6$, $R^2$, $R^3$, and $R^4$ are as described herein.

In embodiments, the targeted autophagy protein binder (e.g., autophagy adapter protein binder) has the formula:

(XIa)

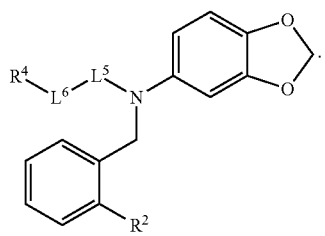

$L^5$, $L^6$, $R^2$, and $R^4$ are as described herein.

In embodiments, the targeted autophagy protein binder (e.g., autophagy adapter protein binder) has the formula:

(XIb)

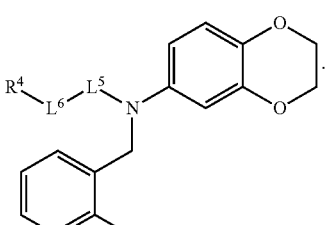

$L^5$, $L^6$, $R^2$, and $R^4$ are as described herein.

In embodiments, the targeted autophagy protein binder (e.g., autophagy adapter protein binder) has the formula:

(XIIa)

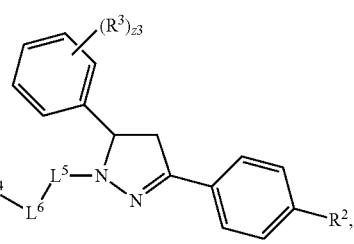

wherein z3 is 2. $L^5$, $L^6$, $R^3$, z3, and $R^4$ are as described herein.

In embodiments, the targeted autophagy protein binder (e.g., autophagy adapter protein binder) has the formula:

(XIIIa)

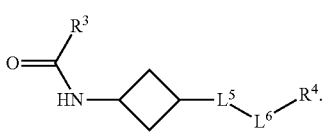

$L^5$, $L^6$, $R^3$, and $R^4$ are as described herein.

In embodiments, the targeted autophagy protein binder (e.g., autophagy adapter protein binder) has the formula:

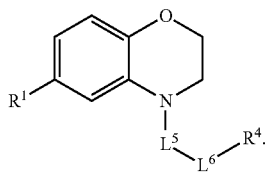

(XIVa)

$L^5$, $L^6$, $R^1$, and $R^4$ are as described herein.

In embodiments, the targeted autophagy protein binder (e.g., autophagy adapter protein binder) has the formula:

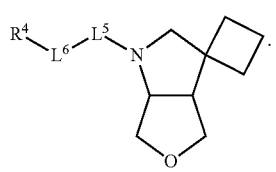

(XVa)

$L^5$, $L^6$, and $R^4$ are as described herein.

In embodiments, the targeted autophagy protein binder (e.g., autophagy adapter protein binder) has the formula:

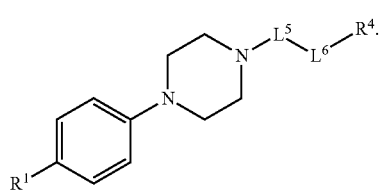

(XVIa)

$L^5$, $L^6$, $R^1$, and $R^4$ are as described herein.

In embodiments, the targeted autophagy protein binder (e.g., autophagy adapter protein binder) has the formula:

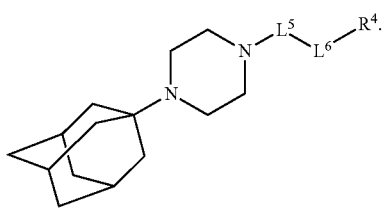

(XVIIa)

$L^5$, $L^6$, and $R^4$ are as described herein.

In embodiments, the targeted autophagy protein binder (e.g., autophagy adapter protein binder) has the formula:

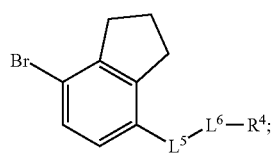

(Ib)

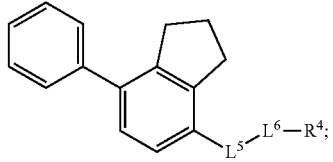

(Ic)

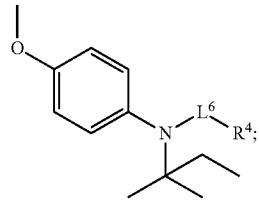

(IIb)

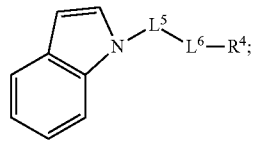

(IIIa)

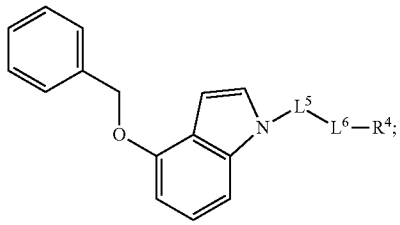

(IIIc)

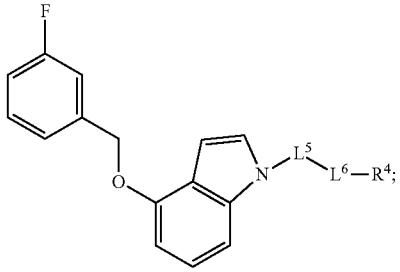

(IIId)

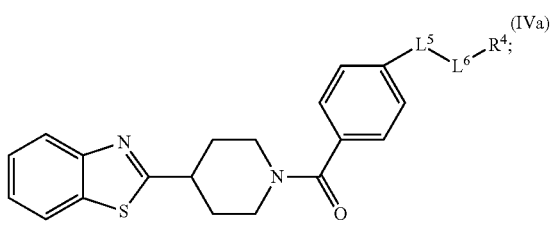

(IVa)

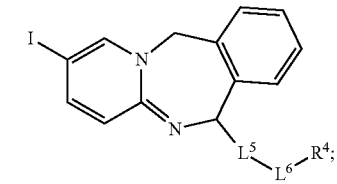

(Vb)

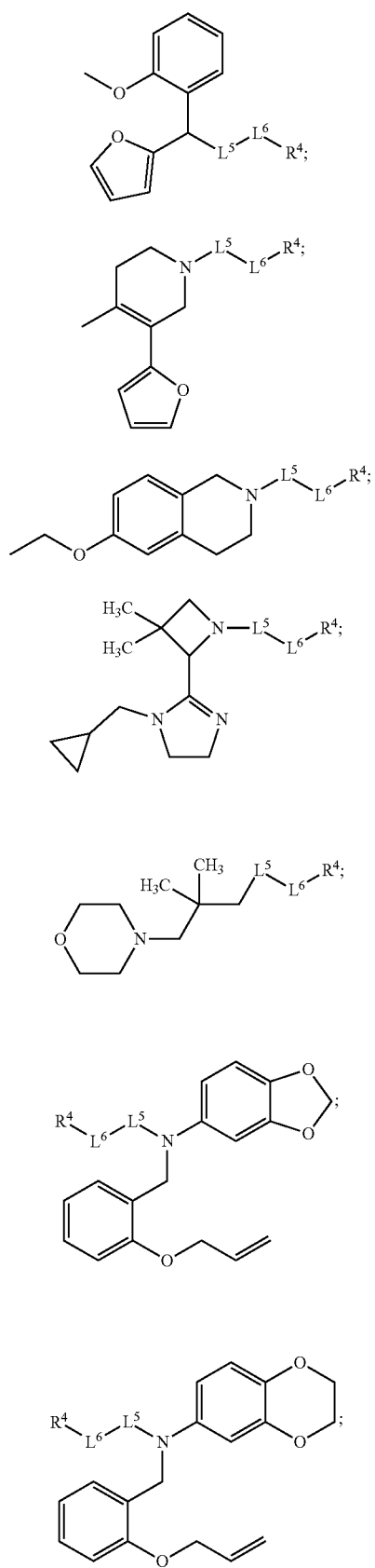
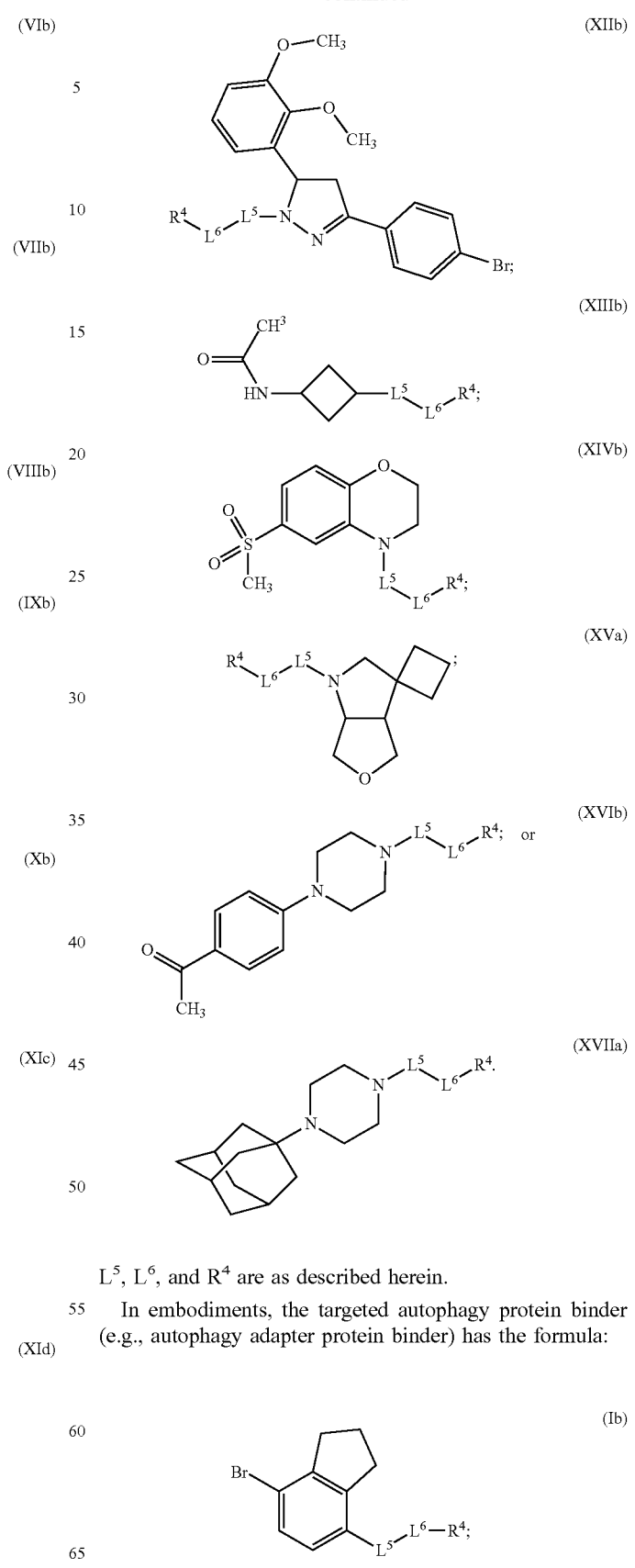
L$^5$, L$^6$, and R$^4$ are as described herein.
In embodiments, the targeted autophagy protein binder (e.g., autophagy adapter protein binder) has the formula:
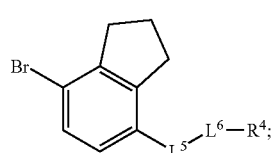

-continued (Ic)

(IIb)

(IIIa)

(IIIc)

(IIId)

(IVa)

(Vb)

-continued (VIb)

(VIIb)

L⁵, L⁶, and R⁴ are as described herein.

In embodiments, the targeted autophagy protein binder (e.g., autophagy adapter protein binder) has the formula:

(Ib)

L⁵, L⁶, and R⁴ are as described herein.

In embodiments, the targeted autophagy protein binder (e.g., autophagy adapter protein binder) has the formula:

(Ic)

L⁵, L⁶, and R⁴ are as described herein.

In embodiments, the targeted autophagy protein binder (e.g., autophagy adapter protein binder) has the formula:

(IIb)

L⁵, L⁶, and R⁴ are as described herein.

In embodiments, the targeted autophagy protein binder (e.g., autophagy adapter protein binder) has the formula:

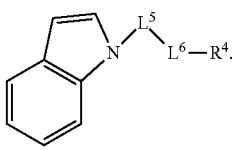 (IIIa)

$L^5$, $L^6$, and $R^4$ are as described herein.

In embodiments, the targeted autophagy protein binder (e.g., autophagy adapter protein binder) has the formula:

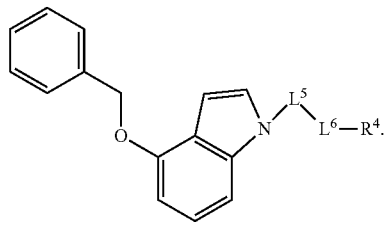 (IIIc)

$L^5$, $L^6$, and $R^4$ are as described herein.

In embodiments, the targeted autophagy protein binder (e.g., autophagy adapter protein binder) has the formula:

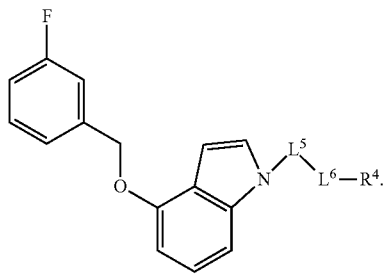 (IIId)

$L^5$, $L^6$, and $R^4$ are as described herein.

In embodiments, the targeted autophagy protein binder (e.g., autophagy adapter protein binder) has the formula:

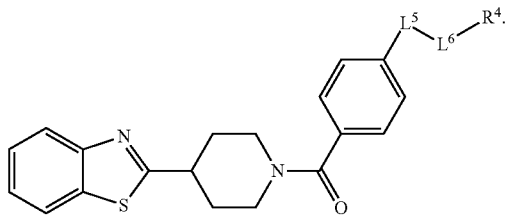 (IVa)

$L^5$, $L^6$, and $R^4$ are as described herein.

In embodiments, the targeted autophagy protein binder (e.g., autophagy adapter protein binder) has the formula:

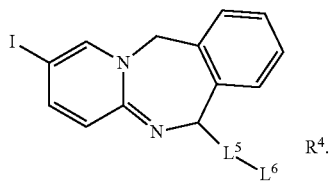 (Vb)

$L^5$, $L^6$, and $R^4$ are as described herein.

In embodiments, the targeted autophagy protein binder (e.g., autophagy adapter protein binder) has the formula:

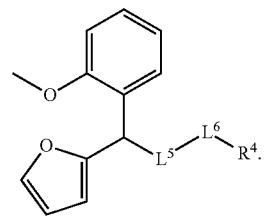 (VIb)

$L^5$, $L^6$, and $R^4$ are as described herein.

In embodiments, the targeted autophagy protein binder (e.g., autophagy adapter protein binder) has the formula:

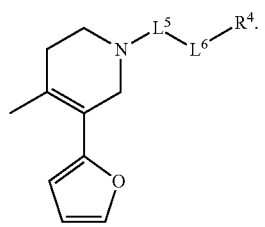 (VIIb)

$L^5$, $L^6$, and $R^4$ are as described herein.

In embodiments, the targeted autophagy protein binder (e.g., autophagy adapter protein binder) has the formula:

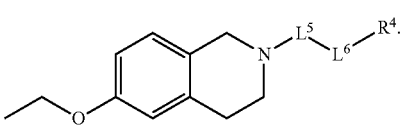 (VIIIb)

$L^5$, $L^6$, and $R^4$ are as described herein.

In embodiments, the targeted autophagy protein binder (e.g., autophagy adapter protein binder) has the formula:

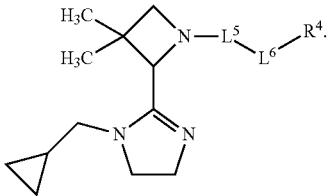 (IXb)

$L^5$, $L^6$, and $R^4$ are as described herein.

In embodiments, the targeted autophagy protein binder (e.g., autophagy adapter protein binder) has the formula:

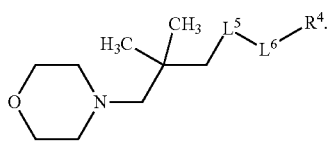
(Xb)

$L^5$, $L^6$, and $R^4$ are as described herein.

In embodiments, the targeted autophagy protein binder (e.g., autophagy adapter protein binder) has the formula:

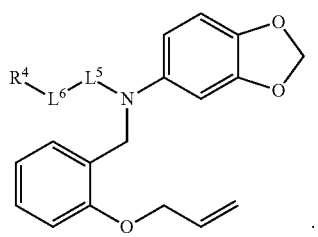
(XIc)

$L^5$, $L^6$, and $R^4$ are as described herein.

In embodiments, the targeted autophagy protein binder (e.g., autophagy adapter protein binder) has the formula:

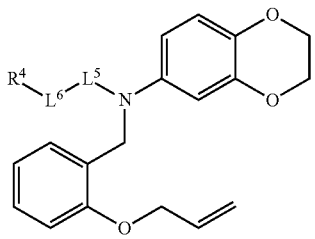
(XId)

$L^5$, $L^6$, and $R^4$ are as described herein.

In embodiments, the targeted autophagy protein binder (e.g., autophagy adapter protein binder) has the formula:

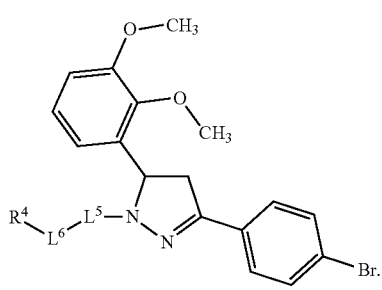
(XIIb)

$L^5$, $L^6$, and $R^4$ are as described herein.

In embodiments, the targeted autophagy protein binder (e.g., autophagy adapter protein binder) has the formula:

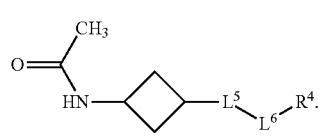
(XIIIb)

$L^5$, $L^6$, and $R^4$ are as described herein.

In embodiments, the targeted autophagy protein binder (e.g., autophagy adapter protein binder) has the formula:

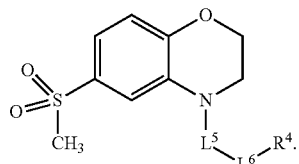
(XIVb)

$L^5$, $L^6$, and $R^4$ are as described herein.

In embodiments, the targeted autophagy protein binder (e.g., autophagy adapter protein binder) has the formula:

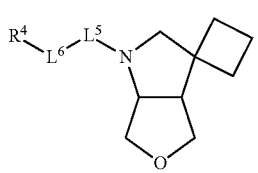
(XVa)

$L^5$, $L^6$, and $R^4$ are as described herein.

In embodiments, the targeted autophagy protein binder (e.g., autophagy adapter protein binder) has the formula:

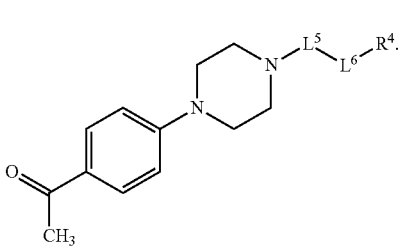
(XVIb)

$L^5$, $L^6$, and $R^4$ are as described herein.

In embodiments, the targeted autophagy protein binder (e.g., autophagy adapter protein binder) has the formula:

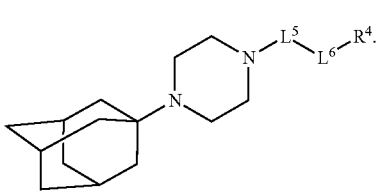
(XVIIa)

$L^5$, $L^6$, and $R^4$ are as described herein.

In embodiments, $R^4$ is E.

In embodiments, E is a covalent cysteine modifier, covalent lysine modifier, covalent serine modifier, or covalent methionine modifier. In embodiments, E is a covalent cysteine modifier. In embodiments, E is a covalent lysine modifier. In embodiments, E is a covalent serine modifier. In embodiments, E is a covalent methionine modifier. In embodiments, E is a covalent methionine modifier described in Lin S, Yang X, Jia S, et al. (Redox-based reagents for chemoselective methionine bioconjugation. Science (New York, N.Y.). 2017; 355(6325):597-602. doi:10.1126/science.aal3316), which is incorporated herein by reference in its entirety for all purposes.

In embodiments, E is

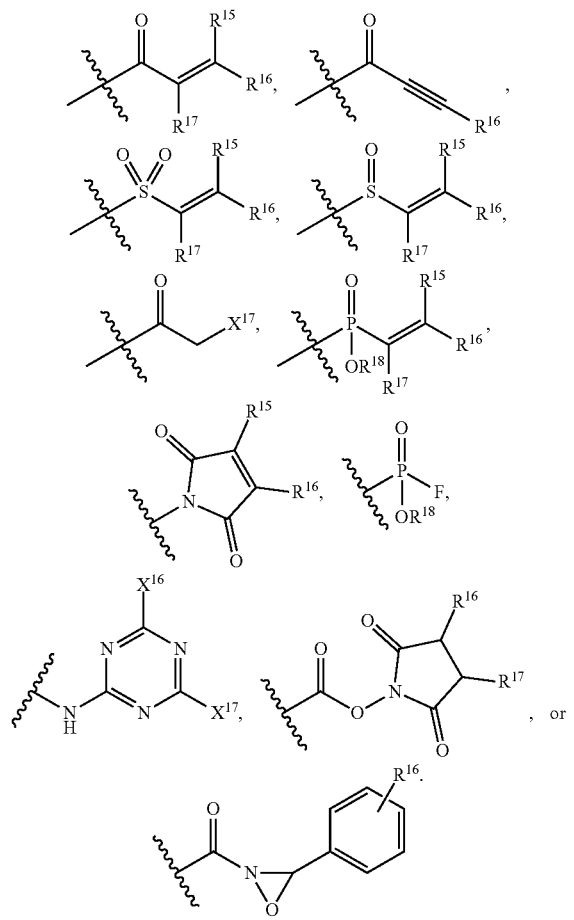

$R^{15}$ is independently hydrogen, halogen, $-CX^{15}_3$, $-CHX^{15}_2$, $-CH_2X^{15}$, $-CN$, $-SO_{n15}R^{15D}$, $-SO_{v15}NR^{15A}R^{15B}$, $-NHC(O)NR^{15A}R^{15B}$, $-ONR^{15A}R^{15B}$, $-NHC=(O)NHNR^{15A}R^{15B}$, $-NHC(O)NR^{15A}R^{15B}$, $-N(O)_{m15}$, $-NR^{15A}R^{15B}$, $-C(O)R^{15C}$, $-C(O)-OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)OR^{15C}$, $-NR^{15A}OR^{15C}$, $-OCX^{15}_3$, $-OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{16}$ is independently hydrogen, halogen, $-CX^{16}_3$, $-CHX^{16}_2$, $-CH_2X^{16}$, $-CN$, $-SO_{n16}R^{16D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}(O)OR^{16C}$, $-NR^{16A}OR^{16C}$, $-OCX^{16}_3$, $-OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{1-7}$ is independently hydrogen, halogen, $-CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}(O)OR^{17C}$, $-NR^{17A}OR^{17C}$, $-OCX^{17}_3$, $-OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{18}$ is independently hydrogen, $-CX^{18}_3$, $-CHX^{18}_2$, $-CH_2X^{18}$, $-C(O)R^{18C}$, $-C(O)OR^{18C}$, $-C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, and $R^{18D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl.

X, $X^{15}$, $X^{16}$, $X^{17}$, and $X^{18}$ are independently $-F$, $-Cl$, $-Br$, or $-I$.

n15, n16, and n17 are independently an integer from 0 to 4.

m15, m16, m17, v15, v16, and v17 are independently and integer from 1 to 2.

In embodiments, E is

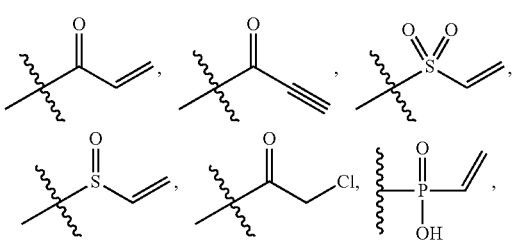

103
-continued

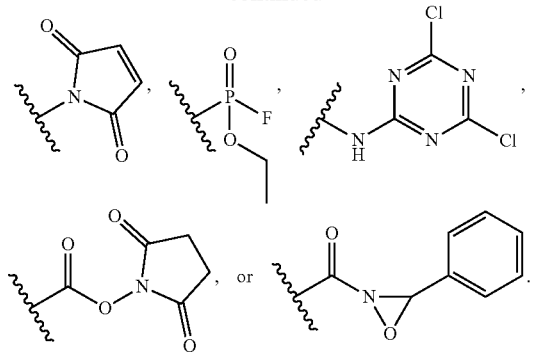

In embodiments, E is

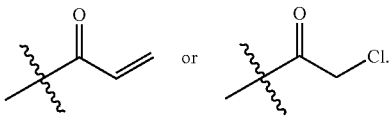

In embodiments, E is

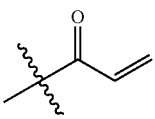

In embodiments, E is

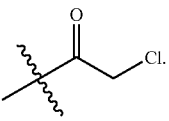 [SMILES: *C(=O)CCl]

In embodiments, -L$^6$-E is

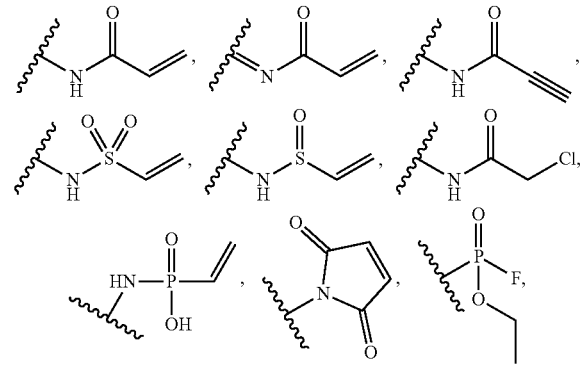

104
-continued

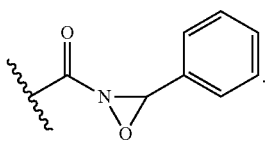

In embodiments, L$^5$-L$^6$-R$^4$ is C(O)CH$_2$-(halogen). In embodiments, L$^5$-L$^6$-R$^4$ is C(O)CH$_2$—Cl. In embodiments, L$^5$-L$^6$-R$^4$ is —C(O)CH$_2$—Br.

In embodiments, the targeted autophagy protein binder (e.g., autophagy adapter protein binder) has the formula:

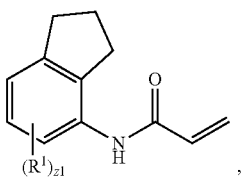
(Id)

wherein z1 is an integer from 0 to 9:

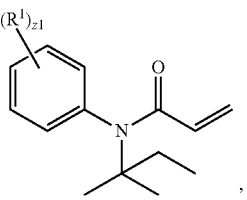
(IIc)

wherein z1 is an integer from 0 to 5;

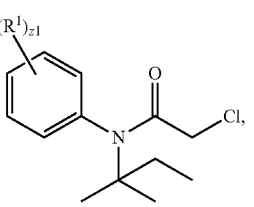
(IId)

wherein z1 is an integer from 0 to 5;

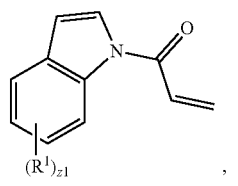
(IIIe)

wherein z1 is an integer from 0 to 6;

(IVb)
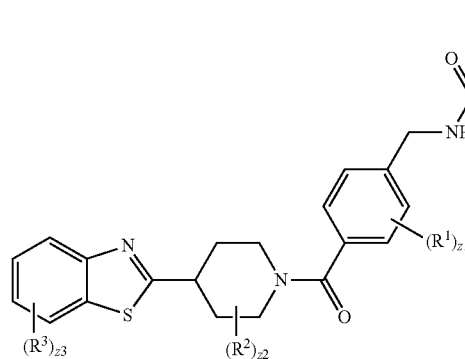

(Vc)
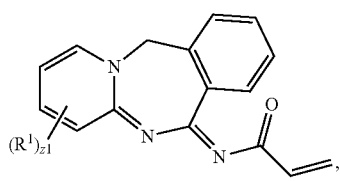

wherein z1 is an integer from 0 to 11;

(VIc)
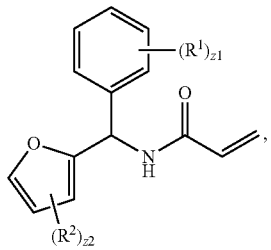

wherein z1 is an integer from 0 to 5 and z2 is an integer from 0 to 3;

(VIIc)
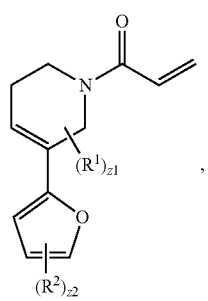

wherein z1 is an integer from 0 to 5 and z2 is an integer from 0 to 3;

(VIIIc)
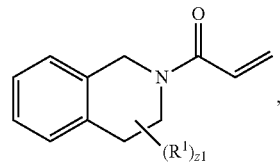

wherein z1 is an integer from 0 to 10;

(IXc)
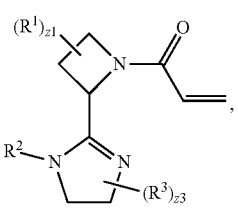

wherein z1 is an integer from 0 to 5 and z3 is an integer from 0 to 4;

(Xc)
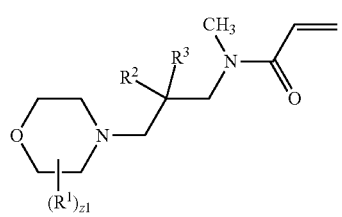

wherein z1 is an integer from 0 to 8;

(XIe)
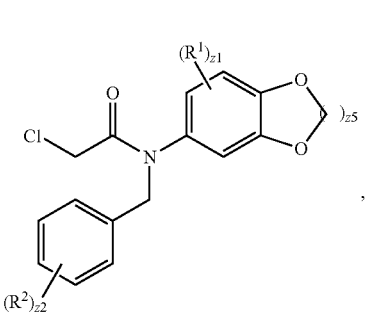

wherein z1 is an integer from 0 to 7, z2 is an integer from 0 to 5, and z5 is 1 or 2;

(XIIc)
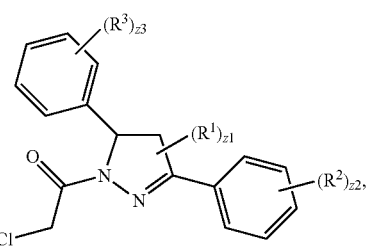

wherein z1 is an integer from 0 to 2, z2 is an integer from 0 to 5, and z3 is an integer from 0 to 5;

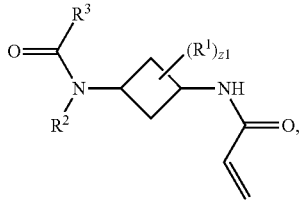
(XIIIc)

wherein z1 is an integer from 0 to 6;

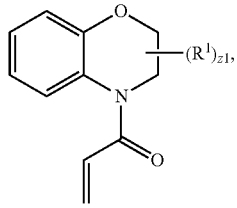
(XIVc)

wherein z1 is an integer from 0 to 6;

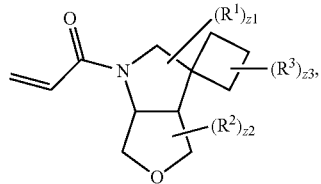
(XVb)

wherein z1 is an integer from 0 to 4, z2 is an integer from 0 to 6, and z3 is an integer from 0 to 6;

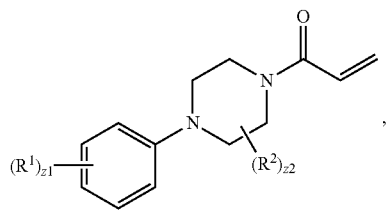
(XVIc)

wherein z1 is an integer from 0 to 5 and z2 is an integer from 0 to 8; or

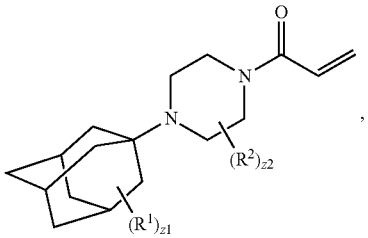
(XVIIb)

wherein z1 is an integer from 0 to 15 and z2 is an integer from 0 to 8. $R^1$, z1, $R^2$, z2, $R^3$, z3 and z5 are as described herein.

In embodiments, the targeted autophagy protein binder (e.g., autophagy adapter protein binder) has the formula:

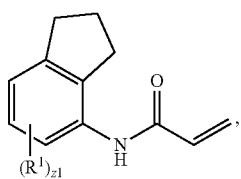
(Id)

wherein z1 is an integer from 0 to 9;

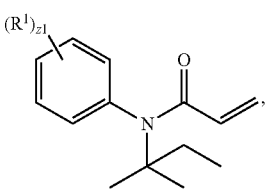
(IIc)

wherein z1 is an integer from 0 to 5;

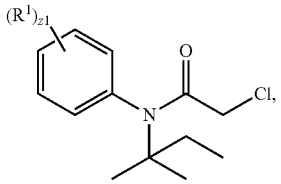
(IId)

wherein z1 is an integer from 0 to 5;

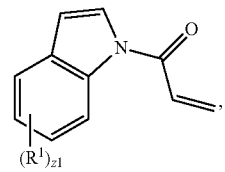
(IIIe)

wherein z1 is an integer from 0 to 6;

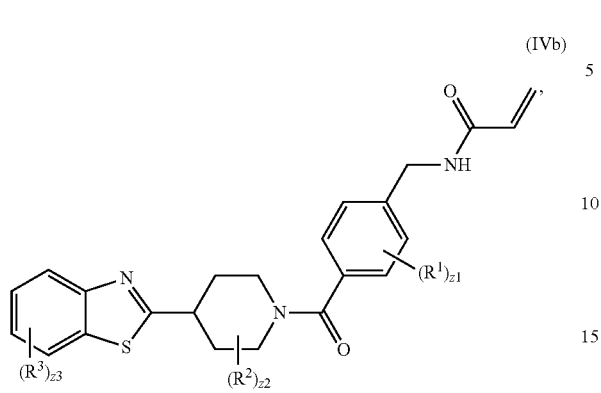
(IVb)

wherein z1 is an integer from 0 to 4, z2 is an integer from 0 to 8, and z3 is an integer from 0 to 4;

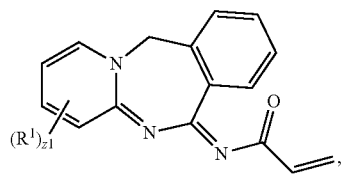
(Vc)

wherein z1 is an integer from 0 to 11;

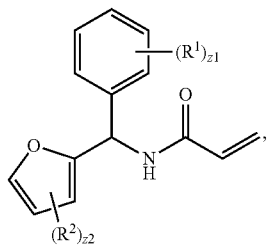
(VIc)

wherein z1 is an integer from 0 to 5 and z2 is an integer from 0 to 3; or

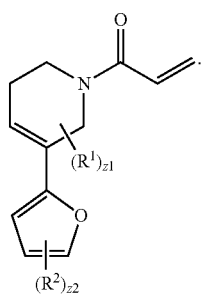
(VIIc)

$R^1$, z1, $R^2$, z2, $R^3$, and z3 are as described herein.

In embodiments, the targeted autophagy protein binder (e.g., autophagy adapter protein binder) has the formula:

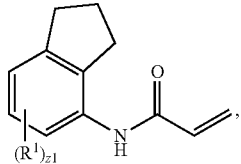
(Id)

wherein z1 is an integer from 0 to 9. $R^1$ and z1 are as described herein.

In embodiments, the targeted autophagy protein binder (e.g., autophagy adapter protein binder) has the formula:

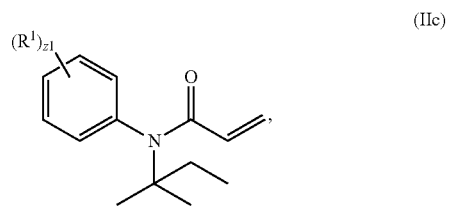
(IIc)

wherein z1 is an integer from 0 to 5. $R^1$ and z1 are as described herein.

In embodiments, the targeted autophagy protein binder (e.g., autophagy adapter protein binder) has the formula:

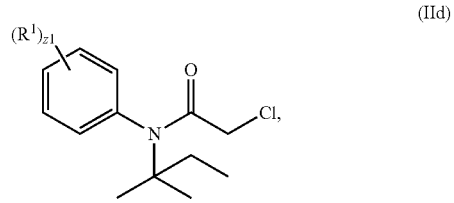
(IId)

wherein z1 is an integer from 0 to 5. $R^1$ and z1 are as described herein.

In embodiments, the targeted autophagy protein binder (e.g., autophagy adapter protein binder) has the formula:

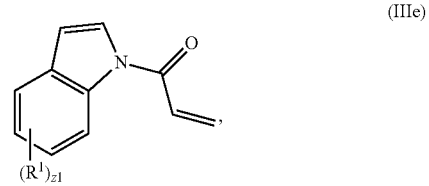
(IIIe)

wherein z1 is an integer from 0 to 6. $R^1$ and z1 are as described herein.

In embodiments, the targeted autophagy protein binder (e.g., autophagy adapter protein binder) has the formula:

(IVb)

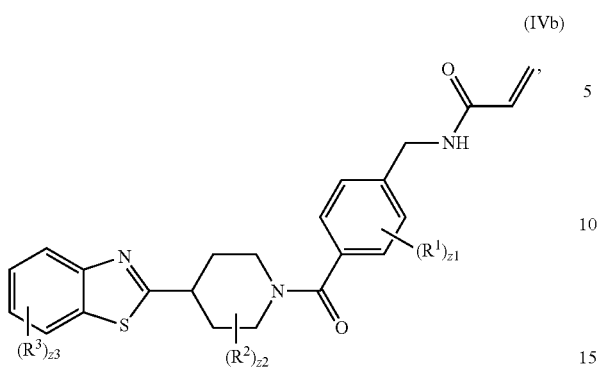

wherein z1 is an integer from 0 to 4, z2 is an integer from 0 to 8, and z3 is an integer from 0 to 4. $R^1$, z1, $R^2$, z2, $R^3$, and z3 are as described herein.

In embodiments, the targeted autophagy protein binder (e.g., autophagy adapter protein binder) has the formula:

(Vc)

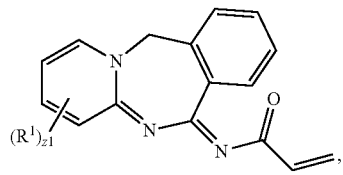

wherein z1 is an integer from 0 to 11. $R^1$ and z1 are as described herein.

In embodiments, the targeted autophagy protein binder (e.g., autophagy adapter protein binder) has the formula:

(VIc)

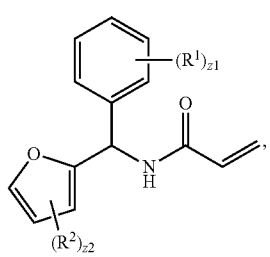

wherein z1 is an integer from 0 to 5 and z2 is an integer from 0 to 3. $R^1$, z1, $R^2$, and z2 are as described herein.

In embodiments, the targeted autophagy protein binder (e.g., autophagy adapter protein binder) has the formula:

(VIIc)

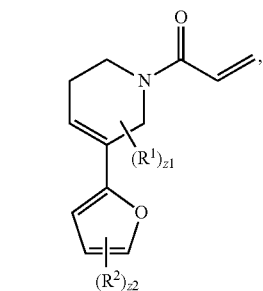

wherein z1 is an integer from 0 to 5 and z2 is an integer from 0 to 3. $R^1$, z1, $R^2$, and z2 are as described herein.

In embodiments, the targeted autophagy protein binder (e.g., autophagy adapter protein binder) has the formula:

(VIIIc)

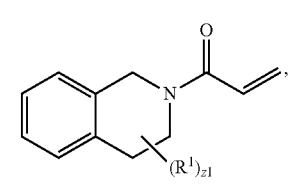

wherein z1 is an integer from 0 to 10. $R^1$ and z1 are as described herein.

In embodiments, the targeted autophagy protein binder (e.g., autophagy adapter protein binder) has the formula:

(IXc)

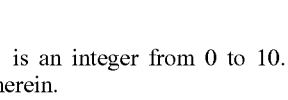

wherein z1 is an integer from 0 to 5 and z3 is an integer from 0 to 4. $R^1$, z1, $R^2$, $R^3$, and z3 are as described herein.

In embodiments, the targeted autophagy protein binder (e.g., autophagy adapter protein binder) has the formula:

(Xc)

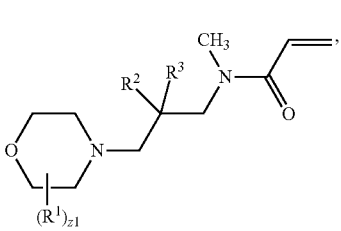

wherein z1 is an integer from 0 to 8. $R^1$, z1, $R^2$, and $R^3$ are as described herein.

In embodiments, the targeted autophagy protein binder (e.g., autophagy adapter protein binder) has the formula:

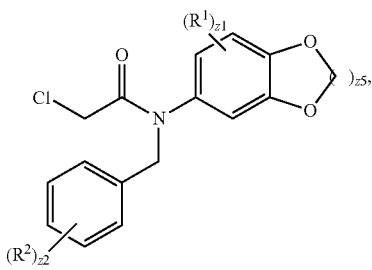

(XIe)

wherein z1 is an integer from 0 to 7, z2 is an integer from 0 to 5, and z5 is 1 or 2. $R^1$, z1, $R^2$, z2, and z5 are as described herein.

In embodiments, the targeted autophagy protein binder (e.g., autophagy adapter protein binder) has the formula:

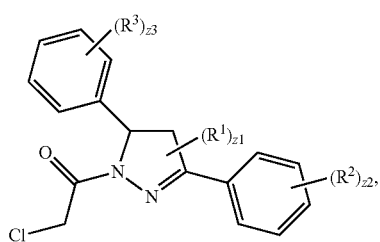

(XIIc)

wherein z1 is an integer from 0 to 2, z2 is an integer from 0 to 5, and z3 is an integer from 0 to 5. $R^1$, z1, $R^2$, z2, $R^3$, and z3 are as described herein.

In embodiments, the targeted autophagy protein binder (e.g., autophagy adapter protein binder) has the formula:

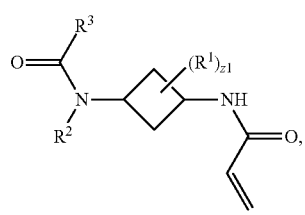

(XIIIc)

wherein z1 is an integer from 0 to 6. $R^1$, z1, $R^2$, and $R^3$ are as described herein.

In embodiments, the targeted autophagy protein binder (e.g., autophagy adapter protein binder) has the formula:

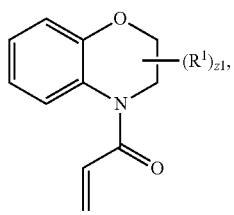

(XIVc)

wherein z1 is an integer from 0 to 6. $R^1$ and z1 are as described herein.

In embodiments, the targeted autophagy protein binder (e.g., autophagy adapter protein binder) has the formula:

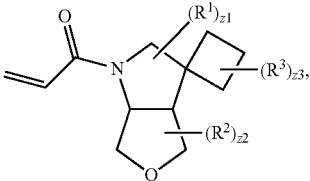

(XVb)

wherein z1 is an integer from 0 to 4, z2 is an integer from 0 to 6, and z3 is an integer from 0 to 6. $R^1$, z1, $R^2$, z2, $R^3$, and z3 are as described herein.

In embodiments, the targeted autophagy protein binder (e.g., autophagy adapter protein binder) has the formula:

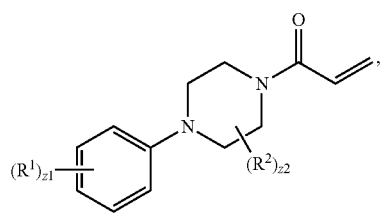

(XVIc)

wherein z1 is an integer from 0 to 5 and z2 is an integer from 0 to 8. $R^1$, z1, $R^2$, and z2 are as described herein.

In embodiments, the targeted autophagy protein binder (e.g., autophagy adapter protein binder) has the formula:

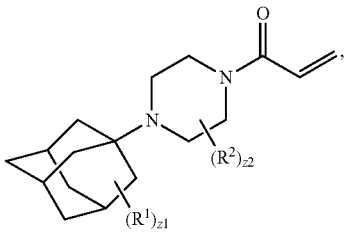

(XVIIb)

wherein z1 is an integer from 0 to 15 and z2 is an integer from 0 to 8. $R^1$, z1, $R^2$, and z2 are as described herein.

In embodiments, the targeted autophagy protein binder (e.g., autophagy adapter protein binder) has the formula:

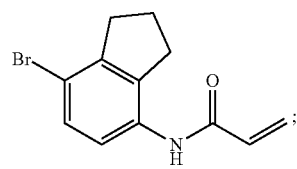

(Ie)

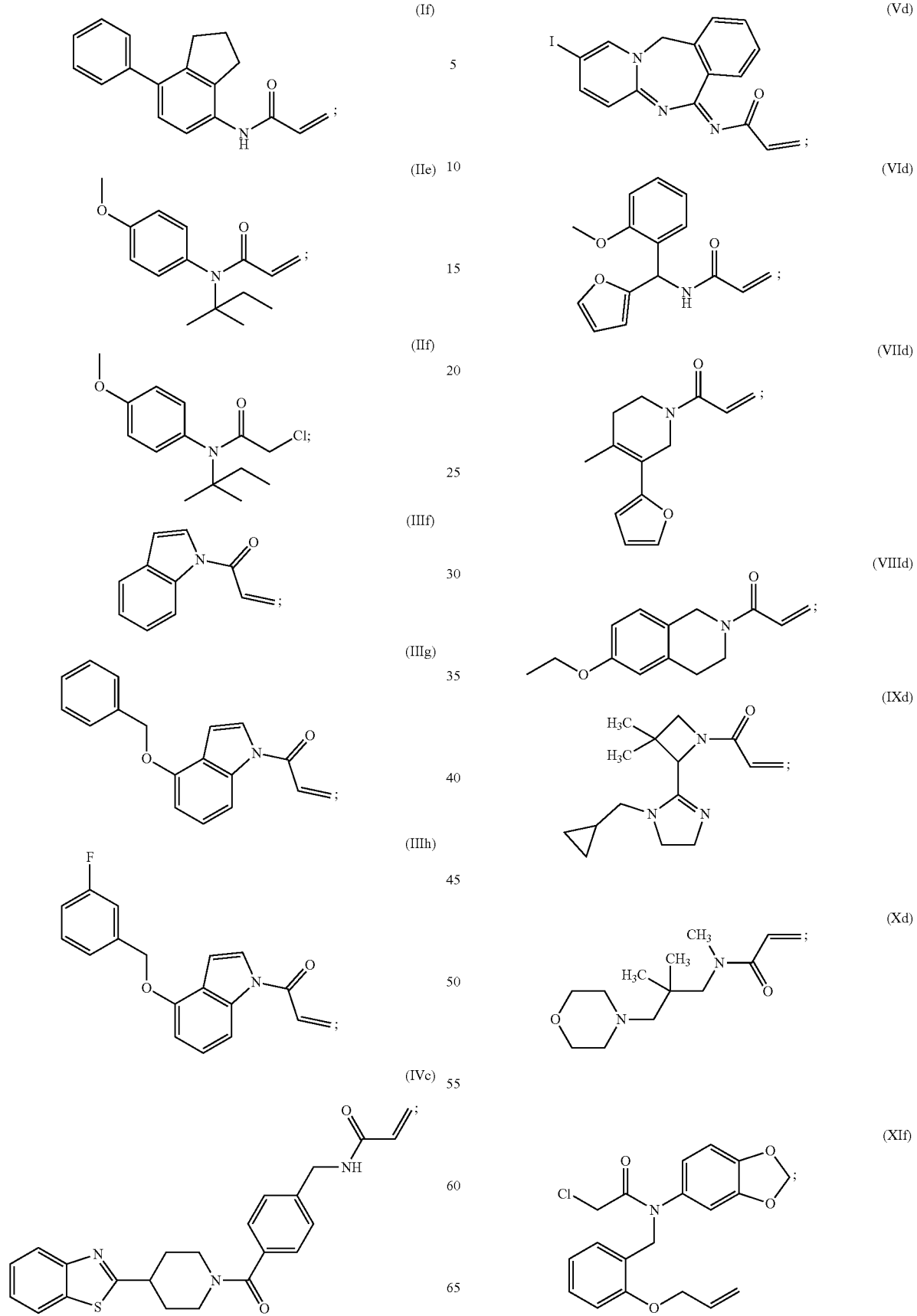

-continued
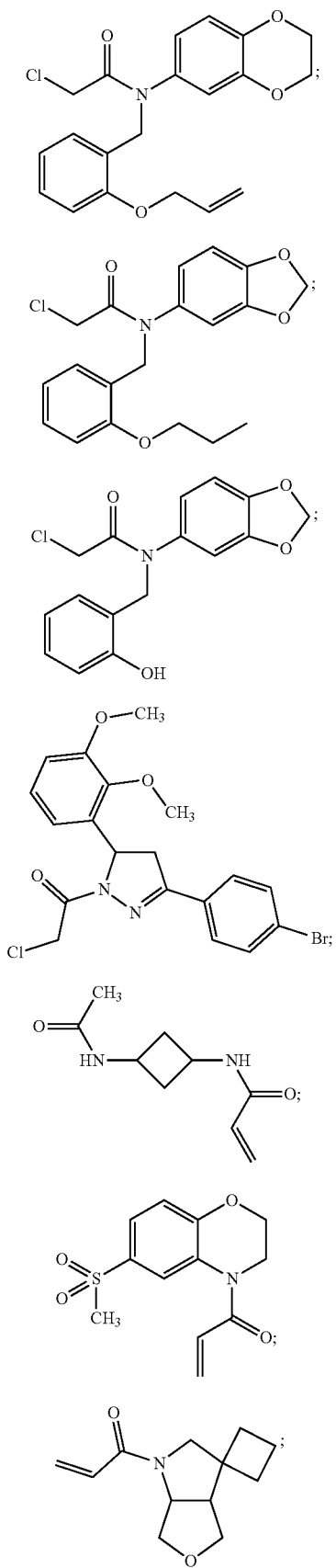
(XIg)
(XIh)
(XIi)
(XIId)
(XIIId)
(XIVd)
(XVc)
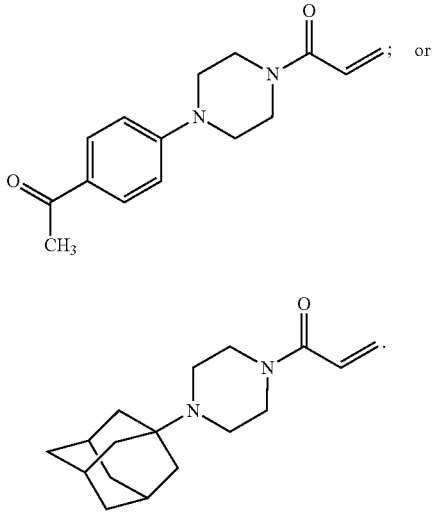
(XVId)
(XVIIc)
In embodiments, the targeted autophagy protein binder (e.g., autophagy adapter protein binder) has the formula:
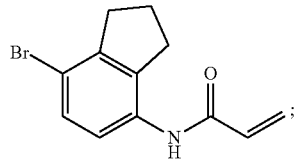
(Ie)
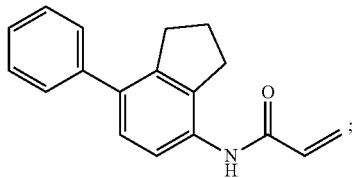
(If)
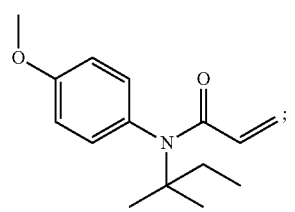
(IIe)
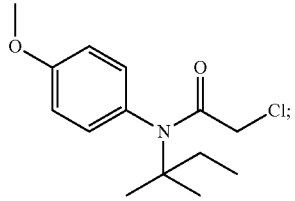
(IIf)
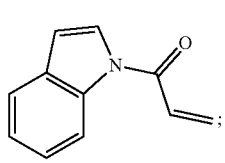
(IIIf)

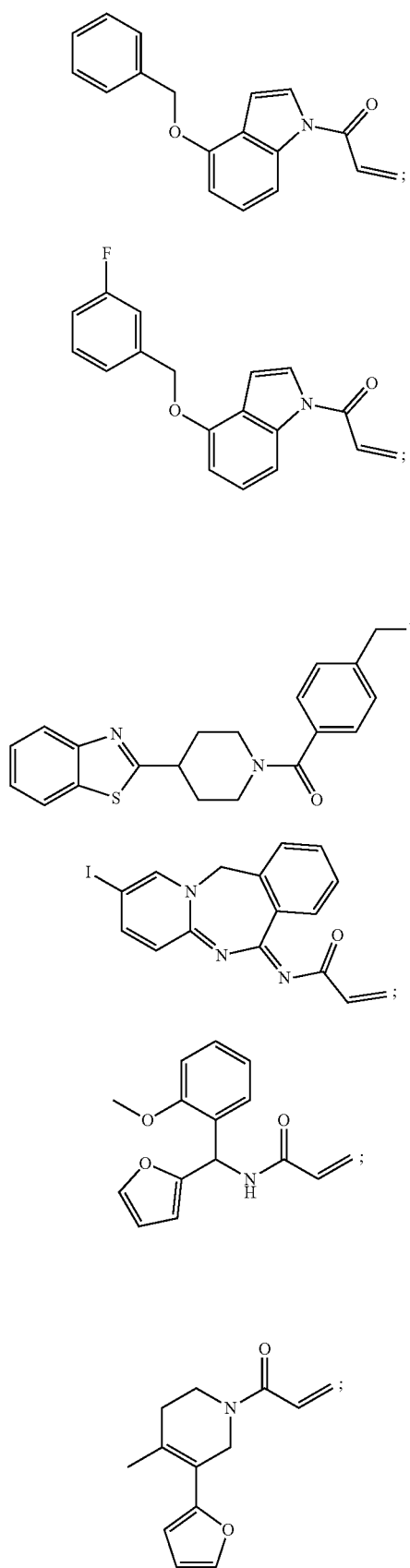
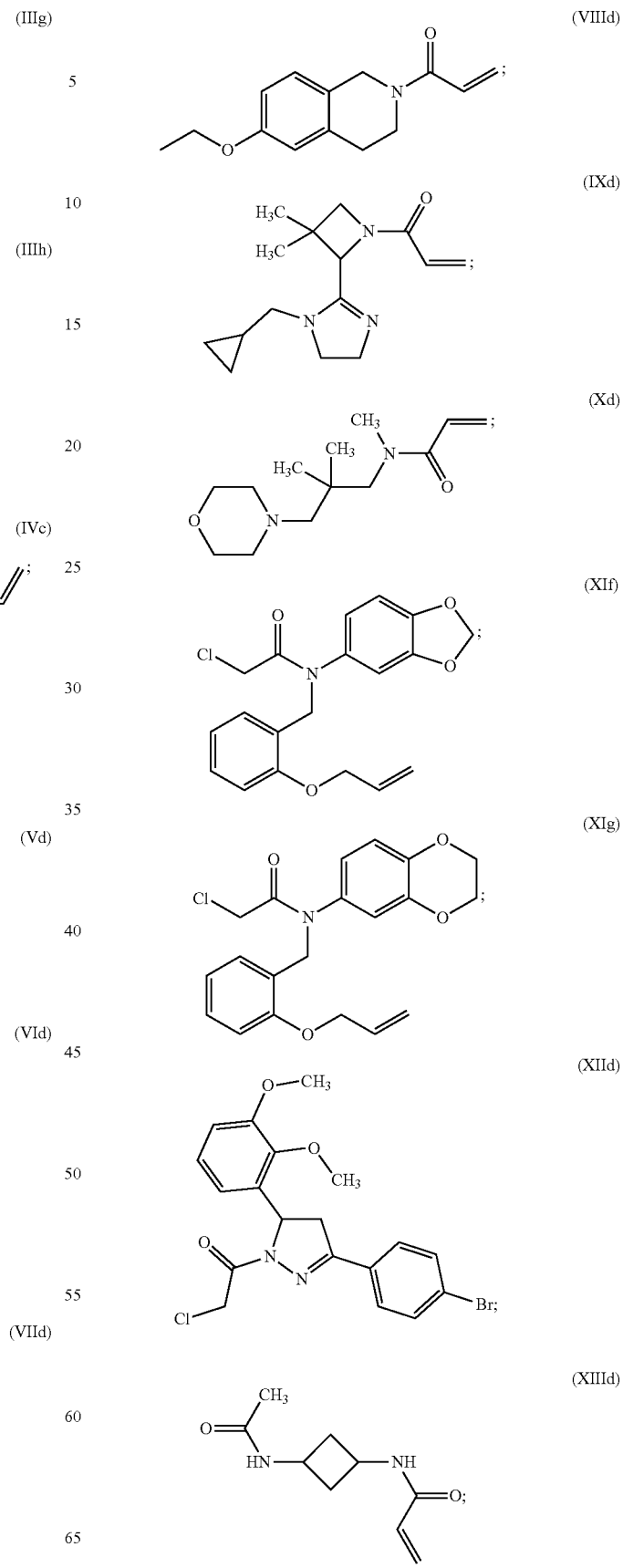

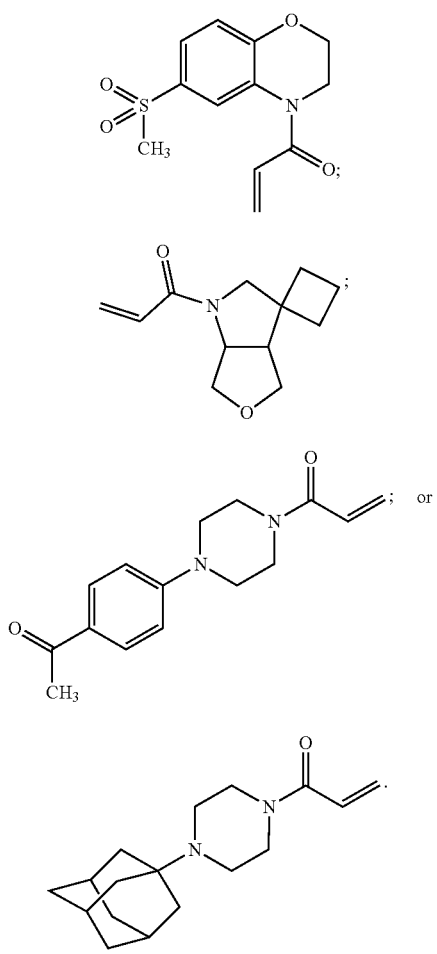
(XIVd); (XVc); (XVId); (XVIIc)
In embodiments, the targeted autophagy protein binder (e.g., autophagy adapter protein binder) has the formula:
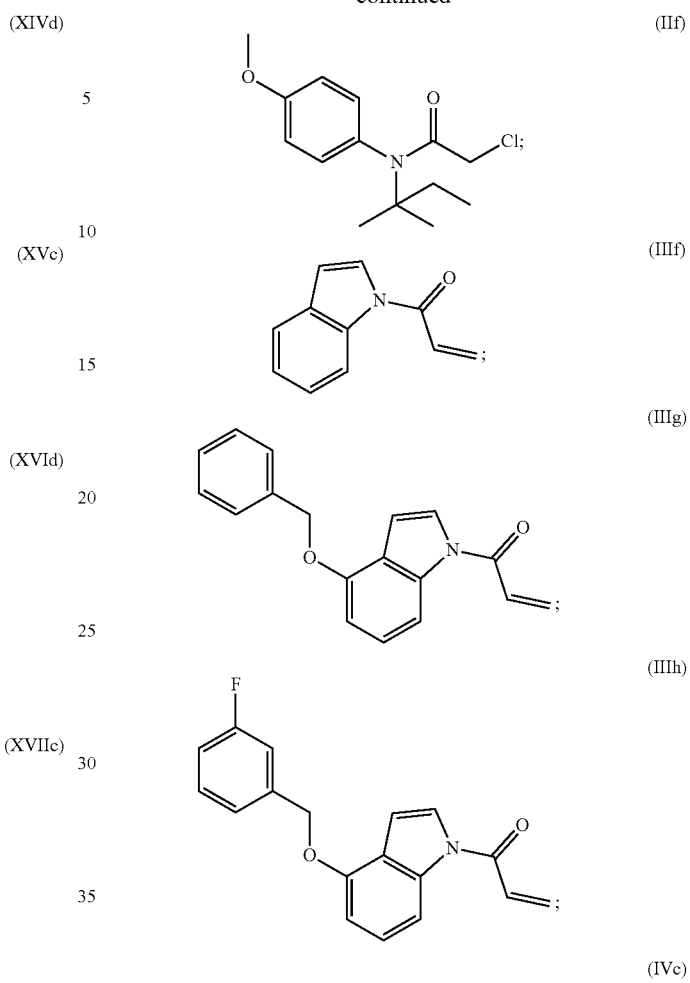
(Ie); (If); (IIe); (IIf); (IIIf); (IIIg); (IIIh); (IVc); (Vd); (VId) or (VIId)

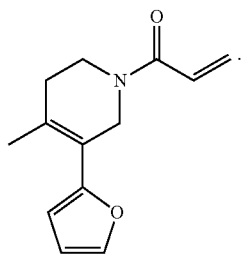

In embodiments, the targeted autophagy protein binder (e.g., autophagy adapter protein binder) has the formula:

(Ie)

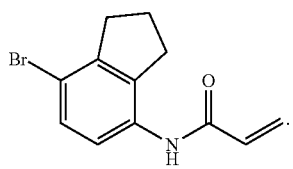

In embodiments, the targeted autophagy protein binder (e.g., autophagy adapter protein binder) has the formula:

(If)

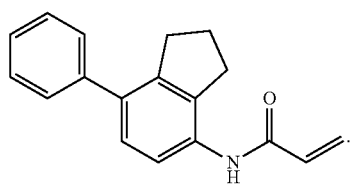

In embodiments, the targeted autophagy protein binder (e.g., autophagy adapter protein binder) has the formula:

(IIe)

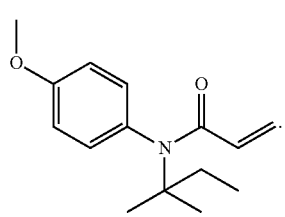

In embodiments, the targeted autophagy protein binder (e.g., autophagy adapter protein binder) has the formula:

(IIf)

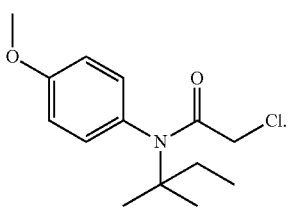

In embodiments, the targeted autophagy protein binder (e.g., autophagy adapter protein binder) has the formula:

(IIIf)

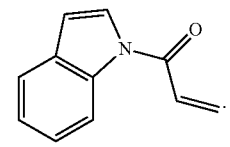

In embodiments, the targeted autophagy protein binder (e.g., autophagy adapter protein binder) has the formula:

(IIIg)

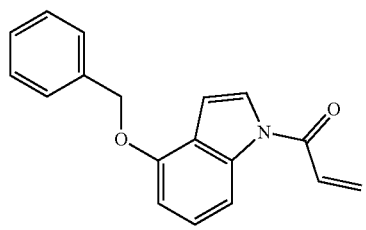

In embodiments, the targeted autophagy protein binder (e.g., autophagy adapter protein binder) has the formula:

(IIIh)

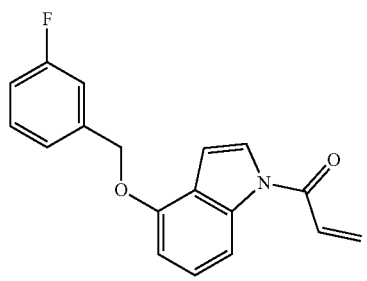

In embodiments, the targeted autophagy protein binder (e.g., autophagy adapter protein binder) has the formula:

(IVc)

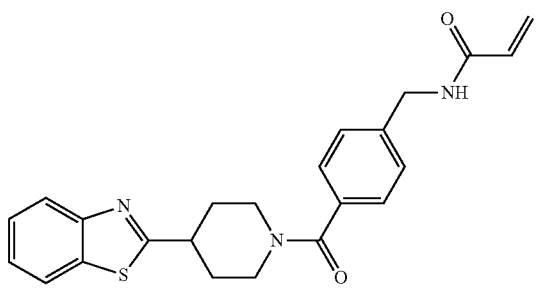

In embodiments, the targeted autophagy protein binder (e.g., autophagy adapter protein binder) has the formula:

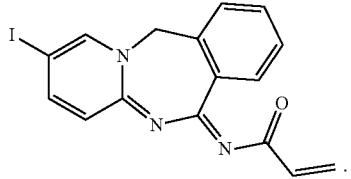

(Vd)

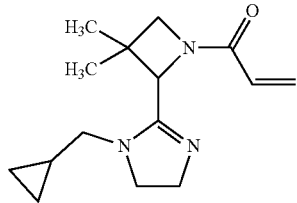

(IXd)

In embodiments, the targeted autophagy protein binder (e.g., autophagy adapter protein binder) has the formula:

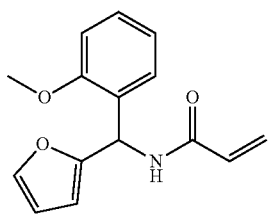

(VId)

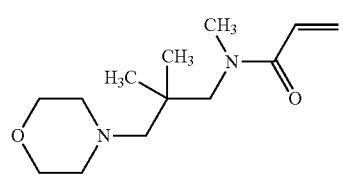

(Xd)

In embodiments, the targeted autophagy protein binder (e.g., autophagy adapter protein binder) has the formula:

In embodiments, the targeted autophagy protein binder (e.g., autophagy adapter protein binder) has the formula:

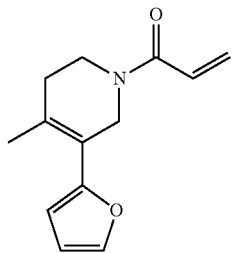

(VIId)

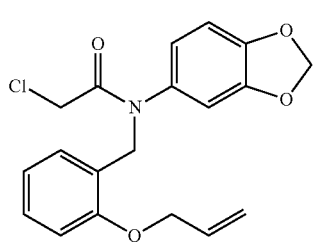

(XIf)

In embodiments, the targeted autophagy protein binder (e.g., autophagy adapter protein binder) has the formula:

In embodiments, the targeted autophagy protein binder (e.g., autophagy adapter protein binder) has the formula:

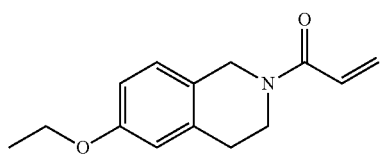

(VIIId)

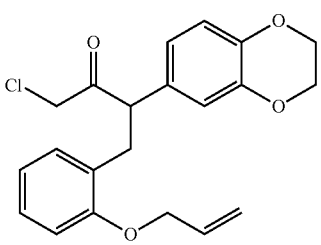

(XIg)

In embodiments, the targeted autophagy protein binder (e.g., autophagy adapter protein binder) has the formula:

In embodiments, the targeted autophagy protein binder (e.g., autophagy adapter protein binder) has the formula:

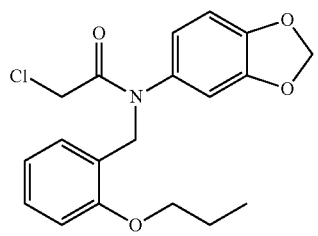
(XIh)

In embodiments, the targeted autophagy protein binder (e.g., autophagy adapter protein binder) has the formula:

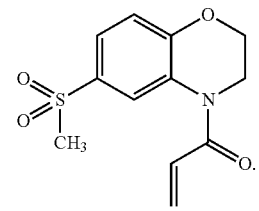
(XIVd)

In embodiments, the targeted autophagy protein binder (e.g., autophagy adapter protein binder) has the formula:

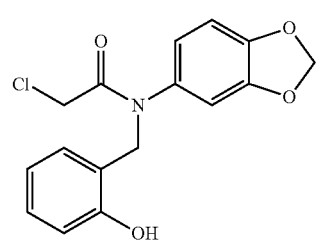
(XIi)

In embodiments, the targeted autophagy protein binder (e.g., autophagy adapter protein binder) has the formula:

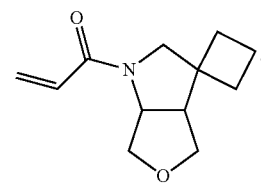
(XVc)

In embodiments, the targeted autophagy protein binder (e.g., autophagy adapter protein binder) has the formula:

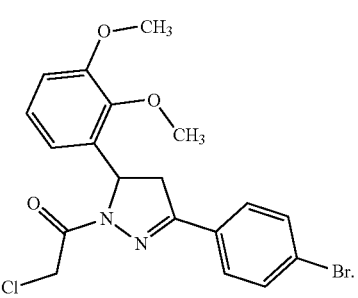
(XIId)

In embodiments, the targeted autophagy protein binder (e.g., autophagy adapter protein binder) has the formula:

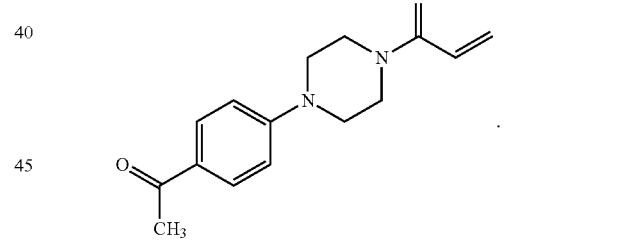
(XVId)

In embodiments, the targeted autophagy protein binder (e.g., autophagy adapter protein binder) has the formula:

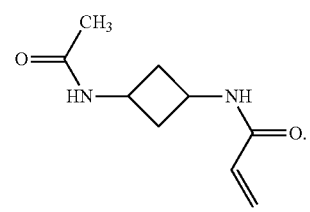
(XIIId)

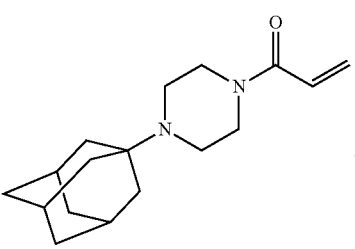
(XVIIc)

In embodiments, the monovalent targeted autophagy protein binder (e.g., monovalent autophagy adapter protein binder) has the formula:

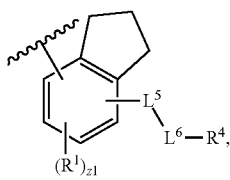
(mI)

wherein z1 is an integer from 0 to 8. $R^1$, z1, $L^5$, $L^6$, and $R^4$ are as described herein.

In embodiments, the monovalent targeted autophagy protein binder (e.g., monovalent autophagy adapter protein binder) has the formula:

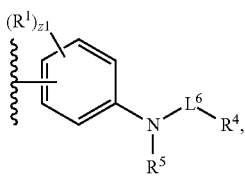
(mII)

wherein z1 is an integer from 0 to 4. $R^1$, z1, $R^5$, $L^6$, and $R^4$ are as described herein.

In embodiments, the monovalent targeted autophagy protein binder (e.g., monovalent autophagy adapter protein binder) has the formula:

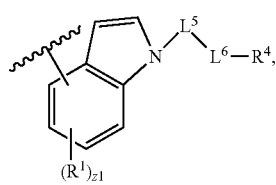
(mIII)

wherein z1 is an integer from 0 to 5. $R^1$, z1, $L^5$, $L^6$, and $R^4$ are as described herein.

In embodiments, the monovalent targeted autophagy protein binder (e.g., monovalent autophagy adapter protein binder) has the formula:

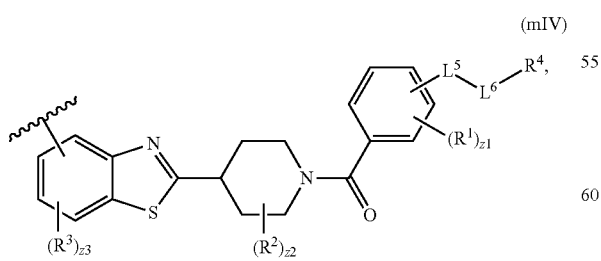
(mIV)

wherein z1 is an integer from 0 to 4, z2 is an integer from 0 to 8, and z3 is an integer from 0 to 3. $R^1$, z1, $R^2$, z2, $R^3$, z3, $L^5$, $L^6$, and $R^4$ are as described herein.

In embodiments, the monovalent targeted autophagy protein binder (e.g., monovalent autophagy adapter protein binder) has the formula:

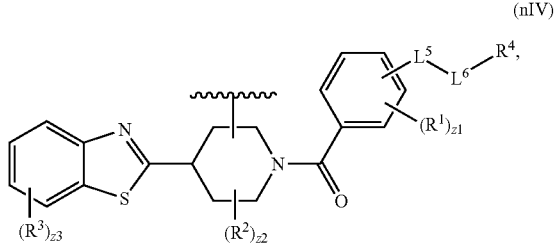
(mIV)

wherein z1 is an integer from 0 to 4, z2 is an integer from 0 to 8, and z3 is an integer from 0 to 3. $R^1$, z1, $R^2$, z2, $R^3$, z3, $L^5$, $L^6$, and $R^4$ are as described herein.

In embodiments, the monovalent targeted autophagy protein binder (e.g., monovalent autophagy adapter protein binder) has the formula:

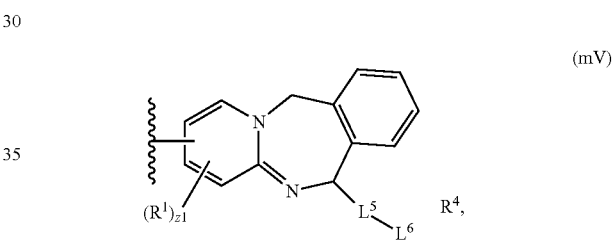
(mV)

wherein z1 is an integer from 0 to 10. $R^1$, z1, $L^5$, $L^6$, and $R^4$ are as described herein.

In embodiments, the monovalent targeted autophagy protein binder (e.g., monovalent autophagy adapter protein binder) has the formula:

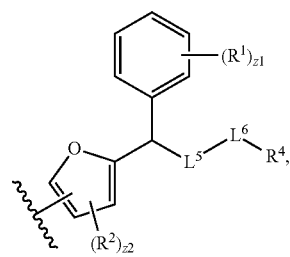
(mVI)

wherein z1 is an integer from 0 to 5 and z2 is an integer from 0 to 2. $R^1$, z1, $R^2$, z2, $L^5$, $L^6$, and $R^4$ are as described herein.

In embodiments, the monovalent targeted autophagy protein binder (e.g., monovalent autophagy adapter protein binder) has the formula:

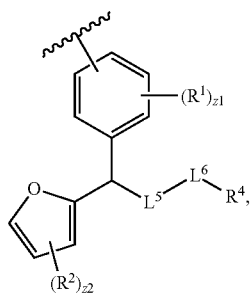

(nVI)

wherein z1 is an integer from 0 to 5 and z2 is an integer from 0 to 2. $R^1$, z1, $R^2$, z2, $L^5$, $L^6$, and $R^4$ are as described herein.

In embodiments, the monovalent targeted autophagy protein binder (e.g., monovalent autophagy adapter protein binder) has the formula:

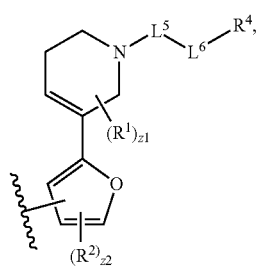

(mVII)

wherein z1 is an integer from 0 to 7 and z2 is an integer from 0 to 2. $R^1$, z1, $R^2$, z2, $L^5$, $L^6$, and $R^4$ are as described herein.

In embodiments, the monovalent targeted autophagy protein binder (e.g., monovalent autophagy adapter protein binder) has the formula:

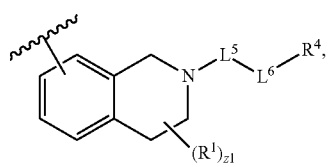

(mVIII)

wherein z1 is an integer from 0 to 10. $R^1$, z1, $L^5$, $L^6$, and $R^4$ are as described herein.

In embodiments, the monovalent targeted autophagy protein binder (e.g., monovalent autophagy adapter protein binder) has the formula:

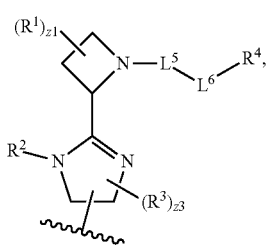

(mIX)

wherein z1 is an integer from 0 to 5 and z3 is an integer from 0 to 4. $R^1$, z1, $R^2$, $R^3$, z3, $L^5$, $L^6$, and $R^4$ are as described herein.

In embodiments, the monovalent targeted autophagy protein binder (e.g., monovalent autophagy adapter protein binder) has the formula:

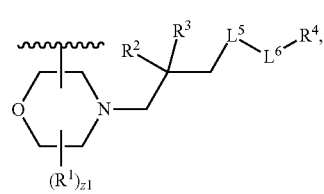

(mX)

wherein z1 is an integer from 0 to 8. $R^1$, z1, $R^2$, $R^3$, $L^5$, $L^6$, and $R^4$ are as described herein.

In embodiments, the monovalent targeted autophagy protein binder (e.g., monovalent autophagy adapter protein binder) has the formula:

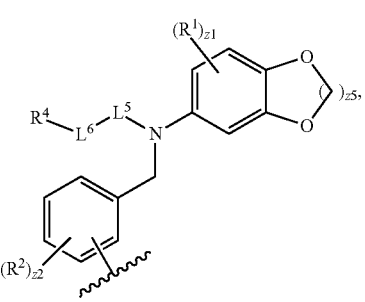

(mXI)

wherein z1 is an integer from 0 to 7, z2 is an integer from 0 to 5, and z4 is 1 or 2. $R^1$, z1, $R^2$, z2, z5, $L^5$, $L^6$, and $R^4$ are as described herein.

In embodiments, the monovalent targeted autophagy protein binder (e.g., monovalent autophagy adapter protein binder) has the formula:

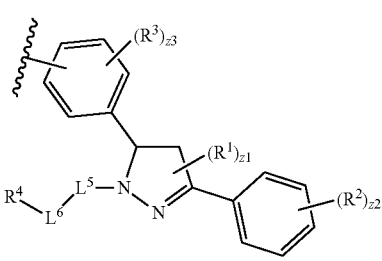

(mXII)

wherein z1 is an integer from 0 to 2, z2 is an integer from 0 to 5, and z3 is an integer from 0 to 5. $R^1$, z1, $R^2$, z2, $R^3$, z3, $L^5$, $L^6$, and $R^4$ are as described herein.

In embodiments, the monovalent targeted autophagy protein binder (e.g., monovalent autophagy adapter protein binder) has the formula:

(nXII)

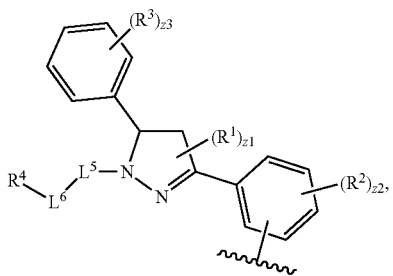

wherein z1 is an integer from 0 to 2, z2 is an integer from 0 to 5, and z3 is an integer from 0 to 5. $R^1$, z1, $R^2$, z2, $R^3$, z3, $L^5$, $L^6$, and $R^4$ are as described herein.

In embodiments, the monovalent targeted autophagy protein binder (e.g., monovalent autophagy adapter protein binder) has the formula:

(mXIII)

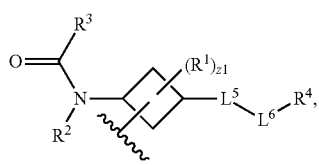

wherein z1 is an integer from 0 to 6. $R^1$, z1, $R^2$, $R^3$, $L^5$, $L^6$, and $R^4$ are as described herein.

In embodiments, the monovalent targeted autophagy protein binder (e.g., monovalent autophagy adapter protein binder) has the formula:

(mXIV)

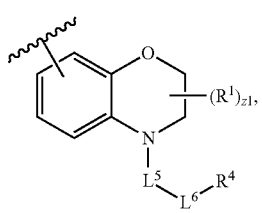

wherein z1 is an integer from 0 to 6. $R^1$, z1, $L^5$, $L^6$, and $R^4$ are as described herein.

In embodiments, the monovalent targeted autophagy protein binder (e.g., monovalent autophagy adapter protein binder) has the formula:

(mXV)

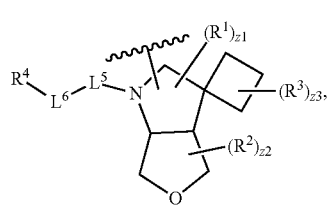

wherein z1 is an integer from 0 to 4, z2 is an integer from 0 to 6, and z3 is an integer from 0 to 6. $R^1$, z1, $R^2$, z2, $R^3$, z3, $L^5$, $L^6$, and $R^4$ are as described herein.

In embodiments, the monovalent targeted autophagy protein binder (e.g., monovalent autophagy adapter protein binder) has the formula:

(nXV)

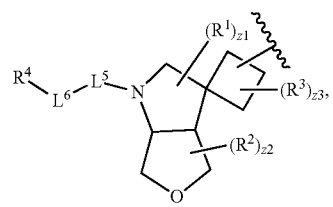

wherein z1 is an integer from 0 to 4, z2 is an integer from 0 to 6, and z3 is an integer from 0 to 6. $R^1$, z1, $R^2$, z2, $R^3$, z3, $L^5$, $L^6$, and $R^4$ are as described herein.

In embodiments, the monovalent targeted autophagy protein binder (e.g., monovalent autophagy adapter protein binder) has the formula:

(mXVI)

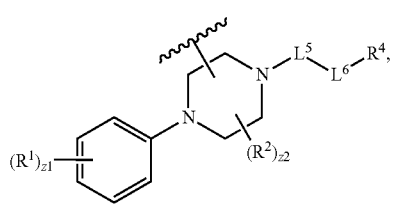

wherein z1 is an integer from 0 to 5 and z2 is an integer from 0 to 8. $R^1$, z1, $R^2$, z2, $L^5$, $L^6$, and $R^4$ are as described herein.

In embodiments, the monovalent targeted autophagy protein binder (e.g., monovalent autophagy adapter protein binder) has the formula:

(nXVI)

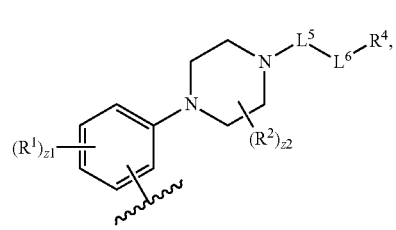

wherein z1 is an integer from 0 to 5 and z2 is an integer from 0 to 8. $R^1$, z1, $R^2$, z2, $L^5$, $L^6$, and $R^4$ are as described herein.

In embodiments, the monovalent targeted autophagy protein binder (e.g., monovalent autophagy adapter protein binder) has the formula:

(mXVII)

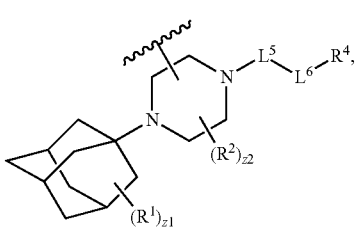

wherein z1 is an integer from 0 to 15 and z2 is an integer from 0 to 8. $R^1$, z1, $R^2$, z2, $L^5$, $L^6$, and $R^4$ are as described herein.

In embodiments, the monovalent targeted autophagy protein binder (e.g., monovalent autophagy adapter protein binder) has the formula:

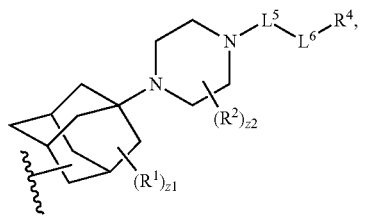

(nXVII)

wherein z1 is an integer from 0 to 15 and z2 is an integer from 0 to 8. $R^1$, z1, $R^2$, z2, $L^5$, $L^6$, and $R^4$ are as described herein.

In embodiments, the monovalent targeted autophagy protein binder (e.g., monovalent autophagy adapter protein binder) has the formula:

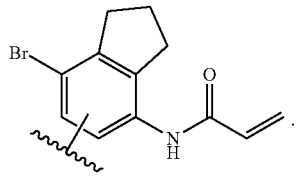

(mIe)

In embodiments, the monovalent targeted autophagy protein binder (e.g., monovalent autophagy adapter protein binder) has the formula:

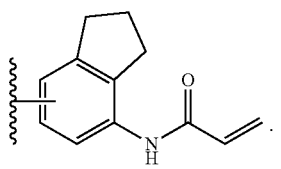

(mIg)

In embodiments, the monovalent targeted autophagy protein binder (e.g., monovalent autophagy adapter protein binder) has the formula:

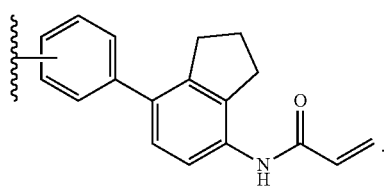

(mIf)

In embodiments, the monovalent targeted autophagy protein binder (e.g., monovalent autophagy adapter protein binder) has the formula:

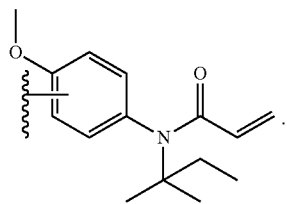

(mIIe)

In embodiments, the monovalent targeted autophagy protein binder (e.g., monovalent autophagy adapter protein binder) has the formula:

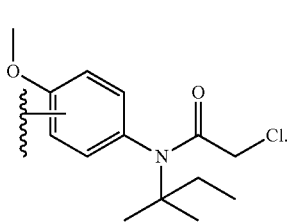

(mIIf)

In embodiments, the monovalent targeted autophagy protein binder (e.g., monovalent autophagy adapter protein binder) has the formula:

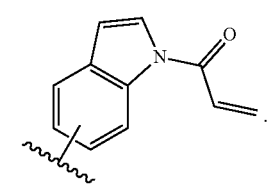

(mIIIf)

In embodiments, the monovalent targeted autophagy protein binder (e.g., monovalent autophagy adapter protein binder) has the formula:

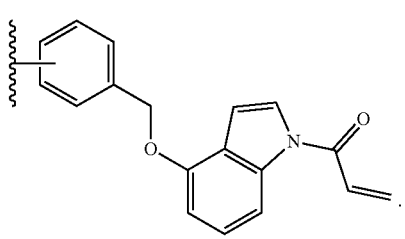

(mIIIg)

In embodiments, the monovalent targeted autophagy protein binder (e.g., monovalent autophagy adapter protein binder) has the formula:

(mIIIh)

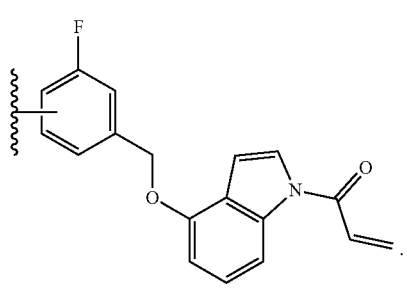

In embodiments, the monovalent targeted autophagy protein binder (e.g., monovalent autophagy adapter protein binder) has the formula:

(mIVc)

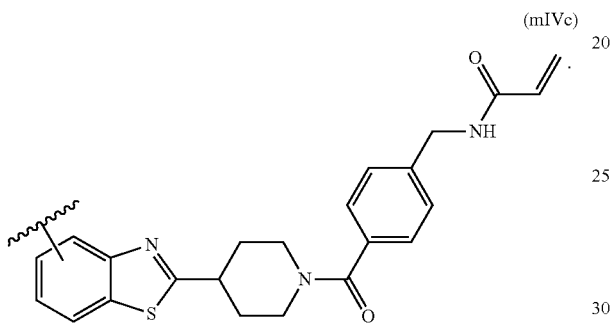

In embodiments, the monovalent targeted autophagy protein binder (e.g., monovalent autophagy adapter protein binder) has the formula:

(nIVc)

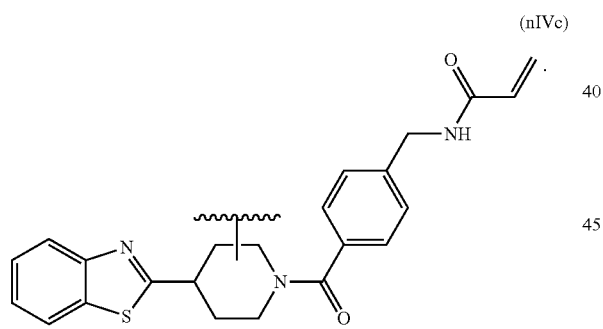

In embodiments, the monovalent targeted autophagy protein binder (e.g., monovalent autophagy adapter protein binder) has the formula:

(mVd)

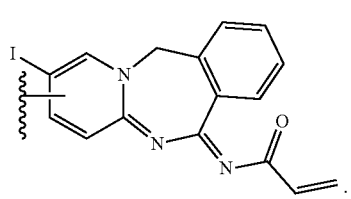

In embodiments, the monovalent targeted autophagy protein binder (e.g., monovalent autophagy adapter protein binder) has the formula:

(mVId)

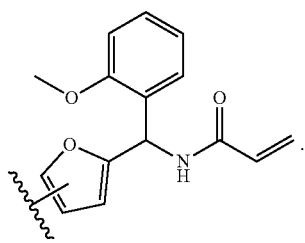

In embodiments, the monovalent targeted autophagy protein binder (e.g., monovalent autophagy adapter protein binder) has the formula:

(nVId)

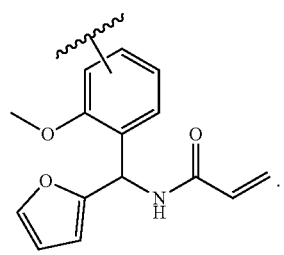

In embodiments, the monovalent targeted autophagy protein binder (e.g., monovalent autophagy adapter protein binder) has the formula:

(mVIId)

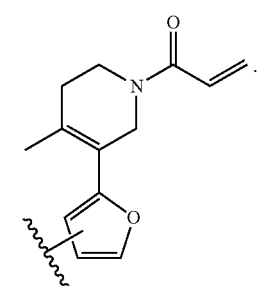

In embodiments, the monovalent targeted autophagy protein binder (e.g., monovalent autophagy adapter protein binder) has the formula:

(mVIIId)

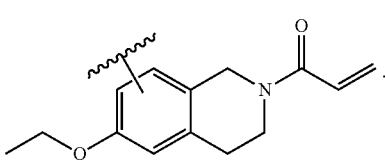

In embodiments, the monovalent targeted autophagy protein binder (e.g., monovalent autophagy adapter protein binder) has the formula:

(mIXd)

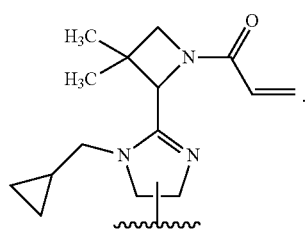

In embodiments, the monovalent targeted autophagy protein binder (e.g., monovalent autophagy adapter protein binder) has the formula:

(mXd)

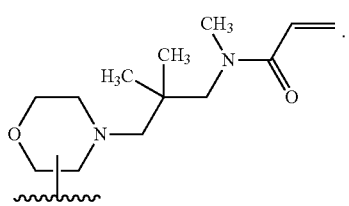

In embodiments, the monovalent targeted autophagy protein binder (e.g., monovalent autophagy adapter protein binder) has the formula:

(mXIf)

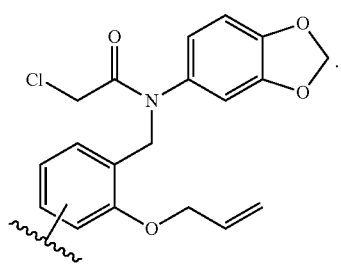

In embodiments, the monovalent targeted autophagy protein binder (e.g., monovalent autophagy adapter protein binder) has the formula:

(mXIg)

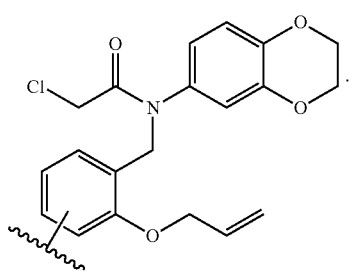

In embodiments, the monovalent targeted autophagy protein binder (e.g., monovalent autophagy adapter protein binder) has the formula:

(mXIId)

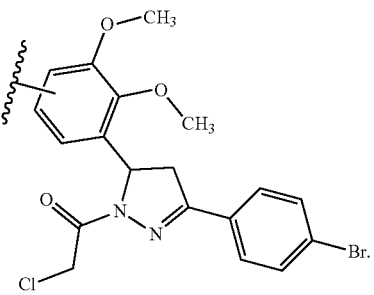

In embodiments, the monovalent targeted autophagy protein binder (e.g., monovalent autophagy adapter protein binder) has the formula:

(nXIId)

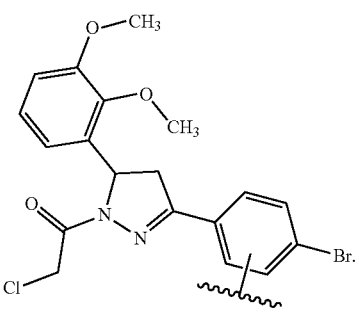

In embodiments, the monovalent targeted autophagy protein binder (e.g., monovalent autophagy adapter protein binder) has the formula:

(mXIIId)

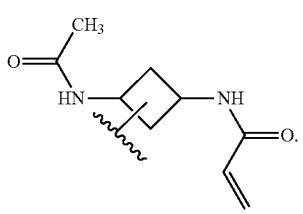

In embodiments, the monovalent targeted autophagy protein binder (e.g., monovalent autophagy adapter protein binder) has the formula:

(mXIVd)

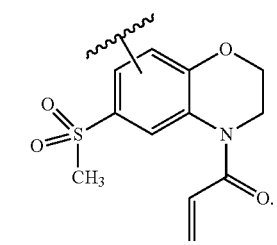

In embodiments, the monovalent targeted autophagy protein binder (e.g., monovalent autophagy adapter protein binder) has the formula:

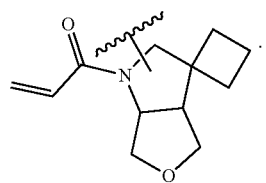
(mXVc)

In embodiments, the monovalent targeted autophagy protein binder (e.g., monovalent autophagy adapter protein binder) has the formula:

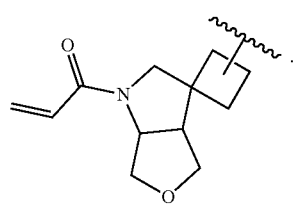
(nXVc)

In embodiments, the monovalent targeted autophagy protein binder (e.g., monovalent autophagy adapter protein binder) has the formula:

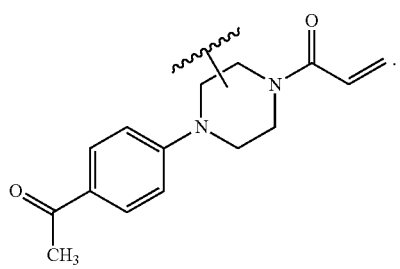
(mXVId)

In embodiments, the monovalent targeted autophagy protein binder (e.g., monovalent autophagy adapter protein binder) has the formula:

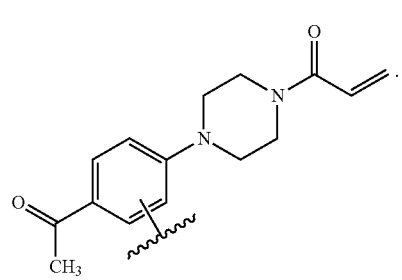
(nXVId)

In embodiments, the monovalent targeted autophagy protein binder (e.g., monovalent autophagy adapter protein binder) has the formula:

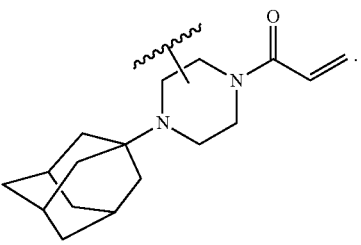
(mXVIIc)

In embodiments, the monovalent targeted autophagy protein binder (e.g., monovalent autophagy adapter protein binder) has the formula:

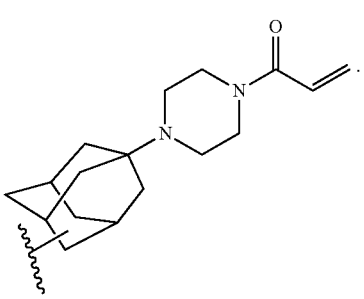
(nXVIIc)

In embodiments, the monovalent targeted autophagy protein binder (e.g., monovalent autophagy adapter protein binder) has the formula:

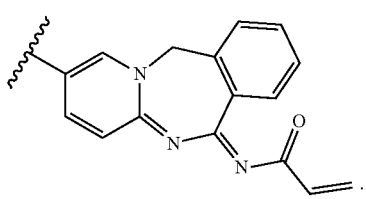
(mVe)

In embodiments, the monovalent targeted autophagy protein binder (e.g., monovalent autophagy adapter protein binder) has the formula:

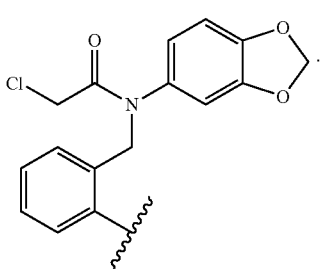
(mXIh)

In embodiments, the monovalent targeted autophagy protein binder (e.g., monovalent autophagy adapter protein binder) has the formula:

(mXIi)

In embodiments, R¹ is independently halogen, —CF₃, —CBr₃, —CCl₃, —CI₃, —CHF₂, —CHBr₂, —CHCl₂, —CHI₂, —CH₂F, —CH₂Br, —CH₂Cl, —CH₂I, —OCF₃, —OCBr₃, —OCCl₃, —OCl₃, —OCHF₂, —OCHBr₂, —OCHCl₂, —OCHI₂, —OCH₂F, —OCH₂Br, —OCH₂Cl, —CN, —OH, —NH₂, —COOH, —CONH₂, —NO₂, —SH, —SO₃H, —SO₄H, —SO₂NH₂, —NHNH₂, ONH₂, —NHC(O)NHNH₂, —N₃, substituted or unsubstituted alkyl (e.g., C₁-C₈ alkyl, C₁-C₆ alkyl, or C₁-C₄ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C₃-C₈ cycloalkyl, C₃-C₆ cycloalkyl, or C₅-C₆ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C₆-C₁₀ aryl, C₁₀ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R¹ is independently substituted or unsubstituted alkyl (e.g., C₁-C₈ alkyl, C₁-C₆ alkyl, or C₁-C₄ alkyl). In embodiments, R¹ is independently substituted alkyl (e.g., C₁-C₈ alkyl, C₁-C₆ alkyl, or C₁-C₄ alkyl). In embodiments, R¹ is independently an unsubstituted alkyl (e.g., C₁-C₈ alkyl, C₁-C₆ alkyl, or C₁-C₄ alkyl). In embodiments, R¹ is independently substituted or unsubstituted heteroalkyl (e.g., 2 to 8 membered heteroalkyl, 2 to 6 membered heteroalkyl, or 2 to 4 membered heteroalkyl). In embodiments, R¹ is independently substituted heteroalkyl (e.g., 2 to 8 membered heteroalkyl, 2 to 6 membered heteroalkyl, or 2 to 4 membered heteroalkyl). In embodiments, R¹ is independently an unsubstituted heteroalkyl (e.g., 2 to 8 membered heteroalkyl, 2 to 6 membered heteroalkyl, or 2 to 4 membered heteroalkyl). In embodiments, R¹ is independently substituted or unsubstituted cycloalkyl (e.g., C₃-C₈ cycloalkyl, C₃-C₆ cycloalkyl, or C₅-C₆ cycloalkyl). In embodiments, R¹ is independently substituted cycloalkyl (e.g., C₃-C₈ cycloalkyl, C₃-C₆ cycloalkyl, or C₅-C₆ cycloalkyl). In embodiments, R¹ is independently an unsubstituted cycloalkyl (e.g., C₃-C₈ cycloalkyl, C₃-C₆ cycloalkyl, or C₅-C₆ cycloalkyl). In embodiments, R¹ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, R¹ is independently substituted heterocycloalkyl (e.g., 3 to 8 membered heterocycloalkyl, 3 to 6 membered heterocycloalkyl, or 5 to 6 membered heterocycloalkyl). In embodiments, R¹ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R¹ is independently substituted or unsubstituted aryl (e.g., C₆-C₁₀ aryl, C₁₀ aryl, or phenyl). In embodiments, R¹ is independently substituted aryl (e.g., C₆-C₁₀ aryl, C₁₀ aryl, or phenyl). In embodiments, R¹ is independently an unsubstituted aryl (e.g., C₆-C₁₀ aryl, C₁₀ aryl, or phenyl). In embodiments, R¹ is independently substituted or unsubstituted heteroaryl (e.g., 5 to 10 membered heteroaryl, 5 to 9 membered heteroaryl, or 5 to 6 membered heteroaryl). In embodiments, R¹ is independently substituted heteroaryl (e.g., 5 to 10 membered heteroaryl, 5 to 9 membered heteroaryl, or 5 to 6 membered heteroaryl). In embodiments, R¹ is independently an unsubstituted heteroaryl (e.g., 5 to 10 membered heteroaryl, 5 to 9 membered heteroaryl, or 5 to 6 membered heteroaryl).

In embodiments, R¹ is independently halogen, —CF₃, —CBr₃, —CCl₃, —CI₃, —CHF₂, —CHBr₂, —CHCl₂, —CHI₂, —CH₂F, —CH₂Br, —CH₂Cl, —CH₂I, —OCF₃, —OCBr₃, —OCCl₃, —OCl₃, —OCHF₂, —OCHBr₂, —OCHCl₂, —OCHI₂, —OCH₂F, —OCH₂Br, —OCH₂Cl, —OCH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, R²¹-substituted or unsubstituted alkyl (e.g., C₁-C₈ alkyl, C₁-C₆ alkyl, or C₁-C₄ alkyl), R²¹-substituted or unsubstituted heteroalkyl (e.g., 2 to 8 membered heteroalkyl, 2 to 6 membered heteroalkyl, or 2 to 4 membered heteroalkyl), R²¹-substituted or unsubstituted cycloalkyl (e.g., C₃-C₈ cycloalkyl, C₃-C₆ cycloalkyl, or C₅-C₆ cycloalkyl), R²¹-substituted or unsubstituted heterocycloalkyl (e.g., 3 to 8 membered heterocycloalkyl, 3 to 6 membered heterocycloalkyl, or 5 to 6 membered heterocycloalkyl), R²¹-substituted or unsubstituted aryl (e.g., C₆-C₁₀ aryl, C₁₀ aryl, or phenyl), or R²¹-substituted or unsubstituted heteroaryl (e.g., 5 to 10 membered heteroaryl, 5 to 9 membered heteroaryl, or 5 to 6 membered heteroaryl). In embodiments, R¹ is independently halogen, —CF₃, —CBr₃, —CCl₃, —CI₃, —CHF₂, —CHBr₂, —CHCl₂, —CHI₂, —CH₂F, —CH₂Br, —CH₂Cl, —CH₂I, —OCF₃, —OCBr₃, —O CCl₃, —OCl₃, —OCHF₂, —OCHBr₂, —OCHCl₂, —OCHI₂, —OCH₂F, —OCH₂Br, —OCH₂Cl, —OCH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, unsubstituted alkyl (e.g., C₁-C₈ alkyl, C₁-C₆ alkyl, or C₁-C₄ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C₃-C₈ cycloalkyl, C₃-C₆ cycloalkyl, or C₅-C₆ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C₆-C₁₀ aryl, C₁₀ aryl, or phenyl), or unsubstituted heteroaryl (e.g., 5 to 10 membered heteroaryl, 5 to 9 membered heteroaryl, or 5 to 6 membered heteroaryl).

In embodiments, R¹ is independently R²¹-substituted or unsubstituted alkyl (e.g., C₁-C₈ alkyl, C₁-C₆ alkyl, or C₁-C₄ alkyl). In embodiments, R¹ is independently 10-substituted alkyl (e.g., C₁-C₈ alkyl, C₁-C₆ alkyl, or C₁-C₄ alkyl). In embodiments, R¹ is independently an unsubstituted alkyl (e.g., C₁-C₈ alkyl, C₁-C₆ alkyl, or C₁-C₄ alkyl). In embodiments, R¹ is independently R²¹-substituted or unsubstituted heteroalkyl (e.g., 2 to 8 membered heteroalkyl, 2 to 6 membered heteroalkyl, or 2 to 4 membered heteroalkyl). In embodiments, R¹ is independently R²¹-substituted heteroalkyl (e.g., 2 to 8 membered heteroalkyl, 2 to 6 membered heteroalkyl, or 2 to 4 membered heteroalkyl). In embodiments, R¹ is independently an unsubstituted heteroalkyl (e.g., 2 to 8 membered heteroalkyl, 2 to 6 membered heteroalkyl, or 2 to 4 membered heteroalkyl). In embodiments, R¹ is independently R²¹-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is independently $R^{21}$-substituted cycloalkyl (e.g., $C_3$-$C_8$ cycloalkyl, $C_3$-$C_6$ cycloalkyl, or $C_5$-$C_6$ cycloalkyl). In embodiments, $R^1$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is independently $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is independently $R^{21}$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is independently $R^{21}$-substituted or unsubstituted aryl (e.g., $C_6$-$C_{10}$ aryl, $C_{10}$ aryl, or phenyl). In embodiments, $R^1$ is independently $R^{21}$-substituted aryl (e.g., $C_6$-$C_{10}$ aryl, $C_{10}$ aryl, or phenyl). In embodiments, $R^1$ is independently an unsubstituted aryl (e.g., $C_6$-$C_{10}$ aryl, $C_{10}$ aryl, or phenyl). In embodiments, $R^1$ is independently $R^{21}$-substituted or unsubstituted heteroaryl (e.g., 5 to 10 membered heteroaryl, 5 to 9 membered heteroaryl, or 5 to 6 membered heteroaryl). In embodiments, $R^1$ is independently $R^{21}$-substituted heteroaryl (e.g., 5 to 10 membered heteroaryl, 5 to 9 membered heteroaryl, or 5 to 6 membered heteroaryl). In embodiments, $R^1$ is independently an unsubstituted heteroaryl (e.g., 5 to 10 membered heteroaryl, 5 to 9 membered heteroaryl, or 5 to 6 membered heteroaryl).

In embodiments, $R^1$ is independently —$CX^1_3$. In embodiments, $R^1$ is independently —$CHX^1_2$. In embodiments, $R^1$ is independently —$CH_2X^1$. In embodiments, $R^1$ is independently —$OCX^1_3$. In embodiments, $R^1$ is independently —$OCH_2X^1$. In embodiments, $R^1$ is independently —$OCHX^1_2$. In embodiments, $R^1$ is independently —CN. In embodiments, $R^1$ is independently —$SR^{1D}$. In embodiments, $R^1$ is independently —$SOR^{1D}$. In embodiments, $R^1$ is independently —$SO_2R^{1D}$. In embodiments, $R^1$ is independently —$SO_3R^{1D}$. In embodiments, $R^1$ is independently —$SO_4R^{1D}$. In embodiments, $R^1$ is independently —$SONR^{1A}R^{1B}$. In embodiments, $R^1$ is independently —$SO_2NR^{1A}R^{1B}$. In embodiments, $R^1$ is independently —$NHC(O)NR^{1A}R^{1B}$. In embodiments, $R^1$ is independently —N(O). In embodiments, $R^1$ is independently —$N(O)_2$. In embodiments, $R^1$ is independently —$NR^{1A}R^{1B}$. In embodiments, $R^1$ is independently —$C(O)R^{1C}$. In embodiments, $R^1$ is independently —C(O)—$OR^{1C}$. In embodiments, $R^1$ is independently —$C(O)NR^{1A}R^{1B}$. In embodiments, $R^1$ is independently —$OR^{1D}$. In embodiments, $R^1$ is independently —$NR^{1A}SO_2R^{1D}$. In embodiments, $R^1$ is independently —$NR^{1A}C(O)R^{1C}$. In embodiments, $R^1$ is independently —$NR^{1A}C(O)OR^{1C}$. In embodiments, $R^1$ is independently —$NR^{1A}OR^{1C}$.

In embodiments, $R^1$ is independently oxo. In embodiments, $R^1$ is independently halogen. In embodiments, $R^1$ is independently —$CCl_3$. In embodiments, $R^1$ is independently —$CBr_3$. In embodiments, $R^1$ is independently —$CF_3$. In embodiments, $R^1$ is independently —$CI_3$. In embodiments, $R^1$ is independently —$CHCl_2$. In embodiments, $R^1$ is independently —$CHBr_2$. In embodiments, $R^1$ is independently —$CHF_2$. In embodiments, $R^1$ is independently —$CHI_2$. In embodiments, $R^1$ is independently —$CH_2Cl$. In embodiments, $R^1$ is independently —$CH_2Br$. In embodiments, $R^1$ is independently —$CH_2F$. In embodiments, $R^1$ is independently —$CH_2I$. In embodiments, $R^1$ is independently —CN. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$NO_2$. In embodiments, $R^1$ is independently —SH. In embodiments, $R^1$ is independently —$SO_3H$. In embodiments, $R^1$ is independently —$SO_4H$. In embodiments, $R^1$ is independently —$SO_2NH_2$. In embodiments, $R^1$ is independently —$NHNH_2$. In embodiments, $R^1$ is independently —$ONH_2$. In embodiments, $R^1$ is independently —NHC(O)$NHNH_2$. In embodiments, $R^1$ is independently —NHC(O)$NH_2$. In embodiments, $R^1$ is independently —$NHSO_2H$. In embodiments, $R^1$ is independently —NHC(O)H. In embodiments, $R^1$ is independently —NHC(O)OH. In embodiments, $R^1$ is independently —NHOH. In embodiments, $R^1$ is independently —$OCCl_3$. In embodiments, $R^1$ is independently —$OCF_3$. In embodiments, $R^1$ is independently —$OCBr_3$. In embodiments, $R^1$ is independently —$OCl_3$. In embodiments, $R^1$ is independently —$OCHCl_2$. In embodiments, $R^1$ is independently —$OCHBr_2$. In embodiments, $R^1$ is independently —$OCHI_2$. In embodiments, $R^1$ is independently —$OCHF_2$. In embodiments, $R^1$ is independently —$OCH_2Cl$. In embodiments, $R^1$ is independently —$OCH_2Br$. In embodiments, $R^1$ is independently —$OCH_2I$. In embodiments, $R^1$ is independently —$OCH_2F$. In embodiments, $R^1$ is independently —$N_3$. In embodiments, $R^1$ is independently —$OCH_3$. In embodiments, $R^1$ is independently —$CH_3$. In embodiments, $R^1$ is independently —$CH_2CH_3$. In embodiments, $R^1$ is independently unsubstituted propyl. In embodiments, $R^1$ is independently unsubstituted isopropyl. In embodiments, $R^1$ is independently unsubstituted butyl. In embodiments, $R^1$ is independently unsubstituted tert-butyl. In embodiments, $R^1$ is independently —F. In embodiments, $R^1$ is independently —Cl. In embodiments, $R^1$ is independently —Br. In embodiments, $R^1$ is independently —I.

$R^{21}$ is independently oxo, halogen, —$CCl_3$, —$CBr_3$, —$CF_3$, —$Cl_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC(O)$NHNH_2$, NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). In embodiments, $R^{21}$ is independently oxo, halogen, —$CF_3$, —$CBr_3$, —$CCl_3$, —$Cl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{21}$ is independently oxo. In embodiments, $R^{21}$ is independently halogen. In embodiments, $R^{21}$ is independently —$CCl_3$. In embodiments, $R^{21}$ is independently —$CBr_3$. In embodiments, $R^{21}$ is independently —$CF_3$. In embodiments, $R^{21}$ is independently —$CI_3$. In embodiments, $R^{21}$ is independently —$CHCl_2$. In embodiments, $R^{21}$ is independently —$CHBr_2$. In embodiments, $R^{21}$ is independently —$CHF_2$. In embodiments, $R^{21}$ is independently —$CHI_2$. In embodiments, $R^{21}$ is independently —$CH_2Cl$. In embodiments, $R^{21}$ is independently —$CH_2Br$. In embodiments, $R^{21}$ is independently —$CH_2F$. In embodiments, $R^{21}$ is independently —$CH_2I$. In embodiments, $R^{21}$ is independently —CN. In embodiments, $R^{21}$ is independently —OH. In embodiments, $R^{21}$ is independently —$NH_2$. In embodiments, $R^{21}$ is independently —COOH. In embodiments, $R^{21}$ is independently —$CONH_2$. In embodiments, $R^{21}$ is independently —$NO_2$. In embodiments, $R^{21}$ is independently —SH. In embodiments, $R^{21}$ is independently —$SO_3H$. In embodiments, $R^{21}$ is independently —$SO_4H$. In embodiments, $R^{21}$ is independently —$SO_2NH_2$. In embodiments, $R^{21}$ is independently —$NHNH_2$. In embodiments, $R^{21}$ is independently —$ONH_2$. In embodiments, $R^{21}$ is independently —$NHC(O)NHNH_2$. In embodiments, $R^{21}$ is independently —$NHC(O)NH_2$. In embodiments, $R^{21}$ is independently —$NHSO_2H$. In embodiments, $R^{21}$ is independently —NHC(O)H. In embodiments, $R^{21}$ is independently —NHC(O)OH. In embodiments, $R^{21}$ is independently —NHOH. In embodiments, $R^{21}$ is independently —$OCCl_3$. In embodiments, $R^{21}$ is independently —$OCF_3$. In embodiments, $R^{21}$ is independently —$OCBr_3$. In embodiments, $R^{21}$ is independently —$OCI_3$. In embodiments, $R^{21}$ is independently —$OCHCl_2$. In embodiments, $R^{21}$ is independently —$OCHBr_2$. In embodiments, $R^{21}$ is independently —$OCHI_2$. In embodiments, $R^{21}$ is independently —$OCHF_2$. In embodiments, $R^{21}$ is independently —$OCH_2Cl$. In embodiments, $R^{21}$ is independently —$OCH_2Br$. In embodiments, $R^{21}$ is independently —$OCH_2I$. In embodiments, $R^{21}$ is independently —$OCH_2F$. In embodiments, $R^{21}$ is independently —$N_3$. In embodiments, $R^{21}$ is independently —$OCH_3$. In embodiments, $R^{21}$ is independently —$CH_3$. In embodiments, $R^{21}$ is independently —$CH_2CH_3$. In embodiments, $R^{21}$ is independently unsubstituted propyl. In embodiments, $R^{21}$ is independently unsubstituted isopropyl. In embodiments, $R^{21}$ is independently unsubstituted butyl. In embodiments, $R^{21}$ is independently unsubstituted tert-butyl. In embodiments, $R^{21}$ is independently —F. In embodiments, $R^{21}$ is independently —Cl. In embodiments, $R^{21}$ is independently —Br. In embodiments, $R^{21}$ is independently —I.

In embodiments, $R^{21}$ is independently $R^{22}$-substituted or unsubstituted alkyl (e.g., $C_1$-$C_8$ alkyl, $C_1$-$C_6$ alkyl, or $C_1$-$C_4$ alkyl). In embodiments, $R^{21}$ is independently $R^{22}$-substituted alkyl (e.g., $C_1$-$C_8$ alkyl, $C_1$-$C_6$ alkyl, or $C_1$-$C_4$ alkyl). In embodiments, $R^{21}$ is independently an unsubstituted alkyl (e.g., $C_1$-$C_8$ alkyl, $C_1$-$C_6$ alkyl, or $C_1$-$C_4$ alkyl). In embodiments, $R^{21}$ is independently $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^{21}$ is independently $R^{22}$-substituted heteroalkyl (e.g., 2 to 8 membered heteroalkyl, 2 to 6 membered heteroalkyl, or 2 to 4 membered heteroalkyl). In embodiments, $R^{21}$ is independently an unsubstituted heteroalkyl (e.g., 2 to 8 membered heteroalkyl, 2 to 6 membered heteroalkyl, or 2 to 4 membered heteroalkyl). In embodiments, $R^{21}$ is independently $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is independently $R^{22}$-substituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{20}$ is independently $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21}$ is independently $R^{22}$-substituted heterocycloalkyl (e.g., 3 to 8 membered heterocycloalkyl, 3 to 6 membered heterocycloalkyl, or 5 to 6 membered heterocycloalkyl). In embodiments, $R^{21}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{21}$ is independently $R^{22}$-substituted or unsubstituted aryl (e.g., $C_6$-$C_{10}$ aryl, $C_{10}$ aryl, or phenyl). In embodiments, $R^{21}$ is independently $R^{22}$-substituted aryl (e.g., $C_6$-$C_{10}$ aryl, $C_{10}$ aryl, or phenyl). In embodiments, $R^{21}$ is independently an unsubstituted aryl (e.g., $C_6$-$C_{10}$ aryl, $C_{10}$ aryl, or phenyl). In embodiments, $R^{21}$ is independently $R^{22}$-substituted or unsubstituted heteroaryl (e.g., 5 to 10 membered heteroaryl, 5 to 9 membered heteroaryl, or 5 to 6 membered heteroaryl). In embodiments, $R^{21}$ is independently $R^{22}$-substituted heteroaryl (e.g., 5 to 10 membered heteroaryl, 5 to 9 membered heteroaryl, or 5 to 6 membered heteroaryl). In embodiments, $R^{21}$ is independently an unsubstituted heteroaryl (e.g., 5 to 10 membered heteroaryl, 5 to 9 membered heteroaryl, or 5 to 6 membered heteroaryl).

$R^{22}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{23}$-substituted or unsubstituted alkyl (e.g., $C_1$-$C_8$ alkyl, $C_1$-$C_6$ alkyl, or $C_1$-$C_4$ alkyl), $R^{23}$-substituted or unsubstituted heteroalkyl (e.g., 2 to 8 membered heteroalkyl, 2 to 6 membered heteroalkyl, or 2 to 4 membered heteroalkyl), $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23}$-substituted or unsubstituted aryl (e.g., $C_6$-$C_{10}$ aryl, $C_{10}$ aryl, or phenyl), or $R^{23}$-substituted or unsubstituted heteroaryl (e.g., 5 to 10 membered heteroaryl, 5 to 9 membered heteroaryl, or 5 to 6 membered heteroaryl). In embodiments, $R^{22}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{22}$ is independently $R^{23}$-substituted or unsubstituted alkyl (e.g., $C_1$-$C_8$ alkyl, $C_1$-$C_6$ alkyl, or $C_1$-$C_4$ alkyl). In embodiments, $R^{22}$ is independently $R^{23}$-substituted alkyl (e.g., $C_1$-$C_8$ alkyl, $C_1$-$C_6$ alkyl, or $C_1$-$C_4$ alkyl). In embodiments, $R^{22}$ is independently an unsubstituted alkyl (e.g., $C_1$-$C_8$ alkyl, $C_1$-$C_6$ alkyl, or $C_1$-$C_4$ alkyl). In embodiments, $R^{22}$ is independently $R^{23}$-substituted or unsubstituted heteroalkyl (e.g., 2 to 8 membered heteroalkyl, 2 to 6 membered heteroalkyl, or 2 to 4 membered heteroalkyl). In embodiments, $R^{22}$ is independently $R^{23}$-substituted heteroalkyl (e.g., 2 to 8 membered heteroalkyl, 2 to 6 membered heteroalkyl, or 2 to 4 membered heteroalkyl). In embodiments, $R^{22}$ is independently an unsubstituted heteroalkyl (e.g., 2 to 8 membered heteroalkyl, 2 to 6 membered heteroalkyl, or 2 to 4 membered heteroalkyl). In embodiments, $R^{22}$ is independently $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{22}$ is independently $R^{23}$-substituted cycloalkyl (e.g., $C_3$-$C_8$ cycloalkyl, $C_3$-$C_6$ cycloalkyl, or $C_5$-$C_6$ cycloalkyl). In embodiments, $R^{22}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{22}$ is independently $R^{23}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{22}$ is independently $R^{23}$-substituted heterocycloalkyl (e.g., 3 to 8 membered heterocycloalkyl, 3 to 6 membered heterocycloalkyl, or 5 to 6 membered heterocycloalkyl). In embodiments, $R^{22}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{22}$ is independently $R^{23}$-substituted or unsubstituted aryl (e.g., $C_6$-$C_{10}$ aryl, $C_{10}$ aryl, or phenyl). In embodiments, $R^{22}$ is independently $R^{23}$-substituted aryl (e.g., $C_6$-$C_{10}$ aryl, $C_{10}$ aryl, or phenyl). In embodiments, $R^{22}$ is independently an unsubstituted aryl (e.g., $C_6$-$C_{10}$ aryl, $C_{10}$ aryl, or phenyl). In embodiments, $R^{22}$ is independently $R^{23}$-substituted or unsubstituted heteroaryl (e.g., 5 to 10 membered heteroaryl, 5 to 9 membered heteroaryl, or 5 to 6 membered heteroaryl). In embodiments, $R^{22}$ is independently $R^{23}$-substituted heteroaryl (e.g., 5 to 10 membered heteroaryl, 5 to 9 membered heteroaryl, or 5 to 6 membered heteroaryl). In embodiments, $R^{22}$ is independently an unsubstituted heteroaryl (e.g., 5 to 10 membered heteroaryl, 5 to 9 membered heteroaryl, or 5 to 6 membered heteroaryl).

In embodiments, $R^{22}$ is independently oxo. In embodiments, $R^{22}$ is independently halogen. In embodiments, $R^{22}$ is independently —$CCl_3$. In embodiments, $R^{22}$ is independently —$CBr_3$. In embodiments, $R^{22}$ is independently —$CF_3$. In embodiments, $R^{22}$ is independently —$CI_3$. In embodiments, $R^{22}$ is independently $CHCl_2$. In embodiments, $R^{22}$ is independently —$CHBr_2$. In embodiments, $R^{22}$ is independently —$CHF_2$. In embodiments, $R^{22}$ is independently —$CHI_2$. In embodiments, $R^{22}$ is independently —$CH_2Cl$. In embodiments, $R^{22}$ is independently —$CH_2Br$. In embodiments, $R^{22}$ is independently —$CH_2F$. In embodiments, $R^{22}$ is independently —$CH_2I$. In embodiments, $R^{22}$ is independently —CN. In embodiments, $R^{22}$ is independently —OH. In embodiments, $R^{22}$ is independently —$NH_2$. In embodiments, $R^{22}$ is independently —COOH. In embodiments, $R^{22}$ is independently —$CONH_2$. In embodiments, $R^{22}$ is independently —$NO_2$. In embodiments, $R^{22}$ is independently —SH. In embodiments, $R^{22}$ is independently —$SO_3H$. In embodiments, $R^{22}$ is independently —$SO_4H$. In embodiments, $R^{22}$ is independently —$SO_2NH_2$. In embodiments, $R^{22}$ is independently —$NHNH_2$. In embodiments, $R^{22}$ is independently —$ONH_2$. In embodiments, $R^{22}$ is independently —$NHC(O)NHNH_2$. In embodiments, $R^{22}$ is independently —$NHC(O)NH_2$. In embodiments, $R^{22}$ is independently —$NHSO_2H$. In embodiments, $R^{22}$ is independently —NHC(O)H. In embodiments, $R^{22}$ is independently —NHC(O)OH. In embodiments, $R^{22}$ is independently —NHOH. In embodiments, $R^{22}$ is independently —$OCCl_3$. In embodiments, $R^{22}$ is independently —$OCF_3$. In embodiments, $R^{22}$ is independently —$OCBr_3$. In embodiments, $R^{22}$ is independently —$OCl_3$. In embodiments, $R^{22}$ is independently —$OCHCl_2$. In embodiments, $R^{22}$ is independently —$OCHBr_2$. In embodiments, $R^{22}$ is independently —$OCHI_2$. In embodiments, $R^{22}$ is independently —$OCHF_2$. In embodiments, $R^{22}$ is independently —$OCH_2Cl$. In embodiments, $R^{22}$ is independently —$OCH_2Br$. In embodiments, $R^{22}$ is independently —$OCH_2I$. In embodiments, $R^{22}$ is independently —$OCH_2F$. In embodiments, $R^{22}$ is independently —$N_3$. In embodiments, $R^{22}$ is independently —$OCH_3$. In embodiments, $R^{22}$ is independently —$CH_3$. In embodiments, $R^{22}$ is independently —$CH_2CH_3$. In embodiments, $R^{22}$ is independently unsubstituted propyl. In embodiments, $R^{22}$ is independently unsubstituted isopropyl. In embodiments, $R^{22}$ is independently unsubstituted butyl. In embodiments, $R^{22}$ is independently unsubstituted tert-butyl. In embodiments, $R^{22}$ is independently —F. In embodiments, $R^{22}$ is independently —Cl. In embodiments, $R^{22}$ is independently —Br. In embodiments, $R^{22}$ is independently —I.

$R^{23}$ is independently oxo, halogen, —$CF_3$, —$CBr_3$, —$CCl_3$, —$CI_3$, —$CHF_2$, —$CHBr_2$, —$CHCl_2$, —$CH_2F$, —$CH_2Br$, —$CH_2Cl$, —$OCF_3$, —$OCBr_3$, —$OCCl_3$, —$OCl_3$, —$OCHF_2$, —$OCHBr_2$, —$OCHCl_2$, —$OCH_2F$, —$OCH_2Br$, —$OCH_2Cl$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{23}$ is independently an unsubstituted alkyl (e.g., $C_1$-$C_8$ alkyl, $C_1$-$C_6$ alkyl, or $C_1$-$C_4$ alkyl). In embodiments, $R^{23}$ is independently an unsubstituted heteroalkyl (e.g., 2 to 8 membered heteroalkyl, 2 to 6 membered heteroalkyl, or 2 to 4 membered heteroalkyl). In embodiments, $R^{23}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{23}$ is independently an unsubstituted aryl (e.g., $C_6$-$C_{10}$ aryl, $C_{10}$ aryl, or phenyl). In embodiments, $R^{23}$ is independently an unsubstituted heteroaryl (e.g., 5 to 10 membered heteroaryl, 5 to 9 membered heteroaryl, or 5 to 6 membered heteroaryl).

In embodiments, $R^{23}$ is independently oxo. In embodiments, $R^{23}$ is independently halogen. In embodiments, $R^{23}$ is independently —$CCl_3$. In embodiments, $R^{23}$ is independently —$CBr_3$. In embodiments, $R^{23}$ is independently —$CF_3$. In embodiments, $R^{23}$ is independently —$CI_3$. In embodiments, $R^{23}$ is independently —$CHCl_2$. In embodiments, $R^{23}$ is independently —$CHBr_2$. In embodiments, $R^{23}$ is independently —$CHF_2$. In embodiments, $R^{23}$ is independently —$CHI_2$. In embodiments, $R^{23}$ is independently —$CH_2Cl$. In embodiments, $R^{23}$ is independently —$CH_2Br$. In embodiments, $R^{23}$ is independently —$CH_2F$. In embodiments, $R^{23}$ is independently —$CH_2I$. In embodiments, $R^{23}$ is independently —CN. In embodiments, $R^{23}$ is independently —OH. In embodiments, $R^{23}$ is independently —$NH_2$. In embodiments, $R^{23}$ is independently —COOH. In embodiments, $R^{23}$ is independently —$CONH_2$. In embodiments, $R^{23}$ is independently —$NO_2$. In embodiments, $R^{23}$ is independently —SH. In embodiments, $R^{23}$ is independently —$SO_3H$. In embodiments, $R^{23}$ is independently —$SO_4H$. In embodiments, $R^{23}$ is independently —$SO_2NH_2$. In embodiments, $R^{23}$ is independently —$NHNH_2$. In embodiments, $R^{23}$ is independently —$ONH_2$. In embodiments, $R^{23}$ is independently —NHC(O)$NHNH_2$. In embodiments, $R^{23}$ is independently —NHC(O)$NH_2$. In embodiments, $R^{23}$ is independently —$NHSO_2H$. In embodiments, $R^{23}$ is independently —NHC(O)H. In embodiments, $R^{23}$ is independently —NHC(O)OH. In embodiments, $R^{23}$ is independently —NHOH. In embodiments, $R^{23}$ is independently —$OCCl_3$. In embodiments, $R^{23}$ is independently —$OCF_3$. In embodiments, $R^{23}$ is independently —$OCBr_3$. In embodiments, $R^{23}$ is independently —$OCI_3$. In embodiments, $R^{23}$ is independently —$OCHCl_2$. In embodiments, $R^{23}$ is independently —$OCHBr_2$. In embodiments, $R^{23}$ is independently —$OCHI_2$. In embodiments, $R^{23}$ is independently —$OCHF_2$. In embodiments, $R^{23}$ is independently —$OCH_2Cl$. In embodiments, $R^{23}$ is independently —$OCH_2Br$. In embodiments, $R^{23}$ is independently —$OCH_2I$. In embodiments, $R^{23}$ is independently —$OCH_2F$. In embodiments, $R^{23}$ is independently —$N_3$. In embodiments, $R^{23}$ is independently —$OCH_3$. In embodiments, $R^{23}$ is independently —$CH_3$. In embodiments, $R^{23}$ is independently —$CH_2CH_3$. In embodiments, $R^{23}$ is independently unsubstituted propyl. In embodiments, $R^{23}$ is independently unsubstituted isopropyl. In embodiments, $R^{23}$ is independently unsubstituted butyl. In embodiments, $R^{23}$ is independently unsubstituted tert-butyl. In embodiments, $R^{23}$ is independently —F. In embodiments, $R^{23}$ is independently —Cl. In embodiments, $R^{23}$ is independently —Br. In embodiments, $R^{23}$ is independently —I.

In embodiments, two (e.g., adjacent) $R^1$ substituents are independently joined to form a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^1$ substituents are independently joined to form a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^1$ substituents are independently joined to form a substituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^1$ substituents are independently joined to form an unsubstituted cycloalkyl (e.g., $C_3$-$C_8$ cycloalkyl, $C_3$-$C_6$ cycloalkyl, or $C_5$-$C_6$ cycloalkyl).

In embodiments, two (e.g., adjacent) $R^1$ substituents are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^1$ substituents are independently joined to form a substituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^1$ substituents are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^1$ substituents are independently joined to form a substituted or unsubstituted aryl (e.g., $C_6$-$C_{10}$ aryl, $C_{10}$ aryl, or phenyl). In embodiments, two (e.g., adjacent) $R^1$ substituents are independently joined to form a substituted aryl (e.g., $C_6$-$C_{10}$ aryl, $C_{10}$ aryl, or phenyl). In embodiments, two (e.g., adjacent) $R^1$ substituents are independently joined to form an unsubstituted aryl (e.g., $C_6$-$C_{10}$ aryl, $C_{10}$ aryl, or phenyl). In embodiments, two (e.g., adjacent) $R^1$ substituents are independently joined to form a substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^1$ substituents are independently joined to form a substituted heteroaryl (e.g., 5 to 10 membered heteroaryl, 5 to 9 membered heteroaryl, or 5 to 6 membered heteroaryl). In embodiments, two (e.g., adjacent) $R^1$ substituents are independently joined to form an unsubstituted heteroaryl (e.g., 5 to 10 membered heteroaryl, 5 to 9 membered heteroaryl, or 5 to 6 membered heteroaryl). In embodiments, two (e.g., adjacent) $R^1$ substituents are independently joined to form an $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) le substituents are independently joined to form an $R^{21}$-substituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) le substituents are independently joined to form an unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^1$ substituents are independently joined to form an $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^1$ substituents are independently joined to form an $R^{21}$-substituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^1$ substituents are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^1$ substituents are independently joined to form an $R^{21}$-substituted or unsubstituted aryl (e.g., $C_6$-$C_{10}$ aryl, $C_{10}$ aryl, or phenyl). In embodiments, two (e.g., adjacent) $R^1$ substituents are independently joined to form an $R^{21}$-substituted aryl (e.g., $C_6$-$C_{10}$ aryl, $C_{10}$ aryl, or phenyl). In embodiments, two (e.g., adjacent) $R^1$ substituents are independently joined to form an unsubstituted aryl (e.g., $C_6$-$C_{10}$ aryl, $C_{10}$ aryl, or phenyl). In embodiments, two (e.g., adjacent) $R^1$ substituents are independently joined to form an $R^{21}$-substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^1$ substituents are independently joined to form an $R^1$ substituted heteroaryl (e.g., 5 to 10 membered heteroaryl, 5 to 9 membered heteroaryl, or 5 to 6 membered heteroaryl). In embodiments, two (e.g., adjacent) $R^1$ substituents are independently joined to form an unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^1$ position. In embodiments, when the divalent linker bonded to both the monovalent cellular component binder and monovalent targeted autophagy protein binder is attached to the monovalent targeted autophagy protein binder at an $R^1$ position, $R^1$ is replaced with a divalent linker, referred to in this embodiment as $L^{R1}$.

$L^{R1}$ is a bond, —S(O)$_2$—, —S(O)—, —NR$^{1A}$—, =N—, —O—, —S—, —C(O)—, —C(O)NR$^{1A}$—, —NR$^{1A}$C(O)—, —NR$^{1A}$C(O)NH—, —NHC(O)NR$^{1A}$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. It will be understood that when -$L^{R1}$- is =N—, one of the two direct covalent connections to $L^{R1}$ shown in "-$L^{R1}$-" is a double bond and $L^{R1}$ may equivalently be shown as "=$L^{R1}$-" and the atom to which the double bond is directly attached must obey standard rules of chemical valency known in the chemical arts and be capable of forming such a double bond.

In embodiments, $L^{R1}$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^{R1}$ is independently a —S(O)$_2$—. In embodiments, $L^{R1}$ is independently a —S(O)—. In embodiments, $L^{R1}$ is independently a —NH—. In embodiments, $L^{R1}$ is independently a —O—. In embodiments, $L^{R1}$ is independently a —S—. In embodiments, $L^{R1}$ is independently a —C(O)—. In embodiments, $L^{R1}$ is independently a —C(O)NH—. In embodiments, $L^{R1}$ is independently a —NHC(O)—. In embodiments, $L^{R1}$ is independently a —NHC(O)NH—. In embodiments, $L^{R1}$ is independently a —C(O)O—. In embodiments, $L^{R1}$ is independently —OC(O)—. In embodiments, $L^{R1}$ is independently —NR$^{1A}$—. In embodiments, $L^{R1}$ is independently —C(O)NR$^{1A}$—. In embodiments, $L^{R1}$ is independently —NR$^{1A}$C(O)—. In embodiments, $L^{R1}$ is independently —NR$^{1A}$C(O)NH—. In embodiments, $L^{R1}$ is independently —NHC(O)NR$^{1A}$—. In embodiments, $L^{R1}$ is independently a bond.

In embodiments, $L^{R1}$ is substituted or unsubstituted alkylene (e.g., $C_1$-$C_8$ alkylene, $C_1$-$C_6$ alkylene, or $C_1$-$C_4$ alkylene). In embodiments, $L^{R1}$ is substituted alkylene (e.g., $C_1$-$C_8$ alkylene, $C_1$-$C_6$ alkylene, or $C_1$-$C_4$ alkylene). In embodiments, $L^{R1}$ is an unsubstituted alkylene (e.g., $C_1$-$C_8$ alkylene, $C_1$-$C_6$ alkylene, or $C_1$-$C_4$ alkylene). In embodiments, $L^{R1}$ is substituted or unsubstituted heteroalkylene (e.g., 2 to 8 membered heteroalkylene, 2 to 6 membered heteroalkylene, or 2 to 4 membered heteroalkylene). In embodiments, $L^{R1}$ is substituted heteroalkylene (e.g., 2 to 8 membered heteroalkylene, 2 to 6 membered heteroalkylene, or 2 to 4 membered heteroalkylene). In embodiments, $L^{R1}$ is an unsubstituted heteroalkylene (e.g., 2 to 8 membered heteroalkylene, 2 to 6 membered heteroalkylene, or 2 to 4 membered heteroalkylene). In embodiments, $L^{R1}$ is substituted or unsubstituted cycloalkylene (e.g., $C_3$-$C_9$ cycloalkylene, $C_3$-$C_6$ cycloalkylene, or $C_5$-$C_6$ cycloalkylene). In embodiments, $L^{R1}$ is substituted cycloalkylene (e.g., $C_3$-$C_8$ cycloalkylene, $C_3$-$C_6$ cycloalkylene, or $C_5$-$C_6$ cycloalkylene). In embodiments, $L^{R1}$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R1}$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^{R1}$ is substituted heterocycloalkylene (e.g., 3 to 8 membered heterocycloalkylene, 3 to 6 membered heterocycloalkylene, or 5 to 6 membered heterocycloalkylene). In embodiments, $L^{R1}$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^{R1}$ is substituted or unsubstituted arylene (e.g., $C_6$-$C_{10}$ arylene, $C_{10}$ arylene, or phenylene). In embodiments, $L^{R1}$ is substituted arylene (e.g., $C_6$-$C_{10}$ arylene, $C_{10}$ arylene, or phenylene). In embodiments, $L^{R1}$ is an unsubstituted arylene (e.g., $C_6$-$C_{10}$ arylene, $C_{10}$ arylene, or phenylene). In embodiments, $L^{R1}$ is substituted or unsubstituted heteroarylene (e.g., 5 to 10 membered heteroarylene, 5 to 9 membered heteroarylene, or 5 to 6 membered heteroarylene). In embodiments, $L^{R1}$ is substituted heteroarylene (e.g., 5 to 10 membered heteroarylene, 5 to 9 membered heteroarylene, or 5 to 6 membered heteroarylene). In embodiments, $L^{R1}$ is an unsubstituted heteroarylene (e.g., 5 to 10 membered heteroarylene, 5 to 9 membered heteroarylene, or 5 to 6 membered heteroarylene).

In embodiments, $L^{R1}$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, $R^{21}$-substituted or unsubstituted alkylene (e.g., $C_1$-$C_8$ alkylene, $C_1$-$C_6$ alkylene, or $C_1$-$C_4$ alkylene), $R^{21}$-substituted or unsubstituted heteroalkylene (e.g., 2 to 8 membered heteroalkylene, 2 to 6 membered heteroalkylene, or 2 to 4 membered heteroalkylene), $R^{21}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{21}$-substituted or unsubstituted heterocycloalkylene (e.g., 3 to 8 membered heterocycloalkylene, 3 to 6 membered heterocycloalkylene, or 5 to 6 membered heterocycloalkylene), $R^{21}$-substituted or unsubstituted arylene (e.g., $C_6$-$C_{10}$ arylene, $C_{10}$ arylene, or phenylene), or $R^{21}$-substituted or unsubstituted heteroarylene (e.g., 5 to 10 membered heteroarylene, 5 to 9 membered heteroarylene, or 5 to 6 membered heteroarylene). In embodiments, $L^{R1}$ is independently a bond —S(O)$_2$—, —S(O)—, —NH—, —O—, —S—, —C(O)—, —C(O)NH—, —NHC(O)—, —NHC(O)NH—, —C(O)O—, —OC(O)—, unsubstituted alkylene (e.g., C$_1$-C$_8$ alkylene, C$_1$-C$_6$ alkylene, or C$_1$-C$_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., C$_3$-C$_8$ cycloalkylene, C$_3$-C$_6$ cycloalkylene, or C$_5$-C$_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., C$_6$-C$_{10}$ arylene, C$_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, L$^{R1}$ is R$^{21}$-substituted or unsubstituted alkylene (e.g., C$_1$-C$_8$ alkylene, C$_1$-C$_6$ alkylene, or C$_1$-C$_4$ alkylene). In embodiments, L$^{R1}$ is R$^{21}$-substituted alkylene (e.g., C$_1$-C$_8$ alkylene, C$_1$-C$_6$ alkylene, or C$_1$-C$_4$ alkylene). In embodiments, L$^{R1}$ is an unsubstituted alkylene (e.g., C$_1$-C$_8$ alkylene, C$_1$-C$_6$ alkylene, or C$_1$-C$_4$ alkylene). In embodiments, L$^{R1}$ is R$^{21}$-substituted or unsubstituted heteroalkylene (e.g., 2 to 8 membered heteroalkylene, 2 to 6 membered heteroalkylene, or 2 to 4 membered heteroalkylene). In embodiments, L$^{R1}$ is R$^{21}$-substituted heteroalkylene (e.g., 2 to 8 membered heteroalkylene, 2 to 6 membered heteroalkylene, or 2 to 4 membered heteroalkylene). In embodiments, L$^{R1}$ is an unsubstituted heteroalkylene (e.g., 2 to 8 membered heteroalkylene, 2 to 6 membered heteroalkylene, or 2 to 4 membered heteroalkylene). In embodiments, L$^{R1}$ is R$^{21}$-substituted or unsubstituted cycloalkylene (e.g., C$_3$-C$_8$ cycloalkylene, C$_3$-C$_6$ cycloalkylene, or C$_5$-C$_6$ cycloalkylene). In embodiments, L$^{R1}$ is R$^{21}$-substituted cycloalkylene (e.g., C$_3$-C$_8$ cycloalkylene, C$_3$-C$_6$ cycloalkylene, or C$_5$-C$_6$ cycloalkylene). In embodiments, L$^{R1}$ is an unsubstituted cycloalkylene (e.g., C$_3$-C$_8$ cycloalkylene, C$_3$-C$_6$ cycloalkylene, or C$_5$-C$_6$ cycloalkylene). In embodiments, L$^{R1}$ is R$^{21}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, L$^{R1}$ is R$^{21}$-substituted heterocycloalkylene (e.g., 3 to 8 membered heterocycloalkylene, 3 to 6 membered heterocycloalkylene, or 5 to 6 membered heterocycloalkylene). In embodiments, L$^{R1}$ is an unsubstituted heterocycloalkylene (e.g., 3 to 8 membered heterocycloalkylene, 3 to 6 membered heterocycloalkylene, or 5 to 6 membered heterocycloalkylene). In embodiments, L$^{R1}$ is R$^{21}$-substituted or unsubstituted arylene (e.g., C$_6$-C$_{10}$ arylene, C$_{10}$ arylene, or phenylene). In embodiments, L$^{R1}$ is R$^{21}$-substituted arylene (e.g., C$_6$-C$_{10}$ arylene, C$_{10}$ arylene, or phenylene). In embodiments, L$^{R1}$ is an unsubstituted arylene (e.g., C$_6$-C$_{10}$ arylene, C$_{10}$ arylene, or phenylene). In embodiments, L$^{R1}$ is R$^{21}$-substituted or unsubstituted heteroarylene (e.g., 5 to 10 membered heteroarylene, 5 to 9 membered heteroarylene, or 5 to 6 membered heteroarylene). In embodiments, L$^{R1}$ is R$^{21}$-substituted heteroarylene (e.g., 5 to 10 membered heteroarylene, 5 to 9 membered heteroarylene, or 5 to 6 membered heteroarylene). In embodiments, L$^{R1}$ is an unsubstituted heteroarylene (e.g., 5 to 10 membered heteroarylene, 5 to 9 membered heteroarylene, or 5 to 6 membered heteroarylene).

In embodiments, R$^{1A}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an R$^{1A}$ position. In embodiments, when the divalent linker bonded to both the monovalent cellular component binder and monovalent targeted autophagy protein binder is attached to the monovalent targeted autophagy protein binder at an R$^{1A}$ position, R$^{1A}$ is replaced with a divalent linker, referred to in this embodiment as L$^{R1}$.

In embodiments, R$^{1B}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an R$^{1B}$ position. In embodiments, when the divalent linker bonded to both the monovalent cellular component binder and monovalent targeted autophagy protein binder is attached to the monovalent targeted autophagy protein binder at an R$^{1B}$ position, R$^{1B}$ is replaced with a divalent linker, referred to in this embodiment as L$^{R1}$.

In embodiments, R$^{1C}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{1C}$ position. In embodiments, when the divalent linker bonded to both the monovalent cellular component binder and monovalent targeted autophagy protein binder is attached to the monovalent targeted autophagy protein binder at an $R^{1C}$ position, $R^{1C}$ is replaced with a divalent linker, referred to in this embodiment as $L^{R1}$.

In embodiments, $R^{1D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{1D}$ position. In embodiments, when the divalent linker bonded to both the monovalent cellular component binder and monovalent targeted autophagy protein binder is attached to the monovalent targeted autophagy protein binder at an $R^{1D}$ position, $R^{1D}$ is replaced with a divalent linker, referred to in this embodiment as $L^{R1}$.

In embodiments, $R^{1A}$ and $R^{1B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{1A}$ and $R^{1B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ and $R^{1B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{1A}$ and $R^{1B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ and $R^{1B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{1A}$ and $R^{1B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{1A}$ and $R^{1B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{1A}$, $R^{1B}$, $R^{1C}$, and $R^{1D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{21}$-substituted or unsubstituted alkyl (e.g., $C_1$-$C_8$ alkyl, $C_1$-$C_6$ alkyl, or $C_1$-$C_4$ alkyl), $R^{21}$-substituted or unsubstituted heteroalkyl (e.g., 2 to 8 membered heteroalkyl, 2 to 6 membered heteroalkyl, or 2 to 4 membered heteroalkyl), $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{21}$-substituted or unsubstituted heterocycloalkyl (e.g., 3 to 8 membered heterocycloalkyl, 3 to 6 membered heterocycloalkyl, or 5 to 6 membered heterocycloalkyl), $R^{21}$-substituted or unsubstituted aryl (e.g., $C_6$-$C_{10}$ aryl, $C_{10}$ aryl, or phenyl), or $R^{21}$-substituted or unsubstituted heteroaryl (e.g., 5 to 10 membered heteroaryl, 5 to 9 membered heteroaryl, or 5 to 6 membered heteroaryl). In embodiments, $R^{1A}$ and $R^{1B}$ substituents bonded to the same nitrogen atom are independently joined to form an $R^{21}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{21}$-substituted or unsubstituted heteroaryl (e.g., 5 to 10 membered heteroaryl, 5 to 9 membered heteroaryl, or 5 to 6 membered heteroaryl). In embodiments, $R^{1A}$ and $R^{1B}$ substituents bonded to the same nitrogen atom are independently joined to form an $R^{21}$-substituted or unsubstituted heterocycloalkyl (e.g., 3 to 8 membered heterocycloalkyl, 3 to 6 membered heterocycloalkyl. In embodiments, $R^{1A}$ and $R^{1B}$ substituents bonded to the same nitrogen atom are independently joined to form an $R^{21}$-substituted or unsubstituted heteroaryl (e.g., 5 to 10 membered heteroaryl, 5 to 9 membered heteroaryl, or 5 to 6 membered heteroaryl).

In embodiments, $R^{1A}$ is independently $R^{21}$-substituted or unsubstituted alkyl (e.g., $C_1$-$C_8$ alkyl, $C_1$-$C_6$ alkyl, or $C_1$-$C_4$ alkyl). In embodiments, $R^{1A}$ is independently $R^{21}$-substituted alkyl (e.g., $C_1$-$C_8$ alkyl, $C_1$-$C_6$ alkyl, or $C_1$-$C_4$ alkyl). In embodiments, $R^{1A}$ is independently an unsubstituted alkyl (e.g., $C_1$-$C_8$ alkyl, $C_1$-$C_6$ alkyl, or $C_1$-$C_4$ alkyl). In embodiments, $R^{1A}$ is independently $R^{21}$-substituted or unsubstituted heteroalkyl (e.g., 2 to 8 membered heteroalkyl, 2 to 6 membered heteroalkyl, or 2 to 4 membered heteroalkyl). In embodiments, $R^{1A}$ is independently $R^{21}$-substituted heteroalkyl (e.g., 2 to 8 membered heteroalkyl, 2 to 6 membered heteroalkyl, or 2 to 4 membered heteroalkyl). In embodiments, $R^{1A}$ is independently an unsubstituted heteroalkyl (e.g., 2 to 8 membered heteroalkyl, 2 to 6 membered heteroalkyl, or 2 to 4 membered heteroalkyl). In embodiments, $R^{1A}$ is independently $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is independently $R^{21}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is independently $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is independently $R^{21}$-substituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is independently $R^{21}$-substituted or unsubstituted aryl (e.g., $C_6$-$C_{10}$ aryl, $C_{10}$ aryl, or phenyl). In embodiments, $R^{1A}$ is independently $R^{21}$-substituted aryl (e.g., $C_6$-$C_{10}$ aryl, $C_{10}$ aryl, or phenyl). In embodiments, $R^{1A}$ is independently an unsubstituted aryl (e.g., $C_6$-$C_{10}$ aryl, $C_{10}$ aryl, or phenyl). In embodiments, $R^{1A}$ is independently $R^{21}$-substituted or unsubstituted heteroaryl (e.g., 5 to 10 membered heteroaryl, 5 to 9 membered heteroaryl, or 5 to 6 membered heteroaryl). In embodiments, $R^{1A}$ is independently $R^{21}$-substituted heteroaryl (e.g., 5 to 10 membered heteroaryl, 5 to 9 membered heteroaryl, or 5 to 6 membered heteroaryl). In embodiments, $R^{1A}$ is independently an unsubstituted heteroaryl (e.g., 5 to 10 membered heteroaryl, 5 to 9 membered heteroaryl, or 5 to 6 membered heteroaryl).

In embodiments, $R^{1A}$ is independently —$CCl_3$. In embodiments, $R^{1A}$ is independently —$CBr_3$. In embodiments, $R^{1A}$ is independently —$CF_3$. In embodiments, $R^{1A}$ is independently —$CI_3$. In embodiments, $R^{1A}$ is independently —$CHCl_2$. In embodiments, $R^{1A}$ is independently —$CHBr_2$. In embodiments, $R^{1A}$ is independently —$CHF_2$. In embodiments, $R^{1A}$ is independently —$CHI_2$. In embodiments, $R^{1A}$ is independently —$CH_2Cl$. In embodiments, $R^{1A}$ is independently —$CH_2Br$. In embodiments, $R^{1A}$ is independently —$CH_2F$. In embodiments, $R^{1A}$ is independently —$CH_2I$. In embodiments, $R^{1A}$ is independently —CN. In embodiments, $R^{1A}$ is independently —OH. In embodiments, $R^{1A}$ is independently —COOH. In embodiments, $R^{1A}$ is independently —$CONH_2$. In embodiments, $R^{1A}$ is independently —$OCCl_3$. In embodiments, $R^{1A}$ is independently —$OCF_3$. In embodiments, $R^{1A}$ is independently —$OCBr_3$. In embodiments, $R^{1A}$ is independently —$OCl_3$. In embodiments, $R^{1A}$ is independently —$OCHCl_2$. In embodiments, $R^{1A}$ is independently —$OCHBr_2$. In embodiments, $R^{1A}$ is independently —$OCHI_2$. In embodiments, $R^{1A}$ is independently —$OCHF_2$. In embodiments, $R^{1A}$ is independently —$OCH_2Cl$. In embodiments, $R^{1A}$ is independently —$OCH_2Br$. In embodiments, $R^{1A}$ is independently —$OCH_2I$. In embodiments, $R^{1A}$ is independently —$OCH_2F$. In embodiments, $R^{1A}$ is independently —$OCH_3$. In embodiments, $R^{1A}$ is independently —$CH_3$. In embodiments, $R^{1A}$ is independently —$CH_2CH_3$. In embodiments, $R^{1A}$ is independently unsubstituted propyl. In embodiments, $R^{1A}$ is independently unsubstituted isopropyl. In embodiments, $R^{1A}$ is independently unsubstituted butyl. In embodiments, $R^{1A}$ is independently unsubstituted tert-butyl. In embodiments, $R^{1A}$ is independently hydrogen.

In embodiments, $R^{1B}$ is independently $R^{21}$-substituted or unsubstituted alkyl (e.g., $C_1$-$C_8$ alkyl, $C_1$-$C_6$ alkyl, or $C_1$-$C_4$ alkyl). In embodiments, $R^{1B}$ is independently $R^{21}$-substituted alkyl (e.g., $C_1$-$C_8$ alkyl, $C_1$-$C_6$ alkyl, or $C_1$-$C_4$ alkyl). In embodiments, $R^{1B}$ is independently an unsubstituted alkyl (e.g., $C_1$-$C_8$ alkyl, $C_1$-$C_6$ alkyl, or $C_1$-$C_4$ alkyl). In embodiments, $R^{1B}$ is independently $R^{21}$-substituted or unsubstituted heteroalkyl (e.g., 2 to 8 membered heteroalkyl, 2 to 6 membered heteroalkyl, or 2 to 4 membered heteroalkyl). In embodiments, $R^{1B}$ is independently $R^{21}$-substituted heteroalkyl (e.g., 2 to 8 membered heteroalkyl, 2 to 6 membered heteroalkyl, or 2 to 4 membered heteroalkyl). In embodiments, $R^{1B}$ is independently an unsubstituted heteroalkyl (e.g., 2 to 8 membered heteroalkyl, 2 to 6 membered heteroalkyl, or 2 to 4 membered heteroalkyl). In embodiments, $R^{1B}$ is independently $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is independently $R^{21}$-substituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1B}$ is independently $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is independently $R^{21}$-substituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{1B}$ is independently $R^{21}$-substituted or unsubstituted aryl (e.g., $C_6$-$C_{10}$ aryl, $C_{10}$ aryl, or phenyl). In embodiments, $R^{1B}$ is independently $R^{21}$-substituted aryl (e.g., $C_6$-$C_{10}$ aryl, $C_{10}$ aryl, or phenyl). In embodiments, $R^{1B}$ is independently an unsubstituted aryl (e.g., $C_6$-$C_{10}$ aryl, $C_{10}$ aryl, or phenyl). In embodiments, $R^{1B}$ is independently $R^{21}$-substituted or unsubstituted heteroaryl (e.g., 5 to 10 membered heteroaryl, 5 to 9 membered heteroaryl, or 5 to 6 membered heteroaryl). In embodiments, $R^{1B}$ is independently $R^{21}$-substituted heteroaryl (e.g., 5 to 10 membered heteroaryl, 5 to 9 membered heteroaryl, or 5 to 6 membered heteroaryl). In embodiments, $R^{1B}$ is independently an unsubstituted heteroaryl (e.g., 5 to 10 membered heteroaryl, 5 to 9 membered heteroaryl, or 5 to 6 membered heteroaryl).

In embodiments, $R^{1B}$ is independently —$CCl_3$. In embodiments, $R^{1B}$ is independently —$CBr_3$. In embodiments, $R^{1B}$ is independently —$CF_3$. In embodiments, $R^{1B}$ is independently —$CI_3$. In embodiments, $R^{1B}$ is independently —$CHCl_2$. In embodiments, $R^{1B}$ is independently —$CHBr_2$. In embodiments, $R^{1B}$ is independently —$CHF_2$. In embodiments, $R^{1B}$ is independently —$CHI_2$. In embodiments, $R^{1B}$ is independently —$CH_2Cl$. In embodiments, $R^{1B}$ is independently —$CH_2Br$. In embodiments, $R^{1B}$ is independently —$CH_2F$. In embodiments, $R^{1B}$ is independently —$CH_2I$. In embodiments, $R^{1B}$ is independently —CN. In embodiments, $R^{1B}$ is independently —OH. In embodiments, $R^{1B}$ is independently —COOH. In embodiments, $R^{1B}$ is independently —$CONH_2$. In embodiments, $R^{1B}$ is independently —$OCCl_3$. In embodiments, $R^{1B}$ is independently —$OCF_3$. In embodiments, $R^{1B}$ is independently —$OCBr_3$. In embodiments, $R^{1B}$ is independently —$OCl_3$. In embodiments, $R^{1B}$ is independently —$OCHCl_2$. In embodiments, $R^{1B}$ is independently —$OCHBr_2$. In embodiments, $R^{1B}$ is independently —$OCHI_2$. In embodiments, $R^{1B}$ is independently —$OCHF_2$. In embodiments, $R^{1B}$ is independently —$OCH_2Cl$. In embodiments, $R^{1B}$ is independently —$OCH_2Br$. In embodiments, $R^{1B}$ is independently —$OCH_2I$. In embodiments, $R^{1B}$ is independently —$OCH_2F$. In embodiments, $R^{1B}$ is independently —$OCH_3$. In embodiments, $R^{1B}$ is independently —CH$_3$. In embodiments, R$^{1B}$ is independently —CH$_2$CH$_3$. In embodiments, R$^{1B}$ is independently unsubstituted propyl. In embodiments, R$^{1B}$ is independently unsubstituted isopropyl. In embodiments, R$^{1B}$ is independently unsubstituted butyl. In embodiments, R$^{1B}$ is independently unsubstituted tert-butyl. In embodiments, R$^{1B}$ is independently hydrogen.

In embodiments, R$^{1C}$ is independently R$^{21}$-substituted or unsubstituted alkyl (e.g., C$_1$-C$_8$ alkyl, C$_1$-C$_6$ alkyl, or C$_1$-C$_4$ alkyl). In embodiments, R$^{1C}$ is independently R$^{21}$-substituted alkyl (e.g., C$_1$-C$_8$ alkyl, C$_1$-C$_6$ alkyl, or C$_1$-C$_4$ alkyl). In embodiments, R$^{1C}$ is independently an unsubstituted alkyl (e.g., C$_1$-C$_8$ alkyl, C$_1$-C$_6$ alkyl, or C$_1$-C$_4$ alkyl). In embodiments, R$^{1C}$ is independently R$^{21}$-substituted or unsubstituted heteroalkyl (e.g., 2 to 8 membered heteroalkyl, 2 to 6 membered heteroalkyl, or 2 to 4 membered heteroalkyl). In embodiments, R$^{1C}$ is independently R$^{21}$-substituted heteroalkyl (e.g., 2 to 8 membered heteroalkyl, 2 to 6 membered heteroalkyl, or 2 to 4 membered heteroalkyl). In embodiments, R$^{1C}$ is independently an unsubstituted heteroalkyl (e.g., 2 to 8 membered heteroalkyl, 2 to 6 membered heteroalkyl, or 2 to 4 membered heteroalkyl). In embodiments, R$^{1C}$ is independently R$^{21}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{1C}$ is independently R$^{21}$-substituted cycloalkyl (e.g., C$_3$-C$_8$ cycloalkyl, C$_3$-C$_6$ cycloalkyl, or C$_5$-C$_6$ cycloalkyl). In embodiments, R$^{1C}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{1C}$ is independently R$^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{1C}$ is independently R$^{21}$-substituted heterocycloalkyl (e.g., 3 to 8 membered heterocycloalkyl, 3 to 6 membered heterocycloalkyl, or 5 to 6 membered heterocycloalkyl). In embodiments, R$^{1C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{1C}$ is independently R$^{21}$-substituted or unsubstituted aryl (e.g., C$_6$-C$_{10}$ aryl, C$_{10}$ aryl, or phenyl). In embodiments, R$^{1C}$ is independently R$^{21}$-substituted aryl (e.g., C$_6$-C$_{10}$ aryl, C$_{10}$ aryl, or phenyl). In embodiments, R$^{1C}$ is independently an unsubstituted aryl (e.g., C$_6$-C$_{10}$ aryl, C$_{10}$ aryl, or phenyl). In embodiments, R$^{1C}$ is independently R$^{21}$-substituted or unsubstituted heteroaryl (e.g., 5 to 10 membered heteroaryl, 5 to 9 membered heteroaryl, or 5 to 6 membered heteroaryl). In embodiments, R$^{1C}$ is independently R$^{21}$-substituted heteroaryl (e.g., 5 to 10 membered heteroaryl, 5 to 9 membered heteroaryl, or 5 to 6 membered heteroaryl). In embodiments, R$^{1C}$ is independently an unsubstituted heteroaryl (e.g., 5 to 10 membered heteroaryl, 5 to 9 membered heteroaryl, or 5 to 6 membered heteroaryl).

In embodiments, R$^{1C}$ is independently —CCl$_3$. In embodiments, R$^{1C}$ is independently —CBr$_3$. In embodiments, R$^{1C}$ is independently —CF$_3$. In embodiments, R$^{1C}$ is independently —CI$_3$. In embodiments, R$^{1C}$ is independently —CHCl$_2$. In embodiments, R$^{1C}$ is independently —CHBr$_2$. In embodiments, R$^{1C}$ is independently —CHF$_2$. In embodiments, R$^{1C}$ is independently —CHI$_2$. In embodiments, R$^{1C}$ is independently —CH$_2$Cl. In embodiments, R$^{1C}$ is independently —CH$_2$Br. In embodiments, R$^{1C}$ is independently —CH$_2$F. In embodiments, R$^{1C}$ is independently —CH$_2$I. In embodiments, R$^{1C}$ is independently —CN. In embodiments, R$^{1C}$ is independently —OH. In embodiments, R$^{1C}$ is independently —COOH. In embodiments, R$^{1C}$ is independently —CONH$_2$. In embodiments, R$^{1C}$ is independently —OCCl$_3$. In embodiments, R$^{1C}$ is independently —OCF$_3$. In embodiments, R$^{1C}$ is independently —OCBr$_3$. In embodiments, R$^{1C}$ is independently —OCl$_3$. In embodiments, R$^{1C}$ is independently —OCHCl$_2$. In embodiments, R$^{1C}$ is independently —OCHBr$_2$. In embodiments, R$^{1C}$ is independently —OCHI$_2$. In embodiments, R$^{1C}$ is independently —OCHF$_2$. In embodiments, R$^{1C}$ is independently —OCH$_2$Cl. In embodiments, R$^{1C}$ is independently —OCH$_2$Br. In embodiments, R$^{1C}$ is independently —OCH$_2$I. In embodiments, R$^{1C}$ is independently —OCH$_2$F. In embodiments, R$^{1C}$ is independently —OCH$_3$. In embodiments, R$^{1C}$ is independently —CH$_3$. In embodiments, R$^{1C}$ is independently —CH$_2$CH$_3$. In embodiments, R$^{1C}$ is independently unsubstituted propyl. In embodiments, R$^{1C}$ is independently unsubstituted isopropyl. In embodiments, R$^{1C}$ is independently unsubstituted butyl. In embodiments, R$^{1C}$ is independently unsubstituted tert-butyl. In embodiments, R$^{1C}$ is independently hydrogen.

In embodiments, R$^{1D}$ is independently R$^{21}$-substituted or unsubstituted alkyl (e.g., C$_1$-C$_8$ alkyl, C$_1$-C$_6$ alkyl, or C$_1$-C$_4$ alkyl). In embodiments, R$^{1D}$ is independently R$^{21}$-substituted alkyl (e.g., C$_1$-C$_8$ alkyl, C$_1$-C$_6$ alkyl, or C$_1$-C$_4$ alkyl). In embodiments, R$^{1D}$ is independently an unsubstituted alkyl (e.g., C$_1$-C$_8$ alkyl, C$_1$-C$_6$ alkyl, or C$_1$-C$_4$ alkyl). In embodiments, R$^{1D}$ is independently R$^{21}$-substituted or unsubstituted heteroalkyl (e.g., 2 to 8 membered heteroalkyl, 2 to 6 membered heteroalkyl, or 2 to 4 membered heteroalkyl). In embodiments, R$^{1D}$ is independently R$^{21}$-substituted heteroalkyl (e.g., 2 to 8 membered heteroalkyl, 2 to 6 membered heteroalkyl, or 2 to 4 membered heteroalkyl). In embodiments, R$^{1D}$ is independently an unsubstituted heteroalkyl (e.g., 2 to 8 membered heteroalkyl, 2 to 6 membered heteroalkyl, or 2 to 4 membered heteroalkyl). In embodiments, R$^{1D}$ is independently R$^{21}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{1D}$ is independently R$^{21}$-substituted cycloalkyl (e.g., C$_3$-C$_8$ cycloalkyl, C$_3$-C$_6$ cycloalkyl, or C$_5$-C$_6$ cycloalkyl). In embodiments, R$^{1D}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{1D}$ is independently R$^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{1D}$ is independently R$^{21}$-substituted heterocycloalkyl (e.g., 3 to 8 membered heterocycloalkyl, 3 to 6 membered heterocycloalkyl, or 5 to 6 membered heterocycloalkyl). In embodiments, R$^{1D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{1D}$ is independently R$^{21}$-substituted or unsubstituted aryl (e.g., C$_6$-C$_{10}$ aryl, C$_{10}$ aryl, or phenyl). In embodiments, R$^{1D}$ is independently R$^{21}$-substituted aryl (e.g., C$_6$-C$_{10}$ aryl, C$_{10}$ aryl, or phenyl). In embodiments, R$^{1D}$ is independently an unsubstituted aryl (e.g., C$_6$-C$_{10}$ aryl, C$_{10}$ aryl, or phenyl). In embodiments, R$^{1D}$ is independently R$^{21}$-substituted or unsubstituted heteroaryl (e.g., 5 to 10 membered heteroaryl, 5 to 9 membered heteroaryl, or 5 to 6 membered heteroaryl). In embodiments, R$^{1D}$ is independently R$^{21}$-substituted heteroaryl (e.g., 5 to 10 membered heteroaryl, 5 to 9 membered heteroaryl, or 5 to 6 membered heteroaryl). In embodiments, R$^{1D}$ is independently an unsubstituted heteroaryl (e.g., 5 to 10 membered heteroaryl, 5 to 9 membered heteroaryl, or 5 to 6 membered heteroaryl).

In embodiments, R$^{1D}$ is independently —CCl$_3$. In embodiments, R$^{1D}$ is independently —CBr$_3$. In embodiments, $R^{1D}$ is independently —$CF_3$. In embodiments, $R^{1D}$ is independently —$CI_3$. In embodiments, $R^{1D}$ is independently —$CHCl_2$. In embodiments, $R^{1D}$ is independently —$CHBr_2$. In embodiments, $R^{1D}$ is independently —$CHF_2$. In embodiments, $R^{1D}$ is independently —$CHI_2$. In embodiments, $R^{1D}$ is independently —$CH_2Cl$. In embodiments, $R^{1D}$ is independently —$CH_2Br$. In embodiments, $R^{1D}$ is independently —$CH_2F$. In embodiments, $R^{1D}$ is independently —$CH_2I$. In embodiments, $R^{1D}$ is independently —$CN$. In embodiments, $R^{1D}$ is independently —$OH$. In embodiments, $R^{1D}$ is independently —$COOH$. In embodiments, $R^{1D}$ is independently —$CONH_2$. In embodiments, $R^{1D}$ is independently —$OCCl_3$. In embodiments, $R^{1D}$ is independently —$OCF_3$. In embodiments, $R^{1D}$ is independently —$OCBr_3$. In embodiments, $R^{1D}$ is independently —$OCl_3$. In embodiments, $R^{1D}$ is independently —$OCHCl_2$. In embodiments, $R^{1D}$ is independently —$OCHBr_2$. In embodiments, $R^{1D}$ is independently —$OCHI_2$. In embodiments, $R^{1D}$ is independently —$OCHF_2$. In embodiments, $R^{1D}$ is independently —$OCH_2Cl$. In embodiments, $R^{1D}$ is independently —$OCH_2Br$. In embodiments, $R^{1D}$ is independently —$OCH_2I$. In embodiments, $R^{1D}$ is independently —$OCH_2F$. In embodiments, $R^{1D}$ is independently —$OCH_3$. In embodiments, $R^{1D}$ is independently —$CH_3$. In embodiments, $R^{1D}$ is independently —$CH_2CH_3$. In embodiments, $R^{1D}$ is independently unsubstituted propyl. In embodiments, $R^{1D}$ is independently unsubstituted isopropyl. In embodiments, $R^{1D}$ is independently unsubstituted butyl. In embodiments, $R^{1D}$ is independently unsubstituted tert-butyl. In embodiments, $R^{1D}$ is independently hydrogen.

In embodiments, $R^2$ is independently halogen, —$CF_3$, —$CBr_3$, —$CCl_3$, —$CCl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, $ONH_2$, $NHC(O)NHNH_2$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^2$ is independently substituted or unsubstituted alkyl (e.g., $C_1$-$C_8$ alkyl, $C_1$-$C_6$ alkyl, or $C_1$-$C_4$ alkyl). In embodiments, $R^2$ is independently substituted alkyl (e.g., $C_1$-$C_8$ alkyl, $C_1$-$C_6$ alkyl, or $C_1$-$C_4$ alkyl). In embodiments, $R^2$ is independently an unsubstituted alkyl (e.g., $C_1$-$C_8$ alkyl, $C_1$-$C_6$ alkyl, or $C_1$-$C_4$ alkyl). In embodiments, $R^2$ is independently substituted or unsubstituted heteroalkyl (e.g., 2 to 8 membered heteroalkyl, 2 to 6 membered heteroalkyl, or 2 to 4 membered heteroalkyl). In embodiments, $R^2$ is independently substituted heteroalkyl (e.g., 2 to 8 membered heteroalkyl, 2 to 6 membered heteroalkyl, or 2 to 4 membered heteroalkyl). In embodiments, $R^2$ is independently an unsubstituted heteroalkyl (e.g., 2 to 8 membered heteroalkyl, 2 to 6 membered heteroalkyl, or 2 to 4 membered heteroalkyl). In embodiments, $R^2$ is independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is independently substituted cycloalkyl (e.g., $C_3$-$C_8$ cycloalkyl, $C_3$-$C_6$ cycloalkyl, or $C_5$-$C_6$ cycloalkyl). In embodiments, $R^2$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is independently substituted heterocycloalkyl (e.g., 3 to 8 membered heterocycloalkyl, 3 to 6 membered heterocycloalkyl, or 5 to 6 membered heterocycloalkyl). In embodiments, $R^2$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is independently substituted or unsubstituted aryl (e.g., $C_6$-$C_{10}$ aryl, $C_{10}$ aryl, or phenyl). In embodiments, $R^2$ is independently substituted aryl (e.g., $C_6$-$C_{10}$ aryl, $C_{10}$ aryl, or phenyl). In embodiments, $R^2$ is independently an unsubstituted aryl (e.g., $C_6$-$C_{10}$ aryl, $C_{10}$ aryl, or phenyl). In embodiments, $R^2$ is independently substituted or unsubstituted heteroaryl (e.g., 5 to 10 membered heteroaryl, 5 to 9 membered heteroaryl, or 5 to 6 membered heteroaryl). In embodiments, $R^2$ is independently substituted heteroaryl (e.g., 5 to 10 membered heteroaryl, 5 to 9 membered heteroaryl, or 5 to 6 membered heteroaryl). In embodiments, $R^2$ is independently an unsubstituted heteroaryl (e.g., 5 to 10 membered heteroaryl, 5 to 9 membered heteroaryl, or 5 to 6 membered heteroaryl).

In embodiments, $R^2$ is independently halogen, —$CF_3$, —$CBr_3$, —$CCl_3$, —$CCl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, $R^{24}$-substituted or unsubstituted alkyl (e.g., $C_1$-$C_8$ alkyl, $C_1$-$C_6$ alkyl, or $C_1$-$C_4$ alkyl), $R^{24}$-substituted or unsubstituted heteroalkyl (e.g., 2 to 8 membered heteroalkyl, 2 to 6 membered heteroalkyl, or 2 to 4 membered heteroalkyl), $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{24}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24}$-substituted or unsubstituted aryl (e.g., $C_6$-$C_{10}$ aryl, $C_{10}$ aryl, or phenyl), or $R^{24}$-substituted or unsubstituted heteroaryl (e.g., 5 to 10 membered heteroaryl, 5 to 9 membered heteroaryl, or 5 to 6 membered heteroaryl). In embodiments, $R^2$ is independently halogen, —$CF_3$, —$CBr_3$, —$CCl_3$, —$Cl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^2$ is independently $R^{24}$-substituted or unsubstituted alkyl (e.g., $C_1$-$C_8$ alkyl, $C_1$-$C_6$ alkyl, or $C_1$-$C_4$ alkyl). In embodiments, $R^2$ is independently $R^{24}$-substituted alkyl (e.g., $C_1$-$C_8$ alkyl, $C_1$-$C_6$ alkyl, or $C_1$-$C_4$ alkyl). In embodiments, $R^2$ is independently an unsubstituted alkyl (e.g., $C_1$-$C_8$ alkyl, $C_1$-$C_6$ alkyl, or $C_1$-$C_4$ alkyl). In embodiments, $R^2$ is independently $R^{24}$-substituted or unsubstituted heteroalkyl (e.g., 2 to 8 membered heteroalkyl, 2 to 6 membered heteroalkyl, or 2 to 4 membered heteroalkyl). In embodiments, $R^2$ is independently $R^{24}$-substituted heteroalkyl (e.g., 2 to 8 membered heteroalkyl, 2 to 6 membered heteroalkyl, or 2 to 4 membered heteroalkyl). In embodiments, $R^2$ is independently an unsubstituted heteroalkyl (e.g., 2 to 8 membered heteroalkyl, 2 to 6 membered heteroalkyl, or 2 to 4 membered heteroalkyl). In embodiments, $R^2$ is independently $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is independently $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, $R^2$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is independently $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is independently $R^{24}$-substituted heterocycloalkyl (e.g., 3 to 8 membered heterocycloalkyl, 3 to 6 membered heterocycloalkyl, or 5 to 6 membered heterocycloalkyl). In embodiments, $R^2$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^2$ is independently $R^{24}$-substituted or unsubstituted aryl (e.g., $C_6$-$C_{10}$ aryl, $C_{10}$ aryl, or phenyl). In embodiments, $R^2$ is independently $R^{24}$-substituted aryl (e.g., $C_6$-$C_{10}$ aryl, $C_{10}$ aryl, or phenyl). In embodiments, $R^2$ is independently an unsubstituted aryl (e.g., $C_6$-$C_{10}$ aryl, $C_{10}$ aryl, or phenyl). In embodiments, $R^2$ is independently $R^{24}$-substituted or unsubstituted heteroaryl (e.g., 5 to 10 membered heteroaryl, 5 to 9 membered heteroaryl, or 5 to 6 membered heteroaryl). In embodiments, $R^2$ is independently $R^{24}$-substituted heteroaryl (e.g., 5 to 10 membered heteroaryl, 5 to 9 membered heteroaryl, or 5 to 6 membered heteroaryl). In embodiments, $R^2$ is independently an unsubstituted heteroaryl (e.g., 5 to 10 membered heteroaryl, 5 to 9 membered heteroaryl, or 5 to 6 membered heteroaryl).

In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$OCX^2_3$. In embodiments, $R^2$ is independently —$OCH_2X^2$. In embodiments, $R^2$ is independently —$OCHX^2_2$. In embodiments, $R^2$ is independently —CN. In embodiments, $R^2$ is independently —$SR^{2D}$. In embodiments, $R^2$ is independently —$SOR^{2D}$. In embodiments, $R^2$ is independently —$SO_2R^{2D}$. In embodiments, $R^2$ is independently —$SO_3R^{2D}$. In embodiments, $R^2$ is independently —$SO_4R^{2D}$. In embodiments, $R^2$ is independently —$SONR^{2A}R^{2B}$. In embodiments, $R^2$ is independently —$SO_2NR^{2A}R^{2B}$. In embodiments, $R^2$ is independently —$NHC(O)NR^{2A}R^{2B}$. In embodiments, $R^2$ is independently —N(O). In embodiments, $R^2$ is independently —$N(O)_2$. In embodiments, $R^2$ is independently —$NR^{2A}R^{2B}$. In embodiments, $R^2$ is independently —$C(O)R^{2C}$. In embodiments, $R^2$ is independently —$C(O)$—$OR^{2C}$. In embodiments, $R^2$ is independently —$C(O)NR^{2A}R^{2C}$. In embodiments, $R^2$ is independently —$OR^{2D}$. In embodiments, $R^2$ is independently —$NR^{2A}SO_2R^{2D}$. In embodiments, $R^2$ is independently —$NR^{2A}C(O)R^{2C}$. In embodiments, $R^2$ is independently —$NR^{2A}C(O)OR^{2C}$. In embodiments, $R^2$ is independently —$NR^{2A}OR^{2C}$.

In embodiments, $R^2$ is independently oxo. In embodiments, $R^2$ is independently halogen. In embodiments, $R^2$ is independently —$CCl_3$. In embodiments, $R^2$ is independently —$CBr_3$. In embodiments, $R^2$ is independently —$CF_3$. In embodiments, $R^2$ is independently —$CI_3$. In embodiments, $R^2$ is independently —$CHCl_2$. In embodiments, $R^2$ is independently —$CHBr_2$. In embodiments, $R^2$ is independently —$CHF_2$. In embodiments, $R^2$ is independently —$CHI_2$. In embodiments, $R^2$ is independently —$CH_2Cl$. In embodiments, $R^2$ is independently —$CH_2Br$. In embodiments, $R^2$ is independently —$CH_2F$. In embodiments, $R^2$ is independently —$CH_2I$. In embodiments, $R^2$ is independently —CN. In embodiments, $R^2$ is independently —OH. In embodiments, $R^2$ is independently —$NH_2$. In embodiments, $R^2$ is independently —COOH. In embodiments, $R^2$ is independently —$CONH_2$. In embodiments, $R^2$ is independently —$NO_2$. In embodiments, $R^2$ is independently —SH. In embodiments, $R^2$ is independently —$SO_3H$. In embodiments, $R^2$ is independently —$SO_4H$. In embodiments, $R^2$ is independently —$SO_2NH_2$. In embodiments, $R^2$ is independently —$NHNH_2$. In embodiments, $R^2$ is independently —$ONH_2$. In embodiments, $R^2$ is independently —$NHC(O)NHNH_2$. In embodiments, $R^2$ is independently —$NHC(O)NH_2$. In embodiments, $R^2$ is independently —$NHSO_2H$. In embodiments, $R^2$ is independently —NHC(O)H. In embodiments, $R^2$ is independently —NHC(O)OH. In embodiments, $R^2$ is independently —NHOH. In embodiments, $R^2$ is independently —$OCCl_3$. In embodiments, $R^2$ is independently —$OCF_3$. In embodiments, $R^2$ is independently —$OCBr_3$. In embodiments, $R^2$ is independently —$OCl_3$. In embodiments, $R^2$ is independently —$OCHCl_2$. In embodiments, $R^2$ is independently —$OCHBr_2$. In embodiments, $R^2$ is independently —$OCHI_2$. In embodiments, $R^2$ is independently —$OCHF_2$. In embodiments, $R^2$ is independently —$OCH_2Cl$. In embodiments, $R^2$ is independently —$OCH_2Br$. In embodiments, $R^2$ is independently —$OCH_2I$. In embodiments, $R^2$ is independently —$OCH_2F$. In embodiments, $R^2$ is independently —$N_3$. In embodiments, $R^2$ is independently —$OCH_3$. In embodiments, $R^2$ is independently —$CH_3$. In embodiments, $R^2$ is independently —$CH_2CH_3$. In embodiments, $R^2$ is independently unsubstituted propyl. In embodiments, $R^2$ is independently unsubstituted isopropyl. In embodiments, $R^2$ is independently unsubstituted butyl. In embodiments, $R^2$ is independently unsubstituted tert-butyl. In embodiments, $R^2$ is independently —F. In embodiments, $R^2$ is independently —Cl. In embodiments, $R^2$ is independently —Br. In embodiments, $R^2$ is independently —I.

$R^{24}$ is independently oxo, halogen, —$CCl_3$, —$CBr_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, $NHC(O)NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHF_2$, —$OCH_2Cl$, —$OCH_2Br$, —$OCH_2F$, —$N_3$, $R^{25}$-substituted or unsubstituted alkyl (e.g., $C_1$-$C_8$ alkyl, $C_1$-$C_6$ alkyl, or $C_1$-$C_4$ alkyl), $R^{25}$-substituted or unsubstituted heteroalkyl (e.g., 2 to 8 membered heteroalkyl, 2 to 6 membered heteroalkyl, or 2 to 4 membered heteroalkyl), $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., $C_6$-$C_{10}$ aryl, $C_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl). In embodiments, $R^{24}$ is independently oxo, halogen, —$CF_3$, —$CBr_3$, —$CCl_3$, —$CCl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{24}$ is independently oxo. In embodiments, $R^{24}$ is independently halogen. In embodiments, $R^{24}$ is independently —$CCl_3$. In embodiments, $R^{24}$ is independently —$CBr_3$. In embodiments, $R^{24}$ is independently —$CF_3$. In embodiments, $R^{24}$ is independently —$CI_3$. In embodiments, $R^{24}$ is independently —$CHCl_2$. In embodiments, $R^{24}$ is independently —$CHBr_2$. In embodiments, $R^{24}$ is independently —$CHF_2$. In embodiments, $R^{24}$ is independently —$CHI_2$. In embodiments, $R^{24}$ is independently —$CH_2Cl$. In embodiments, $R^{24}$ is independently —$CH_2Br$. In embodiments, $R^{24}$ is independently —$CH_2F$. In embodiments, $R^{24}$ is independently —$CH_2I$. In embodiments, $R^{24}$ is independently —CN. In embodiments, $R^{24}$ is independently —OH. In embodiments, $R^{24}$ is independently —$NH_2$. In embodiments, $R^{24}$ is independently —COOH. In embodiments, $R^{24}$ is independently —$CONH_2$. In embodiments, $R^{24}$ is independently —$NO_2$. In embodiments, $R^{24}$ is independently —SH. In embodiments, $R^{24}$ is independently —$SO_3H$. In embodiments, $R^{24}$ is independently —$SO_4H$. In embodiments, $R^{24}$ is independently —$SO_2NH_2$. In embodiments, $R^{24}$ is independently —$NHNH_2$. In embodiments, $R^{24}$ is independently —$ONH_2$. In embodiments, $R^{24}$ is independently —NHC(O)$NHNH_2$. In embodiments, $R^{24}$ is independently —NHC(O)$NH_2$. In embodiments, $R^{24}$ is independently —$NHSO_2H$. In embodiments, $R^{24}$ is independently —NHC(O)H. In embodiments, $R^{24}$ is independently —NHC(O)OH. In embodiments, $R^{24}$ is independently —NHOH. In embodiments, $R^{24}$ is independently —$OCCl_3$. In embodiments, $R^{24}$ is independently —$OCF_3$. In embodiments, $R^{24}$ is independently —$OCBr_3$. In embodiments, $R^{24}$ is independently —$OCl_3$. In embodiments, $R^{24}$ is independently —$OCHCl_2$. In embodiments, $R^{24}$ is independently —$OCHBr_2$. In embodiments, $R^{24}$ is independently —$OCHI_2$. In embodiments, $R^{24}$ is independently —$OCHF_2$. In embodiments, $R^{24}$ is independently —$OCH_2Cl$. In embodiments, $R^{24}$ is independently —$OCH_2Br$. In embodiments, $R^{24}$ is independently —$OCH_2I$. In embodiments, $R^{24}$ is independently —$OCH_2F$. In embodiments, $R^{24}$ is independently —$N_3$. In embodiments, $R^{24}$ is independently —$OCH_3$. In embodiments, $R^{24}$ is independently —$CH_3$. In embodiments, $R^{24}$ is independently —$CH_2CH_3$. In embodiments, $R^{24}$ is independently unsubstituted propyl. In embodiments, $R^{24}$ is independently unsubstituted isopropyl. In embodiments, $R^{24}$ is independently unsubstituted butyl. In embodiments, $R^{24}$ is independently unsubstituted tert-butyl. In embodiments, $R^{24}$ is independently —F. In embodiments, $R^{24}$ is independently —Cl. In embodiments, $R^{24}$ is independently —Br. In embodiments, $R^{24}$ is independently —I.

In embodiments, $R^{24}$ is independently $R^{25}$-substituted or unsubstituted alkyl (e.g., $C_1$-$C_8$ alkyl, $C_1$-$C_6$ alkyl, or $C_1$-$C_4$ alkyl). In embodiments, $R^{24}$ is independently $R^{25}$-substituted alkyl (e.g., $C_1$-$C_8$ alkyl, $C_1$-$C_6$ alkyl, or $C_1$-$C_4$ alkyl). In embodiments, $R^{24}$ is independently an unsubstituted alkyl (e.g., $C_1$-$C_8$ alkyl, $C_1$-$C_6$ alkyl, or $C_1$-$C_4$ alkyl). In embodiments, $R^{24}$ is independently $R^{25}$-substituted or unsubstituted heteroalkyl (e.g., 2 to 8 membered heteroalkyl, 2 to 6 membered heteroalkyl, or 2 to 4 membered heteroalkyl). In embodiments, $R^{24}$ is independently $R^{25}$-substituted heteroalkyl (e.g., 2 to 8 membered heteroalkyl, 2 to 6 membered heteroalkyl, or 2 to 4 membered heteroalkyl). In embodiments, $R^{24}$ is independently an unsubstituted heteroalkyl (e.g., 2 to 8 membered heteroalkyl, 2 to 6 membered heteroalkyl, or 2 to 4 membered heteroalkyl). In embodiments, $R^{24}$ is independently $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{24}$ is independently $R^{25}$-substituted cycloalkyl (e.g., $C_3$-$C_8$ cycloalkyl, $C_3$-$C_6$ cycloalkyl, or $C_5$-$C_6$ cycloalkyl). In embodiments, $R^{24}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{24}$ is independently $R^{25}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{24}$ is independently $R^{25}$-substituted heterocycloalkyl (e.g., 3 to 8 membered heterocycloalkyl, 3 to 6 membered heterocycloalkyl, or 5 to 6 membered heterocycloalkyl). In embodiments, $R^{24}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{24}$ is independently $R^{25}$-substituted or unsubstituted aryl (e.g., $C_6$-$C_{10}$ aryl, $C_{10}$ aryl, or phenyl). In embodiments, $R^{24}$ is independently $R^{25}$-substituted aryl (e.g., $C_6$-$C_{10}$ aryl, $C_{10}$ aryl, or phenyl). In embodiments, $R^{24}$ is independently an unsubstituted aryl (e.g., $C_6$-$C_{10}$ aryl, $C_{10}$ aryl, or phenyl). In embodiments, $R^{24}$ is independently $R^{25}$-substituted or unsubstituted heteroaryl (e.g., 5 to 10 membered heteroaryl, 5 to 9 membered heteroaryl, or 5 to 6 membered heteroaryl). In embodiments, $R^{24}$ is independently $R^{25}$-substituted heteroaryl (e.g., 5 to 10 membered heteroaryl, 5 to 9 membered heteroaryl, or 5 to 6 membered heteroaryl). In embodiments, $R^{24}$ is independently an unsubstituted heteroaryl (e.g., 5 to 10 membered heteroaryl, 5 to 9 membered heteroaryl, or 5 to 6 membered heteroaryl).

$R^{25}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl). In embodiments, $R^{25}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{25}$ is independently $R^{26}$-substituted or unsubstituted alkyl (e.g., $C_1$-$C_8$ alkyl, $C_1$-$C_6$ alkyl, or $C_1$-$C_4$ alkyl). In embodiments, $R^{25}$ is independently $R^{26}$-substituted alkyl (e.g., $C_1$-$C_8$ alkyl, $C_1$-$C_6$ alkyl, or $C_1$-$C_4$ alkyl). In embodiments, $R^{25}$ is independently an unsubstituted alkyl (e.g., $C_1$-$C_8$ alkyl, $C_1$-$C_6$ alkyl, or $C_1$-$C_4$ alkyl). In embodiments, $R^{25}$ is independently $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{25}$ is independently $R^{26}$-substituted heteroalkyl (e.g., 2 to 8 membered heteroalkyl, 2 to 6 membered heteroalkyl, or 2 to 4 membered heteroalkyl). In embodiments, $R^{25}$ is independently an unsubstituted heteroalkyl (e.g., 2 to 8 membered heteroalkyl, 2 to 6 membered heteroalkyl, or 2 to 4 membered heteroalkyl). In embodiments, $R^{25}$ is independently $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is independently $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is independently $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{25}$ is independently $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{25}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{25}$ is independently $R^{26}$-substituted or unsubstituted aryl (e.g., $C_6$-$C_{10}$ aryl, $C_{10}$ aryl, or phenyl). In embodiments, $R^{25}$ is independently $R^{26}$-substituted aryl (e.g., $C_6$-$C_{10}$ aryl, $C_{10}$ aryl, or phenyl). In embodiments, $R^{25}$ is independently an unsubstituted aryl (e.g., $C_6$-$C_{10}$ aryl, $C_{10}$ aryl, or phenyl). In embodiments, $R^{25}$ is independently $R^{26}$-substituted or unsubstituted heteroaryl (e.g., 5 to 10 membered heteroaryl, 5 to 9 membered heteroaryl, or 5 to 6 membered heteroaryl). In embodiments, $R^{25}$ is independently $R^{26}$-substituted heteroaryl (e.g., 5 to 10 membered heteroaryl, 5 to 9 membered heteroaryl, or 5 to 6 membered heteroaryl). In embodiments, $R^{25}$ is independently an unsubstituted heteroaryl (e.g., 5 to 10 membered heteroaryl, 5 to 9 membered heteroaryl, or 5 to 6 membered heteroaryl).

In embodiments, $R^{25}$ is independently oxo. In embodiments, $R^{25}$ is independently halogen. In embodiments, $R^{25}$ is independently —$CCl_3$. In embodiments, $R^{25}$ is independently —$CBr_3$. In embodiments, $R^{25}$ is independently —$CF_3$. In embodiments, $R^{25}$ is independently —$CI_3$. In embodiments, $R^{25}$ is independently —$CHCl_2$. In embodiments, $R^{25}$ is independently —$CHBr_2$. In embodiments, $R^{25}$ is independently —$CHF_2$. In embodiments, $R^{25}$ is independently —$CHI_2$. In embodiments, $R^{25}$ is independently —$CH_2Cl$. In embodiments, $R^{25}$ is independently —$CH_2Br$. In embodiments, $R^{25}$ is independently —$CH_2F$. In embodiments, $R^{25}$ is independently —$CH_2I$. In embodiments, $R^{25}$ is independently —CN. In embodiments, $R^{25}$ is independently —OH. In embodiments, $R^{25}$ is independently —$NH_2$. In embodiments, $R^{25}$ is independently —COOH. In embodiments, $R^{25}$ is independently —$CONH_2$. In embodiments, $R^{25}$ is independently —$NO_2$. In embodiments, $R^{25}$ is independently —SH. In embodiments, $R^{25}$ is independently —$SO_3H$. In embodiments, $R^{25}$ is independently —$SO_4H$. In embodiments, $R^{25}$ is independently —$SO_2NH_2$. In embodiments, $R^{25}$ is independently —$NHNH_2$. In embodiments, $R^{25}$ is independently —$ONH_2$. In embodiments, $R^{25}$ is independently —$NHC(O)NHNH_2$. In embodiments, $R^{25}$ is independently —$NHC(O)NH_2$. In embodiments, $R^{25}$ is independently —$NHSO_2H$. In embodiments, $R^{25}$ is independently —$NHC(O)H$. In embodiments, $R^{25}$ is independently —$NHC(O)OH$. In embodiments, $R^{25}$ is independently —NHOH. In embodiments, $R^{25}$ is independently —$OCCl_3$. In embodiments, $R^{25}$ is independently —$OCF_3$. In embodiments, $R^{25}$ is independently —$OCBr_3$. In embodiments, $R^{25}$ is independently —$OCl_3$. In embodiments, $R^{25}$ is independently —$OCHCl_2$. In embodiments, $R^{25}$ is independently —$OCHBr_2$. In embodiments, $R^{25}$ is independently —$OCHI_2$. In embodiments, $R^{25}$ is independently —$OCHF_2$. In embodiments, $R^{25}$ is independently —$OCH_2Cl$. In embodiments, $R^{25}$ is independently —$OCH_2Br$. In embodiments, $R^{25}$ is independently —$OCH_2I$. In embodiments, $R^{25}$ is independently —$OCH_2F$. In embodiments, $R^{25}$ is independently —$N_3$. In embodiments, $R^{25}$ is independently —$OCH_3$. In embodiments, $R^{25}$ is independently —$CH_3$. In embodiments, $R^{25}$ is independently —$CH_2CH_3$. In embodiments, $R^{25}$ is independently unsubstituted propyl. In embodiments, $R^{25}$ is independently unsubstituted isopropyl. In embodiments, $R^{25}$ is independently unsubstituted butyl. In embodiments, $R^{25}$ is independently unsubstituted tert-butyl. In embodiments, $R^{25}$ is independently —F. In embodiments, $R^{25}$ is independently —Cl. In embodiments, $R^{25}$ is independently —Br. In embodiments, $R^{25}$ is independently —I.

$R^{26}$ is independently oxo, halogen, —$CF_3$, —$CBr_3$, —$CCl_3$, —$CI_3$, —$CHF_2$, —$CHBr_2$, —$CHCl_2$, —$CH_2F$, —$CH_2Br$, —$CH_2Cl$, —$OCF_3$, —$OCBr_3$, —$OCCl_3$, —$OCl_3$, —$OCHF_2$, —$OCHBr_2$, —$OCHCl_2$, —$OCH_2F$, —$OCH_2Br$, —$OCH_2Cl$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{26}$ is independently an unsubstituted alkyl (e.g., $C_1$-$C_8$ alkyl, $C_1$-$C_6$ alkyl, or $C_1$-$C_4$ alkyl). In embodiments, $R^{26}$ is independently an unsubstituted heteroalkyl (e.g., 2 to 8 membered heteroalkyl, 2 to 6 membered heteroalkyl, or 2 to 4 membered heteroalkyl). In embodiments, $R^{26}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{26}$ is independently an unsubstituted aryl (e.g., $C_6$-$C_{10}$ aryl, $C_{10}$ aryl, or phenyl). In embodiments, $R^{26}$ is independently an unsubstituted heteroaryl (e.g., 5 to 10 membered heteroaryl, 5 to 9 membered heteroaryl, or 5 to 6 membered heteroaryl).

In embodiments, $R^{26}$ is independently oxo. In embodiments, $R^{26}$ is independently halogen. In embodiments, $R^{26}$ is independently —$CCl_3$. In embodiments, $R^{26}$ is independently —$CBr_3$. In embodiments, $R^{26}$ is independently —$CF_3$. In embodiments, $R^{26}$ is independently —$CI_3$. In embodiments, $R^{26}$ is independently —$CHCl_2$. In embodiments, $R^{26}$ is independently —$CHBr_2$. In embodiments, $R^{26}$ is independently —$CHF_2$. In embodiments, $R^{26}$ is independently —$CHI_2$. In embodiments, $R^{26}$ is independently —$CH_2Cl$. In embodiments, $R^{26}$ is independently —$CH_2Br$. In embodiments, $R^{26}$ is independently —$CH_2F$. In embodiments, $R^{26}$ is independently —$CH_2I$. In embodiments, $R^{26}$ is independently —CN. In embodiments, $R^{26}$ is independently —OH. In embodiments, $R^{26}$ is independently —$NH_2$. In embodiments, $R^{26}$ is independently —COOH. In embodiments, $R^{26}$ is independently —$CONH_2$. In embodiments, $R^{26}$ is independently —$NO_2$. In embodiments, $R^{26}$ is independently —SH. In embodiments, $R^{26}$ is independently —$SO_3H$. In embodiments, $R^{26}$ is independently —$SO_4H$. In embodiments, $R^{26}$ is independently —$SO_2NH_2$. In embodiments, $R^{26}$ is independently —$NHNH_2$. In embodiments, $R^{26}$ is independently —$ONH_2$. In embodiments, $R^{26}$ is independently —$NHC(O)NHNH_2$. In embodiments, $R^{26}$ is independently —$NHC(O)NH_2$. In embodiments, $R^{26}$ is independently —$NHSO_2H$. In embodiments, $R^{26}$ is independently —NHC(O)H. In embodiments, $R^{26}$ is independently —NHC(O)OH. In embodiments, $R^{26}$ is independently —NHOH. In embodiments, $R^{26}$ is independently —$OCCl_3$. In embodiments, $R^{26}$ is independently —$OCF_3$. In embodiments, $R^{26}$ is independently —$OCBr_3$. In embodiments, $R^{26}$ is independently —$OCI_3$. In embodiments, $R^{26}$ is independently —$OCHCl_2$. In embodiments, $R^{26}$ is independently —$OCHBr_2$. In embodiments, $R^{26}$ is independently —$OCHI_2$. In embodiments, $R^{26}$ is independently —$OCHF_2$. In embodiments, $R^{26}$ is independently —$OCH_2Cl$. In embodiments, $R^{26}$ is independently —$OCH_2Br$. In embodiments, $R^{26}$ is independently —$OCH_2I$. In embodiments, $R^{26}$ is independently —$OCH_2F$. In embodiments, $R^{26}$ is independently —$N_3$. In embodiments, $R^{26}$ is independently —$OCH_3$. In embodiments, $R^{26}$ is independently —$CH_3$. In embodiments, $R^{26}$ is independently —$CH_2CH_3$. In embodiments, $R^{26}$ is independently unsubstituted propyl. In embodiments, $R^{26}$ is independently unsubstituted isopropyl. In embodiments, $R^{26}$ is independently unsubstituted butyl. In embodiments, $R^{26}$ is independently unsubstituted tert-butyl. In embodiments, $R^{26}$ is independently —F. In embodiments, $R^{26}$ is independently —Cl. In embodiments, $R^{26}$ is independently —Br. In embodiments, $R^{26}$ is independently —I.

In embodiments, two (e.g., adjacent) $R^2$ substituents are independently joined to form a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^2$ substituents are independently joined to form a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^2$ substituents are independently joined to form a substituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^2$ substituents are independently joined to form an unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^2$ substituents are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^2$ substituents are independently joined to form a substituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^2$ substituents are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^2$ substituents are independently joined to form a substituted or unsubstituted aryl (e.g., $C_6$-$C_{10}$ aryl, $C_{10}$ aryl, or phenyl). In embodiments, two (e.g., adjacent) $R^2$ substituents are independently joined to form a substituted aryl (e.g., $C_6$-$C_{10}$ aryl, $C_{10}$ aryl, or phenyl). In embodiments, two (e.g., adjacent) $R^2$ substituents are independently joined to form an unsubstituted aryl (e.g., $C_6$-$C_{10}$ aryl, $C_{10}$ aryl, or phenyl). In embodiments, two (e.g., adjacent) $R^2$ substituents are independently joined to form a substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^2$ substituents are independently joined to form a substituted heteroaryl (e.g., 5 to 10 membered heteroaryl, 5 to 9 membered heteroaryl, or 5 to 6 membered heteroaryl). In embodiments, two (e.g., adjacent) $R^2$ substituents are independently joined to form an unsubstituted heteroaryl (e.g., 5 to 10 membered heteroaryl, 5 to 9 membered heteroaryl, or 5 to 6 membered heteroaryl). In embodiments, two (e.g., adjacent) $R^2$ substituents are independently joined to form an $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^2$ substituents are independently joined to form an $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^2$ substituents are independently joined to form an unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^2$ substituents are independently joined to form an $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^2$ substituents are independently joined to form an $R^{24}$-substituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^2$ substituents are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^2$ substituents are independently joined to form an $R^{24}$-substituted or unsubstituted aryl (e.g., $C_6$-$C_{10}$ aryl, $C_{10}$ aryl, or phenyl). In embodiments, two (e.g., adjacent) $R^2$ substituents are independently joined to form an $R^{24}$-substituted aryl (e.g., $C_6$-$C_{10}$ aryl, $C_{10}$ aryl, or phenyl). In embodiments, two (e.g., adjacent) $R^2$ substituents are independently joined to form an unsubstituted aryl (e.g., $C_6$-$C_{10}$ aryl, $C_{10}$ aryl, or phenyl). In embodiments, two (e.g., adjacent) $R^2$ substituents are independently joined to form an $R^{24}$-substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^2$ substituents are independently joined to form an $R^{24}$-substituted heteroaryl (e.g., 5 to 10 membered heteroaryl, 5 to 9 membered heteroaryl, or 5 to 6 membered heteroaryl). In embodiments, two (e.g., adjacent) $R^2$ substituents are independently joined to form an unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^2$ position. In embodiments, when the divalent linker bonded to both the monovalent cellular component binder and monovalent targeted autophagy protein binder is attached to the monovalent targeted autophagy protein binder at an $R^2$ position, $R^2$ is replaced with a divalent linker, referred to in this embodiment as $L^{R2}$.

$L^{R2}$ is a bond, —S(O)$_2$—, —S(O)—, —NR$^{24}$—, =N—, —O—, —S—, —C(O)—, —C(O)NR$^{24}$—, —NR$^{24}$C(O)—, —NR$^{24}$C(O)NH—, —NHC(O)$_{NR}{}^{24}$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. It will be understood that when -$L^{R2}$- is =N—, one of the two direct covalent connections to $L^{R2}$ shown in "-$L^{R2}$-" is a double bond and $L^{R2}$ may equivalently be shown as "=$L^{R2}$-" and the atom to which the double bond is directly attached must obey standard rules of chemical valency known in the chemical arts and be capable of forming such a double bond.

In embodiments, $L^{R2}$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^{R2}$ is independently a —S(O)$_2$—. In embodiments, $L^{R2}$ is independently a —S(O)—. In embodiments, $L^{R2}$ is independently a —NH—. In embodiments, $L^{R2}$ is independently a —O—. In embodiments, $L^{R2}$ is independently a —S—. In embodiments, $L^{R2}$ is independently a —C(O)—. In embodiments, $L^{R2}$ is independently a —C(O)NH—. In embodiments, $L^{R2}$ is independently a —NHC(O)—. In embodiments, $L^{R2}$ is independently a —NHC(O)NH—. In embodiments, $L^{R2}$ is independently a —C(O)O—. In embodiments, $L^{R2}$ is independently —OC(O)—. In embodiments, $L^{R2}$ is independently —NR$^{24}$—. In embodiments, $L^{R2}$ is independently —C(O)NR$^{24}$—. In embodiments, $L^{R2}$ is independently —NR$^{24}$C(O)—. In embodiments, $L^{R2}$ is independently —NR$^{24}$C(O)NH—. In embodiments, $L^{R2}$ is independently —NHC(O)NR$^{24}$—. In embodiments, $L^{R2}$ is independently a bond.

In embodiments, $L^{R2}$ is substituted or unsubstituted alkylene (e.g., $C_1$-$C_8$ alkylene, $C_1$-$C_6$ alkylene, or $C_1$-$C_4$ alkylene). In embodiments, $L^{R2}$ is substituted alkylene (e.g., $C_1$-$C_8$ alkylene, $C_1$-$C_6$ alkylene, or $C_1$-$C_4$ alkylene). In embodiments, $L^{R2}$ is an unsubstituted alkylene (e.g., $C_1$-$C_8$ alkylene, $C_1$-$C_6$ alkylene, or $C_1$-$C_4$ alkylene). In embodiments, $L^{R2}$ is substituted or unsubstituted heteroalkylene (e.g., 2 to 8 membered heteroalkylene, 2 to 6 membered heteroalkylene, or 2 to 4 membered heteroalkylene). In embodiments, $L^{R2}$ is substituted heteroalkylene (e.g., 2 to 8 membered heteroalkylene, 2 to 6 membered heteroalkylene, or 2 to 4 membered heteroalkylene). In embodiments, $L^{R2}$ is an unsubstituted heteroalkylene (e.g., 2 to 8 membered heteroalkylene, 2 to 6 membered heteroalkylene, or 2 to 4 membered heteroalkylene). In embodiments, $L^{R2}$ is substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R2}$ is substituted cycloalkylene (e.g., $C_3$-$C_8$ cycloalkylene, $C_3$-$C_6$ cycloalkylene, or $C_5$-$C_6$ cycloalkylene). In embodiments, $L^{R2}$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R2}$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^{R2}$ is substituted heterocycloalkylene (e.g., 3 to 8 membered heterocycloalkylene, 3 to 6 membered heterocycloalkylene, or 5 to 6 membered heterocycloalkylene). In embodiments, $L^{R2}$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^{R2}$ is substituted or unsubstituted arylene (e.g., $C_6$-$C_{10}$ arylene, $C_{10}$ arylene, or phenylene). In embodiments, $L^{R2}$ is substituted arylene (e.g., $C_6$-$C_{10}$ arylene, $C_{10}$ arylene, or phenylene). In embodiments, $L^{R2}$ is an unsubstituted arylene (e.g., $C_6$-$C_{10}$ arylene, $C_{10}$ arylene, or phenylene). In embodiments, $L^{R2}$ is substituted or unsubstituted heteroarylene (e.g., 5 to 10 membered heteroarylene, 5 to 9 membered heteroarylene, or 5 to 6 membered heteroarylene). In embodiments, $L^{R2}$ is substituted heteroarylene (e.g., 5 to 10 membered heteroarylene, 5 to 9 membered heteroarylene, or 5 to 6 membered heteroarylene). In embodiments, $L^{R2}$ is an unsubstituted heteroarylene (e.g., 5 to 10 membered heteroarylene, 5 to 9 membered heteroarylene, or 5 to 6 membered heteroarylene).

In embodiments, $L^{R2}$ is independently a bond, —S(O)$_2$—, —S(O)—, —NH—, —O—, —S—, —C(O)—, —C(O)NH—, —NHC(O)—, —NHC(O)NH—, —C(O)O—, —OC (O)—, $R^{24}$-substituted or unsubstituted alkylene (e.g., $C_1$-$C_8$ alkylene, $C_1$-$C_6$ alkylene, or $C_1$-$C_4$ alkylene), $R^{24}$-substituted or unsubstituted heteroalkylene (e.g., 2 to 8 membered heteroalkylene, 2 to 6 membered heteroalkylene, or 2 to 4 membered heteroalkylene), $R^{24}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{24}$-substituted or unsubstituted heterocycloalkylene (e.g., 3 to 8 membered heterocycloalkylene, 3 to 6 membered heterocycloalkylene, or 5 to 6 membered heterocycloalkylene), $R^{24}$-substituted or unsubstituted arylene (e.g., $C_6$-$C_{10}$ arylene, $C_{10}$ arylene, or phenylene), or $R^{24}$-substituted or unsubstituted heteroarylene (e.g., 5 to 10 membered heteroarylene, 5 to 9 membered heteroarylene, or 5 to 6 membered heteroarylene). In embodiments, $L^{R2}$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, $L^{R2}$ is $R^{24}$-substituted or unsubstituted alkylene (e.g., $C_1$-$C_8$ alkylene, $C_1$-$C_6$ alkylene, or $C_1$-$C_4$ alkylene). In embodiments, $L^{R2}$ is $R^{24}$-substituted alkylene (e.g., $C_1$-$C_8$ alkylene, $C_1$-$C_6$ alkylene, or $C_1$-$C_4$ alkylene). In embodiments, $L^{R2}$ is an unsubstituted alkylene (e.g., $C_1$-$C_8$ alkylene, $C_1$-$C_6$ alkylene, or $C_1$-$C_4$ alkylene). In embodiments, $L^{R2}$ is $R^{24}$-substituted or unsubstituted heteroalkylene (e.g., 2 to 8 membered heteroalkylene, 2 to 6 membered heteroalkylene, or 2 to 4 membered heteroalkylene). In embodiments, $L^{R2}$ is $R^{24}$-substituted heteroalkylene (e.g., 2 to 8 membered heteroalkylene, 2 to 6 membered heteroalkylene, or 2 to 4 membered heteroalkylene). In embodiments, $L^{R2}$ is an unsubstituted heteroalkylene (e.g., 2 to 8 membered heteroalkylene, 2 to 6 membered heteroalkylene, or 2 to 4 membered heteroalkylene). In embodiments, $L^{R2}$ is $R^{24}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R2}$ is $R^{24}$-substituted cycloalkylene (e.g., $C_3$-$C_8$ cycloalkylene, $C_3$-$C_6$ cycloalkylene, or $C_5$-$C_6$ cycloalkylene). In embodiments, $L^{R2}$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R2}$ is $R^{24}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^{R2}$ is $R^{24}$-substituted heterocycloalkylene (e.g., 3 to 8 membered heterocycloalkylene, 3 to 6 membered heterocycloalkylene, or 5 to 6 membered heterocycloalkylene). In embodiments, $L^{R2}$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^{R2}$ is $R^{24}$-substituted or unsubstituted arylene (e.g., $C_6$-$C_{10}$ arylene, $C_{10}$ arylene, or phenylene). In embodiments, $L^{R2}$ is $R^{24}$-substituted arylene (e.g., $C_6$-$C_{10}$ arylene, $C_{10}$ arylene, or phenylene). In embodiments, $L^{R2}$ is an unsubstituted arylene (e.g., $C_6$-$C_{10}$ arylene, $C_{10}$ arylene, or phenylene). In embodiments, $L^{R2}$ is $R^{24}$-substituted or unsubstituted heteroarylene (e.g., 5 to 10 membered heteroarylene, 5 to 9 membered heteroarylene, or 5 to 6 membered heteroarylene). In embodiments, $L^{R2}$ is $R^{24}$-substituted heteroarylene (e.g., 5 to 10 membered heteroarylene, 5 to 9 membered heteroarylene, or 5 to 6 membered heteroarylene). In embodiments, $L^{R2}$ is an unsubstituted heteroarylene (e.g., 5 to 10 membered heteroarylene, 5 to 9 membered heteroarylene, or 5 to 6 membered heteroarylene).

In embodiments, $R^{2A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{2A}$ position. In embodiments, when the divalent linker bonded to both the monovalent cellular component binder and monovalent targeted autophagy protein binder is attached to the monovalent targeted autophagy protein binder at an $R^{2A}$ position, $R^{2A}$ is replaced with a divalent linker, referred to in this embodiment as $L^{R2}$.

In embodiments, $R^{2B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{2B}$ position. In embodiments, when the divalent linker bonded to both the monovalent cellular component binder and monovalent targeted autophagy protein binder is attached to the monovalent targeted autophagy protein binder at an $R^{2B}$ position, $R^{2B}$ is replaced with a divalent linker, referred to in this embodiment as $L^{R2}$.

In embodiments, $R^{2C}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{2C}$ position. In embodiments, when the divalent linker bonded to both the monovalent cellular component binder and monovalent targeted autophagy protein binder is attached to the monovalent targeted autophagy protein binder at an $R^{2C}$ position, $R^{2C}$ is replaced with a divalent linker, referred to in this embodiment as $L^{R2}$.

In embodiments, $R^{2D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{2D}$ position. In embodiments, when the divalent linker bonded to both the monovalent cellular component binder and monovalent targeted autophagy protein binder is attached to the monovalent targeted autophagy protein binder at an $R^{2D}$ position, $R^{2D}$ is replaced with a divalent linker, referred to in this embodiment as $L^{R2}$.

In embodiments, $R^{2A}$ and $R^{2B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{2A}$ and $R^{2B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ and $R^{2B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{2A}$ and $R^{2B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ and $R^{2B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{2A}$ and $R^{2B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{2A}$ and $R^{2B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{2A}$, $R^{2B}$, $R^{2C}$, and $R^{2D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{24}$-substituted or unsubstituted alkyl (e.g., $C_1$-$C_8$ alkyl, $C_1$-$C_6$ alkyl, or $C_1$-$C_4$ alkyl), $R^{24}$-substituted or unsubstituted heteroalkyl (e.g., 2 to 8 membered heteroalkyl, 2 to 6 membered heteroalkyl, or 2 to 4 membered heteroalkyl), $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{24}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24}$-substituted or unsubstituted aryl (e.g., $C_6$-$C_{10}$ aryl, $C_{10}$ aryl, or phenyl), or $R^{24}$-substituted or unsubstituted heteroaryl (e.g., 5 to 10 membered heteroaryl, 5 to 9 membered heteroaryl, or 5 to 6 membered heteroaryl). In embodiments, $R^{2A}$ and $R^{2B}$ substituents bonded to the same nitrogen atom are independently joined to form an $R^{24}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{24}$-substituted or unsubstituted heteroaryl (e.g., 5 to 10 membered heteroaryl, 5 to 9 membered heteroaryl, or 5 to 6 membered heteroaryl). In embodiments, $R^{2A}$ and $R^{2B}$ substituents bonded to the same nitrogen atom are independently joined to form an $R^{24}$-substituted or unsubstituted heterocycloalkyl (e.g., 3 to 8 membered heterocycloalkyl, 3 to 6 membered heterocycloalkyl. In embodiments, $R^{2A}$ and $R^{2B}$ substituents bonded to the same nitrogen atom are independently joined to form an $R^{24}$-substituted or unsubstituted heteroaryl (e.g., 5 to 10 membered heteroaryl, 5 to 9 membered heteroaryl, or 5 to 6 membered heteroaryl).

In embodiments, $R^{2A}$ is independently $R^{24}$-substituted or unsubstituted alkyl (e.g., $C_1$-$C_8$ alkyl, $C_1$-$C_6$ alkyl, or $C_1$-$C_4$ alkyl). In embodiments, $R^{2A}$ is independently $R^{24}$-substituted alkyl (e.g., $C_1$-$C_8$ alkyl, $C_1$-$C_6$ alkyl, or $C_1$-$C_4$ alkyl). In embodiments, $R^{2A}$ is independently an unsubstituted alkyl (e.g., $C_1$-$C_8$ alkyl, $C_1$-$C_6$ alkyl, or $C_1$-$C_4$ alkyl). In embodiments, $R^{2A}$ is independently $R^{24}$-substituted or unsubstituted heteroalkyl (e.g., 2 to 8 membered heteroalkyl, 2 to 6 membered heteroalkyl, or 2 to 4 membered heteroalkyl). In embodiments, $R^{2A}$ is independently $R^{24}$-substituted heteroalkyl (e.g., 2 to 8 membered heteroalkyl, 2 to 6 membered heteroalkyl, or 2 to 4 membered heteroalkyl). In embodiments, $R^{2A}$ is independently an unsubstituted heteroalkyl (e.g., 2 to 8 membered heteroalkyl, 2 to 6 membered heteroalkyl, or 2 to 4 membered heteroalkyl). In embodiments, $R^{2A}$ is independently $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is independently $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is independently $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is independently $R^{24}$-substituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is independently $R^{24}$-substituted or unsubstituted aryl (e.g., $C_6$-$C_{10}$ aryl, $C_{10}$ aryl, or phenyl). In embodiments, $R^{2A}$ is independently $R^{24}$-substituted aryl (e.g., $C_6$-$C_{10}$ aryl, $C_{10}$ aryl, or phenyl). In embodiments, $R^{2A}$ is independently an unsubstituted aryl (e.g., $C_6$-$C_{10}$ aryl, $C_{10}$ aryl, or phenyl). In embodiments, $R^{2A}$ is independently $R^{24}$-substituted or unsubstituted heteroaryl (e.g., 5 to 10 membered heteroaryl, 5 to 9 membered heteroaryl, or 5 to 6 membered heteroaryl). In embodiments, $R^{2A}$ is independently $R^{24}$-substituted heteroaryl (e.g., 5 to 10 membered heteroaryl, 5 to 9 membered heteroaryl, or 5 to 6 membered heteroaryl). In embodiments, $R^{2A}$ is independently an unsubstituted heteroaryl (e.g., 5 to 10 membered heteroaryl, 5 to 9 membered heteroaryl, or 5 to 6 membered heteroaryl).

In embodiments, $R^{2A}$ is independently —$CCl_3$. In embodiments, $R^{2A}$ is independently —$CBr_3$. In embodiments, $R^{2A}$ is independently —$CF_3$. In embodiments, $R^{2A}$ is independently —$CI_3$. In embodiments, $R^{2A}$ is independently —$CHCl_2$. In embodiments, $R^{2A}$ is independently —$CHBr_2$. In embodiments, $R^{2A}$ is independently —$CHF_2$. In embodiments, $R^{2A}$ is independently —$CHI_2$. In embodiments, $R^{2A}$ is independently —$CH_2Cl$. In embodiments, $R^{2A}$ is independently —$CH_2Br$. In embodiments, $R^{2A}$ is independently —$CH_2F$. In embodiments, $R^{2A}$ is independently —$CH_2I$. In embodiments, $R^{2A}$ is independently —CN. In embodiments, $R^{2A}$ is independently —OH. In embodiments, $R^{2A}$ is independently —COOH. In embodiments, $R^{2A}$ is independently —$CONH_2$. In embodiments, $R^{2A}$ is independently —$OCCl_3$. In embodiments, $R^{2A}$ is independently —$OCF_3$. In embodiments, $R^{2A}$ is independently —$OCBr_3$. In embodiments, $R^{2A}$ is independently —$OCl_3$. In embodiments, $R^{2A}$ is independently —$OCHCl_2$. In embodiments, $R^{2A}$ is independently —$OCHBr_2$. In embodiments, $R^{2A}$ is independently —$OCHI_2$. In embodiments, $R^{2A}$ is independently —$OCHF_2$. In embodiments, $R^{2A}$ is independently —$OCH_2Cl$. In embodiments, $R^{2A}$ is independently —$OCH_2Br$. In embodiments, $R^{2A}$ is independently —$OCH_2I$. In embodiments, $R^{2A}$ is independently —$OCH_2F$. In embodiments, $R^{2A}$ is independently —$OCH_3$. In embodiments, $R^{2A}$ is independently —$CH_3$. In embodiments, $R^{2A}$ is idenpendently —$CH_2CH_3$. In embodiments, $R^{2A}$ is independently unsubstituted propyl. In embodiments, $R^{2A}$ is independently unsubstituted isopropyl. In embodiments, $R^{2A}$ is independently unsubstituted butyl. In embodiments, $R^{2A}$ is independently unsubstituted tert-butyl. In embodiments, $R^{2A}$ is independently hydrogen.

In embodiments, $R^{2B}$ is independently $R^{24}$-substituted or unsubstituted alkyl (e.g., $C_1$-$C_8$ alkyl, $C_1$-$C_6$ alkyl, or $C_1$-$C_4$ alkyl). In embodiments, $R^{2B}$ is independently $R^{24}$-substituted alkyl (e.g., $C_1$-$C_8$ alkyl, $C_1$-$C_6$ alkyl, or $C_1$-$C_4$ alkyl). In embodiments, $R^{2B}$ is independently an unsubstituted alkyl (e.g., $C_1$-$C_8$ alkyl, $C_1$-$C_6$ alkyl, or $C_1$-$C_4$ alkyl). In embodiments, $R^{2B}$ is independently $R^{24}$-substituted or unsubstituted heteroalkyl (e.g., 2 to 8 membered heteroalkyl, 2 to 6 membered heteroalkyl, or 2 to 4 membered heteroalkyl). In embodiments, $R^{2B}$ is independently $R^{24}$-substituted heteroalkyl (e.g., 2 to 8 membered heteroalkyl, 2 to 6 membered heteroalkyl, or 2 to 4 membered heteroalkyl). In embodiments, $R^{2B}$ is independently an unsubstituted heteroalkyl (e.g., 2 to 8 membered heteroalkyl, 2 to 6 membered heteroalkyl, or 2 to 4 membered heteroalkyl). In embodiments, $R^{2B}$ is independently $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2B}$ is independently $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, $R^{2B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2B}$ is independently $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{2B}$ is independently $R^{24}$-substituted heterocycloalkyl (e.g., 3 to 8 membered heterocycloalkyl, 3 to 6 membered heterocycloalkyl, or 5 to 6 membered heterocycloalkyl). In embodiments, $R^{2B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{2B}$ is independently $R^{24}$-substituted or unsubstituted aryl (e.g., $C_6$-$C_{10}$ aryl, $C_{10}$ aryl, or phenyl). In embodiments, $R^{2B}$ is independently $R^{24}$-substituted aryl (e.g., $C_6$-$C_{10}$ aryl, $C_{10}$ aryl, or phenyl). In embodiments, $R^{2B}$ is independently an unsubstituted aryl (e.g., $C_6$-$C_{10}$ aryl, $C_{10}$ aryl, or phenyl). In embodiments, $R^{2B}$ is independently $R^{24}$-substituted or unsubstituted heteroaryl (e.g., 5 to 10 membered heteroaryl, 5 to 9 membered heteroaryl, or 5 to 6 membered heteroaryl). In embodiments, $R^{2B}$ is independently $R^{24}$-substituted heteroaryl (e.g., 5 to 10 membered heteroaryl, 5 to 9 membered heteroaryl, or 5 to 6 membered heteroaryl). In embodiments, $R^{2B}$ is independently an unsubstituted heteroaryl (e.g., 5 to 10 membered heteroaryl, 5 to 9 membered heteroaryl, or 5 to 6 membered heteroaryl).

In embodiments, $R^{2B}$ is independently —$CCl_3$. In embodiments, $R^{2B}$ is independently —$CBr_3$. In embodiments, $R^{2B}$ is independently —$CF_3$. In embodiments, $R^{2B}$ is independently —$CI_3$. In embodiments, $R^{2B}$ is independently —$CHCl_2$. In embodiments, $R^{2B}$ is independently —$CHBr_2$. In embodiments, $R^{2B}$ is independently —$CHF_2$. In embodiments, $R^{2B}$ is independently —$CHI_2$. In embodiments, $R^{2B}$ is independently —$CH_2Cl$. In embodiments, $R^{2B}$ is independently —$CH_2Br$. In embodiments, $R^{2B}$ is independently —CH$_2$F. In embodiments, R$^{2B}$ is independently —CH$_2$I. In embodiments, R$^{2B}$ is independently —CN. In embodiments, R$^{2B}$ is independently —OH. In embodiments, R$^{2B}$ is independently —COOH. In embodiments, R$^{2B}$ is independently —CONH$_2$. In embodiments, R$^{2B}$ is independently —OCCl$_3$. In embodiments, R$^{2B}$ is independently —OCF$_3$. In embodiments, R$^{2B}$ is independently —OCBr$_3$. In embodiments, R$^{2B}$ is independently —OCl$_3$. In embodiments, R$^{2B}$ is independently —OCHCl$_2$. In embodiments, R$^{2B}$ is independently —OCHBr$_2$. In embodiments, R$^{2B}$ is independently —OCHI$_2$. In embodiments, R$^{2B}$ is independently —OCHF$_2$. In embodiments, R$^{2B}$ is independently —OCH$_2$Cl. In embodiments, R$^{2B}$ is independently —OCH$_2$Br. In embodiments, R$^{2B}$ is independently —OCH$_2$I. In embodiments, R$^{2B}$ is independently —OCH$_2$F. In embodiments, R$^{2B}$ is independently —OCH$_3$. In embodiments, R$^{2B}$ is idenpendently —CH$_3$. In embodiments, R$^{2B}$ is idenpendently —CH$_2$CH$_3$. In embodiments, R$^{2B}$ is independently unsubstituted propyl. In embodiments, R$^{2B}$ is independently unsubstituted isopropyl. In embodiments, R$^{2B}$ is independently unsubstituted butyl. In embodiments, R$^{2B}$ is independently unsubstituted tert-butyl. In embodiments, R$^{2B}$ is independently hydrogen.

In embodiments, R$^{2C}$ is independently R$^{24}$-substituted or unsubstituted alkyl (e.g., C$_1$-C$_8$ alkyl, C$_1$-C$_6$ alkyl, or C$_1$-C$_4$ alkyl). In embodiments, R$^{2C}$ is independently R$^{24}$-substituted alkyl (e.g., C$_1$-C$_8$ alkyl, C$_1$-C$_6$ alkyl, or C$_1$-C$_4$ alkyl). In embodiments, R$^{2C}$ is independently an unsubstituted alkyl (e.g., C$_1$-C$_8$ alkyl, C$_1$-C$_6$ alkyl, or C$_1$-C$_4$ alkyl). In embodiments, R$^{2C}$ is independently R$^{24}$-substituted or unsubstituted heteroalkyl (e.g., 2 to 8 membered heteroalkyl, 2 to 6 membered heteroalkyl, or 2 to 4 membered heteroalkyl). In embodiments, R$^{2C}$ is independently R$^{24}$-substituted heteroalkyl (e.g., 2 to 8 membered heteroalkyl, 2 to 6 membered heteroalkyl, or 2 to 4 membered heteroalkyl). In embodiments, R$^{2C}$ is independently an unsubstituted heteroalkyl (e.g., 2 to 8 membered heteroalkyl, 2 to 6 membered heteroalkyl, or 2 to 4 membered heteroalkyl). In embodiments, R$^{2C}$ is independently R$^{24}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{2C}$ is independently R$^{24}$-substituted cycloalkyl (e.g., C$_3$-C$_8$ cycloalkyl, C$_3$-C$_6$ cycloalkyl, or C$_5$-C$_6$ cycloalkyl). In embodiments, R$^{2C}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{2C}$ is independently R$^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{2C}$ is independently R$^{24}$-substituted heterocycloalkyl (e.g., 3 to 8 membered heterocycloalkyl, 3 to 6 membered heterocycloalkyl, or 5 to 6 membered heterocycloalkyl). In embodiments, R$^{2C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{2C}$ is independently R$^{24}$-substituted or unsubstituted aryl (e.g., C$_6$-C$_{10}$ aryl, C$_{10}$ aryl, or phenyl). In embodiments, R$^{2C}$ is independently R$^{24}$-substituted aryl (e.g., C$_6$-C$_{10}$ aryl, C$_{10}$ aryl, or phenyl). In embodiments, R$^{2C}$ is independently an unsubstituted aryl (e.g., C$_6$-C$_{10}$ aryl, C$_{10}$ aryl, or phenyl). In embodiments, R$^{2C}$ is independently R$^{24}$-substituted or unsubstituted heteroaryl (e.g., 5 to 10 membered heteroaryl, 5 to 9 membered heteroaryl, or 5 to 6 membered heteroaryl). In embodiments, R$^{2C}$ is independently R$^{24}$-substituted heteroaryl (e.g., 5 to 10 membered heteroaryl, 5 to 9 membered heteroaryl, or 5 to 6 membered heteroaryl). In embodiments, R$^{2C}$ is independently an unsubstituted heteroaryl (e.g., 5 to 10 membered heteroaryl, 5 to 9 membered heteroaryl, or 5 to 6 membered heteroaryl).

In embodiments, R$^{2C}$ is independently —CCl$_3$. In embodiments, R$^{2C}$ is independently —CBr$_3$. In embodiments, R$^{2C}$ is independently —CF$_3$. In embodiments, R$^{2C}$ is independently —CI$_3$. In embodiments, R$^{2C}$ is independently —CHCl$_2$. In embodiments, R$^{2C}$ is independently —CHBr$_2$. In embodiments, R$^{2C}$ is independently —CHF$_2$. In embodiments, R$^{2C}$ is independently —CHI$_2$. In embodiments, R$^{2C}$ is independently —CH$_2$Cl. In embodiments, R$^{2C}$ is independently —CH$_2$Br. In embodiments, R$^{2C}$ is independently —CH$_2$F. In embodiments, R$^{2C}$ is independently —CH$_2$I. In embodiments, R$^{2C}$ is independently —CN. In embodiments, R$^{2C}$ is independently —OH. In embodiments, R$^{2C}$ is independently —COOH. In embodiments, R$^{2C}$ is independently —CONH$_2$. In embodiments, R$^{2C}$ is independently —OCCl$_3$. In embodiments, R$^{2C}$ is independently —OCF$_3$. In embodiments, R$^{2C}$ is independently —OCBr$_3$. In embodiments, R$^{2C}$ is independently —OCl$_3$. In embodiments, R$^{2C}$ is independently —OCHCl$_2$. In embodiments, R$^{2C}$ is independently —OCHBr$_2$. In embodiments, R$^{2C}$ is independently —OCHI$_2$. In embodiments, R$^{2C}$ is independently —OCHF$_2$. In embodiments, R$^2$ is independently —OCH$_2$Cl. In embodiments, R$^{2C}$ is independently —OCH$_2$Br. In embodiments, R$^{2C}$ is independently —OCH$_2$I. In embodiments, R$^{2C}$ is independently —OCH$_2$F. In embodiments, R$^{2C}$ is independently —OCH$_3$. In embodiments, R$^{2C}$ is idenpendently —CH$_3$. In embodiments, R$^{2C}$ is idenpendently —CH$_2$CH$_3$. In embodiments, R$^{2C}$ is independently unsubstituted propyl. In embodiments, R$^{2C}$ is independently unsubstituted isopropyl. In embodiments, R$^{2C}$ is independently unsubstituted butyl. In embodiments, R$^{2C}$ is independently unsubstituted tert-butyl. In embodiments, R$^{2C}$ is independently hydrogen.

In embodiments, R$^{2D}$ is independently R$^{24}$-substituted or unsubstituted alkyl (e.g., C$_1$-C$_8$ alkyl, C$_1$-C$_6$ alkyl, or C$_1$-C$_4$ alkyl). In embodiments, R$^{2D}$ is independently R$^{24}$-substituted alkyl (e.g., C$_1$-C$_8$ alkyl, C$_1$-C$_6$ alkyl, or C$_1$-C$_4$ alkyl). In embodiments, R$^{2D}$ is independently an unsubstituted alkyl (e.g., C$_1$-C$_8$ alkyl, C$_1$-C$_6$ alkyl, or C$_1$-C$_4$ alkyl). In embodiments, R$^{2D}$ is independently R$^{24}$-substituted or unsubstituted heteroalkyl (e.g., 2 to 8 membered heteroalkyl, 2 to 6 membered heteroalkyl, or 2 to 4 membered heteroalkyl). In embodiments, R$^{2D}$ is independently R$^{24}$-substituted heteroalkyl (e.g., 2 to 8 membered heteroalkyl, 2 to 6 membered heteroalkyl, or 2 to 4 membered heteroalkyl). In embodiments, R$^{2D}$ is independently an unsubstituted heteroalkyl (e.g., 2 to 8 membered heteroalkyl, 2 to 6 membered heteroalkyl, or 2 to 4 membered heteroalkyl). In embodiments, R$^{2D}$ is independently R$^{24}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{2D}$ is independently R$^{24}$-substituted cycloalkyl (e.g., C$_3$-C$_8$ cycloalkyl, C$_3$-C$_6$ cycloalkyl, or C$_5$-C$_6$ cycloalkyl). In embodiments, R$^{2D}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{2D}$ is independently R$^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R' is independently R$^{24}$-substituted heterocycloalkyl (e.g., 3 to 8 membered heterocycloalkyl, 3 to 6 membered heterocycloalkyl, or 5 to 6 membered heterocycloalkyl). In embodiments, R' is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{2D}$ is independently $R^{24}$-substituted or unsubstituted aryl (e.g., $C_6$-$C_{10}$ aryl, $C_{10}$ aryl, or phenyl). In embodiments, $R^{2D}$ is independently $R^{24}$-substituted aryl (e.g., $C_6$-$C_{10}$ aryl, $C_{10}$ aryl, or phenyl). In embodiments, $R^{2D}$ is independently an unsubstituted aryl (e.g., $C_6$-$C_{10}$ aryl, $C_{10}$ aryl, or phenyl). In embodiments, $R^{2D}$ is independently $R^{24}$-substituted or unsubstituted heteroaryl (e.g., 5 to 10 membered heteroaryl, 5 to 9 membered heteroaryl, or 5 to 6 membered heteroaryl). In embodiments, $R^{2D}$ is independently $R^{24}$-substituted heteroaryl (e.g., 5 to 10 membered heteroaryl, 5 to 9 membered heteroaryl, or 5 to 6 membered heteroaryl). In embodiments, $R^{2D}$ is independently an unsubstituted heteroaryl (e.g., 5 to 10 membered heteroaryl, 5 to 9 membered heteroaryl, or 5 to 6 membered heteroaryl).

In embodiments, $R^{2D}$ is independently —$CCl_3$. In embodiments, $R^{2D}$ is independently —$CBr_3$. In embodiments, $R^{2D}$ is independently —$CF_3$. In embodiments, $R^{2D}$ is independently —$CI_3$. In embodiments, $R^{2D}$ is independently —$CHCl_2$. In embodiments, $R^{2D}$ is independently —$CHBr_2$. In embodiments, $R^{2D}$ is independently —$CHF_2$. In embodiments, $R^{2D}$ is independently —$CHI_2$. In embodiments, $R^{2D}$ is independently —$CH_2Cl$. In embodiments, $R^{2D}$ is independently —$CH_2Br$. In embodiments, $R^{2D}$ is independently —$CH_2F$. In embodiments, $R^{2D}$ is independently —$CH_2I$. In embodiments, $R^{2D}$ is independently —CN. In embodiments, $R^{2D}$ is independently —OH. In embodiments, $R^{2D}$ is independently —COOH. In embodiments, $R^{2D}$ is independently —$CONH_2$. In embodiments, $R^{2D}$ is independently —$OCCl_3$. In embodiments, $R^{2D}$ is independently —$OCF_3$. In embodiments, $R^{2D}$ is independently —$OCBr_3$. In embodiments, $R^{2D}$ is independently —$OCl_3$. In embodiments, $R^{2D}$ is independently —$OCHCl_2$. In embodiments, $R^{2D}$ is independently —$OCHBr_2$. In embodiments, $R^{2D}$ is independently —$OCHI_2$. In embodiments, $R^{2D}$ is independently —$OCHF_2$. In embodiments, $R^{2D}$ is independently —$OCH_2Cl$. In embodiments, $R^{2D}$ is independently —$OCH_2Br$. In embodiments, $R^{2D}$ is independently —$OCH_2I$. In embodiments, $R^{2D}$ is independently —$OCH_2F$. In embodiments, $R^{2D}$ is independently —$OCH_3$. In embodiments, $R^{2D}$ is idenpendently —$CH_3$. In embodiments, $R^{2D}$ is idenpendently —$CH_2CH_3$. In embodiments, $R^{2D}$ is independently unsubstituted propyl. In embodiments, $R^{2D}$ is independently unsubstituted isopropyl. In embodiments, $R^{2D}$ is independently unsubstituted butyl. In embodiments, $R^{2D}$ is independently unsubstituted tert-butyl. In embodiments, $R^{2D}$ is independently hydrogen.

In embodiments, $R^3$ is independently halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^3$ is independently substituted or unsubstituted alkyl (e.g., $C_1$-$C_8$ alkyl, $C_1$-$C_6$ alkyl, or $C_1$-$C_4$ alkyl). In embodiments, $R^3$ is independently substituted alkyl (e.g., $C_1$-$C_8$ alkyl, $C_1$-$C_6$ alkyl, or $C_1$-$C_4$ alkyl). In embodiments, $R^3$ is independently an unsubstituted alkyl (e.g., $C_1$-$C_8$ alkyl, $C_1$-$C_6$ alkyl, or $C_1$-$C_4$ alkyl). In embodiments, $R^3$ is independently substituted or unsubstituted heteroalkyl (e.g., 2 to 8 membered heteroalkyl, 2 to 6 membered heteroalkyl, or 2 to 4 membered heteroalkyl). In embodiments, $R^3$ is independently substituted heteroalkyl (e.g., 2 to 8 membered heteroalkyl, 2 to 6 membered heteroalkyl, or 2 to 4 membered heteroalkyl). In embodiments, $R^3$ is independently an unsubstituted heteroalkyl (e.g., 2 to 8 membered heteroalkyl, 2 to 6 membered heteroalkyl, or 2 to 4 membered heteroalkyl). In embodiments, $R^3$ is independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is independently substituted cycloalkyl (e.g., $C_3$-$C_8$ cycloalkyl, $C_3$-$C_6$ cycloalkyl, or $C_5$-$C_6$ cycloalkyl). In embodiments, $R^3$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is independently substituted heterocycloalkyl (e.g., 3 to 8 membered heterocycloalkyl, 3 to 6 membered heterocycloalkyl, or 5 to 6 membered heterocycloalkyl). In embodiments, $R^3$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is independently substituted or unsubstituted aryl (e.g., $C_6$-$C_{10}$ aryl, $C_{10}$ aryl, or phenyl). In embodiments, $R^3$ is independently substituted aryl (e.g., $C_6$-$C_{10}$ aryl, $C_{10}$ aryl, or phenyl). In embodiments, $R^3$ is independently an unsubstituted aryl (e.g., $C_6$-$C_{10}$ aryl, $C_{10}$ aryl, or phenyl). In embodiments, $R^3$ is independently substituted or unsubstituted heteroaryl (e.g., 5 to 10 membered heteroaryl, 5 to 9 membered heteroaryl, or 5 to 6 membered heteroaryl). In embodiments, $R^3$ is independently substituted heteroaryl (e.g., 5 to 10 membered heteroaryl, 5 to 9 membered heteroaryl, or 5 to 6 membered heteroaryl). In embodiments, $R^3$ is independently an unsubstituted heteroaryl (e.g., 5 to 10 membered heteroaryl, 5 to 9 membered heteroaryl, or 5 to 6 membered heteroaryl).

In embodiments, $R^3$ is independently halogen, —$CF_3$, —$CBr_3$, —$CCl_3$, —$CCl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, —$NHC(O)NHNH_2$, $R^{27}$-substituted or unsubstituted alkyl (e.g., $C_1$-$C_8$ alkyl, $C_1$-$C_6$ alkyl, or $C_1$-$C_4$ alkyl), $R^{27}$-substituted or unsubstituted heteroalkyl (e.g., 2 to 8 membered heteroalkyl, 2 to 6 membered heteroalkyl, or 2 to 4 membered heteroalkyl), $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27}$-substituted or unsubstituted aryl (e.g., $C_6$-$C_{10}$ aryl, $C_{10}$ aryl, or phenyl), or $R^{27}$-substituted or unsubstituted heteroaryl (e.g., 5 to 10 membered heteroaryl, 5 to 9 membered heteroaryl, or 5 to 6 membered heteroaryl). In embodiments, $R^3$ is independently halogen, —$CF_3$, —$CBr_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^3$ is independently R$^{27}$-substituted or unsubstituted alkyl (e.g., C$_1$-C$_8$ alkyl, C$_1$-C$_6$ alkyl, or C$_1$-C$_4$ alkyl). In embodiments, R$^3$ is independently R$^{27}$-substituted alkyl (e.g., C$_1$-C$_8$ alkyl, C$_1$-C$_6$ alkyl, or C$_1$-C$_4$ alkyl). In embodiments, R$^3$ is independently an unsubstituted alkyl (e.g., C$_1$-C$_8$ alkyl, C$_1$-C$_6$ alkyl, or C$_1$-C$_4$ alkyl). In embodiments, R$^3$ is independently R$^{27}$-substituted or unsubstituted heteroalkyl (e.g., 2 to 8 membered heteroalkyl, 2 to 6 membered heteroalkyl, or 2 to 4 membered heteroalkyl). In embodiments, R$^3$ is independently R$^{27}$-substituted heteroalkyl (e.g., 2 to 8 membered heteroalkyl, 2 to 6 membered heteroalkyl, or 2 to 4 membered heteroalkyl). In embodiments, R$^3$ is independently an unsubstituted heteroalkyl (e.g., 2 to 8 membered heteroalkyl, 2 to 6 membered heteroalkyl, or 2 to 4 membered heteroalkyl). In embodiments, R$^3$ is independently R$^{27}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^3$ is independently R$^{27}$-substituted cycloalkyl (e.g., C$_3$-C$_8$ cycloalkyl, C$_3$-C$_6$ cycloalkyl, or C$_5$-C$_6$ cycloalkyl). In embodiments, R$^3$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^3$ is independently R$^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^3$ is independently R$^{27}$-substituted heterocycloalkyl (e.g., 3 to 8 membered heterocycloalkyl, 3 to 6 membered heterocycloalkyl, or 5 to 6 membered heterocycloalkyl). In embodiments, R$^3$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^3$ is independently R$^{27}$-substituted or unsubstituted aryl (e.g., C$_6$-C$_{10}$ aryl, C$_{10}$ aryl, or phenyl). In embodiments, R$^3$ is independently R$^{27}$-substituted aryl (e.g., C$_6$-C$_{10}$ aryl, C$_{10}$ aryl, or phenyl). In embodiments, R$^3$ is independently an unsubstituted aryl (e.g., C$_6$-C$_{10}$ aryl, C$_{10}$ aryl, or phenyl). In embodiments, R$^3$ is independently R$^{27}$-substituted or unsubstituted heteroaryl (e.g., 5 to 10 membered heteroaryl, 5 to 9 membered heteroaryl, or 5 to 6 membered heteroaryl). In embodiments, R$^3$ is independently R$^{27}$-substituted heteroaryl (e.g., 5 to 10 membered heteroaryl, 5 to 9 membered heteroaryl, or 5 to 6 membered heteroaryl). In embodiments, R$^3$ is independently an unsubstituted heteroaryl (e.g., 5 to 10 membered heteroaryl, 5 to 9 membered heteroaryl, or 5 to 6 membered heteroaryl).

In embodiments, R$^3$ is independently —CX$^3{}_3$. In embodiments, R$^3$ is independently —CHX$^3{}_2$. In embodiments, R$^3$ is independently —CH$_2$X$^3$. In embodiments, R$^3$ is independently —OCX$^3{}_3$. In embodiments, R$^3$ is independently —OCH$_2$X$^3$. In embodiments, R$^3$ is independently —OCHX$^3{}_2$. In embodiments, R$^3$ is independently —CN. In embodiments, R$^3$ is independently —SR$^{3D}$. In embodiments, R$^3$ is independently —SOR$^{3D}$. In embodiments, R$^3$ is independently SO$_2$R$^{3D}$. In embodiments, R$^3$ is independently SO$_3$R$^{3D}$. In embodiments, R$^3$ is independently SO$_4$R$^{3D}$. In embodiments, R$^3$ is independently —SONR$^{3A}$R$^{3B}$. In embodiments, R$^3$ is independently SO$_2$NR$^{3A}$R$^{3B}$. In embodiments, R$^3$ is independently —NHC(O)NR$^{3A}$R$^{3B}$. In embodiments, R$^3$ is independently —N(O). In embodiments, R$^3$ is independently —N(O)$_2$. In embodiments, R$^3$ is independently —NR$^{3A}$R$^{3B}$. In embodiments, R$^3$ is independently —C(O)R$^{3C}$. In embodiments, R$^3$ is independently —C(O)—OR$^{3C}$. In embodiments, R$^3$ is independently —C(O)NR$^{3A}$R$^{3B}$. In embodiments, R$^3$ is independently —OR$^{3D}$. In embodiments, R$^3$ is independently —NR$^{3A}$SO$_2$R$^{3D}$. In embodiments, R$^3$ is independently —NR$^{3A}$C(O)R$^{3C}$. In embodiments, R$^3$ is independently —NR$^{3A}$C(O)OR$^{3C}$. In embodiments, R$^3$ is independently —NR$^{3A}$OR$^{3C}$.

In embodiments, R$^3$ is independently oxo. In embodiments, R$^3$ is independently halogen. In embodiments, R$^3$ is independently —CCl$_3$. In embodiments, R$^3$ is independently —CBr$_3$. In embodiments, R$^3$ is independently —CF$_3$. In embodiments, R$^3$ is independently —CI$_3$. In embodiments, R$^3$ is independently —CHCl$_2$. In embodiments, R$^3$ is independently —CHBr$_2$. In embodiments, R$^3$ is independently —CHF$_2$. In embodiments, R$^3$ is independently —CHI$_2$. In embodiments, R$^3$ is independently —CH$_2$Cl. In embodiments, R$^3$ is independently —CH$_2$Br. In embodiments, R$^3$ is independently —CH$_2$F. In embodiments, R$^3$ is independently —CH$_2$I. In embodiments, R$^3$ is independently —CN. In embodiments, R$^3$ is independently —OH. In embodiments, R$^3$ is independently —NH$_2$. In embodiments, R$^3$ is independently —COOH. In embodiments, R$^3$ is independently —CONH$_2$. In embodiments, R$^3$ is independently —NO$_2$. In embodiments, R$^3$ is independently —SH. In embodiments, R$^3$ is independently —SO$_3$H. In embodiments, R$^3$ is independently —SO$_4$H. In embodiments, R$^3$ is independently —SO$_2$NH$_2$. In embodiments, R$^3$ is independently —NHNH$_2$. In embodiments, R$^3$ is independently —ONH$_2$. In embodiments, R$^3$ is independently —NHC(O)NHNH$_2$. In embodiments, R$^3$ is independently —NHC(O)NH$_2$. In embodiments, R$^3$ is independently —NHSO$_2$H. In embodiments, R$^3$ is independently —NHC(O)H. In embodiments, R$^3$ is independently —NHC(O)OH. In embodiments, R$^3$ is independently —NHOH. In embodiments, R$^3$ is independently —OCCl$_3$. In embodiments, R$^3$ is independently —OCF$_3$. In embodiments, R$^3$ is independently —OCBr$_3$. In embodiments, R$^3$ is independently —OCI$_3$. In embodiments, R$^3$ is independently —OCHCl$_2$. In embodiments, R$^3$ is independently —OCHBr$_2$. In embodiments, R$^3$ is independently —OCHI$_2$. In embodiments, R$^3$ is independently —OCHF$_2$. In embodiments, R$^3$ is independently —OCH$_2$Cl. In embodiments, R$^3$ is independently —OCH$_2$Br. In embodiments, R$^3$ is independently —OCH$_2$I. In embodiments, R$^3$ is independently —OCH$_2$F. In embodiments, R$^3$ is independently —N$_3$. In embodiments, R$^3$ is independently —OCH$_3$. In embodiments, R$^3$ is idenpendently —CH$_3$. In embodiments, R$^3$ is idenpendently —CH$_2$CH$_3$. In embodiments, R$^3$ is independently unsubstituted propyl. In embodiments, R$^3$ is independently unsubstituted isopropyl. In embodiments, R$^3$ is independently unsubstituted butyl. In embodiments, R$^3$ is independently unsubstituted tert-butyl. In embodiments, R$^3$ is independently —F. In embodiments, $R^3$ is independently —Cl. In embodiments, $R^3$ is independently —Br. In embodiments, $R^3$ is independently —I.

$R^{27}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, $R^{27}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{27}$ is independently oxo. In embodiments, $R^{27}$ is independently halogen. In embodiments, $R^{27}$ is independently —CCl$_3$. In embodiments, $R^{27}$ is independently —CBr$_3$. In embodiments, $R^{27}$ is independently —CF$_3$. In embodiments, $R^{27}$ is independently —CI$_3$. In embodiments, $R^{27}$ is independently —CHCl$_2$. In embodiments, $R^{27}$ is independently —CHBr$_2$. In embodiments, $R^{27}$ is independently —CHF$_2$. In embodiments, $R^{27}$ is independently —CHI$_2$. In embodiments, $R^{27}$ is independently —CH$_2$Cl. In embodiments, $R^{27}$ is independently —CH$_2$Br. In embodiments, $R^{27}$ is independently —CH$_2$F. In embodiments, $R^{27}$ is independently —CH$_2$I. In embodiments, $R^{27}$ is independently —CN. In embodiments, $R^{27}$ is independently —OH. In embodiments, $R^{27}$ is independently —NH$_2$. In embodiments, $R^{27}$ is independently —COOH. In embodiments, $R^{27}$ is independently —CONH$_2$. In embodiments, $R^{27}$ is independently —NO$_2$. In embodiments, $R^{27}$ is independently —SH. In embodiments, $R^{27}$ is independently —SO$_3$H. In embodiments, $R^{27}$ is independently —SO$_4$H. In embodiments, $R^{27}$ is independently —SO$_2$NH$_2$. In embodiments, $R^{27}$ is independently —NHNH$_2$. In embodiments, $R^{27}$ is independently —ONH$_2$. In embodiments, $R^{27}$ is independently —NHC(O)NHNH$_2$. In embodiments, $R^{27}$ is independently —NHC(O)NH$_2$. In embodiments, $R^{27}$ is independently —NHSO$_2$H. In embodiments, $R^{27}$ is independently —NHC(O)H. In embodiments, $R^{27}$ is independently —NHC(O)OH. In embodiments, $R^{27}$ is independently —NHOH. In embodiments, $R^{27}$ is independently —OCCl$_3$. In embodiments, $R^{27}$ is independently —OCF$_3$. In embodiments, $R^{27}$ is independently —OCBr$_3$. In embodiments, $R^{27}$ is independently —OCI$_3$. In embodiments, $R^{27}$ is independently —OCHCl$_2$. In embodiments, $R^{27}$ is independently —OCHBr$_2$. In embodiments, $R^{27}$ is independently —OCHI$_2$. In embodiments, $R^{27}$ is independently —OCHF$_2$. In embodiments, $R^{27}$ is independently —OCH$_2$Cl. In embodiments, $R^{27}$ is independently —OCH$_2$Br. In embodiments, $R^{27}$ is independently —OCH$_2$I. In embodiments, $R^{27}$ is independently —OCH$_2$F. In embodiments, $R^{27}$ is independently —N$_3$. In embodiments, $R^{27}$ is independently —OCH$_3$. In embodiments, $R^{27}$ is independently —CH$_3$. In embodiments, $R^{27}$ is independently —CH$_2$CH$_3$. In embodiments, $R^{27}$ is independently unsubstituted propyl. In embodiments, $R^{27}$ is independently unsubstituted isopropyl. In embodiments, $R^{27}$ is independently unsubstituted butyl. In embodiments, $R^{27}$ is independently unsubstituted tert-butyl. In embodiments, $R^{27}$ is independently —F. In embodiments, $R^{27}$ is independently —Cl. In embodiments, $R^{27}$ is independently —Br. In embodiments, $R^{27}$ is independently —I.

In embodiments, $R^{27}$ is independently $R^{28}$-substituted or unsubstituted alkyl (e.g., $C_1$-$C_8$ alkyl, $C_1$-$C_6$ alkyl, or $C_1$-$C_4$ alkyl). In embodiments, $R^{27}$ is independently $R^{28}$-substituted alkyl (e.g., $C_1$-$C_8$ alkyl, $C_1$-$C_6$ alkyl, or $C_1$-$C_4$ alkyl). In embodiments, $R^{27}$ is independently an unsubstituted alkyl (e.g., $C_1$-$C_8$ alkyl, $C_1$-$C_6$ alkyl, or $C_1$-$C_4$ alkyl). In embodiments, $R^{27}$ is independently $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^{27}$ is independently $R^{28}$-substituted heteroalkyl (e.g., 2 to 8 membered heteroalkyl, 2 to 6 membered heteroalkyl, or 2 to 4 membered heteroalkyl). In embodiments, $R^{27}$ is independently an unsubstituted heteroalkyl (e.g., 2 to 8 membered heteroalkyl, 2 to 6 membered heteroalkyl, or 2 to 4 membered heteroalkyl). In embodiments, $R^{27}$ is independently $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{27}$ is independently $R^{28}$-substituted cycloalkyl (e.g., $C_3$-$C_8$ cycloalkyl, $C_3$-$C_6$ cycloalkyl, or $C_5$-$C_6$ cycloalkyl). In embodiments, $R^{27}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{27}$ is independently $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{27}$ is independently $R^{28}$-substituted heterocycloalkyl (e.g., 3 to 8 membered heterocycloalkyl, 3 to 6 membered heterocycloalkyl, or 5 to 6 membered heterocycloalkyl). In embodiments, $R^{27}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{27}$ is independently $R^{28}$-substituted or unsubstituted aryl (e.g., $C_6$-$C_{10}$ aryl, $C_{10}$ aryl, or phenyl). In embodiments, $R^{27}$ is independently $R^{28}$-substituted aryl (e.g., $C_6$-$C_{10}$ aryl, $C_{10}$ aryl, or phenyl). In embodiments, $R^{27}$ is independently an unsubstituted aryl (e.g., $C_6$-$C_{10}$ aryl, $C_{10}$ aryl, or phenyl). In embodiments, $R^{27}$ is independently $R^{28}$-substituted or unsubstituted heteroaryl (e.g., 5 to 10 membered heteroaryl, 5 to 9 membered heteroaryl, or 5 to 6 membered heteroaryl). In embodiments, $R^{27}$ is independently $R^{28}$-substituted heteroaryl (e.g., 5 to 10 membered heteroaryl, 5 to 9 membered heteroaryl, or 5 to 6 membered heteroaryl). In embodiments, $R^{27}$ is independently an unsubstituted heteroaryl (e.g., 5 to 10 membered heteroaryl, 5 to 9 membered heteroaryl, or 5 to 6 membered heteroaryl).

$R^{28}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{29}$-substituted or unsubstituted alkyl (e.g., C$_1$-C$_8$ alkyl, C$_1$-C$_6$ alkyl, or C$_1$-C$_4$ alkyl), $R^{29}$-substituted or unsubstituted heteroalkyl (e.g., 2 to 8 membered heteroalkyl, 2 to 6 membered heteroalkyl, or 2 to 4 membered heteroalkyl), $R^{29}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{29}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29}$-substituted or unsubstituted aryl (e.g., C$_6$-C$_{10}$ aryl, C$_{10}$ aryl, or phenyl), or $R^{29}$-substituted or unsubstituted heteroaryl (e.g., 5 to 10 membered heteroaryl, 5 to 9 membered heteroaryl, or 5 to 6 membered heteroaryl). In embodiments, $R^{28}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{28}$ is independently $R^{29}$-substituted or unsubstituted alkyl (e.g., C$_1$-C$_8$ alkyl, C$_1$-C$_6$ alkyl, or C$_1$-C$_4$ alkyl). In embodiments, $R^{28}$ is independently $R^{29}$-substituted alkyl (e.g., C$_1$-C$_8$ alkyl, C$_1$-C$_6$ alkyl, or C$_1$-C$_4$ alkyl). In embodiments, $R^{28}$ is independently an unsubstituted alkyl (e.g., C$_1$-C$_8$ alkyl, C$_1$-C$_6$ alkyl, or C$_1$-C$_4$ alkyl). In embodiments, $R^{28}$ is independently $R^{29}$-substituted or unsubstituted heteroalkyl (e.g., 2 to 8 membered heteroalkyl, 2 to 6 membered heteroalkyl, or 2 to 4 membered heteroalkyl). In embodiments, $R^{28}$ is independently $R^{29}$-substituted heteroalkyl (e.g., 2 to 8 membered heteroalkyl, 2 to 6 membered heteroalkyl, or 2 to 4 membered heteroalkyl). In embodiments, $R^{28}$ is independently an unsubstituted heteroalkyl (e.g., 2 to 8 membered heteroalkyl, 2 to 6 membered heteroalkyl, or 2 to 4 membered heteroalkyl). In embodiments, $R^{28}$ is independently $R^{29}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{28}$ is independently $R^{29}$-substituted cycloalkyl (e.g., C$_3$-C$_8$ cycloalkyl, C$_3$-C$_6$ cycloalkyl, or C$_5$-C$_6$ cycloalkyl). In embodiments, $R^{28}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, $R^{28}$ is independently $R^{29}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28}$ is independently $R^{29}$-substituted heterocycloalkyl (e.g., 3 to 8 membered heterocycloalkyl, 3 to 6 membered heterocycloalkyl, or 5 to 6 membered heterocycloalkyl). In embodiments, $R^{28}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{28}$ is independently $R^{29}$-substituted or unsubstituted aryl (e.g., C$_6$-C$_{10}$ aryl, C$_{10}$ aryl, or phenyl). In embodiments, $R^{28}$ is independently $R^{29}$-substituted aryl (e.g., C$_6$-C$_{10}$ aryl, C$_{10}$ aryl, or phenyl). In embodiments, $R^{28}$ is independently an unsubstituted aryl (e.g., C$_6$-C$_{10}$ aryl, C$_{10}$ aryl, or phenyl). In embodiments, $R^{28}$ is independently $R^{29}$-substituted or unsubstituted heteroaryl (e.g., 5 to 10 membered heteroaryl, 5 to 9 membered heteroaryl, or 5 to 6 membered heteroaryl). In embodiments, $R^{28}$ is independently $R^{29}$-substituted heteroaryl (e.g., 5 to 10 membered heteroaryl, 5 to 9 membered heteroaryl, or 5 to 6 membered heteroaryl). In embodiments, $R^{28}$ is independently an unsubstituted heteroaryl (e.g., 5 to 10 membered heteroaryl, 5 to 9 membered heteroaryl, or 5 to 6 membered heteroaryl).

In embodiments, $R^{28}$ is independently oxo. In embodiments, $R^{28}$ is independently halogen. In embodiments, $R^{28}$ is independently —CCl$_3$. In embodiments, $R^{28}$ is independently —CBr$_3$. In embodiments, $R^{28}$ is independently —CF$_3$. In embodiments, $R^{28}$ is independently —CI$_3$. In embodiments, $R^{28}$ is independently —CHCl$_2$. In embodiments, $R^{28}$ is independently —CHBr$_2$. In embodiments, $R^{28}$ is independently —CHF$_2$. In embodiments, $R^{28}$ is independently —CHI$_2$. In embodiments, $R^{28}$ is independently —CH$_2$Cl. In embodiments, $R^{28}$ is independently —CH$_2$Br. In embodiments, $R^{28}$ is independently —CH$_2$F. In embodiments, $R^{28}$ is independently —CH$_2$I. In embodiments, $R^{28}$ is independently —CN. In embodiments, $R^{28}$ is independently —OH. In embodiments, $R^{28}$ is independently —NH$_2$. In embodiments, $R^{28}$ is independently —COOH. In embodiments, $R^{28}$ is independently —CONH$_2$. In embodiments, $R^{28}$ is independently —NO$_2$. In embodiments, $R^{28}$ is independently —SH. In embodiments, $R^{28}$ is independently —SO$_3$H. In embodiments, $R^{28}$ is independently —SO$_4$H. In embodiments, $R^{28}$ is independently —SO$_2$NH$_2$. In embodiments, $R^{28}$ is independently —NHNH$_2$. In embodiments, $R^{28}$ is independently —ONH$_2$. In embodiments, $R^{28}$ is independently —NHC(O)NHNH$_2$. In embodiments, $R^{28}$ is independently —NHC(O)NH$_2$. In embodiments, $R^{28}$ is independently —NHSO$_2$H. In embodiments, $R^{28}$ is independently —NHC(O)H. In embodiments, $R^{28}$ is independently —NHC(O)OH. In embodiments, $R^{28}$ is independently —NHOH. In embodiments, $R^{28}$ is independently —OCCl$_3$. In embodiments, $R^{28}$ is independently —OCF$_3$. In embodiments, $R^{28}$ is independently —OCBr$_3$. In embodiments, $R^{28}$ is independently —OCI$_3$. In embodiments, $R^{28}$ is independently —OCHCl$_2$. In embodiments, $R^{28}$ is independently —OCHBr$_2$. In embodiments, $R^{28}$ is independently —OCHI$_2$. In embodiments, $R^{28}$ is independently —OCHF$_2$. In embodiments, $R^{28}$ is independently —OCH$_2$Cl. In embodiments, $R^{28}$ is independently —OCH$_2$Br. In embodiments, $R^{28}$ is independently —OCH$_2$I. In embodiments, $R^{28}$ is independently —OCH$_2$F. In embodiments, $R^{28}$ is independently —N$_3$. In embodiments, $R^{28}$ is independently —OCH$_3$. In embodiments, $R^{28}$ is idenpendently —CH$_3$. In embodiments, $R^{28}$ is idenpendently —CH$_2$CH$_3$. In embodiments, $R^{28}$ is independently unsubstituted propyl. In embodiments, $R^{28}$ is independently unsubstituted isopropyl.

In embodiments, $R^{28}$ is independently unsubstituted butyl. In embodiments, $R^{28}$ is independently unsubstituted tert-butyl. In embodiments, $R^{28}$ is independently —F. In embodiments, $R^{28}$ is independently —Cl. In embodiments, $R^{28}$ is independently —Br. In embodiments, $R^{28}$ is independently —I.

$R^{29}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{29}$ is independently an unsubstituted alkyl (e.g., $C_1$-$C_8$ alkyl, $C_1$-$C_6$ alkyl, or $C_1$-$C_4$ alkyl). In embodiments, $R^{29}$ is independently an unsubstituted heteroalkyl (e.g., 2 to 8 membered heteroalkyl, 2 to 6 membered heteroalkyl, or 2 to 4 membered heteroalkyl). In embodiments, $R^{29}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{29}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{29}$ is independently an unsubstituted aryl (e.g., $C_6$-$C_{10}$ aryl, $C_{10}$ aryl, or phenyl). In embodiments, $R^{29}$ is independently an unsubstituted heteroaryl (e.g., 5 to 10 membered heteroaryl, 5 to 9 membered heteroaryl, or 5 to 6 membered heteroaryl).

In embodiments, $R^{29}$ is independently oxo. In embodiments, $R^{29}$ is independently halogen. In embodiments, $R^{29}$ is independently —$CCl_3$. In embodiments, $R^{29}$ is independently —$CBr_3$. In embodiments, $R^{29}$ is independently —$CF_3$. In embodiments, $R^{29}$ is independently —$CI_3$. In embodiments, $R^{29}$ is independently —$CHCl_2$. In embodiments, $R^{29}$ is independently —$CHBr_2$. In embodiments, $R^{29}$ is independently —$CHF_2$. In embodiments, $R^{29}$ is independently —$CHI_2$. In embodiments, $R^{29}$ is independently —$CH_2Cl$. In embodiments, $R^{29}$ is independently —$CH_2Br$. In embodiments, $R^{29}$ is independently —$CH_2F$. In embodiments, $R^{29}$ is independently —$CH_2I$. In embodiments, $R^{29}$ is independently —CN. In embodiments, $R^{29}$ is independently —OH. In embodiments, $R^{29}$ is independently —$NH_2$. In embodiments, $R^{29}$ is independently —COOH. In embodiments, $R^{29}$ is independently —$CONH_2$. In embodiments, $R^{29}$ is independently —$NO_2$. In embodiments, $R^{29}$ is independently —SH. In embodiments, $R^{29}$ is independently —$SO_3H$. In embodiments, $R^{29}$ is independently —$SO_4H$. In embodiments, $R^{29}$ is independently —$SO_2NH_2$. In embodiments, $R^{29}$ is independently —$NHNH_2$. In embodiments, $R^{29}$ is independently —$ONH_2$. In embodiments, $R^{29}$ is independently —NHC(O)$NHNH_2$. In embodiments, $R^{29}$ is independently —NHC(O)$NH_2$. In embodiments, $R^{29}$ is independently —$NHSO_2H$. In embodiments, $R^{29}$ is independently —NHC(O)H. In embodiments, $R^{29}$ is independently —NHC(O)OH. In embodiments, $R^{29}$ is independently —NHOH. In embodiments, $R^{29}$ is independently —$OCCl_3$. In embodiments, $R^{29}$ is independently —$OCF_3$. In embodiments, $R^{29}$ is independently —$OCBr_3$. In embodiments, $R^{29}$ is independently —$OCI_3$. In embodiments, $R^{29}$ is independently —$OCHCl_2$. In embodiments, $R^{29}$ is independently —$OCHBr_2$. In embodiments, $R^{29}$ is independently —$OCHI_2$. In embodiments, $R^{29}$ is independently —$OCHF_2$. In embodiments, $R^{29}$ is independently —$OCH_2Cl$. In embodiments, $R^{29}$ is independently —$OCH_2Br$. In embodiments, $R^{29}$ is independently —$OCH_2I$. In embodiments, $R^{29}$ is independently —$OCH_2F$. In embodiments, $R^{29}$ is independently —$N_3$. In embodiments, $R^{29}$ is independently —$OCH_3$. In embodiments, $R^{29}$ is independently —$CH_3$. In embodiments, $R^{29}$ is independently —$CH_2CH_3$. In embodiments, $R^{29}$ is independently unsubstituted propyl. In embodiments, $R^{29}$ is independently unsubstituted isopropyl. In embodiments, $R^{29}$ is independently unsubstituted butyl. In embodiments, $R^{29}$ is independently unsubstituted tert-butyl. In embodiments, $R^{29}$ is independently —F. In embodiments, $R^{29}$ is independently —Cl. In embodiments, $R^{29}$ is independently —Br. In embodiments, $R^{29}$ is independently —I.

In embodiments, two (e.g., adjacent) $R^3$ substituents are independently joined to form a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^3$ substituents are independently joined to form a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^3$ substituents are independently joined to form a substituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^3$ substituents are independently joined to form an unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^3$ substituents are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^3$ substituents are independently joined to form a substituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^3$ substituents are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^3$ substituents are independently joined to form a substituted or unsubstituted aryl (e.g., $C_6$-$C_{10}$ aryl, $C_{10}$ aryl, or phenyl). In embodiments, two (e.g., adjacent) $R^3$ substituents are independently joined to form a substituted aryl (e.g., $C_6$-$C_{10}$ aryl, $C_{10}$ aryl, or phenyl). In embodiments, two (e.g., adjacent) $R^3$ substituents are independently joined to form an unsubstituted aryl (e.g., $C_6$-$C_{10}$ aryl, $C_{10}$ aryl, or phenyl). In embodiments, two (e.g., adjacent) $R^3$ substituents are independently joined to form a substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^3$ substituents are independently joined to form a substituted heteroaryl (e.g., 5 to 10 membered heteroaryl, 5 to 9 membered heteroaryl, or 5 to 6 membered heteroaryl). In embodiments, two (e.g., adjacent) $R^3$ substituents are independently joined to form an unsubstituted heteroaryl (e.g., 5 to 10 membered heteroaryl, 5 to 9 membered heteroaryl, or 5 to 6 membered heteroaryl). In embodiments, two (e.g., adjacent) $R^3$ substituents are independently joined to form an $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^3$ substituents are independently joined to form an $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^3$ substituents are independently joined to form an unsubstituted cycloalkyl (e.g., $C_3$-$C_8$ cycloalkyl, $C_3$-$C_6$ cycloalkyl, or $C_5$-$C_6$ cycloalkyl). In embodiments, two (e.g., adjacent) $R^3$ substituents are independently joined to form an $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^3$ substituents are independently joined to form an $R^{27}$-substituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^3$ substituents are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, two (e.g., adjacent) $R^3$ substituents are independently joined to form an $R^{27}$-substituted or unsubstituted aryl (e.g., $C_6$-$C_{10}$ aryl, $C_{10}$ aryl, or phenyl). In embodiments, two (e.g., adjacent) $R^3$ substituents are independently joined to form an $R^{27}$-substituted aryl (e.g., $C_6$-$C_{10}$ aryl, $C_{10}$ aryl, or phenyl). In embodiments, two (e.g., adjacent) $R^3$ substituents are independently joined to form an unsubstituted aryl (e.g., $C_6$-$C_{10}$ aryl, $C_{10}$ aryl, or phenyl). In embodiments, two (e.g., adjacent) $R^3$ substituents are independently joined to form an $R^{27}$-substituted or unsubstituted heteroaryl (e.g., 5 to 10 membered heteroaryl, 5 to 9 membered heteroaryl, or 5 to 6 membered heteroaryl). In embodiments, two (e.g., adjacent) $R^3$ substituents are independently joined to form an $R^{27}$-substituted heteroaryl (e.g., 5 to 10 membered heteroaryl, 5 to 9 membered heteroaryl, or 5 to 6 membered heteroaryl). In embodiments, two (e.g., adjacent) $R^3$ substituents are independently joined to form an unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^3$ position. In embodiments, when the divalent linker bonded to both the monovalent cellular component binder and monovalent targeted autophagy protein binder is attached to the monovalent targeted autophagy protein binder at an $R^3$ position, $R^3$ is replaced with a divalent linker, referred to in this embodiment as $L^{R3}$.

$L^{R3}$ is a bond, —S(O)$_2$—, —S(O)—, —O—, —S—, —C(O)—, —C(O)NR$^{1A}$—, —NR$^{1A}$C(O)—, —NR$^{1A}$C(O)NH—, —NHC(O)NR$^{1A}$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. It will be understood that when $L^{R3}$- is =N—, one of the two direct covalent connections to $L^{R3}$ shown in "-$L^{R3}$-" is a double bond and $L^{R3}$ may equivalently be shown as "=$L^{R3}$-" and the atom to which the double bond is directly attached must obey standard rules of chemical valency known in the chemical arts and be capable of forming such a double bond.

In embodiments, $L^{R3}$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^{R3}$ is independently a —S(O)$_2$—. In embodiments, $L^{R3}$ is independently a —S(O)—. In embodiments, $L^{R3}$ is independently a —NH—. In embodiments, $L^{R3}$ is independently a —O—. In embodiments, $L^{R3}$ is independently a —S—. In embodiments, $L^{R3}$ is independently a —C(O)—. In embodiments, $L^{R3}$ is independently a —C(O)NH—. In embodiments, $L^{R3}$ is independently a —NHC(O)—. In embodiments, $L^{R3}$ is independently a —NHC(O)NH—. In embodiments, $L^{R3}$ is independently a —C(O)O—. In embodiments, $L^{R3}$ is independently —OC(O)—. In embodiments, $L^{R3}$ is independently —NR$^{3A}$—. In embodiments, $L^{R3}$ is independently —C(O)NR$^{3A}$—. In embodiments, $L^{R3}$ is independently —NR$^{3A}$C(O)—. In embodiments, $L^{R3}$ is independently —NR$^{3A}$C(O)NH—. In embodiments, $L^{R3}$ is independently —NHC(O)NR$^{3A}$—. In embodiments, $L^{R3}$ is independently a bond.

In embodiments, $L^{R3}$ is substituted or unsubstituted alkylene (e.g., $C_1$-$C_8$ alkylene, $C_1$-$C_6$ alkylene, or $C_1$-$C_4$ alkylene). In embodiments, $L^{R3}$ is substituted alkylene (e.g., $C_1$-$C_8$ alkylene, $C_1$-$C_6$ alkylene, or $C_1$-$C_4$ alkylene). In embodiments, $L^{R3}$ is an unsubstituted alkylene (e.g., $C_1$-$C_8$ alkylene, $C_1$-$C_6$ alkylene, or $C_1$-$C_4$ alkylene). In embodiments, $L^{R3}$ is substituted or unsubstituted heteroalkylene (e.g., 2 to 8 membered heteroalkylene, 2 to 6 membered heteroalkylene, or 2 to 4 membered heteroalkylene). In embodiments, $L^{R3}$ is substituted heteroalkylene (e.g., 2 to 8 membered heteroalkylene, 2 to 6 membered heteroalkylene, or 2 to 4 membered heteroalkylene). In embodiments, $L^{R3}$ is an unsubstituted heteroalkylene (e.g., 2 to 8 membered heteroalkylene, 2 to 6 membered heteroalkylene, or 2 to 4 membered heteroalkylene). In embodiments, $L^{R3}$ is substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R1}$ is substituted cycloalkylene (e.g., $C_3$-$C_8$ cycloalkylene, $C_3$-$C_6$ cycloalkylene, or $C_5$-$C_6$ cycloalkylene). In embodiments, $L^{R1}$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R3}$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^{R3}$ is substituted heterocycloalkylene (e.g., 3 to 8 membered heterocycloalkylene, 3 to 6 membered heterocycloalkylene, or 5 to 6 membered heterocycloalkylene). In embodiments, $L^{R3}$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^{R3}$ is substituted or unsubstituted arylene (e.g., $C_6$-$C_{10}$ arylene, $C_{10}$ arylene, or phenylene). In embodiments, $L^{R3}$ is substituted arylene (e.g., $C_6$-$C_{10}$ arylene, $C_{10}$ arylene, or phenylene). In embodiments, $L^{R3}$ is an unsubstituted arylene (e.g., $C_6$-$C_{10}$ arylene, $C_{10}$ arylene, or phenylene). In embodiments, $L^{R3}$ is substituted or unsubstituted heteroarylene (e.g., 5 to 10 membered heteroarylene, 5 to 9 membered heteroarylene, or 5 to 6 membered heteroarylene). In embodiments, $L^{R3}$ is substituted heteroarylene (e.g., 5 to 10 membered heteroarylene, 5 to 9 membered heteroarylene, or 5 to 6 membered heteroarylene). In embodiments, $L^{R3}$ is an unsubstituted heteroarylene (e.g., 5 to 10 membered heteroarylene, 5 to 9 membered heteroarylene, or 5 to 6 membered heteroarylene).

In embodiments, $L^{R3}$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, $R^{27}$-substituted or unsubstituted alkylene (e.g., $C_1$-$C_8$ alkylene, $C_1$-$C_6$ alkylene, or $C_1$-$C_4$ alkylene), $R^{27}$-substituted or unsubstituted heteroalkylene (e.g., 2 to 8 membered heteroalkylene, 2 to 6 membered heteroalkylene, or 2 to 4 membered heteroalkylene), $R^{27}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{27}$-substituted or unsubstituted heterocycloalkylene (e.g., 3 to 8 membered heterocycloalkylene, 3 to 6 membered heterocycloalkylene, or 5 to 6 membered heterocycloalkylene), $R^{27}$-substituted or unsubstituted arylene (e.g., $C_6$-$C_{10}$ arylene, $C_{10}$ arylene, or phenylene), or $R^{27}$-substituted or unsubstituted heteroarylene (e.g., 5 to 10 membered heteroarylene, 5 to 9 membered heteroarylene, or 5 to 6 membered heteroarylene). In embodiments, $L^{R3}$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, $L^{R3}$ is $R^{27}$-substituted or unsubstituted alkylene (e.g., $C_1$-$C_8$ alkylene, $C_1$-$C_6$ alkylene, or $C_1$-$C_4$ alkylene). In embodiments, $L^{R3}$ is $R^{27}$-substituted alkylene (e.g., $C_1$-$C_8$ alkylene, $C_1$-$C_6$ alkylene, or $C_1$-$C_4$ alkylene). In embodiments, $L^{R3}$ is an unsubstituted alkylene (e.g., $C_1$-$C_8$ alkylene, $C_1$-$C_6$ alkylene, or $C_1$-$C_4$ alkylene). In embodiments, $L^{R3}$ is $R^{27}$-substituted or unsubstituted heteroalkylene (e.g., 2 to 8 membered heteroalkylene, 2 to 6 membered heteroalkylene, or 2 to 4 membered heteroalkylene). In embodiments, $L^{R3}$ is $R^{27}$-substituted heteroalkylene (e.g., 2 to 8 membered heteroalkylene, 2 to 6 membered heteroalkylene, or 2 to 4 membered heteroalkylene). In embodiments, $L^{R3}$ is an unsubstituted heteroalkylene (e.g., 2 to 8 membered heteroalkylene, 2 to 6 membered heteroalkylene, or 2 to 4 membered heteroalkylene). In embodiments, $L^{R3}$ is $R^{27}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R3}$ is $R^{27}$-substituted cycloalkylene (e.g., $C_3$-$C_8$ cycloalkylene, $C_3$-$C_6$ cycloalkylene, or $C_5$-$C_6$ cycloalkylene). In embodiments, $L^{R3}$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^{R3}$ is $R^{27}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^{R3}$ is $R^{27}$-substituted heterocycloalkylene (e.g., 3 to 8 membered heterocycloalkylene, 3 to 6 membered heterocycloalkylene, or 5 to 6 membered heterocycloalkylene). In embodiments, $L^{R3}$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^{R3}$ is $R^{27}$-substituted or unsubstituted arylene (e.g., $C_6$-$C_{10}$ arylene, $C_{10}$ arylene, or phenylene). In embodiments, $L^{R3}$ is $R^{27}$-substituted arylene (e.g., $C_6$-$C_{10}$ arylene, $C_{10}$ arylene, or phenylene). In embodiments, $L^{R3}$ is an unsubstituted arylene (e.g., $C_6$-$C_{10}$ arylene, $C_{10}$ arylene, or phenylene). In embodiments, $L^{R3}$ is $R^{27}$-substituted or unsubstituted heteroarylene (e.g., 5 to 10 membered heteroarylene, 5 to 9 membered heteroarylene, or 5 to 6 membered heteroarylene). In embodiments, $L^{R3}$ is $R^{27}$-substituted heteroarylene (e.g., 5 to 10 membered heteroarylene, 5 to 9 membered heteroarylene, or 5 to 6 membered heteroarylene). In embodiments, $L^{R3}$ is an unsubstituted heteroarylene (e.g., 5 to 10 membered heteroarylene, 5 to 9 membered heteroarylene, or 5 to 6 membered heteroarylene).

In embodiments, $R^{3A}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{3A}$ position. In embodiments, when the divalent linker bonded to both the monovalent cellular component binder and monovalent targeted autophagy protein binder is attached to the monovalent targeted autophagy protein binder at an $R^{3A}$ position, $R^{3A}$ is replaced with a divalent linker, referred to in this embodiment as $L^{R3}$.

In embodiments, $R^{3B}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{3B}$ position. In embodiments, when the divalent linker bonded to both the monovalent cellular component binder and monovalent targeted autophagy protein binder is attached to the monovalent targeted autophagy protein binder at an $R^{3B}$ position, $R^{3B}$ is replaced with a divalent linker, referred to in this embodiment as $L^{R3}$.

In embodiments, $R^{3C}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{3C}$ position. In embodiments, when the divalent linker bonded to both the monovalent cellular component binder and monovalent targeted autophagy protein binder is attached to the monovalent targeted autophagy protein binder at an $R^{3C}$ position, $R^{3C}$ is replaced with a divalent linker, referred to in this embodiment as $L^{R3}$.

In embodiments, $R^{3D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, the divalent linker bonded to both the monovalent cellular component binder and monovalent targeted autophagy protein binder is attached to the monovalent targeted autophagy protein binder at an $R^{3D}$ position. In embodiments, when the divalent linker bonded to both the monovalent cellular component binder and monovalent targeted autophagy protein binder is attached to the monovalent targeted autophagy protein binder at an $R^{3D}$ position, $R^{3D}$ is replaced with a divalent linker, referred to in this embodiment as $L^{R3}$.

In embodiments, $R^{3A}$ and $R^{3B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ and $R^{3B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{3A}$ and $R^{3B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ and $R^{3B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{3A}$, $R^{3B}$, $R^{1C}$, and $R^{3D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{27}$-substituted or unsubstituted alkyl (e.g., $C_1$-$C_8$ alkyl, $C_1$-$C_6$ alkyl, or $C_1$-$C_4$ alkyl), $R^{27}$-substituted or unsubstituted heteroalkyl (e.g., 2 to 8 membered heteroalkyl, 2 to 6 membered heteroalkyl, or 2 to 4 membered heteroalkyl), $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27}$-substituted or unsubstituted aryl (e.g., $C_6$-$C_{10}$ aryl, $C_{10}$ aryl, or phenyl), or $R^{27}$-substituted or unsubstituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are independently joined to form an $R^{27}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{27}$-substituted or unsubstituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are independently joined to form an $R^{27}$-substituted or unsubstituted heterocycloalkyl (e.g., 3 to 8 membered heterocycloalkyl, 3 to 6 membered heterocycloalkyl. In embodiments, $R^{3A}$ and $R^{3B}$ substituents bonded to the same nitrogen atom are independently joined to form an $R^{27}$-substituted or unsubstituted heteroaryl (e.g., 5 to 10 membered heteroaryl, 5 to 9 membered heteroaryl, or 5 to 6 membered heteroaryl).

In embodiments, $R^{3A}$ is independently $R^{27}$-substituted or unsubstituted alkyl (e.g., $C_1$-$C_8$ alkyl, $C_1$-$C_6$ alkyl, or $C_1$-$C_4$ alkyl). In embodiments, $R^{3A}$ is independently $R^{27}$-substituted alkyl (e.g., $C_1$-$C_8$ alkyl, $C_1$-$C_6$ alkyl, or $C_1$-$C_4$ alkyl). In embodiments, $R^{3A}$ is independently an unsubstituted alkyl (e.g., $C_1$-$C_8$ alkyl, $C_1$-$C_6$ alkyl, or $C_1$-$C_4$ alkyl). In embodiments, $R^{3A}$ is independently $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^{3A}$ is independently $R^{27}$-substituted heteroalkyl (e.g., 2 to 8 membered heteroalkyl, 2 to 6 membered heteroalkyl, or 2 to 4 membered heteroalkyl). In embodiments, $R^{3A}$ is independently an unsubstituted heteroalkyl (e.g., 2 to 8 membered heteroalkyl, 2 to 6 membered heteroalkyl, or 2 to 4 membered heteroalkyl). In embodiments, $R^{3A}$ is independently $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is independently $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is independently $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is independently $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is independently $R^{27}$-substituted or unsubstituted aryl (e.g., $C_6$-$C_{10}$ aryl, $C_{10}$ aryl, or phenyl). In embodiments, $R^{3A}$ is independently $R^{27}$-substituted aryl (e.g., $C_6$-$C_{10}$ aryl, $C_{10}$ aryl, or phenyl). In embodiments, $R^{3A}$ is independently an unsubstituted aryl (e.g., $C_6$-$C_{10}$ aryl, $C_{10}$ aryl, or phenyl). In embodiments, $R^{3A}$ is independently $R^{27}$-substituted or unsubstituted heteroaryl (e.g., 5 to 10 membered heteroaryl, 5 to 9 membered heteroaryl, or 5 to 6 membered heteroaryl). In embodiments, $R^{3A}$ is independently $R^{27}$-substituted heteroaryl (e.g., 5 to 10 membered heteroaryl, 5 to 9 membered heteroaryl, or 5 to 6 membered heteroaryl). In embodiments, $R^{3A}$ is independently an unsubstituted heteroaryl (e.g., 5 to 10 membered heteroaryl, 5 to 9 membered heteroaryl, or 5 to 6 membered heteroaryl).

In embodiments, $R^{3A}$ is independently —$CCl_3$. In embodiments, $R^{3A}$ is independently —$CBr_3$. In embodiments, $R^{3A}$ is independently —$CF_3$. In embodiments, $R^{3A}$ is independently —$CI_3$. In embodiments, $R^{3A}$ is independently —$CHCl_2$. In embodiments, $R^{3A}$ is independently —$CHBr_2$. In embodiments, $R^{3A}$ is independently —$CHF_2$. In embodiments, $R^{3A}$ is independently —$CHI_2$. In embodiments, $R^{3A}$ is independently —$CH_2Cl$. In embodiments, $R^{3A}$ is independently —$CH_2Br$. In embodiments, $R^{3A}$ is independently —$CH_2F$. In embodiments, $R^{3A}$ is independently —$CH_2I$. In embodiments, $R^{3A}$ is independently —CN. In embodiments, $R^{3A}$ is independently —OH. In embodiments, $R^{3A}$ is independently —COOH. In embodiments, $R^{3A}$ is independently —$CONH_2$. In embodiments, $R^{3A}$ is independently —$OCCl_3$. In embodiments, $R^{3A}$ is independently —$OCF_3$. In embodiments, $R^{3A}$ is independently —$OCBr_3$. In embodiments, $R^{3A}$ is independently —$OCl_3$. In embodiments, $R^{3A}$ is independently —$OCHCl_2$. In embodiments, $R^{3A}$ is independently —$OCHBr_2$. In embodiments, $R^{3A}$ is independently —$OCHI_2$. In embodiments, $R^{3A}$ is independently —$OCHF_2$. In embodiments, $R^{3A}$ is independently —$OCH_2Cl$. In embodiments, $R^{3A}$ is independently —$OCH_2Br$. In embodiments, $R^{3A}$ is independently —$OCH_2I$. In embodiments, $R^{3A}$ is independently —$OCH_2F$. In embodiments, $R^{3A}$ is independently —$OCH_3$. In embodiments, $R^{3A}$ is independently $CH_3$. In embodiments, $R^{3A}$ is idenpendently —$CH_2CH_3$. In embodiments, $R^{3A}$ is independently unsubstituted propyl. In embodiments, $R^{3A}$ is independently unsubstituted isopropyl. In embodiments, $R^{3A}$ is independently unsubstituted butyl. In embodiments, $R^{3A}$ is independently unsubstituted tert-butyl. In embodiments, $R^{3A}$ is independently hydrogen.

In embodiments, $R^{3B}$ is independently $R^{27}$-substituted or unsubstituted alkyl (e.g., $C_1$-$C_8$ alkyl, $C_1$-$C_6$ alkyl, or $C_1$-$C_4$ alkyl). In embodiments, $R^{3B}$ is independently $R^{27}$-substituted alkyl (e.g., $C_1$-$C_8$ alkyl, $C_1$-$C_6$ alkyl, or $C_1$-$C_4$ alkyl). In embodiments, $R^{3B}$ is independently an unsubstituted alkyl (e.g., $C_1$-$C_8$ alkyl, $C_1$-$C_6$ alkyl, or $C_1$-$C_4$ alkyl). In embodiments, $R^{3B}$ is independently $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^{3B}$ is independently $R^{27}$-substituted heteroalkyl (e.g., 2 to 8 membered heteroalkyl, 2 to 6 membered heteroalkyl, or 2 to 4 membered heteroalkyl). In embodiments, $R^{3B}$ is independently an unsubstituted heteroalkyl (e.g., 2 to 8 membered heteroalkyl, 2 to 6 membered heteroalkyl, or 2 to 4 membered heteroalkyl). In embodiments, $R^{3B}$ is independently $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3B}$ is independently $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3B}$ is independently $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3B}$ is independently $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^{3B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{3B}$ is independently $R^{27}$-substituted or unsubstituted aryl (e.g., $C_6$-$C_{10}$ aryl, $C_{10}$ aryl, or phenyl). In embodiments, $R^{3B}$ is independently $R^{27}$-substituted aryl (e.g., $C_6$-$C_{10}$ aryl, $C_{10}$ aryl, or phenyl). In embodiments, $R^{3B}$ is independently an unsubstituted aryl (e.g., $C_6$-$C_{10}$ aryl, $C_{10}$ aryl, or phenyl). In embodiments, $R^{3B}$ is independently $R^{27}$-substituted or unsubstituted heteroaryl (e.g., 5 to 10 membered heteroaryl, 5 to 9 membered heteroaryl, or 5 to 6 membered heteroaryl). In embodiments, $R^{3B}$ is independently $R^{27}$-substituted heteroaryl (e.g., 5 to 10 membered heteroaryl, 5 to 9 membered heteroaryl, or 5 to 6 membered heteroaryl). In embodiments, $R^{3B}$ is independently an unsubstituted heteroaryl (e.g., 5 to 10 membered heteroaryl, 5 to 9 membered heteroaryl, or 5 to 6 membered heteroaryl).

In embodiments, $R^{3B}$ is independently —CCl$_3$. In embodiments, $R^{3B}$ is independently —CBr$_3$. In embodiments, $R^{3B}$ is independently —CF$_3$. In embodiments, $R^{3B}$ is independently —CI$_3$. In embodiments, $R^{3B}$ is independently —CHCl$_2$. In embodiments, $R^{3B}$ is independently —CHBr$_2$. In embodiments, $R^{3B}$ is independently —CHF$_2$. In embodiments, $R^{3B}$ is independently —CHI$_2$. In embodiments, $R^{3B}$ is independently —CH$_2$Cl. In embodiments, $R^{3B}$ is independently —CH$_2$Br. In embodiments, $R^{3B}$ is independently —CH$_2$F. In embodiments, $R^{3B}$ is independently —CH$_2$I. In embodiments, $R^{3B}$ is independently —CN. In embodiments, $R^{3B}$ is independently —OH. In embodiments, $R^{3B}$ is independently —COOH. In embodiments, $R^{3B}$ is independently —CONH$_2$. In embodiments, $R^{3B}$ is independently —OCCl$_3$. In embodiments, $R^{3B}$ is independently —OCF$_3$. In embodiments, $R^{3B}$ is independently —OCBr$_3$. In embodiments, $R^{3B}$ is independently —OCI$_3$. In embodiments, $R^{3B}$ is independently —OCHCl$_2$. In embodiments, $R^{3B}$ is independently —OCHBr$_2$. In embodiments, $R^{3B}$ is independently —OCHI$_2$. In embodiments, $R^{3B}$ is independently —OCHF$_2$. In embodiments, $R^{3B}$ is independently —OCH$_2$Cl. In embodiments, $R^{3B}$ is independently —OCH$_2$Br. In embodiments, $R^{3B}$ is independently —OCH$_2$I. In embodiments, $R^{3B}$ is independently —OCH$_2$F. In embodiments, $R^{3B}$ is independently —OCH$_3$. In embodiments, $R^{3B}$ is independently —CH$_3$. In embodiments, $R^{3B}$ is independently —CH$_2$CH$_3$. In embodiments, $R^{3B}$ is independently unsubstituted propyl. In embodiments, $R^{3B}$ is independently unsubstituted isopropyl. In embodiments, $R^{3B}$ is independently unsubstituted butyl. In embodiments, $R^{3B}$ is independently unsubstituted tert-butyl. In embodiments, $R^{3B}$ is independently hydrogen.

In embodiments, $R^{3C}$ is independently $R^{27}$-substituted or unsubstituted alkyl (e.g., $C_1$-$C_8$ alkyl, $C_1$-$C_6$ alkyl, or $C_1$-$C_4$ alkyl). In embodiments, $R^{3C}$ is independently $R^{27}$-substituted alkyl (e.g., $C_1$-$C_8$ alkyl, $C_1$-$C_6$ alkyl, or $C_1$-$C_4$ alkyl). In embodiments, $R^{3C}$ is independently an unsubstituted alkyl (e.g., $C_1$-$C_8$ alkyl, $C_1$-$C_6$ alkyl, or $C_1$-$C_4$ alkyl). In embodiments, $R^{3C}$ is independently $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^{3C}$ is independently $R^{27}$-substituted heteroalkyl (e.g., 2 to 8 membered heteroalkyl, 2 to 6 membered heteroalkyl, or 2 to 4 membered heteroalkyl). In embodiments, $R^{3C}$ is independently an unsubstituted heteroalkyl (e.g., 2 to 8 membered heteroalkyl, 2 to 6 membered heteroalkyl, or 2 to 4 membered heteroalkyl). In embodiments, $R^{3C}$ is independently $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3C}$ is independently $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3C}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3C}$ is independently $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3C}$ is independently $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^{3C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{3C}$ is independently $R^{27}$-substituted or unsubstituted aryl (e.g., $C_6$-$C_{10}$ aryl, $C_{10}$ aryl, or phenyl). In embodiments, $R^{3C}$ is independently $R^{27}$-substituted aryl (e.g., $C_6$-$C_{10}$ aryl, $C_{10}$ aryl, or phenyl). In embodiments, $R^{3C}$ is independently an unsubstituted aryl (e.g., $C_6$-$C_{10}$ aryl, $C_{10}$ aryl, or phenyl). In embodiments, $R^{3C}$ is independently $R^{27}$-substituted or unsubstituted heteroaryl (e.g., 5 to 10 membered heteroaryl, 5 to 9 membered heteroaryl, or 5 to 6 membered heteroaryl). In embodiments, $R^{3C}$ is independently $R^{27}$-substituted heteroaryl (e.g., 5 to 10 membered heteroaryl, 5 to 9 membered heteroaryl, or 5 to 6 membered heteroaryl). In embodiments, $R^{3C}$ is independently an unsubstituted heteroaryl (e.g., 5 to 10 membered heteroaryl, 5 to 9 membered heteroaryl, or 5 to 6 membered heteroaryl).

In embodiments, $R^{3C}$ is independently —CCl$_3$. In embodiments, $R^{3C}$ is independently —CBr$_3$. In embodiments, $R^{3C}$ is independently —CF$_3$. In embodiments, $R^{3C}$ is independently —CI$_3$. In embodiments, $R^{3C}$ is independently —CHCl$_2$. In embodiments, $R^{3C}$ is independently —CHBr$_2$. In embodiments, $R^{3C}$ is independently —CHF$_2$. In embodiments, $R^{3C}$ is independently —CHI$_2$. In embodiments, $R^{3C}$ is independently —CH$_2$Cl. In embodiments, $R^{3C}$ is independently —CH$_2$Br. In embodiments, $R^{3C}$ is independently —CH$_2$F. In embodiments, $R^{3C}$ is independently —CH$_2$I. In embodiments, $R^{3C}$ is independently —CN. In embodiments, $R^{3C}$ is independently —OH. In embodiments, $R^{3C}$ is independently —COOH. In embodiments, $R^{3C}$ is independently —CONH$_2$. In embodiments, $R^{3C}$ is independently —OCCl$_3$. In embodiments, $R^{3C}$ is independently —OCF$_3$. In embodiments, $R^{3C}$ is independently —OCBr$_3$. In embodiments, $R^{3C}$ is independently —OCI$_3$. In embodiments, $R^{3C}$ is independently —OCHCl$_2$. In embodiments, $R^{3C}$ is independently —OCHBr$_2$. In embodiments, $R^{3C}$ is independently —OCHI$_2$. In embodiments, $R^{3C}$ is independently —OCHF$_2$. In embodiments, $R^{3C}$ is independently —OCH$_2$Cl. In embodiments, $R^{3C}$ is independently —OCH$_2$Br. In embodiments, $R^{3C}$ is independently —OCH$_2$I. In embodiments, $R^{3C}$ is independently —OCH$_2$F. In embodiments, $R^{3C}$ is independently —OCH$_3$. In embodiments, $R^{3C}$ is independently —CH$_3$. In embodiments, $R^{3C}$ is independently —CH$_2$CH$_3$. In embodiments, $R^{3C}$ is independently unsubstituted propyl. In embodiments, $R^{3C}$ is independently unsubstituted isopropyl. In embodiments, $R^{3C}$ is independently unsubstituted butyl. In embodiments, $R^{3C}$ is independently unsubstituted tert-butyl. In embodiments, $R^{3C}$ is independently hydrogen.

In embodiments, $R^{3D}$ is independently $R^{27}$-substituted or unsubstituted alkyl (e.g., $C_1$-$C_8$ alkyl, $C_1$-$C_6$ alkyl, or $C_1$-$C_4$ alkyl). In embodiments, $R^{3D}$ is independently $R^{27}$-substituted alkyl (e.g., $C_1$-$C_8$ alkyl, $C_1$-$C_6$ alkyl, or $C_1$-$C_4$ alkyl). In embodiments, $R^{3D}$ is independently an unsubstituted alkyl (e.g., $C_1$-$C_8$ alkyl, $C_1$-$C_6$ alkyl, or $C_1$-$C_4$ alkyl). In embodiments, $R^{3D}$ is independently $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^{3D}$ is independently $R^{27}$-substituted heteroalkyl (e.g., 2 to 8 membered heteroalkyl, 2 to 6 membered heteroalkyl, or 2 to 4 membered heteroalkyl). In embodiments, $R^{3D}$ is independently an unsubstituted heteroalkyl (e.g., 2 to 8 membered heteroalkyl, 2 to 6 membered heteroalkyl, or 2 to 4 membered heteroalkyl). In embodiments, $R^{3D}$ is independently $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3D}$ is independently $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3D}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3D}$ is independently $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3D}$ is independently $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^{3D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{3D}$ is independently $R^{27}$-substituted or unsubstituted aryl (e.g., $C_6$-$C_{10}$ aryl, $C_{10}$ aryl, or phenyl). In embodiments, $R^{3D}$ is independently $R^{27}$-substituted aryl (e.g., $C_6$-$C_{10}$ aryl, $C_{10}$ aryl, or phenyl). In embodiments, $R^{3D}$ is independently an unsubstituted aryl (e.g., $C_6$-$C_{10}$ aryl, $C_{10}$ aryl, or phenyl). In embodiments, $R^{3D}$ is independently $R^{27}$-substituted or unsubstituted heteroaryl (e.g., 5 to 10 membered heteroaryl, 5 to 9 membered heteroaryl, or 5 to 6 membered heteroaryl). In embodiments, $R^{3D}$ is independently $R^{27}$-substituted heteroaryl (e.g., 5 to 10 membered heteroaryl, 5 to 9 membered heteroaryl, or 5 to 6 membered heteroaryl). In embodiments, $R^{3D}$ is independently an unsubstituted heteroaryl (e.g., 5 to 10 membered heteroaryl, 5 to 9 membered heteroaryl, or 5 to 6 membered heteroaryl).

In embodiments, $R^{3D}$ is independently —$CCl_3$. In embodiments, $R^{3D}$ is independently —$CBr_3$. In embodiments, $R^{3D}$ is independently —$CF_3$. In embodiments, $R^{3D}$ is independently —$CI_3$. In embodiments, $R^{3D}$ is independently —$CHCl_2$. In embodiments, $R^{3D}$ is independently —$CHBr_2$. In embodiments, $R^{3D}$ is independently —$CHF_2$. In embodiments, $R^{3D}$ is independently —$CHI_2$. In embodiments, $R^{3D}$ is independently —$CH_2Cl$. In embodiments, $R^{3D}$ is independently —$CH_2Br$. In embodiments, $R^{3D}$ is independently —$CH_2F$. In embodiments, $R^{3D}$ is independently —$CH_2I$. In embodiments, $R^{3D}$ is independently —CN. In embodiments, $R^{3D}$ is independently —OH. In embodiments, $R^{3D}$ is independently —COOH. In embodiments, $R^{3D}$ is independently —$CONH_2$. In embodiments, $R^{3D}$ is independently —$OCCl_3$. In embodiments, $R^{3D}$ is independently —$OCF_3$. In embodiments, $R^{3D}$ is independently —$OCBr_3$. In embodiments, $R^{3D}$ is independently —$OCl_3$. In embodiments, $R^{3D}$ is independently —$OCHCl_2$. In embodiments, $R^{3D}$ is independently —$OCHBr_2$. In embodiments, $R^{3D}$ is independently —$OCHI_2$. In embodiments, $R^{3D}$ is independently —$OCHF_2$. In embodiments, $R^{3D}$ is independently —$OCH_2Cl$. In embodiments, $R^{3D}$ is independently —$OCH_2Br$. In embodiments, $R^{3D}$ is independently —$OCH_2I$. In embodiments, $R^{3D}$ is independently —$OCH_2F$. In embodiments, $R^{3D}$ is independently —$OCH_3$. In embodiments, $R^{3D}$ is idenpendently —$CH_3$. In embodiments, $R^{3D}$ is independently —$CH_2CH_3$. In embodiments, $R^{3D}$ is independently unsubstituted propyl. In embodiments, $R^{3D}$ is independently unsubstituted isopropyl. In embodiments, $R^{3D}$ is independently unsubstituted butyl. In embodiments, $R^{3D}$ is independently unsubstituted tert-butyl. In embodiments, $R^{3D}$ is independently hydrogen.

In embodiments, $R^4$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, —$NHC(O)NHNH_2$, —$N_3$, E, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^4$ is independently substituted or unsubstituted alkyl (e.g., $C_1$-$C_8$ alkyl, $C_1$-$C_6$ alkyl, or $C_1$-$C_4$ alkyl). In embodiments, $R^4$ is independently substituted alkyl (e.g., $C_1$-$C_8$ alkyl, $C_1$-$C_6$ alkyl, or $C_1$-$C_4$ alkyl). In embodiments, $R^4$ is independently an unsubstituted alkyl (e.g., $C_1$-$C_8$ alkyl, $C_1$-$C_6$ alkyl, or $C_1$-$C_4$ alkyl). In embodiments, $R^4$ is independently substituted or unsubstituted heteroalkyl (e.g., 2 to 8 membered heteroalkyl, 2 to 6 membered heteroalkyl, or 2 to 4 membered heteroalkyl). In embodiments, $R^4$ is independently substituted heteroalkyl (e.g., 2 to 8 membered heteroalkyl, 2 to 6 membered heteroalkyl, or 2 to 4 membered heteroalkyl). In embodiments, $R^4$ is independently an unsubstituted heteroalkyl (e.g., 2 to 8 membered heteroalkyl, 2 to 6 membered heteroalkyl, or 2 to 4 membered heteroalkyl). In embodiments, $R^4$ is independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is independently substituted cycloalkyl (e.g., $C_3$-$C_8$ cycloalkyl, $C_3$-$C_6$ cycloalkyl, or $C_5$-$C_6$ cycloalkyl). In embodiments, $R^4$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ is independently substituted heterocycloalkyl (e.g., 3 to 8 membered heterocycloalkyl, 3 to 6 membered heterocycloalkyl, or 5 to 6 membered heterocycloalkyl). In embodiments, $R^4$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ is independently substituted or unsubstituted aryl (e.g., $C_6$-$C_{10}$ aryl, $C_{10}$ aryl, or phenyl). In embodiments, $R^4$ is independently substituted aryl (e.g., $C_6$-$C_{10}$ aryl, $C_{10}$ aryl, or phenyl). In embodiments, $R^4$ is independently an unsubstituted aryl (e.g., $C_6$-$C_{10}$ aryl, $C_{10}$ aryl, or phenyl). In embodiments, $R^4$ is independently substituted or unsubstituted heteroaryl (e.g., 5 to 10 membered heteroaryl, 5 to 9 membered heteroaryl, or 5 to 6 membered heteroaryl). In embodiments, $R^4$ is independently substituted heteroaryl (e.g., 5 to 10 membered heteroaryl, 5 to 9 membered heteroaryl, or 5 to 6 membered heteroaryl). In embodiments, $R^4$ is independently an unsubstituted heteroaryl (e.g., 5 to 10 membered heteroaryl, 5 to 9 membered heteroaryl, or 5 to 6 membered heteroaryl).

In embodiments, $R^4$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, E, R$^{30}$-substituted or unsubstituted alkyl (e.g., C$_1$-C$_8$ alkyl, C$_1$-C$_6$ alkyl, or C$_1$-C$_4$ alkyl), R$^{30}$-substituted or unsubstituted heteroalkyl (e.g., 2 to 8 membered heteroalkyl, 2 to 6 membered heteroalkyl, or 2 to 4 membered heteroalkyl), R$^{30}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{30}$-substituted or unsubstituted heterocycloalkyl (e.g., 3 to 8 membered heterocycloalkyl, 3 to 6 membered heterocycloalkyl, or 5 to 6 membered heterocycloalkyl), R$^{30}$-substituted or unsubstituted aryl (e.g., C$_6$-C$_{10}$ aryl, C$_{10}$ aryl, or phenyl), or R$^{30}$-substituted or unsubstituted heteroaryl (e.g., 5 to 10 membered heteroaryl, 5 to 9 membered heteroaryl, or 5 to 6 membered heteroaryl). In embodiments, R$^4$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —O CCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, E, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^4$ is independently R$^{30}$-substituted or unsubstituted alkyl (e.g., C$_1$-C$_8$ alkyl, C$_1$-C$_6$ alkyl, or C$_1$-C$_4$ alkyl). In embodiments, R$^4$ is independently R$^{30}$-substituted alkyl (e.g., C$_1$-C$_8$ alkyl, C$_1$-C$_6$ alkyl, or C$_1$-C$_4$ alkyl). In embodiments, R$^4$ is independently an unsubstituted alkyl (e.g., C$_1$-C$_8$ alkyl, C$_1$-C$_6$ alkyl, or C$_1$-C$_4$ alkyl). In embodiments, R$^4$ is independently R$^{30}$-substituted or unsubstituted heteroalkyl (e.g., 2 to 8 membered heteroalkyl, 2 to 6 membered heteroalkyl, or 2 to 4 membered heteroalkyl). In embodiments, R$^4$ is independently R$^{30}$-substituted heteroalkyl (e.g., 2 to 8 membered heteroalkyl, 2 to 6 membered heteroalkyl, or 2 to 4 membered heteroalkyl). In embodiments, R$^4$ is independently an unsubstituted heteroalkyl (e.g., 2 to 8 membered heteroalkyl, 2 to 6 membered heteroalkyl, or 2 to 4 membered heteroalkyl). In embodiments, R$^4$ is independently R$^{30}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^4$ is independently R$^{30}$-substituted cycloalkyl (e.g., C$_3$-C$_8$ cycloalkyl, C$_3$-C$_6$ cycloalkyl, or C$_5$-C$_6$ cycloalkyl). In embodiments, R$^4$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^4$ is independently R$^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^4$ is independently R$^{30}$-substituted heterocycloalkyl (e.g., 3 to 8 membered heterocycloalkyl, 3 to 6 membered heterocycloalkyl, or 5 to 6 membered heterocycloalkyl). In embodiments, R$^4$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^4$ is independently R$^{30}$-substituted or unsubstituted aryl (e.g., C$_6$-C$_{10}$ aryl, C$_{10}$ aryl, or phenyl). In embodiments, R$^4$ is independently R$^{30}$-substituted aryl (e.g., C$_6$-C$_{10}$ aryl, C$_{10}$ aryl, or phenyl). In embodiments, R$^4$ is independently an unsubstituted aryl (e.g., C$_6$-C$_{10}$ aryl, C$_{10}$ aryl, or phenyl). In embodiments, R$^4$ is independently R$^{30}$-substituted or unsubstituted heteroaryl (e.g., 5 to 10 membered heteroaryl, 5 to 9 membered heteroaryl, or 5 to 6 membered heteroaryl). In embodiments, R$^4$ is independently R$^{30}$-substituted heteroaryl (e.g., 5 to 10 membered heteroaryl, 5 to 9 membered heteroaryl, or 5 to 6 membered heteroaryl). In embodiments, R$^4$ is independently an unsubstituted heteroaryl (e.g., 5 to 10 membered heteroaryl, 5 to 9 membered heteroaryl, or 5 to 6 membered heteroaryl).

In embodiments, R$^4$ is independently —CX$^4_3$. In embodiments, R$^4$ is independently —CHX$^4_2$. In embodiments, R$^4$ is independently —CH$_2$X$^4$. In embodiments, R$^4$ is independently —OCX$^4_3$. In embodiments, R$^4$ is independently —OCH$_2$X$^4$. In embodiments, R$^4$ is independently —OCHX$^4_2$. In embodiments, R$^4$ is independently —CN. In embodiments, R$^4$ is independently —SR$^{4D}$. In embodiments, R$^4$ is independently —SOR$^{4D}$. In embodiments, R$^4$ is independently —SO$_2$R$^{4D}$. In embodiments, R$^4$ is independently —SO$_3$R$^{4D}$. In embodiments, R$^4$ is independently —SO$_4$R$^{4D}$. In embodiments, R$^4$ is independently —SONR$^{4A}$R$^{4B}$. In embodiments, R$^4$ is independently SO$_2$NR$^{4A}$R$^{4B}$. In embodiments, R$^4$ is independently —NHC(O)NR$^{4A}$R$^{4B}$. In embodiments, R$^4$ is independently —N(O). In embodiments, R$^4$ is independently —N(O)$_2$. In embodiments, R$^4$ is independently —NR$^{4A}$R$^{4C}$. In embodiments, R$^4$ is independently —C(O)R$^{4C}$. In embodiments, R$^4$ is independently —C(O)—OR$^{4C}$. In embodiments, R$^4$ is independently —C(O)NR$^{4A}$R$^{4B}$. In embodiments, R$^4$ is independently —OR$^{4D}$. In embodiments, R$^4$ is independently —NR$^{4A}$SO$_2$R$^{4D}$. In embodiments, R$^4$ is independently —NR$^{4A}$C(O)R$^{4C}$. In embodiments, R$^4$ is independently —NR$^{4A}$C(O)OR$^{4C}$. In embodiments, R$^4$ is independently —NR$^{4A}$OR$^{4C}$. In embodiments, R$^4$ is independently hydrogen.

In embodiments, R$^4$ is independently halogen. In embodiments, R$^4$ is independently —CCl$_3$. In embodiments, R$^4$ is independently —CBr$_3$. In embodiments, R$^4$ is independently —CF$_3$. In embodiments, R$^4$ is independently —CI$_3$. In embodiments, R$^4$ is independently —CHCl$_2$. In embodiments, R$^4$ is independently —CHBr$_2$. In embodiments, R$^4$ is independently —CHF$_2$. In embodiments, R$^4$ is independently —CHI$_2$. In embodiments, R$^4$ is independently —CH$_2$Cl. In embodiments, R$^4$ is independently —CH$_2$Br. In embodiments, R$^4$ is independently —CH$_2$F. In embodiments, R$^4$ is independently —CH$_2$I. In embodiments, R$^4$ is independently —CN. In embodiments, R$^4$ is independently —OH. In embodiments, R$^4$ is independently —NH$_2$. In embodiments, R$^4$ is independently —COOH. In embodiments, R$^4$ is independently —CONH$_2$. In embodiments, R$^4$ is independently —NO$_2$. In embodiments, R$^4$ is independently —SH. In embodiments, R$^4$ is independently —SO$_3$H. In embodiments, R$^4$ is independently —SO$_4$H. In embodiments, R$^4$ is independently —SO$_2$NH$_2$. In embodiments, R$^4$ is independently —NHNH$_2$. In embodiments, R$^4$ is independently —ONH$_2$. In embodiments, R$^4$ is independently —NHC(O)NHNH$_2$. In embodiments, R$^4$ is independently —NHC(O)NH$_2$. In embodiments, R$^4$ is independently —NHSO$_2$H. In embodiments, R$^4$ is independently —NHC(O)H. In embodiments, R$^4$ is independently —NHC(O)OH. In embodiments, R$^4$ is independently —NHOH. In embodiments, R$^4$ is independently —OCCl$_3$. In embodiments, R$^4$ is independently —OCF$_3$. In embodiments, R$^4$ is independently —OCBr$_3$. In embodiments, R$^4$ is independently —OCI$_3$. In embodiments, R$^4$ is independently —OCHCl$_2$. In embodiments, R$^4$ is independently —OCHBr$_2$. In embodiments, R$^4$ is independently —OCHI$_2$. In embodiments, R$^4$ is independently —OCHF$_2$. In embodiments, R$^4$ is independently —OCH$_2$Cl. In embodiments, R$^4$ is independently —OCH$_2$Br. In embodiments, R$^4$ is independently —OCH$_2$I. In embodiments, R$^4$ is independently —OCH$_2$F. In embodiments, R$^4$ is independently —N$_3$. In embodiments, R$^4$ is independently —OCH$_3$. In embodiments, R$^4$ is independently —CH$_3$. In embodiments, R$^4$ is independently —CH$_2$CH$_3$. In embodiments, R$^4$ is independently unsubstituted propyl. In embodiments, R$^4$ is independently unsubstituted isopropyl. In embodiments, R$^4$ is independently unsubstituted butyl. In embodiments, R$^4$ is independently unsubstituted tert-butyl. In embodiments, R$^4$ is independently —F. In embodiments, R$^4$ is independently —Cl. In embodiments, R$^4$ is independently —Br. In embodiments, R$^4$ is independently —I. In embodiments, R$^4$ is independently E.

R$^{30}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{31}$-substituted or unsubstituted alkyl (e.g., C$_1$-C$_8$ alkyl, C$_1$-C$_6$ alkyl, or C$_1$-C$_4$ alkyl), R$^{31}$-substituted or unsubstituted heteroalkyl (e.g., 2 to 8 membered heteroalkyl, 2 to 6 membered heteroalkyl, or 2 to 4 membered heteroalkyl), R$^{31}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{31}$-substituted or unsubstituted heterocycloalkyl (e.g., 3 to 8 membered heterocycloalkyl, 3 to 6 membered heterocycloalkyl, or 5 to 6 membered heterocycloalkyl), R$^{31}$-substituted or unsubstituted aryl (e.g., C$_6$-C$_{10}$ aryl, C$_{10}$ aryl, or phenyl), or R$^{31}$-substituted or unsubstituted heteroaryl (e.g., 5 to 10 membered heteroaryl, 5 to 9 membered heteroaryl, or 5 to 6 membered heteroaryl). In embodiments, R$^{30}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{30}$ is independently oxo. In embodiments, R$^{30}$ is independently halogen. In embodiments, R$^{30}$ is independently —CCl$_3$. In embodiments, R$^{30}$ is independently —CBr$_3$. In embodiments, R$^{30}$ is independently —CF$_3$. In embodiments, R$^{30}$ is independently —CI$_3$. In embodiments, R$^{30}$ is independently —CHCl$_2$. In embodiments, R$^{30}$ is independently —CHBr$_2$. In embodiments, R$^{30}$ is independently —CHF$_2$. In embodiments, R$^{30}$ is independently —CHI$_2$. In embodiments, R$^{30}$ is independently —CH$_2$Cl. In embodiments, R$^{30}$ is independently —CH$_2$Br. In embodiments, R$^{30}$ is independently —CH$_2$F. In embodiments, R$^{30}$ is independently —CH$_2$I. In embodiments, R$^{30}$ is independently —CN. In embodiments, R$^{30}$ is independently —OH. In embodiments, R$^{30}$ is independently —NH$_2$. In embodiments, R$^{30}$ is independently —COOH. In embodiments, R$^{30}$ is independently —CONH$_2$. In embodiments, R$^{30}$ is independently —NO$_2$. In embodiments, R$^{30}$ is independently —SH. In embodiments, R$^{30}$ is independently —SO$_3$H. In embodiments, R$^{30}$ is independently —SO$_4$H. In embodiments, R$^{30}$ is independently —SO$_2$NH$_2$. In embodiments, R$^{30}$ is independently —NHNH$_2$. In embodiments, R$^{30}$ is independently —ONH$_2$. In embodiments, R$^{30}$ is independently —NHC(O)NHNH$_2$. In embodiments, R$^{30}$ is independently —NHC(O)NH$_2$. In embodiments, R$^{30}$ is independently —NHSO$_2$H. In embodiments, R$^{30}$ is independently —NHC(O)H. In embodiments, R$^{30}$ is independently —NHC(O)OH. In embodiments, R$^{30}$ is independently —NHOH. In embodiments, R$^{30}$ is independently —OCCl$_3$. In embodiments, R$^{30}$ is independently —OCF$_3$. In embodiments, R$^{30}$ is independently —OCBr$_3$. In embodiments, R$^{30}$ is independently —OCI$_3$. In embodiments, R$^{30}$ is independently —OCHCl$_2$. In embodiments, R$^{30}$ is independently —OCHBr$_2$. In embodiments, R$^{30}$ is independently —OCHI$_2$. In embodiments, R$^{30}$ is independently —OCHF$_2$. In embodiments, R$^{30}$ is independently —OCH$_2$Cl. In embodiments, R$^{30}$ is independently —OCH$_2$Br. In embodiments, R$^{30}$ is independently —OCH$_2$I. In embodiments, R$^{30}$ is independently —OCH$_2$F. In embodiments, R$^{30}$ is independently —N$_3$. In embodiments, R$^{30}$ is independently —OCH$_3$. In embodiments, R$^{30}$ is idenpendently —CH$_3$. In embodiments, R$^{30}$ is idenpendently —CH$_2$CH$_3$. In embodiments, R$^{30}$ is independently unsubstituted propyl. In embodiments, R$^{30}$ is independently unsubstituted isopropyl. In embodiments, R$^{30}$ is independently unsubstituted butyl. In embodiments, R$^{30}$ is independently unsubstituted tert-butyl. In embodiments, R$^{30}$ is independently —F. In embodiments, R$^{30}$ is independently —Cl. In embodiments, R$^{30}$ is independently —Br. In embodiments, R$^{30}$ is independently —I.

In embodiments, R$^{30}$ is independently R$^{31}$-substituted or unsubstituted alkyl (e.g., C$_1$-C$_8$ alkyl, C$_1$-C$_6$ alkyl, or C$_1$-C$_4$ alkyl). In embodiments, R$^{30}$ is independently R$^{31}$-substituted alkyl (e.g., C$_1$-C$_8$ alkyl, C$_1$-C$_6$ alkyl, or C$_1$-C$_4$ alkyl). In embodiments, R$^{30}$ is independently an unsubstituted alkyl (e.g., C$_1$-C$_8$ alkyl, C$_1$-C$_6$ alkyl, or C$_1$-C$_4$ alkyl). In embodiments, R$^{30}$ is independently R$^{31}$-substituted or unsubstituted heteroalkyl (e.g., 2 to 8 membered heteroalkyl, 2 to 6 membered heteroalkyl, or 2 to 4 membered heteroalkyl). In embodiments, R$^{30}$ is independently R$^{31}$-substituted heteroalkyl (e.g., 2 to 8 membered heteroalkyl, 2 to 6 membered heteroalkyl, or 2 to 4 membered heteroalkyl). In embodiments, R$^{30}$ is independently an unsubstituted heteroalkyl (e.g., 2 to 8 membered heteroalkyl, 2 to 6 membered heteroalkyl, or 2 to 4 membered heteroalkyl). In embodiments, R$^{30}$ is independently R$^{31}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{30}$ is independently R$^{31}$-substituted cycloalkyl (e.g., C$_3$-C$_8$ cycloalkyl, C$_3$-C$_6$ cycloalkyl, or C$_5$-C$_6$ cycloalkyl). In embodiments, R$^{30}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{30}$ is independently R$^{31}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{30}$ is independently $R^{31}$-substituted heterocycloalkyl (e.g., 3 to 8 membered heterocycloalkyl, 3 to 6 membered heterocycloalkyl, or 5 to 6 membered heterocycloalkyl). In embodiments, $R^{30}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{30}$ is independently $R^{31}$-substituted or unsubstituted aryl (e.g., $C_6$-$C_{10}$ aryl, $C_{10}$ aryl, or phenyl). In embodiments, $R^{30}$ is independently $R^{31}$-substituted aryl (e.g., $C_6$-$C_{10}$ aryl, $C_{10}$ aryl, or phenyl). In embodiments, $R^{30}$ is independently an unsubstituted aryl (e.g., $C_6$-$C_{10}$ aryl, $C_{10}$ aryl, or phenyl). In embodiments, $R^{30}$ is independently $R^{31}$-substituted or unsubstituted heteroaryl (e.g., 5 to 10 membered heteroaryl, 5 to 9 membered heteroaryl, or 5 to 6 membered heteroaryl). In embodiments, $R^{30}$ is independently $R^{31}$-substituted heteroaryl (e.g., 5 to 10 membered heteroaryl, 5 to 9 membered heteroaryl, or 5 to 6 membered heteroaryl). In embodiments, $R^{30}$ is independently an unsubstituted heteroaryl (e.g., 5 to 10 membered heteroaryl, 5 to 9 membered heteroaryl, or 5 to 6 membered heteroaryl).

$R^{31}$ is independently oxo, halogen, —$CCl_3$, —$CBr_3$, —$CF_3$, —$CI_3$, —$CHCl_2$, —$CHBr_2$, —$CHF_2$, —$CH_2Cl$, —$CH_2Br$, —$CH_2F$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, $NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHF_2$, —$OCH_2Cl$, —$OCH_2Br$, —$OCH_2F$, —$N_3$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl). In embodiments, $R^{31}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{31}$ is independently $R^{32}$-substituted or unsubstituted alkyl (e.g., $C_1$-$C_8$ alkyl, $C_1$-$C_6$ alkyl, or $C_1$-$C_4$ alkyl). In embodiments, $R^{31}$ is independently $R^{32}$-substituted alkyl (e.g., $C_1$-$C_8$ alkyl, $C_1$-$C_6$ alkyl, or $C_1$-$C_4$ alkyl). In embodiments, $R^{31}$ is independently an unsubstituted alkyl (e.g., $C_1$-$C_8$ alkyl, $C_1$-$C_6$ alkyl, or $C_1$-$C_4$ alkyl). In embodiments, $R^{31}$ is independently $R^{32}$-substituted or unsubstituted heteroalkyl (e.g., 2 to 8 membered heteroalkyl, 2 to 6 membered heteroalkyl, or 2 to 4 membered heteroalkyl). In embodiments, $R^{31}$ is independently $R^{32}$-substituted heteroalkyl (e.g., 2 to 8 membered heteroalkyl, 2 to 6 membered heteroalkyl, or 2 to 4 membered heteroalkyl). In embodiments, $R^{31}$ is independently an unsubstituted heteroalkyl (e.g., 2 to 8 membered heteroalkyl, 2 to 6 membered heteroalkyl, or 2 to 4 membered heteroalkyl). In embodiments, $R^{31}$ is independently $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is independently $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{31}$ is independently $R^{32}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{31}$ is independently $R^{32}$-substituted heterocycloalkyl (e.g., 3 to 8 membered heterocycloalkyl, 3 to 6 membered heterocycloalkyl, or 5 to 6 membered heterocycloalkyl). In embodiments, $R^{31}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{31}$ is independently $R^{32}$-substituted or unsubstituted aryl (e.g., $C_6$-$C_{10}$ aryl, $C_{10}$ aryl, or phenyl). In embodiments, $R^{31}$ is independently $R^{32}$-substituted aryl (e.g., $C_6$-$C_{10}$ aryl, $C_{10}$ aryl, or phenyl). In embodiments, $R^{31}$ is independently an unsubstituted aryl (e.g., $C_6$-$C_{10}$ aryl, $C_{10}$ aryl, or phenyl). In embodiments, $R^{31}$ is independently $R^{32}$-substituted or unsubstituted heteroaryl (e.g., 5 to 10 membered heteroaryl, 5 to 9 membered heteroaryl, or 5 to 6 membered heteroaryl). In embodiments, $R^{31}$ is independently $R^{32}$-substituted heteroaryl (e.g., 5 to 10 membered heteroaryl, 5 to 9 membered heteroaryl, or 5 to 6 membered heteroaryl). In embodiments, $R^{31}$ is independently an unsubstituted heteroaryl (e.g., 5 to 10 membered heteroaryl, 5 to 9 membered heteroaryl, or 5 to 6 membered heteroaryl).

In embodiments, $R^{31}$ is independently oxo. In embodiments, $R^{31}$ is independently halogen. In embodiments, $R^{31}$ is independently —$CCl_3$. In embodiments, $R^{31}$ is independently —$CBr_3$. In embodiments, $R^{31}$ is independently —$CF_3$. In embodiments, $R^{31}$ is independently —$CI_3$. In embodiments, $R^{31}$ is independently —$CHCl_2$. In embodiments, $R^{31}$ is independently —$CHBr_2$. In embodiments, $R^{31}$ is independently —$CHF_2$. In embodiments, $R^{31}$ is independently —$CHI_2$. In embodiments, $R^{31}$ is independently —$CH_2Cl$. In embodiments, $R^{31}$ is independently —$CH_2Br$. In embodiments, $R^{31}$ is independently —$CH_2F$. In embodiments, $R^{31}$ is independently —$CH_2I$. In embodiments, $R^{31}$ is independently —CN. In embodiments, $R^{31}$ is independently —OH. In embodiments, $R^{31}$ is independently —$NH_2$. In embodiments, $R^{31}$ is independently —COOH. In embodiments, $R^{31}$ is independently —$CONH_2$. In embodiments, $R^{31}$ is independently —$NO_2$. In embodiments, $R^{31}$ is independently —SH. In embodiments, $R^{31}$ is independently —$SO_3H$. In embodiments, $R^{31}$ is independently —$SO_4H$. In embodiments, $R^{31}$ is independently —$SO_2NH_2$. In embodiments, $R^{31}$ is independently —$NHNH_2$. In embodiments, $R^{31}$ is independently —$ONH_2$. In embodiments, $R^{31}$ is independently —$NHC(O)NHNH_2$. In embodiments, $R^{31}$ is independently —$NHC(O)NH_2$. In embodiments, $R^{31}$ is independently —$NHSO_2H$. In embodiments, $R^{30}$ is independently —NHC(O)H. In embodiments, $R^{30}$ is independently —NHC(O)OH. In embodiments, $R^{30}$ is independently —NHOH. In embodiments, $R^{30}$ is independently —OCCl$_3$. In embodiments, $R^{30}$ is independently —OCF$_3$. In embodiments, $R^{30}$ is independently —OCBr$_3$. In embodiments, $R^{30}$ is independently —OCl$_3$. In embodiments, $R^{30}$ is independently —OCHCl$_2$. In embodiments, $R^{30}$ is independently —OCHBr$_2$. In embodiments, $R^{30}$ is independently —OCHI$_2$. In embodiments, $R^{30}$ is independently —OCHF$_2$. In embodiments, $R^{30}$ is independently —OCH$_2$Cl. In embodiments, $R^{30}$ is independently —OCH$_2$Br. In embodiments, $R^{30}$ is independently —OCH$_2$I. In embodiments, $R^{30}$ is independently —OCH$_2$F. In embodiments, $R^{30}$ is independently —N$_3$. In embodiments, $R^{30}$ is independently —OCH$_3$. In embodiments, $R^{30}$ is independently —CH$_3$. In embodiments, $R^{30}$ is independently —CH$_2$CH$_3$. In embodiments, $R^{30}$ is independently unsubstituted propyl. In embodiments, $R^{30}$ is independently unsubstituted isopropyl. In embodiments, $R^{30}$ is independently unsubstituted butyl. In embodiments, $R^{30}$ is independently unsubstituted tert-butyl. In embodiments, $R^{30}$ is independently —F. In embodiments, $R^{31}$ is independently —Cl. In embodiments, $R^{31}$ is independently —Br. In embodiments, $R^{31}$ is independently —I.

$R^{32}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{32}$ is independently an unsubstituted alkyl (e.g., C$_1$-C$_8$ alkyl, C$_1$-C$_6$ alkyl, or C$_1$-C$_4$ alkyl). In embodiments, $R^{32}$ is independently an unsubstituted heteroalkyl (e.g., 2 to 8 membered heteroalkyl, 2 to 6 membered heteroalkyl, or 2 to 4 membered heteroalkyl). In embodiments, $R^{32}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, $R^{32}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{32}$ is independently an unsubstituted aryl (e.g., C$_6$-C$_{10}$ aryl, C$_{10}$ aryl, or phenyl). In embodiments, $R^{32}$ is independently an unsubstituted heteroaryl (e.g., 5 to 10 membered heteroaryl, 5 to 9 membered heteroaryl, or 5 to 6 membered heteroaryl).

In embodiments, $R^{32}$ is independently oxo. In embodiments, $R^{32}$ is independently halogen. In embodiments, $R^{32}$ is independently —CCl$_3$. In embodiments, $R^{32}$ is independently —CBr$_3$. In embodiments, $R^{32}$ is independently —CF$_3$. In embodiments, $R^{32}$ is independently —CI$_3$. In embodiments, $R^{32}$ is independently —CHCl$_2$. In embodiments, $R^{32}$ is independently —CHBr$_2$. In embodiments, $R^{32}$ is independently —CHF$_2$. In embodiments, $R^{32}$ is independently —CHI$_2$. In embodiments, $R^{32}$ is independently —CH$_2$Cl. In embodiments, $R^{32}$ is independently —CH$_2$Br. In embodiments, $R^{32}$ is independently —CH$_2$F. In embodiments, $R^{32}$ is independently —CH$_2$I. In embodiments, $R^{32}$ is independently —CN. In embodiments, $R^{32}$ is independently —OH. In embodiments, $R^{32}$ is independently —NH$_2$. In embodiments, $R^{32}$ is independently —COOH. In embodiments, $R^{32}$ is independently —CONH$_2$. In embodiments, $R^{32}$ is independently —NO$_2$. In embodiments, $R^{32}$ is independently —SH. In embodiments, $R^{32}$ is independently —SO$_3$H. In embodiments, $R^{32}$ is independently —SO$_4$H. In embodiments, $R^{32}$ is independently —SO$_2$NH$_2$. In embodiments, $R^{32}$ is independently —NHNH$_2$. In embodiments, $R^{32}$ is independently —ONH$_2$. In embodiments, $R^{32}$ is independently —NHC(O)NHNH$_2$. In embodiments, $R^{32}$ is independently —NHC(O)NH$_2$. In embodiments, $R^{32}$ is independently —NHSO$_2$H. In embodiments, $R^{32}$ is independently —NHC(O)H. In embodiments, $R^{32}$ is independently —NHC(O)OH. In embodiments, $R^{32}$ is independently —NHOH. In embodiments, $R^{32}$ is independently —OCCl$_3$. In embodiments, $R^{32}$ is independently —OCF$_3$. In embodiments, $R^{32}$ is independently —OCBr$_3$. In embodiments, $R^{32}$ is independently —OCl$_3$. In embodiments, $R^{32}$ is independently —OCHCl$_2$. In embodiments, $R^{32}$ is independently —OCHBr$_2$. In embodiments, $R^{32}$ is independently —OCHI$_2$. In embodiments, $R^{32}$ is independently —OCHF$_2$. In embodiments, $R^{32}$ is independently —OCH$_2$Cl. In embodiments, $R^{32}$ is independently —OCH$_2$Br. In embodiments, $R^{32}$ is independently —OCH$_2$I. In embodiments, $R^{32}$ is independently —OCH$_2$F. In embodiments, $R^{32}$ is independently —N$_3$. In embodiments, $R^{32}$ is independently —OCH$_3$. In embodiments, $R^{32}$ is independently —CH$_3$. In embodiments, $R^{32}$ is independently —CH$_2$CH$_3$. In embodiments, $R^{32}$ is independently unsubstituted propyl. In embodiments, $R^{32}$ is independently unsubstituted isopropyl. In embodiments, $R^{32}$ is independently unsubstituted butyl. In embodiments, $R^{32}$ is independently unsubstituted tert-butyl. In embodiments, $R^{32}$ is independently —F. In embodiments, $R^{32}$ is independently —Cl. In embodiments, $R^{32}$ is independently —Br. In embodiments, $R^{32}$ is independently —I.

In embodiments, $R^{4A}$ is independently hydrogen, halogen, —CF$_3$, —CBr$_3$, —CCl$_3$, —CI$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCl$_3$, —OCHF$_2$, —OCHBr$_2$, —OCHCl$_2$, —OCH$_2$F, —OCH$_2$Br, —OCH$_2$Cl, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{4B}$ is independently hydrogen, halogen, —CF$_3$, —CBr$_3$, —CCl$_3$, —CI$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCl$_3$, —OCHF$_2$, —OCHBr$_2$, —OCHCl$_2$, —OCH$_2$F, —OCH$_2$Br, —OCH$_2$Cl, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{4C}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{4D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{4A}$ and $R^{4B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{4A}$ and $R^{4B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ and $R^{4B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{4A}$ and $R^{4B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ and $R^{4B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{4A}$ and $R^{4B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{4A}$ and $R^{4B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{4A}$, $R^{4B}$, $R^{4C}$ and $R^{4D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{30}$-substituted or unsubstituted alkyl (e.g., $C_1$-$C_8$ alkyl, $C_1$-$C_6$ alkyl, or $C_1$-$C_4$ alkyl), $R^{30}$-substituted or unsubstituted heteroalkyl (e.g., 2 to 8 membered heteroalkyl, 2 to 6 membered heteroalkyl, or 2 to 4 membered heteroalkyl), $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{30}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30}$-substituted or unsubstituted aryl (e.g., $C_6$-$C_{10}$ aryl, $C_{10}$ aryl, or phenyl), or $R^{30}$-substituted or unsubstituted heteroaryl (e.g., 5 to 10 membered heteroaryl, 5 to 9 membered heteroaryl, or 5 to 6 membered heteroaryl). In embodiments, $R^{4A}$ and $R^{4B}$ substituents bonded to the same nitrogen atom are independently joined to form an $R^{30}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{30}$-substituted or unsubstituted heteroaryl (e.g., 5 to 10 membered heteroaryl, 5 to 9 membered heteroaryl, or 5 to 6 membered heteroaryl). In embodiments, $R^{4A}$ and $R^{4B}$ substituents bonded to the same nitrogen atom are independently joined to form an $R^{30}$-substituted or unsubstituted heterocycloalkyl (e.g., 3 to 8 membered heterocycloalkyl, 3 to 6 membered heterocycloalkyl. In embodiments, $R^{4A}$ and $R^{4B}$ substituents bonded to the same nitrogen atom are independently joined to form an $R^{30}$-substituted or unsubstituted heteroaryl (e.g., 5 to 10 membered heteroaryl, 5 to 9 membered heteroaryl, or 5 to 6 membered heteroaryl).

In embodiments, $R^{4A}$ is independently $R^{30}$-substituted or unsubstituted alkyl (e.g., $C_1$-$C_8$ alkyl, $C_1$-$C_6$ alkyl, or $C_1$-$C_4$ alkyl). In embodiments, $R^{4A}$ is independently $R^{30}$-substituted alkyl (e.g., $C_1$-$C_8$ alkyl, $C_1$-$C_6$ alkyl, or $C_1$-$C_4$ alkyl). In embodiments, $R^{4A}$ is independently an unsubstituted alkyl (e.g., $C_1$-$C_8$ alkyl, $C_1$-$C_6$ alkyl, or $C_1$-$C_4$ alkyl). In embodiments, $R^{4A}$ is independently $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^{4A}$ is independently $R^{30}$-substituted heteroalkyl (e.g., 2 to 8 membered heteroalkyl, 2 to 6 membered heteroalkyl, or 2 to 4 membered heteroalkyl). In embodiments, $R^{4A}$ is independently an unsubstituted heteroalkyl (e.g., 2 to 8 membered heteroalkyl, 2 to 6 membered heteroalkyl, or 2 to 4 membered heteroalkyl). In embodiments, $R^{4A}$ is independently $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4A}$ is independently $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{4A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4A}$ is independently $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ is independently $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{4A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{4A}$ is independently $R^{30}$-substituted or unsubstituted aryl (e.g., $C_6$-$C_{10}$ aryl, $C_{10}$ aryl, or phenyl). In embodiments, $R^{4A}$ is independently $R^{30}$-substituted aryl (e.g., $C_6$-$C_{10}$ aryl, $C_{10}$ aryl, or phenyl). In embodiments, $R^{4A}$ is independently an unsubstituted aryl (e.g., $C_6$-$C_{10}$ aryl, $C_{10}$ aryl, or phenyl). In embodiments, $R^{4A}$ is independently $R^{30}$-substituted or unsubstituted heteroaryl (e.g., 5 to 10 membered heteroaryl, 5 to 9 membered heteroaryl, or 5 to 6 membered heteroaryl). In embodiments, $R^{4A}$ is independently $R^{30}$-substituted heteroaryl (e.g., 5 to 10 membered heteroaryl, 5 to 9 membered heteroaryl, or 5 to 6 membered heteroaryl). In embodiments, $R^{4A}$ is independently an unsubstituted heteroaryl (e.g., 5 to 10 membered heteroaryl, 5 to 9 membered heteroaryl, or 5 to 6 membered heteroaryl).

In embodiments, $R^{4A}$ is independently —$CCl_3$. In embodiments, $R^{4A}$ is independently —$CBr_3$. In embodiments, $R^{4A}$ is independently —$CF_3$. In embodiments, $R^{4A}$ is independently —$CI_3$. In embodiments, $R^{4A}$ is independently —$CHCl_2$. In embodiments, $R^{4A}$ is independently —$CHBr_2$. In embodiments, $R^{4A}$ is independently —$CHF_2$. In embodiments, $R^{4A}$ is independently —$CHI_2$. In embodiments, $R^{4A}$ is independently —$CH_2Cl$. In embodiments, $R^{4A}$ is independently —$CH_2Br$. In embodiments, $R^{4A}$ is independently —$CH_2F$. In embodiments, $R^{4A}$ is independently —$CH_2I$. In embodiments, $R^{4A}$ is independently —CN. In embodiments, $R^{4A}$ is independently —OH. In embodiments, $R^{4A}$ is independently —COOH. In embodiments, $R^{4A}$ is independently —$CONH_2$. In embodiments, $R^{4A}$ is independently —$OCCl_3$. In embodiments, $R^{4A}$ is independently —$OCF_3$. In embodiments, $R^{4A}$ is independently —$OCBr_3$. In embodiments, $R^{4A}$ is independently —$OCI_3$. In embodiments, $R^{4A}$ is independently —$OCHCl_2$. In embodiments, $R^{4A}$ is independently —$OCHBr_2$. In embodiments, $R^{4A}$ is independently —$OCHI_2$. In embodiments, $R^{4A}$ is independently —$OCHF_2$. In embodiments, $R^{4A}$ is independently —$OCH_2Cl$. In embodiments, $R^{4A}$ is independently —$OCH_2Br$. In embodiments, $R^{4A}$ is independently —$OCH_2I$. In embodiments, $R^{4A}$ is independently —$OCH_2F$. In embodiments, $R^{4A}$ is independently —$OCH_3$. In embodiments, $R^{4A}$ is independently —$CH_3$. In embodiments, $R^{4A}$ is independently —$CH_2CH_3$. In embodiments, $R^{4A}$ is independently unsubstituted propyl. In embodiments, $R^{4A}$ is independently unsubstituted isopropyl. In embodiments, $R^{4A}$ is independently unsubstituted butyl. In embodiments, $R^{4A}$ is independently unsubstituted tert-butyl. In embodiments, $R^{4A}$ is independently hydrogen.

In embodiments, $R^{4B}$ is independently $R^{30}$-substituted or unsubstituted alkyl (e.g., $C_1$-$C_8$ alkyl, $C_1$-$C_6$ alkyl, or $C_1$-$C_4$ alkyl). In embodiments, $R^{4B}$ is independently $R^{30}$-substituted alkyl (e.g., $C_1$-$C_8$ alkyl, $C_1$-$C_6$ alkyl, or $C_1$-$C_4$ alkyl). In embodiments, $R^{4B}$ is independently an unsubstituted alkyl (e.g., $C_1$-$C_8$ alkyl, $C_1$-$C_6$ alkyl, or $C_1$-$C_4$ alkyl). In embodiments, $R^{4B}$ is independently $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^{4B}$ is independently $R^{30}$-substituted heteroalkyl (e.g., 2 to 8 membered heteroalkyl, 2 to 6 membered heteroalkyl, or 2 to 4 membered heteroalkyl). In embodiments, $R^{4B}$ is independently an unsubstituted heteroalkyl (e.g., 2 to 8 membered heteroalkyl, 2 to 6 membered heteroalkyl, or 2 to 4 membered heteroalkyl). In embodiments, $R^{4B}$ is independently $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4B}$ is independently $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{4B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4B}$ is independently $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4B}$ is independently $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{4B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{4B}$ is independently $R^{30}$-substituted or unsubstituted aryl (e.g., $C_6$-$C_{10}$ aryl, $C_{10}$ aryl, or phenyl). In embodiments, $R^{4B}$ is independently $R^{30}$-substituted aryl (e.g., $C_6$-$C_{10}$ aryl, $C_{10}$ aryl, or phenyl). In embodiments, $R^{4B}$ is independently an unsubstituted aryl (e.g., $C_6$-$C_{10}$ aryl, $C_{10}$ aryl, or phenyl). In embodiments, $R^{4B}$ is independently $R^{30}$-substituted or unsubstituted heteroaryl (e.g., 5 to 10 membered heteroaryl, 5 to 9 membered heteroaryl, or 5 to 6 membered heteroaryl). In embodiments, $R^{4B}$ is independently $R^{30}$-substituted heteroaryl (e.g., 5 to 10 membered heteroaryl, 5 to 9 membered heteroaryl, or 5 to 6 membered heteroaryl). In embodiments, $R^{4B}$ is independently an unsubstituted heteroaryl (e.g., 5 to 10 membered heteroaryl, 5 to 9 membered heteroaryl, or 5 to 6 membered heteroaryl).

In embodiments, $R^{4B}$ is independently —$CCl_3$. In embodiments, $R^{4B}$ is independently —$CBr_3$. In embodiments, $R^{4B}$ is independently —$CF_3$. In embodiments, $R^{4B}$ is independently —$CI_3$. In embodiments, $R^{4B}$ is independently —$CHCl_2$. In embodiments, $R^{4B}$ is independently —$CHBr_2$. In embodiments, $R^{4B}$ is independently —$CHF_2$. In embodiments, $R^{4B}$ is independently —$CHI_2$. In embodiments, $R^{4B}$ is independently —$CH_2Cl$. In embodiments, $R^{4B}$ is independently —$CH_2Br$. In embodiments, $R^{4B}$ is independently —$CH_2F$. In embodiments, $R^{4B}$ is independently —$CH_2I$. In embodiments, $R^{4B}$ is independently —CN. In embodiments, $R^{4B}$ is independently —OH. In embodiments, $R^{4B}$ is independently —COOH. In embodiments, $R^{4B}$ is independently —$CONH_2$. In embodiments, $R^{4B}$ is independently —$OCCl_3$. In embodiments, $R^{4B}$ is independently —$OCF_3$. In embodiments, $R^{4B}$ is independently —$OCBr_3$. In embodiments, $R^{4B}$ is independently —$OCI_3$. In embodiments, $R^{4B}$ is independently —$OCHCl_2$. In embodiments, $R^{4B}$ is independently —$OCHBr_2$. In embodiments, $R^{4B}$ is independently —$OCHI_2$. In embodiments, $R^{4B}$ is independently —$OCHF_2$. In embodiments, $R^{4B}$ is independently —$OCH_2Cl$. In embodiments, $R^{4B}$ is independently —$OCH_2Br$. In embodiments, $R^{4B}$ is independently —OCH$_2$I. In embodiments, $R^{4B}$ is independently —OCH$_2$F. In embodiments, $R^{4B}$ is independently —OCH$_3$. In embodiments, $R^{4B}$ is independently —CH$_3$. In embodiments, $R^{4B}$ is independently —CH$_2$CH$_3$. In embodiments, $R^{4B}$ is independently unsubstituted propyl. In embodiments, $R^{4B}$ is independently unsubstituted isopropyl. In embodiments, $R^{4B}$ is independently unsubstituted butyl. In embodiments, $R^{4B}$ is independently unsubstituted tert-butyl. In embodiments, $R^{4B}$ is independently hydrogen.

In embodiments, $R^{4C}$ is independently $R^{30}$-substituted or unsubstituted alkyl (e.g., $C_1$-$C_8$ alkyl, $C_1$-$C_6$ alkyl, or $C_1$-$C_4$ alkyl). In embodiments, $R^{4C}$ is independently $R^{30}$-substituted alkyl (e.g., $C_1$-$C_8$ alkyl, $C_1$-$C_6$ alkyl, or $C_1$-$C_4$ alkyl). In embodiments, $R^{4C}$ is independently an unsubstituted alkyl (e.g., $C_1$-$C_8$ alkyl, $C_1$-$C_6$ alkyl, or $C_1$-$C_4$ alkyl). In embodiments, $R^{4C}$ is independently $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^{4C}$ is independently $R^{30}$-substituted heteroalkyl (e.g., 2 to 8 membered heteroalkyl, 2 to 6 membered heteroalkyl, or 2 to 4 membered heteroalkyl). In embodiments, $R^{4C}$ is independently an unsubstituted heteroalkyl (e.g., 2 to 8 membered heteroalkyl, 2 to 6 membered heteroalkyl, or 2 to 4 membered heteroalkyl). In embodiments, $R^{4C}$ is independently $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4C}$ is independently $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{4C}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4C}$ is independently $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4C}$ is independently $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{4C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{4C}$ is independently $R^{30}$-substituted or unsubstituted aryl (e.g., $C_6$-$C_{10}$ aryl, $C_{10}$ aryl, or phenyl). In embodiments, $R^{4C}$ is independently $R^{30}$-substituted aryl (e.g., $C_6$-$C_{10}$ aryl, $C_{10}$ aryl, or phenyl). In embodiments, $R^{4C}$ is independently an unsubstituted aryl (e.g., $C_6$-$C_{10}$ aryl, $C_{10}$ aryl, or phenyl). In embodiments, $R^{4C}$ is independently $R^{30}$-substituted or unsubstituted heteroaryl (e.g., 5 to 10 membered heteroaryl, 5 to 9 membered heteroaryl, or 5 to 6 membered heteroaryl). In embodiments, $R^{4C}$ is independently $R^{30}$-substituted heteroaryl (e.g., 5 to 10 membered heteroaryl, 5 to 9 membered heteroaryl, or 5 to 6 membered heteroaryl). In embodiments, $R^{4C}$ is independently an unsubstituted heteroaryl (e.g., 5 to 10 membered heteroaryl, 5 to 9 membered heteroaryl, or 5 to 6 membered heteroaryl).

In embodiments, $R^{4C}$ is independently —CCl$_3$. In embodiments, $R^{4C}$ is independently —CBr$_3$. In embodiments, $R^{4C}$ is independently —CF$_3$. In embodiments, $R^{4C}$ is independently —CI$_3$. In embodiments, $R^{4C}$ is independently —CHCl$_2$. In embodiments, $R^{4C}$ is independently —CHBr$_2$. In embodiments, $R^{4C}$ is independently —CHF$_2$. In embodiments, $R^{4C}$ is independently —CHI$_2$. In embodiments, $R^{4C}$ is independently —CH$_2$Cl. In embodiments, $R^{4C}$ is independently —CH$_2$Br. In embodiments, $R^{4C}$ is independently —CH$_2$F. In embodiments, $R^{4C}$ is independently —CH$_2$I. In embodiments, $R^{4C}$ is independently —CN. In embodiments, $R^{4C}$ is independently —OH. In embodiments, $R^{4C}$ is independently —COOH. In embodiments, $R^{4C}$ is independently —CONH$_2$. In embodiments, $R^{4C}$ is independently —OCCl$_3$. In embodiments, $R^{4C}$ is independently —OCF$_3$. In embodiments, $R^{4C}$ is independently —OCBr$_3$. In embodiments, $R^{4C}$ is independently —OCI$_3$. In embodiments, $R^{4C}$ is independently —OCHCl$_2$. In embodiments, $R^{4C}$ is independently —OCHBr$_2$. In embodiments, $R^{4C}$ is independently —OCHI$_2$. In embodiments, $R^{4C}$ is independently —OCHF$_2$. In embodiments, $R^{4C}$ is independently —OCH$_2$Cl. In embodiments, $R^{4C}$ is independently —OCH$_2$Br. In embodiments, $R^{4C}$ is independently —OCH$_2$I. In embodiments, $R^{4C}$ is independently —OCH$_2$F. In embodiments, $R^{4C}$ is independently —OCH$_3$. In embodiments, $R^{4C}$ is idenpendently —CH$_3$. In embodiments, $R^{4C}$ is independently —CH$_2$CH$_3$. In embodiments, $R^{4C}$ is independently unsubstituted propyl. In embodiments, $R^{4C}$ is independently unsubstituted isopropyl. In embodiments, $R^{4C}$ is independently unsubstituted butyl. In embodiments, $R^{4C}$ is independently unsubstituted tert-butyl. In embodiments, $R^{4C}$ is independently hydrogen.

In embodiments, $R^{4D}$ is independently $R^{30}$-substituted or unsubstituted alkyl (e.g., $C_1$-$C_8$ alkyl, $C_1$-$C_6$ alkyl, or $C_1$-$C_4$ alkyl). In embodiments, $R^{4D}$ is independently $R^{30}$-substituted alkyl (e.g., $C_1$-$C_8$ alkyl, $C_1$-$C_6$ alkyl, or $C_1$-$C_4$ alkyl). In embodiments, $R^{4D}$ is independently an unsubstituted alkyl (e.g., $C_1$-$C_8$ alkyl, $C_1$-$C_6$ alkyl, or $C_1$-$C_4$ alkyl). In embodiments, $R^{4D}$ is independently $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^{4D}$ is independently $R^{30}$-substituted heteroalkyl (e.g., 2 to 8 membered heteroalkyl, 2 to 6 membered heteroalkyl, or 2 to 4 membered heteroalkyl). In embodiments, $R^{4D}$ is independently an unsubstituted heteroalkyl (e.g., 2 to 8 membered heteroalkyl, 2 to 6 membered heteroalkyl, or 2 to 4 membered heteroalkyl). In embodiments, $R^{4D}$ is independently $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4D}$ is independently $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{4D}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{4D}$ is independently $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{4D}$ is independently $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{4D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{4D}$ is independently $R^{30}$-substituted or unsubstituted aryl (e.g., $C_6$-$C_{10}$ aryl, $C_{10}$ aryl, or phenyl). In embodiments, $R^{4D}$ is independently $R^{30}$-substituted aryl (e.g., $C_6$-$C_{10}$ aryl, $C_{10}$ aryl, or phenyl). In embodiments, $R^{4D}$ is independently an unsubstituted aryl (e.g., $C_6$-$C_{10}$ aryl, $C_{10}$ aryl, or phenyl). In embodiments, $R^{4D}$ is independently $R^{30}$-substituted or unsubstituted heteroaryl (e.g., 5 to 10 membered heteroaryl, 5 to 9 membered heteroaryl, or 5 to 6 membered heteroaryl). In embodiments, $R^{4D}$ is independently $R^{30}$-substituted heteroaryl (e.g., 5 to 10 membered heteroaryl, 5 to 9 membered heteroaryl, or 5 to 6 membered heteroaryl). In embodiments, $R^{4D}$ is independently an unsubstituted heteroaryl (e.g., 5 to 10 membered heteroaryl, 5 to 9 membered heteroaryl, or 5 to 6 membered heteroaryl).

In embodiments, $R^{4D}$ is independently —CCl$_3$. In embodiments, $R^{4D}$ is independently —CBr$_3$. In embodiments, $R^{4D}$ is independently —CF$_3$. In embodiments, $R^{4D}$ is independently —CI$_3$. In embodiments, $R^{4D}$ is independently —CHCl$_2$. In embodiments, $R^{4D}$ is independently —CHBr$_2$. In embodiments, $R^{4D}$ is independently —CHF$_2$. In embodiments, $R^{4D}$ is independently —CHI$_2$. In embodiments, $R^{4D}$ is independently —CH$_2$Cl. In embodiments, $R^{4D}$ is independently —CH$_2$Br. In embodiments, $R^{4D}$ is independently —CH$_2$F. In embodiments, $R^{4D}$ is independently —CH$_2$I. In embodiments, $R^{4D}$ is independently —CN. In embodiments, $R^{4D}$ is independently —OH. In embodiments, $R^{4D}$ is independently —COOH. In embodiments, $R^{4D}$ is independently —CONH$_2$. In embodiments, $R^{4D}$ is independently —OCCl$_3$. In embodiments, $R^{4D}$ is independently —OCF$_3$. In embodiments, $R^{4D}$ is independently —OCBr$_3$. In embodiments, $R^{4D}$ is independently —OCl$_3$. In embodiments, $R^{4D}$ is independently —OCHCl$_2$. In embodiments, $R^{4D}$ is independently —OCHBr$_2$. In embodiments, $R^{4D}$ is independently —OCHI$_2$. In embodiments, $R^{4D}$ is independently —OCHF$_2$. In embodiments, $R^{4D}$ is independently —OCH$_2$Cl. In embodiments, $R^{4D}$ is independently —OCH$_2$Br. In embodiments, $R^{4D}$ is independently —OCH$_2$I. In embodiments, $R^{4D}$ is independently —OCH$_2$F. In embodiments, $R^{4D}$ is independently —OCH$_3$. In embodiments, $R^{4D}$ is independently CH$_3$. In embodiments, $R^{4D}$ is independently —CH$_2$CH$_3$. In embodiments, $R^{4D}$ is independently unsubstituted propyl. In embodiments, $R^{4D}$ is independently unsubstituted isopropyl. In embodiments, $R^{4D}$ is independently unsubstituted butyl. In embodiments, $R^{4D}$ is independently unsubstituted tert-butyl. In embodiments, $R^{4D}$ is independently hydrogen.

In embodiments, $R^5$ is independently hydrogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —COOH, —CONH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^5$ is independently substituted or unsubstituted alkyl (e.g., C$_1$-C$_8$ alkyl, C$_1$-C$_6$ alkyl, or C$_1$-C$_4$ alkyl). In embodiments, $R^5$ is independently substituted alkyl (e.g., C$_1$-C$_8$ alkyl, C$_1$-C$_6$ alkyl, or C$_1$-C$_4$ alkyl). In embodiments, $R^5$ is independently an unsubstituted alkyl (e.g., C$_1$-C$_8$ alkyl, C$_1$-C$_6$ alkyl, or C$_1$-C$_4$ alkyl). In embodiments, $R^5$ is independently substituted or unsubstituted heteroalkyl (e.g., 2 to 8 membered heteroalkyl, 2 to 6 membered heteroalkyl, or 2 to 4 membered heteroalkyl). In embodiments, $R^5$ is independently substituted heteroalkyl (e.g., 2 to 8 membered heteroalkyl, 2 to 6 membered heteroalkyl, or 2 to 4 membered heteroalkyl). In embodiments, $R^5$ is independently an unsubstituted heteroalkyl (e.g., 2 to 8 membered heteroalkyl, 2 to 6 membered heteroalkyl, or 2 to 4 membered heteroalkyl). In embodiments, $R^5$ is independently substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^5$ is independently substituted cycloalkyl (e.g., C$_3$-C$_8$ cycloalkyl, C$_3$-C$_6$ cycloalkyl, or C$_5$-C$_6$ cycloalkyl). In embodiments, $R^5$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, $R^5$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is independently substituted heterocycloalkyl (e.g., 3 to 8 membered heterocycloalkyl, 3 to 6 membered heterocycloalkyl, or 5 to 6 membered heterocycloalkyl). In embodiments, $R^5$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is independently substituted or unsubstituted aryl (e.g., C$_6$-C$_{10}$ aryl, C$_{10}$ aryl, or phenyl). In embodiments, $R^5$ is independently substituted aryl (e.g., C$_6$-C$_{10}$ aryl, C$_{10}$ aryl, or phenyl). In embodiments, $R^5$ is independently an unsubstituted aryl (e.g., C$_6$-C$_{10}$ aryl, C$_{10}$ aryl, or phenyl). In embodiments, $R^5$ is independently substituted or unsubstituted heteroaryl (e.g., 5 to 10 membered heteroaryl, 5 to 9 membered heteroaryl, or 5 to 6 membered heteroaryl). In embodiments, $R^5$ is independently substituted heteroaryl (e.g., 5 to 10 membered heteroaryl, 5 to 9 membered heteroaryl, or 5 to 6 membered heteroaryl). In embodiments, $R^5$ is independently an unsubstituted heteroaryl (e.g., 5 to 10 membered heteroaryl, 5 to 9 membered heteroaryl, or 5 to 6 membered heteroaryl).

In embodiments, $R^5$ is independently hydrogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —COOH, —CONH$_2$, $R^{33}$-substituted or unsubstituted alkyl (e.g., C$_1$-C$_8$ alkyl, C$_1$-C$_6$ alkyl, or C$_1$-C$_4$ alkyl), $R^{33}$-substituted or unsubstituted heteroalkyl (e.g., 2 to 8 membered heteroalkyl, 2 to 6 membered heteroalkyl, or 2 to 4 membered heteroalkyl), $R^{33}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{33}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33}$-substituted or unsubstituted aryl (e.g., C$_6$-C$_{10}$ aryl, C$_{10}$ aryl, or phenyl), or $R^{33}$-substituted or unsubstituted heteroaryl (e.g., 5 to 10 membered heteroaryl, 5 to 9 membered heteroaryl, or 5 to 6 membered heteroaryl). In embodiments, $R^5$ is independently hydrogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —COOH, —CONH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^5$ is independently $R^{33}$-substituted or unsubstituted alkyl (e.g., $C_1$-$C_8$ alkyl, $C_1$-$C_6$ alkyl, or $C_1$-$C_4$ alkyl). In embodiments, $R^5$ is independently $R^{33}$-substituted alkyl (e.g., $C_1$-$C_8$ alkyl, $C_1$-$C_6$ alkyl, or $C_1$-$C_4$ alkyl). In embodiments, $R^5$ is independently an unsubstituted alkyl (e.g., $C_1$-$C_8$ alkyl, $C_1$-$C_6$ alkyl, or $C_1$-$C_4$ alkyl). In embodiments, $R^5$ is independently $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^5$ is independently $R^{33}$-substituted heteroalkyl (e.g., 2 to 8 membered heteroalkyl, 2 to 6 membered heteroalkyl, or 2 to 4 membered heteroalkyl). In embodiments, $R^5$ is independently an unsubstituted heteroalkyl (e.g., 2 to 8 membered heteroalkyl, 2 to 6 membered heteroalkyl, or 2 to 4 membered heteroalkyl). In embodiments, $R^5$ is independently $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is independently $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^5$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is independently $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is independently $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^5$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is independently $R^{33}$-substituted or unsubstituted aryl (e.g., $C_6$-$C_{10}$ aryl, $C_{10}$ aryl, or phenyl). In embodiments, $R^5$ is independently $R^{33}$-substituted aryl (e.g., $C_6$-$C_{10}$ aryl, $C_{10}$ aryl, or phenyl). In embodiments, $R^5$ is independently an unsubstituted aryl (e.g., $C_6$-$C_{10}$ aryl, $C_{10}$ aryl, or phenyl). In embodiments, $R^5$ is independently $R^{33}$-substituted or unsubstituted heteroaryl (e.g., 5 to 10 membered heteroaryl, 5 to 9 membered heteroaryl, or 5 to 6 membered heteroaryl). In embodiments, $R^5$ is independently $R^{33}$-substituted heteroaryl (e.g., 5 to 10 membered heteroaryl, 5 to 9 membered heteroaryl, or 5 to 6 membered heteroaryl). In embodiments, $R^5$ is independently an unsubstituted heteroaryl (e.g., 5 to 10 membered heteroaryl, 5 to 9 membered heteroaryl, or 5 to 6 membered heteroaryl).

In embodiments, $R^5$ is independently —$CX^5_3$. In embodiments, $R^5$ is independently —$CHX^5_2$. In embodiments, $R^5$ is independently —$CH_2X^5$. In embodiments, $R^5$ is independently —$OCX^5_3$. In embodiments, $R^5$ is independently —$OCH_2X^5$. In embodiments, $R^5$ is independently —$OCHX^5_2$. In embodiments, $R^5$ is independently —CN. In embodiments, $R^5$ is independently —$C(O)R^{5C}$. In embodiments, $R^5$ is independently —$C(O)$—$OR^{5C}$. In embodiments, $R^5$ is independently —$C(O)NR^{5A}R^{5B}$. In embodiments, $R^5$ is independently —$OR^{5D}$. In embodiments, $R^5$ is independently hydrogen. $X^5$ is independently halogen.

In embodiments, $R^5$ is independently —$CCl_3$. In embodiments, $R^5$ is independently —$CBr_3$. In embodiments, $R^5$ is independently —$CF_3$. In embodiments, $R^5$ is independently —$CI_3$. In embodiments, $R^5$ is independently —$CHCl_2$. In embodiments, $R^5$ is independently —$CHBr_2$. In embodiments, $R^5$ is independently —$CHF_2$. In embodiments, $R^5$ is independently —$CHI_2$. In embodiments, $R^5$ is independently —$CH_2Cl$. In embodiments, $R^5$ is independently —$CH_2Br$. In embodiments, $R^5$ is independently —$CH_2F$. In embodiments, $R^5$ is independently —$CH_2I$. In embodiments, $R^5$ is independently —CN. In embodiments, $R^5$ is independently —OH. In embodiments, $R^5$ is independently —COOH. In embodiments, $R^5$ is independently —$CONH_2$. In embodiments, $R^5$ is independently —$OCCl_3$. In embodiments, $R^5$ is independently —$OCF_3$. In embodiments, $R^5$ is independently —$OCBr_3$. In embodiments, $R^5$ is independently —$OCl_3$. In embodiments, $R^5$ is independently —$OCHCl_2$. In embodiments, $R^5$ is independently —$OCHBr_2$. In embodiments, $R^5$ is independently —$OCHI_2$. In embodiments, $R^5$ is independently —$OCHF_2$. In embodiments, $R^5$ is independently —$OCH_2Cl$. In embodiments, $R^5$ is independently —$OCH_2Br$. In embodiments, $R^5$ is independently —$OCH_2I$. In embodiments, $R^5$ is independently —$OCH_2F$. In embodiments, $R^5$ is independently —$OCH_3$. In embodiments, $R^5$ is independently —$CH_3$. In embodiments, $R^5$ is independently —$CH_2CH_3$. In embodiments, $R^5$ is independently unsubstituted propyl. In embodiments, $R^5$ is independently unsubstituted isopropyl. In embodiments, $R^5$ is independently unsubstituted butyl. In embodiments, $R^5$ is independently unsubstituted tert-butyl. In embodiments, $X^5$ is independently —F. In embodiments, $X^5$ is independently —Cl. In embodiments, $X^5$ is independently —Br. In embodiments, $X^5$ is independently —I.

$R^{33}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, $NHC(O)NH_2$, —$NHSO_2H$, —$NHC(O)H$, —$NHC(O)OH$, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl). In embodiments, $R^{33}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{33}$ is independently oxo. In embodiments, $R^{33}$ is independently halogen. In embodiments, $R^{33}$ is independently —$CCl_3$. In embodiments, $R^{33}$ is independently —CBr$_3$. In embodiments, R$^{33}$ is independently —CF$_3$. In embodiments, R$^{33}$ is independently —CI$_3$. In embodiments, R$^{33}$ is independently —CHCl$_2$. In embodiments, R$^{33}$ is independently —CHBr$_2$. In embodiments, R$^{33}$ is independently —CHF$_2$. In embodiments, R$^{33}$ is independently —CHI$_2$. In embodiments, R$^{33}$ is independently —CH$_2$Cl. In embodiments, R$^{33}$ is independently —CH$_2$Br. In embodiments, R$^{33}$ is independently —CH$_2$F. In embodiments, R$^{33}$ is independently —CH$_2$I. In embodiments, R$^{33}$ is independently —CN. In embodiments, R$^{33}$ is independently —OH. In embodiments, R$^{33}$ is independently —NH$_2$. In embodiments, R$^{33}$ is independently —COOH. In embodiments, R$^{33}$ is independently —CONH$_2$. In embodiments, R$^{33}$ is independently —NO$_2$. In embodiments, R$^{33}$ is independently —SH. In embodiments, R$^{33}$ is independently —SO$_3$H. In embodiments, R$^{33}$ is independently —SO$_4$H. In embodiments, R$^{33}$ is independently —SO$_2$NH$_2$. In embodiments, R$^{33}$ is independently —NHNH$_2$. In embodiments, R$^{33}$ is independently —ONH$_2$. In embodiments, R$^{33}$ is independently —NHC(O)NHNH$_2$. In embodiments, R$^{33}$ is independently —NHC(O)NH$_2$. In embodiments, R$^{33}$ is independently —NHSO$_2$H. In embodiments, R$^{33}$ is independently —NHC(O)H. In embodiments, R$^{33}$ is independently —NHC(O)OH. In embodiments, R$^{33}$ is independently —NHOH. In embodiments, R$^{33}$ is independently —OCCl$_3$. In embodiments, R$^{33}$ is independently —OCF$_3$. In embodiments, R$^{33}$ is independently —OCBr$_3$. In embodiments, R$^{33}$ is independently —OCI$_3$. In embodiments, R$^{33}$ is independently —OCHCl$_2$. In embodiments, R$^{33}$ is independently —OCHBr$_2$. In embodiments, R$^{33}$ is independently —OCHI$_2$. In embodiments, R$^{33}$ is independently —OCHF$_2$.

In embodiments, R$^{33}$ is independently —OCH$_2$Cl. In embodiments, R$^{33}$ is independently —OCH$_2$Br. In embodiments, R$^{33}$ is independently —OCH$_2$I. In embodiments, R$^{33}$ is independently —OCH$_2$F. In embodiments, R$^{33}$ is independently —N$_3$. In embodiments, R$^{33}$ is independently —OCH$_3$. In embodiments, R$^{33}$ is independently —CH$_3$. In embodiments, R$^{33}$ is independently —CH$_2$CH$_3$. In embodiments, R$^{33}$ is independently unsubstituted propyl. In embodiments, R$^{33}$ is independently unsubstituted isopropyl. In embodiments, R$^{33}$ is independently unsubstituted butyl. In embodiments, R$^{33}$ is independently unsubstituted tert-butyl. In embodiments, R$^{33}$ is independently —F. In embodiments, R$^{33}$ is independently —Cl. In embodiments, R$^{33}$ is independently —Br. In embodiments, R$^{33}$ is independently —I.

In embodiments, R$^{33}$ is independently R$^{34}$-substituted or unsubstituted alkyl (e.g., C$_1$-C$_8$ alkyl, C$_1$-C$_6$ alkyl, or C$_1$-C$_4$ alkyl). In embodiments, R$^{33}$ is independently R$^{34}$-substituted alkyl (e.g., C$_1$-C$_8$ alkyl, C$_1$-C$_6$ alkyl, or C$_1$-C$_4$ alkyl). In embodiments, R$^{33}$ is independently an unsubstituted alkyl (e.g., C$_1$-C$_8$ alkyl, C$_1$-C$_6$ alkyl, or C$_1$-C$_4$ alkyl). In embodiments, R$^{33}$ is independently R$^{34}$-substituted or unsubstituted heteroalkyl (e.g., 2 to 8 membered heteroalkyl, 2 to 6 membered heteroalkyl, or 2 to 4 membered heteroalkyl). In embodiments, R$^{33}$ is independently R$^{34}$-substituted heteroalkyl (e.g., 2 to 8 membered heteroalkyl, 2 to 6 membered heteroalkyl, or 2 to 4 membered heteroalkyl). In embodiments, R$^{33}$ is independently an unsubstituted heteroalkyl (e.g., 2 to 8 membered heteroalkyl, 2 to 6 membered heteroalkyl, or 2 to 4 membered heteroalkyl). In embodiments, R$^{33}$ is independently R$^{34}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{33}$ is independently R$^{34}$-substituted cycloalkyl (e.g., C$_3$-C$_8$ cycloalkyl, C$_3$-C$_6$ cycloalkyl, or C$_5$-C$_6$ cycloalkyl). In embodiments, R$^{33}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{33}$ is independently R$^{34}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{33}$ is independently R$^{34}$-substituted heterocycloalkyl (e.g., 3 to 8 membered heterocycloalkyl, 3 to 6 membered heterocycloalkyl, or 5 to 6 membered heterocycloalkyl). In embodiments, R$^{33}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{33}$ is independently R$^{34}$-substituted or unsubstituted aryl (e.g., C$_6$-C$_{10}$ aryl, C$_{10}$ aryl, or phenyl). In embodiments, R$^{33}$ is independently R$^{34}$-substituted aryl (e.g., C$_6$-C$_{10}$ aryl, C$_{10}$ aryl, or phenyl). In embodiments, R$^{33}$ is independently an unsubstituted aryl (e.g., C$_6$-C$_{10}$ aryl, C$_{10}$ aryl, or phenyl). In embodiments, R$^{33}$ is independently R$^{34}$-substituted or unsubstituted heteroaryl (e.g., 5 to 10 membered heteroaryl, 5 to 9 membered heteroaryl, or 5 to 6 membered heteroaryl). In embodiments, R$^{33}$ is independently R$^{34}$-substituted heteroaryl (e.g., 5 to 10 membered heteroaryl, 5 to 9 membered heteroaryl, or 5 to 6 membered heteroaryl). In embodiments, R$^{33}$ is independently an unsubstituted heteroaryl (e.g., 5 to 10 membered heteroaryl, 5 to 9 membered heteroaryl, or 5 to 6 membered heteroaryl).

R$^{34}$ is independently oxo, halogen, —CCl$_3$, —CBr$_3$, —CF$_3$, —CI$_3$, —CHCl$_2$, —CHBr$_2$, —CHF$_2$, —CH$_2$Cl, —CH$_2$Br, —CH$_2$F, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHF$_2$, —OCH$_2$Cl, —OCH$_2$Br, —OCH$_2$F, —N$_3$, R$^{35}$-substituted or unsubstituted alkyl (e.g., C$_1$-C$_8$ alkyl, C$_1$-C$_6$ alkyl, or C$_1$-C$_4$ alkyl), R$^{35}$-substituted or unsubstituted heteroalkyl (e.g., 2 to 8 membered heteroalkyl, 2 to 6 membered heteroalkyl, or 2 to 4 membered heteroalkyl), R$^{35}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{35}$-substituted or unsubstituted heterocycloalkyl (e.g., 3 to 8 membered heterocycloalkyl, 3 to 6 membered heterocycloalkyl, or 5 to 6 membered heterocycloalkyl), R$^{35}$-substituted or unsubstituted aryl (e.g., C$_6$-C$_{10}$ aryl, C$_{10}$ aryl, or phenyl), or R$^{35}$-substituted or unsubstituted heteroaryl (e.g., 5 to 10 membered heteroaryl, 5 to 9 membered heteroaryl, or 5 to 6 membered heteroaryl). In embodiments, R$^{34}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{34}$ is independently R$^{35}$-substituted or unsubstituted alkyl (e.g., C$_1$-C$_8$ alkyl, C$_1$-C$_6$ alkyl, or C$_1$-C$_4$ alkyl). In embodiments, $R^{34}$ is independently $R^{35}$-substituted alkyl (e.g., $C_1$-$C_8$ alkyl, $C_1$-$C_6$ alkyl, or $C_1$-$C_4$ alkyl). In embodiments, $R^{34}$ is independently an unsubstituted alkyl (e.g., $C_1$-$C_8$ alkyl, $C_1$-$C_6$ alkyl, or $C_1$-$C_4$ alkyl). In embodiments, $R^{34}$ is independently $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^{34}$ is independently $R^{35}$-substituted heteroalkyl (e.g., 2 to 8 membered heteroalkyl, 2 to 6 membered heteroalkyl, or 2 to 4 membered heteroalkyl). In embodiments, $R^{34}$ is independently an unsubstituted heteroalkyl (e.g., 2 to 8 membered heteroalkyl, 2 to 6 membered heteroalkyl, or 2 to 4 membered heteroalkyl). In embodiments, $R^{34}$ is independently $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{34}$ is independently $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^{34}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{34}$ is independently $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{34}$ is independently $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^{34}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{34}$ is independently $R^{35}$-substituted or unsubstituted aryl (e.g., $C_6$-$C_{10}$ aryl, $C_{10}$ aryl, or phenyl). In embodiments, $R^{34}$ is independently $R^{35}$-substituted aryl (e.g., $C_6$-$C_{10}$ aryl, $C_{10}$ aryl, or phenyl). In embodiments, $R^{34}$ is independently an unsubstituted aryl (e.g., $C_6$-$C_{10}$ aryl, $C_{10}$ aryl, or phenyl). In embodiments, $R^{34}$ is independently $R^{35}$-substituted or unsubstituted heteroaryl (e.g., 5 to 10 membered heteroaryl, 5 to 9 membered heteroaryl, or 5 to 6 membered heteroaryl). In embodiments, $R^{34}$ is independently $R^{35}$-substituted heteroaryl (e.g., 5 to 10 membered heteroaryl, 5 to 9 membered heteroaryl, or 5 to 6 membered heteroaryl). In embodiments, $R^{34}$ is independently an unsubstituted heteroaryl (e.g., 5 to 10 membered heteroaryl, 5 to 9 membered heteroaryl, or 5 to 6 membered heteroaryl).

In embodiments, $R^{34}$ is independently oxo. In embodiments, $R^{34}$ is independently halogen. In embodiments, $R^{34}$ is independently —$CCl_3$. In embodiments, $R^{34}$ is independently —$CBr_3$. In embodiments, $R^{34}$ is independently —$CF_3$. In embodiments, $R^{34}$ is independently —$CI_3$. In embodiments, $R^{34}$ is independently —$CHCl_2$. In embodiments, $R^{34}$ is independently —$CHBr_2$. In embodiments, $R^{34}$ is independently —$CHF_2$. In embodiments, $R^{34}$ is independently —$CHI_2$. In embodiments, $R^{34}$ is independently —$CH_2Cl$. In embodiments, $R^{34}$ is independently —$CH_2Br$. In embodiments, $R^{34}$ is independently —$CH_2F$. In embodiments, $R^{34}$ is independently —$CH_2I$. In embodiments, $R^{34}$ is independently —CN. In embodiments, $R^{34}$ is independently —OH. In embodiments, $R^{34}$ is independently —$NH_2$. In embodiments, $R^{34}$ is independently —COOH. In embodiments, $R^{34}$ is independently —$CONH_2$. In embodiments, $R^{34}$ is independently —$NO_2$. In embodiments, $R^{34}$ is independently —SH. In embodiments, $R^{34}$ is independently —$SO_3H$. In embodiments, $R^{34}$ is independently —$SO_4H$. In embodiments, $R^{34}$ is independently —$SO_2NH_2$. In embodiments, $R^{34}$ is independently —$NHNH_2$. In embodiments, $R^{34}$ is independently —$ONH_2$. In embodiments, $R^{34}$ is independently —$NHC(O)NHNH_2$. In embodiments, $R^{34}$ is independently —$NHC(O)NH_2$. In embodiments, $R^{34}$ is independently —$NHSO_2H$. In embodiments, $R^{34}$ is independently —NHC(O)H. In embodiments, $R^{34}$ is independently —NHC(O)OH. In embodiments, $R^{34}$ is independently —NHOH. In embodiments, $R^{34}$ is independently —$OCCl_3$. In embodiments, $R^{34}$ is independently —$OCF_3$. In embodiments, $R^{34}$ is independently —$OCBr_3$. In embodiments, $R^{34}$ is independently —$OCI_3$. In embodiments, $R^{34}$ is independently —$OCHCl_2$. In embodiments, $R^{34}$ is independently —$OCHBr_2$. In embodiments, $R^{34}$ is independently —$OCHI_2$. In embodiments, $R^{34}$ is independently —$OCHF_2$. In embodiments, $R^{34}$ is independently —$OCH_2Cl$. In embodiments, $R^{34}$ is independently —$OCH_2Br$. In embodiments, $R^{34}$ is independently —$OCH_2I$. In embodiments, $R^{34}$ is independently —$OCH_2F$. In embodiments, $R^{34}$ is independently —$N_3$. In embodiments, $R^{34}$ is independently —$OCH_3$. In embodiments, $R^{34}$ is independently —$CH_3$. In embodiments, $R^{34}$ is independently —$CH_2CH_3$. In embodiments, $R^{34}$ is independently unsubstituted propyl. In embodiments, $R^{34}$ is independently unsubstituted isopropyl. In embodiments, $R^{34}$ is independently unsubstituted butyl. In embodiments, $R^{34}$ is independently unsubstituted tert-butyl. In embodiments, $R^{34}$ is independently —F. In embodiments, $R^{34}$ is independently —Cl. In embodiments, $R^{34}$ is independently —Br. In embodiments, $R^{34}$ is independently —I.

$R^{35}$ is independently oxo, halogen, —$CF_3$, —$CBr_3$, —$CCl_3$, —$CI_3$, —$CHF_2$, —$CHBr_2$, —$CHCl_2$, —$CH_2F$, —$CH_2Br$, —$CH_2Cl$, —$OCF_3$, —$OCBr_3$, —$OCCl_3$, —$OCI_3$, —$OCHF_2$, —$OCHBr_2$, —$OCHCl_2$, —$OCH_2F$, —$OCH_2Br$, —$OCH_2Cl$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{35}$ is independently an unsubstituted alkyl (e.g., $C_1$-$C_8$ alkyl, $C_1$-$C_6$ alkyl, or $C_1$-$C_4$ alkyl). In embodiments, $R^{35}$ is independently an unsubstituted heteroalkyl (e.g., 2 to 8 membered heteroalkyl, 2 to 6 membered heteroalkyl, or 2 to 4 membered heteroalkyl). In embodiments, $R^{35}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{35}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{35}$ is independently an unsubstituted aryl (e.g., $C_6$-$C_{10}$ aryl, $C_{10}$ aryl, or phenyl). In embodiments, $R^{35}$ is independently an unsubstituted heteroaryl (e.g., 5 to 10 membered heteroaryl, 5 to 9 membered heteroaryl, or 5 to 6 membered heteroaryl).

In embodiments, $R^{35}$ is independently oxo. In embodiments, $R^{35}$ is independently halogen. In embodiments, $R^{35}$ is independently —$CCl_3$. In embodiments, $R^{35}$ is independently —$CBr_3$. In embodiments, $R^{35}$ is independently —$CF_3$. In embodiments, $R^{35}$ is independently —$CI_3$. In embodiments, $R^{35}$ is independently —$CHCl_2$. In embodiments, $R^{35}$ is independently —$CHBr_2$. In embodiments, $R^{35}$ is independently —$CHF_2$. In embodiments, $R^{35}$ is independently —CHI$_2$. In embodiments, R$^{35}$ is independently —CH$_2$Cl. In embodiments, R$^{35}$ is independently —CH$_2$Br. In embodiments, R$^{35}$ is independently —CH$_2$F. In embodiments, R$^{35}$ is independently —CH$_2$I. In embodiments, R$^{35}$ is independently —CN. In embodiments, R$^{35}$ is independently —OH. In embodiments, R$^{35}$ is independently —NH$_2$. In embodiments, R$^{35}$ is independently —COOH. In embodiments, R$^{35}$ is independently —CONH$_2$. In embodiments, R$^{35}$ is independently —NO$_2$. In embodiments, R$^{35}$ is independently —SH. In embodiments, R$^{35}$ is independently —SO$_3$H. In embodiments, R$^{35}$ is independently —SO$_4$H. In embodiments, R$^{35}$ is independently —SO$_2$NH$_2$. In embodiments, R$^{35}$ is independently —NHNH$_2$. In embodiments, R$^{35}$ is independently —ONH$_2$. In embodiments, R$^{35}$ is independently —NHC(O)NHNH$_2$. In embodiments, R$^{35}$ is independently —NHC(O)NH$_2$. In embodiments, R$^{35}$ is independently —NHSO$_2$H. In embodiments, R$^{35}$ is independently —NHC(O)H. In embodiments, R$^{35}$ is independently —NHC(O)OH. In embodiments, R$^{35}$ is independently —NHOH. In embodiments, R$^{35}$ is independently —OCCl$_3$. In embodiments, R$^{35}$ is independently —OCF$_3$. In embodiments, R$^{35}$ is independently —OCBr$_3$. In embodiments, R$^{35}$ is independently —OCI$_3$. In embodiments, R$^{35}$ is independently —OCHCl$_2$. In embodiments, R$^{35}$ is independently —OCHBr$_2$. In embodiments, R$^{35}$ is independently —OCHI$_2$. In embodiments, R$^{35}$ is independently —OCHF$_2$. In embodiments, R$^{35}$ is independently —OCH$_2$Cl. In embodiments, R$^{35}$ is independently —OCH$_2$Br. In embodiments, R$^{35}$ is independently —OCH$_2$I. In embodiments, R$^{35}$ is independently —OCH$_2$F. In embodiments, R$^{35}$ is independently —N$_3$. In embodiments, R$^{35}$ is independently —OCH$_3$. In embodiments, R$^{35}$ is independently —CH$_3$. In embodiments, R$^{35}$ is independently —CH$_2$CH$_3$. In embodiments, R$^{35}$ is independently unsubstituted propyl. In embodiments, R$^{35}$ is independently unsubstituted isopropyl. In embodiments, R$^{35}$ is independently unsubstituted butyl. In embodiments, R$^{35}$ is independently unsubstituted tert-butyl. In embodiments, R$^{35}$ is independently —F. In embodiments, R$^{35}$ is independently —Cl. In embodiments, R$^{35}$ is independently —Br. In embodiments, R$^{35}$ is independently —I.

In embodiments, R$^{5A}$ is independently hydrogen, halogen, —CF$_3$, —CBr$_3$, —CCl$_3$, —CI$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCI$_3$, —OCHF$_2$, —OCHBr$_2$, —OCHCl$_2$, —OCH$_2$F, —OCH$_2$Br, —OCH$_2$Cl, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{5B}$ is independently hydrogen, halogen, —CF$_3$, —CBr$_3$, —CCl$_3$, —CI$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCI$_3$, —OCHF$_2$, —OCHBr$_2$, —OCHCl$_2$, —OCH$_2$F, —OCH$_2$Br, —OCH$_2$Cl, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{5C}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{5D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{5A}$ and R$^{5B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, R$^{5A}$ and R$^{5B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{5A}$ and R$^{5B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{5A}$ and $R^{5B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{5A}$ and $R^{5B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{5A}$ and $R^{5B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{5A}$ and $R^{5B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{5A}$, $R^{5B}$, $R^{5C}$, and $R^{5D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{33}$-substituted or unsubstituted alkyl (e.g., $C_1$-$C_8$ alkyl, $C_1$-$C_6$ alkyl, or $C_1$-$C_4$ alkyl), $R^{33}$-substituted or unsubstituted heteroalkyl (e.g., 2 to 8 membered heteroalkyl, 2 to 6 membered heteroalkyl, or 2 to 4 membered heteroalkyl), $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{33}$-substituted or unsubstituted heterocycloalkyl (e.g., 3 to 8 membered heterocycloalkyl, 3 to 6 membered heterocycloalkyl, or 5 to 6 membered heterocycloalkyl), $R^{33}$-substituted or unsubstituted aryl (e.g., $C_6$-$C_{10}$ aryl, $C_{10}$ aryl, or phenyl), or $R^{33}$-substituted or unsubstituted heteroaryl (e.g., 5 to 10 membered heteroaryl, 5 to 9 membered heteroaryl, or 5 to 6 membered heteroaryl). In embodiments, $R^{5A}$ and $R^{5B}$ substituents bonded to the same nitrogen atom are independently joined to form an $R^{33}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{33}$-substituted or unsubstituted heteroaryl (e.g., 5 to 10 membered heteroaryl, 5 to 9 membered heteroaryl, or 5 to 6 membered heteroaryl). In embodiments, $R^{5A}$ and $R^{5B}$ substituents bonded to the same nitrogen atom are independently joined to form an $R^{33}$-substituted or unsubstituted heterocycloalkyl (e.g., 3 to 8 membered heterocycloalkyl, 3 to 6 membered heterocycloalkyl. In embodiments, $R^{5A}$ and $R^{5B}$ substituents bonded to the same nitrogen atom are independently joined to form an $R^{33}$-substituted or unsubstituted heteroaryl (e.g., 5 to 10 membered heteroaryl, 5 to 9 membered heteroaryl, or 5 to 6 membered heteroaryl).

In embodiments, $R^{5A}$ is independently $R^{33}$-substituted or unsubstituted alkyl (e.g., $C_1$-$C_8$ alkyl, $C_1$-$C_6$ alkyl, or $C_1$-$C_4$ alkyl). In embodiments, $R^{5A}$ is independently $R^{33}$-substituted alkyl (e.g., $C_1$-$C_8$ alkyl, $C_1$-$C_6$ alkyl, or $C_1$-$C_4$ alkyl). In embodiments, $R^{5A}$ is independently an unsubstituted alkyl (e.g., $C_1$-$C_8$ alkyl, $C_1$-$C_6$ alkyl, or $C_1$-$C_4$ alkyl). In embodiments, $R^{5A}$ is independently $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{5A}$ is independently $R^{33}$-substituted heteroalkyl (e.g., 2 to 8 membered heteroalkyl, 2 to 6 membered heteroalkyl, or 2 to 4 membered heteroalkyl). In embodiments, $R^{5A}$ is independently an unsubstituted heteroalkyl (e.g., 2 to 8 membered heteroalkyl, 2 to 6 membered heteroalkyl, or 2 to 4 membered heteroalkyl). In embodiments, $R^{5A}$ is independently $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5A}$ is independently $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5A}$ is independently $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5A}$ is independently $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{5A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{5A}$ is independently $R^{33}$-substituted or unsubstituted aryl (e.g., $C_6$-$C_{10}$ aryl, $C_{10}$ aryl, or phenyl). In embodiments, $R^{5A}$ is independently $R^{33}$-substituted aryl (e.g., $C_6$-$C_{10}$ aryl, $C_{10}$ aryl, or phenyl). In embodiments, $R^{5A}$ is independently an unsubstituted aryl (e.g., $C_6$-$C_{10}$ aryl, $C_{10}$ aryl, or phenyl). In embodiments, $R^{5A}$ is independently $R^{33}$-substituted or unsubstituted heteroaryl (e.g., 5 to 10 membered heteroaryl, 5 to 9 membered heteroaryl, or 5 to 6 membered heteroaryl). In embodiments, $R^{5A}$ is independently $R^{33}$-substituted heteroaryl (e.g., 5 to 10 membered heteroaryl, 5 to 9 membered heteroaryl, or 5 to 6 membered heteroaryl). In embodiments, $R^{5A}$ is independently an unsubstituted heteroaryl (e.g., 5 to 10 membered heteroaryl, 5 to 9 membered heteroaryl, or 5 to 6 membered heteroaryl).

In embodiments, $R^{5A}$ is independently —$CCl_3$. In embodiments, $R^{5A}$ is independently —$CBr_3$. In embodiments, $R^{5A}$ is independently —$CF_3$. In embodiments, $R^{5A}$ is independently —$CI_3$. In embodiments, $R^{5A}$ is independently —$CHCl_2$. In embodiments, $R^{5A}$ is independently —$CHBr_2$. In embodiments, $R^{5A}$ is independently —$CHF_2$. In embodiments, $R^{5A}$ is independently —$CHI_2$. In embodiments, $R^{5A}$ is independently —$CH_2Cl$. In embodiments, $R^{5A}$ is independently —$CH_2Br$. In embodiments, $R^{5A}$ is independently —$CH_2F$. In embodiments, $R^{5A}$ is independently —$CH_2I$. In embodiments, $R^{5A}$ is independently —CN. In embodiments, $R^{5A}$ is independently —OH. In embodiments, $R^{5A}$ is independently —COOH. In embodiments, $R^{5A}$ is independently —$CONH_2$. In embodiments, $R^{5A}$ is independently —$OCCl_3$. In embodiments, $R^{5A}$ is independently —$OCF_3$. In embodiments, $R^{5A}$ is independently —$OCBr_3$. In embodiments, $R^{5A}$ is independently —$OCI_3$. In embodiments, $R^{5A}$ is independently —$OCHCl_2$. In embodiments, $R^{5A}$ is independently —$OCHBr_2$. In embodiments, $R^{5A}$ is independently —$OCHI_2$. In embodiments, $R^{5A}$ is independently —$OCHF_2$. In embodiments, $R^{5A}$ is independently —$OCH_2Cl$. In embodiments, $R^{5A}$ is independently —$OCH_2Br$. In embodiments, $R^{5A}$ is independently —$OCH_2I$. In embodiments, $R^{5A}$ is independently —$OCH_2F$. In embodiments, $R^{5A}$ is independently —$OCH_3$. In embodiments, $R^{5A}$ is independently —$CH_3$. In embodiments, $R^{5A}$ is independently —$CH_2CH_3$. In embodiments, $R^{5A}$ is independently unsubstituted propyl. In embodiments, $R^{5A}$ is independently unsubstituted isopropyl. In embodiments, $R^{5A}$ is independently unsubstituted butyl. In embodiments, $R^{5A}$ is independently unsubstituted tert-butyl. In embodiments, $R^{5A}$ is independently hydrogen.

In embodiments, $R^{5B}$ is independently $R^{33}$-substituted or unsubstituted alkyl (e.g., $C_1$-$C_8$ alkyl, $C_1$-$C_6$ alkyl, or $C_1$-$C_4$ alkyl). In embodiments, $R^{5B}$ is independently $R^{33}$-substituted alkyl (e.g., $C_1$-$C_8$ alkyl, $C_1$-$C_6$ alkyl, or $C_1$-$C_4$ alkyl). In embodiments, $R^{5B}$ is independently an unsubstituted alkyl (e.g., $C_1$-$C_8$ alkyl, $C_1$-$C_6$ alkyl, or $C_1$-$C_4$ alkyl). In embodiments, $R^{5B}$ is independently $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{5B}$ is independently $R^{33}$-substituted heteroalkyl (e.g., 2 to 8 membered heteroalkyl, 2 to 6 membered heteroalkyl, or 2 to 4 membered heteroalkyl). In embodiments, $R^{5B}$ is independently an unsubstituted heteroalkyl (e.g., 2 to 8 membered heteroalkyl, 2 to 6 membered heteroalkyl, or 2 to 4 membered heteroalkyl). In embodiments, $R^{5B}$ is independently $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5B}$ is independently $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5B}$ is independently $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5B}$ is independently $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{5B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{5B}$ is independently $R^{33}$-substituted or unsubstituted aryl (e.g., $C_6$-$C_{10}$ aryl, $C_{10}$ aryl, or phenyl). In embodiments, $R^{5B}$ is independently $R^{33}$-substituted aryl (e.g., $C_6$-$C_{10}$ aryl, $C_{10}$ aryl, or phenyl). In embodiments, $R^{5B}$ is independently an unsubstituted aryl (e.g., $C_6$-$C_{10}$ aryl, $C_{10}$ aryl, or phenyl). In embodiments, $R^{5B}$ is independently $R^{33}$-substituted or unsubstituted heteroaryl (e.g., 5 to 10 membered heteroaryl, 5 to 9 membered heteroaryl, or 5 to 6 membered heteroaryl). In embodiments, $R^{5B}$ is independently $R^{33}$-substituted heteroaryl (e.g., 5 to 10 membered heteroaryl, 5 to 9 membered heteroaryl, or 5 to 6 membered heteroaryl). In embodiments, $R^{5B}$ is independently an unsubstituted heteroaryl (e.g., 5 to 10 membered heteroaryl, 5 to 9 membered heteroaryl, or 5 to 6 membered heteroaryl).

In embodiments, $R^{5B}$ is independently —$CCl_3$. In embodiments, $R^{5B}$ is independently —$CBr_3$. In embodiments, $R^{5B}$ is independently —$CF_3$. In embodiments, $R^{5B}$ is independently —$CI_3$. In embodiments, $R^{5B}$ is independently —$CHCl_2$. In embodiments, $R^{5B}$ is independently —$CHBr_2$. In embodiments, $R^{5B}$ is independently —$CHF_2$. In embodiments, $R^{5B}$ is independently —$CHI_2$. In embodiments, $R^{5B}$ is independently —$CH_2Cl$. In embodiments, $R^{5B}$ is independently —$CH_2Br$. In embodiments, $R^{5B}$ is independently —$CH_2F$. In embodiments, $R^{5B}$ is independently —$CH_2I$. In embodiments, $R^{5B}$ is independently —CN. In embodiments, $R^{5B}$ is independently —OH. In embodiments, $R^{5B}$ is independently —COOH. In embodiments, $R^{5B}$ is independently —$CONH_2$. In embodiments, $R^{5B}$ is independently —$OCCl_3$. In embodiments, $R^{5B}$ is independently —$OCF_3$. In embodiments, $R^{5B}$ is independently —$OCBr_3$. In embodiments, $R^{5B}$ is independently —$OCI_3$. In embodiments, $R^{5B}$ is independently —$OCHCl_2$. In embodiments, $R^{5B}$ is independently —$OCHBr_2$. In embodiments, $R^{5B}$ is independently —$OCHI_2$. In embodiments, $R^{5B}$ is independently —$OCHF_2$. In embodiments, $R^{5B}$ is independently —$OCH_2Cl$. In embodiments, $R^{5B}$ is independently —$OCH_2Br$. In embodiments, $R^{5B}$ is independently —$OCH_2I$. In embodiments, $R^{5B}$ is independently —$OCH_2F$. In embodiments, $R^{5B}$ is independently —$OCH_3$. In embodiments, $R^{5B}$ is independently —$CH_3$. In embodiments, $R^{5B}$ is independently —$CH_2CH_3$. In embodiments, $R^{5B}$ is independently unsubstituted propyl. In embodiments, $R^{5B}$ is independently unsubstituted isopropyl. In embodiments, $R^{5B}$ is independently unsubstituted butyl. In embodiments, $R^{5B}$ is independently unsubstituted tert-butyl. In embodiments, $R^{5B}$ is independently hydrogen.

In embodiments, $R^{5C}$ is independently $R^{33}$-substituted or unsubstituted alkyl (e.g., $C_1$-$C_8$ alkyl, $C_1$-$C_6$ alkyl, or $C_1$-$C_4$ alkyl). In embodiments, $R^{5C}$ is independently $R^{33}$-substituted alkyl (e.g., $C_1$-$C_8$ alkyl, $C_1$-$C_6$ alkyl, or $C_1$-$C_4$ alkyl). In embodiments, $R^{5C}$ is independently an unsubstituted alkyl (e.g., $C_1$-$C_8$ alkyl, $C_1$-$C_6$ alkyl, or $C_1$-$C_4$ alkyl). In embodiments, $R^{5C}$ is independently $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{5C}$ is independently $R^{33}$-substituted heteroalkyl (e.g., 2 to 8 membered heteroalkyl, 2 to 6 membered heteroalkyl, or 2 to 4 membered heteroalkyl). In embodiments, $R^{5C}$ is independently an unsubstituted heteroalkyl (e.g., 2 to 8 membered heteroalkyl, 2 to 6 membered heteroalkyl, or 2 to 4 membered heteroalkyl). In embodiments, $R^{5C}$ is independently $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5C}$ is independently $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5C}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is independently $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5C}$ is independently $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{5C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{5C}$ is independently $R^{33}$-substituted or unsubstituted aryl (e.g., $C_6$-$C_{10}$ aryl, $C_{10}$ aryl, or phenyl). In embodiments, $R^{5C}$ is independently $R^{33}$-substituted aryl (e.g., $C_6$-$C_{10}$ aryl, $C_{10}$ aryl, or phenyl). In embodiments, $R^{5C}$ is independently an unsubstituted aryl (e.g., $C_6$-$C_{10}$ aryl, $C_{10}$ aryl, or phenyl). In embodiments, $R^{5C}$ is independently $R^{33}$-substituted or unsubstituted heteroaryl (e.g., 5 to 10 membered heteroaryl, 5 to 9 membered heteroaryl, or 5 to 6 membered heteroaryl). In embodiments, $R^{5C}$ is independently $R^{33}$-substituted heteroaryl (e.g., 5 to 10 membered heteroaryl, 5 to 9 membered heteroaryl, or 5 to 6 membered heteroaryl). In embodiments, $R^{5C}$ is independently an unsubstituted heteroaryl (e.g., 5 to 10 membered heteroaryl, 5 to 9 membered heteroaryl, or 5 to 6 membered heteroaryl).

In embodiments, $R^{5C}$ is independently —$CCl_3$. In embodiments, $R^{5C}$ is independently —$CBr_3$. In embodiments, $R^{5C}$ is independently —$CF_3$. In embodiments, $R^{5C}$ is independently —$CI_3$. In embodiments, $R^{5C}$ is independently —$CHCl_2$. In embodiments, $R^{5C}$ is independently —$CHBr_2$. In embodiments, $R^{5C}$ is independently —$CHF_2$. In embodiments, $R^{5C}$ is independently —$CHI_2$. In embodiments, $R^{5C}$ is independently —CH$_2$Cl. In embodiments, R$^{5C}$ is independently —CH$_2$Br. In embodiments, R$^{5C}$ is independently —CH$_2$F. In embodiments, R$^{5C}$ is independently —CH$_2$I. In embodiments, R$^{5C}$ is independently —CN. In embodiments, R$^{5C}$ is independently —OH. In embodiments, R$^{5C}$ is independently —COOH. In embodiments, R$^{5C}$ is independently —CONH$_2$. In embodiments, R$^{5C}$ is independently —OCCl$_3$. In embodiments, R$^{5C}$ is independently —OCF$_3$. In embodiments, R$^{5C}$ is independently —OCBr$_3$. In embodiments, R$^{5C}$ is independently —OCI$_3$. In embodiments, R$^{5C}$ is independently —OCHCl$_2$. In embodiments, R$^{5C}$ is independently —OCHBr$_2$. In embodiments, R$^{5C}$ is independently —OCHI$_2$. In embodiments, R$^{5C}$ is independently —OCHF$_2$. In embodiments, R$^{5C}$ is independently —OCH$_2$Cl. In embodiments, R$^{5C}$ is independently —OCH$_2$Br. In embodiments, R$^{5C}$ is independently —OCH$_2$I. In embodiments, R$^{5C}$ is independently —OCH$_2$F. In embodiments, R$^{5C}$ is independently —OCH$_3$. In embodiments, R$^{5C}$ is independently —CH$_3$. In embodiments, R$^{5C}$ is independently —CH$_2$CH$_3$. In embodiments, R$^{5C}$ is independently unsubstituted propyl. In embodiments, R$^{5C}$ is independently unsubstituted isopropyl. In embodiments, R$^{5C}$ is independently unsubstituted butyl. In embodiments, R$^5$ is independently unsubstituted tert-butyl. In embodiments, R$^{5C}$ is independently hydrogen.

In embodiments, R$^{5D}$ is independently R$^{33}$-substituted or unsubstituted alkyl (e.g., C$_1$-C$_8$ alkyl, C$_1$-C$_6$ alkyl, or C$_1$-C$_4$ alkyl). In embodiments, R$^{5D}$ is independently R$^{33}$-substituted alkyl (e.g., C$_1$-C$_8$ alkyl, C$_1$-C$_6$ alkyl, or C$_1$-C$_4$ alkyl). In embodiments, R$^{5D}$ is independently an unsubstituted alkyl (e.g., C$_1$-C$_8$ alkyl, C$_1$-C$_6$ alkyl, or C$_1$-C$_4$ alkyl). In embodiments, R$^{5D}$ is independently R$^{33}$-substituted or unsubstituted heteroalkyl (e.g., 2 to 8 membered heteroalkyl, 2 to 6 membered heteroalkyl, or 2 to 4 membered heteroalkyl). In embodiments, R$^{5D}$ is independently R$^{33}$-substituted heteroalkyl (e.g., 2 to 8 membered heteroalkyl, 2 to 6 membered heteroalkyl, or 2 to 4 membered heteroalkyl). In embodiments, R$^{5D}$ is independently an unsubstituted heteroalkyl (e.g., 2 to 8 membered heteroalkyl, 2 to 6 membered heteroalkyl, or 2 to 4 membered heteroalkyl). In embodiments, R$^{5D}$ is independently R$^{33}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{5D}$ is independently R$^{33}$-substituted cycloalkyl (e.g., C$_3$-C$_8$ cycloalkyl, C$_3$-C$_6$ cycloalkyl, or C$_5$-C$_6$ cycloalkyl). In embodiments, R$^{5D}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{5D}$ is independently R$^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{5D}$ is independently R$^{33}$-substituted heterocycloalkyl (e.g., 3 to 8 membered heterocycloalkyl, 3 to 6 membered heterocycloalkyl, or 5 to 6 membered heterocycloalkyl). In embodiments, R$^{5D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{5D}$ is independently R$^{33}$-substituted or unsubstituted aryl (e.g., C$_6$-C$_{10}$ aryl, C$_{10}$ aryl, or phenyl). In embodiments, R$^{5D}$ is independently R$^{33}$-substituted aryl (e.g., C$_6$-C$_{10}$ aryl, C$_{10}$ aryl, or phenyl). In embodiments, R$^{5D}$ is independently an unsubstituted aryl (e.g., C$_6$-C$_{10}$ aryl, C$_{10}$ aryl, or phenyl). In embodiments, R$^{5D}$ is independently R$^{33}$-substituted or unsubstituted heteroaryl (e.g., 5 to 10 membered heteroaryl, 5 to 9 membered heteroaryl, or 5 to 6 membered heteroaryl). In embodiments, R$^{5D}$ is independently R$^{33}$-substituted heteroaryl (e.g., 5 to 10 membered heteroaryl, 5 to 9 membered heteroaryl, or 5 to 6 membered heteroaryl). In embodiments, R$^{5D}$ is independently an unsubstituted heteroaryl (e.g., 5 to 10 membered heteroaryl, 5 to 9 membered heteroaryl, or 5 to 6 membered heteroaryl).

In embodiments, R$^{5D}$ is independently —CCl$_3$. In embodiments, R$^{5D}$ is independently —CBr$_3$. In embodiments, R$^{5D}$ is independently —CF$_3$. In embodiments, R$^{5D}$ is independently —CI$_3$. In embodiments, R$^{5D}$ is independently —CHCl$_2$. In embodiments, R$^{5D}$ is independently —CHBr$_2$. In embodiments, R$^{5D}$ is independently —CHF$_2$. In embodiments, R$^{5D}$ is independently —CHI$_2$. In embodiments, R$^{5D}$ is independently —CH$_2$Cl. In embodiments, R$^{5D}$ is independently —CH$_2$Br. In embodiments, R$^{5D}$ is independently —CH$_2$F. In embodiments, R$^{5D}$ is independently —CH$_2$I. In embodiments, R$^{5D}$ is independently —CN. In embodiments, R$^{5D}$ is independently —OH. In embodiments, R$^{5D}$ is independently —COOH. In embodiments, R$^{5D}$ is independently —CONH$_2$. In embodiments, R$^{5D}$ is independently —OCCl$_3$. In embodiments, R$^{5D}$ is independently —OCF$_3$. In embodiments, R$^{5D}$ is independently —OCBr$_3$. In embodiments, R$^{5D}$ is independently —OCI$_3$. In embodiments, R$^{5D}$ is independently —OCHCl$_2$. In embodiments, R$^{5D}$ is independently —OCHBr$_2$. In embodiments, R$^{5D}$ is independently —OCHI$_2$. In embodiments, R$^{5D}$ is independently —OCHF$_2$. In embodiments, R$^{5D}$ is independently —OCH$_2$Cl. In embodiments, R$^{5D}$ is independently —OCH$_2$Br. In embodiments, R$^{5D}$ is independently —OCH$_2$I. In embodiments, R$^{5D}$ is independently —OCH$_2$F. In embodiments, R$^{5D}$ is independently —OCH$_3$. In embodiments, R$^{5D}$ is independently —CH$_3$. In embodiments, R$^{5D}$ is independently —CH$_2$CH$_3$. In embodiments, R$^{5D}$ is independently unsubstituted propyl. In embodiments, R$^{5D}$ is independently unsubstituted isopropyl. In embodiments, R$^{5D}$ is independently unsubstituted butyl. In embodiments, R$^{5D}$ is independently unsubstituted tert-butyl. In embodiments, R$^{5D}$ is independently hydrogen.

In embodiments, R$^6$ is independently hydrogen, —CF$_3$, —CBr$_3$, —CCl$_3$, —CCl$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCl$_3$, —OCHF$_2$, —OCHBr$_2$, —OCHCl$_2$, —OCH$_2$F, —OCH$_2$Br, —OCH$_2$Cl, —CN, —OH, —COOH, —CONH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^6$ is independently substituted or unsubstituted alkyl (e.g., C$_1$-C$_8$ alkyl, C$_1$-C$_6$ alkyl, or C$_1$-C$_4$ alkyl). In embodiments, R$^6$ is independently substituted alkyl (e.g., C$_1$-C$_8$ alkyl, C$_1$-C$_6$ alkyl, or C$_1$-C$_4$ alkyl). In embodiments, R$^6$ is independently an unsubstituted alkyl (e.g., C$_1$-C$_8$ alkyl, C$_1$-C$_6$ alkyl, or C$_1$-C$_4$ alkyl). In embodiments, R$^6$ is independently substituted or unsubstituted heteroalkyl (e.g., 2 to 8 membered heteroalkyl, 2 to 6 membered heteroalkyl, or 2 to 4 membered heteroalkyl). In embodiments, R$^6$ is independently substituted heteroalkyl (e.g., 2 to 8 membered heteroalkyl, 2 to 6 membered heteroalkyl, or 2 to 4 membered heteroalkyl). In embodiments, $R^6$ is independently an unsubstituted heteroalkyl (e.g., 2 to 8 membered heteroalkyl, 2 to 6 membered heteroalkyl, or 2 to 4 membered heteroalkyl). In embodiments, $R^6$ is independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently substituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is independently substituted heterocycloalkyl (e.g., 3 to 8 membered heterocycloalkyl, 3 to 6 membered heterocycloalkyl, or 5 to 6 membered heterocycloalkyl). In embodiments, $R^6$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is independently substituted or unsubstituted aryl (e.g., $C_6$-$C_{10}$ aryl, $C_{10}$ aryl, or phenyl). In embodiments, $R^6$ is independently substituted aryl (e.g., $C_6$-$C_{10}$ aryl, $C_{10}$ aryl, or phenyl). In embodiments, $R^6$ is independently an unsubstituted aryl (e.g., $C_6$-$C_{10}$ aryl, $C_{10}$ aryl, or phenyl). In embodiments, $R^6$ is independently substituted or unsubstituted heteroaryl (e.g., 5 to 10 membered heteroaryl, 5 to 9 membered heteroaryl, or 5 to 6 membered heteroaryl). In embodiments, $R^6$ is independently substituted heteroaryl (e.g., 5 to 10 membered heteroaryl, 5 to 9 membered heteroaryl, or 5 to 6 membered heteroaryl). In embodiments, $R^6$ is independently an unsubstituted heteroaryl (e.g., 5 to 10 membered heteroaryl, 5 to 9 membered heteroaryl, or 5 to 6 membered heteroaryl).

In embodiments, $R^6$ is independently hydrogen, —$CF_3$, —$CBr_3$, —$CCl_3$, —$CCl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —COOH, —$CONH_2$, $R^{36}$-substituted or unsubstituted alkyl (e.g., $C_1$-$C_8$ alkyl, $C_1$-$C_6$ alkyl, or $C_1$-$C_4$ alkyl), $R^{36}$-substituted or unsubstituted heteroalkyl (e.g., 2 to 8 membered heteroalkyl, 2 to 6 membered heteroalkyl, or 2 to 4 membered heteroalkyl), $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted or unsubstituted aryl (e.g., $C_6$-$C_{10}$ aryl, $C_{10}$ aryl, or phenyl), or $R^{36}$-substituted or unsubstituted heteroaryl (e.g., 5 to 10 membered heteroaryl, 5 to 9 membered heteroaryl, or 5 to 6 membered heteroaryl). In embodiments, $R^6$ is independently hydrogen, —$CF_3$, —$CBr_3$, —$CCl_3$, —$Cl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —COOH, —$CONH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^6$ is independently $R^{36}$-substituted or unsubstituted alkyl (e.g., $C_1$-$C_8$ alkyl, $C_1$-$C_6$ alkyl, or $C_1$-$C_4$ alkyl). In embodiments, $R^6$ is independently $R^{36}$-substituted alkyl (e.g., $C_1$-$C_8$ alkyl, $C_1$-$C_6$ alkyl, or $C_1$-$C_4$ alkyl). In embodiments, $R^6$ is independently an unsubstituted alkyl (e.g., $C_1$-$C_8$ alkyl, $C_1$-$C_6$ alkyl, or $C_1$-$C_4$ alkyl). In embodiments, $R^6$ is independently $R^{36}$-substituted or unsubstituted heteroalkyl (e.g., 2 to 8 membered heteroalkyl, 2 to 6 membered heteroalkyl, or 2 to 4 membered heteroalkyl). In embodiments, $R^6$ is independently $R^{36}$-substituted heteroalkyl (e.g., 2 to 8 membered heteroalkyl, 2 to 6 membered heteroalkyl, or 2 to 4 membered heteroalkyl). In embodiments, $R^6$ is independently an unsubstituted heteroalkyl (e.g., 2 to 8 membered heteroalkyl, 2 to 6 membered heteroalkyl, or 2 to 4 membered heteroalkyl). In embodiments, $R^6$ is independently $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently $R^{36}$-substituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is independently $R^{36}$-substituted heterocycloalkyl (e.g., 3 to 8 membered heterocycloalkyl, 3 to 6 membered heterocycloalkyl, or 5 to 6 membered heterocycloalkyl). In embodiments, $R^6$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is independently $R^{36}$-substituted or unsubstituted aryl (e.g., $C_6$-$C_{10}$ aryl, $C_{10}$ aryl, or phenyl). In embodiments, $R^6$ is independently $R^{36}$-substituted aryl (e.g., $C_6$-$C_{10}$ aryl, $C_{10}$ aryl, or phenyl). In embodiments, $R^6$ is independently an unsubstituted aryl (e.g., $C_6$-$C_{10}$ aryl, $C_{10}$ aryl, or phenyl). In embodiments, $R^6$ is independently $R^{36}$-substituted or unsubstituted heteroaryl (e.g., 5 to 10 membered heteroaryl, 5 to 9 membered heteroaryl, or 5 to 6 membered heteroaryl). In embodiments, $R^6$ is independently $R^{36}$-substituted heteroaryl (e.g., 5 to 10 membered heteroaryl, 5 to 9 membered heteroaryl, or 5 to 6 membered heteroaryl). In embodiments, $R^6$ is independently an unsubstituted heteroaryl (e.g., 5 to 10 membered heteroaryl, 5 to 9 membered heteroaryl, or 5 to 6 membered heteroaryl).

In embodiments, $R^6$ is independently —$CX^6_3$. In embodiments, $R^6$ is independently —$CHX^6_2$. In embodiments, $R^6$ is independently —$CH_2X^6$. In embodiments, $R^6$ is independently —$OCX^6_3$. In embodiments, $R^6$ is independently —$OCH_2X^6$. In embodiments, $R^6$ is independently —$OCHX^6_2$. In embodiments, $R^6$ is independently —CN. In embodiments, $R^6$ is independently —C(O)$R^{6C}$. In embodiments, $R^6$ is independently —C(O)—$OR^{6C}$. In embodiments, $R^6$ is independently —C(O)$NR^{6A}R^{6B}$. In embodiments, $R^6$ is independently —$OR^{6D}$. In embodiments, $R^6$ is independently hydrogen. $X^6$ is independently halogen.

In embodiments, $R^6$ is independently —$CCl_3$. In embodiments, $R^6$ is independently —$CBr_3$. In embodiments, $R^6$ is independently —$CF_3$. In embodiments, $R^6$ is independently —$CI_3$. In embodiments, $R^6$ is independently —$CHCl_2$. In embodiments, $R^6$ is independently —$CHBr_2$. In embodiments, $R^6$ is independently —$CHF_2$. In embodiments, $R^6$ is independently —$CHI_2$. In embodiments, $R^6$ is independently —CH$_2$Cl. In embodiments, R$^6$ is independently —CH$_2$Br. In embodiments, R$^6$ is independently —CH$_2$F. In embodiments, R$^6$ is independently —CH$_2$I. In embodiments, R$^6$ is independently —CN. In embodiments, R$^6$ is independently —OH. In embodiments, R$^6$ is independently —COOH. In embodiments, R$^6$ is independently —CONH$_2$. In embodiments, R$^6$ is independently —OCCl$_3$. In embodiments, R$^6$ is independently —OCF$_3$. In embodiments, R$^6$ is independently —OCBr$_3$. In embodiments, R$^6$ is independently —OCl$_3$. In embodiments, R$^6$ is independently —OCHCl$_2$. In embodiments, R$^6$ is independently —OCHBr$_2$. In embodiments, R$^6$ is independently —OCHI$_2$. In embodiments, R$^6$ is independently —OCHF$_2$. In embodiments, R$^6$ is independently —OCH$_2$Cl. In embodiments, R$^6$ is independently —OCH$_2$Br. In embodiments, R$^6$ is independently —OCH$_2$I. In embodiments, R$^6$ is independently —OCH$_2$F. In embodiments, R$^6$ is independently —OCH$_3$. In embodiments, R$^6$ is independently —CH$_3$. In embodiments, R$^6$ is independently —CH$_2$CH$_3$. In embodiments, R$^6$ is independently unsubstituted propyl. In embodiments, R$^6$ is independently unsubstituted isopropyl. In embodiments, R$^6$ is independently unsubstituted butyl. In embodiments, R$^6$ is independently unsubstituted tert-butyl. In embodiments, X$^6$ is independently —F. In embodiments, X$^6$ is independently —Cl. In embodiments, X$^6$ is independently —Br. In embodiments, X$^6$ is independently —I.

R$^{36}$ is independently oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, R$^{37}$-substituted or unsubstituted alkyl (e.g., C$_1$-C$_8$ alkyl, C$_1$-C$_6$ alkyl, or C$_1$-C$_4$ alkyl), R$^{37}$-substituted or unsubstituted heteroalkyl (e.g., 2 to 8 membered heteroalkyl, 2 to 6 membered heteroalkyl, or 2 to 4 membered heteroalkyl), R$^{37}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{37}$-substituted or unsubstituted heterocycloalkyl (e.g., 3 to 8 membered heterocycloalkyl, 3 to 6 membered heterocycloalkyl, or 5 to 6 membered heterocycloalkyl), R$^{37}$-substituted or unsubstituted aryl (e.g., C$_6$-C$_{10}$ aryl, C$_{10}$ aryl, or phenyl), or R$^{37}$-substituted or unsubstituted heteroaryl (e.g., 5 to 10 membered heteroaryl, 5 to 9 membered heteroaryl, or 5 to 6 membered heteroaryl). In embodiments, R$^{36}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{36}$ is independently oxo. In embodiments, R$^{36}$ is independently halogen. In embodiments, R$^{36}$ is independently —CCl$_3$. In embodiments, R$^{36}$ is independently —CBr$_3$. In embodiments, R$^{36}$ is independently —CF$_3$. In embodiments, R$^{36}$ is independently —CI$_3$. In embodiments, R$^{36}$ is independently —CHCl$_2$. In embodiments, R$^{36}$ is independently —CHBr$_2$. In embodiments, R$^{36}$ is independently —CHF$_2$. In embodiments, R$^{36}$ is independently —CHI$_2$. In embodiments, R$^{36}$ is independently —CH$_2$Cl. In embodiments, R$^{36}$ is independently —CH$_2$Br. In embodiments, R$^{36}$ is independently —CH$_2$F. In embodiments, R$^{36}$ is independently —CH$_2$I. In embodiments, R$^{36}$ is independently —CN. In embodiments, R$^{36}$ is independently —OH. In embodiments, R$^{36}$ is independently —NH$_2$. In embodiments, R$^{36}$ is independently —COOH. In embodiments, R$^{36}$ is independently —CONH$_2$. In embodiments, R$^{36}$ is independently —NO$_2$. In embodiments, R$^{36}$ is independently —SH. In embodiments, R$^{36}$ is independently —SO$_3$H. In embodiments, R$^{36}$ is independently —SO$_4$H. In embodiments, R$^{36}$ is independently —SO$_2$NH$_2$. In embodiments, R$^{36}$ is independently —NHNH$_2$. In embodiments, R$^{36}$ is independently —ONH$_2$. In embodiments, R$^{36}$ is independently —NHC(O)NHNH$_2$. In embodiments, R$^{36}$ is independently —NHC(O)NH$_2$. In embodiments, R$^{36}$ is independently —NHSO$_2$H. In embodiments, R$^{36}$ is independently —NHC(O)H. In embodiments, R$^{36}$ is independently —NHC(O)OH. In embodiments, R$^{36}$ is independently —NHOH. In embodiments, R$^{36}$ is independently —OCCl$_3$. In embodiments, R$^{36}$ is independently —OCF$_3$. In embodiments, R$^{36}$ is independently —OCBr$_3$. In embodiments, R$^{36}$ is independently —OCl$_3$. In embodiments, R$^{36}$ is independently —OCHCl$_2$. In embodiments, R$^{36}$ is independently —OCHBr$_2$. In embodiments, R$^{36}$ is independently —OCHI$_2$. In embodiments, R$^{36}$ is independently —OCHF$_2$. In embodiments, R$^{36}$ is independently —OCH$_2$Cl. In embodiments, R$^{36}$ is independently —OCH$_2$Br. In embodiments, R$^{36}$ is independently —OCH$_2$I. In embodiments, R$^{36}$ is independently —OCH$_2$F. In embodiments, R$^{36}$ is independently —N$_3$. In embodiments, R$^{36}$ is independently —OCH$_3$. In embodiments, R$^{36}$ is idenpendently —CH$_3$. In embodiments, R$^{36}$ is independently —CH$_2$CH$_3$. In embodiments, R$^{36}$ is independently unsubstituted propyl. In embodiments, R$^{36}$ is independently unsubstituted isopropyl. In embodiments, R$^{36}$ is independently unsubstituted butyl. In embodiments, R$^{36}$ is independently unsubstituted tert-butyl. In embodiments, R$^{36}$ is independently —F. In embodiments, R$^{36}$ is independently —Cl. In embodiments, R$^{36}$ is independently —Br. In embodiments, R$^{36}$ is independently —I.

In embodiments, R$^{36}$ is independently R$^{37}$-substituted or unsubstituted alkyl (e.g., C$_1$-C$_8$ alkyl, C$_1$-C$_6$ alkyl, or C$_1$-C$_4$ alkyl). In embodiments, R$^{36}$ is independently R$^{37}$-substituted alkyl (e.g., C$_1$-C$_8$ alkyl, C$_1$-C$_6$ alkyl, or C$_1$-C$_4$ alkyl). In embodiments, R$^{36}$ is independently an unsubstituted alkyl (e.g., C$_1$-C$_8$ alkyl, C$_1$-C$_6$ alkyl, or C$_1$-C$_4$ alkyl). In embodiments, R$^{36}$ is independently R$^{37}$-substituted or unsubstituted heteroalkyl (e.g., 2 to 8 membered heteroalkyl, 2 to 6 membered heteroalkyl, or 2 to 4 membered heteroalkyl). In embodiments, R$^{36}$ is independently R$^{37}$-substituted heteroalkyl (e.g., 2 to 8 membered heteroalkyl, 2 to 6 membered heteroalkyl, or 2 to 4 membered heteroalkyl). In embodiments, R$^{36}$ is independently an unsubstituted heteroalkyl (e.g., 2 to 8 membered heteroalkyl, 2 to 6 membered heteroalkyl, or 2 to 4 membered heteroalkyl). In embodiments, R$^{36}$ is independently R$^{37}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{36}$ is independently R$^{37}$-substituted cycloalkyl (e.g., C$_3$-C$_8$ cycloalkyl, C$_3$-C$_6$ cycloalkyl, or C$_5$-C$_6$ cycloalkyl). In embodiments, $R^{36}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{36}$ is independently $R^{37}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{36}$ is independently $R^{37}$-substituted heterocycloalkyl (e.g., 3 to 8 membered heterocycloalkyl, 3 to 6 membered heterocycloalkyl, or 5 to 6 membered heterocycloalkyl). In embodiments, $R^{36}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{36}$ is independently $R^{37}$-substituted or unsubstituted aryl (e.g., $C_6$-$C_{10}$ aryl, $C_{10}$ aryl, or phenyl). In embodiments, $R^{36}$ is independently $R^{37}$-substituted aryl (e.g., $C_6$-$C_{10}$ aryl, $C_{10}$ aryl, or phenyl). In embodiments, $R^{36}$ is independently an unsubstituted aryl (e.g., $C_6$-$C_{10}$ aryl, $C_{10}$ aryl, or phenyl). In embodiments, $R^{36}$ is independently $R^{37}$-substituted or unsubstituted heteroaryl (e.g., 5 to 10 membered heteroaryl, 5 to 9 membered heteroaryl, or 5 to 6 membered heteroaryl). In embodiments, $R^{36}$ is independently $R^{37}$-substituted heteroaryl (e.g., 5 to 10 membered heteroaryl, 5 to 9 membered heteroaryl, or 5 to 6 membered heteroaryl). In embodiments, $R^{36}$ is independently an unsubstituted heteroaryl (e.g., 5 to 10 membered heteroaryl, 5 to 9 membered heteroaryl, or 5 to 6 membered heteroaryl).

$R^{37}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{38}$-substituted or unsubstituted alkyl (e.g., $C_1$-$C_8$ alkyl, $C_1$-$C_6$ alkyl, or $C_1$-$C_4$ alkyl), $R^{38}$-substituted or unsubstituted heteroalkyl (e.g., 2 to 8 membered heteroalkyl, 2 to 6 membered heteroalkyl, or 2 to 4 membered heteroalkyl), $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted or unsubstituted aryl (e.g., $C_6$-$C_{10}$ aryl, $C_{10}$ aryl, or phenyl), or $R^{38}$-substituted or unsubstituted heteroaryl (e.g., 5 to 10 membered heteroaryl, 5 to 9 membered heteroaryl, or 5 to 6 membered heteroaryl). In embodiments, $R^{37}$ is independently oxo, halogen, —$CF_3$, —$CBr_3$, —$CCl_3$, —$CCl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{37}$ is independently $R^{38}$-substituted or unsubstituted alkyl (e.g., $C_1$-$C_8$ alkyl, $C_1$-$C_6$ alkyl, or $C_1$-$C_4$ alkyl). In embodiments, $R^{37}$ is independently $R^{38}$-substituted alkyl (e.g., $C_1$-$C_8$ alkyl, $C_1$-$C_6$ alkyl, or $C_1$-$C_4$ alkyl). In embodiments, $R^{37}$ is independently an unsubstituted alkyl (e.g., $C_1$-$C_8$ alkyl, $C_1$-$C_6$ alkyl, or $C_1$-$C_4$ alkyl). In embodiments, $R^{37}$ is independently $R^{38}$-substituted or unsubstituted heteroalkyl (e.g., 2 to 8 membered heteroalkyl, 2 to 6 membered heteroalkyl, or 2 to 4 membered heteroalkyl). In embodiments, $R^{37}$ is independently $R^{38}$-substituted heteroalkyl (e.g., 2 to 8 membered heteroalkyl, 2 to 6 membered heteroalkyl, or 2 to 4 membered heteroalkyl). In embodiments, $R^{37}$ is independently an unsubstituted heteroalkyl (e.g., 2 to 8 membered heteroalkyl, 2 to 6 membered heteroalkyl, or 2 to 4 membered heteroalkyl). In embodiments, $R^{37}$ is independently $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{37}$ is independently $R^{38}$-substituted cycloalkyl (e.g., $C_3$-$C_8$ cycloalkyl, $C_3$-$C_6$ cycloalkyl, or $C_5$-$C_6$ cycloalkyl). In embodiments, $R^{37}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{37}$ is independently $R^{38}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{37}$ is independently $R^{38}$-substituted heterocycloalkyl (e.g., 3 to 8 membered heterocycloalkyl, 3 to 6 membered heterocycloalkyl, or 5 to 6 membered heterocycloalkyl). In embodiments, $R^{37}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{37}$ is independently $R^{38}$-substituted or unsubstituted aryl (e.g., $C_6$-$C_{10}$ aryl, $C_{10}$ aryl, or phenyl). In embodiments, $R^{37}$ is independently $R^{38}$-substituted aryl (e.g., $C_6$-$C_{10}$ aryl, $C_{10}$ aryl, or phenyl). In embodiments, $R^{37}$ is independently an unsubstituted aryl (e.g., $C_6$-$C_{10}$ aryl, $C_{10}$ aryl, or phenyl). In embodiments, $R^{37}$ is independently $R^{38}$-substituted or unsubstituted heteroaryl (e.g., 5 to 10 membered heteroaryl, 5 to 9 membered heteroaryl, or 5 to 6 membered heteroaryl). In embodiments, $R^{37}$ is independently $R^{38}$-substituted heteroaryl (e.g., 5 to 10 membered heteroaryl, 5 to 9 membered heteroaryl, or 5 to 6 membered heteroaryl). In embodiments, $R^{37}$ is independently an unsubstituted heteroaryl (e.g., 5 to 10 membered heteroaryl, 5 to 9 membered heteroaryl, or 5 to 6 membered heteroaryl).

In embodiments, $R^{37}$ is independently oxo. In embodiments, $R^{37}$ is independently halogen. In embodiments, $R^{37}$ is independently —$CCl_3$. In embodiments, $R^{37}$ is independently —$CBr_3$. In embodiments, $R^{37}$ is independently —$CF_3$. In embodiments, $R^{37}$ is independently —$CI_3$. In embodiments, $R^{37}$ is independently —$CHCl_2$. In embodiments, $R^{37}$ is independently —$CHBr_2$. In embodiments, $R^{37}$ is independently —$CHF_2$. In embodiments, $R^{37}$ is independently —$CHI_2$. In embodiments, $R^{37}$ is independently —$CH_2Cl$. In embodiments, $R^{37}$ is independently —$CH_2Br$. In embodiments, $R^{37}$ is independently —$CH_2F$. In embodiments, $R^{37}$ is independently —$CH_2I$. In embodiments, $R^{37}$ is independently —CN. In embodiments, $R^{37}$ is independently —OH. In embodiments, $R^{37}$ is independently —$NH_2$. In embodiments, $R^{37}$ is independently —COOH. In embodiments, $R^{37}$ is independently —$CONH_2$. In embodiments, $R^{37}$ is independently —$NO_2$. In embodiments, $R^{37}$ is independently —SH. In embodiments, $R^{37}$ is independently —$SO_3H$. In embodiments, $R^{37}$ is independently —$SO_4H$. In embodiments, $R^{37}$ is independently —$SO_2NH_2$. In embodiments, $R^{37}$ is independently —NHNH$_2$. In embodiments, $R^{37}$ is independently —ONH$_2$. In embodiments, $R^{37}$ is independently —NHC(O)NHNH$_2$. In embodiments, $R^{37}$ is independently —NHC(O)NH$_2$. In embodiments, $R^{37}$ is independently —NHSO$_2$H. In embodiments, $R^{37}$ is independently —NHC(O)H. In embodiments, $R^{37}$ is independently —NHC(O)OH. In embodiments, $R^{37}$ is independently —NHOH. In embodiments, $R^{37}$ is independently —OCCl$_3$. In embodiments, $R^{37}$ is independently —OCF$_3$. In embodiments, $R^{37}$ is independently —OCBr$_3$. In embodiments, $R^{37}$ is independently —OCl$_3$. In embodiments, $R^{37}$ is independently —OCHCl$_2$. In embodiments, $R^{37}$ is independently —OCHBr$_2$. In embodiments, $R^{37}$ is independently —OCHI$_2$. In embodiments, $R^{37}$ is independently —OCHF$_2$. In embodiments, $R^{37}$ is independently —OCH$_2$Cl. In embodiments, $R^{37}$ is independently —OCH$_2$Br. In embodiments, $R^{37}$ is independently —OCH$_2$I. In embodiments, $R^{37}$ is independently —OCH$_2$F. In embodiments, $R^{37}$ is independently —N$_3$. In embodiments, $R^{37}$ is independently —OCH$_3$. In embodiments, $R^{37}$ is independently —CH$_3$. In embodiments, $R^{37}$ is independently —CH$_2$CH$_3$. In embodiments, $R^{37}$ is independently unsubstituted propyl. In embodiments, $R^{37}$ is independently unsubstituted isopropyl. In embodiments, $R^{37}$ is independently unsubstituted butyl. In embodiments, $R^{37}$ is independently unsubstituted tert-butyl. In embodiments, $R^{37}$ is independently —F. In embodiments, $R^{37}$ is independently —Cl. In embodiments, $R^{37}$ is independently —Br. In embodiments, $R^{37}$ is independently —I.

$R^{38}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{38}$ is independently an unsubstituted alkyl (e.g., C$_1$-C$_8$ alkyl, C$_1$-C$_6$ alkyl, or C$_1$-C$_4$ alkyl). In embodiments, $R^{38}$ is independently an unsubstituted heteroalkyl (e.g., 2 to 8 membered heteroalkyl, 2 to 6 membered heteroalkyl, or 2 to 4 membered heteroalkyl). In embodiments, $R^{38}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, $R^{38}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{38}$ is independently an unsubstituted aryl (e.g., C$_6$-C$_{10}$ aryl, C$_{10}$ aryl, or phenyl). In embodiments, $R^{38}$ is independently an unsubstituted heteroaryl (e.g., 5 to 10 membered heteroaryl, 5 to 9 membered heteroaryl, or 5 to 6 membered heteroaryl).

In embodiments, $R^{38}$ is independently oxo. In embodiments, $R^{38}$ is independently halogen. In embodiments, $R^{38}$ is independently —CCl$_3$. In embodiments, $R^{38}$ is independently —CBr$_3$. In embodiments, $R^{38}$ is independently —CF$_3$. In embodiments, $R^{38}$ is independently —CI$_3$. In embodiments, $R^{38}$ is independently —CHCl$_2$. In embodiments, $R^{38}$ is independently —CHBr$_2$. In embodiments, $R^{38}$ is independently —CHF$_2$. In embodiments, $R^{38}$ is independently —CHI$_2$. In embodiments, $R^{38}$ is independently —CH$_2$Cl. In embodiments, $R^{38}$ is independently —CH$_2$Br. In embodiments, $R^{38}$ is independently —CH$_2$F. In embodiments, $R^{38}$ is independently —CH$_2$I. In embodiments, $R^{38}$ is independently —CN. In embodiments, $R^{38}$ is independently —OH. In embodiments, $R^{38}$ is independently —NH$_2$. In embodiments, $R^{38}$ is independently —COOH. In embodiments, $R^{38}$ is independently —CONH$_2$. In embodiments, $R^{38}$ is independently —NO$_2$. In embodiments, $R^{38}$ is independently —SH. In embodiments, $R^{38}$ is independently —SO$_3$H. In embodiments, $R^{38}$ is independently —SO$_4$H. In embodiments, $R^{38}$ is independently —SO$_2$NH$_2$. In embodiments, $R^{38}$ is independently —NHNH$_2$. In embodiments, $R^{38}$ is independently —ONH$_2$. In embodiments, $R^{38}$ is independently —NHC(O)NHNH$_2$. In embodiments, $R^{38}$ is independently —NHC(O)NH$_2$. In embodiments, $R^{38}$ is independently —NHSO$_2$H. In embodiments, $R^{38}$ is independently —NHC(O)H. In embodiments, $R^{38}$ is independently —NHC(O)OH. In embodiments, $R^{38}$ is independently —NHOH. In embodiments, $R^{38}$ is independently —OCCl$_3$. In embodiments, $R^{38}$ is independently —OCF$_3$. In embodiments, $R^{38}$ is independently —OCBr$_3$. In embodiments, $R^{38}$ is independently —OCl$_3$. In embodiments, $R^{38}$ is independently —OCHCl$_2$. In embodiments, $R^{38}$ is independently —OCHBr$_2$. In embodiments, $R^{38}$ is independently —OCHI$_2$. In embodiments, $R^{38}$ is independently —OCHF$_2$. In embodiments, $R^{38}$ is independently —OCH$_2$Cl. In embodiments, $R^{38}$ is independently —OCH$_2$Br. In embodiments, $R^{38}$ is independently —OCH$_2$I. In embodiments, $R^{38}$ is independently —OCH$_2$F. In embodiments, $R^{38}$ is independently —N$_3$. In embodiments, $R^{38}$ is independently —OCH$_3$. In embodiments, $R^{38}$ is idenpendently —CH$_3$. In embodiments, $R^{38}$ is idenpendently —CH$_2$CH$_3$. In embodiments, $R^{38}$ is independently unsubstituted propyl. In embodiments, $R^{38}$ is independently unsubstituted isopropyl. In embodiments, $R^{38}$ is independently unsubstituted butyl. In embodiments, $R^{38}$ is independently unsubstituted tert-butyl. In embodiments, $R^{38}$ is independently —F. In embodiments, $R^{38}$ is independently —Cl. In embodiments, $R^{38}$ is independently —Br. In embodiments, $R^{38}$ is independently —I.

In embodiments, $R^{6A}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{6B}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{6C}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{6D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{6A}$ and R$^{6B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, R$^{6A}$ and R$^{6B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{6A}$ and R$^{6B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, R$^{6A}$ and R$^{6B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, R$^{6A}$ and R$^{6B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, R$^{6A}$ and R$^{6B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, R$^{6A}$ and R$^{6B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, R$^{6A}$, R$^{6B}$, R$^{6C}$ and R$^{6D}$ are independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{36}$-substituted or unsubstituted alkyl (e.g., C$_1$-C$_8$ alkyl, C$_1$-C$_6$ alkyl, or C$_1$-C$_4$ alkyl), R$^{36}$-substituted or unsubstituted heteroalkyl (e.g., 2 to 8 membered heteroalkyl, 2 to 6 membered heteroalkyl, or 2 to 4 membered heteroalkyl), R$^{36}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{36}$-substituted or unsubstituted heterocycloalkyl (e.g., 3 to 8 membered heterocycloalkyl, 3 to 6 membered heterocycloalkyl, or 5 to 6 membered heterocycloalkyl), R$^{36}$-substituted or unsubstituted aryl (e.g., C$_6$-C$_{10}$ aryl, C$_{10}$ aryl, or phenyl), or R$^{36}$-substituted or unsubstituted heteroaryl (e.g., 5 to 10 membered heteroaryl, 5 to 9 membered heteroaryl, or 5 to 6 membered heteroaryl). In embodiments, R$^{6A}$ and R$^{6B}$ substituents bonded to the same nitrogen atom are independently joined to form an R$^{36}$-substituted or unsubstituted heterocycloalkyl (e.g., 3 to 8 membered heterocycloalkyl, 3 to 6 membered heterocycloalkyl, or 5 to 6 membered heterocycloalkyl) or R$^{36}$-substituted or unsubstituted heteroaryl (e.g., 5 to 10 membered heteroaryl, 5 to 9 membered heteroaryl, or 5 to 6 membered heteroaryl). In embodiments, R$^{6A}$ and R$^{6B}$ substituents bonded to the same nitrogen atom are independently joined to form an R$^{36}$-substituted or unsubstituted heterocycloalkyl (e.g., 3 to 8 membered heterocycloalkyl, 3 to 6 membered heterocycloalkyl. In embodiments, R$^{6A}$ and R$^{6B}$ substituents bonded to the same nitrogen atom are independently joined to form an R$^{36}$-substituted or unsubstituted heteroaryl (e.g., 5 to 10 membered heteroaryl, 5 to 9 membered heteroaryl, or 5 to 6 membered heteroaryl).

In embodiments, R$^{6A}$ is independently R$^{36}$-substituted or unsubstituted alkyl (e.g., C$_1$-C$_8$ alkyl, C$_1$-C$_6$ alkyl, or C$_1$-C$_4$ alkyl). In embodiments, R$^{6A}$ is independently R$^{36}$-substituted alkyl (e.g., C$_1$-C$_8$ alkyl, C$_1$-C$_6$ alkyl, or C$_1$-C$_4$ alkyl). In embodiments, R$^{6A}$ is independently an unsubstituted alkyl (e.g., C$_1$-C$_8$ alkyl, C$_1$-C$_6$ alkyl, or C$_1$-C$_4$ alkyl). In embodiments, R$^{6A}$ is independently R$^{36}$-substituted or unsubstituted heteroalkyl (e.g., 2 to 8 membered heteroalkyl, 2 to 6 membered heteroalkyl, or 2 to 4 membered heteroalkyl). In embodiments, $R^{6A}$ is independently $R^{36}$-substituted heteroalkyl (e.g., 2 to 8 membered heteroalkyl, 2 to 6 membered heteroalkyl, or 2 to 4 membered heteroalkyl). In embodiments, $R^{6A}$ is independently an unsubstituted heteroalkyl (e.g., 2 to 8 membered heteroalkyl, 2 to 6 membered heteroalkyl, or 2 to 4 membered heteroalkyl). In embodiments, $R^{6A}$ is independently $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6A}$ is independently $R^{36}$-substituted cycloalkyl (e.g., $C_3$-$C_8$ cycloalkyl, $C_3$-$C_6$ cycloalkyl, or $C_5$-$C_6$ cycloalkyl). In embodiments, $R^{6A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6A}$ is independently $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6A}$ is independently $R^{36}$-substituted heterocycloalkyl (e.g., 3 to 8 membered heterocycloalkyl, 3 to 6 membered heterocycloalkyl, or 5 to 6 membered heterocycloalkyl). In embodiments, $R^{6A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{6A}$ is independently $R^{36}$-substituted or unsubstituted aryl (e.g., $C_6$-$C_{10}$ aryl, $C_{10}$ aryl, or phenyl). In embodiments, $R^{6A}$ is independently $R^{36}$-substituted aryl (e.g., $C_6$-$C_{10}$ aryl, $C_{10}$ aryl, or phenyl). In embodiments, $R^{6A}$ is independently an unsubstituted aryl (e.g., $C_6$-$C_{10}$ aryl, $C_{10}$ aryl, or phenyl). In embodiments, $R^{6A}$ is independently $R^{36}$-substituted or unsubstituted heteroaryl (e.g., 5 to 10 membered heteroaryl, 5 to 9 membered heteroaryl, or 5 to 6 membered heteroaryl). In embodiments, $R^{6A}$ is independently $R^{36}$-substituted heteroaryl (e.g., 5 to 10 membered heteroaryl, 5 to 9 membered heteroaryl, or 5 to 6 membered heteroaryl). In embodiments, $R^{6A}$ is independently an unsubstituted heteroaryl (e.g., 5 to 10 membered heteroaryl, 5 to 9 membered heteroaryl, or 5 to 6 membered heteroaryl).

In embodiments, $R^{6A}$ is independently —CCl$_3$. In embodiments, $R^{6A}$ is independently —CBr$_3$. In embodiments, $R^{6A}$ is independently —CF$_3$. In embodiments, $R^{6A}$ is independently —CI$_3$. In embodiments, $R^{6A}$ is independently —CHCl$_2$. In embodiments, $R^{6A}$ is independently —CHBr$_2$. In embodiments, $R^{6A}$ is independently —CHF$_2$. In embodiments, $R^{6A}$ is independently —CHI$_2$. In embodiments, $R^{6A}$ is independently —CH$_2$Cl. In embodiments, $R^{6A}$ is independently —CH$_2$Br. In embodiments, $R^{6A}$ is independently —CH$_2$F. In embodiments, $R^{6A}$ is independently —CH$_2$I. In embodiments, $R^{6A}$ is independently —CN. In embodiments, $R^{6A}$ is independently —OH. In embodiments, $R^{6A}$ is independently —COOH. In embodiments, $R^{6A}$ is independently —CONH$_2$. In embodiments, $R^{6A}$ is independently —OCCl$_3$. In embodiments, $R^{6A}$ is independently —OCF$_3$. In embodiments, $R^{6A}$ is independently —OCBr$_3$. In embodiments, $R^{6A}$ is independently —OCI$_3$. In embodiments, $R^{6A}$ is independently —OCHCl$_2$. In embodiments, $R^{6A}$ is independently —OCHBr$_2$. In embodiments, $R^{6A}$ is independently —OCHI$_2$. In embodiments, $R^{6A}$ is independently —OCHF$_2$. In embodiments, $R^{6A}$ is independently —OCH$_2$Cl. In embodiments, $R^{6A}$ is independently —OCH$_2$Br. In embodiments, $R^{6A}$ is independently —OCH$_2$I. In embodiments, $R^{6A}$ is independently —OCH$_2$F. In embodiments, $R^{6A}$ is idenpendently —OCH$_3$. In embodiments, $R^{6A}$ is idenpendently —CH$_3$. In embodiments, $R^{6A}$ is idenpendently —CH$_2$CH$_3$. In embodiments, $R^{6A}$ is independently unsubstituted propyl. In embodiments, $R^{6A}$ is independently unsubstituted isopropyl. In embodiments, $R^{6A}$ is independently unsubstituted butyl. In embodiments, $R^{6A}$ is independently unsubstituted tert-butyl. In embodiments, $R^{6A}$ is independently hydrogen.

In embodiments, $R^{6B}$ is independently $R^{36}$-substituted or unsubstituted alkyl (e.g., $C_1$-$C_8$ alkyl, $C_1$-$C_6$ alkyl, or $C_1$-$C_4$ alkyl). In embodiments, $R^{6B}$ is independently $R^{36}$-substituted alkyl (e.g., $C_1$-$C_8$ alkyl, $C_1$-$C_6$ alkyl, or $C_1$-$C_4$ alkyl). In embodiments, $R^{6B}$ is independently an unsubstituted alkyl (e.g., $C_1$-$C_8$ alkyl, $C_1$-$C_6$ alkyl, or $C_1$-$C_4$ alkyl). In embodiments, $R^{6B}$ is independently $R^{36}$-substituted or unsubstituted heteroalkyl (e.g., 2 to 8 membered heteroalkyl, 2 to 6 membered heteroalkyl, or 2 to 4 membered heteroalkyl). In embodiments, $R^{6B}$ is independently $R^{36}$-substituted heteroalkyl (e.g., 2 to 8 membered heteroalkyl, 2 to 6 membered heteroalkyl, or 2 to 4 membered heteroalkyl). In embodiments, $R^{6B}$ is independently an unsubstituted heteroalkyl (e.g., 2 to 8 membered heteroalkyl, 2 to 6 membered heteroalkyl, or 2 to 4 membered heteroalkyl). In embodiments, $R^{6B}$ is independently $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6B}$ is independently $R^{36}$-substituted cycloalkyl (e.g., $C_3$-$C_8$ cycloalkyl, $C_3$-$C_6$ cycloalkyl, or $C_5$-$C_6$ cycloalkyl). In embodiments, $R^{6B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{6B}$ is independently $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{6B}$ is independently $R^{36}$-substituted heterocycloalkyl (e.g., 3 to 8 membered heterocycloalkyl, 3 to 6 membered heterocycloalkyl, or 5 to 6 membered heterocycloalkyl). In embodiments, $R^{6B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{6B}$ is independently $R^{36}$-substituted or unsubstituted aryl (e.g., $C_6$-$C_{10}$ aryl, $C_{10}$ aryl, or phenyl). In embodiments, $R^{6B}$ is independently $R^{36}$-substituted aryl (e.g., $C_6$-$C_{10}$ aryl, $C_{10}$ aryl, or phenyl). In embodiments, $R^{6B}$ is independently an unsubstituted aryl (e.g., $C_6$-$C_{10}$ aryl, $C_{10}$ aryl, or phenyl). In embodiments, $R^{6B}$ is independently $R^{36}$-substituted or unsubstituted heteroaryl (e.g., 5 to 10 membered heteroaryl, 5 to 9 membered heteroaryl, or 5 to 6 membered heteroaryl). In embodiments, $R^{6B}$ is independently $R^{36}$-substituted heteroaryl (e.g., 5 to 10 membered heteroaryl, 5 to 9 membered heteroaryl, or 5 to 6 membered heteroaryl). In embodiments, $R^{6B}$ is independently an unsubstituted heteroaryl (e.g., 5 to 10 membered heteroaryl, 5 to 9 membered heteroaryl, or 5 to 6 membered heteroaryl).

In embodiments, $R^{6B}$ is independently —CCl$_3$. In embodiments, $R^{6B}$ is independently —CBr$_3$. In embodiments, $R^{6B}$ is independently —CF$_3$. In embodiments, $R^{6B}$ is independently —CI$_3$. In embodiments, $R^{6B}$ is independently —CHCl$_2$. In embodiments, $R^{6B}$ is independently —CHBr$_2$. In embodiments, $R^{6B}$ is independently —CHF$_2$. In embodiments, $R^{6B}$ is independently —CHI$_2$. In embodiments, $R^{6B}$ is independently —CH$_2$Cl. In embodiments, $R^{6B}$ is independently —CH$_2$Br. In embodiments, $R^{6B}$ is independently —CH$_2$F. In embodiments, $R^{6B}$ is independently —CH$_2$I. In embodiments, $R^{6B}$ is independently —CN. In embodiments, $R^{6B}$ is independently —OH. In embodiments, $R^{6B}$ is independently —COOH. In embodiments, $R^{6B}$ is independently —CONH$_2$. In embodiments, $R^{6B}$ is independently —OCCl$_3$. In embodiments, $R^{6B}$ is independently —OCF$_3$. In embodiments, $R^{6B}$ is independently —OCBr$_3$. In embodiments, $R^{6B}$ is independently —OCl$_3$. In embodiments, R$^{6B}$ is independently —OCHCl$_2$. In embodiments, R$^{6B}$ is independently —OCHBr$_2$. In embodiments, R$^{6B}$ is independently —OCHI$_2$. In embodiments, R$^{6B}$ is independently —OCHF$_2$. In embodiments, R$^{6B}$ is independently —OCH$_2$Cl. In embodiments, R$^{6B}$ is independently —OCH$_2$Br. In embodiments, R$^{6B}$ is independently —OCH$_2$I. In embodiments, R$^{6B}$ is independently —OCH$_2$F. In embodiments, R$^{6B}$ is independently —OCH$_3$. In embodiments, R$^{6B}$ is idenpendently —CH$_3$. In embodiments, R$^{6B}$ is idenpendently —CH$_2$CH$_3$. In embodiments, R$^{6B}$ is independently unsubstituted propyl. In embodiments, R$^{6B}$ is independently unsubstituted isopropyl. In embodiments, R$^{6B}$ is independently unsubstituted butyl. In embodiments, R$^{6B}$ is independently unsubstituted tert-butyl. In embodiments, R$^{6B}$ is independently hydrogen.

In embodiments, R$^{6C}$ is independently R$^{36}$-substituted or unsubstituted alkyl (e.g., C$_1$-C$_8$ alkyl, C$_1$-C$_6$ alkyl, or C$_1$-C$_4$ alkyl). In embodiments, R$^{6C}$ is independently R$^{36}$-substituted alkyl (e.g., C$_1$-C$_8$ alkyl, C$_1$-C$_6$ alkyl, or C$_1$-C$_4$ alkyl). In embodiments, R$^{6C}$ is independently an unsubstituted alkyl (e.g., C$_1$-C$_8$ alkyl, C$_1$-C$_6$ alkyl, or C$_1$-C$_4$ alkyl). In embodiments, R$^{6C}$ is independently R$^{36}$-substituted or unsubstituted heteroalkyl (e.g., 2 to 8 membered heteroalkyl, 2 to 6 membered heteroalkyl, or 2 to 4 membered heteroalkyl). In embodiments, R$^{6C}$ is independently R$^{36}$-substituted heteroalkyl (e.g., 2 to 8 membered heteroalkyl, 2 to 6 membered heteroalkyl, or 2 to 4 membered heteroalkyl). In embodiments, R$^{6C}$ is independently an unsubstituted heteroalkyl (e.g., 2 to 8 membered heteroalkyl, 2 to 6 membered heteroalkyl, or 2 to 4 membered heteroalkyl). In embodiments, R$^{6C}$ is independently R$^{36}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6C}$ is independently R$^{36}$-substituted cycloalkyl (e.g., C$_3$-C$_8$ cycloalkyl, C$_3$-C$_6$ cycloalkyl, or C$_5$-C$_6$ cycloalkyl). In embodiments, R$^{6C}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6C}$ is independently R$^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{6C}$ is independently R$^{36}$-substituted heterocycloalkyl (e.g., 3 to 8 membered heterocycloalkyl, 3 to 6 membered heterocycloalkyl, or 5 to 6 membered heterocycloalkyl). In embodiments, R$^{6C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{6C}$ is independently R$^{36}$-substituted or unsubstituted aryl (e.g., C$_6$-C$_{10}$ aryl, C$_{10}$ aryl, or phenyl). In embodiments, R$^{6C}$ is independently R$^{36}$-substituted aryl (e.g., C$_6$-C$_{10}$ aryl, C$_{10}$ aryl, or phenyl). In embodiments, R$^{6C}$ is independently an unsubstituted aryl (e.g., C$_6$-C$_{10}$ aryl, C$_{10}$ aryl, or phenyl). In embodiments, R$^{6C}$ is independently R$^{36}$-substituted or unsubstituted heteroaryl (e.g., 5 to 10 membered heteroaryl, 5 to 9 membered heteroaryl, or 5 to 6 membered heteroaryl). In embodiments, R$^{6C}$ is independently R$^{36}$-substituted heteroaryl (e.g., 5 to 10 membered heteroaryl, 5 to 9 membered heteroaryl, or 5 to 6 membered heteroaryl). In embodiments, R$^{6C}$ is independently an unsubstituted heteroaryl (e.g., 5 to 10 membered heteroaryl, 5 to 9 membered heteroaryl, or 5 to 6 membered heteroaryl).

In embodiments, R$^{6C}$ is independently —CCl$_3$. In embodiments, R$^{6C}$ is independently —CBr$_3$. In embodiments, R$^{6C}$ is independently —CF$_3$. In embodiments, R$^{6C}$ is independently —CI$_3$. In embodiments, R$^{6C}$ is independently —CHCl$_2$. In embodiments, R$^{6C}$ is independently —CHBr$_2$. In embodiments, R$^{6C}$ is independently —CHF$_2$. In embodiments, R$^{6C}$ is independently —CHI$_2$. In embodiments, R$^{6C}$ is independently —CH$_2$Cl. In embodiments, R$^{6C}$ is independently —CH$_2$Br. In embodiments, R$^{6C}$ is independently —CH$_2$F. In embodiments, R$^{6C}$ is independently —CH$_2$I. In embodiments, R$^{6C}$ is independently —CN. In embodiments, R$^{6C}$ is independently —OH. In embodiments, R$^{6C}$ is independently —COOH. In embodiments, R$^{6C}$ is independently —CONH$_2$. In embodiments, R$^{6C}$ is independently —OCCl$_3$. In embodiments, R$^{6C}$ is independently —OCF$_3$. In embodiments, R$^{6C}$ is independently —OCBr$_3$. In embodiments, R$^{6C}$ is independently —OCl$_3$. In embodiments, R$^{6C}$ is independently —OCHCl$_2$. In embodiments, R$^{6C}$ is independently —OCHBr$_2$. In embodiments, R$^{6C}$ is independently —OCHI$_2$. In embodiments, R$^{6C}$ is independently —OCHF$_2$. In embodiments, R$^{6C}$ is independently —OCH$_2$Cl. In embodiments, R$^{6C}$ is independently —OCH$_2$Br. In embodiments, R$^{6C}$ is independently —OCH$_2$I. In embodiments, R$^{6C}$ is independently —OCH$_2$F. In embodiments, R$^{6C}$ is independently —OCH$_3$. In embodiments, R$^{6C}$ is idenpendently —CH$_3$. In embodiments, R$^{6C}$ is idenpendently —CH$_2$CH$_3$. In embodiments, R$^{6C}$ is independently unsubstituted propyl. In embodiments, R$^{6C}$ is independently unsubstituted isopropyl. In embodiments, R$^{6C}$ is independently unsubstituted butyl. In embodiments, R$^{6C}$ is independently unsubstituted tert-butyl. In embodiments, R$^{6C}$ is independently hydrogen.

In embodiments, R$^{6D}$ is independently R$^{36}$-substituted or unsubstituted alkyl (e.g., C$_1$-C$_8$ alkyl, C$_1$-C$_6$ alkyl, or C$_1$-C$_4$ alkyl). In embodiments, R$^{6D}$ is independently R$^{36}$-substituted alkyl (e.g., C$_1$-C$_8$ alkyl, C$_1$-C$_6$ alkyl, or C$_1$-C$_4$ alkyl). In embodiments, R$^{6D}$ is independently an unsubstituted alkyl (e.g., C$_1$-C$_8$ alkyl, C$_1$-C$_6$ alkyl, or C$_1$-C$_4$ alkyl). In embodiments, R$^{6D}$ is independently R$^{36}$-substituted or unsubstituted heteroalkyl (e.g., 2 to 8 membered heteroalkyl, 2 to 6 membered heteroalkyl, or 2 to 4 membered heteroalkyl). In embodiments, R' is independently R$^{36}$-substituted heteroalkyl (e.g., 2 to 8 membered heteroalkyl, 2 to 6 membered heteroalkyl, or 2 to 4 membered heteroalkyl). In embodiments, R$^{6D}$ is independently an unsubstituted heteroalkyl (e.g., 2 to 8 membered heteroalkyl, 2 to 6 membered heteroalkyl, or 2 to 4 membered heteroalkyl). In embodiments, R$^{6D}$ is independently R$^{36}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6D}$ is independently R$^{36}$-substituted cycloalkyl (e.g., C$_3$-C$_8$ cycloalkyl, C$_3$-C$_6$ cycloalkyl, or C$_5$-C$_6$ cycloalkyl). In embodiments, R$^{6D}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6D}$ is independently R$^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{6D}$ is independently R$^{36}$-substituted heterocycloalkyl (e.g., 3 to 8 membered heterocycloalkyl, 3 to 6 membered heterocycloalkyl, or 5 to 6 membered heterocycloalkyl). In embodiments, R$^{6D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{6D}$ is independently R$^{36}$-substituted or unsubstituted aryl (e.g., C$_6$-C$_{10}$ aryl, C$_{10}$ aryl, or phenyl). In embodiments, R$^{6D}$ is independently R$^{36}$-substituted aryl (e.g., C$_6$-C$_{10}$ aryl, C$_{10}$ aryl, or phenyl). In embodiments, R$^{6D}$ is independently an unsubstituted aryl (e.g., C$_6$-C$_{10}$ aryl, C$_{10}$ aryl, or phenyl). In embodiments, R$^{6D}$ is independently R$^{36}$-substituted or unsubstituted heteroaryl (e.g., 5 to 10 membered heteroaryl, 5 to 9 membered heteroaryl, or 5 to 6 membered heteroaryl). In embodiments, $R^{6D}$ is independently $R^{36}$-substituted heteroaryl (e.g., 5 to 10 membered heteroaryl, 5 to 9 membered heteroaryl, or 5 to 6 membered heteroaryl). In embodiments, $R^{6D}$ is independently an unsubstituted heteroaryl (e.g., 5 to 10 membered heteroaryl, 5 to 9 membered heteroaryl, or 5 to 6 membered heteroaryl).

In embodiments, $R^{6D}$ is independently —CCl$_3$. In embodiments, $R^{6D}$ is independently —CBr$_3$. In embodiments, $R^{6D}$ is independently —CF$_3$. In embodiments, $R^{6D}$ is independently —CI$_3$. In embodiments, $R^{6D}$ is independently —CHCl$_2$. In embodiments, $R^{6D}$ is independently —CHBr$_2$. In embodiments, $R^{6D}$ is independently —CHF$_2$. In embodiments, $R^{6D}$ is independently —CHI$_2$. In embodiments, $R^{6D}$ is independently —CH$_2$Cl. In embodiments, $R^{6D}$ is independently —CH$_2$Br. In embodiments, $R^{6D}$ is independently —CH$_2$F. In embodiments, $R^{6D}$ is independently —CH$_2$I. In embodiments, $R^{6D}$ is independently —CN. In embodiments, $R^{6D}$ is independently —OH. In embodiments, $R^{6D}$ is independently —COOH. In embodiments, $R^{6D}$ is independently —CONH$_2$. In embodiments, $R^{6D}$ is independently —OCCl$_3$. In embodiments, $R^{6D}$ is independently —OCF$_3$. In embodiments, $R^{6D}$ is independently —OCBr$_3$. In embodiments, $R^{6D}$ is independently —OCI$_3$. In embodiments, $R^{6D}$ is independently —OCHCl$_2$. In embodiments, $R^{6D}$ is independently —OCHBr$_2$. In embodiments, $R^{6D}$ is independently —OCHI$_2$. In embodiments, $R^{6D}$ is independently —OCHF$_2$. In embodiments, $R^{6D}$ is independently —OCH$_2$Cl. In embodiments, $R^{6D}$ is independently —OCH$_2$Br. In embodiments, $R^{6D}$ is independently —OCH$_2$I. In embodiments, $R^{6D}$ is independently —OCH$_2$F. In embodiments, $R^{6D}$ is independently —OCH$_3$. In embodiments, $R^{6D}$ is independently CH$_3$. In embodiments, $R^{6D}$ is idenpendently —CH$_2$CH$_3$. In embodiments, $R^{6D}$ is independently unsubstituted propyl. In embodiments, $R^{6D}$ is independently unsubstituted isopropyl. In embodiments, $R^{6D}$ is independently unsubstituted butyl. In embodiments, $R^{6D}$ is independently unsubstituted tert-butyl. In embodiments, $R^{6D}$ is independently hydrogen.

In embodiments, $R^{15}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, —NHC(O)NHNH$_2$, —N$_3$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{15}$ is independently substituted or unsubstituted alkyl (e.g., C$_1$-C$_8$ alkyl, C$_1$-C$_6$ alkyl, or C$_1$-C$_4$ alkyl). In embodiments, $R^{15}$ is independently substituted alkyl (e.g., C$_1$-C$_8$ alkyl, C$_1$-C$_6$ alkyl, or C$_1$-C$_4$ alkyl). In embodiments, $R^{15}$ is independently an unsubstituted alkyl (e.g., C$_1$-C$_8$ alkyl, C$_1$-C$_6$ alkyl, or C$_1$-C$_4$ alkyl). In embodiments, $R^{15}$ is independently substituted or unsubstituted heteroalkyl (e.g., 2 to 8 membered heteroalkyl, 2 to 6 membered heteroalkyl, or 2 to 4 membered heteroalkyl). In embodiments, $R^{15}$ is independently substituted heteroalkyl (e.g., 2 to 8 membered heteroalkyl, 2 to 6 membered heteroalkyl, or 2 to 4 membered heteroalkyl). In embodiments, $R^{15}$ is independently an unsubstituted heteroalkyl (e.g., 2 to 8 membered heteroalkyl, 2 to 6 membered heteroalkyl, or 2 to 4 membered heteroalkyl). In embodiments, $R^{15}$ is independently substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{15}$ is independently substituted cycloalkyl (e.g., C$_3$-C$_8$ cycloalkyl, C$_3$-C$_6$ cycloalkyl, or C$_5$-C$_6$ cycloalkyl). In embodiments, $R^{15}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, $R^{15}$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is independently substituted heterocycloalkyl (e.g., 3 to 8 membered heterocycloalkyl, 3 to 6 membered heterocycloalkyl, or 5 to 6 membered heterocycloalkyl). In embodiments, $R^{15}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is independently substituted or unsubstituted aryl (e.g., C$_6$-C$_{10}$ aryl, C$_{10}$ aryl, or phenyl). In embodiments, $R^{15}$ is independently substituted aryl (e.g., C$_6$-C$_{10}$ aryl, C$_{10}$ aryl, or phenyl). In embodiments, $R^{15}$ is independently an unsubstituted aryl (e.g., C$_6$-C$_{10}$ aryl, C$_{10}$ aryl, or phenyl). In embodiments, $R^{15}$ is independently substituted or unsubstituted heteroaryl (e.g., 5 to 10 membered heteroaryl, 5 to 9 membered heteroaryl, or 5 to 6 membered heteroaryl). In embodiments, $R^{15}$ is independently substituted heteroaryl (e.g., 5 to 10 membered heteroaryl, 5 to 9 membered heteroaryl, or 5 to 6 membered heteroaryl). In embodiments, $R^{15}$ is independently an unsubstituted heteroaryl (e.g., 5 to 10 membered heteroaryl, 5 to 9 membered heteroaryl, or 5 to 6 membered heteroaryl).

In embodiments, $R^{15}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, —NHC(O)NHNH$_2$, $R^{39}$-substituted or unsubstituted alkyl (e.g., C$_1$-C$_8$ alkyl, C$_1$-C$_6$ alkyl, or C$_1$-C$_4$ alkyl), $R^{39}$-substituted or unsubstituted heteroalkyl (e.g., 2 to 8 membered heteroalkyl, 2 to 6 membered heteroalkyl, or 2 to 4 membered heteroalkyl), $R^{39}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{39}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted or unsubstituted aryl (e.g., C$_6$-C$_{10}$ aryl, C$_{10}$ aryl, or phenyl), or $R^{39}$-substituted or unsubstituted heteroaryl (e.g., 5 to 10 membered heteroaryl, 5 to 9 membered heteroaryl, or 5 to 6 membered heteroaryl).

In embodiments, $R^{15}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{15}$ is independently $R^{39}$-substituted or unsubstituted alkyl (e.g., $C_1$-$C_4$ alkyl, $C_1$-$C_6$ alkyl, or $C_1$-$C_4$ alkyl). In embodiments, $R^{15}$ is independently $R^{39}$-substituted alkyl (e.g., $C_1$-$C_8$ alkyl, $C_1$-$C_6$ alkyl, or $C_1$-$C_4$ alkyl). In embodiments, $R^{15}$ is independently an unsubstituted alkyl (e.g., $C_1$-$C_8$ alkyl, $C_1$-$C_6$ alkyl, or $C_1$-$C_4$ alkyl). In embodiments, $R^{15}$ is independently $R^{39}$-substituted or unsubstituted heteroalkyl (e.g., 2 to 8 membered heteroalkyl, 2 to 6 membered heteroalkyl, or 2 to 4 membered heteroalkyl). In embodiments, $R^{15}$ is independently $R^{39}$-substituted heteroalkyl (e.g., 2 to 8 membered heteroalkyl, 2 to 6 membered heteroalkyl, or 2 to 4 membered heteroalkyl). In embodiments, $R^{15}$ is independently an unsubstituted heteroalkyl (e.g., 2 to 8 membered heteroalkyl, 2 to 6 membered heteroalkyl, or 2 to 4 membered heteroalkyl). In embodiments, $R^{15}$ is independently $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is independently $R^{39}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is independently $R^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is independently $R^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{15}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is independently $R^{39}$-substituted or unsubstituted aryl (e.g., $C_6$-$C_{10}$ aryl, $C_{10}$ aryl, or phenyl). In embodiments, $R^{15}$ is independently $R^{39}$-substituted aryl (e.g., $C_6$-$C_{10}$ aryl, $C_{10}$ aryl, or phenyl). In embodiments, $R^{15}$ is independently an unsubstituted aryl (e.g., $C_6$-$C_{10}$ aryl, $C_{10}$ aryl, or phenyl). In embodiments, $R^{15}$ is independently $R^{39}$-substituted or unsubstituted heteroaryl (e.g., 5 to 10 membered heteroaryl, 5 to 9 membered heteroaryl, or 5 to 6 membered heteroaryl). In embodiments, $R^{15}$ is independently $R^{39}$-substituted heteroaryl (e.g., 5 to 10 membered heteroaryl, 5 to 9 membered heteroaryl, or 5 to 6 membered heteroaryl). In embodiments, $R^{15}$ is independently an unsubstituted heteroaryl (e.g., 5 to 10 membered heteroaryl, 5 to 9 membered heteroaryl, or 5 to 6 membered heteroaryl).

In embodiments, $R^{15}$ is independently —$CX^{15}_3$. In embodiments, $R^{15}$ is independently —$CHX^{15}_2$. In embodiments, $R^{15}$ is independently —$CH_2X^{15}$. In embodiments, $R^{15}$ is independently —$OCX^{15}_3$. In embodiments, $R^{15}$ is independently —$OCH_2X^{15}$. In embodiments, $R^{15}$ is independently —$OCHX^{15}_2$. In embodiments, $R^{15}$ is independently —CN. In embodiments, $R^{15}$ is independently —$SR^{15D}$. In embodiments, $R^{15}$ is independently —$SOR^{15D}$. In embodiments, $R^{15}$ is independently $SO_2R^{15D}$. In embodiments, $R^{15}$ is independently $SO_3R^{15D}$. In embodiments, $R^{15}$ is independently $SO_4R^{15D}$. In embodiments, $R^{15}$ is independently —$SONR^{15A}R^{15B}$. In embodiments, $R^{15}$ is independently —$SO_2NR^{15A}R^{15B}$. In embodiments, $R^{15}$ is independently —$NHC(O)NR^{15A}R^{15B}$. In embodiments, $R^{15}$ is independently —N(O). In embodiments, $R^{15}$ is independently —$N(O)_2$. In embodiments, $R^{15}$ is independently —$NR^{15A}R^{15B}$. In embodiments, $R^{15}$ is independently —$C(O)R^{15C}$. In embodiments, $R^{15}$ is independently —C(O)—$OR^{15C}$. In embodiments, $R^{15}$ is independently —$C(O)NR^{15A}R^{15B}$. In embodiments, $R^{15}$ is independently —$OR^{15D}$. In embodiments, $R^{15}$ is independently —$NR^{15A}SO_2R^{15D}$. In embodiments, $R^{15}$ is independently —$NR^{15A}C(O)R^{15C}$. In embodiments, $R^{15}$ is independently —$NR^{15A}C(O)OR^{15C}$. In embodiments, $R^{15}$ is independently —$NR^{15A}OR^{15C}$. In embodiments, $R^{15}$ is independently hydrogen.

In embodiments, $R^{15}$ is independently oxo. In embodiments, $R^{15}$ is independently halogen. In embodiments, $R^{15}$ is independently —$CCl_3$. In embodiments, $R^{15}$ is independently —$CBr_3$. In embodiments, $R^{15}$ is independently —$CF_3$. In embodiments, $R^{15}$ is independently —$CI_3$. In embodiments, $R^{15}$ is independently —$CHCl_2$. In embodiments, $R^{15}$ is independently —$CHBr_2$. In embodiments, $R^{15}$ is independently —$CHF_2$. In embodiments, $R^{15}$ is independently —$CHI_2$. In embodiments, $R^{15}$ is independently —$CH_2Cl$. In embodiments, $R^{15}$ is independently —$CH_2Br$. In embodiments, $R^{15}$ is independently —$CH_2F$. In embodiments, $R^{15}$ is independently —$CH_2I$. In embodiments, $R^{15}$ is independently —CN. In embodiments, $R^{15}$ is independently —OH. In embodiments, $R^{15}$ is independently —$NH_2$. In embodiments, $R^{15}$ is independently —COOH. In embodiments, $R^{15}$ is independently —$CONH_2$. In embodiments, $R^{15}$ is independently —$NO_2$. In embodiments, $R^{15}$ is independently —SH. In embodiments, $R^{15}$ is independently —$SO_3H$. In embodiments, $R^{15}$ is independently —$SO_4H$. In embodiments, $R^{15}$ is independently —$SO_2NH_2$. In embodiments, $R^{15}$ is independently —$NHNH_2$. In embodiments, $R^{15}$ is independently —$ONH_2$. In embodiments, $R^{15}$ is independently —$NHC(O)NHNH_2$. In embodiments, $R^{15}$ is independently —$NHC(O)NH_2$. In embodiments, $R^{15}$ is independently —$NHSO_2H$. In embodiments, $R^{15}$ is independently —NHC(O)H. In embodiments, $R^{15}$ is independently —NHC(O)OH. In embodiments, $R^{15}$ is independently —NHOH. In embodiments, $R^{15}$ is independently —$OCCl_3$. In embodiments, $R^{15}$ is independently —$OCF_3$. In embodiments, $R^{15}$ is independently —$OCBr_3$. In embodiments, $R^{15}$ is independently —$OCI_3$. In embodiments, $R^{15}$ is independently —$OCHCl_2$. In embodiments, $R^{15}$ is independently —$OCHBr_2$. In embodiments, $R^{15}$ is independently —$OCHI_2$. In embodiments, $R^{15}$ is independently —$OCHF_2$. In embodiments, $R^{15}$ is independently —$OCH_2Cl$. In embodiments, $R^{15}$ is independently —$OCH_2Br$. In embodiments, $R^{15}$ is independently —$OCH_2I$. In embodiments, $R^{15}$ is independently —$OCH_2F$. In embodiments, $R^{15}$ is independently —$N_3$. In embodiments, $R^{15}$ is independently —$OCH_3$. In embodiments, $R^{15}$ is independently —$CH_3$. In embodiments, $R^{15}$ is independently —$CH_2CH_3$. In embodiments, $R^{15}$ is independently unsubstituted propyl. In embodiments, $R^{15}$ is independently unsubstituted isopropyl. In embodiments, $R^{15}$ is independently unsubstituted butyl. In embodiments, $R^{15}$ is independently unsubstituted tert-butyl. In embodiments, $R^{15}$ is independently —F. In embodiments, $R^{15}$ is independently —Cl. In embodiments, $R^{15}$ is independently —Br. In embodiments, $R^{15}$ is independently —I.

$R^{39}$ is independently oxo, halogen, —$CF_3$, —$CBr_3$, —$CCl_3$, —$CI_3$, —$CHF_2$, —$CHBr_2$, —$CHCl_2$, —$CHI_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{39}$ is independently oxo. In embodiments, R$^{39}$ is independently halogen. In embodiments, R$^{39}$ is independently —CCl$_3$. In embodiments, R$^{39}$ is independently —CBr$_3$. In embodiments, R$^{39}$ is independently —CF$_3$. In embodiments, R$^{39}$ is independently —CI$_3$. In embodiments, R$^{39}$ is independently —CHCl$_2$. In embodiments, R$^{39}$ is independently —CHBr$_2$. In embodiments, R$^{39}$ is independently —CHF$_2$. In embodiments, R$^{39}$ is independently —CHI$_2$. In embodiments, R$^{39}$ is independently —CH$_2$Cl. In embodiments, R$^{39}$ is independently —CH$_2$Br. In embodiments, R$^{39}$ is independently —CH$_2$F. In embodiments, R$^{39}$ is independently —CH$_2$I. In embodiments, R$^{39}$ is independently —CN. In embodiments, R$^{39}$ is independently —OH. In embodiments, R$^{39}$ is independently —NH$_2$. In embodiments, R$^{39}$ is independently —COOH. In embodiments, R$^{39}$ is independently —CONH$_2$. In embodiments, R$^{39}$ is independently —NO$_2$. In embodiments, R$^{39}$ is independently —SH. In embodiments, R$^{39}$ is independently —SO$_3$H. In embodiments, R$^{39}$ is independently —SO$_4$H. In embodiments, R$^{39}$ is independently —SO$_2$NH$_2$. In embodiments, R$^{39}$ is independently —NHNH$_2$. In embodiments, R$^{39}$ is independently —ONH$_2$. In embodiments, R$^{39}$ is independently —NHC(O)NHNH$_2$. In embodiments, R$^{39}$ is independently —NHC(O)NH$_2$. In embodiments, R$^{39}$ is independently —NHSO$_2$H. In embodiments, R$^{39}$ is independently —NHC(O)H. In embodiments, R$^{39}$ is independently —NHC(O)OH. In embodiments, R$^{39}$ is independently —NHOH. In embodiments, R$^{39}$ is independently —OCCl$_3$. In embodiments, R$^{39}$ is independently —OCF$_3$. In embodiments, R$^{39}$ is independently —OCBr$_3$. In embodiments, R$^{39}$ is independently —OCI$_3$. In embodiments, R$^{39}$ is independently —OCHCl$_2$. In embodiments, R$^{39}$ is independently —OCHBr$_2$. In embodiments, R$^{39}$ is independently —OCHI$_2$. In embodiments, R$^{39}$ is independently —OCHF$_2$. In embodiments, R$^{39}$ is independently —OCH$_2$Cl. In embodiments, R$^{39}$ is independently —OCH$_2$Br. In embodiments, R$^{39}$ is independently —OCH$_2$I. In embodiments, R$^{39}$ is independently —OCH$_2$F. In embodiments, R$^{39}$ is independently —N$_3$. In embodiments, R$^{39}$ is independently —OCH$_3$. In embodiments, R$^{39}$ is independently —CH$_3$. In embodiments, R$^{39}$ is independently —CH$_2$CH$_3$. In embodiments, R$^{39}$ is independently unsubstituted propyl. In embodiments, R$^{39}$ is independently unsubstituted isopropyl. In embodiments, R$^{39}$ is independently unsubstituted butyl. In embodiments, R$^{39}$ is independently unsubstituted tert-butyl. In embodiments, R$^{39}$ is independently —F. In embodiments, R$^{39}$ is independently —Cl. In embodiments, R$^{39}$ is independently —Br. In embodiments, R$^{39}$ is independently —I.

In embodiments, R$^{15A}$ is independently hydrogen, halogen, —CF$_3$, —CBr$_3$, —CCl$_3$, —CI$_3$, —CHBr$_2$, —CHCl$_2$, —CHI$_2$, —CH$_2$Br, —CH$_2$Cl, —CH$_2$I, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{15B}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$Br, —CH$_2$Cl, —CH$_2$I, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{15C}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{15D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{15A}$ and $R^{15B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{15A}$ and $R^{15B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15A}$ and $R^{15B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{15A}$ and $R^{15B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{15A}$ and $R^{15B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{15A}$ and $R^{15B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{15A}$ and $R^{15B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{15A}$, $R^{15B}$, $R^{15C}$, and $R^{15D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{39}$-substituted or unsubstituted alkyl (e.g., $C_1$-$C_8$ alkyl, $C_1$-$C_6$ alkyl, or $C_1$-$C_4$ alkyl), $R^{39}$-substituted or unsubstituted heteroalkyl (e.g., 2 to 8 membered heteroalkyl, 2 to 6 membered heteroalkyl, or 2 to 4 membered heteroalkyl), $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{39}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted or unsubstituted aryl (e.g., $C_6$-$C_{10}$ aryl, $C_{10}$ aryl, or phenyl), or $R^{39}$-substituted or unsubstituted heteroaryl (e.g., 5 to 10 membered heteroaryl, 5 to 9 membered heteroaryl, or 5 to 6 membered heteroaryl). In embodiments, $R^{15A}$ and $R^{15B}$ substituents bonded to the same nitrogen atom are independently joined to form an $R^{39}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{39}$-substituted or unsubstituted heteroaryl (e.g., 5 to 10 membered heteroaryl, 5 to 9 membered heteroaryl, or 5 to 6 membered heteroaryl). In embodiments, $R^{15A}$ and $R^{15B}$ substituents bonded to the same nitrogen atom are independently joined to form an $R^{39}$-substituted or unsubstituted heterocycloalkyl (e.g., 3 to 8 membered heterocycloalkyl, 3 to 6 membered heterocycloalkyl. In embodiments, $R^{15A}$ and $R^{15B}$ substituents bonded to the same nitrogen atom are independently joined to form an $R^{39}$-substituted or unsubstituted heteroaryl (e.g., 5 to 10 membered heteroaryl, 5 to 9 membered heteroaryl, or 5 to 6 membered heteroaryl).

In embodiments, $R^{15A}$ is independently $R^{39}$-substituted or unsubstituted alkyl (e.g., $C_1$-$C_8$ alkyl, $C_1$-$C_6$ alkyl, or $C_1$-$C_4$ alkyl). In embodiments, $R^{15A}$ is independently $R^{39}$-substituted alkyl (e.g., $C_1$-$C_8$ alkyl, $C_1$-$C_6$ alkyl, or $C_1$-$C_4$ alkyl). In embodiments, $R^{15A}$ is independently an unsubstituted alkyl (e.g., $C_1$-$C_8$ alkyl, $C_1$-$C_6$ alkyl, or $C_1$-$C_4$ alkyl). In embodiments, $R^{15A}$ is independently $R^{39}$-substituted or unsubstituted heteroalkyl (e.g., 2 to 8 membered heteroalkyl, 2 to 6 membered heteroalkyl, or 2 to 4 membered heteroalkyl). In embodiments, $R^{15A}$ is independently $R^{39}$-substituted heteroalkyl (e.g., 2 to 8 membered heteroalkyl, 2 to 6 membered heteroalkyl, or 2 to 4 membered heteroalkyl). In embodiments, $R^{15A}$ is independently an unsubstituted heteroalkyl (e.g., 2 to 8 membered heteroalkyl, 2 to 6 membered heteroalkyl, or 2 to 4 membered heteroalkyl). In embodiments, $R^{15A}$ is independently $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15A}$ is independently $R^{39}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15A}$ is independently $R^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15A}$ is independently $R^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{15A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{15A}$ is independently $R^{39}$-substituted or unsubstituted aryl (e.g., $C_6$-$C_{10}$ aryl, $C_{10}$ aryl, or phenyl). In embodiments, $R^{15A}$ is independently $R^{39}$-substituted aryl (e.g., $C_6$-$C_{10}$ aryl, $C_{10}$ aryl, or phenyl). In embodiments, $R^{15A}$ is independently an unsubstituted aryl (e.g., $C_6$-$C_{10}$ aryl, $C_{10}$ aryl, or phenyl). In embodiments, $R^{15A}$ is independently $R^{39}$-substituted or unsubstituted heteroaryl (e.g., 5 to 10 membered heteroaryl, 5 to 9 membered heteroaryl, or 5 to 6 membered heteroaryl). In embodiments, $R^{15A}$ is independently $R^{39}$-substituted heteroaryl (e.g., 5 to 10 membered heteroaryl, 5 to 9 membered heteroaryl, or 5 to 6 membered heteroaryl). In embodiments, $R^{15A}$ is independently an unsubstituted heteroaryl (e.g., 5 to 10 membered heteroaryl, 5 to 9 membered heteroaryl, or 5 to 6 membered heteroaryl).

In embodiments, $R^{15A}$ is independently —$CCl_3$. In embodiments, $R^{15A}$ is independently —$CBr_3$. In embodiments, $R^{15A}$ is independently —$CF_3$. In embodiments, $R^{15A}$ is independently —$CI_3$. In embodiments, $R^{15A}$ is independently —$CHCl_2$. In embodiments, $R^{15A}$ is independently —CHBr$_2$. In embodiments, R$^{15A}$ is independently —CHF$_2$. In embodiments, R$^{15A}$ is independently —CHI$_2$. In embodiments, R$^{15A}$ is independently —CH$_2$Cl. In embodiments, R$^{15A}$ is independently —CH$_2$Br. In embodiments, R$^{15A}$ is independently —CH$_2$F. In embodiments, R$^{15A}$ is independently —CH$_2$I. In embodiments, R$^{15A}$ is independently —CN. In embodiments, R$^{15A}$ is independently —OH. In embodiments, R$^{15A}$ is independently —COOH. In embodiments, R$^{15A}$ is independently —CONH$_2$. In embodiments, R$^{15A}$ is independently —OCCl$_3$. In embodiments, R$^{15A}$ is independently —OCF$_3$. In embodiments, R$^{15A}$ is independently —OCBr$_3$. In embodiments, R$^{15A}$ is independently —OCl$_3$. In embodiments, R$^{15A}$ is independently —OCHCl$_2$. In embodiments, R$^{15A}$ is independently —OCHBr$_2$. In embodiments, R$^{15A}$ is independently —OCHI$_2$. In embodiments, R$^{15A}$ is independently —OCHF$_2$. In embodiments, R$^{15A}$ is independently —OCH$_2$Cl. In embodiments, R$^{15A}$ is independently —OCH$_2$Br. In embodiments, R$^{15A}$ is independently —OCH$_2$I. In embodiments, R$^{15A}$ is independently —OCH$_2$F. In embodiments, R$^{15A}$ is independently OCH$_3$. In embodiments, R$^{15A}$ is idenpendently —CH$_3$. In embodiments, R$^{15A}$ is independently CH$_2$CH$_3$. In embodiments, R$^{15A}$ is independently unsubstituted propyl. In embodiments, R$^{15A}$ is independently unsubstituted isopropyl. In embodiments, R$^{15A}$ is independently unsubstituted butyl. In embodiments, R$^{15A}$ is independently unsubstituted tert-butyl. In embodiments, R$^{15A}$ is independently hydrogen.

In embodiments, R$^{15B}$ is independently R$^{39}$-substituted or unsubstituted alkyl (e.g., C$_1$-C$_8$ alkyl, C$_1$-C$_6$ alkyl, or C$_1$-C$_4$ alkyl). In embodiments, R$^{15B}$ is independently R$^{39}$-substituted alkyl (e.g., C$_1$-C$_8$ alkyl, C$_1$-C$_6$ alkyl, or C$_1$-C$_4$ alkyl). In embodiments, R$^{15B}$ is independently an unsubstituted alkyl (e.g., C$_1$-C$_8$ alkyl, C$_1$-C$_6$ alkyl, or C$_1$-C$_4$ alkyl). In embodiments, R$^{15B}$ is independently R$^{39}$-substituted or unsubstituted heteroalkyl (e.g., 2 to 8 membered heteroalkyl, 2 to 6 membered heteroalkyl, or 2 to 4 membered heteroalkyl). In embodiments, R$^{15B}$ is independently R$^{39}$-substituted heteroalkyl (e.g., 2 to 8 membered heteroalkyl, 2 to 6 membered heteroalkyl, or 2 to 4 membered heteroalkyl). In embodiments, R$^{15B}$ is independently an unsubstituted heteroalkyl (e.g., 2 to 8 membered heteroalkyl, 2 to 6 membered heteroalkyl, or 2 to 4 membered heteroalkyl). In embodiments, R$^{15B}$ is independently R$^{39}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{15B}$ is independently R$^{39}$-substituted cycloalkyl (e.g., C$_3$-C$_8$ cycloalkyl, C$_3$-C$_6$ cycloalkyl, or C$_5$-C$_6$ cycloalkyl). In embodiments, R$^{15B}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{15B}$ is independently R$^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{15B}$ is independently R$^{39}$-substituted heterocycloalkyl (e.g., 3 to 8 membered heterocycloalkyl, 3 to 6 membered heterocycloalkyl, or 5 to 6 membered heterocycloalkyl). In embodiments, R$^{15B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{15B}$ is independently R$^{39}$-substituted or unsubstituted aryl (e.g., C$_6$-C$_{10}$ aryl, C$_{10}$ aryl, or phenyl). In embodiments, R$^{15B}$ is independently R$^{39}$-substituted aryl (e.g., C$_6$-C$_{10}$ aryl, C$_{10}$ aryl, or phenyl). In embodiments, R$^{15B}$ is independently an unsubstituted aryl (e.g., C$_6$-C$_{10}$ aryl, C$_{10}$ aryl, or phenyl). In embodiments, R$^{15B}$ is independently R$^{39}$-substituted or unsubstituted heteroaryl (e.g., 5 to 10 membered heteroaryl, 5 to 9 membered heteroaryl, or 5 to 6 membered heteroaryl). In embodiments, R$^{15B}$ is independently R$^{39}$-substituted heteroaryl (e.g., 5 to 10 membered heteroaryl, 5 to 9 membered heteroaryl, or 5 to 6 membered heteroaryl). In embodiments, R$^{15B}$ is independently an unsubstituted heteroaryl (e.g., 5 to 10 membered heteroaryl, 5 to 9 membered heteroaryl, or 5 to 6 membered heteroaryl).

In embodiments, R$^{15B}$ is independently —CCl$_3$. In embodiments, R$^{15B}$ is independently —CBr$_3$. In embodiments, R$^{15B}$ is independently —CF$_3$. In embodiments, R$^{15B}$ is independently —CI$_3$. In embodiments, R$^{15B}$ is independently —CHCl$_2$. In embodiments, R$^{15B}$ is independently —CHBr$_2$. In embodiments, R$^{15B}$ is independently —CHF$_2$. In embodiments, R$^{15B}$ is independently —CHI$_2$. In embodiments, R$^{15B}$ is independently —CH$_2$Cl. In embodiments, R$^{15B}$ is independently —CH$_2$Br. In embodiments, R$^{15B}$ is independently —CH$_2$F. In embodiments, R$^{15B}$ is independently —CH$_2$I. In embodiments, R$^{15B}$ is independently —CN. In embodiments, R$^{15B}$ is independently —OH. In embodiments, R$^{15B}$ is independently —COOH. In embodiments, R$^{15B}$ is independently —CONH$_2$. In embodiments, R$^{15B}$ is independently —OCCl$_3$. In embodiments, R$^{15B}$ is independently —OCF$_3$. In embodiments, R$^{15B}$ is independently —OCBr$_3$. In embodiments, R$^{15B}$ is independently —OCl$_3$. In embodiments, R$^{15B}$ is independently —OCHCl$_2$. In embodiments, R$^{15B}$ is independently —OCHBr$_2$. In embodiments, R$^{15B}$ is independently —OCHI$_2$. In embodiments, R$^{15B}$ is independently —OCHF$_2$. In embodiments, R$^{15B}$ is independently —OCH$_2$Cl. In embodiments, R$^{15B}$ is independently —OCH$_2$Br. In embodiments, R$^{15B}$ is independently —OCH$_2$I. In embodiments, R$^{15B}$ is independently —OCH$_2$F. In embodiments, R$^{15B}$ is independently —OCH$_3$. In embodiments, R$^{15B}$ is independently CH$_3$. In embodiments, R$^{15B}$ is independently CH$_2$CH$_3$. In embodiments, R$^{15B}$ is independently unsubstituted propyl. In embodiments, R$^{15B}$ is independently unsubstituted isopropyl. In embodiments, R$^{15B}$ is independently unsubstituted butyl. In embodiments, R$^{15B}$ is independently unsubstituted tert-butyl. In embodiments, R$^{15B}$ is independently hydrogen.

In embodiments, R$^{15C}$ is independently R$^{39}$-substituted or unsubstituted alkyl (e.g., C$_1$-C$_8$ alkyl, C$_1$-C$_6$ alkyl, or C$_1$-C$_4$ alkyl). In embodiments, R$^{15C}$ is independently R$^{39}$-substituted alkyl (e.g., C$_1$-C$_8$ alkyl, C$_1$-C$_6$ alkyl, or C$_1$-C$_4$ alkyl). In embodiments, R$^{15C}$ is independently an unsubstituted alkyl (e.g., C$_1$-C$_8$ alkyl, C$_1$-C$_6$ alkyl, or C$_1$-C$_4$ alkyl). In embodiments, R$^{15C}$ is independently R$^{39}$-substituted or unsubstituted heteroalkyl (e.g., 2 to 8 membered heteroalkyl, 2 to 6 membered heteroalkyl, or 2 to 4 membered heteroalkyl). In embodiments, R$^{15C}$ is independently R$^{39}$-substituted heteroalkyl (e.g., 2 to 8 membered heteroalkyl, 2 to 6 membered heteroalkyl, or 2 to 4 membered heteroalkyl). In embodiments, R$^{15C}$ is independently an unsubstituted heteroalkyl (e.g., 2 to 8 membered heteroalkyl, 2 to 6 membered heteroalkyl, or 2 to 4 membered heteroalkyl). In embodiments, R$^{15C}$ is independently R$^{39}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{15C}$ is independently R$^{39}$-substituted cycloalkyl (e.g., C$_3$-C$_8$ cycloalkyl, C$_3$-C$_6$ cycloalkyl, or C$_5$-C$_6$ cycloalkyl). In embodiments, R$^{15C}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{15C}$ is independently R$^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{15C}$ is independently R$^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{15C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{15C}$ is independently $R^{39}$-substituted or unsubstituted aryl (e.g., $C_6$-$C_{10}$ aryl, $C_{10}$ aryl, or phenyl). In embodiments, $R^{15C}$ is independently $R^{39}$-substituted aryl (e.g., $C_6$-$C_{10}$ aryl, $C_{10}$ aryl, or phenyl). In embodiments, $R^{15C}$ is independently an unsubstituted aryl (e.g., $C_6$-$C_{10}$ aryl, $C_{10}$ aryl, or phenyl). In embodiments, $R^{15C}$ is independently $R^{39}$-substituted or unsubstituted heteroaryl (e.g., 5 to 10 membered heteroaryl, 5 to 9 membered heteroaryl, or 5 to 6 membered heteroaryl). In embodiments, $R^{15C}$ is independently $R^{39}$-substituted heteroaryl (e.g., 5 to 10 membered heteroaryl, 5 to 9 membered heteroaryl, or 5 to 6 membered heteroaryl). In embodiments, $R^{15C}$ is independently an unsubstituted heteroaryl (e.g., 5 to 10 membered heteroaryl, 5 to 9 membered heteroaryl, or 5 to 6 membered heteroaryl).

In embodiments, $R^{15C}$ is independently —$CCl_3$. In embodiments, $R^{15C}$ is independently —$CBr_3$. In embodiments, $R^{15C}$ is independently —$CF_3$. In embodiments, $R^{15C}$ is independently —$CI_3$. In embodiments, $R^{15C}$ is independently —$CHCl_2$. In embodiments, $R^{15C}$ is independently —$CHBr_2$. In embodiments, $R^{15C}$ is independently —$CHF_2$. In embodiments, $R^{15C}$ is independently —$CHI_2$. In embodiments, $R^{15C}$ is independently —$CH_2Cl$. In embodiments, $R^{15C}$ is independently —$CH_2Br$. In embodiments, $R^{15C}$ is independently —$CH_2F$. In embodiments, $R^{15C}$ is independently —$CH_2I$. In embodiments, $R^{15C}$ is independently —CN. In embodiments, $R^{15C}$ is independently —OH. In embodiments, $R^{15C}$ is independently —COOH. In embodiments, $R^{15C}$ is independently —$CONH_2$. In embodiments, $R^{15C}$ is independently —$OCCl_3$. In embodiments, $R^{15C}$ is independently —$OCF_3$. In embodiments, $R^{15C}$ is independently —$OCBr_3$. In embodiments, $R^{15C}$ is independently —$OCI_3$. In embodiments, $R^{15C}$ is independently —$OCHCl_2$. In embodiments, $R^{15C}$ is independently —$OCHBr_2$. In embodiments, $R^{15C}$ is independently —$OCHI_2$. In embodiments, $R^{15C}$ is independently —$OCHF_2$. In embodiments, $R^{15C}$ is independently —$OCH_2Cl$. In embodiments, $R^{15C}$ is independently —$OCH_2Br$. In embodiments, $R^{15C}$ is independently —$OCH_2I$. In embodiments, $R^{15C}$ is independently —$OCH_2F$. In embodiments, $R^{15C}$ is independently —$OCH_3$. In embodiments, $R^{15C}$ is idenpendently —$CH_3$. In embodiments, $R^{15C}$ is idenpendently —$CH_2CH_3$. In embodiments, $R^{15C}$ is independently unsubstituted propyl. In embodiments, $R^{15C}$ is independently unsubstituted isopropyl. In embodiments, $R^{15C}$ is independently unsubstituted butyl. In embodiments, $R^{15C}$ is independently unsubstituted tert-butyl. In embodiments, $R^{15C}$ is independently hydrogen.

In embodiments, $R^{15D}$ is independently $R^{39}$-substituted or unsubstituted alkyl (e.g., $C_1$-$C_8$ alkyl, $C_1$-$C_6$ alkyl, or $C_1$-$C_4$ alkyl). In embodiments, $R^{15D}$ is independently $R^{39}$-substituted alkyl (e.g., $C_1$-$C_8$ alkyl, $C_1$-$C_6$ alkyl, or $C_1$-$C_4$ alkyl). In embodiments, $R^{15D}$ is independently an unsubstituted alkyl (e.g., $C_1$-$C_8$ alkyl, $C_1$-$C_6$ alkyl, or $C_1$-$C_4$ alkyl). In embodiments, $R^{15D}$ is independently $R^{39}$-substituted or unsubstituted heteroalkyl (e.g., 2 to 8 membered heteroalkyl, 2 to 6 membered heteroalkyl, or 2 to 4 membered heteroalkyl). In embodiments, $R^{15D}$ is independently $R^{39}$-substituted heteroalkyl (e.g., 2 to 8 membered heteroalkyl, 2 to 6 membered heteroalkyl, or 2 to 4 membered heteroalkyl). In embodiments, $R^{15D}$ is independently an unsubstituted heteroalkyl (e.g., 2 to 8 membered heteroalkyl, 2 to 6 membered heteroalkyl, or 2 to 4 membered heteroalkyl). In embodiments, $R^{15D}$ is independently $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15D}$ is independently $R^{39}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15D}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15D}$ is independently $R^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15D}$ is independently $R^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{15D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{15D}$ is independently $R^{39}$-substituted or unsubstituted aryl (e.g., $C_6$-$C_{10}$ aryl, $C_{10}$ aryl, or phenyl). In embodiments, $R^{15D}$ is independently $R^{39}$-substituted aryl (e.g., $C_6$-$C_{10}$ aryl, $C_{10}$ aryl, or phenyl). In embodiments, $R^{15D}$ is independently an unsubstituted aryl (e.g., $C_6$-$C_{10}$ aryl, $C_{10}$ aryl, or phenyl). In embodiments, $R^{15D}$ is independently $R^{39}$-substituted or unsubstituted heteroaryl (e.g., 5 to 10 membered heteroaryl, 5 to 9 membered heteroaryl, or 5 to 6 membered heteroaryl). In embodiments, $R^{15D}$ is independently $R^{39}$-substituted heteroaryl (e.g., 5 to 10 membered heteroaryl, 5 to 9 membered heteroaryl, or 5 to 6 membered heteroaryl). In embodiments, $R^{15D}$ is independently an unsubstituted heteroaryl (e.g., 5 to 10 membered heteroaryl, 5 to 9 membered heteroaryl, or 5 to 6 membered heteroaryl).

In embodiments, $R^{15D}$ is independently —$CCl_3$. In embodiments, $R^{15D}$ is independently —$CBr_3$. In embodiments, $R^{15D}$ is independently —$CF_3$. In embodiments, $R^{15D}$ is independently —$CI_3$. In embodiments, $R^{15D}$ is independently —$CHCl_2$. In embodiments, $R^{15D}$ is independently —$CHBr_2$. In embodiments, $R^{15D}$ is independently —$CHF_2$. In embodiments, $R^{15D}$ is independently —$CHI_2$. In embodiments, $R^{15D}$ is independently —$CH_2Cl$. In embodiments, $R^{15D}$ is independently —$CH_2Br$. In embodiments, $R^{15D}$ is independently —$CH_2F$. In embodiments, $R^{15D}$ is independently —$CH_2I$. In embodiments, $R^{15D}$ is independently —CN. In embodiments, $R^{15D}$ is independently —OH. In embodiments, $R^{15D}$ is independently —COOH. In embodiments, $R^{15D}$ is independently —$CONH_2$. In embodiments, $R^{15D}$ is independently —$OCCl_3$. In embodiments, $R^{15D}$ is independently —$OCF_3$. In embodiments, $R^{15D}$ is independently —$OCBr_3$. In embodiments, $R^{15D}$ is independently —$OCI_3$. In embodiments, $R^{15D}$ is independently —$OCHCl_2$. In embodiments, $R^{15D}$ is independently —$OCHBr_2$. In embodiments, $R^{15D}$ is independently —$OCHI_2$. In embodiments, $R^{15D}$ is independently —$OCHF_2$. In embodiments, $R^{15D}$ is independently —$OCH_2Cl$. In embodiments, $R^{15D}$ is independently —$OCH_2Br$. In embodiments, $R^{15D}$ is independently —$OCH_2I$. In embodiments, $R^{15D}$ is independently —$OCH_2F$. In embodiments, $R^{15D}$ is independently —$OCH_3$. In embodiments, $R^{15D}$ is idenpendently —$CH_3$. In embodiments, $R^{15D}$ is idenpendently —$CH_2CH_3$. In embodiments, $R^{15D}$ is independently unsubstituted propyl. In embodiments, $R^{15D}$ is independently unsubstituted isopropyl. In embodiments, $R^{15D}$ is independently unsubstituted butyl. In embodiments, $R^{15D}$ is independently unsubstituted tert-butyl. In embodiments, $R^{15D}$ is independently hydrogen.

In embodiments, $R^{16}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, —N$_3$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{16}$ is independently substituted or unsubstituted alkyl (e.g., C$_1$-C$_8$ alkyl, C$_1$-C$_6$ alkyl, or C$_1$-C$_4$ alkyl). In embodiments, R$^{16}$ is independently substituted alkyl (e.g., C$_1$-C$_8$ alkyl, C$_1$-C$_6$ alkyl, or C$_1$-C$_4$ alkyl). In embodiments, R$^{16}$ is independently an unsubstituted alkyl (e.g., C$_1$-C$_8$ alkyl, C$_1$-C$_6$ alkyl, or C$_1$-C$_4$ alkyl). In embodiments, R$^{16}$ is independently substituted or unsubstituted heteroalkyl (e.g., 2 to 8 membered heteroalkyl, 2 to 6 membered heteroalkyl, or 2 to 4 membered heteroalkyl). In embodiments, R$^{16}$ is independently substituted heteroalkyl (e.g., 2 to 8 membered heteroalkyl, 2 to 6 membered heteroalkyl, or 2 to 4 membered heteroalkyl). In embodiments, R$^{16}$ is independently an unsubstituted heteroalkyl (e.g., 2 to 8 membered heteroalkyl, 2 to 6 membered heteroalkyl, or 2 to 4 membered heteroalkyl). In embodiments, R$^{16}$ is independently substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{16}$ is independently substituted cycloalkyl (e.g., C$_3$-C$_8$ cycloalkyl, C$_3$-C$_6$ cycloalkyl, or C$_5$-C$_6$ cycloalkyl). In embodiments, R$^{16}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, 10$^6$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{16}$ is independently substituted heterocycloalkyl (e.g., 3 to 8 membered heterocycloalkyl, 3 to 6 membered heterocycloalkyl, or 5 to 6 membered heterocycloalkyl). In embodiments, R$^{16}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{16}$ is independently substituted or unsubstituted aryl (e.g., C$_6$-C$_{10}$ aryl, C$_{10}$ aryl, or phenyl). In embodiments, 10$^6$ is independently substituted aryl (e.g., C$_6$-C$_{10}$ aryl, C$_{10}$ aryl, or phenyl). In embodiments, R$^{16}$ is independently an unsubstituted aryl (e.g., C$_6$-C$_{10}$ aryl, C$_{10}$ aryl, or phenyl). In embodiments, 10$^6$ is independently substituted or unsubstituted heteroaryl (e.g., 5 to 10 membered heteroaryl, 5 to 9 membered heteroaryl, or 5 to 6 membered heteroaryl). In embodiments, R$^{16}$ is independently substituted heteroaryl (e.g., 5 to 10 membered heteroaryl, 5 to 9 membered heteroaryl, or 5 to 6 membered heteroaryl). In embodiments, 10$^6$ is independently an unsubstituted heteroaryl (e.g., 5 to 10 membered heteroaryl, 5 to 9 membered heteroaryl, or 5 to 6 membered heteroaryl).

In embodiments, R$^{16}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, R$^{40}$-substituted or unsubstituted alkyl (e.g., C$_1$-C$_8$ alkyl, C$_1$-C$_6$ alkyl, or C$_1$-C$_4$ alkyl), R$^{40}$-substituted or unsubstituted heteroalkyl (e.g., 2 to 8 membered heteroalkyl, 2 to 6 membered heteroalkyl, or 2 to 4 membered heteroalkyl), R$^{40}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{40}$-substituted or unsubstituted heterocycloalkyl (e.g., 3 to 8 membered heterocycloalkyl, 3 to 6 membered heterocycloalkyl, or 5 to 6 membered heterocycloalkyl), R$^{40}$-substituted or unsubstituted aryl (e.g., C$_6$-C$_{10}$ aryl, C$_{10}$ aryl, or phenyl), or R$^{40}$-substituted or unsubstituted heteroaryl (e.g., 5 to 10 membered heteroaryl, 5 to 9 membered heteroaryl, or 5 to 6 membered heteroaryl). In embodiments, 10$^6$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{16}$ is independently R$^{40}$-substituted or unsubstituted alkyl (e.g., C$_1$-C$_8$ alkyl, C$_1$-C$_6$ alkyl, or C$_1$-C$_4$ alkyl). In embodiments, R$^{16}$ is independently R$^{40}$-substituted alkyl (e.g., C$_1$-C$_8$ alkyl, C$_1$-C$_6$ alkyl, or C$_1$-C$_4$ alkyl). In embodiments, R$^{16}$ is independently an unsubstituted alkyl (e.g., C$_1$-C$_8$ alkyl, C$_1$-C$_6$ alkyl, or C$_1$-C$_4$ alkyl). In embodiments, R$^{16}$ is independently R$^{40}$-substituted or unsubstituted heteroalkyl (e.g., 2 to 8 membered heteroalkyl, 2 to 6 membered heteroalkyl, or 2 to 4 membered heteroalkyl). In embodiments, R$^{16}$ is independently R$^{40}$-substituted heteroalkyl (e.g., 2 to 8 membered heteroalkyl, 2 to 6 membered heteroalkyl, or 2 to 4 membered heteroalkyl). In embodiments, R$^{16}$ is independently an unsubstituted heteroalkyl (e.g., 2 to 8 membered heteroalkyl, 2 to 6 membered heteroalkyl, or 2 to 4 membered heteroalkyl). In embodiments, R$^{16}$ is independently R$^{40}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{16}$ is independently R$^{40}$-substituted cycloalkyl (e.g., C$_3$-C$_8$ cycloalkyl, C$_3$-C$_6$ cycloalkyl, or C$_5$-C$_6$ cycloalkyl). In embodiments, R$^{16}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{16}$ is independently R$^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{16}$ is independently R$^{40}$-substituted heterocycloalkyl (e.g., 3 to 8 membered heterocycloalkyl, 3 to 6 membered heterocycloalkyl, or 5 to 6 membered heterocycloalkyl). In embodiments, R$^{16}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{16}$ is independently $R^{16}$-substituted or unsubstituted aryl (e.g., $C_6$-$C_{10}$ aryl, $C_{10}$ aryl, or phenyl). In embodiments, $R^{16}$ is independently $R^{16}$-substituted aryl (e.g., $C_6$-$C_{10}$ aryl, $C_{10}$ aryl, or phenyl). In embodiments, $R^{16}$ is independently an unsubstituted aryl (e.g., $C_6$-$C_{10}$ aryl, $C_{10}$ aryl, or phenyl). In embodiments, $R^{16}$ is independently $R^{40}$-substituted or unsubstituted heteroaryl (e.g., 5 to 10 membered heteroaryl, 5 to 9 membered heteroaryl, or 5 to 6 membered heteroaryl). In embodiments, $R^{16}$ is independently $R^{16}$-substituted heteroaryl (e.g., 5 to 10 membered heteroaryl, 5 to 9 membered heteroaryl, or 5 to 6 membered heteroaryl). In embodiments, $R^{16}$ is independently an unsubstituted heteroaryl (e.g., 5 to 10 membered heteroaryl, 5 to 9 membered heteroaryl, or 5 to 6 membered heteroaryl).

In embodiments, $R^{16}$ is independently —$CX^{16}{}_3$. In embodiments, $R^{16}$ is independently —$CHX^{16}{}_2$. In embodiments, $R^{16}$ is independently —$CH_2X^{16}$. In embodiments, $R^{16}$ is independently —$OCX^{16}{}_3$. In embodiments, $R^{16}$ is independently —$OCH_2X^{16}$. In embodiments, $R^{16}$ is independently —$OCHX^{16}{}_2$. In embodiments, $R^{16}$ is independently —CN. In embodiments, $R^{16}$ is independently —$SR^{16D}$. In embodiments, $R^{16}$ is independently —$SOR^{16D}$. In embodiments, $R^{1-6}$ is independently $SO_2R^{16D}$. In embodiments, $R^{16}$ is independently $SO_3R^{16D}$. In embodiments, $R^{16}$ is independently $SO_4R^{16D}$. In embodiments, $R^{16}$ is independently —$SONR^{16A}R^{16B}$. In embodiments, $R^{16}$ is independently $SO_2NR^{16A}R^{16B}$. In embodiments, $R^{16}$ is independently —$NHC(O)NR^{16A}R^{16B}$. In embodiments, $R^{16}$ is independently —N(O). In embodiments, $R^{16}$ is independently —$N(O)_2$. In embodiments, $R^{16}$ is independently —$NR^{16A}R^{16B}$. In embodiments, $R^{16}$ is independently —$C(O)R^{16C}$. In embodiments, $R^{16}$ is independently —C(O)—$OR^{16C}$. In embodiments, $R^{16}$ is independently —$C(O)NR^{16A}R^{16B}$. In embodiments, $R^{16}$ is independently —$OR^{16D}$. In embodiments, $R^{16}$ is independently —$NR^{16}SO_2R^{16D}$. In embodiments, $R^{16}$ is independently —$NR^{16A}C(O)R^{16C}$. In embodiments, $R^{16}$ is independently —$NR^{16A}C(O)OR^{16C}$. In embodiments, $R^{16}$ is independently —$NR^{16A}OR^{16C}$. In embodiments, $R^{16}$ is independently hydrogen.

In embodiments, $R^{16}$ is independently oxo. In embodiments, $R^{16}$ is independently halogen. In embodiments, $R^{16}$ is independently —$CCl_3$. In embodiments, $R^{16}$ is independently —$CBr_3$. In embodiments, $R^{16}$ is independently —$CF_3$. In embodiments, $R^{16}$ is independently —$CI_3$. In embodiments, $R^{16}$ is independently —$CHCl_2$. In embodiments, $R^{16}$ is independently —$CHBr_2$. In embodiments, $R^{16}$ is independently —$CHF_2$. In embodiments, $R^{16}$ is independently —$CHI_2$. In embodiments, $R^{16}$ is independently —$CH_2Cl$. In embodiments, $R^{16}$ is independently —$CH_2Br$. In embodiments, $R^{16}$ is independently —$CH_2F$. In embodiments, $R^{16}$ is independently —$CH_2I$. In embodiments, $R^{16}$ is independently —CN. In embodiments, $R^{16}$ is independently —OH. In embodiments, $R^{16}$ is independently —$NH_2$. In embodiments, $R^{16}$ is independently —COOH. In embodiments, $R^{16}$ is independently —$CONH_2$. In embodiments, $R^{16}$ is independently —$NO_2$. In embodiments, $R^{16}$ is independently —SH. In embodiments, $R^{16}$ is independently —$SO_3H$. In embodiments, $R^{16}$ is independently —$SO_4H$. In embodiments, $R^{16}$ is independently —$SO_2NH_2$. In embodiments, $R^{16}$ is independently —$NHNH_2$. In embodiments, $R^{16}$ is independently —$ONH_2$. In embodiments, $R^{16}$ is independently —$NHC(O)NHNH_2$. In embodiments, $R^{16}$ is independently —$NHC(O)NH_2$. In embodiments, $R^{16}$ is independently —$NHSO_2H$. In embodiments, $R^{16}$ is independently —NHC(O)H. In embodiments, $R^{16}$ is independently —NHC(O)OH. In embodiments, $R^{16}$ is independently —NHOH. In embodiments, $R^{16}$ is independently —$OCCl_3$. In embodiments, $R^{16}$ is independently —$OCF_3$. In embodiments, $R^{16}$ is independently —$OCBr_3$. In embodiments, $R^{16}$ is independently —$OCI_3$. In embodiments, $R^{16}$ is independently —$OCHCl_2$. In embodiments, $R^{16}$ is independently —$OCHBr_2$. In embodiments, $R^{16}$ is independently —$OCHI_2$. In embodiments, $R^{16}$ is independently —$OCHF_2$. In embodiments, $R^{16}$ is independently —$OCH_2Cl$. In embodiments, $R^{16}$ is independently —$OCH_2Br$. In embodiments, $R^{16}$ is independently —$OCH_2I$. In embodiments, $R^{16}$ is independently —$OCH_2F$. In embodiments, $R^{16}$ is independently —$N_3$. In embodiments, $R^{16}$ is independently —$OCH_3$. In embodiments, $R^{16}$ is idenpendently —$CH_3$. In embodiments, $R^{16}$ is idenpendently —$CH_2CH_3$. In embodiments, $R^{16}$ is independently unsubstituted propyl. In embodiments, $R^{16}$ is independently unsubstituted isopropyl. In embodiments, $R^{16}$ is independently unsubstituted butyl. In embodiments, $R^{16}$ is independently unsubstituted tert-butyl. In embodiments, $R^{16}$ is independently —F. In embodiments, $R^{16}$ is independently —Cl. In embodiments, $R^{16}$ is independently —Br. In embodiments, $R^{16}$ is independently —I.

$R^{40}$ is independently oxo, halogen, —$CF_3$, —$CBr_3$, —$CCl_3$, —$CI_3$, —$CHBr_2$, —$CHCl_2$, —$CHI_2$, —$CH_2Br$, —$CH_2Cl$, —$CH_2I$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{40}$ is independently oxo. In embodiments, $R^{40}$ is independently halogen. In embodiments, $R^{40}$ is independently —$CCl_3$. In embodiments, $R^{40}$ is independently —$CBr_3$. In embodiments, $R^{40}$ is independently —$CF_3$. In embodiments, $R^{40}$ is independently —$CI_3$. In embodiments, $R^{40}$ is independently —$CHCl_2$. In embodiments, $R^{40}$ is independently —$CHBr_2$. In embodiments, $R^{40}$ is independently —$CHF_2$. In embodiments, $R^{40}$ is independently —$CHI_2$. In embodiments, $R^{40}$ is independently —$CH_2Cl$. In embodiments, $R^{40}$ is independently —$CH_2Br$. In embodiments, $R^{40}$ is independently —$CH_2F$. In embodiments, $R^{40}$ is independently —$CH_2I$. In embodiments, $R^{40}$ is independently —CN. In embodiments, $R^{40}$ is independently —OH. In embodiments, $R^{40}$ is independently —$NH_2$. In embodiments, $R^{40}$ is independently —COOH. In embodiments, $R^{40}$ is independently —$CONH_2$. In embodiments, $R^{40}$ is independently —$NO_2$. In embodiments, $R^{40}$ is independently —SH. In embodiments, $R^{40}$ is independently —$SO_3H$. In embodiments, $R^{40}$ is independently —$SO_4H$. In embodiments, $R^{40}$ is independently —$SO_2NH_2$. In embodiments, $R^{40}$ is independently —$NHNH_2$. In embodiments, $R^{40}$ is independently —$ONH_2$. In embodiments, $R^{40}$ is independently —$NHC(O)NHNH_2$. In embodiments, $R^{40}$ is independently —$NHC(O)NH_2$. In embodiments, $R^{40}$ is independently —$NHSO_2H$. In embodiments, $R^{40}$ is independently —NHC(O)H. In embodiments, $R^{40}$ is independently —NHC(O)OH. In embodiments, $R^{40}$ is independently —NHOH. In embodiments, $R^{40}$ is independently —OCCl$_3$. In embodiments, $R^{40}$ is independently —OCF$_3$. In embodiments, $R^{40}$ is independently —OCBr$_3$. In embodiments, $R^{40}$ is independently —OCI$_3$. In embodiments, $R^{40}$ is independently —OCHCl$_2$. In embodiments, $R^{40}$ is independently —OCHBr$_2$. In embodiments, $R^{40}$ is independently —OCHI$_2$. In embodiments, $R^{40}$ is independently —OCHF$_2$. In embodiments, $R^{40}$ is independently —OCH$_2$Cl. In embodiments, $R^{40}$ is independently —OCH$_2$Br. In embodiments, $R^{40}$ is independently —OCH$_2$I. In embodiments, $R^{40}$ is independently —OCH$_2$F. In embodiments, $R^{40}$ is independently —N$_3$. In embodiments, $R^{40}$ is independently —OCH$_3$. In embodiments, $R^{40}$ is independently —CH$_3$. In embodiments, $R^{40}$ is independently —CH$_2$CH$_3$. In embodiments, $R^{40}$ is independently unsubstituted propyl. In embodiments, $R^{40}$ is independently unsubstituted isopropyl. In embodiments, $R^{40}$ is independently unsubstituted butyl. In embodiments, $R^{40}$ is independently unsubstituted tert-butyl. In embodiments, $R^{40}$ is independently —F. In embodiments, $R^{40}$ is independently —Cl. In embodiments, $R^{40}$ is independently —Br. In embodiments, $R^{40}$ is independently —I.

In embodiments, $R^{16A}$ is independently hydrogen, halogen, —CF$_3$, —CBr$_3$, —CCl$_3$, —CI$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCI$_3$, —OCHF$_2$, —OCHBr$_2$, —OCHCl$_2$, —OCH$_2$F, —OCH$_2$Br, —OCH$_2$Cl, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{16B}$ is independently hydrogen, halogen, —CF$_3$, —CBr$_3$, —CCl$_3$, —CI$_3$, —CHF$_2$, —CHBr$_2$, —CHCl$_2$, —CH$_2$F, —CH$_2$Br, —CH$_2$Cl, —OCF$_3$, —OCBr$_3$, —OCCl$_3$, —OCI$_3$, —OCHF$_2$, —OCHBr$_2$, —OCHCl$_2$, —OCH$_2$F, —OCH$_2$Br, —OCH$_2$Cl, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{16C}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{16D}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{16A}$ and $R^{16B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{16A}$ and $R^{16B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{16A}$ and $R^{16B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{16A}$ and $R^{16B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{16A}$ and $R^{16B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{16A}$ and $R^{16B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{16A}$ and $R^{16B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{16A}$, $R^{16B}$, $R^{16C}$, and $R^{16D}$ are independently hydrogen, halogen, —$CF_3$, —$CBr_3$, —$CCl_3$, —$CCl_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{40}$-substituted or unsubstituted alkyl (e.g., $C_1$-$C_8$ alkyl, $C_1$-$C_6$ alkyl, or $C_1$-$C_4$ alkyl), $R^{40}$-substituted or unsubstituted heteroalkyl (e.g., 2 to 8 membered heteroalkyl, 2 to 6 membered heteroalkyl, or 2 to 4 membered heteroalkyl), $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted or unsubstituted aryl (e.g., $C_6$-$C_{10}$ aryl, $C_{10}$ aryl, or phenyl), or $R^{40}$-substituted or unsubstituted heteroaryl (e.g., 5 to 10 membered heteroaryl, 5 to 9 membered heteroaryl, or 5 to 6 membered heteroaryl). In embodiments, $R^{16A}$ and $R^{16B}$ substituents bonded to the same nitrogen atom are independently joined to form an $R^{40}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{40}$-substituted or unsubstituted heteroaryl (e.g., 5 to 10 membered heteroaryl, 5 to 9 membered heteroaryl, or 5 to 6 membered heteroaryl). In embodiments, $R^{16A}$ and $R^{16B}$ substituents bonded to the same nitrogen atom are independently joined to form an $R^{40}$-substituted or unsubstituted heterocycloalkyl (e.g., 3 to 8 membered heterocycloalkyl, 3 to 6 membered heterocycloalkyl. In embodiments, $R^{16A}$ and $R^{16B}$ substituents bonded to the same nitrogen atom are independently joined to form an $R^{40}$-substituted or unsubstituted heteroaryl (e.g., 5 to 10 membered heteroaryl, 5 to 9 membered heteroaryl, or 5 to 6 membered heteroaryl).

In embodiments, $R^{16A}$ is independently $R^{40}$-substituted or unsubstituted alkyl (e.g., $C_1$-$C_8$ alkyl, $C_1$-$C_6$ alkyl, or $C_1$-$C_4$ alkyl). In embodiments, $R^{16A}$ is independently $R^{40}$-substituted alkyl (e.g., $C_1$-$C_8$ alkyl, $C_1$-$C_6$ alkyl, or $C_1$-$C_4$ alkyl). In embodiments, $R^{16A}$ is independently an unsubstituted alkyl (e.g., $C_1$-$C_8$ alkyl, $C_1$-$C_6$ alkyl, or $C_1$-$C_4$ alkyl). In embodiments, $R^{16A}$ is independently $R^{40}$-substituted or unsubstituted heteroalkyl (e.g., 2 to 8 membered heteroalkyl, 2 to 6 membered heteroalkyl, or 2 to 4 membered heteroalkyl). In embodiments, $R^{16A}$ is independently $R^{40}$-substituted heteroalkyl (e.g., 2 to 8 membered heteroalkyl, 2 to 6 membered heteroalkyl, or 2 to 4 membered heteroalkyl). In embodiments, $R^{16A}$ is independently an unsubstituted heteroalkyl (e.g., 2 to 8 membered heteroalkyl, 2 to 6 membered heteroalkyl, or 2 to 4 membered heteroalkyl). In embodiments, $R^{16A}$ is independently $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16A}$ is independently $R^{40}$-substituted cycloalkyl (e.g., $C_3$-$C_8$ cycloalkyl, $C_3$-$C_6$ cycloalkyl, or $C_5$-$C_6$ cycloalkyl). In embodiments, $R^{16A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16A}$ is independently $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{16A}$ is independently $R^{40}$-substituted heterocycloalkyl (e.g., 3 to 8 membered heterocycloalkyl, 3 to 6 membered heterocycloalkyl, or 5 to 6 membered heterocycloalkyl). In embodiments, $R^{16A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{16A}$ is independently $R^{40}$-substituted or unsubstituted aryl (e.g., $C_6$-$C_{10}$ aryl, $C_{10}$ aryl, or phenyl). In embodiments, $R^{16A}$ is independently $R^{40}$-substituted aryl (e.g., $C_6$-$C_{10}$ aryl, $C_{10}$ aryl, or phenyl). In embodiments, $R^{16A}$ is independently an unsubstituted aryl (e.g., $C_6$-$C_{10}$ aryl, $C_{10}$ aryl, or phenyl). In embodiments, $R^{16A}$ is independently $R^{40}$-substituted or unsubstituted heteroaryl (e.g., 5 to 10 membered heteroaryl, 5 to 9 membered heteroaryl, or 5 to 6 membered heteroaryl). In embodiments, $R^{16A}$ is independently $R^{40}$-substituted heteroaryl (e.g., 5 to 10 membered heteroaryl, 5 to 9 membered heteroaryl, or 5 to 6 membered heteroaryl). In embodiments, $R^{16A}$ is independently an unsubstituted heteroaryl (e.g., 5 to 10 membered heteroaryl, 5 to 9 membered heteroaryl, or 5 to 6 membered heteroaryl).

In embodiments, $R^{16A}$ is independently —$CCl_3$. In embodiments, $R^{16A}$ is independently —$CBr_3$. In embodiments, $R^{16A}$ is independently —$CF_3$. In embodiments, $R^{16A}$ is independently —$Cl_3$. In embodiments, $R^{16A}$ is independently —$CHCl_2$. In embodiments, $R^{16A}$ is independently —$CHBr_2$. In embodiments, $R^{16A}$ is independently —$CHF_2$. In embodiments, $R^{16A}$ is independently —$CHI_2$. In embodiments, $R^{16A}$ is independently —$CH_2Cl$. In embodiments, $R^{16A}$ is independently —$CH_2Br$. In embodiments, $R^{16A}$ is independently —$CH_2F$. In embodiments, $R^{16A}$ is independently —$CH_2I$. In embodiments, $R^{16A}$ is independently —CN. In embodiments, $R^{16A}$ is independently —OH. In embodiments, $R^{16A}$ is independently —COOH. In embodiments, $R^{16A}$ is independently —$CONH_2$. In embodiments, $R^{16A}$ is independently —$OCCl_3$. In embodiments, $R^{16A}$ is independently —$OCF_3$. In embodiments, $R^{16A}$ is independently —$OCBr_3$. In embodiments, $R^{16A}$ is independently —$OCl_3$. In embodiments, $R^{16A}$ is independently —$OCHCl_2$. In embodiments, $R^{16A}$ is independently —$OCHBr_2$. In embodiments, $R^{16A}$ is independently —$OCHI_2$. In embodiments, $R^{16A}$ is independently —$OCHF_2$. In embodiments, $R^{16A}$ is independently —$OCH_2Cl$. In embodiments, $R^{16A}$ is independently —$OCH_2Br$. In embodiments, $R^{16A}$ is independently —$OCH_2I$. In embodiments, $R^{16A}$ is independently —$OCH_2F$. In embodiments, $R^{16A}$ is independently —$OCH_3$. In embodiments, $R^{16A}$ is independently $CH_3$. In embodiments, $R^{16A}$ is idenpendently —$CH_2CH_3$. In embodiments, $R^{16A}$ is independently unsubstituted propyl. In embodiments, $R^{16A}$ is independently unsubstituted isopropyl. In embodiments, $R^{16A}$ is independently unsubstituted butyl. In embodiments, $R^{16A}$ is independently unsubstituted tert-butyl. In embodiments, $R^{16A}$ is independently hydrogen.

In embodiments, $R^{16B}$ is independently $R^{40}$-substituted or unsubstituted alkyl (e.g., $C_1$-$C_8$ alkyl, $C_1$-$C_6$ alkyl, or $C_1$-$C_4$ alkyl). In embodiments, $R^{16B}$ is independently $R^{40}$-substituted alkyl (e.g., $C_1$-$C_8$ alkyl, $C_1$-$C_6$ alkyl, or $C_1$-$C_4$ alkyl). In embodiments, $R^{16B}$ is independently an unsubstituted alkyl (e.g., $C_1$-$C_8$ alkyl, $C_1$-$C_6$ alkyl, or $C_1$-$C_4$ alkyl). In embodiments, $R^{16B}$ is independently $R^{40}$-substituted or unsubstituted heteroalkyl (e.g., 2 to 8 membered heteroalkyl, 2 to 6 membered heteroalkyl, or 2 to 4 membered heteroalkyl). In embodiments, $R^{16B}$ is independently $R^{40}$-substituted heteroalkyl (e.g., 2 to 8 membered heteroalkyl, 2 to 6 membered heteroalkyl, or 2 to 4 membered heteroalkyl). In embodiments, $R^{16B}$ is independently an unsubstituted heteroalkyl (e.g., 2 to 8 membered heteroalkyl, 2 to 6 membered heteroalkyl, or 2 to 4 membered heteroalkyl). In embodiments, $R^{16B}$ is independently $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16B}$ is independently $R^{40}$-substituted cycloalkyl (e.g., $C_3$-$C_8$ cycloalkyl, $C_3$-$C_6$ cycloalkyl, or $C_5$-$C_6$ cycloalkyl). In embodiments, $R^{16B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16B}$ is independently $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{16B}$ is independently $R^{40}$-substituted heterocycloalkyl (e.g., 3 to 8 membered heterocycloalkyl, 3 to 6 membered heterocycloalkyl, or 5 to 6 membered heterocycloalkyl). In embodiments, $R^{16B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{16B}$ is independently $R^{40}$-substituted or unsubstituted aryl (e.g., $C_6$-$C_{10}$ aryl, $C_{10}$ aryl, or phenyl). In embodiments, $R^{16B}$ is independently $R^{40}$-substituted aryl (e.g., $C_6$-$C_{10}$ aryl, $C_{10}$ aryl, or phenyl). In embodiments, $R^{16B}$ is independently an unsubstituted aryl (e.g., $C_6$-$C_{10}$ aryl, $C_{10}$ aryl, or phenyl). In embodiments, $R^{16B}$ is independently $R^{40}$-substituted or unsubstituted heteroaryl (e.g., 5 to 10 membered heteroaryl, 5 to 9 membered heteroaryl, or 5 to 6 membered heteroaryl). In embodiments, $R^{16B}$ is independently $R^{40}$-substituted heteroaryl (e.g., 5 to 10 membered heteroaryl, 5 to 9 membered heteroaryl, or 5 to 6 membered heteroaryl). In embodiments, $R^{16B}$ is independently an unsubstituted heteroaryl (e.g., 5 to 10 membered heteroaryl, 5 to 9 membered heteroaryl, or 5 to 6 membered heteroaryl).

In embodiments, $R^{16B}$ is independently —$CCl_3$. In embodiments, $R^{16B}$ is independently —$CBr_3$. In embodiments, $R^{16B}$ is independently —$CF_3$. In embodiments, $R^{16B}$ is independently —$CI_3$. In embodiments, $R^{16B}$ is independently —$CHCl_2$. In embodiments, $R^{16B}$ is independently —$CHBr_2$. In embodiments, $R^{16B}$ is independently —$CHF_2$. In embodiments, $R^{16B}$ is independently —$CHI_2$. In embodiments, $R^{16B}$ is independently —$CH_2Cl$. In embodiments, $R^{16B}$ is independently —$CH_2Br$. In embodiments, $R^{16B}$ is independently —$CH_2F$. In embodiments, $R^{16B}$ is independently —$CH_2I$. In embodiments, $R^{16B}$ is independently —CN. In embodiments, $R^{16B}$ is independently —OH. In embodiments, $R^{16B}$ is independently —COOH. In embodiments, $R^{16B}$ is independently —$CONH_2$. In embodiments, $R^{16B}$ is independently —$OCCl_3$. In embodiments, $R^{16B}$ is independently —$OCF_3$. In embodiments, $R^{16B}$ is independently —$OCBr_3$. In embodiments, $R^{16B}$ is independently —$OCl_3$. In embodiments, $R^{16B}$ is independently —$OCHCl_2$. In embodiments, $R^{16B}$ is independently —$OCHBr_2$. In embodiments, $R^{16B}$ is independently —$OCHI_2$. In embodiments, $R^{16B}$ is independently —$OCHF_2$. In embodiments, $R^{16B}$ is independently —$OCH_2Cl$. In embodiments, $R^{16B}$ is independently —$OCH_2Br$. In embodiments, $R^{16B}$ is independently —$OCH_2I$. In embodiments, $R^{16B}$ is independently —$OCH_2F$. In embodiments, $R^{16B}$ is independently —$OCH_3$. In embodiments, $R^{16B}$ is independently $CH_3$. In embodiments, $R^{16B}$ is idenpendently —$CH_2CH_3$. In embodiments, $R^{16B}$ is independently unsubstituted propyl. In embodiments, $R^{16B}$ is independently unsubstituted isopropyl. In embodiments, $R^{16B}$ is independently unsubstituted butyl. In embodiments, $R^{16B}$ is independently unsubstituted tert-butyl. In embodiments, $R^{16B}$ is independently hydrogen.

In embodiments, $R^{16C}$ is independently $R^{40}$-substituted or unsubstituted alkyl (e.g., $C_1$-$C_8$ alkyl, $C_1$-$C_6$ alkyl, or $C_1$-$C_4$ alkyl). In embodiments, $R^{16C}$ is independently $R^{40}$-substituted alkyl (e.g., $C_1$-$C_8$ alkyl, $C_1$-$C_6$ alkyl, or $C_1$-$C_4$ alkyl). In embodiments, $R^{16C}$ is independently an unsubstituted alkyl (e.g., $C_1$-$C_8$ alkyl, $C_1$-$C_6$ alkyl, or $C_1$-$C_4$ alkyl). In embodiments, $R^{16C}$ is independently $R^{40}$-substituted or unsubstituted heteroalkyl (e.g., 2 to 8 membered heteroalkyl, 2 to 6 membered heteroalkyl, or 2 to 4 membered heteroalkyl). In embodiments, $R^{16C}$ is independently $R^{40}$-substituted heteroalkyl (e.g., 2 to 8 membered heteroalkyl, 2 to 6 membered heteroalkyl, or 2 to 4 membered heteroalkyl). In embodiments, $R^{16C}$ is independently an unsubstituted heteroalkyl (e.g., 2 to 8 membered heteroalkyl, 2 to 6 membered heteroalkyl, or 2 to 4 membered heteroalkyl). In embodiments, $R^{16C}$ is independently $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16C}$ is independently $R^{40}$-substituted cycloalkyl (e.g., $C_3$-$C_8$ cycloalkyl, $C_3$-$C_6$ cycloalkyl, or $C_5$-$C_6$ cycloalkyl). In embodiments, $R^{16C}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{16C}$ is independently $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{16C}$ is independently $R^{40}$-substituted heterocycloalkyl (e.g., 3 to 8 membered heterocycloalkyl, 3 to 6 membered heterocycloalkyl, or 5 to 6 membered heterocycloalkyl). In embodiments, $R^{16C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{16C}$ is independently $R^{40}$-substituted or unsubstituted aryl (e.g., $C_6$-$C_{10}$ aryl, $C_{10}$ aryl, or phenyl). In embodiments, $R^{16C}$ is independently $R^{40}$-substituted aryl (e.g., $C_6$-$C_{10}$ aryl, $C_{10}$ aryl, or phenyl). In embodiments, $R^{16C}$ is independently an unsubstituted aryl (e.g., $C_6$-$C_{10}$ aryl, $C_{10}$ aryl, or phenyl). In embodiments, $R^{16C}$ is independently $R^{40}$-substituted or unsubstituted heteroaryl (e.g., 5 to 10 membered heteroaryl, 5 to 9 membered heteroaryl, or 5 to 6 membered heteroaryl). In embodiments, $R^{16C}$ is independently $R^{40}$-substituted heteroaryl (e.g., 5 to 10 membered heteroaryl, 5 to 9 membered heteroaryl, or 5 to 6 membered heteroaryl). In embodiments, $R^{16C}$ is independently an unsubstituted heteroaryl (e.g., 5 to 10 membered heteroaryl, 5 to 9 membered heteroaryl, or 5 to 6 membered heteroaryl).

In embodiments, $R^{16C}$ is independently —$CCl_3$. In embodiments, $R^{16C}$ is independently —$CBr_3$. In embodiments, $R^{16C}$ is independently —$CF_3$. In embodiments, $R^{16C}$ is independently —$CI_3$. In embodiments, $R^{16C}$ is independently —$CHCl_2$. In embodiments, $R^{16C}$ is independently —$CHBr_2$. In embodiments, $R^{16C}$ is independently —$CHF_2$. In embodiments, $R^{16C}$ is independently —$CHI_2$. In embodiments, $R^{16C}$ is independently —$CH_2Cl$. In embodiments, $R^{16C}$ is independently —$CH_2Br$. In embodiments, $R^{16C}$ is independently —$CH_2F$. In embodiments, $R^{16C}$ is independently —$CH_2I$. In embodiments, $R^{16C}$ is independently —CN. In embodiments, $R^{16C}$ is independently —OH. In embodiments, $R^{16C}$ is independently —COOH. In embodiments, $R^{16C}$ is independently —$CONH_2$. In embodiments, $R^{16C}$ is independently —$OCCl_3$. In embodiments, $R^{16C}$ is independently —$OCF_3$. In embodiments, $R^{16C}$ is independently —$OCBr_3$. In embodiments, $R^{16C}$ is independently —$OCl_3$. In embodiments, $R^{16C}$ is independently —$OCHCl_2$. In embodiments, $R^{16C}$ is independently —$OCHBr_2$. In embodiments, $R^{16C}$ is independently —$OCHI_2$. In embodiments, $R^{16C}$ is independently —$OCHF_2$. In embodiments, $R^{16C}$ is independently —$OCH_2Cl$. In embodiments, $R^{16C}$ is independently —$OCH_2Br$. In embodiments, $R^{16C}$ is independently —OCH$_2$I. In embodiments, R$^{16C}$ is independently —OCH$_2$F. In embodiments, R$^{16C}$ is independently —OCH$_3$. In embodiments, R$^{16C}$ is idenpendently —CH$_3$. In embodiments, R$^{16C}$ is idenpendently —CH$_2$CH$_3$. In embodiments, R$^{16C}$ is independently unsubstituted propyl. In embodiments, R$^{16C}$ is independently unsubstituted isopropyl. In embodiments, R$^{16C}$ is independently unsubstituted butyl. In embodiments, R$^{16C}$ is independently unsubstituted tert-butyl. In embodiments, R$^{16C}$ is independently hydrogen.

In embodiments, R$^{16D}$ is independently R$^{40}$-substituted or unsubstituted alkyl (e.g., C$_1$-C$_8$ alkyl, C$_1$-C$_6$ alkyl, or C$_1$-C$_4$ alkyl). In embodiments, R$^{16D}$ is independently R$^{40}$-substituted alkyl (e.g., C$_1$-C$_8$ alkyl, C$_1$-C$_6$ alkyl, or C$_1$-C$_4$ alkyl). In embodiments, R$^{16D}$ is independently an unsubstituted alkyl (e.g., C$_1$-C$_8$ alkyl, C$_1$-C$_6$ alkyl, or C$_1$-C$_4$ alkyl). In embodiments, R$^{16D}$ is independently R$^{40}$-substituted or unsubstituted heteroalkyl (e.g., 2 to 8 membered heteroalkyl, 2 to 6 membered heteroalkyl, or 2 to 4 membered heteroalkyl). In embodiments, R$^{16D}$ is independently R$^{40}$-substituted heteroalkyl (e.g., 2 to 8 membered heteroalkyl, 2 to 6 membered heteroalkyl, or 2 to 4 membered heteroalkyl). In embodiments, R$^{16D}$ is independently an unsubstituted heteroalkyl (e.g., 2 to 8 membered heteroalkyl, 2 to 6 membered heteroalkyl, or 2 to 4 membered heteroalkyl). In embodiments, R$^{16D}$ is independently R$^{40}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{16D}$ is independently R$^{40}$-substituted cycloalkyl (e.g., C$_3$-C$_8$ cycloalkyl, C$_3$-C$_6$ cycloalkyl, or C$_5$-C$_6$ cycloalkyl). In embodiments, R$^{16D}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{16D}$ is independently R$^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{16D}$ is independently R$^{40}$-substituted heterocycloalkyl (e.g., 3 to 8 membered heterocycloalkyl, 3 to 6 membered heterocycloalkyl, or 5 to 6 membered heterocycloalkyl). In embodiments, R$^{16D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, R$^{16D}$ is independently R$^{40}$-substituted or unsubstituted aryl (e.g., C$_6$-C$_{10}$ aryl, C$_{10}$ aryl, or phenyl). In embodiments, R$^{16D}$ is independently R$^{40}$-substituted aryl (e.g., C$_6$-C$_{10}$ aryl, C$_{10}$ aryl, or phenyl). In embodiments, R$^{16D}$ is independently an unsubstituted aryl (e.g., C$_6$-C$_{10}$ aryl, C$_{10}$ aryl, or phenyl). In embodiments, R$^{16D}$ is independently R$^{40}$-substituted or unsubstituted heteroaryl (e.g., 5 to 10 membered heteroaryl, 5 to 9 membered heteroaryl, or 5 to 6 membered heteroaryl). In embodiments, R$^{16D}$ is independently R$^{40}$-substituted heteroaryl (e.g., 5 to 10 membered heteroaryl, 5 to 9 membered heteroaryl, or 5 to 6 membered heteroaryl). In embodiments, R$^{16D}$ is independently an unsubstituted heteroaryl (e.g., 5 to 10 membered heteroaryl, 5 to 9 membered heteroaryl, or 5 to 6 membered heteroaryl).

In embodiments, R$^{16D}$ is independently —CCl$_3$. In embodiments, R$^{16D}$ is independently —CBr$_3$. In embodiments, R$^{16D}$ is independently —CF$_3$. In embodiments, R$^{16D}$ is independently —CI$_3$. In embodiments, R$^{16D}$ is independently —CHCl$_2$. In embodiments, R$^{16D}$ is independently —CHBr$_2$. In embodiments, R$^{16D}$ is independently —CHF$_2$. In embodiments, R$^{16D}$ is independently —CHI$_2$. In embodiments, R$^{16D}$ is independently —CH$_2$Cl. In embodiments, R$^{16D}$ is independently —CH$_2$Br. In embodiments, R$^{16D}$ is independently —CH$_2$F. In embodiments, R$^{16D}$ is independently —CH$_2$I. In embodiments, R$^{16D}$ is independently —CN. In embodiments, R$^{16D}$ is independently —OH. In embodiments, R$^{16D}$ is independently —COOH. In embodiments, R$^{16D}$ is independently —CONH$_2$. In embodiments, R$^{16D}$ is independently —OCCl$_3$. In embodiments, R$^{16D}$ is independently —OCF$_3$. In embodiments, R$^{16D}$ is independently —OCBr$_3$. In embodiments, R$^{16D}$ is independently —OCI$_3$. In embodiments, R$^{16D}$ is independently —OCHCl$_2$. In embodiments, R$^{16D}$ is independently —OCHBr$_2$. In embodiments, R$^{16D}$ is independently —OCHI$_2$. In embodiments, R$^{16D}$ is independently —OCHF$_2$. In embodiments, R$^{16D}$ is independently —OCH$_2$Cl. In embodiments, R$^{16D}$ is independently —OCH$_2$Br. In embodiments, R$^{16D}$ is independently —OCH$_2$I. In embodiments, R$^{16D}$ is independently —OCH$_2$F. In embodiments, R$^{16D}$ is independently —OCH$_3$. In embodiments, R$^{16D}$ is independently CH$_3$. In embodiments, R$^{16D}$ is idenpendently —CH$_2$CH$_3$. In embodiments, R$^{16D}$ is independently unsubstituted propyl. In embodiments, R$^{16D}$ is independently unsubstituted isopropyl. In embodiments, R$^{16D}$ is independently unsubstituted butyl. In embodiments, R$^{16D}$ is independently unsubstituted tert-butyl. In embodiments, R$^{16D}$ is independently hydrogen.

In embodiments, R$^{17}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, —N$_3$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, R$^{17}$ is independently substituted or unsubstituted alkyl (e.g., C$_1$-C$_8$ alkyl, C$_1$-C$_6$ alkyl, or C$_1$-C$_4$ alkyl). In embodiments, R$^{17}$ is independently substituted alkyl (e.g., C$_1$-C$_8$ alkyl, C$_1$-C$_6$ alkyl, or C$_1$-C$_4$ alkyl). In embodiments, R$^{17}$ is independently an unsubstituted alkyl (e.g., C$_1$-C$_8$ alkyl, C$_1$-C$_6$ alkyl, or C$_1$-C$_4$ alkyl). In embodiments, R$^{17}$ is independently substituted or unsubstituted heteroalkyl (e.g., 2 to 8 membered heteroalkyl, 2 to 6 membered heteroalkyl, or 2 to 4 membered heteroalkyl). In embodiments, R$^{17}$ is independently substituted heteroalkyl (e.g., 2 to 8 membered heteroalkyl, 2 to 6 membered heteroalkyl, or 2 to 4 membered heteroalkyl). In embodiments, R$^{17}$ is independently an unsubstituted heteroalkyl (e.g., 2 to 8 membered heteroalkyl, 2 to 6 membered heteroalkyl, or 2 to 4 membered heteroalkyl). In embodiments, R$^{17}$ is independently substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{17}$ is independently substituted cycloalkyl (e.g., C$_3$-C$_8$ cycloalkyl, C$_3$-C$_6$ cycloalkyl, or C$_5$-C$_6$ cycloalkyl). In embodiments, R$^{17}$ is independently an unsubstituted cycloalkyl (e.g., C$_3$-C$_8$ cycloalkyl, C$_3$-C$_6$ cycloalkyl, or C$_5$-C$_6$ cycloalkyl). In embodiments, R$^{17}$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{17}$ is independently substituted heterocycloalkyl (e.g., 3 to 8 membered heterocycloalkyl, 3 to 6 membered heterocycloalkyl, or 5 to 6 membered heterocycloalkyl). In embodiments, $R^{17}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{17}$ is independently substituted or unsubstituted aryl (e.g., $C_6$-$C_{10}$ aryl, $C_{10}$ aryl, or phenyl). In embodiments, $R^{17}$ is independently substituted aryl (e.g., $C_6$-$C_{10}$ aryl, $C_{10}$ aryl, or phenyl). In embodiments, $R^{17}$ is independently an unsubstituted aryl (e.g., $C_6$-$C_{10}$ aryl, $C_{10}$ aryl, or phenyl). In embodiments, $R^{17}$ is independently substituted or unsubstituted heteroaryl (e.g., 5 to 10 membered heteroaryl, 5 to 9 membered heteroaryl, or 5 to 6 membered heteroaryl). In embodiments, $R^{17}$ is independently substituted heteroaryl (e.g., 5 to 10 membered heteroaryl, 5 to 9 membered heteroaryl, or 5 to 6 membered heteroaryl). In embodiments, $R^{17}$ is independently an unsubstituted heteroaryl (e.g., 5 to 10 membered heteroaryl, 5 to 9 membered heteroaryl, or 5 to 6 membered heteroaryl).

In embodiments, $R^{17}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{41}$-substituted or unsubstituted alkyl (e.g., $C_1$-$C_8$ alkyl, $C_1$-$C_6$ alkyl, or $C_1$-$C_4$ alkyl), $R^{41}$-substituted or unsubstituted heteroalkyl (e.g., 2 to 8 membered heteroalkyl, 2 to 6 membered heteroalkyl, or 2 to 4 membered heteroalkyl), $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41}$-substituted or unsubstituted aryl (e.g., $C_6$-$C_{10}$ aryl, $C_{10}$ aryl, or phenyl), or $R^{41}$-substituted or unsubstituted heteroaryl (e.g., 5 to 10 membered heteroaryl, 5 to 9 membered heteroaryl, or 5 to 6 membered heteroaryl). In embodiments, $R^{17}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{17}$ is independently $R^{41}$-substituted or unsubstituted alkyl (e.g., $C_1$-$C_8$ alkyl, $C_1$-$C_6$ alkyl, or $C_1$-$C_4$ alkyl). In embodiments, $R^{17}$ is independently $R^{41}$-substituted alkyl (e.g., $C_1$-$C_8$ alkyl, $C_1$-$C_6$ alkyl, or $C_1$-$C_4$ alkyl). In embodiments, $R^{17}$ is independently an unsubstituted alkyl (e.g., $C_1$-$C_8$ alkyl, $C_1$-$C_6$ alkyl, or $C_1$-$C_4$ alkyl). In embodiments, $R^{17}$ is independently $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{17}$ is independently $R^{41}$-substituted heteroalkyl (e.g., 2 to 8 membered heteroalkyl, 2 to 6 membered heteroalkyl, or 2 to 4 membered heteroalkyl). In embodiments, $R^{17}$ is independently an unsubstituted heteroalkyl (e.g., 2 to 8 membered heteroalkyl, 2 to 6 membered heteroalkyl, or 2 to 4 membered heteroalkyl). In embodiments, $R^{17}$ is independently $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17}$ is independently $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17}$ is independently $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17}$ is independently $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{17}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{17}$ is independently $R^{41}$-substituted or unsubstituted aryl (e.g., $C_6$-$C_{10}$ aryl, $C_{10}$ aryl, or phenyl). In embodiments, $R^{17}$ is independently $R^{41}$-substituted aryl (e.g., $C_6$-$C_{10}$ aryl, $C_{10}$ aryl, or phenyl). In embodiments, $R^{17}$ is independently an unsubstituted aryl (e.g., $C_6$-$C_{10}$ aryl, $C_{10}$ aryl, or phenyl). In embodiments, $R^{17}$ is independently $R^{41}$-substituted or unsubstituted heteroaryl (e.g., 5 to 10 membered heteroaryl, 5 to 9 membered heteroaryl, or 5 to 6 membered heteroaryl). In embodiments, $R^{17}$ is independently $R^{41}$-substituted heteroaryl (e.g., 5 to 10 membered heteroaryl, 5 to 9 membered heteroaryl, or 5 to 6 membered heteroaryl). In embodiments, $R^{17}$ is independently an unsubstituted heteroaryl (e.g., 5 to 10 membered heteroaryl, 5 to 9 membered heteroaryl, or 5 to 6 membered heteroaryl).

In embodiments, $R^{17}$ is independently —$CX^{17}_3$. In embodiments, $R^{17}$ is independently —$CHX^{17}_2$. In embodiments, $R^{17}$ is independently —$CH_2X^{17}$. In embodiments, $R^{17}$ is independently —$OCX^{17}_3$. In embodiments, $R^{17}$ is independently —$OCH_2X'$. In embodiments, $R^{17}$ is independently —$OCHX^{17}_2$. In embodiments, $R^{17}$ is independently —CN. In embodiments, $R^{17}$ is independently —$SR^{17D}$. In embodiments, $R^{17}$ is independently —$SOR^{17D}$. In embodiments, $R^{17}$ is independently —$SO_2R^{17D}$. In embodiments, $R^{17}$ is independently —$SO_3R^{17D}$. In embodiments, $R^{17}$ is independently —$SO_4R^{17D}$. In embodiments, $R^{17}$ is independently —$SONR^{17A}R^{17B}$. In embodiments, $R^{17}$ is independently —$SO_2NR^{17A}R^{17B}$. In embodiments, $R^{17}$ is independently —$NHC(O)NR^{17A}R^{17B}$. In embodiments, $R^{17}$ is independently —N(O). In embodiments, $R^{17}$ is independently —$N(O)_2$. In embodiments, $R^{17}$ is independently —$NR^{17A}R^{17B}$. In embodiments, $R^{17}$ is independently —$C(O)R^{17C}$. In embodiments, $R^{17}$ is independently —C(O)—$OR^{17C}$. In embodiments, $R^{17}$ is independently —$C(O)NR^{17A}R^{17B}$. In embodiments, $R^{17}$ is independently —$OR^{17D}$. In embodiments, $R^{17}$ is independently —$NR^{17A}SO_2R^{17D}$. In embodiments, $R^{17}$ is independently —$NR^{17A}C(O)R^{17C}$. In embodiments, $R^{17}$ is independently —$NR^{17A}C(O)OR^{17C}$. In embodiments, $R^{17}$ is independently —$NR^{17A}OR^{17C}$. In embodiments, $R^{17}$ is independently hydrogen.

In embodiments, $R^{17}$ is independently oxo. In embodiments, $R^{17}$ is independently halogen. In embodiments, $R^{17}$ is independently —CCl$_3$. In embodiments, R$^{17}$ is independently —CBr$_3$. In embodiments, R$^{17}$ is independently —CF$_3$. In embodiments, R$^{17}$ is independently —CI$_3$. In embodiments, R$^{17}$ is independently —CHCl$_2$. In embodiments, R$^{17}$ is independently —CHBr$_2$. In embodiments, R$^{17}$ is independently —CHF$_2$. In embodiments, R$^{17}$ is independently —CHI$_2$. In embodiments, R$^{17}$ is independently —CH$_2$Cl. In embodiments, R$^{17}$ is independently —CH$_2$Br. In embodiments, R$^{17}$ is independently —CH$_2$F. In embodiments, R$^{17}$ is independently —CH$_2$I. In embodiments, R$^{17}$ is independently —CN. In embodiments, R$^{17}$ is independently —OH. In embodiments, R$^{17}$ is independently —NH$_2$. In embodiments, R$^{17}$ is independently —COOH. In embodiments, R$^{17}$ is independently —CONH$_2$. In embodiments, R$^{17}$ is independently —NO$_2$. In embodiments, R$^{17}$ is independently —SH. In embodiments, R$^{17}$ is independently —SO$_3$H. In embodiments, R$^{17}$ is independently —SO$_4$H. In embodiments, R$^{17}$ is independently —SO$_2$NH$_2$. In embodiments, R$^{17}$ is independently —NHNH$_2$. In embodiments, R$^{17}$ is independently —ONH$_2$. In embodiments, R$^{17}$ is independently —NHC(O)NHNH$_2$. In embodiments, R$^{17}$ is independently —NHC(O)NH$_2$. In embodiments, R$^{17}$ is independently —NHSO$_2$H. In embodiments, R$^{17}$ is independently —NHC(O)H. In embodiments, R$^{17}$ is independently —NHC(O)OH. In embodiments, R$^{17}$ is independently —NHOH. In embodiments, R$^{17}$ is independently —OCCl$_3$. In embodiments, R$^{17}$ is independently —OCF$_3$. In embodiments, R$^{17}$ is independently —OCBr$_3$. In embodiments, R$^{17}$ is independently —OCI$_3$. In embodiments, R$^{17}$ is independently —OCHCl$_2$. In embodiments, R$^{17}$ is independently —OCHBr$_2$. In embodiments, R$^{17}$ is independently —OCHI$_2$. In embodiments, R$^{17}$ is independently —OCHF$_2$. In embodiments, R$^{17}$ is independently —OCH$_2$Cl. In embodiments, R$^{17}$ is independently —OCH$_2$Br. In embodiments, R$^{17}$ is independently —OCH$_2$I. In embodiments, R$^{17}$ is independently —OCH$_2$F. In embodiments, R$^{17}$ is independently —N$_3$. In embodiments, R$^{17}$ is independently —OCH$_3$. In embodiments, R$^{17}$ is idenpendently —CH$_3$. In embodiments, R$^{17}$ is idenpendently —CH$_2$CH$_3$. In embodiments, R$^{17}$ is independently unsubstituted propyl. In embodiments, R$^{17}$ is independently unsubstituted isopropyl. In embodiments, R$^{17}$ is independently unsubstituted butyl. In embodiments, R$^{17}$ is independently unsubstituted tert-butyl. In embodiments, R$^{17}$ is independently —F. In embodiments, R$^{17}$ is independently —Cl. In embodiments, R$^{17}$ is independently —Br. In embodiments, R$^{17}$ is independently —I.

R$^{41}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{41}$ is independently oxo. In embodiments, R$^{41}$ is independently halogen. In embodiments, R$^{41}$ is independently —CCl$_3$. In embodiments, R$^{41}$ is independently —CBr$_3$. In embodiments, R$^{41}$ is independently —CF$_3$. In embodiments, R$^{41}$ is independently —CI$_3$. In embodiments, R$^{41}$ is independently —CHCl$_2$. In embodiments, R$^{41}$ is independently —CHBr$_2$. In embodiments, R$^{41}$ is independently —CHF$_2$. In embodiments, R$^{41}$ is independently —CHI$_2$. In embodiments, R$^{41}$ is independently —CH$_2$Cl. In embodiments, R$^{41}$ is independently —CH$_2$Br. In embodiments, R$^{41}$ is independently —CH$_2$F. In embodiments, R$^{41}$ is independently —CH$_2$I. In embodiments, R$^{41}$ is independently —CN. In embodiments, R$^{41}$ is independently —OH. In embodiments, R$^{41}$ is independently —NH$_2$. In embodiments, R$^{41}$ is independently —COOH. In embodiments, R$^{41}$ is independently —CONH$_2$. In embodiments, R$^{41}$ is independently —NO$_2$. In embodiments, R$^{41}$ is independently —SH. In embodiments, R$^{41}$ is independently —SO$_3$H. In embodiments, R$^{41}$ is independently —SO$_4$H. In embodiments, R$^{41}$ is independently —SO$_2$NH$_2$. In embodiments, R$^{41}$ is independently —NHNH$_2$. In embodiments, R$^{41}$ is independently —ONH$_2$. In embodiments, R$^{41}$ is independently —NHC(O)NHNH$_2$. In embodiments, R$^{41}$ is independently —NHC(O)NH$_2$. In embodiments, R$^{41}$ is independently —NHSO$_2$H. In embodiments, R$^{41}$ is independently —NHC(O)H. In embodiments, R$^{41}$ is independently —NHC(O)OH. In embodiments, R$^{41}$ is independently —NHOH. In embodiments, R$^{41}$ is independently —OCCl$_3$. In embodiments, R$^{41}$ is independently —OCF$_3$. In embodiments, R$^{41}$ is independently —OCBr$_3$. In embodiments, R$^{41}$ is independently —OCI$_3$. In embodiments, R$^{41}$ is independently —OCHCl$_2$. In embodiments, R$^{41}$ is independently —OCHBr$_2$. In embodiments, R$^{41}$ is independently —OCHI$_2$. In embodiments, R$^{41}$ is independently —OCHF$_2$. In embodiments, R$^{41}$ is independently —OCH$_2$Cl. In embodiments, R$^{41}$ is independently —OCH$_2$Br. In embodiments, R$^{41}$ is independently —OCH$_2$I. In embodiments, R$^{41}$ is independently —OCH$_2$F. In embodiments, R$^{41}$ is independently —N$_3$. In embodiments, R$^{41}$ is independently —OCH$_3$. In embodiments, R$^{41}$ is independently —CH$_3$. In embodiments, R$^{41}$ is independently —CH$_2$CH$_3$. In embodiments, R$^{41}$ is independently unsubstituted propyl. In embodiments, R$^{41}$ is independently unsubstituted isopropyl. In embodiments, R$^{41}$ is independently unsubstituted butyl. In embodiments, R$^{41}$ is independently unsubstituted tert-butyl. In embodiments, R$^{41}$ is independently —F. In embodiments, R$^{41}$ is independently —Cl. In embodiments, R$^{41}$ is independently —Br. In embodiments, R$^{41}$ is independently —I.

In embodiments, R$^{17A}$ is independently hydrogen, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{17B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{17C}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2T$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{17D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{17A}$ and $R^{17B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{17A}$ and $R^{17B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17A}$ and $R^{17B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{17A}$ and $R^{17B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{17A}$ and $R^{17B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{17A}$ and $R^{17B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{17A}$ and $R^{17B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{17A}$, $R^{17B}$, $R^{17C}$, and $R^{17D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{41}$-substituted or unsubstituted alkyl (e.g., $C_1$-$C_8$ alkyl, $C_1$-$C_6$ alkyl, or $C_1$-$C_4$ alkyl), $R^{41}$-substituted or unsubstituted heteroalkyl (e.g., 2 to 8 membered heteroalkyl, 2 to 6 membered heteroalkyl, or 2 to 4 membered heteroalkyl), $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{41}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41}$-substituted or unsubstituted aryl (e.g., $C_6$-$C_{10}$ aryl, $C_{10}$ aryl, or phenyl), or $R^{41}$-substituted or unsubstituted heteroaryl (e.g., 5 to 10 membered heteroaryl, 5 to 9 membered heteroaryl, or 5 to 6 membered heteroaryl). In embodiments, $R^{17A}$ and $R^{17B}$ substituents bonded to the same nitrogen atom are independently joined to form an $R^{41}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{41}$-substituted or unsubstituted heteroaryl (e.g., 5 to 10 membered heteroaryl, 5 to 9 membered heteroaryl, or 5 to 6 membered heteroaryl). In embodiments, $R^{17A}$ and $R^{17B}$ substituents bonded to the same nitrogen atom are independently joined to form an $R^{41}$-substituted or unsubstituted heterocycloalkyl (e.g., 3 to 8 membered heterocycloalkyl, 3 to 6 membered heterocycloalkyl. In embodiments, $R^{17A}$ and $R^{17B}$ substituents bonded to the same nitrogen atom are independently joined to form an $R^{41}$-substituted or unsubstituted heteroaryl (e.g., 5 to 10 membered heteroaryl, 5 to 9 membered heteroaryl, or 5 to 6 membered heteroaryl).

In embodiments, $R^{17A}$ is independently $R^{41}$-substituted or unsubstituted alkyl (e.g., $C_1$-$C_8$ alkyl, $C_1$-$C_6$ alkyl, or $C_1$-$C_4$ alkyl). In embodiments, $R^{17A}$ is independently $R^{41}$-substituted alkyl (e.g., $C_1$-$C_8$ alkyl, $C_1$-$C_6$ alkyl, or $C_1$-$C_4$ alkyl). In embodiments, $R^{17A}$ is independently an unsubstituted alkyl (e.g., $C_1$-$C_8$ alkyl, $C_1$-$C_6$ alkyl, or $C_1$-$C_4$ alkyl). In embodiments, $R^{17A}$ is independently $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{17A}$ is independently $R^{41}$-substituted heteroalkyl (e.g., 2 to 8 membered heteroalkyl, 2 to 6 membered heteroalkyl, or 2 to 4 membered heteroalkyl). In embodiments, $R^{17A}$ is independently an unsubstituted heteroalkyl (e.g., 2 to 8 membered heteroalkyl, 2 to 6 membered heteroalkyl, or 2 to 4 membered heteroalkyl). In embodiments, $R^{17A}$ is independently $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17A}$ is independently $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17A}$ is independently $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17A}$ is independently $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{17A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{17A}$ is independently $R^{41}$-substituted or unsubstituted aryl (e.g., $C_6$-$C_{10}$ aryl, $C_{10}$ aryl, or phenyl). In embodiments, $R^{17A}$ is independently $R^{41}$-substituted aryl (e.g., $C_6$-$C_{10}$ aryl, $C_{10}$ aryl, or phenyl). In embodiments, $R^{17A}$ is independently an unsubstituted aryl (e.g., $C_6$-$C_{10}$ aryl, $C_{10}$ aryl, or phenyl). In embodiments, $R^{17A}$ is independently $R^{41}$-substituted or unsubstituted heteroaryl (e.g., 5 to 10 membered heteroaryl, 5 to 9 membered heteroaryl, or 5 to 6 membered heteroaryl). In embodiments, $R^{17A}$ is independently $R^{41}$-substituted heteroaryl (e.g., 5 to 10 membered heteroaryl, 5 to 9 membered heteroaryl, or 5 to 6 membered heteroaryl). In embodiments, $R^{17A}$ is independently an unsubstituted heteroaryl (e.g., 5 to 10 membered heteroaryl, 5 to 9 membered heteroaryl, or 5 to 6 membered heteroaryl).

In embodiments, $R^{17A}$ is independently —$CCl_3$. In embodiments, $R^{17A}$ is independently —$CBr_3$. In embodiments, $R^{17A}$ is independently —$CF_3$. In embodiments, $R^{17A}$ is independently —$CI_3$. In embodiments, $R^{17A}$ is independently —$CHCl_2$. In embodiments, $R^{17A}$ is independently —$CHBr_2$. In embodiments, $R^{17A}$ is independently —$CHF_2$. In embodiments, $R^{17A}$ is independently —$CHI_2$. In embodiments, $R^{17A}$ is independently —$CH_2Cl$. In embodiments, $R^{17A}$ is independently —$CH_2Br$. In embodiments, $R^{17A}$ is independently —$CH_2F$. In embodiments, $R^{17A}$ is independently —$CH_2I$. In embodiments, $R^{17A}$ is independently —CN. In embodiments, $R^{17A}$ is independently —OH. In embodiments, $R^{17A}$ is independently —COOH. In embodiments, $R^{17A}$ is independently —$CONH_2$. In embodiments, $R^{17A}$ is independently —$OCCl_3$. In embodiments, $R^{17A}$ is independently —$OCF_3$. In embodiments, $R^{17A}$ is independently —$OCBr_3$. In embodiments, $R^{17A}$ is independently —$OCI_3$. In embodiments, $R^{17A}$ is independently —$OCHCl_2$. In embodiments, $R^{17A}$ is independently —$OCHBr_2$. In embodiments, $R^{17A}$ is independently —$OCHI_2$. In embodiments, $R^{17A}$ is independently —$OCHF_2$. In embodiments, $R^{17A}$ is independently —$OCH_2Cl$. In embodiments, $R^{17A}$ is independently —$OCH_2Br$. In embodiments, $R^{17A}$ is independently —$OCH_2I$. In embodiments, $R^{17A}$ is independently —$OCH_2F$. In embodiments, $R^{17A}$ is independently —$OCH_3$. In embodiments, $R^{17A}$ is idenpendently —$CH_3$. In embodiments, $R^{17A}$ is idenpendently —$CH_2CH_3$. In embodiments, $R^{17A}$ is independently unsubstituted propyl. In embodiments, $R^{17A}$ is independently unsubstituted isopropyl. In embodiments, $R^{17A}$ is independently unsubstituted butyl. In embodiments, $R^{17A}$ is independently unsubstituted tert-butyl. In embodiments, $R^{17A}$ is independently hydrogen.

In embodiments, $R^{17B}$ is independently $R^{41}$-substituted or unsubstituted alkyl (e.g., $C_1$-$C_8$ alkyl, $C_1$-$C_6$ alkyl, or $C_1$-$C_4$ alkyl). In embodiments, $R^{17B}$ is independently $R^{41}$-substituted alkyl (e.g., $C_1$-$C_8$ alkyl, $C_1$-$C_6$ alkyl, or $C_1$-$C_4$ alkyl). In embodiments, $R^{17B}$ is independently an unsubstituted alkyl (e.g., $C_1$-$C_8$ alkyl, $C_1$-$C_6$ alkyl, or $C_1$-$C_4$ alkyl). In embodiments, $R^{17B}$ is independently $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{17B}$ is independently $R^{41}$-substituted heteroalkyl (e.g., 2 to 8 membered heteroalkyl, 2 to 6 membered heteroalkyl, or 2 to 4 membered heteroalkyl). In embodiments, $R^{17B}$ is independently an unsubstituted heteroalkyl (e.g., 2 to 8 membered heteroalkyl, 2 to 6 membered heteroalkyl, or 2 to 4 membered heteroalkyl). In embodiments, $R^{17B}$ is independently $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17B}$ is independently $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17B}$ is independently $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17B}$ is independently $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{17B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{17B}$ is independently $R^{41}$-substituted or unsubstituted aryl (e.g., $C_6$-$C_{10}$ aryl, $C_{10}$ aryl, or phenyl). In embodiments, $R^{17B}$ is independently $R^{41}$-substituted aryl (e.g., $C_6$-$C_{10}$ aryl, $C_{10}$ aryl, or phenyl). In embodiments, $R^{17B}$ is independently an unsubstituted aryl (e.g., $C_6$-$C_{10}$ aryl, $C_{10}$ aryl, or phenyl). In embodiments, $R^{17B}$ is independently $R^{41}$-substituted or unsubstituted heteroaryl (e.g., 5 to 10 membered heteroaryl, 5 to 9 membered heteroaryl, or 5 to 6 membered heteroaryl). In embodiments, $R^{17B}$ is independently $R^{41}$-substituted heteroaryl (e.g., 5 to 10 membered heteroaryl, 5 to 9 membered heteroaryl, or 5 to 6 membered heteroaryl). In embodiments, $R^{17B}$ is independently an unsubstituted heteroaryl (e.g., 5 to 10 membered heteroaryl, 5 to 9 membered heteroaryl, or 5 to 6 membered heteroaryl).

In embodiments, $R^{17B}$ is independently —$CCl_3$. In embodiments, $R^{17B}$ is independently —$CBr_3$. In embodiments, $R^{17B}$ is independently —$CF_3$. In embodiments, $R^{17B}$ is independently —$CI_3$. In embodiments, $R^{17B}$ is independently —$CHCl_2$. In embodiments, $R^{17B}$ is independently —$CHBr_2$. In embodiments, $R^{17B}$ is independently —$CHF_2$. In embodiments, $R^{17B}$ is independently —$CHI_2$. In embodiments, $R^{17B}$ is independently —$CH_2Cl$. In embodiments, $R^{17B}$ is independently —$CH_2Br$. In embodiments, $R^{17B}$ is independently —$CH_2F$. In embodiments, $R^{17B}$ is independently —$CH_2I$. In embodiments, $R^{17B}$ is independently —CN. In embodiments, $R^{17B}$ is independently —OH. In embodiments, $R^{17B}$ is independently —COOH. In embodiments, $R^{17B}$ is independently —CONH$_2$. In embodiments, $R^{17B}$ is independently —OCCl$_3$. In embodiments, $R^{17B}$ is independently —OCF$_3$. In embodiments, $R^{17B}$ is independently —OCBr$_3$. In embodiments, $R^{17B}$ is independently —OCI$_3$. In embodiments, $R^{17B}$ is independently —OCHCl$_2$. In embodiments, $R^{17B}$ is independently —OCHBr$_2$. In embodiments, $R^{17B}$ is independently —OCHI$_2$. In embodiments, $R^{17B}$ is independently —OCHF$_2$. In embodiments, $R^{17B}$ is independently —OCH$_2$Cl. In embodiments, $R^{17B}$ is independently —OCH$_2$Br. In embodiments, $R^{17B}$ is independently —OCH$_2$I. In embodiments, $R^{17B}$ is independently —OCH$_2$F. In embodiments, $R^{17B}$ is independently —OCH$_3$. In embodiments, $R^{17B}$ is idenpendently —CH$_3$. In embodiments, $R^{17B}$ is idenpendently —CH$_2$CH$_3$. In embodiments, $R^{17B}$ is independently unsubstituted propyl. In embodiments, $R^{17B}$ is independently unsubstituted isopropyl. In embodiments, $R^{17B}$ is independently unsubstituted butyl. In embodiments, $R^{17B}$ is independently unsubstituted tert-butyl. In embodiments, $R^{17B}$ is independently hydrogen.

In embodiments, $R^{17C}$ is independently $R^{41}$-substituted or unsubstituted alkyl (e.g., $C_1$-$C_8$ alkyl, $C_1$-$C_6$ alkyl, or $C_1$-$C_4$ alkyl). In embodiments, $R^{17C}$ is independently $R^{41}$-substituted alkyl (e.g., $C_1$-$C_8$ alkyl, $C_1$-$C_6$ alkyl, or $C_1$-$C_4$ alkyl). In embodiments, $R^{17C}$ is independently an unsubstituted alkyl (e.g., $C_1$-$C_8$ alkyl, $C_1$-$C_6$ alkyl, or $C_1$-$C_4$ alkyl). In embodiments, $R^{17C}$ is independently $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{17C}$ is independently $R^{41}$-substituted heteroalkyl (e.g., 2 to 8 membered heteroalkyl, 2 to 6 membered heteroalkyl, or 2 to 4 membered heteroalkyl). In embodiments, $R^{17C}$ is independently an unsubstituted heteroalkyl (e.g., 2 to 8 membered heteroalkyl, 2 to 6 membered heteroalkyl, or 2 to 4 membered heteroalkyl). In embodiments, $R^{17C}$ is independently $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17C}$ is independently $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17C}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17C}$ is independently $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17C}$ is independently $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{17C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{17C}$ is independently $R^{41}$-substituted or unsubstituted aryl (e.g., $C_6$-$C_{10}$ aryl, $C_{10}$ aryl, or phenyl). In embodiments, $R^{17C}$ is independently $R^{41}$-substituted aryl (e.g., $C_6$-$C_{10}$ aryl, $C_{10}$ aryl, or phenyl). In embodiments, $R^{17C}$ is independently an unsubstituted aryl (e.g., $C_6$-$C_{10}$ aryl, $C_{10}$ aryl, or phenyl). In embodiments, $R^{17C}$ is independently $R^{41}$-substituted or unsubstituted heteroaryl (e.g., 5 to 10 membered heteroaryl, 5 to 9 membered heteroaryl, or 5 to 6 membered heteroaryl). In embodiments, $R^{17C}$ is independently $R^{41}$-substituted heteroaryl (e.g., 5 to 10 membered heteroaryl, 5 to 9 membered heteroaryl, or 5 to 6 membered heteroaryl). In embodiments, $R^{17C}$ is independently an unsubstituted heteroaryl (e.g., 5 to 10 membered heteroaryl, 5 to 9 membered heteroaryl, or 5 to 6 membered heteroaryl).

In embodiments, $R^{17C}$ is independently —CCl$_3$. In embodiments, $R^{17C}$ is independently —CBr$_3$. In embodiments, $R^{17C}$ is independently —CF$_3$. In embodiments, $R^{17C}$ is independently —CI$_3$. In embodiments, $R^{17C}$ is independently —CHCl$_2$. In embodiments, $R^{17C}$ is independently —CHBr$_2$. In embodiments, $R^{17C}$ is independently —CHF$_2$. In embodiments, $R^{17C}$ is independently —CHI$_2$. In embodiments, $R^{17C}$ is independently —CH$_2$Cl. In embodiments, $R^{17C}$ is independently —CH$_2$Br. In embodiments, $R^{17C}$ is independently —CH$_2$F. In embodiments, $R^{17C}$ is independently —CH$_2$I. In embodiments, $R^{17C}$ is independently —CN. In embodiments, $R^{17C}$ is independently —OH. In embodiments, $R^{17C}$ is independently —COOH. In embodiments, $R^{17C}$ is independently —CONH$_2$. In embodiments, $R^{17C}$ is independently —OCCl$_3$. In embodiments, $R^{17C}$ is independently —OCF$_3$. In embodiments, $R^{17C}$ is independently —OCBr$_3$. In embodiments, $R^{17C}$ is independently —OCI$_3$. In embodiments, $R^{17C}$ is independently —OCHCl$_2$. In embodiments, $R^{17C}$ is independently —OCHBr$_2$. In embodiments, $R^{17C}$ is independently —OCHI$_2$. In embodiments, $R^{17C}$ is independently —OCHF$_2$. In embodiments, $R^{17C}$ is independently —OCH$_2$Cl. In embodiments, $R^{17C}$ is independently —OCH$_2$Br. In embodiments, $R^{17C}$ is independently —OCH$_2$I. In embodiments, $R^{17C}$ is independently —OCH$_2$F. In embodiments, $R^{17C}$ is independently —OCH$_3$. In embodiments, $R^{17C}$ is idenpendently —CH$_3$. In embodiments, $R^{17C}$ is idenpendently —CH$_2$CH$_3$. In embodiments, $R^{17C}$ is independently unsubstituted propyl. In embodiments, $R^{17C}$ is independently unsubstituted isopropyl. In embodiments, $R^{17C}$ is independently unsubstituted butyl. In embodiments, $R^{17C}$ is independently unsubstituted tert-butyl. In embodiments, $R^{17C}$ is independently hydrogen.

In embodiments, $R^{17D}$ is independently $R^{41}$-substituted or unsubstituted alkyl (e.g., $C_1$-$C_8$ alkyl, $C_1$-$C_6$ alkyl, or $C_1$-$C_4$ alkyl). In embodiments, $R^{17D}$ is independently $R^{41}$-substituted alkyl (e.g., $C_1$-$C_8$ alkyl, $C_1$-$C_6$ alkyl, or $C_1$-$C_4$ alkyl). In embodiments, $R^{17D}$ is independently an unsubstituted alkyl (e.g., $C_1$-$C_8$ alkyl, $C_1$-$C_6$ alkyl, or $C_1$-$C_4$ alkyl). In embodiments, $R^{17D}$ is independently $R^{41}$-substituted or unsubstituted heteroalkyl (e.g., 2 to 8 membered heteroalkyl, 2 to 6 membered heteroalkyl, or 2 to 4 membered heteroalkyl). In embodiments, $R^{17D}$ is independently $R^{41}$-substituted heteroalkyl (e.g., 2 to 8 membered heteroalkyl, 2 to 6 membered heteroalkyl, or 2 to 4 membered heteroalkyl). In embodiments, $R^{17D}$ is independently an unsubstituted heteroalkyl (e.g., 2 to 8 membered heteroalkyl, 2 to 6 membered heteroalkyl, or 2 to 4 membered heteroalkyl). In embodiments, $R^{17D}$ is independently $R^{41}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17D}$ is independently $R^{41}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17D}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17D}$ is independently $R^{41}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17D}$ is independently $R^{41}$-substituted heterocycloalkyl (e.g., 3 to 8 membered heterocycloalkyl, 3 to 6 membered heterocycloalkyl, or 5 to 6 membered heterocycloalkyl). In embodiments, $R^{17D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{17D}$ is independently $R^{41}$-substituted or unsubstituted aryl (e.g., $C_6$-$C_{10}$ aryl, $C_{10}$ aryl, or phenyl). In embodiments, $R^{17D}$ is independently $R^{41}$-substituted aryl (e.g., $C_6$-$C_{10}$ aryl, $C_{10}$ aryl, or phenyl). In embodiments, $R^{17D}$ is independently an unsubstituted aryl (e.g., $C_6$-$C_{10}$ aryl, $C_{10}$ aryl, or phenyl). In embodiments, $R^{17D}$ is independently $R^{41}$-substituted or unsubstituted heteroaryl (e.g., 5 to 10 membered heteroaryl, 5 to 9 membered heteroaryl, or 5 to 6 membered heteroaryl). In embodiments, $R^{17D}$ is independently $R^{41}$-substituted heteroaryl (e.g., 5 to 10 membered heteroaryl, 5 to 9 membered heteroaryl, or 5 to 6 membered heteroaryl). In embodiments, $R^{17D}$ is independently an unsubstituted heteroaryl (e.g., 5 to 10 membered heteroaryl, 5 to 9 membered heteroaryl, or 5 to 6 membered heteroaryl).

In embodiments, $R^{17D}$ is independently —$CCl_3$. In embodiments, $R^{17D}$ is independently —$CBr_3$. In embodiments, $R^{17D}$ is independently —$CF_3$. In embodiments, $R^{17D}$ is independently —$CI_3$. In embodiments, $R^{17D}$ is independently —$CHCl_2$. In embodiments, $R^{17D}$ is independently —$CHBr_2$. In embodiments, $R^{17D}$ is independently —$CHF_2$. In embodiments, $R^{17D}$ is independently —$CHI_2$. In embodiments, $R^{17D}$ is independently —$CH_2Cl$. In embodiments, $R^{17D}$ is independently —$CH_2Br$. In embodiments, $R^{17D}$ is independently —$CH_2F$. In embodiments, $R^{17D}$ is independently —$CH_2I$. In embodiments, $R^{17D}$ is independently —CN. In embodiments, $R^{17D}$ is independently —OH. In embodiments, $R^{17D}$ is independently —COOH. In embodiments, $R^{17D}$ is independently —$CONH_2$. In embodiments, $R^{17D}$ is independently —$OCCl_3$. In embodiments, $R^{17D}$ is independently —$OCF_3$. In embodiments, $R^{17D}$ is independently —$OCBr_3$. In embodiments, $R^{17D}$ is independently —$OCI_3$. In embodiments, $R^{17D}$ is independently —$OCHCl_2$. In embodiments, $R^{17D}$ is independently —$OCHBr_2$. In embodiments, $R^{17D}$ is independently —$OCHI_2$. In embodiments, $R^{17D}$ is independently —$OCHF_2$. In embodiments, $R^{17D}$ is independently —$OCH_2Cl$. In embodiments, $R^{17D}$ is independently —$OCH_2Br$. In embodiments, $R^{17D}$ is independently —$OCH_2I$. In embodiments, $R^{17D}$ is independently —$OCH_2F$. In embodiments, $R^{17D}$ is independently —$OCH_3$. In embodiments, $R^{17D}$ is idenpendently —$CH_3$. In embodiments, $R^{17D}$ is idenpendently —$CH_2CH_3$. In embodiments, $R^{17D}$ is independently unsubstituted propyl. In embodiments, $R^{17D}$ is independently unsubstituted isopropyl. In embodiments, $R^{17B}$ is independently unsubstituted butyl. In embodiments, $R^{17D}$ is independently unsubstituted tert-butyl. In embodiments, $R^{17D}$ is independently hydrogen.

In embodiments, $R^{18}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2T$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, —$N_3$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{18}$ is independently substituted or unsubstituted alkyl (e.g., $C_1$-$C_8$ alkyl, $C_1$-$C_6$ alkyl, or $C_1$-$C_4$ alkyl). In embodiments, $R^{18}$ is independently substituted alkyl (e.g., $C_1$-$C_8$ alkyl, $C_1$-$C_6$ alkyl, or $C_1$-$C_4$ alkyl). In embodiments, $R^{18}$ is independently an unsubstituted alkyl (e.g., $C_1$-$C_8$ alkyl, $C_1$-$C_6$ alkyl, or $C_1$-$C_4$ alkyl). In embodiments, $R^{18}$ is independently substituted or unsubstituted heteroalkyl (e.g., 2 to 8 membered heteroalkyl, 2 to 6 membered heteroalkyl, or 2 to 4 membered heteroalkyl). In embodiments, $R^{18}$ is independently substituted heteroalkyl (e.g., 2 to 8 membered heteroalkyl, 2 to 6 membered heteroalkyl, or 2 to 4 membered heteroalkyl). In embodiments, $R^{18}$ is independently an unsubstituted heteroalkyl (e.g., 2 to 8 membered heteroalkyl, 2 to 6 membered heteroalkyl, or 2 to 4 membered heteroalkyl). In embodiments, $R^{18}$ is independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is independently substituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18}$ is independently substituted heterocycloalkyl (e.g., 3 to 8 membered heterocycloalkyl, 3 to 6 membered heterocycloalkyl, or 5 to 6 membered heterocycloalkyl). In embodiments, $R^{18}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{18}$ is independently substituted or unsubstituted aryl (e.g., $C_6$-$C_{10}$ aryl, $C_{10}$ aryl, or phenyl). In embodiments, $R^{18}$ is independently substituted aryl (e.g., $C_6$-$C_{10}$ aryl, $C_{10}$ aryl, or phenyl). In embodiments, $R^{18}$ is independently an unsubstituted aryl (e.g., $C_6$-$C_{10}$ aryl, $C_{10}$ aryl, or phenyl). In embodiments, $R^{18}$ is independently substituted or unsubstituted heteroaryl (e.g., 5 to 10 membered heteroaryl, 5 to 9 membered heteroaryl, or 5 to 6 membered heteroaryl). In embodiments, $R^{18}$ is independently substituted heteroaryl (e.g., 5 to 10 membered heteroaryl, 5 to 9 membered heteroaryl, or 5 to 6 membered heteroaryl). In embodiments, $R^{18}$ is independently an unsubstituted heteroaryl (e.g., 5 to 10 membered heteroaryl, 5 to 9 membered heteroaryl, or 5 to 6 membered heteroaryl).

In embodiments, $R^{18}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{42}$-substituted or unsubstituted alkyl (e.g., $C_1$-$C_8$ alkyl, $C_1$-$C_6$ alkyl, or $C_1$-$C_4$ alkyl), $R^{42}$-substituted or unsubstituted heteroalkyl (e.g., 2 to 8 membered heteroalkyl, 2 to 6 membered heteroalkyl, or 2 to 4 membered heteroalkyl), $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42}$-substituted or unsubstituted aryl (e.g., $C_6$-$C_{10}$ aryl, $C_{10}$ aryl, or phenyl), or $R^{42}$-substituted or unsubstituted heteroaryl (e.g., 5 to 10 membered heteroaryl, 5 to 9 membered heteroaryl, or 5 to 6 membered heteroaryl). In embodiments, $R^{18}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{18}$ is independently $R^{42}$-substituted or unsubstituted alkyl (e.g., $C_1$-$C_8$ alkyl, $C_1$-$C_6$ alkyl, or $C_1$-$C_4$ alkyl). In embodiments, $R^{18}$ is independently $R^{42}$-substituted alkyl (e.g., $C_1$-$C_8$ alkyl, $C_1$-$C_6$ alkyl, or $C_1$-$C_4$ alkyl). In embodiments, $R^{18}$ is independently an unsubstituted alkyl (e.g., $C_1$-$C_8$ alkyl, $C_1$-$C_6$ alkyl, or $C_1$-$C_4$ alkyl). In embodiments, $R^{18}$ is independently $R^{42}$-substituted or unsubstituted heteroalkyl (e.g., 2 to 8 membered heteroalkyl, 2 to 6 membered heteroalkyl, or 2 to 4 membered heteroalkyl). In embodiments, $R^{18}$ is independently $R^{42}$-substituted heteroalkyl (e.g., 2 to 8 membered heteroalkyl, 2 to 6 membered heteroalkyl, or 2 to 4 membered heteroalkyl). In embodiments, $R^{18}$ is independently an unsubstituted heteroalkyl (e.g., 2 to 8 membered heteroalkyl, 2 to 6 membered heteroalkyl, or 2 to 4 membered heteroalkyl). In embodiments, $R^{18}$ is independently $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is independently $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is independently $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18}$ is independently $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{18}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{18}$ is independently $R^{42}$-substituted or unsubstituted aryl (e.g., $C_6$-$C_{10}$ aryl, $C_{10}$ aryl, or phenyl). In embodiments, $R^{18}$ is independently $R^{42}$-substituted aryl (e.g., $C_6$-$C_{10}$ aryl, $C_{10}$ aryl, or phenyl). In embodiments, $R^{18}$ is independently an unsubstituted aryl (e.g., $C_6$-$C_{10}$ aryl, $C_{10}$ aryl, or phenyl). In embodiments, $R^{18}$ is independently $R^{42}$-substituted or unsubstituted heteroaryl (e.g., 5 to 10 membered heteroaryl, 5 to 9 membered heteroaryl, or 5 to 6 membered heteroaryl). In embodiments, $R^{18}$ is independently $R^{42}$-substituted heteroaryl (e.g., 5 to 10 membered heteroaryl, 5 to 9 membered heteroaryl, or 5 to 6 membered heteroaryl). In embodiments, $R^{18}$ is independently an unsubstituted heteroaryl (e.g., 5 to 10 membered heteroaryl, 5 to 9 membered heteroaryl, or 5 to 6 membered heteroaryl).

In embodiments, $R^{18}$ is independently —$CX^{18}_3$. In embodiments, $R^{18}$ is independently —$CHX^{18}_2$. In embodiments, $R^{18}$ is independently —$CH_2X^{18}$. In embodiments, $R^{18}$ is independently —$OCX^{18}_3$. In embodiments, $R^{18}$ is independently —$OCH_2X^{18}$. In embodiments, $R^{18}$ is independently —$OCHX^{18}_2$. In embodiments, $R^{18}$ is independently —CN. In embodiments, $R^{18}$ is independently —$SR^{18D}$. In embodiments, $R^{18}$ is independently —$SOR^{18D}$. In embodiments, $R^{18}$ is independently $SO_2R^{18D}$. In embodiments, $R^{18}$ is independently —$SO_3R^{18D}$. In embodiments, $R^{18}$ is independently $SO_4R^{18D}$. In embodiments, $R^{18}$ is independently —$SONR^{18A}R^{18B}$. In embodiments, $R^{18}$ is independently —$SO_2NR^{18A}R^{18B}$. In embodiments, $R^{18}$ is independently —$NHC(O)NR^{18A}R^{18B}$. In embodiments, $R^{18}$ is independently —N(O). In embodiments, $R^{18}$ is independently —$N(O)_2$. In embodiments, $R^{18}$ is independently —$NR^{18A}R^{18B}$. In embodiments, $R^{18}$ is independently —$C(O)R^{18C}$. In embodiments, $R^{18}$ is independently —C(O)—$OR^{18C}$. In embodiments, $R^{18}$ is independently —$C(O)NR^{18A}R^{18B}$. In embodiments, $R^{18}$ is independently —$OR^{18D}$. In embodiments, $R^{18}$ is independently —$NR^{18A}SO_2R^{18D}$. In embodiments, $R^{18}$ is independently —$NR^{18A}C(O)R^{18C}$. In embodiments, $R^{18}$ is independently —$NR^{18A}C(O)OR^{18C}$. In embodiments, $R^{18}$ is independently —$NR^{18A}OR^{18C}$. In embodiments, $R^{18}$ is independently hydrogen.

In embodiments, $R^{18}$ is independently oxo. In embodiments, $R^{18}$ is independently halogen. In embodiments, $R^{18}$ is independently —$CCl_3$. In embodiments, $R^{18}$ is independently —$CBr_3$. In embodiments, $R^{18}$ is independently —$CF_3$. In embodiments, $R^{18}$ is independently —$CI_3$. In embodiments, $R^{18}$ is independently —$CHCl_2$. In embodiments, $R^{18}$ is independently —$CHBr_2$. In embodiments, $R^{18}$ is independently —$CHF_2$. In embodiments, $R^{18}$ is independently —$CHI_2$. In embodiments, $R^{18}$ is independently —$CH_2Cl$. In embodiments, $R^{18}$ is independently —$CH_2Br$. In embodiments, $R^{18}$ is independently —$CH_2F$. In embodiments, $R^{18}$ is independently —$CH_2I$. In embodiments, $R^{18}$ is independently —CN. In embodiments, $R^{18}$ is independently —OH. In embodiments, $R^{18}$ is independently —$NH_2$. In embodiments, $R^{18}$ is independently —COOH. In embodiments, $R^{18}$ is independently —$CONH_2$. In embodiments, $R^{18}$ is independently —$NO_2$. In embodiments, $R^{18}$ is independently —SH. In embodiments, $R^{18}$ is independently —$SO_3H$. In embodiments, $R^{18}$ is independently —$SO_4H$. In embodiments, $R^{18}$ is independently —$SO_2NH_2$. In embodiments, $R^{18}$ is independently —$NHNH_2$. In embodiments, $R^{18}$ is independently —$ONH_2$. In embodiments, $R^{18}$ is independently —$NHC(O)NHNH_2$. In embodiments, $R^{18}$ is independently —$NHC(O)NH_2$. In embodiments, $R^{18}$ is independently —$NHSO_2H$. In embodiments, $R^{18}$ is independently —NHC(O)H. In embodiments, $R^{1D}$ is independently —NHC(O)OH. In embodiments, $R^{18}$ is independently —NHOH. In embodiments, $R^{18}$ is independently —$OCCl_3$. In embodiments, $R^{18}$ is independently —$OCF_3$. In embodiments, $R^{18}$ is independently —$OCBr_3$. In embodiments, $R^{18}$ is independently —$OCI_3$. In embodiments, $R^{18}$ is independently —$OCHCl_2$. In embodiments, $R^{18}$ is independently —$OCHBr_2$. In embodiments, $R^{18}$ is independently —$OCHI_2$. In embodiments, $R^{18}$ is independently —$OCHF_2$. In embodiments, $R^{18}$ is independently —$OCH_2Cl$. In embodiments, $R^{18}$ is independently —$OCH_2Br$. In embodiments, $R^{18}$ is independently —$OCH_2I$. In embodiments, $R^{18}$ is independently —$OCH_2F$. In embodiments, $R^{18}$ is independently —$N_3$. In embodiments, $R^{18}$ is independently —$OCH_3$. In embodiments, $R^{18}$ is idenpendently —$CH_3$. In embodiments, $R^{18}$ is idenpendently —$CH_2CH_3$. In embodiments, $R^{18}$ is independently unsubstituted propyl. In embodiments, $R^{18}$ is independently unsubstituted isopropyl. In embodiments, $R^{18}$ is independently unsubstituted butyl. In embodiments, $R^{18}$ is independently unsubstituted tert-butyl. In embodiments, $R^{18}$ is independently —F. In embodiments, $R^{18}$ is independently —Cl. In embodiments, $R^{18}$ is independently —Br. In embodiments, $R^{18}$ is independently —I.

$R^{42}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{42}$ is independently oxo. In embodiments, $R^{42}$ is independently halogen. In embodiments, $R^{42}$ is independently —$CCl_3$. In embodiments, $R^{42}$ is independently —$CBr_3$. In embodiments, $R^{42}$ is independently —$CF_3$. In embodiments, $R^{42}$ is independently —$CI_3$. In embodiments, $R^{42}$ is independently —$CHCl_2$. In embodiments, $R^{42}$ is independently —$CHBr_2$. In embodiments, $R^{42}$ is independently —$CHF_2$. In embodiments, $R^{42}$ is independently —$CHI_2$. In embodiments, $R^{42}$ is independently —$CH_2Cl$. In embodiments, $R^{42}$ is independently —$CH_2Br$. In embodiments, $R^{42}$ is independently —$CH_2F$. In embodiments, $R^{42}$ is independently —$CH_2I$. In embodiments, $R^{42}$ is independently —CN. In embodiments, $R^{42}$ is independently —OH. In embodiments, $R^{42}$ is independently —$NH_2$. In embodiments, $R^{42}$ is independently —COOH. In embodiments, $R^{42}$ is independently —$CONH_2$. In embodiments, $R^{42}$ is independently —$NO_2$. In embodiments, $R^{42}$ is independently —SH. In embodiments, $R^{42}$ is independently —$SO_3H$. In embodiments, $R^{42}$ is independently —$SO_4H$. In embodiments, $R^{42}$ is independently —$SO_2NH_2$. In embodiments, $R^{42}$ is independently —$NHNH_2$. In embodiments, $R^{42}$ is independently —$ONH_2$. In embodiments, $R^{42}$ is independently —$NHC(O)NHNH_2$. In embodiments, $R^{42}$ is independently —$NHC(O)NH_2$. In embodiments, $R^{42}$ is independently —$NHSO_2H$. In embodiments, $R^{42}$ is independently —NHC(O)H. In embodiments, $R^{42}$ is independently —NHC(O)OH. In embodiments, $R^{42}$ is independently —NHOH. In embodiments, $R^{42}$ is independently —$OCCl_3$. In embodiments, $R^{42}$ is independently —$OCF_3$. In embodiments, $R^{42}$ is independently —$OCBr_3$. In embodiments, $R^{42}$ is independently —$OCI_3$. In embodiments, $R^{42}$ is independently —$OCHCl_2$. In embodiments, $R^{42}$ is independently —$OCHBr_2$. In embodiments, $R^{42}$ is independently —$OCHI_2$. In embodiments, $R^{42}$ is independently —$OCHF_2$. In embodiments, $R^{42}$ is independently —$OCH_2Cl$. In embodiments, $R^{42}$ is independently —$OCH_2Br$. In embodiments, $R^{42}$ is independently —$OCH_2I$. In embodiments, $R^{42}$ is independently —$OCH_2F$. In embodiments, $R^{42}$ is independently —$N_3$. In embodiments, $R^{42}$ is independently —$OCH_3$. In embodiments, $R^{42}$ is idenpendently —$CH_3$. In embodiments, $R^{42}$ is idenpendently —$CH_2CH_3$. In embodiments, $R^{42}$ is independently unsubstituted propyl. In embodiments, $R^{42}$ is independently unsubstituted isopropyl. In embodiments, $R^{42}$ is independently unsubstituted butyl. In embodiments, $R^{42}$ is independently unsubstituted tert-butyl. In embodiments, $R^{42}$ is independently —F. In embodiments, $R^{42}$ is independently —Cl. In embodiments, $R^{42}$ is independently —Br. In embodiments, $R^{42}$ is independently —I.

In embodiments, $R^{18A}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{18B}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{18C}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{18D}$ is independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2T$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{18A}$ and $R^{18B}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl). In embodiments, $R^{18A}$ and $R^{18D}$ substituents bonded to the same nitrogen atom are independently joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18A}$ and $R^{18B}$ substituents bonded to the same nitrogen atom are independently joined to form a substituted heterocycloalkyl (e.g., 3 to 8 membered heterocycloalkyl, 3 to 6 membered heterocycloalkyl, or 5 to 6 membered heterocycloalkyl). In embodiments, $R^{18A}$ and $R^{18B}$ substituents bonded to the same nitrogen atom are independently joined to form an unsubstituted heterocycloalkyl (e.g., 3 to 8 membered heterocycloalkyl, 3 to 6 membered heterocycloalkyl, or 5 to 6 membered heterocycloalkyl). In embodiments, $R^{18A}$ and $R^{18B}$ substituents bonded to the same nitrogen atom are independently joined to form a substituted or unsubstituted heteroaryl (e.g., 5 to 10 membered heteroaryl, 5 to 9 membered heteroaryl, or 5 to 6 membered heteroaryl). In embodiments, $R^{18A}$ and $R^{18B}$ substituents bonded to the same nitrogen atom are independently joined to form a substituted heteroaryl (e.g., 5 to 10 membered heteroaryl, 5 to 9 membered heteroaryl, or 5 to 6 membered heteroaryl). In embodiments, $R^{18A}$ and $R^{18B}$ substituents bonded to the same nitrogen atom are independently joined to form an unsubstituted heteroaryl (e.g., 5 to 10 membered heteroaryl, 5 to 9 membered heteroaryl, or 5 to 6 membered heteroaryl).

In embodiments, $R^{18A}$, $R^{18B}$, $R^{18C}$, and $R^{18D}$ are independently hydrogen, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{42}$-substituted or unsubstituted alkyl (e.g., $C_1$-$C_8$ alkyl, $C_1$-$C_6$ alkyl, or $C_1$-$C_4$ alkyl), $R^{42}$-substituted or unsubstituted heteroalkyl (e.g., 2 to 8 membered heteroalkyl, 2 to 6 membered heteroalkyl, or 2 to 4 membered heteroalkyl), $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{42}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42}$-substituted or unsubstituted aryl (e.g., $C_6$-$C_{10}$ aryl, $C_{10}$ aryl, or phenyl), or $R^{42}$-substituted or unsubstituted heteroaryl (e.g., 5 to 10 membered heteroaryl, 5 to 9 membered heteroaryl, or 5 to 6 membered heteroaryl). In embodiments, $R^{18A}$ and $R^{18B}$ substituents bonded to the same nitrogen atom are independently joined to form an $R^{42}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{42}$-substituted or unsubstituted heteroaryl (e.g., 5 to 10 membered heteroaryl, 5 to 9 membered heteroaryl, or 5 to 6 membered heteroaryl). In embodiments, $R^{18A}$ and $R^{18B}$ substituents bonded to the same nitrogen atom are independently joined to form an $R^{42}$-substituted or unsubstituted heterocycloalkyl (e.g., 3 to 8 membered heterocycloalkyl, 3 to 6 membered heterocycloalkyl. In embodiments, $R^{18A}$ and $R^{18B}$ substituents bonded to the same nitrogen atom are independently joined to form an $R^{42}$-substituted or unsubstituted heteroaryl (e.g., 5 to 10 membered heteroaryl, 5 to 9 membered heteroaryl, or 5 to 6 membered heteroaryl).

In embodiments, $R^{18A}$ is independently $R^{42}$-substituted or unsubstituted alkyl (e.g., $C_1$-$C_8$ alkyl, $C_1$-$C_6$ alkyl, or $C_1$-$C_4$ alkyl). In embodiments, $R^{18A}$ is independently $R^{42}$-substituted alkyl (e.g., $C_1$-$C_8$ alkyl, $C_1$-$C_6$ alkyl, or $C_1$-$C_4$ alkyl). In embodiments, $R^{18A}$ is independently an unsubstituted alkyl (e.g., $C_1$-$C_8$ alkyl, $C_1$-$C_6$ alkyl, or $C_1$-$C_4$ alkyl). In embodiments, $R^{18A}$ is independently $R^{42}$-substituted or unsubstituted heteroalkyl (e.g., 2 to 8 membered heteroalkyl, 2 to 6 membered heteroalkyl, or 2 to 4 membered heteroalkyl). In embodiments, $R^{18A}$ is independently $R^{42}$-substituted heteroalkyl (e.g., 2 to 8 membered heteroalkyl, 2 to 6 membered heteroalkyl, or 2 to 4 membered heteroalkyl). In embodiments, $R^{18A}$ is independently an unsubstituted heteroalkyl (e.g., 2 to 8 membered heteroalkyl, 2 to 6 membered heteroalkyl, or 2 to 4 membered heteroalkyl). In embodiments, $R^{18A}$ is independently $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18A}$ is independently $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18A}$ is independently $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18A}$ is independently $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{18A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{18A}$ is independently $R^{42}$-substituted or unsubstituted aryl (e.g., $C_6$-$C_{10}$ aryl, $C_{10}$ aryl, or phenyl). In embodiments, $R^{18A}$ is independently $R^{42}$-substituted aryl (e.g., $C_6$-$C_{10}$ aryl, $C_{10}$ aryl, or phenyl). In embodiments, $R^{18A}$ is independently an unsubstituted aryl (e.g., $C_6$-$C_{10}$ aryl, $C_{10}$ aryl, or phenyl). In embodiments, $R^{18A}$ is independently $R^{42}$-substituted or unsubstituted heteroaryl (e.g., 5 to 10 membered heteroaryl, 5 to 9 membered heteroaryl, or 5 to 6 membered heteroaryl).

In embodiments, $R^{18A}$ is independently $R^{42}$-substituted heteroaryl (e.g., 5 to 10 membered heteroaryl, 5 to 9 membered heteroaryl, or 5 to 6 membered heteroaryl). In embodiments, $R^{18A}$ is independently an unsubstituted heteroaryl (e.g., 5 to 10 membered heteroaryl, 5 to 9 membered heteroaryl, or 5 to 6 membered heteroaryl).

In embodiments, $R^{18A}$ is independently —CCl$_3$. In embodiments, $R^{18A}$ is independently —CBr$_3$. In embodiments, $R^{18A}$ is independently —CF$_3$. In embodiments, $R^{18A}$ is independently —CI$_3$. In embodiments, $R^{18A}$ is independently —CHCl$_2$. In embodiments, $R^{18A}$ is independently —CHBr$_2$. In embodiments, $R^{18A}$ is independently —CHF$_2$. In embodiments, $R^{18A}$ is independently —CHI$_2$. In embodiments, $R^{18A}$ is independently —CH$_2$Cl. In embodiments, $R^{18A}$ is independently —CH$_2$Br. In embodiments, $R^{18A}$ is independently —CH$_2$F. In embodiments, $R^{18A}$ is independently —CH$_2$I. In embodiments, $R^{18A}$ is independently —CN. In embodiments, $R^{18A}$ is independently —OH. In embodiments, $R^{18A}$ is independently —COOH. In embodiments, $R^{18A}$ is independently —CONH$_2$. In embodiments, $R^{18A}$ is independently —OCCl$_3$. In embodiments, $R^{18A}$ is independently —OCF$_3$. In embodiments, $R^{18A}$ is independently —OCBr$_3$. In embodiments, $R^{18A}$ is independently —OCI$_3$. In embodiments, $R^{18A}$ is independently —OCHCl$_2$. In embodiments, $R^{18A}$ is independently —OCHBr$_2$. In embodiments, $R^{18A}$ is independently —OCHI$_2$. In embodiments, $R^{18A}$ is independently —OCHF$_2$. In embodiments, $R^{18A}$ is independently —OCH$_2$Cl. In embodiments, $R^{18A}$ is independently —OCH$_2$Br. In embodiments, $R^{18A}$ is independently —OCH$_2$I. In embodiments, $R^{18A}$ is independently —OCH$_2$F. In embodiments, $R^{18A}$ is independently —OCH$_3$. In embodiments, $R^{18A}$ is idenpendently —CH$_3$. In embodiments, $R^{18A}$ is idenpendently —CH$_2$CH$_3$. In embodiments, $R^{18A}$ is independently unsubstituted propyl. In embodiments, $R^{18A}$ is independently unsubstituted isopropyl. In embodiments, $R^{18A}$ is independently unsubstituted butyl. In embodiments, $R^{18A}$ is independently unsubstituted tert-butyl. In embodiments, $R^{18A}$ is independently hydrogen.

In embodiments, $R^{18B}$ is independently $R^{42}$-substituted or unsubstituted alkyl (e.g., $C_1$-$C_8$ alkyl, $C_1$-$C_6$ alkyl, or $C_1$-$C_4$ alkyl). In embodiments, $R^{18B}$ is independently $R^{42}$-substituted alkyl (e.g., $C_1$-$C_8$ alkyl, $C_1$-$C_6$ alkyl, or $C_1$-$C_4$ alkyl). In embodiments, $R^{18B}$ is independently an unsubstituted alkyl (e.g., $C_1$-$C_8$ alkyl, $C_1$-$C_6$ alkyl, or $C_1$-$C_4$ alkyl). In embodiments, $R^{18B}$ is independently $R^{42}$-substituted or unsubstituted heteroalkyl (e.g., 2 to 8 membered heteroalkyl, 2 to 6 membered heteroalkyl, or 2 to 4 membered heteroalkyl). In embodiments, $R^{18B}$ is independently $R^{42}$-substituted heteroalkyl (e.g., 2 to 8 membered heteroalkyl, 2 to 6 membered heteroalkyl, or 2 to 4 membered heteroalkyl). In embodiments, $R^{18B}$ is independently an unsubstituted heteroalkyl (e.g., 2 to 8 membered heteroalkyl, 2 to 6 membered heteroalkyl, or 2 to 4 membered heteroalkyl). In embodiments, $R^{18B}$ is independently $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18B}$ is independently $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18B}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18B}$ is independently $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18B}$ is independently $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{18B}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{18B}$ is independently $R^{42}$-substituted or unsubstituted aryl (e.g., $C_6$-$C_{10}$ aryl, $C_{10}$ aryl, or phenyl). In embodiments, $R^{18B}$ is independently $R^{42}$-substituted aryl (e.g., $C_6$-$C_{10}$ aryl, $C_{10}$ aryl, or phenyl). In embodiments, $R^{18B}$ is independently an unsubstituted aryl (e.g., $C_6$-$C_{10}$ aryl, $C_{10}$ aryl, or phenyl). In embodiments, $R^{18B}$ is independently $R^{42}$-substituted or unsubstituted heteroaryl (e.g., 5 to 10 membered heteroaryl, 5 to 9 membered heteroaryl, or 5 to 6 membered heteroaryl). In embodiments, $R^{18B}$ is independently $R^{42}$-substituted heteroaryl (e.g., 5 to 10 membered heteroaryl, 5 to 9 membered heteroaryl, or 5 to 6 membered heteroaryl). In embodiments, $R^{18B}$ is independently an unsubstituted heteroaryl (e.g., 5 to 10 membered heteroaryl, 5 to 9 membered heteroaryl, or 5 to 6 membered heteroaryl).

In embodiments, $R^{18B}$ is independently —CCl$_3$. In embodiments, $R^{18B}$ is independently —CBr$_3$. In embodiments, $R^{18B}$ is independently —CF$_3$. In embodiments, $R^{18B}$ is independently —CI$_3$. In embodiments, $R^{18B}$ is independently —CHCl$_2$. In embodiments, $R^{18B}$ is independently —CHBr$_2$. In embodiments, $R^{18B}$ is independently —CHF$_2$. In embodiments, $R^{18B}$ is independently —CHI$_2$. In embodiments, $R^{18B}$ is independently —CH$_2$Cl. In embodiments, $R^{18B}$ is independently —CH$_2$Br. In embodiments, $R^{18B}$ is independently —CH$_2$F. In embodiments, $R^{18B}$ is independently —CH$_2$I. In embodiments, $R^{18B}$ is independently —CN. In embodiments, $R^{18B}$ is independently —OH. In embodiments, $R^{18B}$ is independently —COOH. In embodiments, $R^{18B}$ is independently —CONH$_2$. In embodiments, $R^{18B}$ is independently —OCCl$_3$. In embodiments, $R^{18B}$ is independently —OCF$_3$. In embodiments, $R^{18B}$ is independently —OCBr$_3$. In embodiments, $R^{18B}$ is independently —OCI$_3$. In embodiments, $R^{18B}$ is independently —OCHCl$_2$. In embodiments, $R^{18B}$ is independently —OCHBr$_2$. In embodiments, $R^{18B}$ is independently —OCHI$_2$. In embodiments, $R^{18B}$ is independently —OCHF$_2$. In embodiments, $R^{18B}$ is independently —OCH$_2$Cl. In embodiments, $R^{18B}$ is independently —OCH$_2$Br. In embodiments, $R^{18B}$ is independently —OCH$_2$I. In embodiments, $R^{18B}$ is independently —OCH$_2$F. In embodiments, $R^{18B}$ is independently OCH$_3$. In embodiments, $R^{18B}$ is idenpendently —CH$_3$. In embodiments, $R^{18B}$ is independently CH$_2$CH$_3$. In embodiments, $R^{18B}$ is independently unsubstituted propyl. In embodiments, $R^{18B}$ is independently unsubstituted isopropyl. In embodiments, $R^{18B}$ is independently unsubstituted butyl. In embodiments, $R^{18B}$ is independently unsubstituted tert-butyl. In embodiments, $R^{18B}$ is independently hydrogen.

In embodiments, $R^{18C}$ is independently $R^{42}$-substituted or unsubstituted alkyl (e.g., $C_1$-$C_8$ alkyl, $C_1$-$C_6$ alkyl, or $C_1$-$C_4$ alkyl). In embodiments, $R^{18C}$ is independently $R^{42}$-substituted alkyl (e.g., $C_1$-$C_8$ alkyl, $C_1$-$C_6$ alkyl, or $C_1$-$C_4$ alkyl). In embodiments, $R^{18C}$ is independently an unsubstituted alkyl (e.g., $C_1$-$C_8$ alkyl, $C_1$-$C_6$ alkyl, or $C_1$-$C_4$ alkyl). In embodiments, $R^{18C}$ is independently $R^{42}$-substituted or unsubstituted heteroalkyl (e.g., 2 to 8 membered heteroalkyl, 2 to 6 membered heteroalkyl, or 2 to 4 membered heteroalkyl). In embodiments, $R^{18C}$ is independently $R^{42}$-substituted heteroalkyl (e.g., 2 to 8 membered heteroalkyl, 2 to 6 membered heteroalkyl, or 2 to 4 membered heteroalkyl). In embodiments, $R^{18C}$ is independently an unsubstituted heteroalkyl (e.g., 2 to 8 membered heteroalkyl, 2 to 6 membered heteroalkyl, or 2 to 4 membered heteroalkyl). In embodiments, $R^{18C}$ is independently $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18C}$ is independently $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18C}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18C}$ is independently $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18C}$ is independently $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{18C}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{18C}$ is independently $R^{42}$-substituted or unsubstituted aryl (e.g., $C_6$-$C_{10}$ aryl, $C_{10}$ aryl, or phenyl). In embodiments, $R^{18C}$ is independently $R^{42}$-substituted aryl (e.g., $C_6$-$C_{10}$ aryl, $C_{10}$ aryl, or phenyl). In embodiments, $R^{18C}$ is independently an unsubstituted aryl (e.g., $C_6$-$C_{10}$ aryl, $C_{10}$ aryl, or phenyl). In embodiments, $R^{18C}$ is independently $R^{42}$-substituted or unsubstituted heteroaryl (e.g., 5 to 10 membered heteroaryl, 5 to 9 membered heteroaryl, or 5 to 6 membered heteroaryl). In embodiments, $R^{18C}$ is independently $R^{42}$-substituted heteroaryl (e.g., 5 to 10 membered heteroaryl, 5 to 9 membered heteroaryl, or 5 to 6 membered heteroaryl). In embodiments, $R^{18C}$ is independently an unsubstituted heteroaryl (e.g., 5 to 10 membered heteroaryl, 5 to 9 membered heteroaryl, or 5 to 6 membered heteroaryl).

In embodiments, $R^{18C}$ is independently —$CCl_3$. In embodiments, $R^{18C}$ is independently —$CBr_3$. In embodiments, $R^{18C}$ is independently —$CF_3$. In embodiments, $R^{18C}$ is independently —$CI_3$. In embodiments, $R^{18C}$ is independently —$CHCl_2$. In embodiments, $R^{18C}$ is independently —$CHBr_2$. In embodiments, $R^{18C}$ is independently —$CHF_2$. In embodiments, $R^{18C}$ is independently —$CHI_2$. In embodiments, $R^{18C}$ is independently —$CH_2Cl$. In embodiments, $R^{18C}$ is independently —$CH_2Br$. In embodiments, $R^{18C}$ is independently —$CH_2F$. In embodiments, $R^{18C}$ is independently —$CH_2I$. In embodiments, $R^{18C}$ is independently —CN. In embodiments, $R^{18C}$ is independently —OH. In embodiments, $R^{18C}$ is independently —COOH. In embodiments, $R^{18C}$ is independently —$CONH_2$. In embodiments, $R^{18C}$ is independently —$OCCl_3$. In embodiments, $R^{18C}$ is independently —$OCF_3$. In embodiments, $R^{18C}$ is independently —$OCBr_3$. In embodiments, $R^{18C}$ is independently —$OCl_3$. In embodiments, $R^{18C}$ is independently —$OCHCl_2$. In embodiments, $R^{18C}$ is independently —$OCHBr_2$. In embodiments, $R^{18C}$ is independently —$OCHI_2$. In embodiments, $R^{18C}$ is independently —$OCHF_2$. In embodiments, $R^{18C}$ is independently —$OCH_2Cl$. In embodiments, $R^{18C}$ is independently —$OCH_2Br$. In embodiments, $R^{18C}$ is independently —$OCH_2I$. In embodiments, $R^{18C}$ is independently —$OCH_2F$. In embodiments, $R^{18C}$ is independently —$OCH_3$. In embodiments, $R^{18C}$ is independently $CH_3$. In embodiments, $R^{18C}$ is idenpendently —$CH_2CH_3$. In embodiments, $R^{18C}$ is independently unsubstituted propyl. In embodiments, $R^{18C}$ is independently unsubstituted isopropyl. In embodiments, $R^{18C}$ is independently unsubstituted butyl. In embodiments, $R^{18C}$ is independently unsubstituted tert-butyl. In embodiments, $R^{18C}$ is independently hydrogen.

In embodiments, $R^{18D}$ is independently $R^{42}$-substituted or unsubstituted alkyl (e.g., $C_1$-$C_8$ alkyl, $C_1$-$C_6$ alkyl, or $C_1$-$C_4$ alkyl). In embodiments, $R^{18D}$ is independently $R^{42}$-substituted alkyl (e.g., $C_1$-$C_8$ alkyl, $C_1$-$C_6$ alkyl, or $C_1$-$C_4$ alkyl). In embodiments, $R^{18D}$ is independently an unsubstituted alkyl (e.g., $C_1$-$C_8$ alkyl, $C_1$-$C_6$ alkyl, or $C_1$-$C_4$ alkyl). In embodiments, $R^{18D}$ is independently $R^{42}$-substituted or unsubstituted heteroalkyl (e.g., 2 to 8 membered heteroalkyl, 2 to 6 membered heteroalkyl, or 2 to 4 membered heteroalkyl). In embodiments, $R^{18D}$ is independently $R^{42}$-substituted heteroalkyl (e.g., 2 to 8 membered heteroalkyl, 2 to 6 membered heteroalkyl, or 2 to 4 membered heteroalkyl). In embodiments, $R^{18D}$ is independently an unsubstituted heteroalkyl (e.g., 2 to 8 membered heteroalkyl, 2 to 6 membered heteroalkyl, or 2 to 4 membered heteroalkyl). In embodiments, $R^{18D}$ is independently $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18D}$ is independently $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18D}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18D}$ is independently $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18D}$ is independently $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{18D}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{18D}$ is independently $R^{42}$-substituted or unsubstituted aryl (e.g., $C_6$-$C_{10}$ aryl, $C_{10}$ aryl, or phenyl). In embodiments, $R^{18D}$ is independently $R^{42}$-substituted aryl (e.g., $C_6$-$C_{10}$ aryl, $C_{10}$ aryl, or phenyl). In embodiments, $R^{18D}$ is independently an unsubstituted aryl (e.g., $C_6$-$C_{10}$ aryl, $C_{10}$ aryl, or phenyl). In embodiments, $R^{18D}$ is independently $R^{42}$-substituted or unsubstituted heteroaryl (e.g., 5 to 10 membered heteroaryl, 5 to 9 membered heteroaryl, or 5 to 6 membered heteroaryl). In embodiments, $R^{18D}$ is independently $R^{42}$-substituted heteroaryl (e.g., 5 to 10 membered heteroaryl, 5 to 9 membered heteroaryl, or 5 to 6 membered heteroaryl). In embodiments, $R^{18D}$ is independently an unsubstituted heteroaryl (e.g., 5 to 10 membered heteroaryl, 5 to 9 membered heteroaryl, or 5 to 6 membered heteroaryl).

In embodiments, $R^{18D}$ is independently —$CCl_3$. In embodiments, $R^{18D}$ is independently —$CBr_3$. In embodiments, $R^{18D}$ is independently —$CF_3$. In embodiments, $R^{18D}$ is independently —$CI_3$. In embodiments, $R^{18D}$ is independently —$CHCl_2$. In embodiments, $R^{18D}$ is independently —$CHBr_2$. In embodiments, $R^{18D}$ is independently —$CHF_2$. In embodiments, $R^{18D}$ is independently —$CHI_2$. In embodiments, $R^{18D}$ is independently —$CH_2Cl$. In embodiments, $R^{18D}$ is independently —$CH_2Br$. In embodiments, $R^{18D}$ is independently —$CH_2F$. In embodiments, $R^{18D}$ is independently —$CH_2I$. In embodiments, $R^{18D}$ is independently —CN. In embodiments, $R^{18D}$ is independently —OH. In embodiments, $R^{18D}$ is independently —COOH. In embodiments, $R^{18D}$ is independently —$CONH_2$. In embodiments, $R^{18D}$ is independently —$OCCl_3$. In embodiments, $R^{18D}$ is independently —$OCF_3$. In embodiments, $R^{18D}$ is independently —$OCBr_3$. In embodiments, $R^{18D}$ is independently —$OCl_3$. In embodiments, $R^{18D}$ is independently —$OCHCl_2$. In embodiments, $R^{18D}$ is independently —$OCHBr_2$. In embodiments, $R^{18D}$ is independently —$OCHI_2$. In embodiments, $R^{18D}$ is independently —$OCHF_2$. In embodiments, $R^{18D}$ is independently —$OCH_2Cl$. In embodiments, $R^{18D}$ is independently —$OCH_2Br$. In embodiments, $R^{18D}$ is independently —$OCH_2I$. In embodiments, $R^{18D}$ is independently —OCH$_2$F. In embodiments, R$^{18D}$ is independently —OCH$_3$. In embodiments, R$^{18D}$ is idenpendently —CH$_3$. In embodiments, R$^{18D}$ is idenpendently —CH$_2$CH$_3$. In embodiments, R$^{18D}$ is independently unsubstituted propyl. In embodiments, R$^{18D}$ is independently unsubstituted isopropyl. In embodiments, R$^{18D}$ is independently unsubstituted butyl. In embodiments, R$^{18D}$ is independently unsubstituted tert-butyl. In embodiments, R$^{18D}$ is independently hydrogen.

In embodiments, L$^1$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene (e.g., C$_1$-C$_8$ alkylene, C$_1$-C$_6$ alkylene, or C$_1$-C$_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., C$_3$-C$_8$ cycloalkylene, C$_3$-C$_6$ cycloalkylene, or C$_5$-C$_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., C$_6$-C$_{10}$ arylene, C$_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, L$^1$ is independently a —S(O)$_2$—. In embodiments, L$^1$ is independently a —S(O)—. In embodiments, L$^1$ is independently a —NH—. In embodiments, L$^1$ is independently a —O—. In embodiments, L$^1$ is independently a —S—. In embodiments, L$^1$ is independently a —C(O)—. In embodiments, L$^1$ is independently a —C(O)NH—. In embodiments, L$^1$ is independently a —NHC(O)—. In embodiments, L$^1$ is independently a —NHC(O)NH—. In embodiments, L$^1$ is independently a —C(O)O—. In embodiments, L$^1$ is independently —OC(O)—.

In embodiments, L$^1$ is substituted or unsubstituted alkylene (e.g., C$_1$-C$_8$ alkylene, C$_1$-C$_6$ alkylene, or C$_1$-C$_4$ alkylene). In embodiments, L$^1$ is substituted alkylene (e.g., C$_1$-C$_8$ alkylene, C$_1$-C$_6$ alkylene, or C$_1$-C$_4$ alkylene). In embodiments, L$^1$ is an unsubstituted alkylene (e.g., C$_1$-C$_8$ alkylene, C$_1$-C$_6$ alkylene, or C$_1$-C$_4$ alkylene). In embodiments, L$^1$ is substituted or unsubstituted heteroalkylene (e.g., 2 to 8 membered heteroalkylene, 2 to 6 membered heteroalkylene, or 2 to 4 membered heteroalkylene). In embodiments, L$^1$ is substituted heteroalkylene (e.g., 2 to 8 membered heteroalkylene, 2 to 6 membered heteroalkylene, or 2 to 4 membered heteroalkylene). In embodiments, L$^1$ is an unsubstituted heteroalkylene (e.g., 2 to 8 membered heteroalkylene, 2 to 6 membered heteroalkylene, or 2 to 4 membered heteroalkylene). In embodiments, L$^1$ is substituted or unsubstituted cycloalkylene (e.g., C$_3$-C$_8$ cycloalkylene, C$_3$-C$_6$ cycloalkylene, or C$_5$-C$_6$ cycloalkylene). In embodiments, L$^1$ is substituted cycloalkylene (e.g., C$_3$-C$_8$ cycloalkylene, C$_3$-C$_6$ cycloalkylene, or C$_5$-C$_6$ cycloalkylene). In embodiments, L$^1$ is an unsubstituted cycloalkylene (e.g., C$_3$-C$_8$ cycloalkylene, C$_3$-C$_6$ cycloalkylene, or C$_5$-C$_6$ cycloalkylene). In embodiments, L$^1$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, L$^1$ is substituted heterocycloalkylene (e.g., 3 to 8 membered heterocycloalkylene, 3 to 6 membered heterocycloalkylene, or 5 to 6 membered heterocycloalkylene). In embodiments, L$^1$ is an unsubstituted heterocycloalkylene (e.g., 3 to 8 membered heterocycloalkylene, 3 to 6 membered heterocycloalkylene, or 5 to 6 membered heterocycloalkylene). In embodiments, L$^1$ is substituted or unsubstituted arylene (e.g., C$_6$-C$_{10}$ arylene, C$_{10}$ arylene, or phenylene). In embodiments, L$^1$ is substituted arylene (e.g., C$_6$-C$_{10}$ arylene, C$_{10}$ arylene, or phenylene). In embodiments, L$^1$ is an unsubstituted arylene (e.g., C$_6$-C$_{10}$ arylene, C$_{10}$ arylene, or phenylene). In embodiments, L$^1$ is substituted or unsubstituted heteroarylene (e.g., 5 to 10 membered heteroarylene, 5 to 9 membered heteroarylene, or 5 to 6 membered heteroarylene). In embodiments, L$^1$ is substituted heteroarylene (e.g., 5 to 10 membered heteroarylene, 5 to 9 membered heteroarylene, or 5 to 6 membered heteroarylene). In embodiments, L$^1$ is an unsubstituted heteroarylene (e.g., 5 to 10 membered heteroarylene, 5 to 9 membered heteroarylene, or 5 to 6 membered heteroarylene).

In embodiments, L$^1$ is independently —S(O)$_2$—, —S(O)—, —NH—, —O—, —S—, —C(O)—, —C(O)NH—, —NHC(O)—, —NHC(O)NH—, —C(O)O—, —OC(O)—, R$^{43}$-substituted or unsubstituted alkylene (e.g., C$_1$-C$_8$ alkylene, C$_1$-C$_6$ alkylene, or C$_1$-C$_4$ alkylene), R$^{43}$-substituted or unsubstituted heteroalkylene (e.g., 2 to 8 membered heteroalkylene, 2 to 6 membered heteroalkylene, or 2 to 4 membered heteroalkylene), R$^{43}$-substituted or unsubstituted cycloalkylene (e.g., C$_3$-C$_8$ cycloalkylene, C$_3$-C$_6$ cycloalkylene, or C$_5$-C$_6$ cycloalkylene), R$^{43}$-substituted or unsubstituted heterocycloalkylene (e.g., 3 to 8 membered heterocycloalkylene, 3 to 6 membered heterocycloalkylene, or 5 to 6 membered heterocycloalkylene), R$^{43}$-substituted or unsubstituted arylene (e.g., C$_6$-C$_{10}$ arylene, C$_{10}$ arylene, or phenylene), or R$^{43}$-substituted or unsubstituted heteroarylene (e.g., 5 to 10 membered heteroarylene, 5 to 9 membered heteroarylene, or 5 to 6 membered heteroarylene). In embodiments, L$^1$ is independently —S(O)$_2$—, —S(O)—, —NH—, —O—, —S—, —C(O)—, —C(O)NH—, —NHC(O)—, —NHC(O)NH—, —C(O)O—, —OC(O)—, unsubstituted alkylene (e.g., C$_1$-C$_8$ alkylene, C$_1$-C$_6$ alkylene, or C$_1$-C$_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., C$_3$-C$_8$ cycloalkylene, C$_3$-C$_6$ cycloalkylene, or C$_5$-C$_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., C$_6$-C$_{10}$ arylene, C$_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, L$^1$ is R$^{43}$-substituted or unsubstituted alkylene (e.g., C$_1$-C$_8$ alkylene, C$_1$-C$_6$ alkylene, or C$_1$-C$_4$ alkylene). In embodiments, L$^1$ is R$^{43}$-substituted alkylene (e.g., C$_1$-C$_8$ alkylene, C$_1$-C$_6$ alkylene, or C$_1$-C$_4$ alkylene). In embodiments, L$^1$ is an unsubstituted alkylene (e.g., C$_1$-C$_8$ alkylene, C$_1$-C$_6$ alkylene, or C$_1$-C$_4$ alkylene). In embodiments, L$^1$ is R$^{43}$-substituted or unsubstituted heteroalkylene (e.g., 2 to 8 membered heteroalkylene, 2 to 6 membered heteroalkylene, or 2 to 4 membered heteroalkylene). In embodiments, L$^1$ is R$^{43}$-substituted heteroalkylene (e.g., 2 to 8 membered heteroalkylene, 2 to 6 membered heteroalkylene, or 2 to 4 membered heteroalkylene). In embodiments, L$^1$ is an unsubstituted heteroalkylene (e.g., 2 to 8 membered heteroalkylene, 2 to 6 membered heteroalkylene, or 2 to 4 membered heteroalkylene). In embodiments, L$^1$ is R$^{43}$-substituted or unsubstituted cycloalkylene (e.g., C$_3$-C$_8$ cycloalkylene, C$_3$-C$_6$ cycloalkylene, or C$_5$-C$_6$ cycloalkylene). In embodiments, L$^1$ is R$^{43}$-substituted cycloalkylene (e.g., C$_3$-C$_8$ cycloalkylene, C$_3$-C$_6$ cycloalkylene, or C$_5$-C$_6$ cycloalkylene). In embodiments, L$^1$ is an unsubstituted cycloalkylene (e.g., C$_3$-C$_8$ cycloalkylene, C$_3$-C$_6$ cycloalkylene, or $C_5$-$C_6$ cycloalkylene). In embodiments, $L^1$ is $R^{43}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^1$ is $R^{43}$-substituted heterocycloalkylene (e.g., 3 to 8 membered heterocycloalkylene, 3 to 6 membered heterocycloalkylene, or 5 to 6 membered heterocycloalkylene). In embodiments, $L^1$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^1$ is $R^{43}$-substituted or unsubstituted arylene (e.g., $C_6$-$C_{10}$ arylene, $C_{10}$ arylene, or phenylene). In embodiments, 12 is $R^{43}$-substituted arylene (e.g., $C_6$-$C_{10}$ arylene, $C_{10}$ arylene, or phenylene). In embodiments, 12 is an unsubstituted arylene (e.g., $C_6$-$C_{10}$ arylene, $C_{10}$ arylene, or phenylene). In embodiments, 12 is $R^{43}$-substituted or unsubstituted heteroarylene (e.g., 5 to 10 membered heteroarylene, 5 to 9 membered heteroarylene, or 5 to 6 membered heteroarylene). In embodiments, 12 is $R^{43}$-substituted heteroarylene (e.g., 5 to 10 membered heteroarylene, 5 to 9 membered heteroarylene, or 5 to 6 membered heteroarylene). In embodiments, 12 is an unsubstituted heteroarylene (e.g., 5 to 10 membered heteroarylene, 5 to 9 membered heteroarylene, or 5 to 6 membered heteroarylene).

$R^{43}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, $NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{43}$ is independently oxo. In embodiments, $R^{43}$ is independently halogen. In embodiments, $R^{43}$ is independently —$CCl_3$. In embodiments, $R^{43}$ is independently —$CBr_3$. In embodiments, $R^{43}$ is independently —$CF_3$. In embodiments, $R^{43}$ is independently —$CI_3$. In embodiments, $R^{43}$ is independently —$CHCl_2$. In embodiments, $R^{43}$ is independently —$CHBr_2$. In embodiments, $R^{43}$ is independently —$CHF_2$. In embodiments, $R^{43}$ is independently —$CHI_2$. In embodiments, $R^{43}$ is independently —$CH_2Cl$. In embodiments, $R^{43}$ is independently —$CH_2Br$. In embodiments, $R^{43}$ is independently —$CH_2F$. In embodiments, $R^{43}$ is independently —$CH_2I$. In embodiments, $R^{43}$ is independently —CN. In embodiments, $R^{43}$ is independently —OH. In embodiments, $R^{43}$ is independently —$NH_2$. In embodiments, $R^{43}$ is independently —COOH. In embodiments, $R^{43}$ is independently —$CONH_2$. In embodiments, $R^{43}$ is independently —$NO_2$. In embodiments, $R^{43}$ is independently —SH. In embodiments, $R^{43}$ is independently —$SO_3H$. In embodiments, $R^{43}$ is independently —$SO_4H$. In embodiments, $R^{43}$ is independently —$SO_2NH_2$. In embodiments, $R^{43}$ is independently —$NHNH_2$. In embodiments, $R^{43}$ is independently —$ONH_2$. In embodiments, $R^{43}$ is independently —$NHC(O)NHNH_2$. In embodiments, $R^{43}$ is independently —$NHC(O)NH_2$. In embodiments, $R^{43}$ is independently —$NHSO_2H$. In embodiments, $R^{43}$ is independently —$NHC(O)H$. In embodiments, $R^{43}$ is independently —$NHC(O)OH$. In embodiments, $R^{43}$ is independently —NHOH. In embodiments, $R^{43}$ is independently —$OCCl_3$. In embodiments, $R^{43}$ is independently —$OCF_3$. In embodiments, $R^{43}$ is independently —$OCBr_3$. In embodiments, $R^{43}$ is independently —$OCI_3$. In embodiments, $R^{43}$ is independently —$OCHCl_2$. In embodiments, $R^{43}$ is independently —$OCHBr_2$. In embodiments, $R^{43}$ is independently —$OCHI_2$. In embodiments, $R^{43}$ is independently —$OCHF_2$. In embodiments, $R^{43}$ is independently —$OCH_2Cl$. In embodiments, $R^{43}$ is independently —$OCH_2Br$. In embodiments, $R^{43}$ is independently —$OCH_2I$. In embodiments, $R^{43}$ is independently —$OCH_2F$. In embodiments, $R^{43}$ is independently —$N_3$. In embodiments, $R^{43}$ is independently —$OCH_3$. In embodiments, $R^{43}$ is independently —$CH_3$. In embodiments, $R^{43}$ is independently —$CH_2CH_3$. In embodiments, $R^{43}$ is independently unsubstituted propyl. In embodiments, $R^{43}$ is independently unsubstituted isopropyl. In embodiments, $R^{43}$ is independently unsubstituted butyl. In embodiments, $R^{43}$ is independently unsubstituted tert-butyl. In embodiments, $R^{43}$ is independently —F. In embodiments, $R^{43}$ is independently —Cl. In embodiments, $R^{43}$ is independently —Br. In embodiments, $R^{43}$ is independently —I.

In embodiments, $L^2$ is independently a bond, —$S(O)_2$—, —$S(O)$—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^2$ is independently a —$S(O)_2$—. In embodiments, $L^2$ is independently a —$S(O)$—. In embodiments, $L^2$ is independently a —NH—. In embodiments, $L^2$ is independently a —O—. In embodiments, $L^2$ is independently a —S—. In embodiments, $L^2$ is independently a —C(O)—. In embodiments, $L^2$ is independently a —C(O)NH—. In embodiments, $L^2$ is independently a —NHC(O)—. In embodiments, $L^2$ is independently a —NHC(O)NH—. In embodiments, $L^2$ is independently a —C(O)O—. In embodiments, $L^2$ is independently —OC(O)—. In embodiments, $L^2$ is independently a bond.

In embodiments, $L^2$ is substituted or unsubstituted alkylene (e.g., $C_1$-$C_8$ alkylene, $C_1$-$C_6$ alkylene, or $C_1$-$C_4$ alkylene). In embodiments, $L^2$ is substituted alkylene (e.g., $C_1$-$C_8$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene). In embodiments, $L^2$ is substituted or unsubstituted heteroalkylene (e.g., 2 to 8 membered heteroalkylene, 2 to 6 membered heteroalkylene, or 2 to 4 membered heteroalkylene). In embodiments, $L^2$ is substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene). In embodiments, $L^2$ is substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is substituted cycloalkylene (e.g., $C_3$-$C_8$ cycloalkylene, $C_3$-$C_6$ cycloalkylene, or $C_5$-$C_6$ cycloalkylene). In embodiments, $L^2$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is substituted heterocycloalkylene (e.g., 3 to 8 membered heterocycloalkylene, 3 to 6 membered heterocycloalkylene, or 5 to 6 membered heterocycloalkylene). In embodiments, $L^2$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is substituted or unsubstituted arylene (e.g., $C_6$-$C_{10}$ arylene, $C_{10}$ arylene, or phenylene). In embodiments, $L^2$ is substituted arylene (e.g., $C_6$-$C_{10}$ arylene, $C_{10}$ arylene, or phenylene). In embodiments, $L^2$ is an unsubstituted arylene (e.g., $C_6$-$C_{10}$ arylene, $C_{10}$ arylene, or phenylene). In embodiments, $L^2$ is substituted or unsubstituted heteroarylene (e.g., 5 to 10 membered heteroarylene, 5 to 9 membered heteroarylene, or 5 to 6 membered heteroarylene). In embodiments, $L^2$ is substituted heteroarylene (e.g., 5 to 10 membered heteroarylene, 5 to 9 membered heteroarylene, or 5 to 6 membered heteroarylene). In embodiments, $L^2$ is an unsubstituted heteroarylene (e.g., 5 to 10 membered heteroarylene, 5 to 9 membered heteroarylene, or 5 to 6 membered heteroarylene).

In embodiments, $L^2$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, $R^{44}$-substituted or unsubstituted alkylene (e.g., $C_1$-$C_8$ alkylene, $C_1$-$C_6$ alkylene, or $C_1$-$C_4$ alkylene), $R^{44}$-substituted or unsubstituted heteroalkylene (e.g., 2 to 8 membered heteroalkylene, 2 to 6 membered heteroalkylene, or 2 to 4 membered heteroalkylene), $R^{44}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{44}$-substituted or unsubstituted heterocycloalkylene (e.g., 3 to 8 membered heterocycloalkylene, 3 to 6 membered heterocycloalkylene, or 5 to 6 membered heterocycloalkylene), $R^{44}$-substituted or unsubstituted arylene (e.g., $C_6$-$C_{10}$ arylene, $C_{10}$ arylene, or phenylene), or $R^{44}$-substituted or unsubstituted heteroarylene (e.g., 5 to 10 membered heteroarylene, 5 to 9 membered heteroarylene, or 5 to 6 membered heteroarylene). In embodiments, $L^2$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, $L^2$ is $R^{44}$-substituted or unsubstituted alkylene (e.g., $C_1$-$C_8$ alkylene, $C_1$-$C_6$ alkylene, or $C_1$-$C_4$ alkylene). In embodiments, $L^2$ is $R^{44}$-substituted alkylene (e.g., $C_1$-$C_6$ alkylene, $C_1$-$C_6$ alkylene, or $C_1$-$C_4$ alkylene). In embodiments, $L^2$ is an unsubstituted alkylene (e.g., $C_1$-$C_8$ alkylene, $C_1$-$C_6$ alkylene, or $C_1$-$C_4$ alkylene). In embodiments, $L^2$ is $R^{44}$-substituted or unsubstituted heteroalkylene (e.g., 2 to 8 membered heteroalkylene, 2 to 6 membered heteroalkylene, or 2 to 4 membered heteroalkylene). In embodiments, $L^2$ is $R^{44}$-substituted heteroalkylene (e.g., 2 to 8 membered heteroalkylene, 2 to 6 membered heteroalkylene, or 2 to 4 membered heteroalkylene). In embodiments, $L^2$ is an unsubstituted heteroalkylene (e.g., 2 to 8 membered heteroalkylene, 2 to 6 membered heteroalkylene, or 2 to 4 membered heteroalkylene). In embodiments, $L^2$ is $R^{44}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is $R^{44}$-substituted cycloalkylene (e.g., $C_3$-$C_8$ cycloalkylene, $C_3$-$C_6$ cycloalkylene, or $C_5$-$C_6$ cycloalkylene). In embodiments, $L^2$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^2$ is $R^{44}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is $R^{44}$-substituted heterocycloalkylene (e.g., 3 to 8 membered heterocycloalkylene, 3 to 6 membered heterocycloalkylene, or 5 to 6 membered heterocycloalkylene). In embodiments, $L^2$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^2$ is $R^{44}$-substituted or unsubstituted arylene (e.g., $C_6$-$C_{10}$ arylene, $C_{10}$ arylene, or phenylene). In embodiments, $L^2$ is $R^{44}$-substituted arylene (e.g., $C_6$-$C_{10}$ arylene, $C_{10}$ arylene, or phenylene). In embodiments, $L^2$ is an unsubstituted arylene (e.g., $C_6$-$C_{10}$ arylene, $C_{10}$ arylene, or phenylene). In embodiments, $L^2$ is $R^{44}$-substituted or unsubstituted heteroarylene (e.g., 5 to 10 membered heteroarylene, 5 to 9 membered heteroarylene, or 5 to 6 membered heteroarylene). In embodiments, $L^2$ is $R^{44}$-substituted heteroarylene (e.g., 5 to 10 membered heteroarylene, 5 to 9 membered heteroarylene, or 5 to 6 membered heteroarylene). In embodiments, $L^2$ is an unsubstituted heteroarylene (e.g., 5 to 10 membered heteroarylene, 5 to 9 membered heteroarylene, or 5 to 6 membered heteroarylene).

$R^{44}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{44}$ is independently oxo. In embodiments, $R^{44}$ is independently halogen. In embodiments, $R^{44}$ is independently —CCl$_3$. In embodiments, $R^{44}$ is independently —CBr$_3$. In embodiments, $R^{44}$ is independently —CF$_3$. In embodiments, $R^{44}$ is independently —CI$_3$. In embodiments, $R^{44}$ is independently —CHCl$_2$. In embodiments, $R^{44}$ is independently —CHBr$_2$. In embodiments, $R^{44}$ is independently —CHF$_2$. In embodiments, $R^{44}$ is independently —CHI$_2$. In embodiments, $R^{44}$ is independently —CH$_2$Cl. In embodiments, $R^{44}$ is independently —CH$_2$Br. In embodiments, $R^{44}$ is independently —CH$_2$F. In embodiments, $R^{44}$ is independently —CH$_2$I. In embodiments, $R^{44}$ is independently —CN. In embodiments, $R^{44}$ is independently —OH. In embodiments, $R^{44}$ is independently —NH$_2$. In embodiments, $R^{44}$ is independently —COOH. In embodiments, $R^{44}$ is independently —CONH$_2$. In embodiments, $R^{44}$ is independently —NO$_2$. In embodiments, $R^{44}$ is independently —SH. In embodiments, $R^{44}$ is independently —SO$_3$H. In embodiments, $R^{44}$ is independently —SO$_4$H. In embodiments, $R^{44}$ is independently —SO$_2$NH$_2$. In embodiments, $R^{44}$ is independently —NHNH$_2$. In embodiments, $R^{44}$ is independently —ONH$_2$. In embodiments, $R^{44}$ is independently —NHC(O)NHNH$_2$. In embodiments, $R^{44}$ is independently —NHC(O)NH$_2$. In embodiments, $R^{44}$ is independently —NHSO$_2$H. In embodiments, $R^{44}$ is independently —NHC(O)H. In embodiments, $R^{44}$ is independently —NHC(O)OH. In embodiments, $R^{44}$ is independently —NHOH. In embodiments, $R^{44}$ is independently —OCCl$_3$. In embodiments, $R^{44}$ is independently —OCF$_3$. In embodiments, $R^{44}$ is independently —OCBr$_3$. In embodiments, $R^{44}$ is independently —OCI$_3$. In embodiments, $R^{44}$ is independently —OCHCl$_2$. In embodiments, $R^{44}$ is independently —OCHBr$_2$. In embodiments, $R^{44}$ is independently —OCHI$_2$. In embodiments, $R^{44}$ is independently —OCHF$_2$. In embodiments, $R^{44}$ is independently —OCH$_2$Cl. In embodiments, $R^{44}$ is independently —OCH$_2$Br. In embodiments, $R^{44}$ is independently —OCH$_2$I. In embodiments, $R^{44}$ is independently —OCH$_2$F. In embodiments, $R^{44}$ is independently —N$_3$. In embodiments, $R^{44}$ is independently —OCH$_3$. In embodiments, $R^{44}$ is idenpendently —CH$_3$. In embodiments, $R^{44}$ is idenpendently —CH$_2$CH$_3$. In embodiments, $R^{44}$ is independently unsubstituted propyl. In embodiments, $R^{44}$ is independently unsubstituted isopropyl. In embodiments, $R^{44}$ is independently unsubstituted butyl. In embodiments, $R^{44}$ is independently unsubstituted tert-butyl. In embodiments, $R^{44}$ is independently —F. In embodiments, $R^{44}$ is independently —Cl. In embodiments, $R^{44}$ is independently —Br. In embodiments, $R^{44}$ is independently —I.

In embodiments, $L^3$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^3$ is independently a —S(O)$_2$—. In embodiments, $L^3$ is independently a —S(O)—. In embodiments, $L^3$ is independently a —NH—. In embodiments, $L^3$ is independently a —O—. In embodiments, $L^3$ is independently a —S—. In embodiments, $L^3$ is independently a —C(O)—. In embodiments, $L^3$ is independently a —C(O)NH—. In embodiments, $L^3$ is independently a —NHC(O)—. In embodiments, $L^3$ is independently a —NHC(O)NH—. In embodiments, $L^3$ is independently a —C(O)O—. In embodiments, $L^3$ is independently —OC(O)—. In embodiments, $L^3$ is independently a bond.

In embodiments, $L^3$ is substituted or unsubstituted alkylene (e.g., $C_1$-$C_8$ alkylene, $C_1$-$C_6$ alkylene, or $C_1$-$C_4$ alkylene). In embodiments, $L^3$ is substituted alkylene (e.g., $C_1$-$C_8$ alkylene, $C_1$-$C_6$ alkylene, or $C_1$-$C_4$ alkylene). In embodiments, $L^3$ is an unsubstituted alkylene (e.g., $C_1$-$C_8$ alkylene, $C_1$-$C_6$ alkylene, or $C_1$-$C_4$ alkylene). In embodiments, $L^3$ is substituted or unsubstituted heteroalkylene (e.g., 2 to 8 membered heteroalkylene, 2 to 6 membered heteroalkylene, or 2 to 4 membered heteroalkylene). In embodiments, $L^3$ is substituted heteroalkylene (e.g., 2 to 8 membered heteroalkylene, 2 to 6 membered heteroalkylene, or 2 to 4 membered heteroalkylene). In embodiments, $L^3$ is an unsubstituted heteroalkylene (e.g., 2 to 8 membered heteroalkylene, 2 to 6 membered heteroalkylene, or 2 to 4 membered heteroalkylene). In embodiments, $L^3$ is substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^3$ is substituted cycloalkylene (e.g., $C_3$-$C_8$ cycloalkylene, $C_3$-$C_6$ cycloalkylene, or $C_5$-$C_6$ cycloalkylene). In embodiments, $L^3$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^3$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^3$ is substituted heterocycloalkylene (e.g., 3 to 8 membered heterocycloalkylene, 3 to 6 membered heterocycloalkylene, or 5 to 6 membered heterocycloalkylene). In embodiments, $L^3$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^3$ is substituted or unsubstituted arylene (e.g., C6-$C_{10}$ arylene, $C_{10}$ arylene, or phenylene). In embodiments, $L^3$ is substituted arylene (e.g., $C_6$-$C_{10}$ arylene, $C_{10}$ arylene, or phenylene). In embodiments, $L^3$ is an unsubstituted arylene (e.g., $C_6$-$C_{10}$ arylene, $C_{10}$ arylene, or phenylene). In embodiments, $L^3$ is substituted or unsubstituted heteroarylene (e.g., 5 to 10 membered heteroarylene, 5 to 9 membered heteroarylene, or 5 to 6 membered heteroarylene). In embodiments, $L^3$ is substituted heteroarylene (e.g., 5 to 10 membered heteroarylene, 5 to 9 membered heteroarylene, or 5 to 6 membered heteroarylene). In embodiments, $L^3$ is an unsubstituted heteroarylene (e.g., 5 to 10 membered heteroarylene, 5 to 9 membered heteroarylene, or 5 to 6 membered heteroarylene).

In embodiments, $L^3$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, $R^{45}$-substituted or unsubstituted alkylene (e.g., $C_1$-$C_8$ alkylene, $C_1$-$C_6$ alkylene, or $C_1$-$C_4$ alkylene), $R^{45}$-substituted or unsubstituted heteroalkylene (e.g., 2 to 8 membered heteroalkylene, 2 to 6 membered heteroalkylene, or 2 to 4 membered heteroalkylene), $R^{45}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{45}$-substituted or unsubstituted heterocycloalkylene (e.g., 3 to 8 membered heterocycloalkylene, 3 to 6 membered heterocycloalkylene, or 5 to 6 membered heterocycloalkylene), $R^{45}$-substituted or unsubstituted arylene (e.g., $C_6$-$C_{10}$ arylene, $C_{10}$ arylene, or phenylene), or $R^{45}$-substituted or unsubstituted heteroarylene (e.g., 5 to 10 membered heteroarylene, 5 to 9 membered heteroarylene, or 5 to 6 membered heteroarylene). In embodiments, $L^3$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, unsubstituted alkylene (e.g., C$_1$-C$_8$ alkylene, C$_1$-C$_6$ alkylene, or C$_1$-C$_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., C$_3$-C$_8$ cycloalkylene, C$_3$-C$_6$ cycloalkylene, or C$_5$-C$_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., C$_6$-C$_{10}$ arylene, C$_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, L$^3$ is R$^{45}$-substituted or unsubstituted alkylene (e.g., C$_1$-C$_8$ alkylene, C$_1$-C$_6$ alkylene, or C$_1$-C$_4$ alkylene). In embodiments, L$^3$ is R$^{45}$-substituted alkylene (e.g., C$_1$-C$_8$ alkylene, C$_1$-C$_6$ alkylene, or C$_1$-C$_4$ alkylene). In embodiments, L$^3$ is an unsubstituted alkylene (e.g., C$_1$-C$_8$ alkylene, C$_1$-C$_6$ alkylene, or C$_1$-C$_4$ alkylene). In embodiments, L$^3$ is R$^{45}$-substituted or unsubstituted heteroalkylene (e.g., 2 to 8 membered heteroalkylene, 2 to 6 membered heteroalkylene, or 2 to 4 membered heteroalkylene). In embodiments, L$^3$ is R$^{45}$-substituted heteroalkylene (e.g., 2 to 8 membered heteroalkylene, 2 to 6 membered heteroalkylene, or 2 to 4 membered heteroalkylene). In embodiments, L$^3$ is an unsubstituted heteroalkylene (e.g., 2 to 8 membered heteroalkylene, 2 to 6 membered heteroalkylene, or 2 to 4 membered heteroalkylene). In embodiments, L$^3$ is R$^{45}$-substituted or unsubstituted cycloalkylene (e.g., C$_3$-C$_8$ cycloalkylene, C$_3$-C$_6$ cycloalkylene, or C$_5$-C$_6$ cycloalkylene). In embodiments, L$^3$ is R$^{45}$-substituted cycloalkylene (e.g., C$_3$-C$_8$ cycloalkylene, C$_3$-C$_6$ cycloalkylene, or C$_5$-C$_6$ cycloalkylene). In embodiments, L$^3$ is an unsubstituted cycloalkylene (e.g., C$_3$-C$_8$ cycloalkylene, C$_3$-C$_6$ cycloalkylene, or C$_5$-C$_6$ cycloalkylene). In embodiments, L$^3$ is R$^{45}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, L$^3$ is R$^{45}$-substituted heterocycloalkylene (e.g., 3 to 8 membered heterocycloalkylene, 3 to 6 membered heterocycloalkylene, or 5 to 6 membered heterocycloalkylene). In embodiments, L$^3$ is an unsubstituted heterocycloalkylene (e.g., 3 to 8 membered heterocycloalkylene, 3 to 6 membered heterocycloalkylene, or 5 to 6 membered heterocycloalkylene). In embodiments, L$^3$ is R$^{45}$-substituted or unsubstituted arylene (e.g., C$_6$-C$_{10}$ arylene, C$_{10}$ arylene, or phenylene). In embodiments, L$^3$ is R$^{45}$-substituted arylene (e.g., C$_6$-C$_{10}$ arylene, C$_{10}$ arylene, or phenylene). In embodiments, L$^3$ is an unsubstituted arylene (e.g., C$_6$-C$_{10}$ arylene, C$_{10}$ arylene, or phenylene). In embodiments, L$^3$ is R$^{45}$-substituted or unsubstituted heteroarylene (e.g., 5 to 10 membered heteroarylene, 5 to 9 membered heteroarylene, or 5 to 6 membered heteroarylene). In embodiments, L$^3$ is R$^{45}$-substituted heteroarylene (e.g., 5 to 10 membered heteroarylene, 5 to 9 membered heteroarylene, or 5 to 6 membered heteroarylene). In embodiments, L$^3$ is an unsubstituted heteroarylene (e.g., 5 to 10 membered heteroarylene, 5 to 9 membered heteroarylene, or 5 to 6 membered heteroarylene).

R$^{45}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, ONH$_2$, NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{45}$ is independently oxo. In embodiments, R$^{45}$ is independently halogen. In embodiments, R$^{45}$ is independently —CCl$_3$. In embodiments, R$^{45}$ is independently —CBr$_3$. In embodiments, R$^{45}$ is independently —CF$_3$. In embodiments, R$^{45}$ is independently —CI$_3$. In embodiments, R$^{45}$ is independently —CHCl$_2$. In embodiments, R$^{45}$ is independently —CHBr$_2$. In embodiments, R$^{45}$ is independently —CHF$_2$. In embodiments, R$^{45}$ is independently —CHI$_2$. In embodiments, R$^{45}$ is independently —CH$_2$Cl. In embodiments, R$^{45}$ is independently —CH$_2$Br. In embodiments, R$^{45}$ is independently —CH$_2$F. In embodiments, R$^{45}$ is independently —CH$_2$I. In embodiments, R$^{45}$ is independently —CN. In embodiments, R$^{45}$ is independently —OH. In embodiments, R$^{45}$ is independently —NH$_2$. In embodiments, R$^{45}$ is independently —COOH. In embodiments, R$^{45}$ is independently —CONH$_2$. In embodiments, R$^{45}$ is independently —NO$_2$. In embodiments, R$^{45}$ is independently —SH. In embodiments, R$^{45}$ is independently —SO$_3$H. In embodiments, R$^{45}$ is independently —SO$_4$H. In embodiments, R$^{45}$ is independently —SO$_2$NH$_2$. In embodiments, R$^{45}$ is independently —NHNH$_2$. In embodiments, R$^{45}$ is independently —ONH$_2$. In embodiments, R$^{45}$ is independently —NHC(O)NHNH$_2$. In embodiments, R$^{45}$ is independently —NHC(O)NH$_2$. In embodiments, R$^{45}$ is independently —NHSO$_2$H. In embodiments, R$^{45}$ is independently —NHC(O)H. In embodiments, R$^{45}$ is independently —NHC(O)OH. In embodiments, R$^{45}$ is independently —NHOH. In embodiments, R$^{45}$ is independently —OCCl$_3$. In embodiments, R$^{45}$ is independently —OCF$_3$. In embodiments, R$^{45}$ is independently —OCBr$_3$. In embodiments, R$^{45}$ is independently —OCI$_3$. In embodiments, R$^{45}$ is independently —OCHCl$_2$. In embodiments, R$^{45}$ is independently —OCHBr$_2$. In embodiments, R$^{45}$ is independently —OCHI$_2$. In embodiments, R$^{45}$ is independently —OCHF$_2$. In embodiments, R$^{45}$ is independently —OCH$_2$Cl. In embodiments, R$^{45}$ is independently —OCH$_2$Br. In embodiments, R$^{45}$ is independently —OCH$_2$I. In embodiments, R$^{45}$ is independently —OCH$_2$F. In embodiments, R$^{45}$ is independently —N$_3$. In embodiments, R$^{45}$ is independently —OCH$_3$. In embodiments, R$^{45}$ is independently —CH$_3$. In embodiments, R$^{45}$ is independently —CH$_2$CH$_3$. In embodiments, R$^{45}$ is independently unsubstituted propyl. In embodiments, R$^{45}$ is independently unsubstituted isopropyl. In embodiments, R$^{45}$ is independently unsubstituted butyl. In embodiments, R$^{45}$ is independently unsubstituted tert-butyl. In embodiments, R$^{45}$ is independently —F. In embodiments, R$^{45}$ is independently —Cl. In embodiments, R$^{45}$ is independently —Br. In embodiments, R$^{45}$ is independently —I.

In embodiments, L$^4$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene (e.g., C$_1$-C$_8$ alkylene, C$_1$-C$_6$ alkylene, or C$_1$-C$_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^4$ is independently a —S(O)$_2$—. In embodiments, $L^4$ is independently a —S(O)—. In embodiments, $L^4$ is independently a —NH—. In embodiments, $L^4$ is independently a —O—. In embodiments, $L^4$ is independently a —S—. In embodiments, $L^4$ is independently a —C(O)—. In embodiments, $L^4$ is independently a —C(O)NH—. In embodiments, $L^4$ is independently a —NHC(O)—. In embodiments, $L^4$ is independently a —NHC(O)NH—. In embodiments, $L^4$ is independently a —C(O)O—. In embodiments, $L^4$ is independently —OC(O)—. In embodiments, $L^4$ is independently a bond.

In embodiments, $L^4$ is substituted or unsubstituted alkylene (e.g., $C_1$-$C_8$ alkylene, $C_1$-$C_6$ alkylene, or $C_1$-$C_4$ alkylene). In embodiments, $L^4$ is substituted alkylene (e.g., $C_1$-$C_8$ alkylene, $C_1$-$C_6$ alkylene, or $C_1$-$C_4$ alkylene). In embodiments, $L^4$ is an unsubstituted alkylene (e.g., $C_1$-$C_8$ alkylene, $C_1$-$C_6$ alkylene, or $C_1$-$C_4$ alkylene). In embodiments, $L^4$ is substituted or unsubstituted heteroalkylene (e.g., 2 to 8 membered heteroalkylene, 2 to 6 membered heteroalkylene, or 2 to 4 membered heteroalkylene). In embodiments, $L^4$ is substituted heteroalkylene (e.g., 2 to 8 membered heteroalkylene, 2 to 6 membered heteroalkylene, or 2 to 4 membered heteroalkylene). In embodiments, $L^4$ is an unsubstituted heteroalkylene (e.g., 2 to 8 membered heteroalkylene, 2 to 6 membered heteroalkylene, or 2 to 4 membered heteroalkylene). In embodiments, $L^4$ is substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is substituted cycloalkylene (e.g., $C_3$-$C_8$ cycloalkylene, $C_3$-$C_6$ cycloalkylene, or $C_5$-$C_6$ cycloalkylene). In embodiments, $L^4$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^4$ is substituted heterocycloalkylene (e.g., 3 to 8 membered heterocycloalkylene, 3 to 6 membered heterocycloalkylene, or 5 to 6 membered heterocycloalkylene). In embodiments, $L^4$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^4$ is substituted or unsubstituted arylene (e.g., $C_6$-$C_{10}$ arylene, $C_{10}$ arylene, or phenylene). In embodiments, $L^4$ is substituted arylene (e.g., $C_6$-$C_{10}$ arylene, $C_{10}$ arylene, or phenylene). In embodiments, $L^4$ is an unsubstituted arylene (e.g., $C_6$-$C_{10}$ arylene, $C_{10}$ arylene, or phenylene). In embodiments, $L^4$ is substituted or unsubstituted heteroarylene (e.g., 5 to 10 membered heteroarylene, 5 to 9 membered heteroarylene, or 5 to 6 membered heteroarylene). In embodiments, $L^4$ is substituted heteroarylene (e.g., 5 to 10 membered heteroarylene, 5 to 9 membered heteroarylene, or 5 to 6 membered heteroarylene). In embodiments, $L^4$ is an unsubstituted heteroarylene (e.g., 5 to 10 membered heteroarylene, 5 to 9 membered heteroarylene, or 5 to 6 membered heteroarylene).

In embodiments, $L^4$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, $R^{46}$-substituted or unsubstituted alkylene (e.g., $C_1$-$C_8$ alkylene, $C_1$-$C_6$ alkylene, or $C_1$-$C_4$ alkylene), $R^{46}$-substituted or unsubstituted heteroalkylene (e.g., 2 to 8 membered heteroalkylene, 2 to 6 membered heteroalkylene, or 2 to 4 membered heteroalkylene), $R^{46}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{46}$-substituted or unsubstituted heterocycloalkylene (e.g., 3 to 8 membered heterocycloalkylene, 3 to 6 membered heterocycloalkylene, or 5 to 6 membered heterocycloalkylene), $R^{46}$-substituted or unsubstituted arylene (e.g., $C_6$-$C_{10}$ arylene, $C_{10}$ arylene, or phenylene), or $R^{46}$-substituted or unsubstituted heteroarylene (e.g., 5 to 10 membered heteroarylene, 5 to 9 membered heteroarylene, or 5 to 6 membered heteroarylene). In embodiments, $L^4$ is independently a bond, —S(O)$_2$—, —S(O)—, —NH—, —O—, —S—, —C(O)—, —C(O)NH—, —NHC(O)—, —NHC(O)NH—, —C(O)O—, —OC(O)—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, $L^4$ is $R^{46}$-substituted or unsubstituted alkylene (e.g., $C_1$-$C_8$ alkylene, $C_1$-$C_6$ alkylene, or $C_1$-$C_4$ alkylene). In embodiments, $L^4$ is $R^{46}$-substituted alkylene (e.g., $C_1$-$C_8$ alkylene, $C_1$-$C_6$ alkylene, or $C_1$-$C_4$ alkylene). In embodiments, $L^4$ is an unsubstituted alkylene (e.g., $C_1$-$C_8$ alkylene, $C_1$-$C_6$ alkylene, or $C_1$-$C_4$ alkylene). In embodiments, $L^4$ is $R^{46}$-substituted or unsubstituted heteroalkylene (e.g., 2 to 8 membered heteroalkylene, 2 to 6 membered heteroalkylene, or 2 to 4 membered heteroalkylene). In embodiments, $L^4$ is $R^{46}$-substituted heteroalkylene (e.g., 2 to 8 membered heteroalkylene, 2 to 6 membered heteroalkylene, or 2 to 4 membered heteroalkylene). In embodiments, $L^4$ is an unsubstituted heteroalkylene (e.g., 2 to 8 membered heteroalkylene, 2 to 6 membered heteroalkylene, or 2 to 4 membered heteroalkylene). In embodiments, $L^4$ is $R^{46}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is $R^{46}$-substituted cycloalkylene (e.g., $C_3$-$C_8$ cycloalkylene, $C_3$-$C_6$ cycloalkylene, or $C_5$-$C_6$ cycloalkylene). In embodiments, $L^4$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^4$ is $R^{46}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^4$ is $R^{46}$-substituted heterocycloalkylene (e.g., 3 to 8 membered heterocycloalkylene, 3 to 6 membered heterocycloalkylene, or 5 to 6 membered heterocycloalkylene). In embodiments, $L^4$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^4$ is $R^{46}$-substituted or unsubstituted arylene (e.g., $C_6$-$C_{10}$ arylene, $C_{10}$ arylene, or phenylene). In embodiments, $L^4$ is $R^{46}$- substituted arylene (e.g., $C_6$-$C_{10}$ arylene, $C_{10}$ arylene, or phenylene). In embodiments, $L^4$ is an unsubstituted arylene (e.g., $C_6$-$C_{10}$ arylene, $C_{10}$ arylene, or phenylene). In embodiments, $L^4$ is $R^{46}$-substituted or unsubstituted heteroarylene (e.g., 5 to 10 membered heteroarylene, 5 to 9 membered heteroarylene, or 5 to 6 membered heteroarylene). In embodiments, $L^4$ is $R^{46}$-substituted heteroarylene (e.g., 5 to 10 membered heteroarylene, 5 to 9 membered heteroarylene, or 5 to 6 membered heteroarylene). In embodiments, $L^4$ is an unsubstituted heteroarylene (e.g., 5 to 10 membered heteroarylene, 5 to 9 membered heteroarylene, or 5 to 6 membered heteroarylene).

$R^{46}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{46}$ is independently oxo. In embodiments, $R^{46}$ is independently halogen. In embodiments, $R^{46}$ is independently —$CCl_3$. In embodiments, $R^{46}$ is independently —$CBr_3$. In embodiments, $R^{46}$ is independently —$CF_3$. In embodiments, $R^{46}$ is independently —$CI_3$. In embodiments, $R^{46}$ is independently —$CHCl_2$. In embodiments, $R^{46}$ is independently —$CHBr_2$. In embodiments, $R^{46}$ is independently —$CHF_2$. In embodiments, $R^{46}$ is independently —$CHI_2$. In embodiments, $R^{46}$ is independently —$CH_2Cl$. In embodiments, $R^{46}$ is independently —$CH_2Br$. In embodiments, $R^{46}$ is independently —$CH_2F$. In embodiments, $R^{46}$ is independently —$CH_2I$. In embodiments, $R^{46}$ is independently —CN. In embodiments, $R^{46}$ is independently —OH. In embodiments, $R^{46}$ is independently —$NH_2$. In embodiments, $R^{46}$ is independently —COOH. In embodiments, $R^{46}$ is independently —$CONH_2$. In embodiments, $R^{46}$ is independently —$NO_2$. In embodiments, $R^{46}$ is independently —SH. In embodiments, $R^{46}$ is independently —$SO_3H$. In embodiments, $R^{46}$ is independently —$SO_4H$. In embodiments, $R^{46}$ is independently —$SO_2NH_2$. In embodiments, $R^{46}$ is independently —$NHNH_2$. In embodiments, $R^{46}$ is independently —$ONH_2$. In embodiments, $R^{46}$ is independently —NHC(O)$NHNH_2$. In embodiments, $R^{46}$ is independently —NHC(O)$NH_2$. In embodiments, $R^{46}$ is independently —$NHSO_2H$. In embodiments, $R^{46}$ is independently —NHC(O)H. In embodiments, $R^{46}$ is independently —NHC(O)OH. In embodiments, $R^{46}$ is independently —NHOH. In embodiments, $R^{46}$ is independently —$OCCl_3$. In embodiments, $R^{46}$ is independently —$OCF_3$. In embodiments, $R^{46}$ is independently —$OCBr_3$. In embodiments, $R^{46}$ is independently —$OCI_3$. In embodiments, $R^{46}$ is independently —$OCHCl_2$. In embodiments, $R^{46}$ is independently —$OCHBr_2$. In embodiments, $R^{46}$ is independently —$OCHI_2$. In embodiments, $R^{46}$ is independently —$OCHF_2$. In embodiments, $R^{46}$ is independently —$OCH_2Cl$. In embodiments, $R^{46}$ is independently —$OCH_2Br$. In embodiments, $R^{46}$ is independently —$OCH_2I$. In embodiments, $R^{46}$ is independently —$OCH_2F$. In embodiments, $R^{46}$ is independently —$N_3$. In embodiments, $R^{46}$ is independently —$OCH_3$. In embodiments, $R^{46}$ is idenpendently —$CH_3$. In embodiments, $R^{46}$ is idenpendently —$CH_2CH_3$. In embodiments, $R^{46}$ is independently unsubstituted propyl. In embodiments, $R^{46}$ is independently unsubstituted isopropyl. In embodiments, $R^{46}$ is independently unsubstituted butyl. In embodiments, $R^{46}$ is independently unsubstituted tert-butyl. In embodiments, $R^{46}$ is independently —F. In embodiments, $R^{46}$ is independently —Cl. In embodiments, $R^{46}$ is independently —Br. In embodiments, $R^{46}$ is independently —I.

In embodiments, $L^5$ is independently a bond, —$S(O)_2$—, —S(O)—, =N—, —NH—, —O—, —S—, —C(O)—, —C(O)NH—, —NHC(O)—, —NHC(O)NH—, —C(O)O—, —OC(O)—, substituted or unsubstituted alkylene (e.g., $C_1$-$C_8$ alkylene, $C_1$-$C_6$ alkylene, or $C_1$-$C_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., $C_3$-$C_8$ cycloalkylene, $C_3$-$C_6$ cycloalkylene, or $C_5$-$C_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., $C_6$-$C_{10}$ arylene, $C_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^5$ is independently a —$S(O)_2$—. In embodiments, $L^5$ is independently a —S(O)—. In embodiments, $L^5$ is independently a —NH—. In embodiments, $L^5$ is independently a —O—. In embodiments, $L^5$ is independently a —S—. In embodiments, $L^5$ is independently a —C(O)—. In embodiments, $L^5$ is independently a —C(O)NH—. In embodiments, $L^5$ is independently a —NHC(O)—. In embodiments, $L^5$ is independently a —NHC(O)NH—. In embodiments, $L^5$ is independently a —C(O)O—. In embodiments, $L^5$ is independently —OC(O)—. In embodiments, $L^5$ is independently a bond. In embodiments, $L^5$ is independently —$NR^5$—. In embodiments, $L^5$ is independently =N—. In embodiments, $L^5$ is independently —C(O)$NR^5$—. In embodiments, $L^5$ is independently —$NR^5$C(O)—. In embodiments, $L^5$ is independently —$NR^5$C(O)NH—. In embodiments, $L^5$ is independently —NHC(O)$NR^5$—.

In embodiments, $L^5$ is substituted or unsubstituted alkylene (e.g., $C_1$-$C_8$ alkylene, $C_1$-$C_6$ alkylene, or $C_1$-$C_4$ alkylene). In embodiments, $L^5$ is substituted alkylene (e.g., $C_1$-$C_8$ alkylene, $C_1$-$C_6$ alkylene, or $C_1$-$C_4$ alkylene). In embodiments, $L^5$ is an unsubstituted alkylene (e.g., $C_1$-$C_8$ alkylene, $C_1$-$C_6$ alkylene, or $C_1$-$C_4$ alkylene). In embodiments, $L^5$ is substituted or unsubstituted heteroalkylene (e.g., 2 to 8 membered heteroalkylene, 2 to 6 membered heteroalkylene, or 2 to 4 membered heteroalkylene). In embodiments, $L^5$ is substituted heteroalkylene (e.g., 2 to 8 membered heteroalkylene, 2 to 6 membered heteroalkylene, or 2 to 4 membered heteroalkylene). In embodiments, $L^5$ is an unsubstituted heteroalkylene (e.g., 2 to 8 membered heteroalkylene, 2 to 6 membered heteroalkylene, or 2 to 4 membered heteroalkylene). In embodiments, $L^5$ is substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^5$ is substituted cycloalkylene (e.g., $C_3$-$C_8$ cycloalkylene, $C_3$-$C_6$ cycloalkylene, or $C_5$-$C_6$ cycloalkylene). In embodiments, $L^5$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^5$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^5$ is substituted heterocycloalkylene (e.g., 3 to 8 membered heterocycloalkylene, 3 to 6 membered heterocycloalkylene, or 5 to 6 membered heterocycloalkylene). In embodiments, $L^5$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^5$ is substituted or unsubstituted arylene (e.g., $C_6$-$C_{10}$ arylene, $C_{10}$ arylene, or phenylene). In embodiments, $L^5$ is substituted arylene (e.g., $C_6$-$C_{10}$ arylene, $C_{10}$ arylene, or phenylene). In embodiments, $L^5$ is an unsubstituted arylene (e.g., $C_6$-$C_{10}$ arylene, $C_{10}$ arylene, or phenylene). In embodiments, $L^5$ is substituted or unsubstituted heteroarylene (e.g., 5 to 10 membered heteroarylene, 5 to 9 membered heteroarylene, or 5 to 6 membered heteroarylene). In embodiments, $L^5$ is substituted heteroarylene (e.g., 5 to 10 membered heteroarylene, 5 to 9 membered heteroarylene, or 5 to 6 membered heteroarylene). In embodiments, $L^5$ is an unsubstituted heteroarylene (e.g., 5 to 10 membered heteroarylene, 5 to 9 membered heteroarylene, or 5 to 6 membered heteroarylene).

In embodiments, $L^5$ is independently a bond, —S(O)$_2$—, —S(O)—, =N—, —NH—, —O—, —S—, —C(O)—, —C(O)NH—, —NHC(O)—, —NHC(O)NH—, —C(O)O—, —OC(O)—, $R^{47}$-substituted or unsubstituted alkylene (e.g., $C_1$-$C_8$ alkylene, $C_1$-$C_6$ alkylene, or $C_1$-$C_4$ alkylene), $R^{47}$-substituted or unsubstituted heteroalkylene (e.g., 2 to 8 membered heteroalkylene, 2 to 6 membered heteroalkylene, or 2 to 4 membered heteroalkylene), $R^{47}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{47}$-substituted or unsubstituted heterocycloalkylene (e.g., 3 to 8 membered heterocycloalkylene, 3 to 6 membered heterocycloalkylene, or 5 to 6 membered heterocycloalkylene), $R^{47}$-substituted or unsubstituted arylene (e.g., $C_6$-$C_{10}$ arylene, $C_{10}$ arylene, or phenylene), or $R^{47}$-substituted or unsubstituted heteroarylene (e.g., 5 to 10 membered heteroarylene, 5 to 9 membered heteroarylene, or 5 to 6 membered heteroarylene). In embodiments, $L^5$ is independently a bond, —S(O)$_2$—, —S(O)—, —NH—, =N—, —O—, —S—, —C(O)—, —C(O)NH—, —NHC(O)—, —NHC(O)NH—, —C(O)O—, —OC(O)—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, $L^5$ is $R^{47}$-substituted or unsubstituted alkylene (e.g., $C_1$-$C_8$ alkylene, $C_1$-$C_6$ alkylene, or $C_1$-$C_4$ alkylene). In embodiments, $L^5$ is $R^{47}$-substituted alkylene (e.g., $C_1$-$C_8$ alkylene, $C_1$-$C_6$ alkylene, or $C_1$-$C_4$ alkylene). In embodiments, $L^5$ is an unsubstituted alkylene (e.g., $C_1$-$C_8$ alkylene, $C_1$-$C_6$ alkylene, or $C_1$-$C_4$ alkylene). In embodiments, $L^5$ is $R^{47}$-substituted or unsubstituted heteroalkylene (e.g., 2 to 8 membered heteroalkylene, 2 to 6 membered heteroalkylene, or 2 to 4 membered heteroalkylene). In embodiments, $L^5$ is $R^{47}$-substituted heteroalkylene (e.g., 2 to 8 membered heteroalkylene, 2 to 6 membered heteroalkylene, or 2 to 4 membered heteroalkylene). In embodiments, $L^5$ is an unsubstituted heteroalkylene (e.g., 2 to 8 membered heteroalkylene, 2 to 6 membered heteroalkylene, or 2 to 4 membered heteroalkylene). In embodiments, $L^5$ is $R^{47}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^5$ is $R^{47}$-substituted cycloalkylene (e.g., $C_3$-$C_8$ cycloalkylene, $C_3$-$C_6$ cycloalkylene, or $C_5$-$C_6$ cycloalkylene). In embodiments, $L^5$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^5$ is $R^{47}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^5$ is $R^{47}$-substituted heterocycloalkylene (e.g., 3 to 8 membered heterocycloalkylene, 3 to 6 membered heterocycloalkylene, or 5 to 6 membered heterocycloalkylene). In embodiments, $L^5$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^5$ is $R^{47}$-substituted or unsubstituted arylene (e.g., $C_6$-$C_{10}$ arylene, $C_{10}$ arylene, or phenylene). In embodiments, $L^5$ is $R^{47}$-substituted arylene (e.g., $C_6$-$C_{10}$ arylene, $C_{10}$ arylene, or phenylene). In embodiments, $L^5$ is an unsubstituted arylene (e.g., $C_6$-$C_{10}$ arylene, $C_{10}$ arylene, or phenylene). In embodiments, $L^5$ is $R^{47}$-substituted or unsubstituted heteroarylene (e.g., 5 to 10 membered heteroarylene, 5 to 9 membered heteroarylene, or 5 to 6 membered heteroarylene). In embodiments, $L^5$ is $R^{47}$-substituted heteroarylene (e.g., 5 to 10 membered heteroarylene, 5 to 9 membered heteroarylene, or 5 to 6 membered heteroarylene). In embodiments, $L^5$ is an unsubstituted heteroarylene (e.g., 5 to 10 membered heteroarylene, 5 to 9 membered heteroarylene, or 5 to 6 membered heteroarylene).

$R^{47}$ is independently oxo, halogen, —CF$_3$, —CBr$_3$, —CCl$_3$, —CI$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{47}$ is independently oxo. In embodiments, $R^{47}$ is independently halogen. In embodiments, $R^{47}$ is independently —CCl$_3$. In embodiments, $R^{47}$ is independently —CBr$_3$. In embodiments, $R^{47}$ is independently —CF$_3$. In embodiments, $R^{47}$ is independently —CI$_3$. In embodiments, $R^{47}$ is independently —CHCl$_2$. In embodiments, $R^{47}$ is independently —CHBr$_2$. In embodiments, $R^{47}$ is independently —CHF$_2$. In embodiments, $R^{47}$ is independently —CHI$_2$. In embodiments, $R^{47}$ is independently —CH$_2$Cl. In embodiments, $R^{47}$ is independently —CH$_2$Br. In embodiments, $R^{47}$ is independently —CH$_2$F. In embodiments, $R^{47}$ is independently —CH$_2$I. In embodiments, $R^{47}$ is independently —CN. In embodiments, $R^{47}$ is independently —OH. In embodiments, $R^{47}$ is independently —NH$_2$. In embodiments, $R^{47}$ is independently —COOH. In embodiments, $R^{47}$ is independently —CONH$_2$. In embodiments, $R^{47}$ is independently —NO$_2$. In embodiments, $R^{47}$ is independently —SH. In embodiments, $R^{47}$ is independently —SO$_3$H. In embodiments, $R^{47}$ is independently —SO$_4$H. In embodiments, $R^{47}$ is independently —SO$_2$NH$_2$. In embodiments, $R^{47}$ is independently —NHNH$_2$. In embodiments, $R^{47}$ is independently —ONH$_2$. In embodiments, $R^{47}$ is independently —NHC(O)NHNH$_2$. In embodiments, $R^{47}$ is independently —NHC(O)NH$_2$. In embodiments, $R^{47}$ is independently —NHSO$_2$H. In embodiments, $R^{47}$ is independently —NHC(O)H. In embodiments, $R^{47}$ is independently —NHC(O)OH. In embodiments, $R^{47}$ is independently —NHOH. In embodiments, $R^{47}$ is independently —OCCl$_3$. In embodiments, $R^{47}$ is independently —OCF$_3$. In embodiments, $R^{47}$ is independently —OCBr$_3$. In embodiments, $R^{47}$ is independently —OCI$_3$. In embodiments, $R^{47}$ is independently —OCHCl$_2$. In embodiments, $R^{47}$ is independently —OCHBr$_2$. In embodiments, $R^{47}$ is independently —OCHI$_2$. In embodiments, $R^{47}$ is independently —OCHF$_2$. In embodiments, $R^{47}$ is independently —OCH$_2$Cl. In embodiments, $R^{47}$ is independently —OCH$_2$Br. In embodiments, $R^{47}$ is independently —OCH$_2$I. In embodiments, $R^{47}$ is independently —OCH$_2$F. In embodiments, $R^{47}$ is independently —N$_3$. In embodiments, $R^{47}$ is independently —OCH$_3$. In embodiments, $R^{47}$ is idenpendently —CH$_3$. In embodiments, $R^{47}$ is idenpendently —CH$_2$CH$_3$. In embodiments, $R^{47}$ is independently unsubstituted propyl. In embodiments, $R^{47}$ is independently unsubstituted isopropyl. In embodiments, $R^{47}$ is independently unsubstituted butyl. In embodiments, $R^{47}$ is independently unsubstituted tert-butyl. In embodiments, $R^{47}$ is independently —F. In embodiments, $R^{47}$ is independently —Cl. In embodiments, $R^{47}$ is independently —Br. In embodiments, $R^{47}$ is independently —I.

In embodiments, $L^6$ is independently a bond, —S(O)$_2$—, —S(O)—, =N—, —NH—, —O—, —S—, —C(O)—, —C(O)NH—, —NHC(O)—, —NHC(O)NH—, —C(O)O—, —OC(O)—, substituted or unsubstituted alkylene (e.g., C$_1$-C$_8$ alkylene, C$_1$-C$_6$ alkylene, or C$_1$-C$_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., C$_3$-C$_8$ cycloalkylene, C$_3$-C$_6$ cycloalkylene, or C$_5$-C$_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., C$_6$-C$_{10}$ arylene, C$_{10}$ arylene, or phenylene), or substituted or unsubstituted heteroarylene (e.g., 5 to 10 membered heteroarylene, 5 to 9 membered heteroarylene, or 5 to 6 membered heteroarylene). In embodiments, $L^6$ is independently a —S(O)$_2$—. In embodiments, $L^6$ is independently a —S(O)—. In embodiments, $L^6$ is independently a —NH—. In embodiments, $L^6$ is independently a —O—. In embodiments, $L^6$ is independently a —S—. In embodiments, $L^6$ is independently a —C(O)—. In embodiments, $L^6$ is independently a —C(O)NH—. In embodiments, $L^6$ is independently a —NHC(O)—. In embodiments, $L^6$ is independently a —NHC(O)NH—. In embodiments, $L^6$ is independently a —C(O)O—. In embodiments, $L^6$ is independently —OC(O)—. In embodiments, $L^6$ is independently a bond. In embodiments, $L^6$ is independently —NR$^6$—. In embodiments, $L^6$ is independently =N—. In embodiments, $L^6$ is independently —C(O)NR$^6$—. In embodiments, $L^6$ is independently —NR$^6$C(O)—. In embodiments, $L^6$ is independently —NR$^6$C(O)NH—. In embodiments, $L^6$ is independently —NHC(O)NR$^6$—.

In embodiments, $L^6$ is substituted or unsubstituted alkylene (e.g., C$_1$-C$_8$ alkylene, C$_1$-C$_6$ alkylene, or C$_1$-C$_4$ alkylene). In embodiments, $L^6$ is substituted alkylene (e.g., C$_1$-C$_8$ alkylene, C$_1$-C$_6$ alkylene, or C$_1$-C$_4$ alkylene). In embodiments, $L^6$ is an unsubstituted alkylene (e.g., C$_1$-C$_8$ alkylene, C$_1$-C$_6$ alkylene, or C$_1$-C$_4$ alkylene). In embodiments, $L^6$ is substituted or unsubstituted heteroalkylene (e.g., 2 to 8 membered heteroalkylene, 2 to 6 membered heteroalkylene, or 2 to 4 membered heteroalkylene). In embodiments, $L^6$ is substituted heteroalkylene (e.g., 2 to 8 membered heteroalkylene, 2 to 6 membered heteroalkylene, or 2 to 4 membered heteroalkylene). In embodiments, $L^6$ is an unsubstituted heteroalkylene (e.g., 2 to 8 membered heteroalkylene, 2 to 6 membered heteroalkylene, or 2 to 4 membered heteroalkylene). In embodiments, $L^6$ is substituted or unsubstituted cycloalkylene (e.g., C$_3$-C$_8$ cycloalkylene, C$_3$-C$_6$ cycloalkylene, or C$_5$-C$_6$ cycloalkylene). In embodiments, $L^6$ is substituted cycloalkylene (e.g., C$_3$-C$_8$ cycloalkylene, C$_3$-C$_6$ cycloalkylene, or C$_5$-C$_6$ cycloalkylene). In embodiments, $L^6$ is an unsubstituted cycloalkylene (e.g., C$_3$-C$_8$ cycloalkylene, C$_3$-C$_6$ cycloalkylene, or C$_5$-C$_6$ cycloalkylene). In embodiments, $L^6$ is substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^6$ is substituted heterocycloalkylene (e.g., 3 to 8 membered heterocycloalkylene, 3 to 6 membered heterocycloalkylene, or 5 to 6 membered heterocycloalkylene). In embodiments, $L^6$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^6$ is substituted or unsubstituted arylene (e.g., C$_6$-C$_{10}$ arylene, C$_{10}$ arylene, or phenylene). In embodiments, $L^6$ is substituted arylene (e.g., C$_6$-C$_{10}$ arylene, C$_{10}$ arylene, or phenylene). In embodiments, $L^6$ is an unsubstituted arylene (e.g., C$_6$-C$_{10}$ arylene, C$_{10}$ arylene, or phenylene). In embodiments, $L^6$ is substituted or unsubstituted heteroarylene (e.g., 5 to 10 membered heteroarylene, 5 to 9 membered heteroarylene, or 5 to 6 membered heteroarylene). In embodiments, $L^6$ is substituted heteroarylene (e.g., 5 to 10 membered heteroarylene, 5 to 9 membered heteroarylene, or 5 to 6 membered heteroarylene). In embodiments, $L^6$ is an unsubstituted heteroarylene (e.g., 5 to 10 membered heteroarylene, 5 to 9 membered heteroarylene, or 5 to 6 membered heteroarylene).

In embodiments, $L^6$ is independently a bond, —S(O)$_2$—, —S(O)—, =N—, —NH—, —O—, —S—, —C(O)—, —C(O)NH—, —NHC(O)—, —NHC(O)NH—, —C(O)O—, —OC(O)—, $R^{48}$-substituted or unsubstituted alkylene (e.g., C$_1$-C$_8$ alkylene, C$_1$-C$_6$ alkylene, or C$_1$-C$_4$ alkylene), $R^{48}$-substituted or unsubstituted heteroalkylene (e.g., 2 to 8 membered heteroalkylene, 2 to 6 membered heteroalkylene, or 2 to 4 membered heteroalkylene), $R^{48}$-substituted or unsubstituted cycloalkylene (e.g., C$_3$-C$_8$ cycloalkylene, C$_3$-C$_6$ cycloalkylene, or C$_5$-C$_6$ cycloalkylene), $R^{48}$-substituted or unsubstituted heterocycloalkylene (e.g., 3 to 8 membered heterocycloalkylene, 3 to 6 membered heterocycloalkylene, or 5 to 6 membered heterocycloalkylene), $R^{48}$-substituted or unsubstituted arylene (e.g., C$_6$-C$_{10}$ arylene, C$_{10}$ arylene, or phenylene), or $R^{48}$-substituted or unsubstituted heteroarylene (e.g., 5 to 10 membered heteroarylene, 5 to 9 membered heteroarylene, or 5 to 6 membered heteroarylene). In embodiments, $L^6$ is independently a bond, —S(O)$_2$—, —S(O)—, —NH—, =N—, —O—, —S—, —C(O)—, —C(O)NH—, —NHC(O)—, —NHC(O)NH—, —C(O)O—, —OC(O)—, unsubstituted alkylene (e.g., $C_1$-$C_8$ alkylene, $C_1$-$C_6$ alkylene, or $C_1$-$C_4$ alkylene), unsubstituted heteroalkylene (e.g., 2 to 8 membered heteroalkylene, 2 to 6 membered heteroalkylene, or 2 to 4 membered heteroalkylene), unsubstituted cycloalkylene (e.g., $C_3$-$C_8$ cycloalkylene, $C_3$-$C_6$ cycloalkylene, or $C_5$-$C_6$ cycloalkylene), unsubstituted heterocycloalkylene (e.g., 3 to 8 membered heterocycloalkylene, 3 to 6 membered heterocycloalkylene, or 5 to 6 membered heterocycloalkylene), unsubstituted arylene (e.g., $C_6$-$C_{10}$ arylene, $C_{10}$ arylene, or phenylene), or unsubstituted heteroarylene (e.g., 5 to 10 membered heteroarylene, 5 to 9 membered heteroarylene, or 5 to 6 membered heteroarylene).

In embodiments, $L^6$ is $R^{48}$-substituted or unsubstituted alkylene (e.g., $C_1$-$C_8$ alkylene, $C_1$-$C_6$ alkylene, or $C_1$-$C_4$ alkylene). In embodiments, $L^6$ is $R^{48}$-substituted alkylene (e.g., $C_1$-$C_8$ alkylene, $C_1$-$C_6$ alkylene, or $C_1$-$C_4$ alkylene). In embodiments, $L^6$ is an unsubstituted alkylene (e.g., $C_1$-$C_8$ alkylene, $C_1$-$C_6$ alkylene, or $C_1$-$C_4$ alkylene). In embodiments, $L^6$ is $R^{48}$-substituted or unsubstituted heteroalkylene (e.g., 2 to 8 membered heteroalkylene, 2 to 6 membered heteroalkylene, or 2 to 4 membered heteroalkylene). In embodiments, $L^6$ is $R^{48}$-substituted heteroalkylene (e.g., 2 to 8 membered heteroalkylene, 2 to 6 membered heteroalkylene, or 2 to 4 membered heteroalkylene). In embodiments, $L^6$ is an unsubstituted heteroalkylene (e.g., 2 to 8 membered heteroalkylene, 2 to 6 membered heteroalkylene, or 2 to 4 membered heteroalkylene). In embodiments, $L^6$ is $R^{48}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^6$ is $R^{48}$-substituted cycloalkylene (e.g., $C_3$-$C_8$ cycloalkylene, $C_3$-$C_6$ cycloalkylene, or $C_5$-$C_6$ cycloalkylene). In embodiments, $L^6$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^6$ is $R^{48}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^6$ is $R^{48}$-substituted heterocycloalkylene (e.g., 3 to 8 membered heterocycloalkylene, 3 to 6 membered heterocycloalkylene, or 5 to 6 membered heterocycloalkylene). In embodiments, $L^6$ is an unsubstituted heterocycloalkylene (e.g., 3 to 8 membered heterocycloalkylene, 3 to 6 membered heterocycloalkylene, or 5 to 6 membered heterocycloalkylene). In embodiments, $L^6$ is $R^{48}$-substituted or unsubstituted arylene (e.g., $C_6$-$C_{10}$ arylene, $C_{10}$ arylene, or phenylene). In embodiments, $L^6$ is $R^{48}$-substituted arylene (e.g., $C_6$-$C_{10}$ arylene, $C_{10}$ arylene, or phenylene). In embodiments, $L^6$ is an unsubstituted arylene (e.g., $C_6$-$C_{10}$ arylene, $C_{10}$ arylene, or phenylene). In embodiments, $L^6$ is $R^{48}$-substituted or unsubstituted heteroarylene (e.g., 5 to 10 membered heteroarylene, 5 to 9 membered heteroarylene, or 5 to 6 membered heteroarylene). In embodiments, $L^6$ is $R^{48}$-substituted heteroarylene (e.g., 5 to 10 membered heteroarylene, 5 to 9 membered heteroarylene, or 5 to 6 membered heteroarylene). In embodiments, $L^6$ is an unsubstituted heteroarylene (e.g., 5 to 10 membered heteroarylene, 5 to 9 membered heteroarylene, or 5 to 6 membered heteroarylene).

$R^{48}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{48}$ is independently oxo. In embodiments, $R^{48}$ is independently halogen. In embodiments, $R^{48}$ is independently —$CCl_3$. In embodiments, $R^{48}$ is independently —$CBr_3$. In embodiments, $R^{48}$ is independently —$CF_3$. In embodiments, $R^{48}$ is independently —$CI_3$. In embodiments, $R^{48}$ is independently —$CHCl_2$. In embodiments, $R^{48}$ is independently —$CHBr_2$. In embodiments, $R^{48}$ is independently —$CHF_2$. In embodiments, $R^{48}$ is independently —$CHI_2$. In embodiments, $R^{48}$ is independently —$CH_2Cl$. In embodiments, $R^{48}$ is independently —$CH_2Br$. In embodiments, $R^{48}$ is independently —$CH_2F$. In embodiments, $R^{48}$ is independently —$CH_2I$. In embodiments, $R^{48}$ is independently —CN. In embodiments, $R^{48}$ is independently —OH. In embodiments, $R^{48}$ is independently —$NH_2$. In embodiments, $R^{48}$ is independently —COOH. In embodiments, $R^{48}$ is independently —$CONH_2$. In embodiments, $R^{48}$ is independently —$NO_2$. In embodiments, $R^{48}$ is independently —SH. In embodiments, $R^{48}$ is independently —$SO_3H$. In embodiments, $R^{48}$ is independently —$SO_4H$. In embodiments, $R^{48}$ is independently —$SO_2NH_2$. In embodiments, $R^{48}$ is independently —$NHNH_2$. In embodiments, $R^{48}$ is independently —$ONH_2$. In embodiments, $R^{48}$ is independently —NHC(O)$NHNH_2$. In embodiments, $R^{48}$ is independently —NHC(O)$NH_2$. In embodiments, $R^{48}$ is independently —$NHSO_2H$. In embodiments, $R^{48}$ is independently —NHC(O)H. In embodiments, $R^{48}$ is independently —NHC(O)OH. In embodiments, $R^{48}$ is independently —NHOH. In embodiments, $R^{48}$ is independently —$OCCl_3$. In embodiments, $R^{48}$ is independently —$OCF_3$. In embodiments, $R^{48}$ is independently —$OCBr_3$. In embodiments, $R^{48}$ is independently —$OCl_3$. In embodiments, $R^{48}$ is independently —$OCHCl_2$. In embodiments, $R^{48}$ is independently —$OCHBr_2$. In embodiments, $R^{48}$ is independently —$OCHI_2$. In embodiments, $R^{48}$ is independently —$OCHF_2$. In embodiments, $R^{48}$ is independently —$OCH_2Cl$. In embodiments, $R^{48}$ is independently —$OCH_2Br$. In embodiments, $R^{48}$ is independently —$OCH_2I$. In embodiments, $R^{48}$ is independently —$OCH_2F$. In embodiments, $R^{48}$ is independently —$N_3$. In embodiments, $R^{48}$ is independently —$OCH_3$. In embodiments, $R^{48}$ is independently —$CH_3$. In embodiments, $R^{48}$ is independently —$CH_2CH_3$. In embodiments, $R^{48}$ is independently unsubstituted propyl. In embodiments, $R^{48}$ is independently unsubstituted isopropyl. In embodiments, $R^{48}$ is independently unsubstituted butyl. In embodiments, $R^{48}$ is independently unsubstituted tert-butyl. In embodiments, $R^{48}$ is independently —F. In embodiments, $R^{48}$ is independently —Cl. In embodiments, $R^{48}$ is independently —Br. In embodiments, $R^{48}$ is independently —I.

In embodiments, X is independently —F. In embodiments, X is independently —Cl. In embodiments, X is independently —Br. In embodiments, X is independently —I. In embodiments, $X^1$ is independently —F. In embodiments, $X^1$ is independently —Cl. In embodiments, $X^1$ is independently —Br. In embodiments, $X^1$ is independently —I. In embodiments, $X^2$ is independently —F. In embodiments, $X^2$ is independently —Cl. In embodiments, $X^2$ is independently —Br. In embodiments, $X^2$ is independently —I. In embodiments, $X^3$ is independently —F. In embodiments, $X^3$ is independently —Cl. In embodiments, $X^3$ is independently —Br. In embodiments, $X^3$ is independently —I. In embodiments, $X^4$ is independently —F. In embodiments, $X^4$ is independently —Cl. In embodiments, $X^4$ is independently —Br. In embodiments, $X^4$ is independently —I. In embodiments, $X^5$ is independently —F. In embodiments, $X^5$ is independently —Cl. In embodiments, $X^5$ is independently —Br. In embodiments, $X^5$ is independently —I. In embodiments, $X^6$ is independently —F. In embodiments, $X^6$ is independently —Cl. In embodiments, $X^6$ is independently —Br. In embodiments, $X^6$ is independently —I. In embodiments, $X^{15}$ is independently —F. In embodiments, $X^{15}$ is independently —Cl. In embodiments, $X^{15}$ is independently —Br. In embodiments, $X^{15}$ is independently —I. In embodiments, $X^{16}$ is independently —F. In embodiments, $X^{16}$ is independently —Cl. In embodiments, $X^{16}$ is independently —Br. In embodiments, $X^{16}$ is independently —I. In embodiments, $X^{17}$ is independently —F. In embodiments, $X^{17}$ is independently —Cl. In embodiments, $X^{17}$ is independently —Br. In embodiments, $X^{17}$ is independently —I. In embodiments, $X^{18}$ is independently —F. In embodiments, $X^{18}$ is independently —Cl. In embodiments, $X^{18}$ is independently —Br. In embodiments, $X^{18}$ is independently —I.

In embodiments, n1 is independently 0. In embodiments, n1 is independently 1. In embodiments, n1 is independently 2. In embodiments, n1 is independently 3. In embodiments, n1 is independently 4. In embodiments, n2 is independently 0. In embodiments, n2 is independently 1. In embodiments, n2 is independently 2. In embodiments, n2 is independently 3. In embodiments, n2 is independently 4. In embodiments, n3 is independently 0. In embodiments, n3 is independently 1. In embodiments, n3 is independently 2. In embodiments, n3 is independently 3. In embodiments, n3 is independently 4. In embodiments, n4 is independently 0. In embodiments, n4 is independently 1. In embodiments, n4 is independently 2. In embodiments, n4 is independently 3. In embodiments, n4 is independently 4. In embodiments, n5 is independently 0. In embodiments, n5 is independently 1. In embodiments, n5 is independently 2. In embodiments, n5 is independently 3. In embodiments, n5 is independently 4. In embodiments, n6 is independently 0. In embodiments, n6 is independently 1. In embodiments, n6 is independently 2. In embodiments, n6 is independently 3. In embodiments, n6 is independently 4. In embodiments, n15 is independently 0. In embodiments, n15 is independently 1. In embodiments, n15 is independently 2. In embodiments, n15 is independently 3. In embodiments, n15 is independently 4. In embodiments, n16 is independently 0. In embodiments, n16 is independently 1. In embodiments, n16 is independently 2. In embodiments, n16 is independently 3. In embodiments, n16 is independently 4. In embodiments, n17 is independently 0. In embodiments, n17 is independently 1. In embodiments, n17 is independently 2. In embodiments, n17 is independently 3. In embodiments, n17 is independently 4. In embodiments, n18 is independently 0. In embodiments, n18 is independently 1. In embodiments, n18 is independently 2. In embodiments, n18 is independently 3. In embodiments, n18 is independently 4.

In embodiments, m1 is independently 1. In embodiments, m1 is independently 2. In embodiments, m2 is independently 1. In embodiments, m2 is independently 2. In embodiments, m3 is independently 1. In embodiments, m3 is independently 2. In embodiments, m4 is independently 1. In embodiments, m4 is independently 2. In embodiments, m5 is independently 1. In embodiments, m5 is independently 2. In embodiments, m6 is independently 1. In embodiments, m6 is independently 2. In embodiments, m15 is independently 1. In embodiments, m15 is independently 2. In embodiments, m16 is independently 1. In embodiments, m16 is independently 2. In embodiments, m17 is independently 1. In embodiments, m17 is independently 2. In embodiments, m18 is independently 1. In embodiments, m18 is independently 2.

In embodiments, v1 is independently 1. In embodiments, v1 is independently 2. In embodiments, v2 is independently 1. In embodiments, v2 is independently 2. In embodiments, v3 is independently 1. In embodiments, v3 is independently 2. In embodiments, v4 is independently 1. In embodiments, v4 is independently 2. In embodiments, v5 is independently 1. In embodiments, v5 is independently 2. In embodiments, v6 is independently 1. In embodiments, v6 is independently 2. In embodiments, v15 is independently 1. In embodiments, v15 is independently 2. In embodiments, v16 is independently 1. In embodiments, v16 is independently 2. In embodiments, v17 is independently 1. In embodiments, v17 is independently 2. In embodiments, v18 is independently 1. In embodiments, v18 is independently 2.

In embodiments, z1 is independently 0. In embodiments, z1 is independently 1. In embodiments, z1 is independently 2. In embodiments, z1 is independently 3. In embodiments, z1 is independently 4. In embodiments, z1 is independently 5. In embodiments, z1 is independently 6. In embodiments, z1 is independently 7. In embodiments, z1 is independently 8. In embodiments, z1 is independently 9. In embodiments, z1 is independently 10. In embodiments, z1 is independently 11.

In embodiments, z2 is independently 0. In embodiments, z2 is independently 1. In embodiments, z2 is independently 2. In embodiments, z2 is independently 3. In embodiments, z2 is independently 4. In embodiments, z2 is independently 5. In embodiments, z2 is independently 6. In embodiments, z2 is independently 7. In embodiments, z2 is independently 8.

In embodiments, z3 is independently 0. In embodiments, z3 is independently 1. In embodiments, z3 is independently 2. In embodiments, z3 is independently 3. In embodiments, z3 is independently 4.

In embodiments z5 is independently 1. In embodiments z5 is independently 2.

In embodiments, the compound is
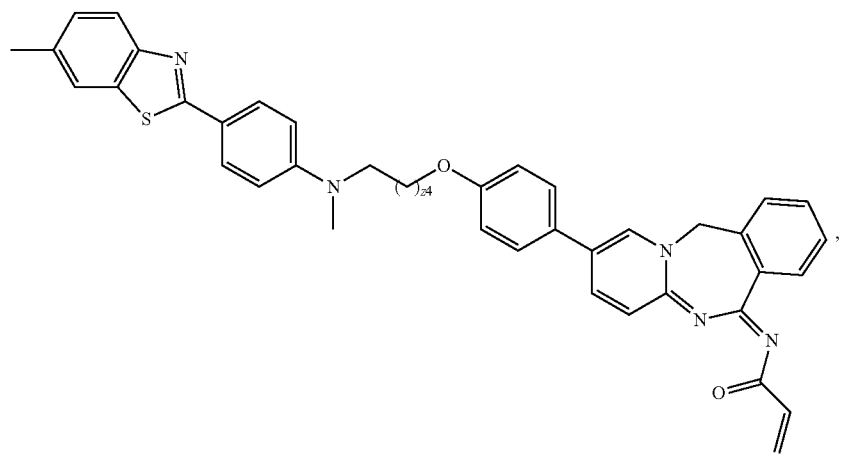
wherein z4 is an integer from 0 to 100. In embodiments, the compound is
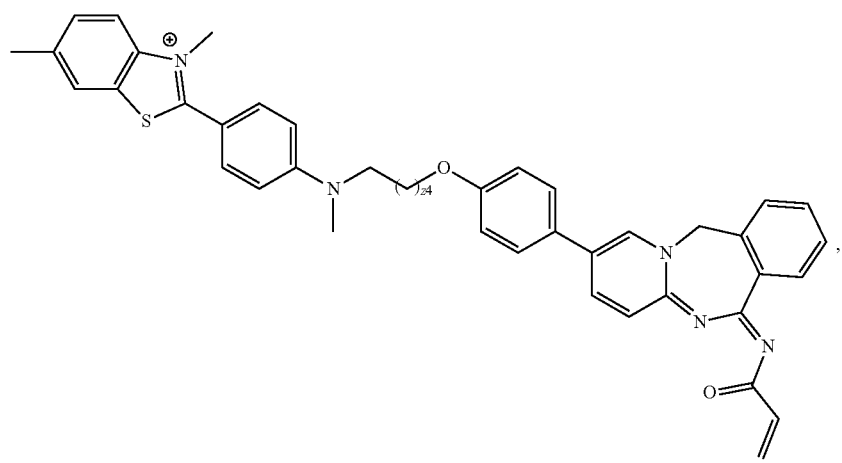
wherein z4 is an integer from 0 to 100. In embodiments, the compound is
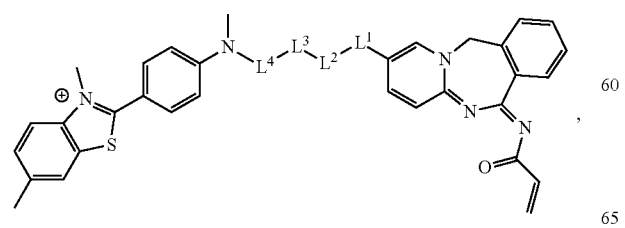

where $L^1$, $L^2$, $L^3$, and $L^4$ are as described herein. In embodiments, the compound is

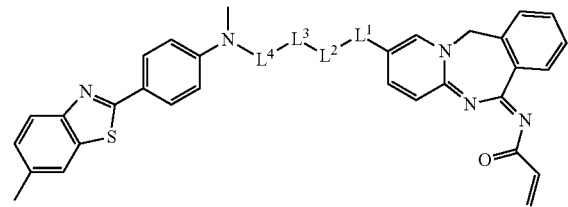

where $L^1$, $L^2$, $L^3$, and $L^4$ are as described herein. In embodiments, the compound is

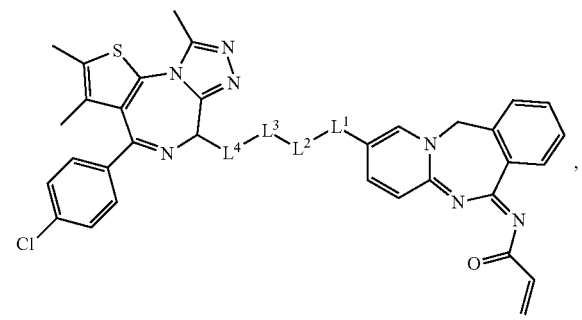

where $L^1$, $L^2$, $L^3$, and $L^4$ are as described herein. In embodiments, the compound is

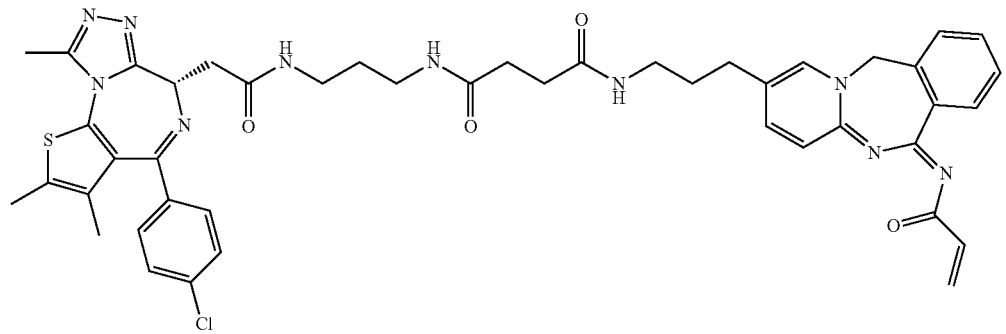

In embodiments, the compound is

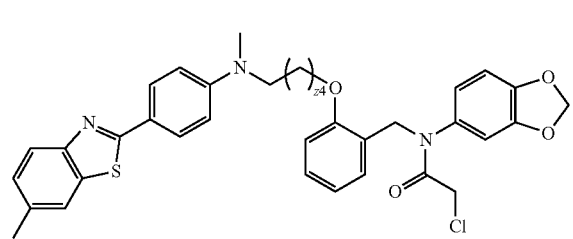

wherein z4 is an integer from 0 to 100. In embodiments, the compound is

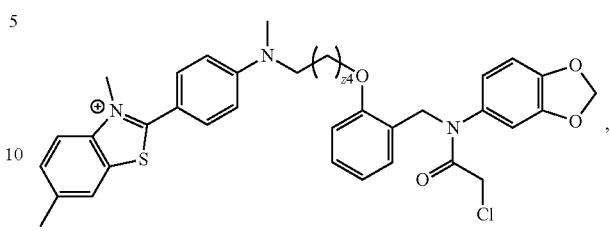

wherein z4 is an integer from 0 to 100. In embodiments, the compound is

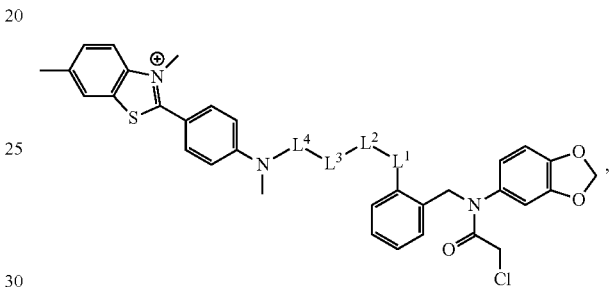

wherein $L^1$, $L^2$, $L^3$, and $L^4$ are as described herein. In embodiments, the compound is

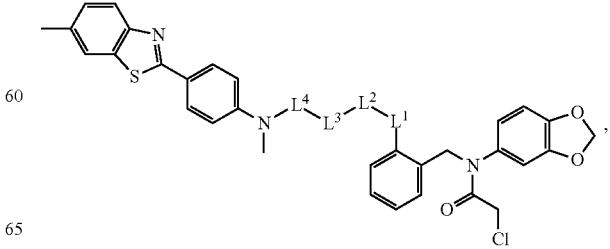

wherein $L^1$, $L^2$, $L^3$, and $L^4$ are as described herein. In embodiments, the compound is
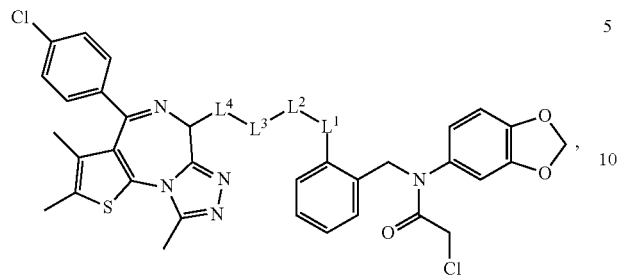
wherein $L^1$, $L^2$, $L^3$, and $L^4$ are as described herein. In embodiments, the compound is
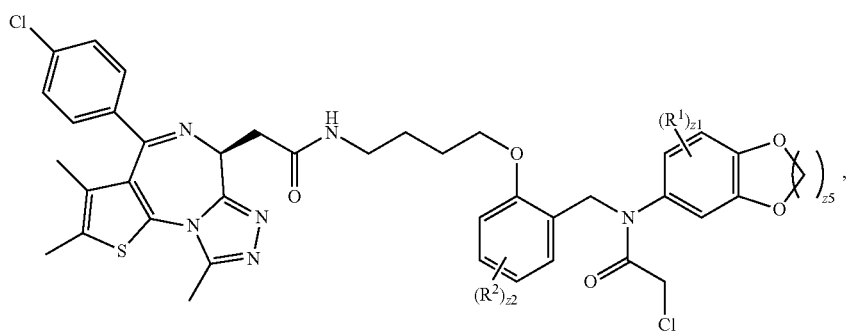
wherein z1 is an integer from 0 to 7, z2 is an integer from 0 to 5, and z5 is 1 or 2. $R^1$, z1, $R^2$, z2, and z5 are as described herein. In embodiments, the compound is
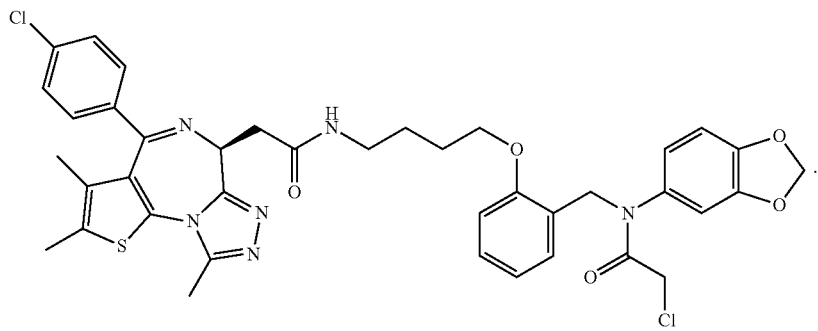 [SMILES: Cc1sc2c(c1C)C(c1ccc(Cl)cc1)=N[C@@H](CC(=O)NCCCCOc1ccccc1CN(C(=O)CCl)c1ccc3c(c1)OCO3)c1nnc(C)n1-2]
In embodiments, the compound is
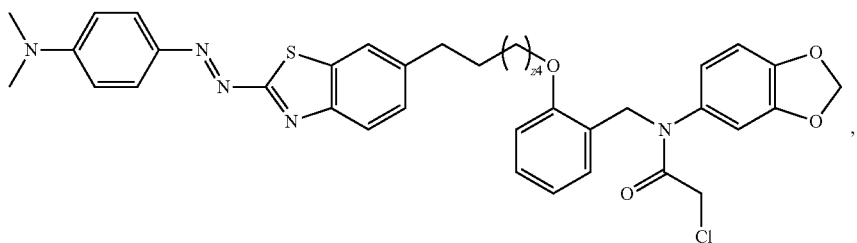

wherein z4 is an integer from 0 to 100. In embodiments, the compound is

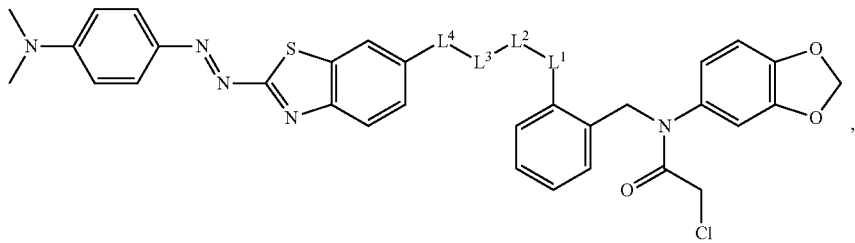

wherein $L^1$, $L^2$, $L^3$, and $L^4$ are as described herein. In embodiments, the compound is

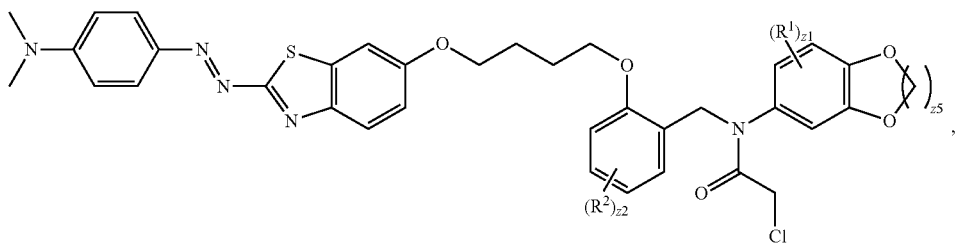

wherein z1 is an integer from 0 to 7, z2 is an integer from 0 to 5, and z5 is 1 or 2. $R^1$, z1, $R^2$, z2, and z5 are as described herein. In embodiments, the compound is

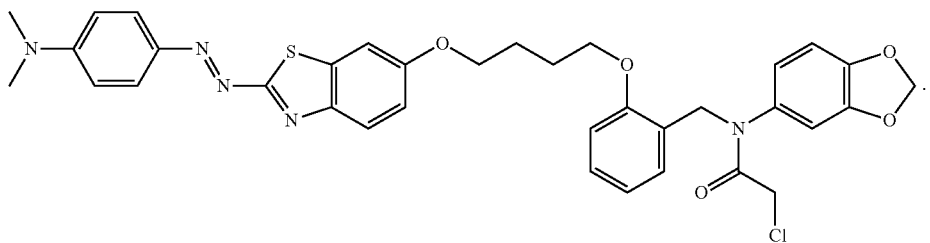 [SMILES: CN(C)c1ccc(/N=N/c2nc3ccc(OCCCCOc4ccccc4CN(C(=O)CCl)c4ccc5c(c4)OCO5)cc3s2)cc1]

In embodiments, z4 is an integer from 0 to 50. In embodiments, z4 is an integer from 0 to 40. In embodiments, z4 is an integer from 0 to 30. In embodiments, z4 is an integer from 0 to 20. In embodiments, z4 is an integer from 0 to 10. In embodiments, z4 is an integer from 0 to 5. In embodiments, z4 is 0. In embodiments, z4 is 1. In embodiments, z4 is 2. In embodiments, z4 is 3. In embodiments, z4 is 4. In embodiments, z4 is 5.

If a substituent (e.g., R') is floating for an aromatic ring (e.g., aryl, heteroaryl, arylene, or heteroarylene) it is understood to obey the rules of chemical valency. For example, in the formula

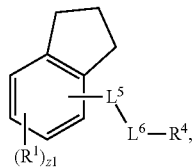

R[1] may not be oxo when attached to the aromatic ring, however R[1] may be oxo if attached to the nonaromatic ring,

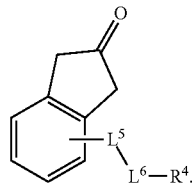

In an aspect is provided an autophagy adapter protein (e.g., LC3, p62, NBR1, NDP52, Optineurin, NUFIP1, WDFY3, RETREG1, Nix, TOLLIP, or TAX1BP1) covalently bonded to a compound described herein. In embodiments, the compound is covalently bonded to a cysteine residue of the protein. In embodiments, the compound is irreversibly covalently bonded to a cysteine residue of the protein. In embodiments, the compound is a targeted autophagy degrader (e.g., as described herein, for example a compound including a monovalent cellular component binder (e.g., as described herein) and a monovalent autophagy adapter protein binder (e.g., as described herein)).

In embodiments, the compound is covalently (e.g., irreversibly) bonded to an amino acid corresponding to C17 of human LC3A protein. In embodiments, the compound is covalently (e.g., irreversibly) bonded to an amino acid corresponding to C26 of human p62/SQSTM1 protein. In embodiments, the compound is covalently (e.g., irreversibly) bonded to an amino acid corresponding to C27 of human p62/SQSTM1protein. In embodiments, the compound is covalently (e.g., irreversibly) bonded to an amino acid corresponding to C113 of human p62/SQSTM1protein. In embodiments, the compound is covalently (e.g., irreversibly) bonded to an amino acid corresponding to C120 of human NBR1 protein. In embodiments, the compound is covalently (e.g., irreversibly) bonded to an amino acid corresponding to C321 of human NDP52/CALCOCO2 protein. In embodiments, the compound is covalently (e.g., irreversibly) bonded to an amino acid corresponding to C558 of human OPTN protein.

In an aspect is provided an autophagy adapter protein (e.g., LC3, p62, NBR1, NDP52, Optineurin, NUFIP1, WDFY3, RETREG1, Nix, TOLLIP, or TAX1BP1) covalently bonded to a fragment (e.g., moiety, moiety of a fragment) of a compound described herein.

In embodiments, the compound fragment is covalently (e.g., irreversibly) bonded to an amino acid corresponding to C17 of human LC3A protein. In embodiments, the compound fragment is covalently (e.g., irreversibly) bonded to an amino acid corresponding to C26 of human p62/SQSTM1 protein. In embodiments, the compound fragment is covalently (e.g., irreversibly) bonded to an amino acid corresponding to C27 of human p62/SQSTM1protein. In embodiments, the compound fragment is covalently (e.g., irreversibly) bonded to an amino acid corresponding to C113 of human p62/SQSTM1protein. In embodiments, the compound fragment is covalently (e.g., irreversibly) bonded to an amino acid corresponding to C120 of human NBR1 protein. In embodiments, the compound fragment is covalently (e.g., irreversibly) bonded to an amino acid corresponding to C321 of human NDP52/CALCOCO2 protein. In embodiments, the compound fragment is covalently (e.g., irreversibly) bonded to an amino acid corresponding to C558 of human OPTN protein. In embodiments, the compound fragment is the remnant of the compound after the compound has covalently reacted with the amino acid of the protein to form a covalent bond (e.g., the compound fragment is formed by removal of a leaving group in the covalent bond formation).

In embodiments, the autophagy adapter protein covalently bonded to a autophagy adapter protein binder or compound described herein is the product of a reaction between the autophagy adapter protein and a autophagy adapter protein binder or compound described herein. It will be understood that the covalently bonded autophagy adapter protein and autophagy adapter protein binder (e.g., compound described herein) are the remnants of the reactant autophagy adapter protein and autophagy adapter protein binder or compound, wherein each reactant now participates in the covalent bond between the autophagy adapter protein and autophagy adapter protein binder or compound. In embodiments of the covalently bonded autophagy adapter protein and compound described herein, the remnant of the E substituent is a linker including a covalent bond between the autophagy adapter protein and the remainder of the compound described herein. It will be understood by a person of ordinary skill in the art that when a autophagy adapter protein is covalently bonded to a autophagy adapter protein binder (e.g., compound described herein), the autophagy adapter protein binder (e.g., compound described herein) forms a remnant of the pre-reacted autophagy adapter protein binder (e.g., compound described herein) wherein a bond connects the remnant of the autophagy adapter protein binder (e.g., compound described herein) to the remnant of the autophagy adapter protein (e.g., cysteine sulfur, sulfur of amino acid corresponding to C17 of human LC3A protein, sulfur of amino acid corresponding to C26 of human p62/SQSTM1 protein, sulfur of amino acid corresponding to C27 of human p62/SQSTM1protein, sulfur of amino acid corresponding to C120 of human NBR1 protein, sulfur of amino acid corresponding to C321 of human NDP52/CALCOCO2 protein, sulfur of amino acid corresponding to C558 of human OPTN protein, sulfur of C17 of human LC3A protein, sulfur of C26 of human p62/SQSTM1 protein, sulfur of C27 of human p62/SQSTM1protein, sulfur of C113 of human p62/SQSTM1protein, sulfur of C120 of human NBR1 protein, sulfur of C321 of human NDP52/CALCOCO2 protein, or sulfur of C558 of human OPTN protein). The remnant of the autophagy adapter protein binder (e.g., a compound described herein) may also be called a portion of the autophagy adapter protein binder. In embodiments, the remnant of the E substituent is a linker selected from a bond, —S(O)$_2$—, —NH—, —O—, —S—, —C(O)—, —C(O)NH—, —NHC(O)—, —NHC(O)NH—, —NHC(O)NH—, —C(O)O—, —OC(O)—, —CH$_2$NH—, substituted (e.g., substituted with a substituent group, a size-limited substituent group, or lower substituent group) or unsubstituted alkylene (e.g., C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkylene (e.g., 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkylene (e.g., 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{10}$ or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered). As a non-limiting example, the autophagy adapter protein covalently bonded to a monovalent autophagy adapter protein binder may have the formula:

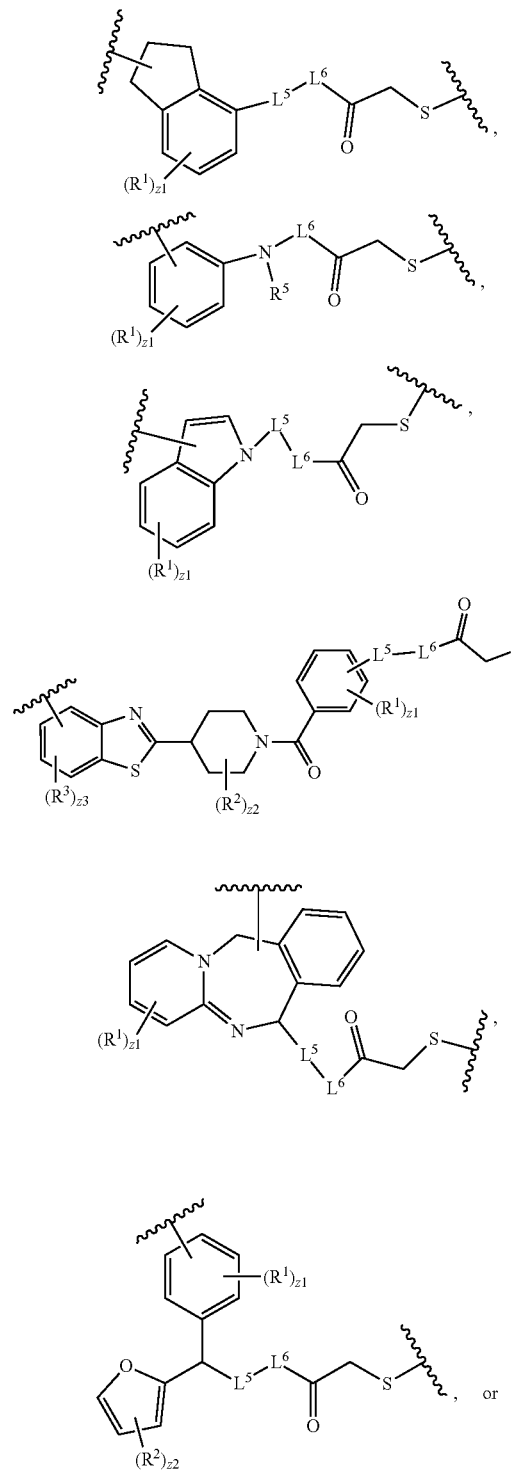

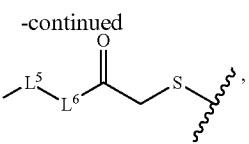

wherein S is the sulfur of an autophagy adapter protein cysteine (e.g., sulfur of amino acid corresponding to C17 of human LC3A protein, sulfur of amino acid corresponding to C26 of human p62/SQSTM1 protein, sulfur of amino acid corresponding to C27 of human p62/SQSTM1protein, sulfur of amino acid corresponding to C120 of human NBR1 protein, sulfur of amino acid corresponding to C321 of human NDP52/CALCOCO2 protein, sulfur of amino acid corresponding to C558 of human OPTN protein, sulfur of C17 of human LC3A protein, sulfur of C26 of human p62/SQSTM1 protein, sulfur of C27 of human p62/SQSTM1protein, sulfur of C113 of human p62/SQSTM1protein, sulfur of C120 of human NBR1 protein, sulfur of C321 of human NDP52/CALCOCO2 protein, or sulfur of C558 of human OPTN protein), which is bonded to the remainder of the autophagy adapter protein and wherein $R^5$, $R^1$, $R^2$, z2, $R^3$, z3, $L^5$, $L^6$, and z1 are as described herein.

As a non-limiting example, the autophagy adapter protein covalently bonded to a monovalent autophagy adapter protein binder may have the formula:

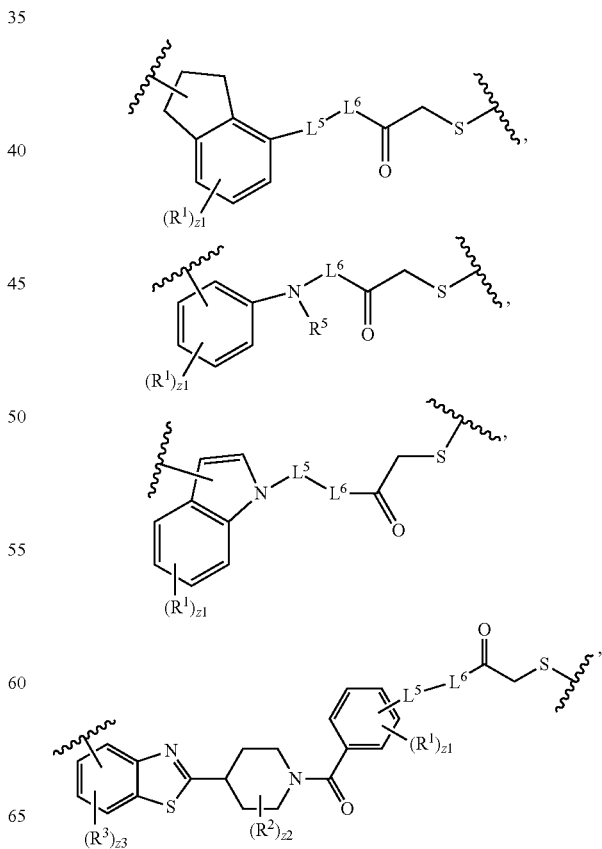

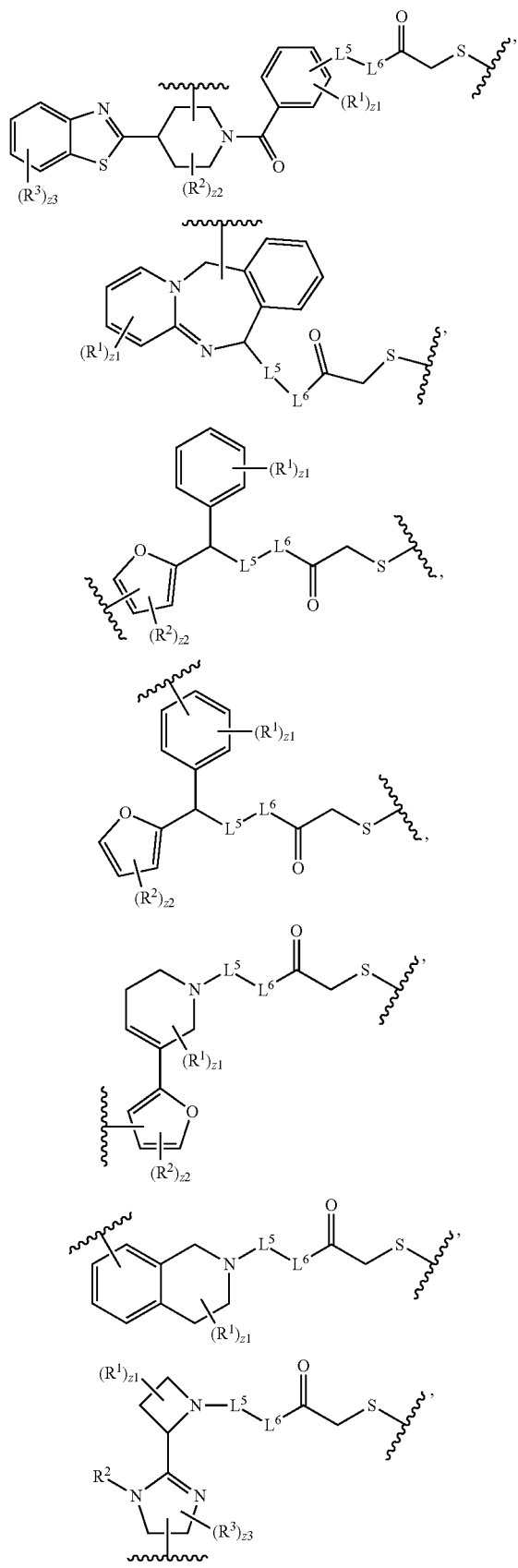
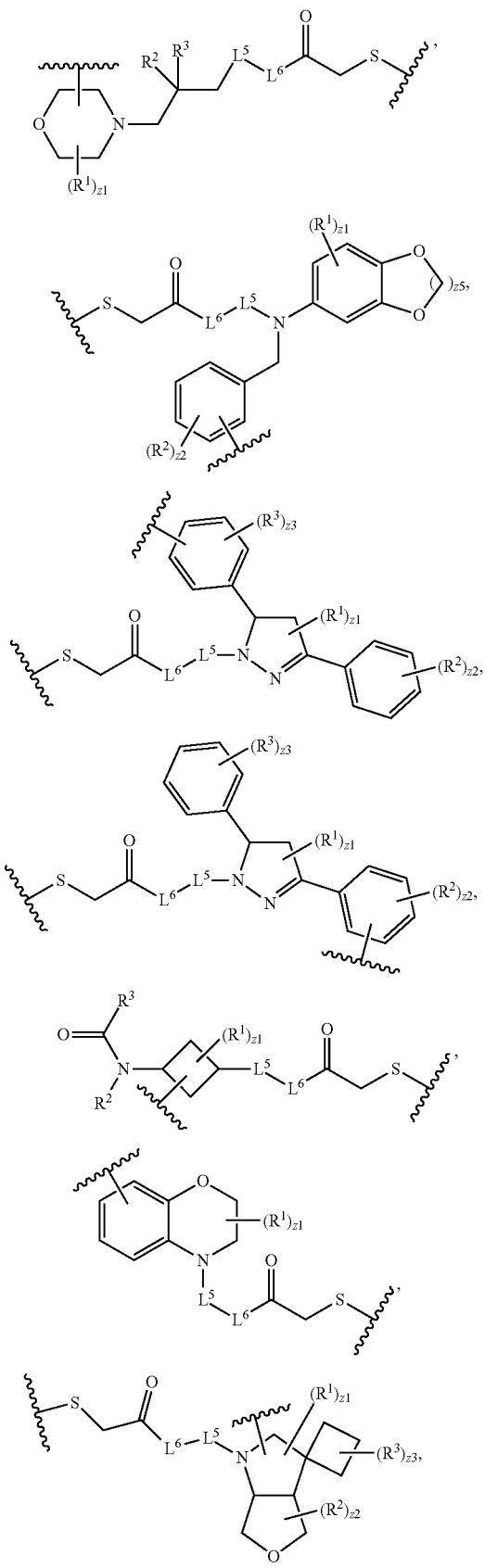

-continued

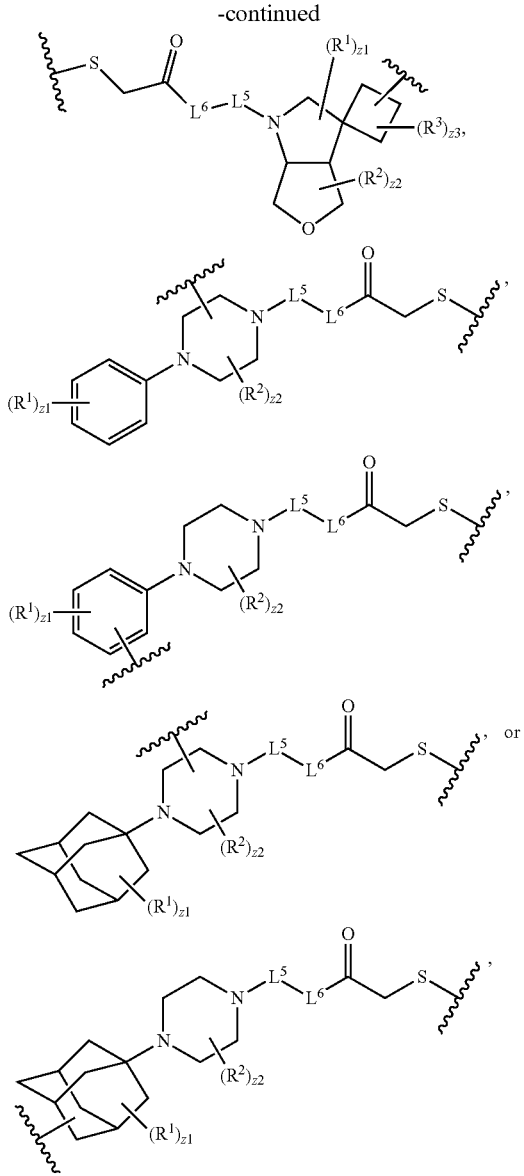

wherein S is the sulfur of an autophagy adapter protein cysteine (e.g., sulfur of amino acid corresponding to C17 of human LC3A protein, sulfur of amino acid corresponding to C26 of human p62/SQSTM1 protein, sulfur of amino acid corresponding to C27 of human p62/SQSTM1protein, sulfur of amino acid corresponding to C113 of human p62/SQSTM1 protein, sulfur of amino acid corresponding to C120 of human NBR1 protein, sulfur of amino acid corresponding to C321 of human NDP52/CALCOCO2 protein, sulfur of amino acid corresponding to C558 of human OPTN protein, sulfur of C17 of human LC3A protein, sulfur of C26 of human p62/SQSTM1 protein, sulfur of C27 of human p62/SQSTM1protein, sulfur of C113 of human p62/SQSTM1 protein, sulfur of C120 of human NBR1 protein, sulfur of C321 of human NDP52/CALCOCO2 protein, or sulfur of C558 of human OPTN protein), which is bonded to the remainder of the autophagy adapter protein and wherein $R^5$, $R^1$, $R^2$, z2, $R^3$, z3, $L^5$, $L^6$, and z1 are as described herein.

As a non-limiting example, the autophagy adapter protein covalently bonded to a monovalent autophagy adapter protein binder may have the formula:

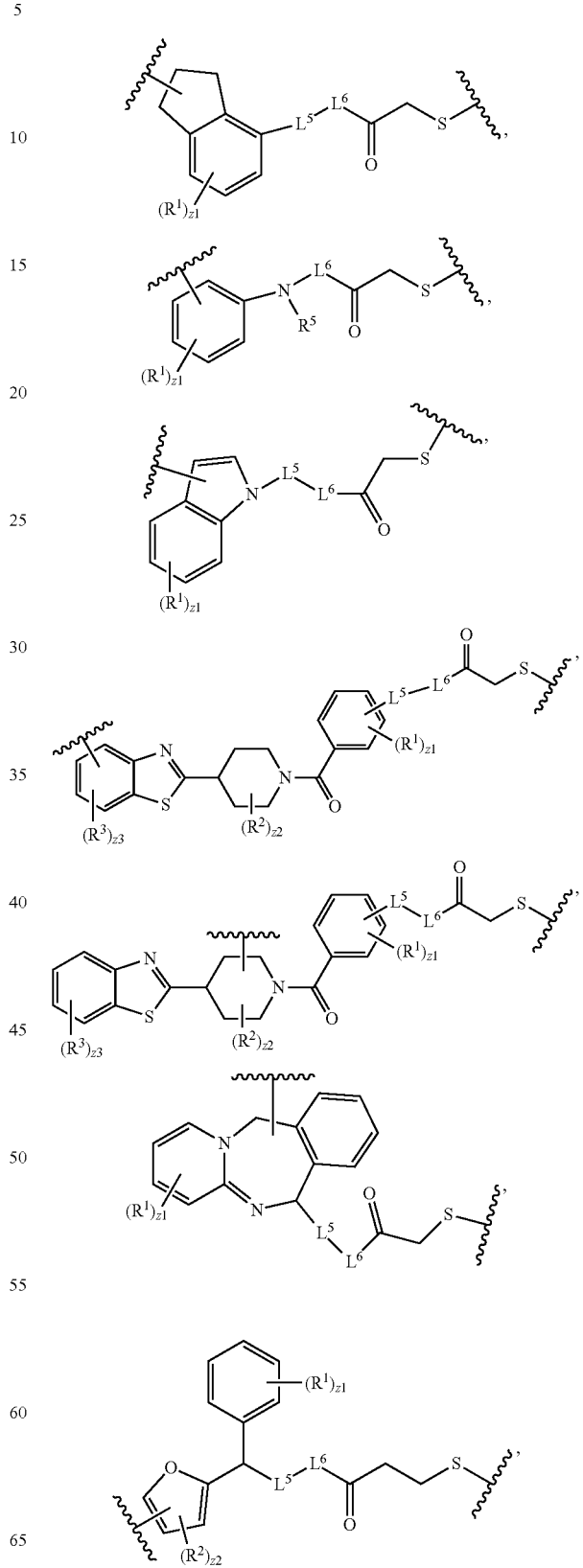

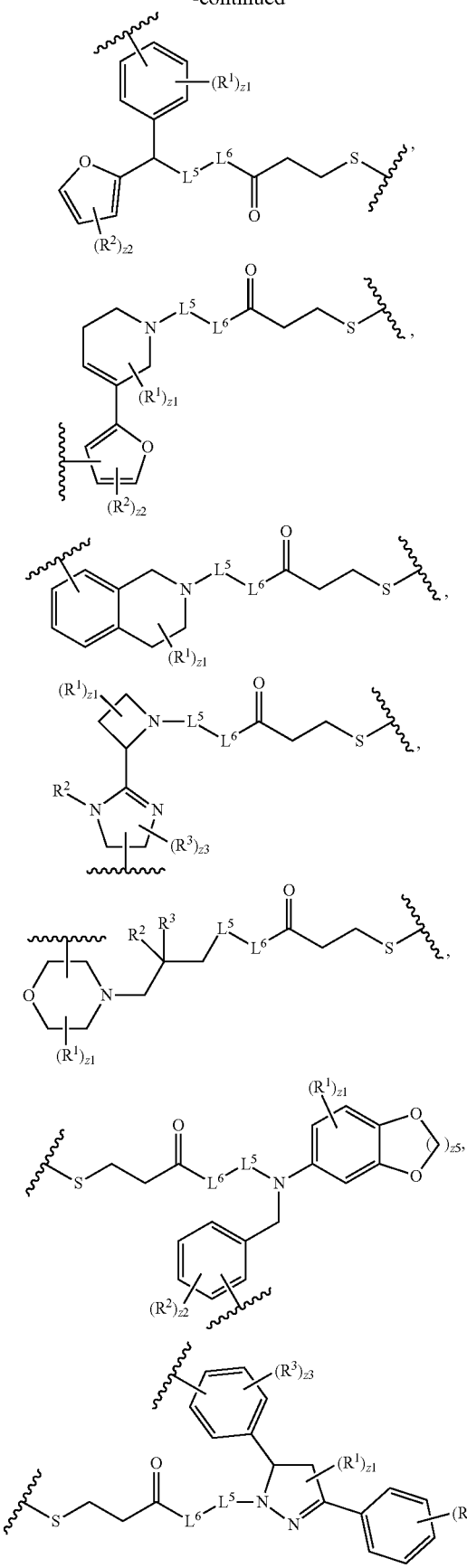
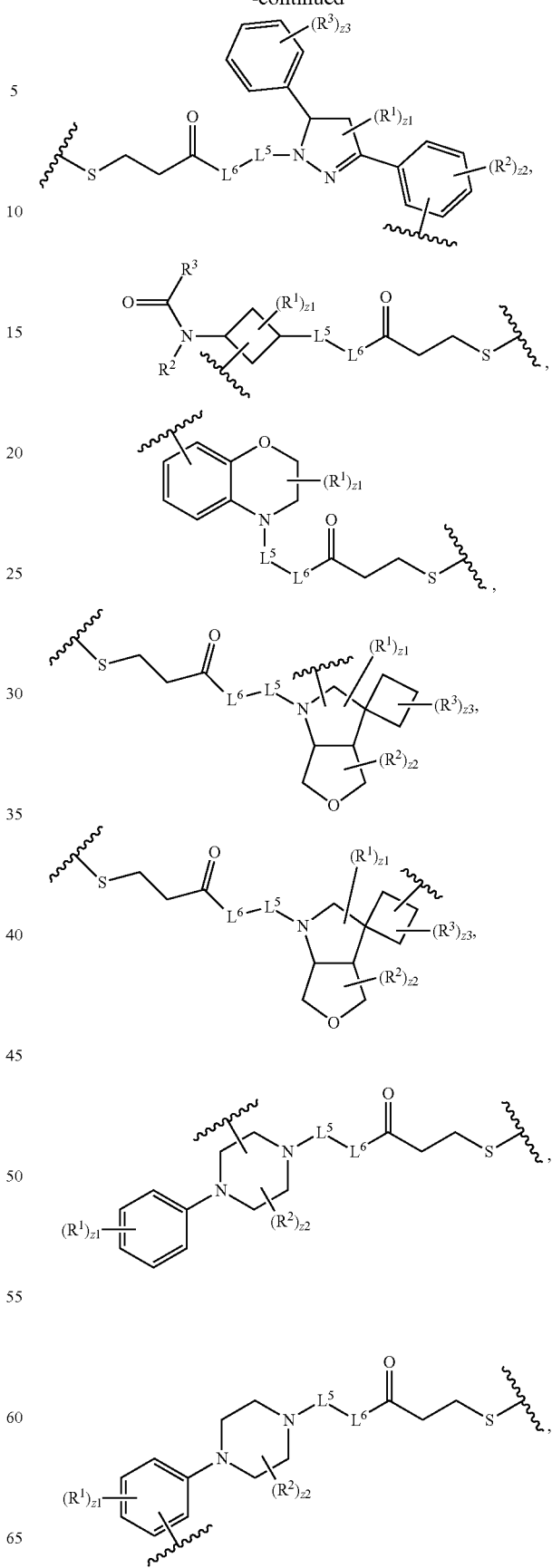

335
-continued

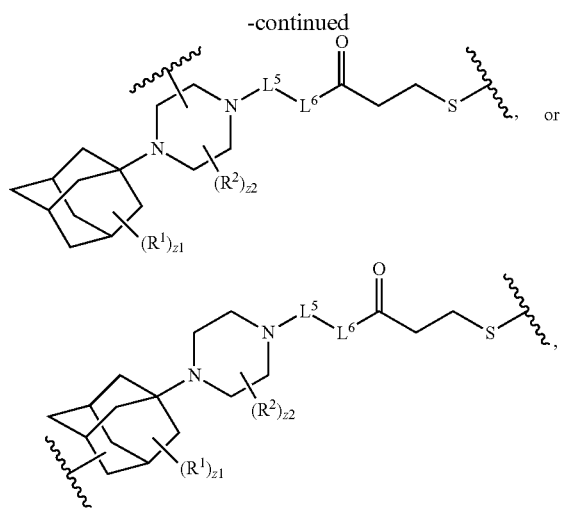

wherein S is the sulfur of an autophagy adapter protein cysteine (e.g., sulfur of amino acid corresponding to C17 of human LC3A protein, sulfur of amino acid corresponding to C26 of human p62/SQSTM1 protein, sulfur of amino acid corresponding to C27 of human p62/SQSTM1protein, sulfur of amino acid corresponding to C113 of human p62/SQSTM1 protein, sulfur of amino acid corresponding to C120 of human NBR1 protein, sulfur of amino acid corresponding to C321 of human NDP52/CALCOCO2 protein, sulfur of amino acid corresponding to C558 of human OPTN protein, sulfur of C17 of human LC3A protein, sulfur of C26 of human p62/SQSTM1 protein, sulfur of C27 of human p62/SQSTM1protein, sulfur of C113 of human p62/SQSTM1 protein, sulfur of C120 of human NBR1 protein, sulfur of C321 of human NDP52/CALCOCO2 protein, or sulfur of C558 of human OPTN protein), which is bonded to the remainder of the autophagy adapter protein and wherein $R^5$, $R^1$, $R^2$, z2, $R^3$, z3, $L^5$, $L^6$, and z1 are as described herein.

As a non-limiting example, the autophagy adapter protein covalently bonded to a monovalent autophagy adapter protein binder may have the formula:

336
-continued

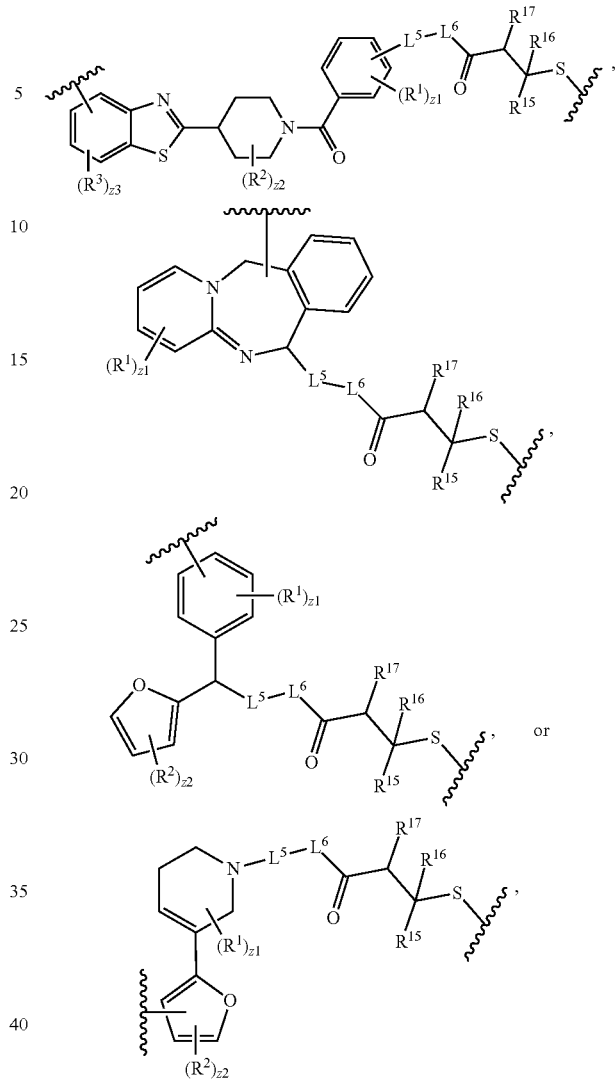

wherein S is the sulfur of an autophagy adapter protein cysteine (e.g., sulfur of amino acid corresponding to C17 of human LC3A protein, sulfur of amino acid corresponding to C26 of human p62/SQSTM1 protein, sulfur of amino acid corresponding to C27 of human p62/SQSTM1protein, sulfur of amino acid corresponding to C113 of human p62/SQSTM1 protein, sulfur of amino acid corresponding to C120 of human NBR1 protein, sulfur of amino acid corresponding to C321 of human NDP52/CALCOCO2 protein, sulfur of amino acid corresponding to C558 of human OPTN protein, sulfur of C17 of human LC3A protein, sulfur of C26 of human p62/SQSTM1 protein, sulfur of C27 of human p62/SQSTM1protein, sulfur of C113 of human p62/SQSTM1 protein, sulfur of C120 of human NBR1 protein, sulfur of C321 of human NDP52/CALCOCO2 protein, or sulfur of C558 of human OPTN protein), which is bonded to the remainder of the autophagy adapter protein and wherein $R^{15}$, $R^{16}$, $R^{17}$, $R^5$, $R^1$, $R^2$, z2, $R^3$, z3, $L^5$, $L^6$, and z1 are as described herein.

As a non-limiting example, the autophagy adapter protein covalently bonded to a monovalent autophagy adapter protein binder may have the formula:

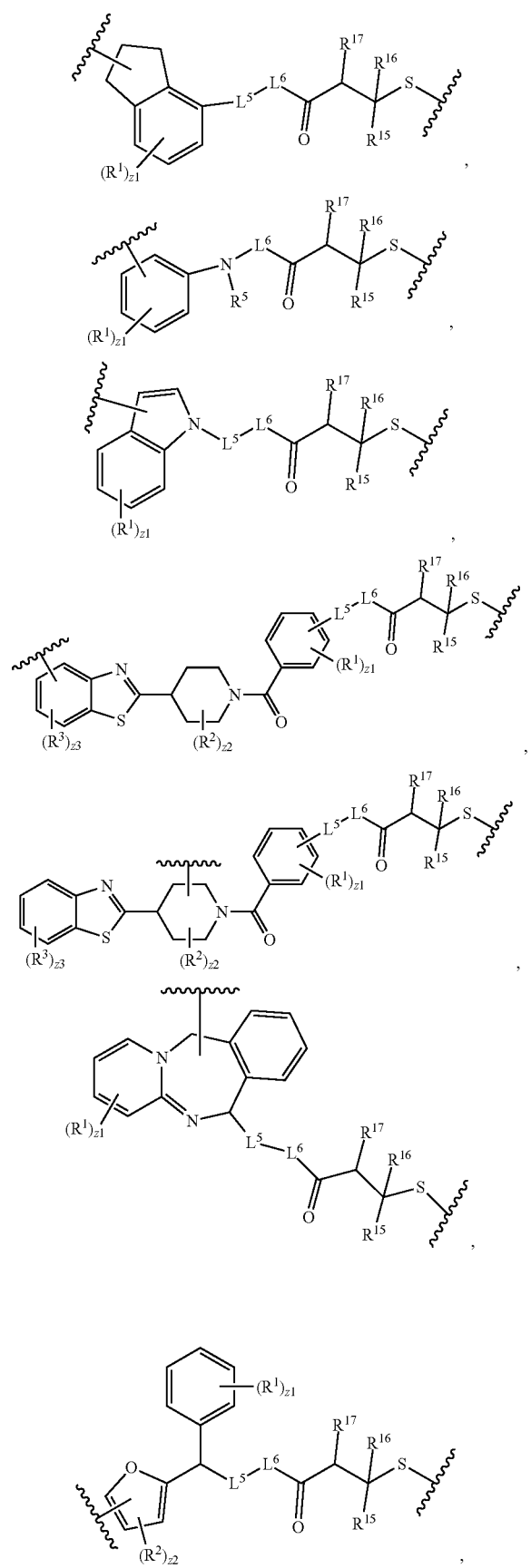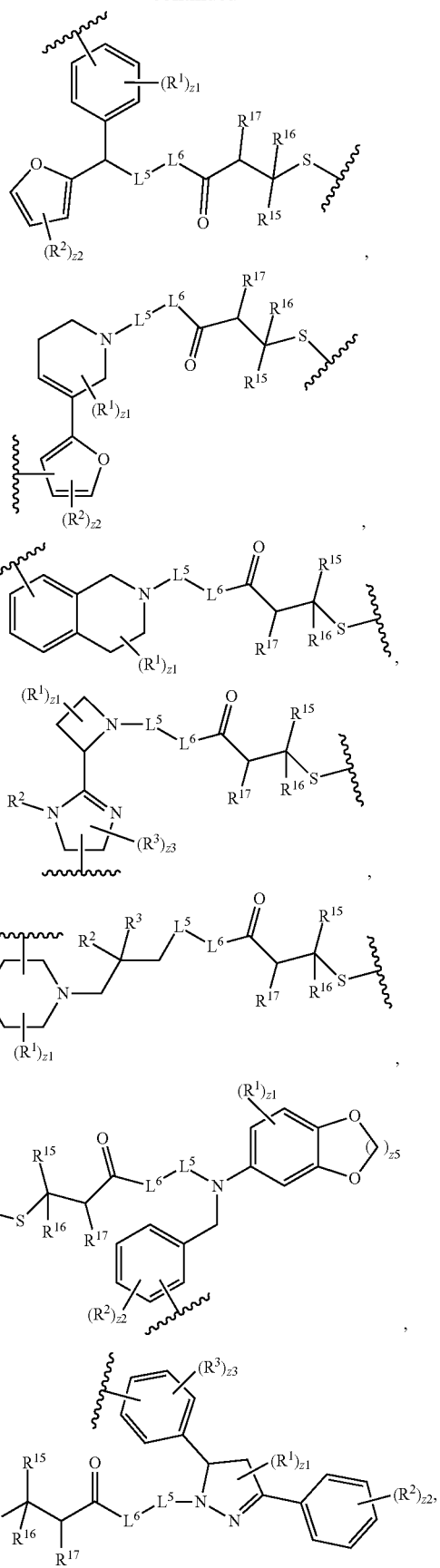

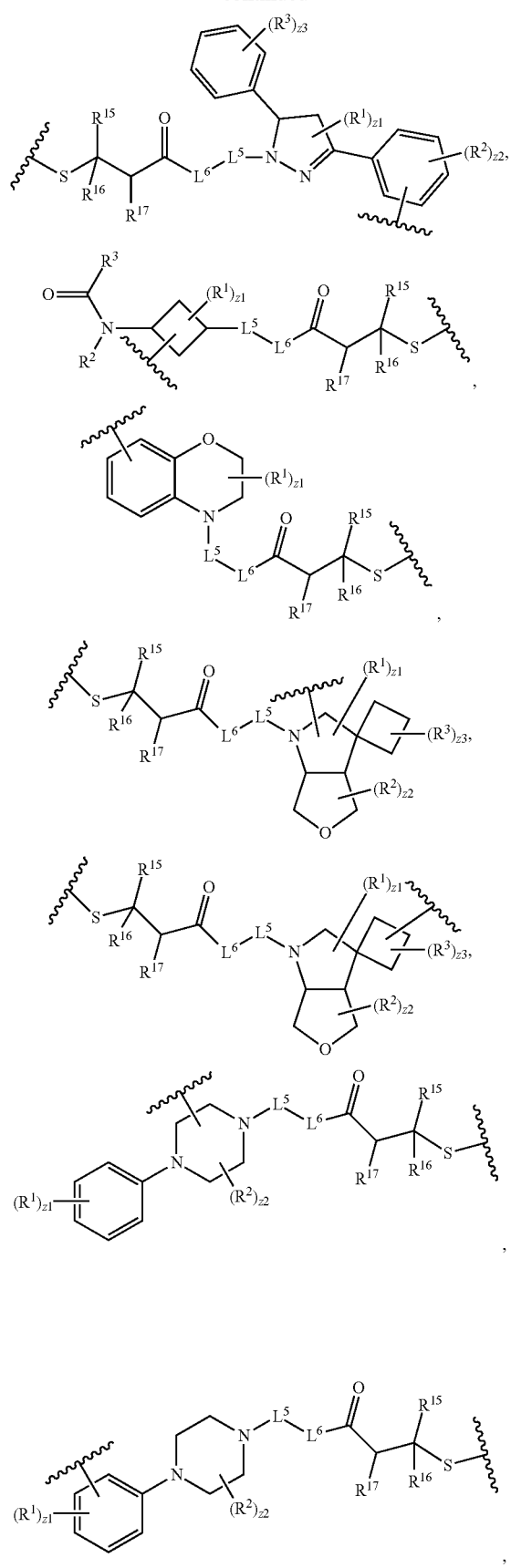

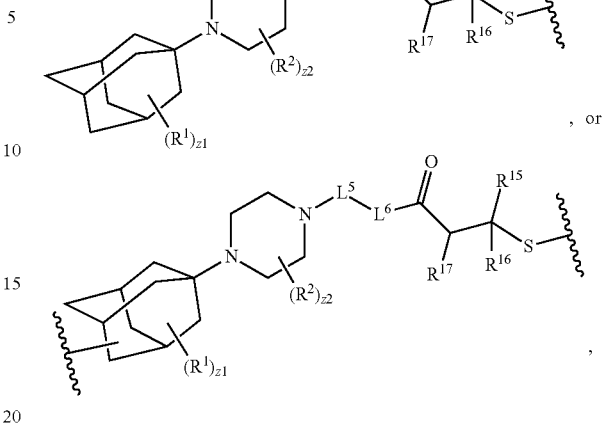

wherein S is the sulfur of an autophagy adapter protein cysteine (e.g., sulfur of amino acid corresponding to C17 of human LC3A protein, sulfur of amino acid corresponding to C26 of human p62/SQSTM1 protein, sulfur of amino acid corresponding to C27 of human p62/SQSTM1protein, sulfur of amino acid corresponding to C113 of human p62/SQSTM1 protein, sulfur of amino acid corresponding to C120 of human NBR1 protein, sulfur of amino acid corresponding to C321 of human NDP52/CALCOCO2 protein, sulfur of amino acid corresponding to C558 of human OPTN protein, sulfur of C17 of human LC3A protein, sulfur of C26 of human p62/SQSTM1 protein, sulfur of C27 of human p62/SQSTM1protein, sulfur of C113 of human p62/SQSTM1 protein, sulfur of C120 of human NBR1 protein, sulfur of C321 of human NDP52/CALCOCO2 protein, or sulfur of C558 of human OPTN protein), which is bonded to the remainder of the autophagy adapter protein and wherein $R^{15}$, $R^{16}$, $R^{17}$, $R^5$, $R^1$, z2, $R^3$, z3, $L^5$, $L^6$, and z1 are as described herein.

In embodiments, the monovalent cellular component binder is a monovalent compound described herein (e.g., in a claim, example, table, figure, or embodiment). In embodiments, the monovalent targeted autophagy protein binder is a monovalent compound described herein (e.g., in a claim, example, table, figure, or embodiment).

A person of ordinary skill in the art will understand when a compound or a compound genus (e.g., a genus described herein) is described by a name or formula of a standalone compound with all valencies filled, the valencie(s) will be dictated by the context in which the compound is used. For example, when a compound (e.g., cellular component binder or targeted autophagy protein binder) as described herein is connected (e.g., bonded) through a linker, it is understood the compound represents a monovalent form of the standalone compound. The compounds provided herein may be depicted as standalone compounds with all valencies filled, for example

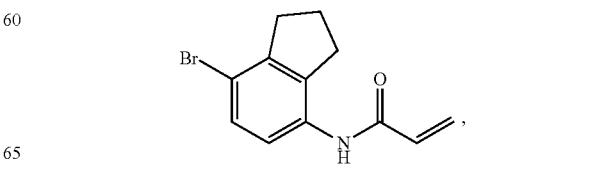

however when it is intended to be a monovalent compound (e.g., monovalent targeted autophagy protein binder) it is understood that a substituent (e.g., hydrogen, halogen, methyl, $R^1$, $R^2$, or $R^3$) may be removed to accommodate the linker, see for example:

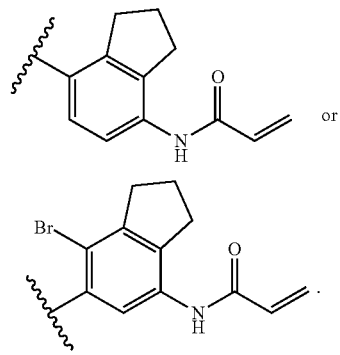

It is understood that when a compound as shown anywhere in the specification is connected (e.g., bonded) to another moiety through a linker, the compound is intended to be a monovalent form of the standalone compound at any attachment point following the replacement of a substituent (e.g., hydrogen or halogen) with a bond to the linker connected to the other moiety, for example, a monovalent form of

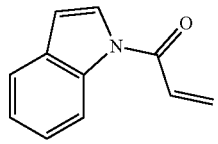

may be understood as

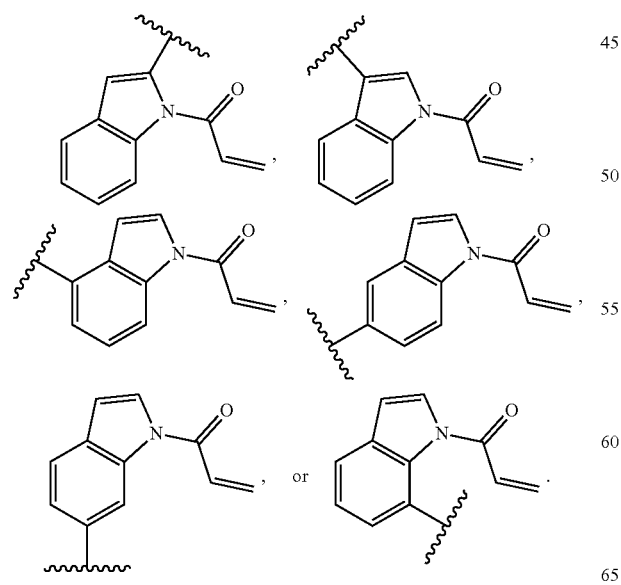

As another example, a monovalent form of

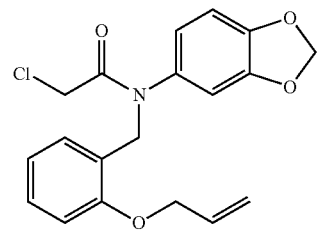 [SMILES: C=CCOc1ccccc1CN(C(=O)CCl)c1ccc2c(c1)OCO2]

may be understood as

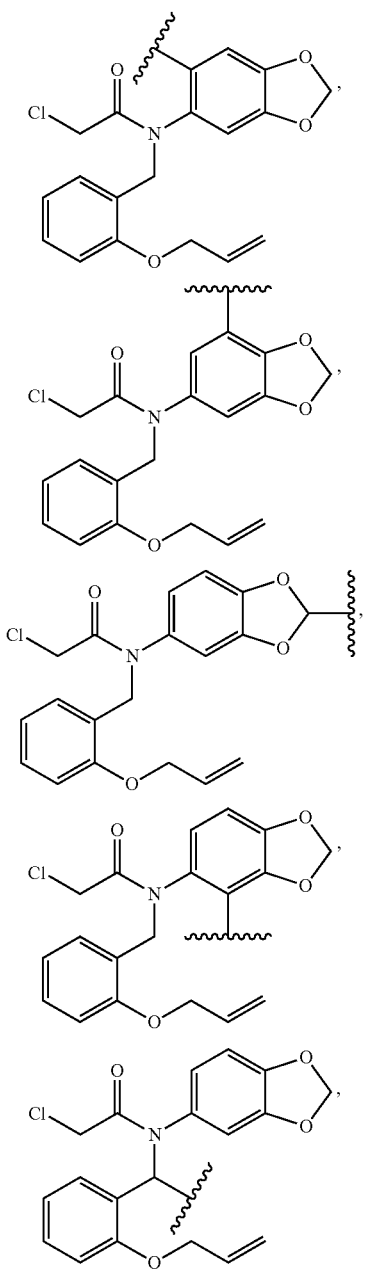

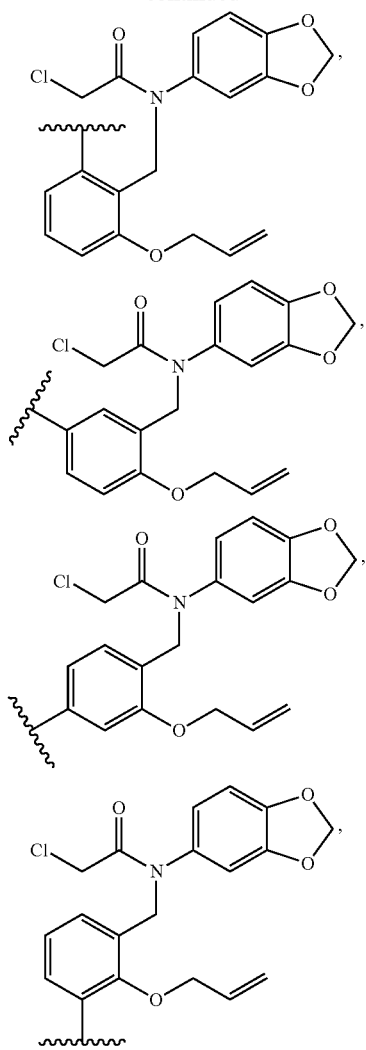

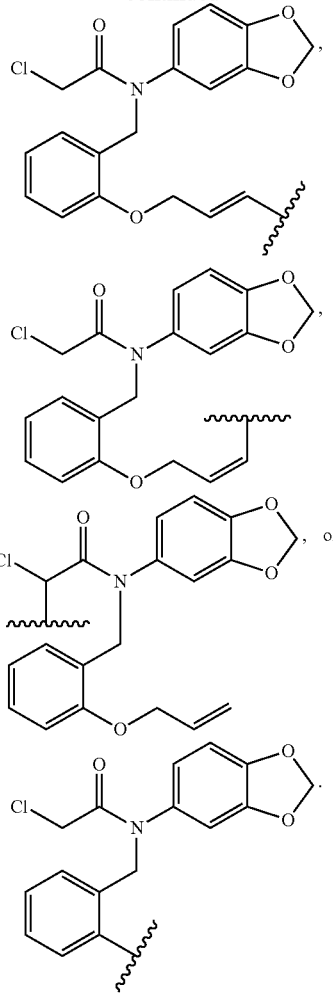

In embodiments, the monovalent targeted autophagy protein binder is a monovalent form of the formula I, II, III, IV, V, VI, VII, VIII, IX, X, XI, XII, XIII, XIV, XV, XVI, XVII, Ia, IIa, IIIa, IVa, Va, VIa, VIIa, VIIIa, IXa, Xa, XIa, XIIa, XIIIa, XIVa, XVa, XVIa, XVIIa, Ib, IIb, IIIb, IVb, Vb, VIb, VIIb, VIIIb, IXb, Xb, XIb, XIII), XIIIb, XIVb, XVb, XVIb, XVIIb, Ic, IIc, IIIc, IVc, Vc, VIc, VIIc, VIIIc, IXc, Xc, XIc, XIIc, XIIIc, XIVc, XVc, XVIc, XVIIc, Id, Ie, If, IId, IIe, IIf, IIId, IIIe, IIIf, IIIg, IIIh, Vd, VId, VIId, VIIId, IXd, Xd, XId, XIe, XIf, XIg, XIh, XIi, XIId, XIIId, XIVd, XVId, mI, mII, mIII, mIV, nIV, mV, mVI, nVI, mVII, mVIII, mIX, mX, mXI, mXII, nXII, mXIII, mXIV, mXV, nXV, mXVI, nXVI, mXVII, nXVII, mIe, mIf, mIg, mIIe, mIIf, mIIIf, mIIIg, mIIIh, mIVc, nIVc, mVd, mVId, nVId, mVIId, mVIIId, mIXd, mXd, mXIf, mXIg, mXIId, nXIId, mXIIId, mXIVd, mXVc, nXVc, mXVId, nXVId, mXVIIc, nXVIIc, mVe, mXIh, or mXIi. In embodiments, the monovalent targeted autophagy protein binder is a monovalent form of the formula I. In embodiments, the monovalent targeted autophagy protein binder is a monovalent form of the formula II. In embodiments, the monovalent targeted autophagy protein binder is a monovalent form of the formula III. In embodiments, the monovalent targeted autophagy protein binder is a monovalent form of the formula IV. In embodiments, the monovalent targeted autophagy protein binder is a monovalent form of the formula V. In embodiments, the monovalent targeted autophagy protein binder is a monovalent form of the formula VI. In embodiments, the monovalent targeted autophagy protein binder is a monovalent form of the formula VII. In embodiments, the monovalent targeted autophagy protein binder is a monovalent form of the formula VIII. In embodiments, the monovalent targeted autophagy protein binder is a monovalent form of the formula IX. In embodiments, the monovalent targeted autophagy protein binder is a monovalent form of the formula X. In embodiments, the monovalent targeted autophagy protein binder is a monovalent form of the formula XI. In embodiments, the monovalent targeted autophagy protein binder is a monovalent form of the formula XII. In embodiments, the monovalent targeted autophagy protein binder is a monovalent form of the formula XIII In embodiments, the monovalent targeted autophagy protein binder is a monovalent form of the formula XIV. In embodiments, the monovalent targeted autophagy protein binder is a monovalent form of the formula XV. In embodiments, the monovalent targeted autophagy protein binder is a monovalent form of the formula XVI. In embodiments, the monovalent targeted autophagy protein binder is a monovalent form of the formula XVII. In embodiments, the monovalent targeted autophagy protein binder is a monovalent form of the formula Ia. In embodiments, the monovalent targeted autophagy protein binder is a monovalent form of the formula IIa. In embodiments, the monovalent targeted autophagy protein binder is a monovalent form of the formula IIIa. In embodiments, the monovalent targeted autophagy protein binder is a monovalent form of the formula IVa. In embodiments, the monovalent targeted autophagy protein binder is a monovalent form of the formula Va. In embodiments, the monovalent targeted autophagy protein binder is a monovalent form of the formula VIa. In embodiments, the monovalent targeted autophagy protein binder is a monovalent form of the formula VIIa. In embodiments, the monovalent targeted autophagy protein binder is a monovalent form of the formula VIIIa. In embodiments, the monovalent targeted autophagy protein binder is a monovalent form of the formula IXa. In embodiments, the monovalent targeted autophagy protein binder is a monovalent form of the formula Xa. In embodiments, the monovalent targeted autophagy protein binder is a monovalent form of the formula XIa. In embodiments, the monovalent targeted autophagy protein binder is a monovalent form of the formula XIIa. In embodiments, the monovalent targeted autophagy protein binder is a monovalent form of the formula XIIIa. In embodiments, the monovalent targeted autophagy protein binder is a monovalent form of the formula XIVa. In embodiments, the monovalent targeted autophagy protein binder is a monovalent form of the formula XVa. In embodiments, the monovalent targeted autophagy protein binder is a monovalent form of the formula XVIa. In embodiments, the monovalent targeted autophagy protein binder is a monovalent form of the formula XVIIa. In embodiments, the monovalent targeted autophagy protein binder is a monovalent form of the formula Ib. In embodiments, the monovalent targeted autophagy protein binder is a monovalent form of the formula IIb. In embodiments, the monovalent targeted autophagy protein binder is a monovalent form of the formula IIIb. In embodiments, the monovalent targeted autophagy protein binder is a monovalent form of the formula IVb. In embodiments, the monovalent targeted autophagy protein binder is a monovalent form of the formula Vb. In embodiments, the monovalent targeted autophagy protein binder is a monovalent form of the formula VIb. In embodiments, the monovalent targeted autophagy protein binder is a monovalent form of the formula VIIb. In embodiments, the monovalent targeted autophagy protein binder is a monovalent form of the formula VIIIb. In embodiments, the monovalent targeted autophagy protein binder is a monovalent form of the formula IXb. In embodiments, the monovalent targeted autophagy protein binder is a monovalent form of the formula Xb. In embodiments, the monovalent targeted autophagy protein binder is a monovalent form of the formula XIb. In embodiments, the monovalent targeted autophagy protein binder is a monovalent form of the formula XIII). In embodiments, the monovalent targeted autophagy protein binder is a monovalent form of the formula XIIIb. In embodiments, the monovalent targeted autophagy protein binder is a monovalent form of the formula XIVb. In embodiments, the monovalent targeted autophagy protein binder is a monovalent form of the formula XVb. In embodiments, the monovalent targeted autophagy protein binder is a monovalent form of the formula XVIb. In embodiments, the monovalent targeted autophagy protein binder is a monovalent form of the formula XVIIb. In embodiments, the monovalent targeted autophagy protein binder is a monovalent form of the formula Ic. In embodiments, the monovalent targeted autophagy protein binder is a monovalent form of the formula IIc. In embodiments, the monovalent targeted autophagy protein binder is a monovalent form of the formula IIIc. In embodiments, the monovalent targeted autophagy protein binder is a monovalent form of the formula IVc. In embodiments, the monovalent targeted autophagy protein binder is a monovalent form of the formula Vc. In embodiments, the monovalent targeted autophagy protein binder is a monovalent form of the formula VIc. In embodiments, the monovalent targeted autophagy protein binder is a monovalent form of the formula VIII. In embodiments, the monovalent targeted autophagy protein binder is a monovalent form of the formula VIIIc. In embodiments, the monovalent targeted autophagy protein binder is a monovalent form of the formula IXc. In embodiments, the monovalent targeted autophagy protein binder is a monovalent form of the formula Xc. In embodiments, the monovalent targeted autophagy protein binder is a monovalent form of the formula XIc. In embodiments, the monovalent targeted autophagy protein binder is a monovalent form of the formula XIIc. In embodiments, the monovalent targeted autophagy protein binder is a monovalent form of the formula XIIIc. In embodiments, the monovalent targeted autophagy protein binder is a monovalent form of the formula XIVc. In embodiments, the monovalent targeted autophagy protein binder is a monovalent form of the formula XVc. In embodiments, the monovalent targeted autophagy protein binder is a monovalent form of the formula XVIc. In embodiments, the monovalent targeted autophagy protein binder is a monovalent form of the formula XVIIc. In embodiments, the monovalent targeted autophagy protein binder is a monovalent form of the formula Id. In embodiments, the monovalent targeted autophagy protein binder is a monovalent form of the formula Ie. In embodiments, the monovalent targeted autophagy protein binder is a monovalent form of the formula If. In embodiments, the monovalent targeted autophagy protein binder is a monovalent form of the formula IId. In embodiments, the monovalent targeted autophagy protein binder is a monovalent form of the formula IIe. In embodiments, the monovalent targeted autophagy protein binder is a monovalent form of the formula IIf. In embodiments, the monovalent targeted autophagy protein binder is a monovalent form of the formula IIId. In embodiments, the monovalent targeted autophagy protein binder is a monovalent form of the formula IIIe. In embodiments, the monovalent targeted autophagy protein binder is a monovalent form of the formula IIIf. In embodiments, the monovalent targeted autophagy protein binder is a monovalent form of the formula IIIg. In embodiments, the monovalent targeted autophagy protein binder is a monovalent form of the formula IIIh. In embodiments, the monovalent targeted autophagy protein binder is a monovalent form of the formula Vd. In embodiments, the monovalent targeted autophagy protein binder is a monovalent form of the formula VId. In embodiments, the monovalent targeted autophagy protein binder is a monovalent form of the formula VIId. In embodiments, the monovalent targeted autophagy protein binder is a monovalent form of the formula VIIId. In embodiments, the monovalent targeted autophagy protein binder is a monovalent form of the formula IXd. In embodiments, the monovalent targeted autophagy protein binder is a monovalent form of the formula Xd. In embodiments, the monovalent targeted autophagy protein binder is a monovalent form of the formula XId. In embodiments, the monovalent targeted autophagy protein binder is a monovalent form of the formula XIe. In embodiments, the monovalent targeted autophagy protein binder is a monovalent form of the formula XIf. In embodiments, the monovalent targeted autophagy protein binder is a monovalent form of the formula XIg. In embodiments, the monovalent targeted autophagy protein binder is a monovalent form of the formula XIh. In embodiments, the monovalent targeted autophagy protein binder is a monovalent form of the formula XIi. In embodiments, the monovalent targeted autophagy protein binder is a monovalent form of the formula XIId. In embodiments, the monovalent targeted autophagy protein binder is a monovalent form of the formula XIIId. In embodiments, the monovalent targeted autophagy protein binder is a monovalent form of the formula XIVd. In embodiments, the monovalent targeted autophagy protein binder is a monovalent form of the formula XVId. In embodiments, the monovalent targeted autophagy protein binder is a monovalent form of the formula mI. In embodiments, the monovalent targeted autophagy protein binder is a monovalent form of the formula mII. In embodiments, the monovalent targeted autophagy protein binder is a monovalent form of the formula mIII. In embodiments, the monovalent targeted autophagy protein binder is a monovalent form of the formula mIV. In embodiments, the monovalent targeted autophagy protein binder is a monovalent form of the formula nIV. In embodiments, the monovalent targeted autophagy protein binder is a monovalent form of the formula mV. In embodiments, the monovalent targeted autophagy protein binder is a monovalent form of the formula mVI. In embodiments, the monovalent targeted autophagy protein binder is a monovalent form of the formula nVI. In embodiments, the monovalent targeted autophagy protein binder is a monovalent form of the formula mVII. In embodiments, the monovalent targeted autophagy protein binder is a monovalent form of the formula mVIII. In embodiments, the monovalent targeted autophagy protein binder is a monovalent form of the formula mIX. In embodiments, the monovalent targeted autophagy protein binder is a monovalent form of the formula mX. In embodiments, the monovalent targeted autophagy protein binder is a monovalent form of the formula mXI. In embodiments, the monovalent targeted autophagy protein binder is a monovalent form of the formula mXII. In embodiments, the monovalent targeted autophagy protein binder is a monovalent form of the formula nXII. In embodiments, the monovalent targeted autophagy protein binder is a monovalent form of the formula mXIII. In embodiments, the monovalent targeted autophagy protein binder is a monovalent form of the formula mXIV. In embodiments, the monovalent targeted autophagy protein binder is a monovalent form of the formula mXV. In embodiments, the monovalent targeted autophagy protein binder is a monovalent form of the formula nXV. In embodiments, the monovalent targeted autophagy protein binder is a monovalent form of the formula mXVI. In embodiments, the monovalent targeted autophagy protein binder is a monovalent form of the formula nXVI. In embodiments, the monovalent targeted autophagy protein binder is a monovalent form of the formula mXVII. In embodiments, the monovalent targeted autophagy protein binder is a monovalent form of the formula nXVII. In embodiments, the monovalent targeted autophagy protein binder is a monovalent form of the formula mIe. In embodiments, the monovalent targeted autophagy protein binder is a monovalent form of the formula mIf. In embodiments, the monovalent targeted autophagy protein binder is a monovalent form of the formula mIg. In embodiments, the monovalent targeted autophagy protein binder is a monovalent form of the formula mIIe. In embodiments, the monovalent targeted autophagy protein binder is a monovalent form of the formula mIIf. In embodiments, the monovalent targeted autophagy protein binder is a monovalent form of the formula mIIIf. In embodiments, the monovalent targeted autophagy protein binder is a monovalent form of the formula mIIIg. In embodiments, the monovalent targeted autophagy protein binder is a monovalent form of the formula mIIIh. In embodiments, the monovalent targeted autophagy protein binder is a monovalent form of the formula mIVc. In embodiments, the monovalent targeted autophagy protein binder is a monovalent form of the formula nIVc. In embodiments, the monovalent targeted autophagy protein binder is a monovalent form of the formula mVd. In embodiments, the monovalent targeted autophagy protein binder is a monovalent form of the formula mVId. In embodiments, the monovalent targeted autophagy protein binder is a monovalent form of the formula nVId. In embodiments, the monovalent targeted autophagy protein binder is a monovalent form of the formula mVIId. In embodiments, the monovalent targeted autophagy protein binder is a monovalent form of the formula mVIIId. In embodiments, the monovalent targeted autophagy protein binder is a monovalent form of the formula mIXd. In embodiments, the monovalent targeted autophagy protein binder is a monovalent form of the formula mXd. In embodiments, the monovalent targeted autophagy protein binder is a monovalent form of the formula mXIf. In embodiments, the monovalent targeted autophagy protein binder is a monovalent form of the formula mXIg. In embodiments, the monovalent targeted autophagy protein binder is a monovalent form of the formula mXIId. In embodiments, the monovalent targeted autophagy protein binder is a monovalent form of the formula nXIId. In embodiments, the monovalent targeted autophagy protein binder is a monovalent form of the formula mXIIId. In embodiments, the monovalent targeted autophagy protein binder is a monovalent form of the formula mXIVd. In embodiments, the monovalent targeted autophagy protein binder is a monovalent form of the formula mXVc. In embodiments, the monovalent targeted autophagy protein binder is a monovalent form of the formula nXVc. In embodiments, the monovalent targeted autophagy protein binder is a monovalent form of the formula mXVId. In embodiments, the monovalent targeted autophagy protein binder is a monovalent form of the formula nXVId. In embodiments, the monovalent targeted autophagy protein binder is a monovalent form of the formula mXVIIc. In embodiments, the monovalent targeted autophagy protein binder is a monovalent form of the formula nXVIIc. In embodiments, the monovalent targeted autophagy protein binder is a monovalent form of the formula mVe. In embodiments, the monovalent targeted autophagy protein binder is a monovalent form of the formula mXIh. In embodiments, the monovalent targeted autophagy protein binder is a monovalent form of the formula mXIi.

TABLE 1

Figure 4:
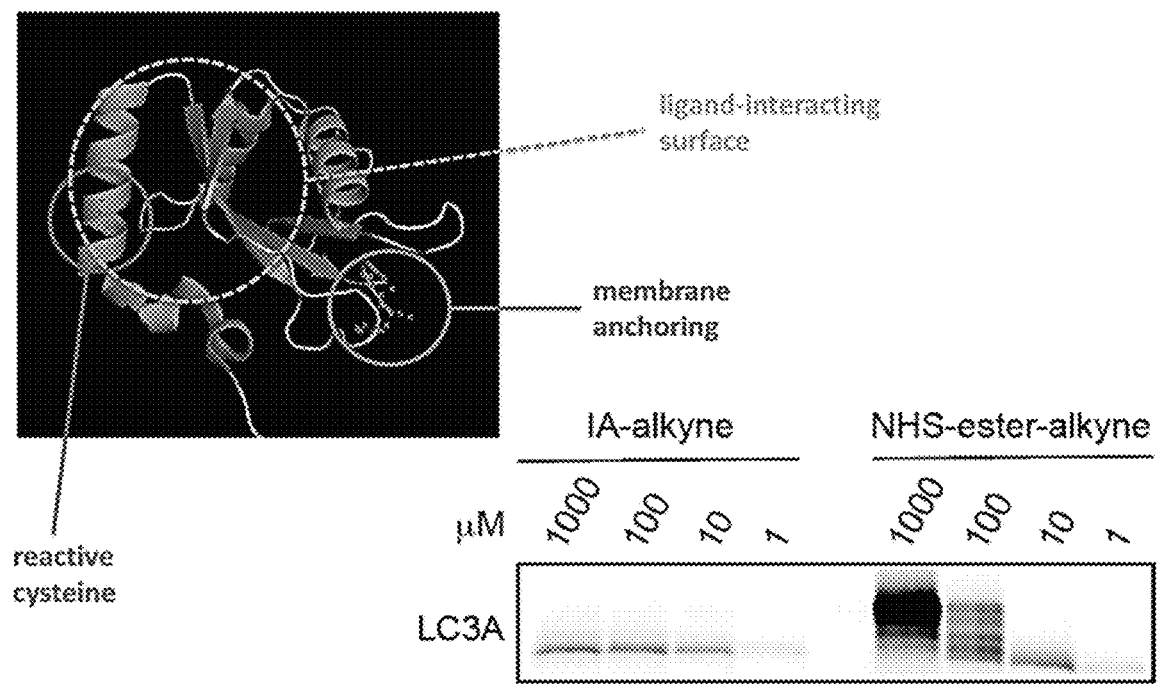
FIG. 4. LC3A is ligandable. LC3A pure protein was incubated with various concentration of the IA-alkyne or NHS-ester-alkyne probe for 30 min at room temperature before appending rhodamine-azide using copper-catalyzed click chemistry. Proteins were separated by SDS/PAGE and in-gel fluorescence was analyzed.
Figure 5A:
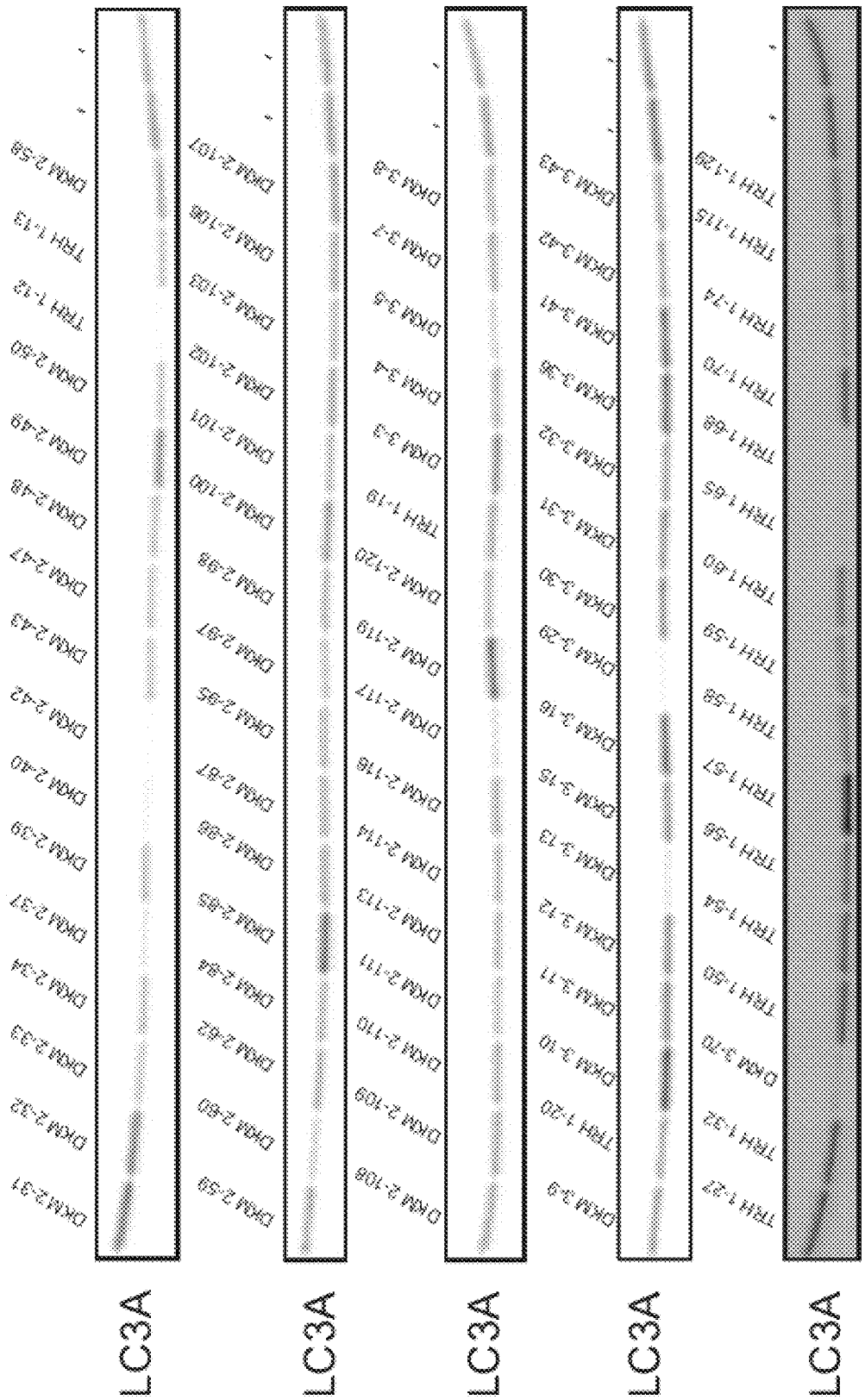
FIGS. 5A-5D. Covalent ligand screen against LC3A. Gel-based ABPP screen of cysteine-reactive ligand library against IA-alkyne labeling of LC3A. Cysteine-reactive covalent ligands were pre-incubated with LC3A pure protein (50 microM) for 30 min at room temperature prior to IA-alkyne labeling of the protein (10 microM) for 30 min at room temperature. Proteins were run on SDS/PAGE and in-gel fluorescence was analyzed. Hits refer to compounds that showed displacement of probe labeling resulting in loss of fluorescence by gel.
Figure 5B:
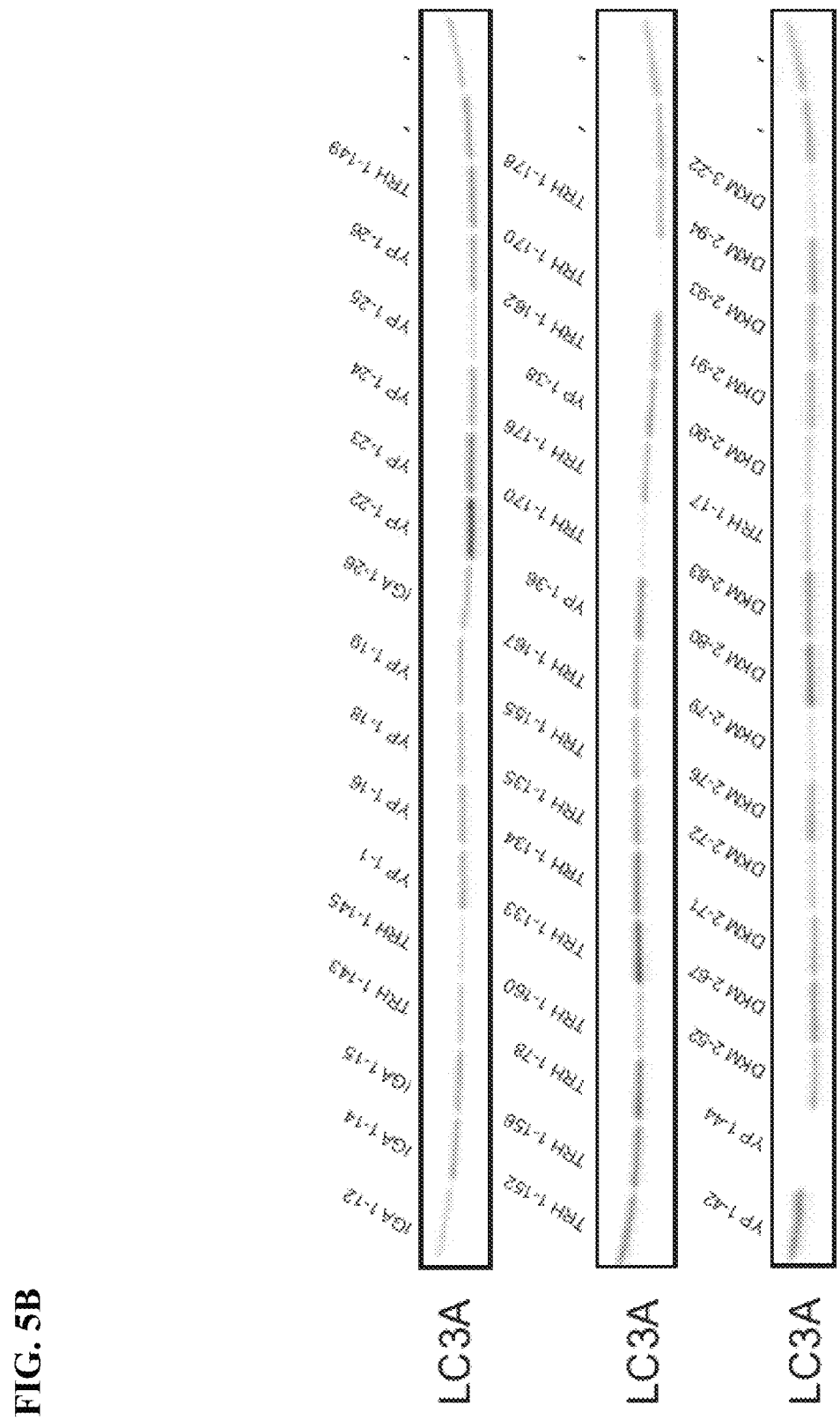
Figure 5C:
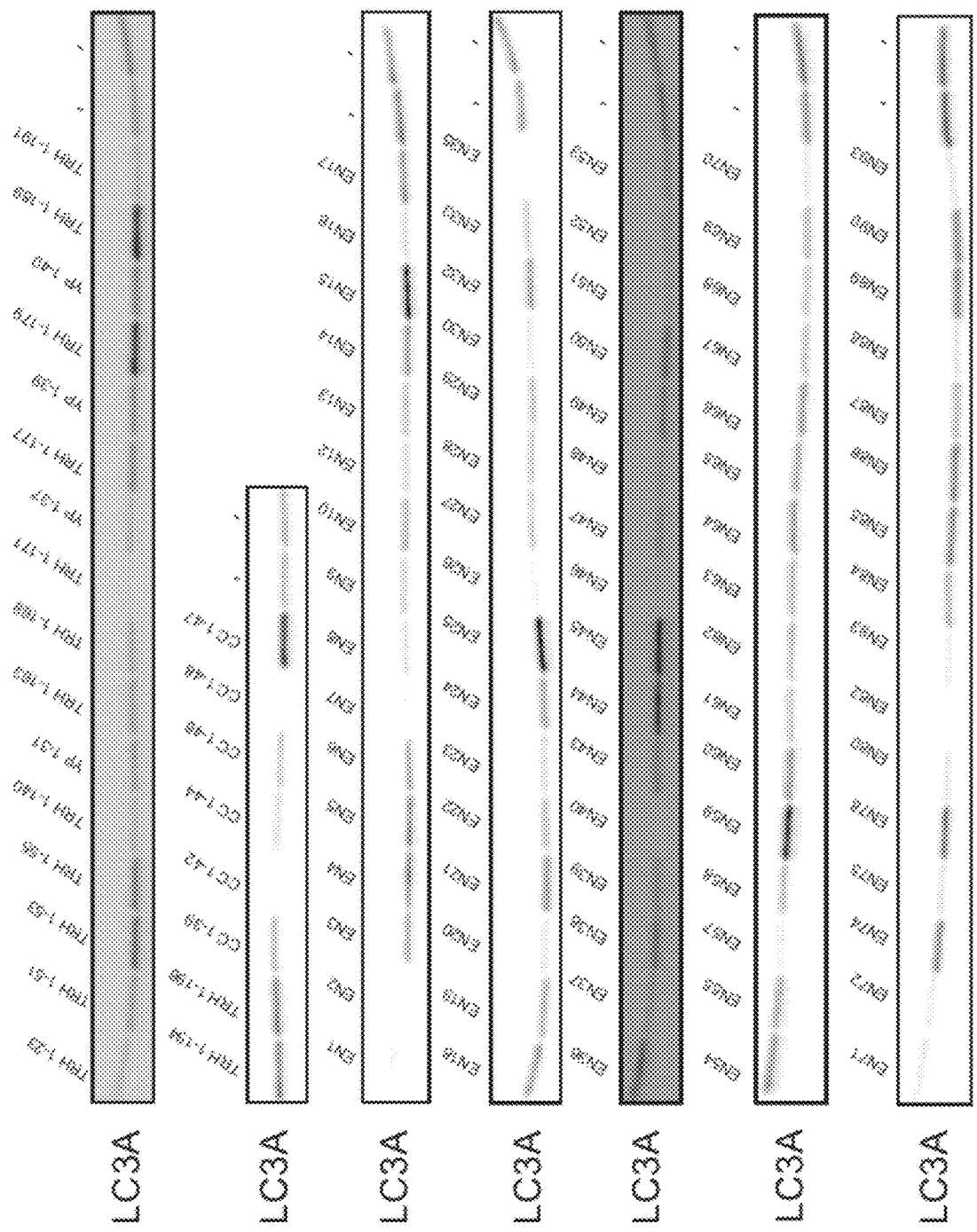
Figure 5D:
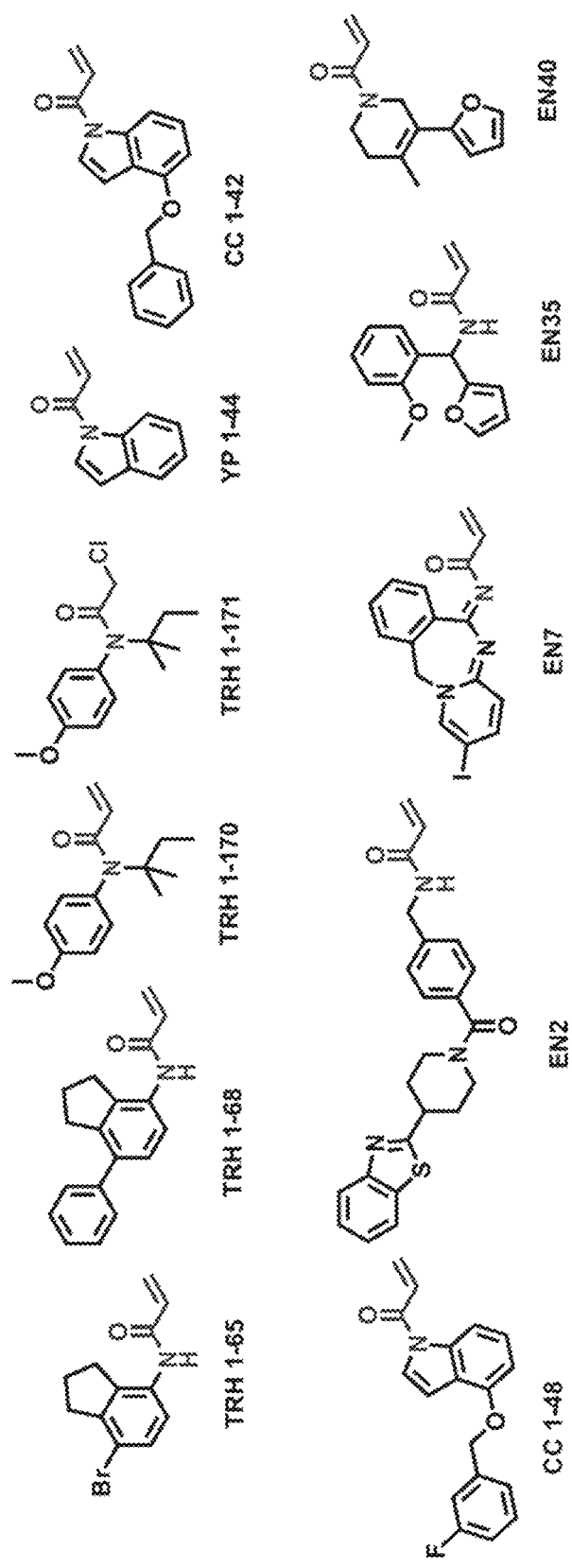

Additional compounds used in the gel-based ABPP screen of LC3A depicted in FIG. 4, in combination with FIGS. 9A-9G.

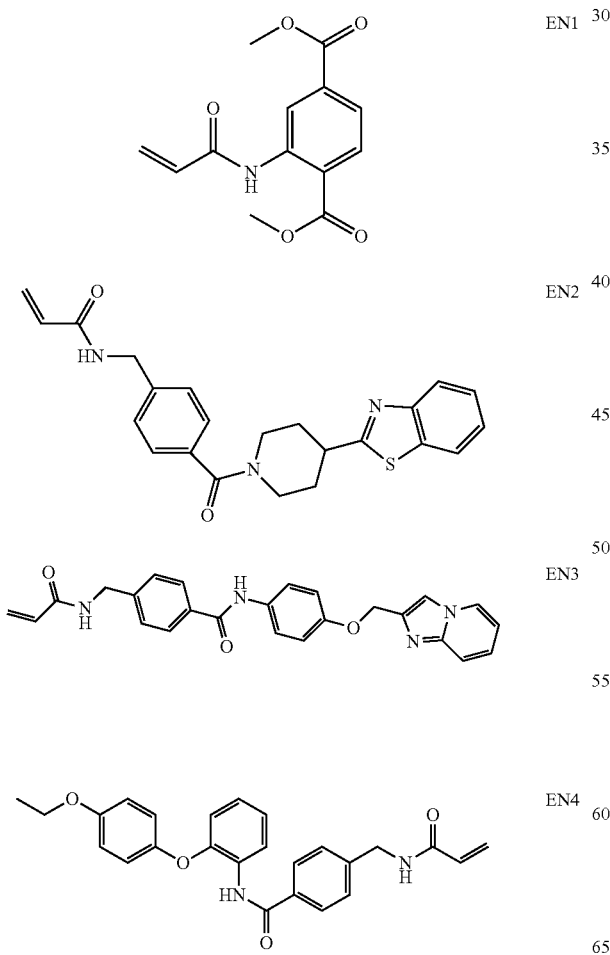

TABLE 1-continued

Additional compounds used in the gel-based ABPP screen of LC3A depicted in FIG. 4, in combination with FIGS. 9A-9G.

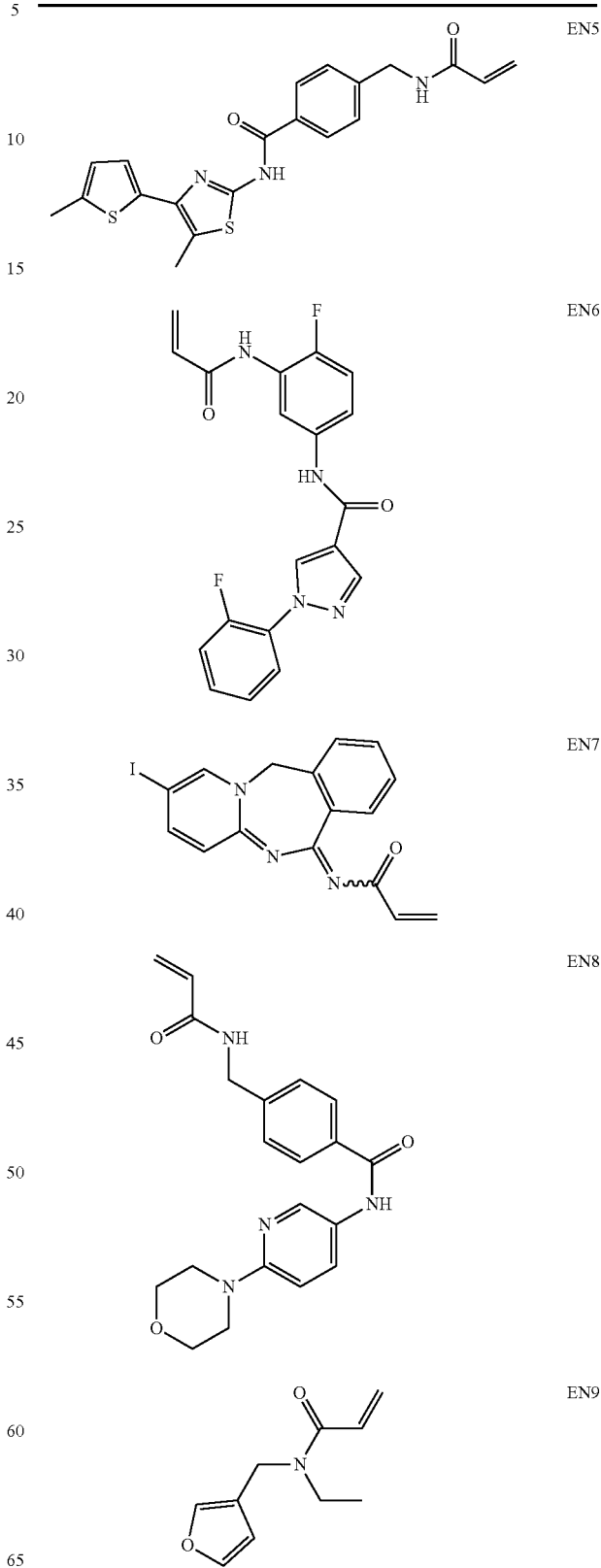

TABLE 1-continued
Additional compounds used in the gel-based ABPP screen of LC3A depicted in FIG. 4, in combination with FIGS. 9A-9G.
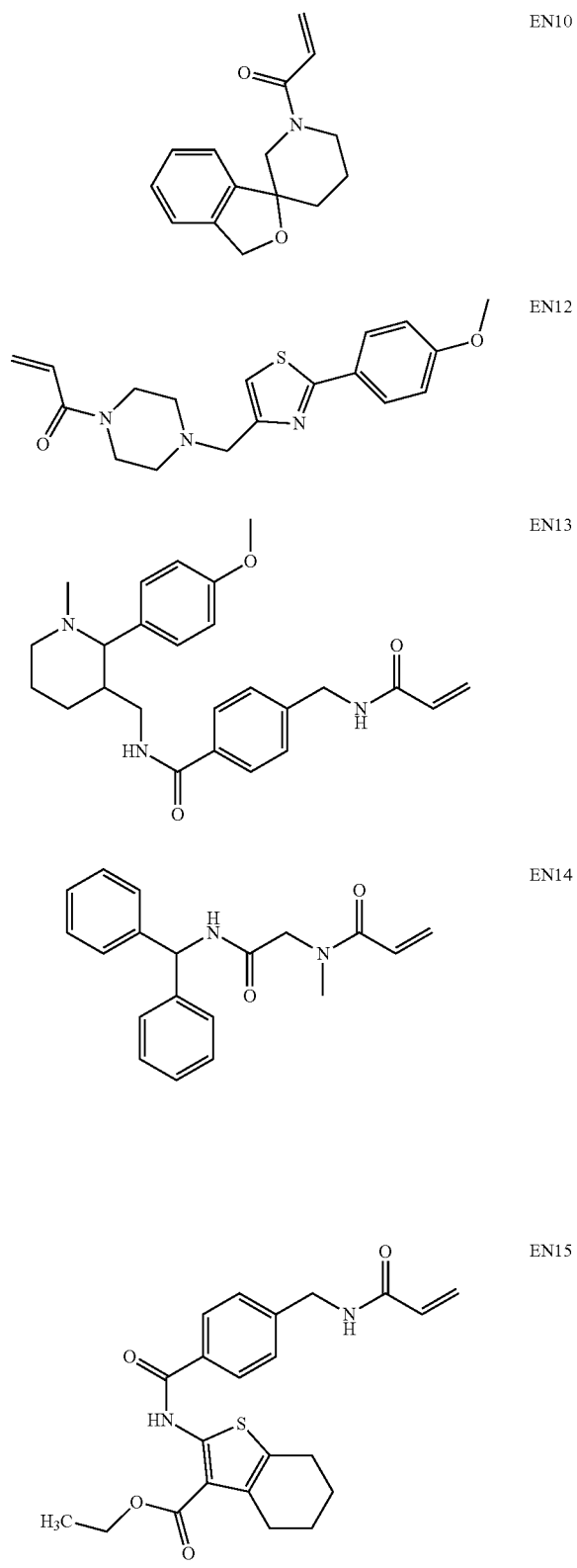

TABLE 1-continued
Additional compounds used in the gel-based ABPP screen of LC3A depicted in FIG. 4, in combination with FIGS. 9A-9G.
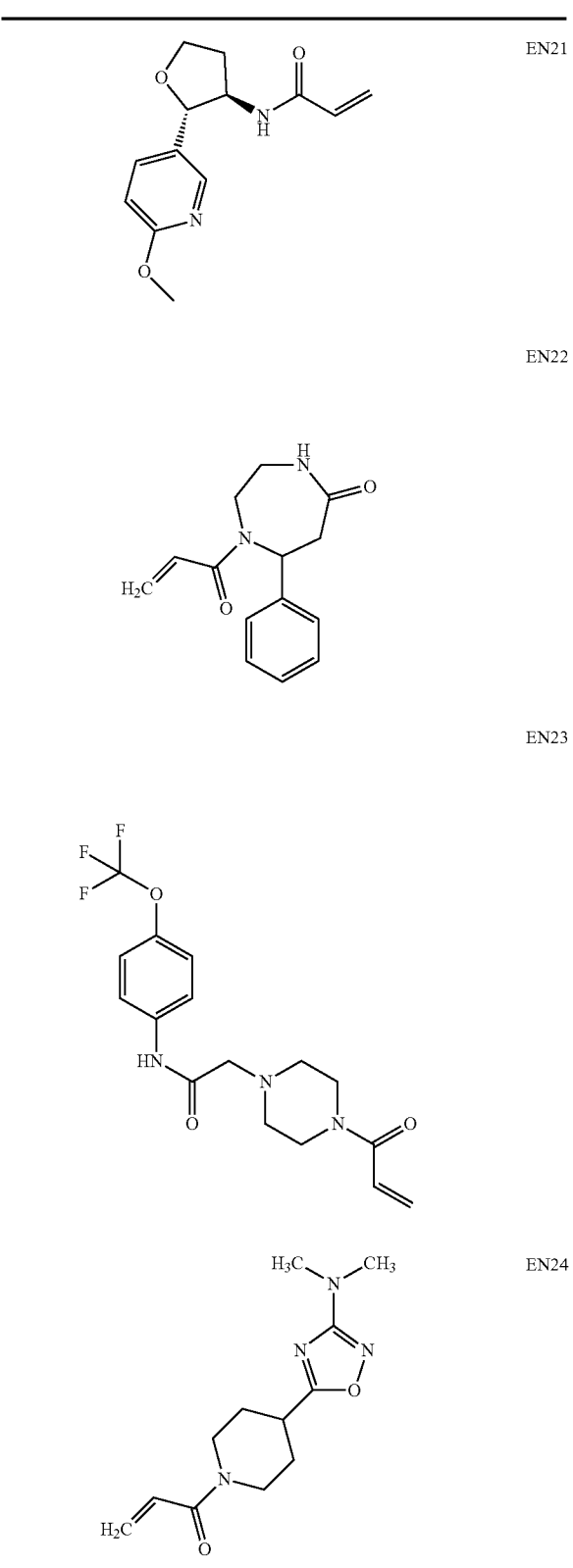
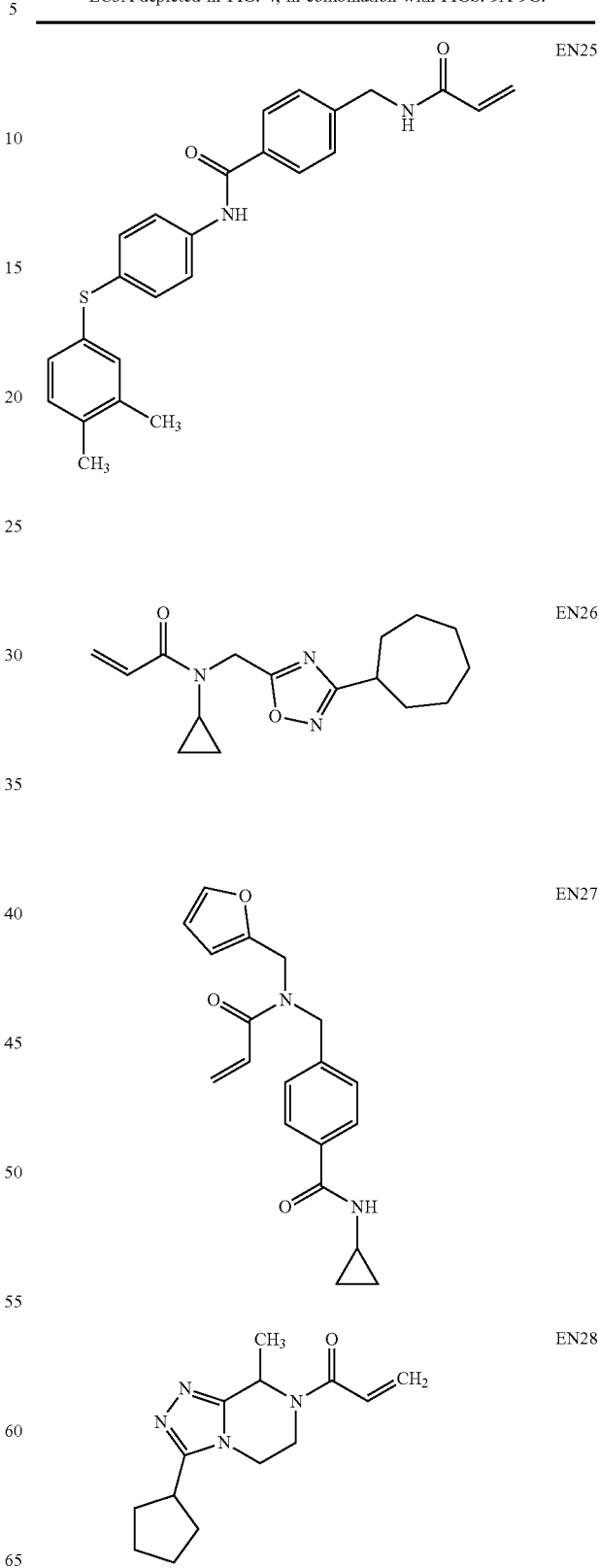

TABLE 1-continued
Additional compounds used in the gel-based ABPP screen of LC3A depicted in FIG. 4, in combination with FIGS. 9A-9G.
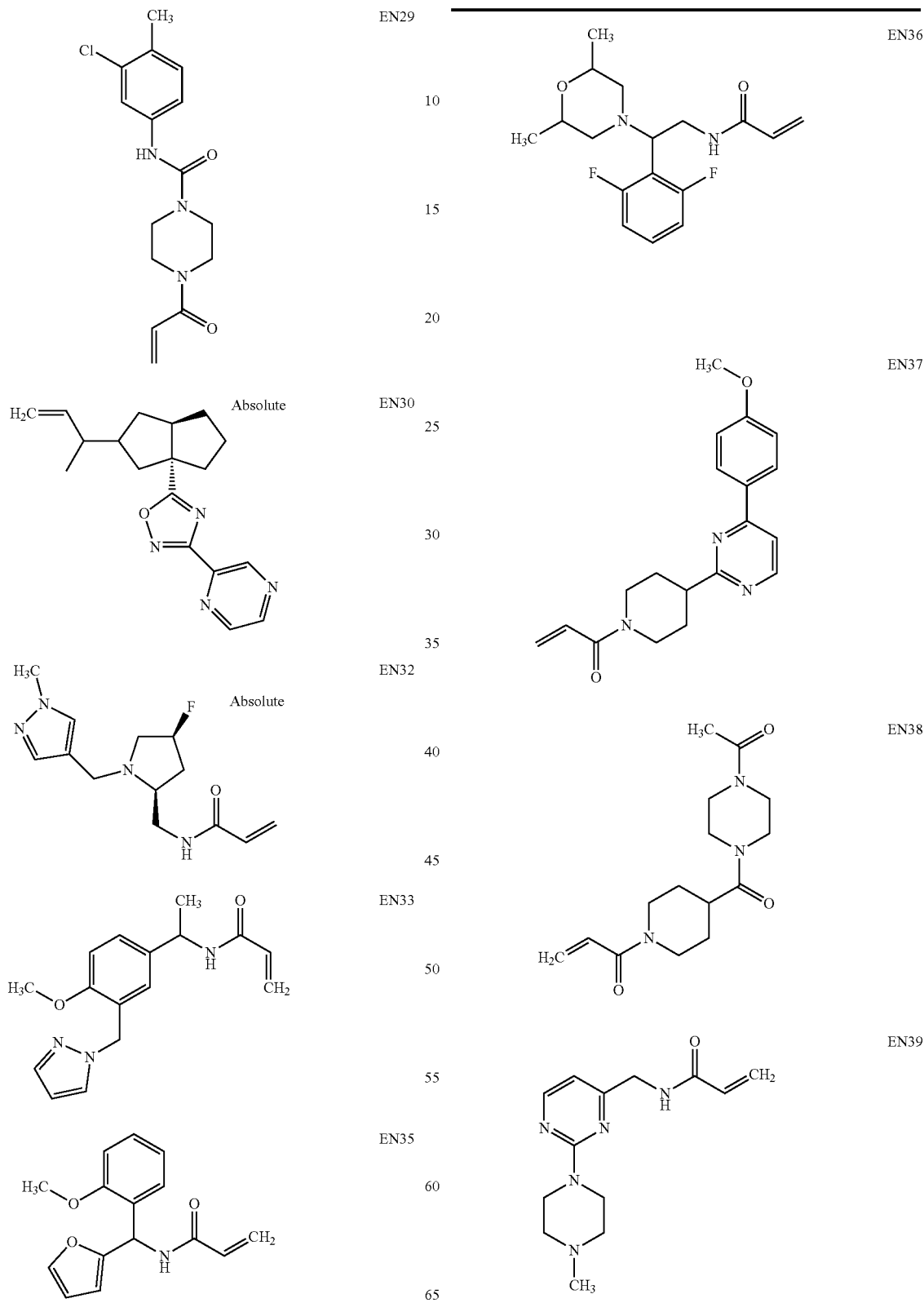

TABLE 1-continued
Additional compounds used in the gel-based ABPP screen of LC3A depicted in FIG. 4, in combination with FIGS. 9A-9G.
EN40
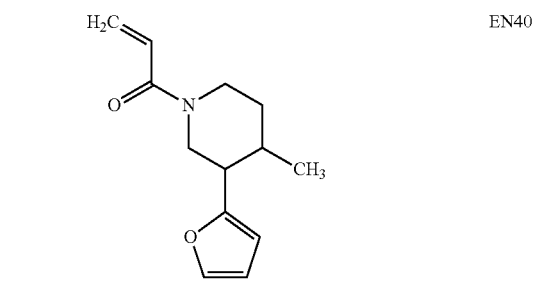
EN43
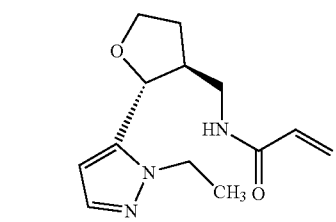 [SMILES: C=CC(=O)NC[C@@H]1CCO[C@H]1c1ccnn1CC]
EN44
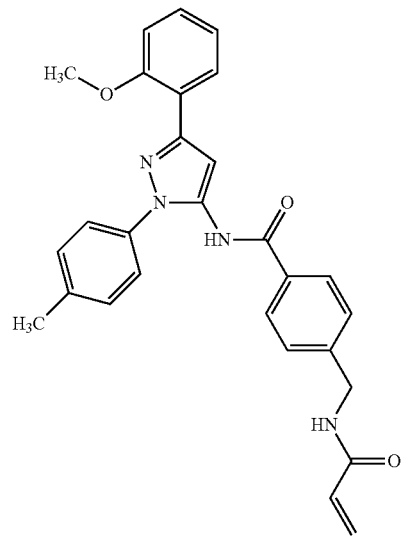 [SMILES: C=CC(=O)NCc1ccc(C(=O)Nc2cc(-c3ccccc3OC)nn2-c2ccc(C)cc2)cc1]
TABLE 1-continued
Additional compounds used in the gel-based ABPP screen of LC3A depicted in FIG. 4, in combination with FIGS. 9A-9G.
EN45
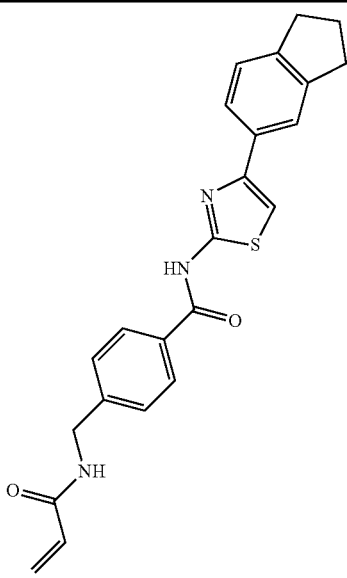
EN46
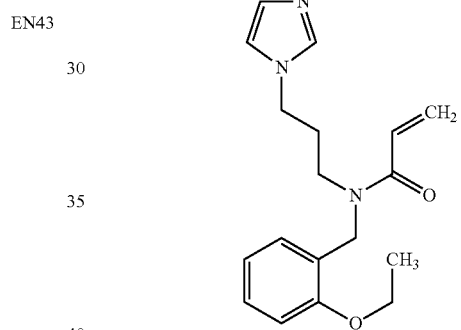
EN47
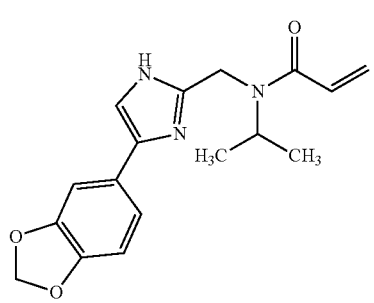 [SMILES: C=CC(=O)N(Cc1nc(-c2ccc3c(c2)OCO3)c[nH]1)C(C)C]
EN48
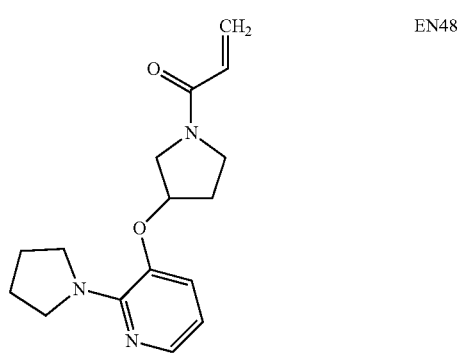

TABLE 1-continued
Additional compounds used in the gel-based ABPP screen of LC3A depicted in FIG. 4, in combination with FIGS. 9A-9G.
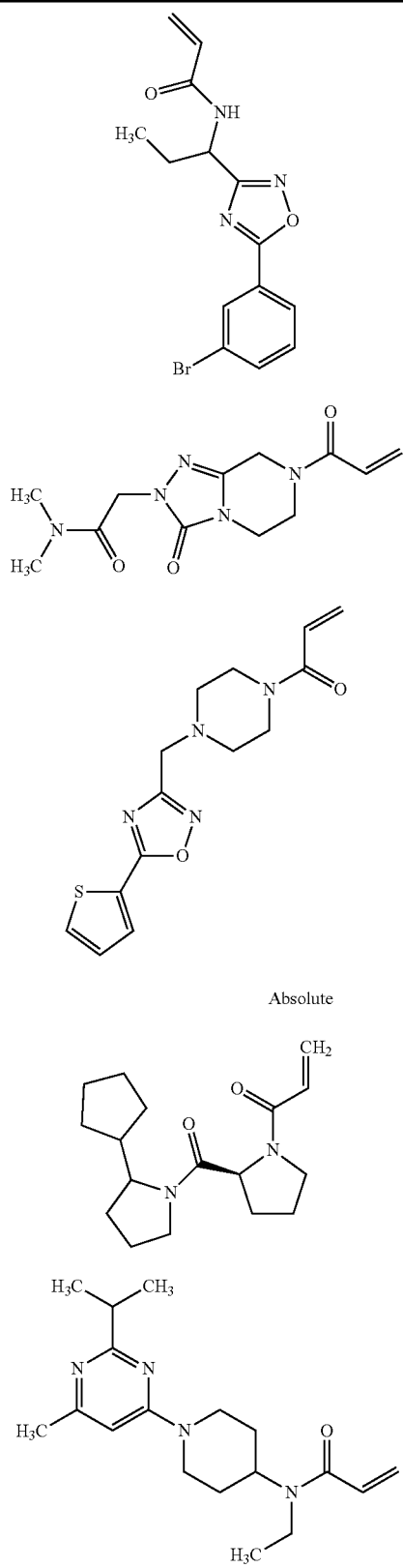
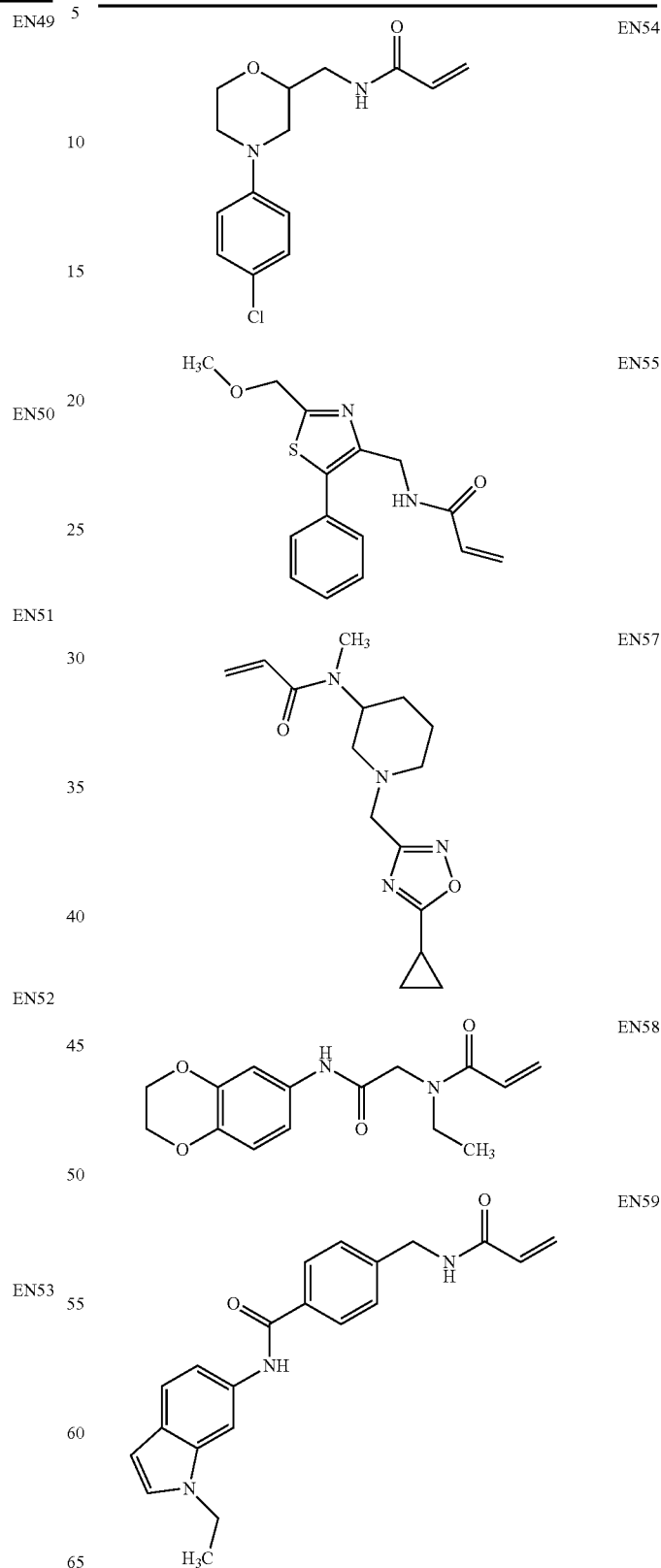

TABLE 1-continued
Additional compounds used in the gel-based ABPP screen of LC3A depicted in FIG. 4, in combination with FIGS. 9A-9G.
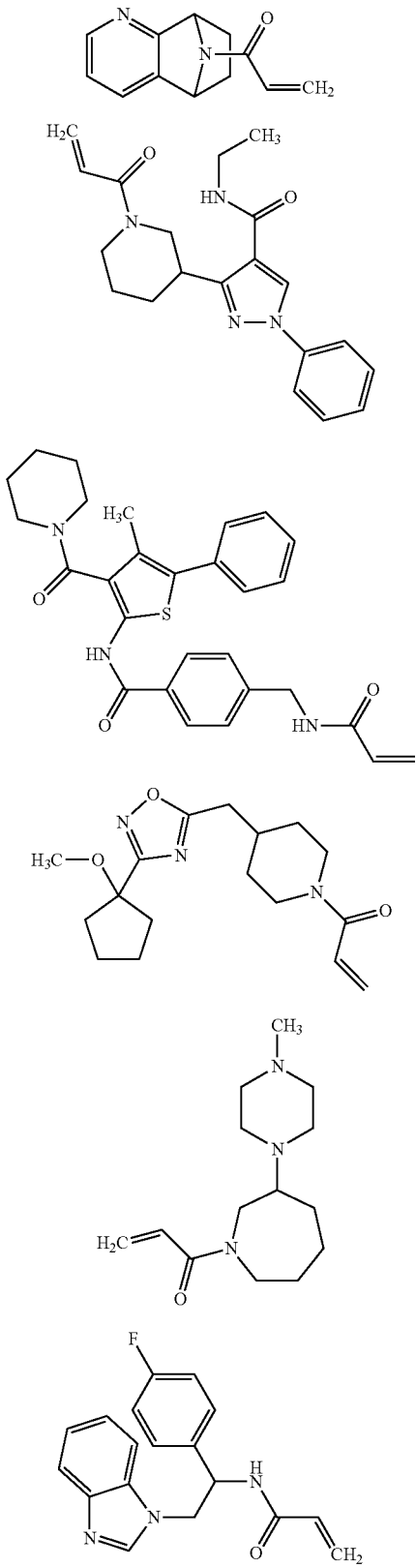
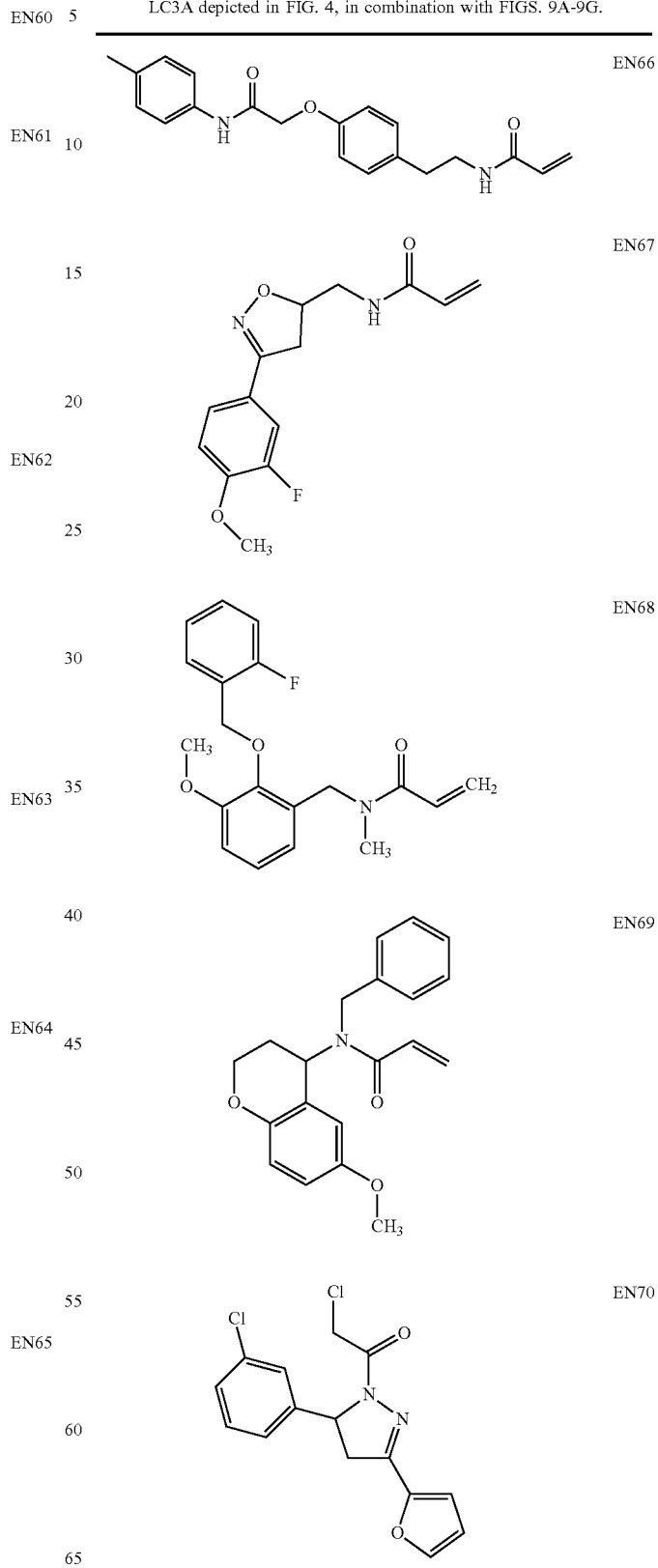

TABLE 1-continued
Additional compounds used in the gel-based ABPP screen of LC3A depicted in FIG. 4, in combination with FIGS. 9A-9G.
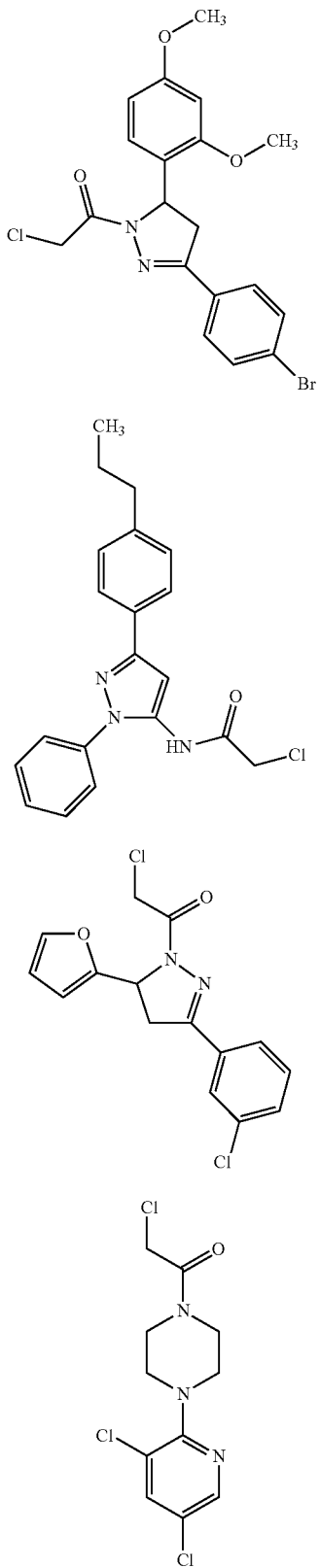
EN71
EN72
EN74
EN75
TABLE 1-continued
Additional compounds used in the gel-based ABPP screen of LC3A depicted in FIG. 4, in combination with FIGS. 9A-9G.
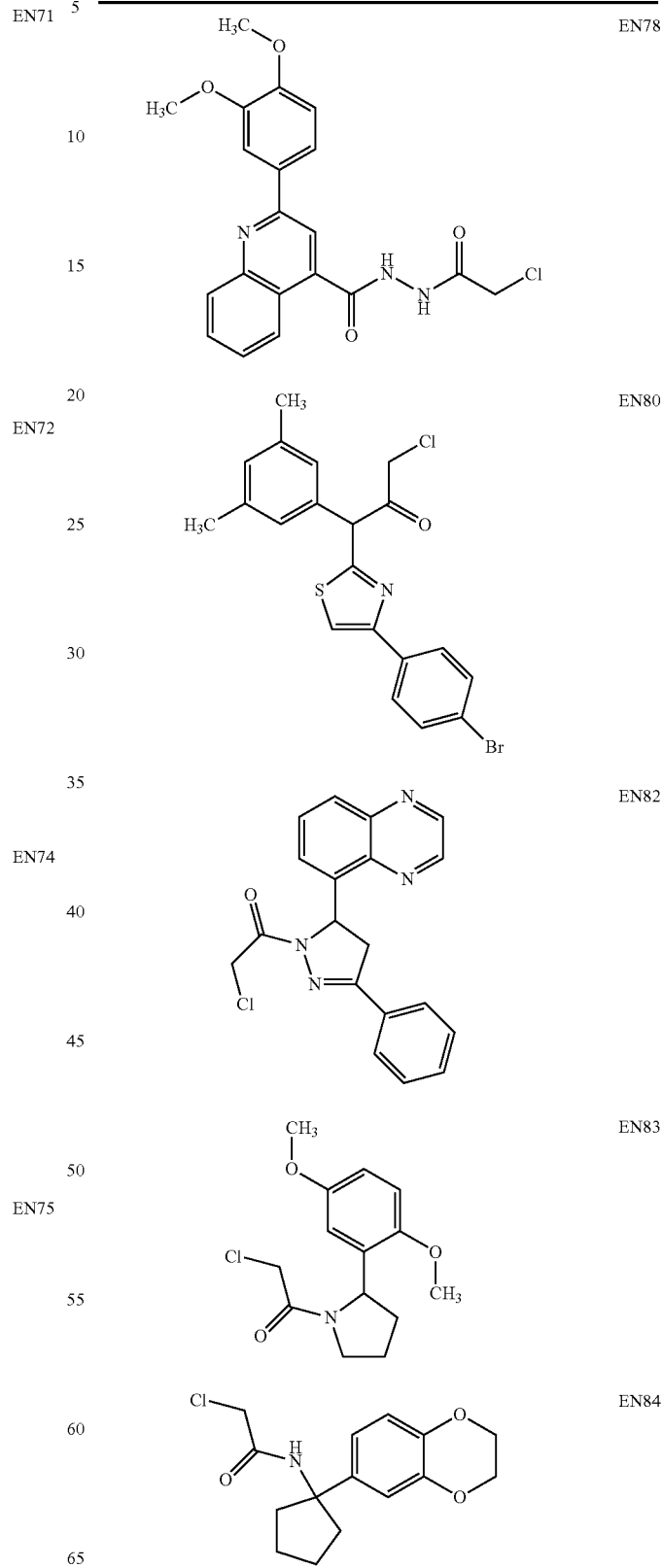
EN78
EN80
EN82
EN83
EN84

TABLE 1-continued
Additional compounds used in the gel-based ABPP screen of LC3A depicted in FIG. 4, in combination with FIGS. 9A-9G.
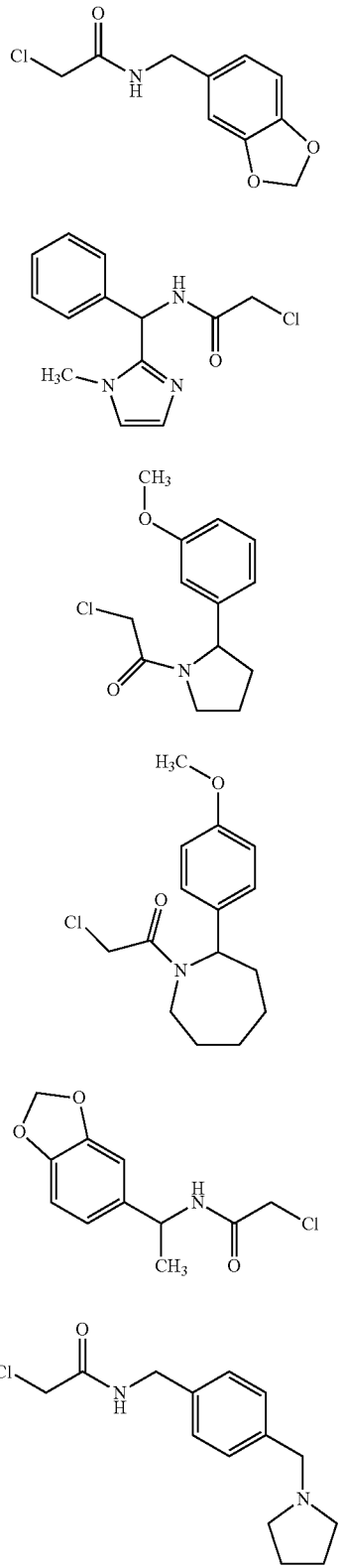
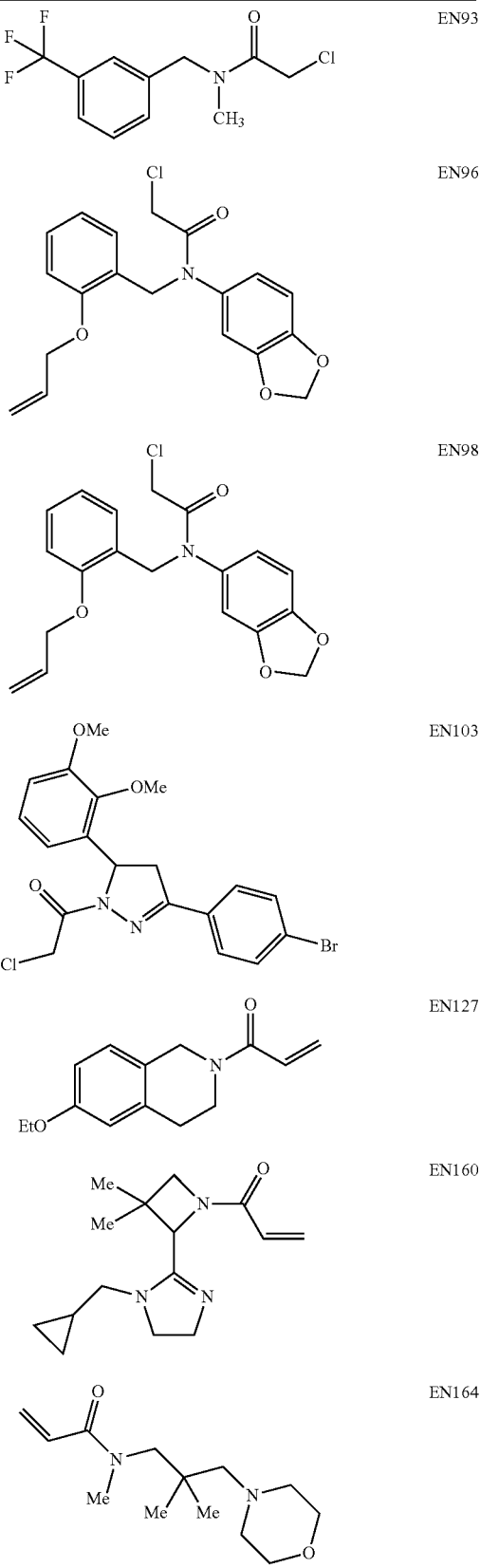

TABLE 1-continued

Additional compounds used in the gel-based ABPP screen of LC3A depicted in FIG. 4, in combination with FIGS. 9A-9G.

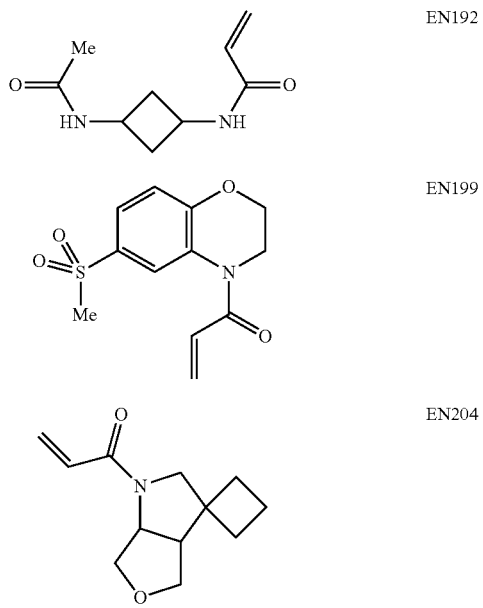

It is understood that when a compound as shown anywhere in the specification (e.g., in Table 1) is connected (e.g., bonded) to a linker, it is understood the compound is intended to be a monovalent form of the standalone compound at any attachment point following the replacement of a substituent (e.g., hydrogen or halogen) with the bond to the linker. In embodiments, the targeted autophagy binder may be a compound in the table below. In embodiments, the monovalent targeted autophagy binder may be a monovalent form of a compound in the table below.

In embodiments, the compound is a compound described herein. In embodiments, the compound is a derivative, analogue, or prodrug of a compound described herein. In embodiments, the compound is a derivative of a compound described herein. In embodiments, the compound is an analogue of a compound described herein. In embodiments, the compound is a prodrug of a compound described herein.

In an aspect is provide an autophagy adapter protein binder (e.g., a compound described herein).

III. Pharmaceutical Compositions

In an aspect is provided a pharmaceutical composition including a compound described herein (e.g., a targeted autophagy degrader) and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent. In embodiments of the pharmaceutical compositions, the pharmaceutical composition includes a second agent in a therapeutically effective amount.

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

In an aspect is provided a pharmaceutical composition including a targeted autophagy degrader (e.g., as described herein or a compound described herein) and a pharmaceutically acceptable excipient.

In embodiments, the pharmaceutical composition includes an effective amount of the targeted autophagy degrader. In embodiments, the pharmaceutical composition includes a therapeutically effective amount of the targeted autophagy degrader. In embodiments, the pharmaceutical composition includes a second agent. In embodiments of the pharmaceutical compositions, the pharmaceutical composition includes a second agent in a therapeutically effective amount. In embodiments, the second agent is an agent for treating cancer. In embodiments, the second agent is an agent for treating a neurodegenerative disease (e.g., Huntington's Disease, Alzheimer Disease, or Parkinson's Disease). In embodiments, the second agent is an agent for treating a disease associated with a protein aggregate. In embodiments, the second agent is an agent for treating a metabolic disease. In embodiments, the second agent is an agent for treating an autoimmune disease. In embodiments, the second agent is an agent for treating an infectious disease. In embodiments, the second agent is an agent for treating an inflammatory disease. In embodiments, the second agent is an agent for treating Huntington's disease.

IV. Methods for Treating Diseases

In an aspect is provided a method for treating a disease associated with a cellular component (e.g., aberrant level of a cellular component), the method including contacting the cellular component with a targeted autophagy degrader (e.g., as described herein). In an aspect is provided a method for treating a disease associated with a cellular component (e.g., aberrant level of a cellular component), the method including administering to a subject in need thereof a therapeutically effective amount of a compound described herein.

In an aspect is provided a method for treating cancer, the method including contacting a cellular component associated with cancer with a targeted autophagy degrader (e.g., as described herein).

In an aspect is provided a method for treating cancer, the method including administering to a subject in need thereof a therapeutically effective amount of a compound described herein. In an aspect is provided a method for treating cancer, the method including administering to a subject in need thereof a therapeutically effective amount of a targeted autophagy degrader (e.g., as described herein).

In an aspect is provided a method for treating neurodegenerative disease, the method including contacting a cellular component associated with the neurodegenerative disease with a targeted autophagy degrader (e.g., as described herein).

In an aspect is provided a method for treating a neurodegenerative disease, the method including administering to a subject in need thereof a therapeutically effective amount of a compound described herein. In an aspect is provided a method for treating a neurodegenerative disease, the method including administering to a subject in need thereof a therapeutically effective amount of a targeted autophagy degrader (e.g., as described herein). In embodiments, the neurodegenerative disease is Huntington Disease, Alzheimer Disease, or Parkinson's Disease.

In an aspect is provided a method for treating a metabolic disease, the method including contacting a cellular component associated with the metabolic disease with a targeted autophagy degrader (e.g., as described herein).

In an aspect is provided a method for treating a metabolic disease, the method including administering to a subject in need thereof a therapeutically effective amount of a compound described herein. In an aspect is provided a method for treating a metabolic disease, the method including administering to a subject in need thereof a therapeutically effective amount of a targeted autophagy degrader (e.g., as described herein).

In an aspect is provided a method for treating an infectious disease, the method including contacting a cellular component associated with the infectious disease with a targeted autophagy degrader (e.g., as described herein).

In an aspect is provided a method for treating an infectious disease, the method including administering to a subject in need thereof a therapeutically effective amount of a compound described herein. In an aspect is provided a method for treating an infectious disease, the method including administering to a subject in need thereof a therapeutically effective amount of a targeted autophagy degrader (e.g., as described herein).

In an aspect is provided a method for treating an autoimmune disease, the method including contacting a cellular component associated with the autoimmune disease with a targeted autophagy degrader (e.g., as described herein).

In an aspect is provided a method for treating an autoimmune disease, the method including administering to a subject in need thereof a therapeutically effective amount of a compound described herein. In an aspect is provided a method for treating an autoimmune disease, the method including administering to a subject in need thereof a therapeutically effective amount of a targeted autophagy degrader (e.g., as described herein).

In an aspect is provided a method for treating an inflammatory disease, the method including contacting a cellular component associated with the inflammatory disease with a targeted autophagy degrader (e.g., as described herein).

In an aspect is provided a method for treating an inflammatory disease, the method including administering to a subject in need thereof a therapeutically effective amount of a compound described herein. In an aspect is provided a method for treating an inflammatory disease, the method including administering to a subject in need thereof a therapeutically effective amount of a targeted autophagy degrader (e.g., as described herein).

In embodiments, the method includes modulating (e.g., inhibiting relative to a control) the level or activity of a protein (e.g., BRD4, KRAS, MYC, YAP, TAZ, CTNNB1, APP, HTT, SNCA, NRF2, or MAPT).

In embodiments, the method includes modulating (e.g., inhibiting relative to a control) the level or activity of a protein aggregate (e.g., HTT, APP, SNCA, or MAPT).

In embodiments, the method includes modulating (e.g., inhibiting relative to a control) the level or activity of a protein associated with an organelle (e.g., PINK1, ATG32, ESYT, PI3KC3, RAB10, or ATGL). In embodiments, the method includes modulating (e.g., inhibiting relative to a control) the level or activity of a protein associated with the mitochondria (e.g., ATG32). In embodiments, the method includes modulating (e.g., inhibiting relative to a control) the level or activity of a protein associated with the endoplasmic reticuluum (e.g., ESYT or PI3KC3). In embodiments, the method includes modulating (e.g., inhibiting relative to a control) the level or activity of an organelle. In embodiments, the method includes modulating (e.g., inhibiting relative to a control) the level or activity of a mitochondria. In embodiments, the method includes modulating (e.g., inhibiting relative to a control) the level or activity of an endoplasmic reticuluum.

The compounds of the invention (i.e., compounds described herein, including in embodiments, examples, figures, tables) can be administered alone or can be coadministered to the patient. Co-administration is meant to include simultaneous or sequential administration of the compounds individually or in combination (more than one compound). Thus, the preparations can also be combined, when desired, with other active substances (e.g., to reduce metabolic degradation or anti-cancer agents).

In an aspect is provided a method for treating a disease associated with a protein aggregate, the method including administering to a subject in need thereof a therapeutically effective amount of a compound described herein. In an aspect is provided a method for treating a disease associated with a protein aggregate, the method including administering to a subject in need thereof a therapeutically effective amount of a targeted autophagy degrader (e.g., as described herein). In embodiments, the disease associated with a protein aggregate is a neurodegenerative disease (e.g., Huntington's Disease, Alzheimer Disease, or Parkinson's Disease). In embodiments, the disease associated with a protein aggregate is Alzheimer's disease and the protein aggregate is an aggregate including beta amyloid. In embodiments, the disease associated with a protein aggregate is diabetes mellitus type 2 and the protein aggregate is an aggregate including IAPP. In embodiments, the disease associated with a protein aggregate is Parkinson's disease and the protein aggregate is an aggregate including alpha-synuclein. In embodiments, the disease associated with a protein aggregate is transmissible spongiform encephalopathy and the protein aggregate is an aggregate including PrP (e.g., PrP (Sc)). In embodiments, the disease associated with a protein aggregate is fatal familial insomnia and the protein aggregate is an aggregate including PrP (e.g., PrP(Sc)). In embodiments, the disease associated with a protein aggregate is Huntington's disease and the protein aggregate is an aggregate including Huntingtin. In embodiments, the disease associated with a protein aggregate is medullary carcinoma of the thyroid and the protein aggregate is an aggregate including calcitonin. In embodiments, the disease associated with a protein aggregate is cardiac arrhythmia (e.g., isolated atrial amyloidosis) and the protein aggregate is an aggregate including atrial natriuretic factor. In embodiments, the disease associated with a protein aggregate is atherosclerosis and the protein aggregate is an aggregate including apolipoprotein A1. In embodiments, the disease associated with a protein aggregate is rheumatoid arthritis and the protein aggregate is an aggregate including serum amyloid A. In embodiments, the disease associated with a protein aggregate is aortic medial amyloid and the protein aggregate is an aggregate including medin. In embodiments, the disease associated with a protein aggregate is prolactinomas and the protein aggregate is an aggregate including prolactin. In embodiments, the disease associated with a protein aggregate is familial amyloid polyneuropathy and the protein aggregate is an aggregate including transthyretin. In embodiments, the disease associated with a protein aggregate is hereditary non-neuropathic systemic amyloidosis and the protein aggregate is an aggregate including lysozyme. In embodiments, the disease associated with a protein aggregate is dialysis related amyloidosis and the protein aggregate is an aggregate including beta-2 microglobulin. In embodiments, the disease associated with a protein aggregate is Finnish amyloidosis and the protein aggregate is an aggregate including gelsolin. In embodiments, the disease associated with a protein aggregate is lattice corneal dystrophy and the protein aggregate is an aggregate including keratoepithelin. In embodiments, the disease associated with a protein aggregate is cerebral amyloid angiopathy and the protein aggregate is an aggregate including beta amyloid. In embodiments, the disease associated with a protein aggregate is cerebral amyloid angiopathy (Icelandic type) and the protein aggregate is an aggregate including cystatin. In embodiments, the disease associated with a protein aggregate is systemic AL amyloidosis and the protein aggregate is an aggregate including immunoglobulin light chain AL. In embodiments, the disease associated with a protein aggregate is sporadic inclusion body myositis and the protein aggregate is an aggregate including S-IBM. In embodiments, the disease associated with a protein aggregate is a tauopathy and the protein aggregate is an aggregate including tau protein. In embodiments, the tauopathy is primary age-related tauopathy, CTE, progressive supranuclear palsy, corticobasal degeneration, frontotemporal demential and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, pantothenate kinase-associated neurodegeneration, lipofuscinosis, or Pick's disease. In embodiments, the disease associated with a protein aggregate is amyloidosis. In embodiments, the disease associated with a protein aggregate is a proteinopathy. In embodiments, the disease associated with a protein aggregate is amyotrophic lateral sclerosis and the protein aggregate is an aggregate including superoxide dismutase, TDP043, FUS, C90RF72, and/or ubiquilin-2 (UBQLN2). In embodiments, the disease associated with a protein aggregate is a trinucleotide repeat disorder. In embodiments, the disease associated with a protein aggregate is a synucleinopathy. In embodiments, the disease associated with a protein aggregate is prion disease and the protein aggregate is an aggregate including prion protein. In embodiments, the method includes reducing the protein aggregate (e.g., reducing aggregate size, number of aggregates, or occurrence of aggregates).

V. Methods of Modulating Activity

In an aspect is provided a method of reducing the level of a cellular component, the method including contacting the cellular component with a targeted autophagy degrader (e.g., as described herein).

In embodiments, the targeted autophagy degrader (e.g., as described herein) includes a monovalent cellular component binder (e.g., as described herein) and a monovalent autophagy adapter protein binder (e.g., as described herein). In embodiments, the monovalent cellular component binder and monovalent autophagy adapter protein binder are covalently bonded by a linker (e.g., as described herein).

In embodiments, the cellular component is a protein. In embodiments, the cellular component is an organelle. In embodiments, the cellular component is a complex of a plurality of optionally different proteins. In embodiments, the cellular component is a protein aggregate. In embodiments, the cellular component is a macromolecule. In embodiments, the cellular component is an ion, lipid, nucleic acid, nucleotide, amino acid, protein, particle, organelle, cellular compartment, microorganism, vesicle, or small molecule.

In embodiments, the method includes modulating (e.g., inhibiting relative to a control) the level or activity of a protein associated with an organelle (e.g., PINK1ATG32, ESYT, PI3KC3, RAB10, or ATGL). In embodiments, the method includes modulating (e.g., inhibiting relative to a control) the level or activity of a protein associated with the mitochondria (e.g., ATG32). In embodiments, the method includes modulating (e.g., inhibiting relative to a control) the level or activity of a protein associated with the endoplasmic reticuluum (e.g., ESYT or PI3KC3). In embodiments, the method includes modulating (e.g., inhibiting relative to a control) the level or activity of an organelle. In embodiments, the method includes modulating (e.g., inhibiting relative to a control) the level or activity of a mitochondria. In embodiments, the method includes modulating (e.g., inhibiting relative to a control) the level or activity of an endoplasmic reticuluum.

In an aspect is provided a method of reducing the level of a cellular component, the method including contacting the cellular component with a targeted autophagy degrader, wherein the targeted autophagy degrader is a compound described herein.

In embodiments, the method further including the steps: A) allowing formation of an autophagosome including the cellular component-targeted autophagy degrader-autophagy adapter protein complex; B) allowing the autophagosome to acidify; and C) allowing degradation of the cellular component.

VI. Process

In an aspect is provided a method of reducing the level of a cellular component, the method including contacting a cellular component with a targeted autophagy degrader; wherein the targeted autophagy degrader includes: i) a monovalent autophagy associated protein binder; ii) a monovalent cellular component binder; and iii) a covalent linker directly bonded to the monovalent autophagy associated protein binder and the monovalent cellular component binder.

In embodiments, the autophagy associated protein is an autophagy adapter protein. In embodiments, the cellular component is a protein, ion, lipid, nucleic acid, nucleotide, amino acid, particle, organelle, cellular compartment, microorganism, virus, vesicle, small molecule, protein complex, protein aggregate, or macromolecule.

In embodiments, prior to the contacting, the targeted autophagy degrader is synthesized by reacting a cellular component binder, a linker, and an autophagy associated protein binder to produce the targeted autophagy degrader (e.g., a compound or composition described herein).

In embodiments, prior to the contacting, the targeted autophagy degrader is synthesized by covalently reacting a cellular component binder, a linker, and an autophagy associated protein binder to produce the targeted autophagy degrader.

In embodiments, prior to the synthesizing, the autophagy associated protein binder is identified. In embodiments, prior to the synthesizing, the autophagy associated protein binder is selected and ranked according to a quantifiable property (e.g., binding ability, Lipinski's rule, or level of inhibition).

In embodiments, the autophagy associated protein binder is identified by a method including the steps: i) mixing an autophagy associated protein with a library of candidate autophagy associated protein binders (e.g., in a reaction vessel); and ii) identifying the candidate autophagy associated protein binders that bind to the autophagy associated protein. In embodiments, the candidate autophagy associated protein binders include a covalent cysteine modifier moiety and a candidate autophagy associated protein binder is identified as an autophagy associated protein binder by detection of covalent binding of the autophagy associated protein binder to the autophagy associated protein. In embodiments, the method follows substantially similar steps to those described in the Example section (see for example the IsoTOP-ABPP method described herein). In embodiments, the detection of covalent binding of the candidate autophagy associated protein binder to the autophagy associated protein includes use of a detectable label or mass spectroscopic detection of the covalent binding. In embodiments, prior to the synthesizing, the cellular component binder is identified.

In embodiments, the detection of covalent binding of the candidate autophagy associated protein binder to the autophagy associated protein includes competing candidate autophagy associated protein binders against reactivity-based probes (e.g., probes described herein) in the autophagy associated protein. In embodiments, the detection includes comparing isotopically light to heavy ratios of probe-modified autophagy associated proteins.

In embodiments, the cellular component binder is identified by a method including the steps: i) mixing a cellular component protein with a library of candidate cellular component binders; and ii) identifying the candidate cellular component binders that bind to the cellular component. In embodiments, the candidate cellular component binders include a covalent cysteine modifier moiety and a candidate cellular component binder is identified as a cellular component binder by detection of covalent binding of the cellular component binder to the cellular component. In embodiments, the detection of covalent binding of the candidate cellular component binder to the cellular component includes use of a detectable label or mass spectroscopic detection of the covalent binding.

In embodiments, prior to synthesizing, the autophagy associated protein binder is modified to remove a covalent cysteine modifier moiety.

In embodiments, the targeted autophagy degrader is a compound as described herein, including embodiments, tables, and figures.

VII. Embodiments

Embodiment P1. A compound comprising a monovalent cellular component binder covalently bound to a monovalent targeted autophagy protein binder.

Embodiment P2. The compound of embodiment P1, wherein a divalent linker binds said monovalent cellular component binder to said monovalent targeted autophagy protein binder.

Embodiment P3. The compound of one of embodiments P1 to P2, wherein the cellular component is a protein, ion, lipid, nucleic acid, nucleotide, amino acid, particle, organelle, cellular compartment, microorganism, virus, lipid droplet, vesicle, small molecule, protein complex, protein aggregate, or macromolecule.

Embodiment P4. The compound of one of embodiments P1 to P3, wherein the monovalent targeted autophagy protein binder is a monovalent autophagy adapter protein binder.

Embodiment P5. The compound of embodiment P4, wherein the autophagy adapter protein is LC3, p62, NBR1, NDP52, Optineurin, or a derivative, fragment, or homolog thereof.

Embodiment P6. The compound of one of embodiments P2 to P5, wherein the divalent linker has the formula:

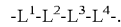

$L^1$ is connected directly to the monovalent targeted autophagy protein binder;

$L^1$ is —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^2$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^4$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P7. The compound of one of embodiments P1 to P6, wherein the targeted autophagy protein binder is capable of contacting an amino acid corresponding to C17 of human LC3A protein.

Embodiment P8. The compound of one of embodiments P1 to P6, wherein the targeted autophagy protein binder is capable of contacting an amino acid corresponding to C26 of human p62/SQSTM1 protein.

Embodiment P9. The compound of one of embodiments P1 to P6, wherein the targeted autophagy protein binder is capable of contacting an amino acid corresponding to C27 of human p62/SQSTM1protein.

Embodiment P10. The compound of one of embodiments P1 to P6, wherein the targeted autophagy protein binder is capable of contacting an amino acid corresponding to C120 of human NBR1 protein.

Embodiment P11. The compound of one of embodiments P1 to P6, wherein the targeted autophagy protein binder is capable of contacting an amino acid corresponding to C321 of human NDP52/CALCOCO2 protein.

Embodiment P12. The compound of one of embodiments P1 to P6, wherein the targeted autophagy protein binder is capable of contacting an amino acid corresponding to C558 of human OPTN protein.

Embodiment P13. The compound of one of embodiments P7 to P12, wherein the targeted autophagy protein binder is capable of forming a covalent bond to the cysteine.

Embodiment P14. The compound of one of embodiments P1 to P7, wherein the targeted autophagy protein binder has the formula:

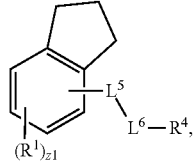
(I)

wherein z1 is an integer from 0 to 9;

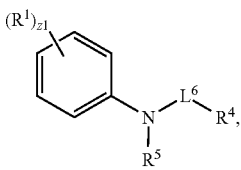
(II)

wherein z1 is an integer from 0 to 5;

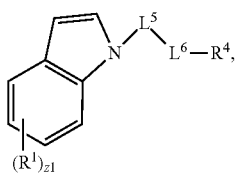
(III)

wherein z1 is an integer from 0 to 6;

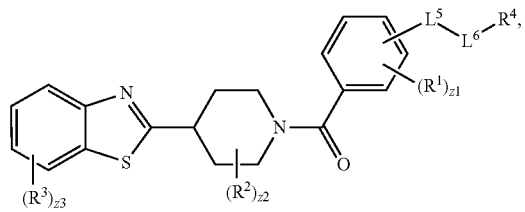
(IV)

wherein z1 is an integer from 0 to 4, z2 is an integer from 0 to 8, and z3 is an integer from 0 to 4;

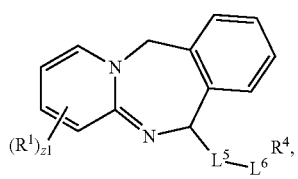
(V)

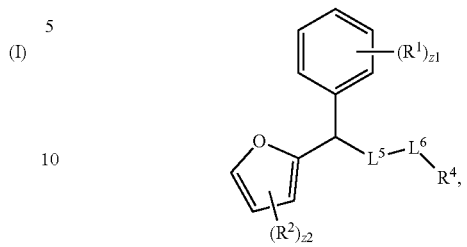
(VI)

wherein z1 is an integer from 0 to 5 and z2 is an integer from 0 to 3; or

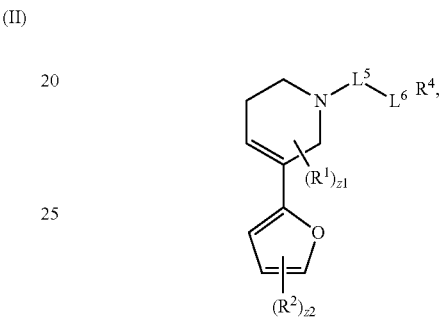
(VII)

wherein z1 is an integer from 0 to 11;

wherein z1 is an integer from 0 to 7 and z2 is an integer from 0 to 3;

$R^1$ is independently oxo, halogen, $-CX^1{}_3$, $-CHX^1{}_2$, $-CH_2X^1$, $-OCX^1{}_3$, $-OCH_2X^1$, $-OCHX^1{}_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently oxo, halogen, $-CX^2{}_3$, $-CHX^2{}_2$, $-CH_2X^2$, $-OCX^2{}_3$, $-OCH_2X^2$, $-OCHX^2{}_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^3$ is independently oxo, halogen, $-CX^3{}_3$, $-CHX^3{}_2$, $-CH_3X^2$, $-OCX^3{}_3$, $-OCH_2X^3$, $-OCHX^3{}_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two R³ substituents may optionally be joined to form a substituted or unsubstituted cycloalkyl, substituted or unsubstituted heterocycloalkyl, substituted or unsubstituted aryl, or substituted or unsubstituted heteroaryl;

R⁴ is hydrogen, halogen, —CX⁴₃, —CHX⁴₂, —CH₂X⁴, —OCX⁴₃, —OCH₂X⁴, —OCHX⁴₂, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO₂R$^{4D}$, —NR$^{4A}$C(O)R$^{4C}$, —NR$^{4A}$C(O)OR$^{4C}$, —NR$^{4A}$OR$^{4C}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

L⁵ is a bond, —S(O)₂—, —S(O)—, —NR⁵—, =N—, —O—, —S—, —C(O)—, —C(O)NR⁵—, —NR⁵C(O)—, —NR⁵C(O)NH—, —NHC(O)NR⁵—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R⁵ is hydrogen, —CX⁵₃, —CHX⁵₂, —CH₂X⁵, —OCX⁵₃, —OCH₂X⁵, —OCHX⁵₂, —CN, —C(O)R$^{5C}$, —C(O)—OR$^{5C}$, —C(O)NR$^{5A}$R$^{5B}$, —OR$^{5D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L⁶ is a bond, —S(O)₂—, —S(O)—, —NR⁶—, =N—, —O—, —S—, —C(O)—, —C(O)NR⁶—, —NR⁶C(O)—, —NR⁶C(O)NH—, —NHC(O)NR⁶—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R⁶ is hydrogen, —CX⁶₃, —CHX⁶₂, —CH₂X⁶, —OCX⁶₃, —OCH₂X⁶, —OCHX⁶₂, —CN, —C(O)R$^{6C}$, —C(O)—OR$^{6C}$, —C(O)NR$^{6A}$R$^{6B}$, —OR$^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, and R$^{6D}$ are independently hydrogen, —CX₃, —CN, —COOH, —CONH₂, —CHX₂, —CH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl;

X, X¹, X², X³, X⁴, X⁵, and X⁶ are independently F, —Cl, —Br, or —I;

n1, n2, n3, n4, n5, and n6 are independently an integer from 0 to 4; and m1, m2, m3, m4, m5, m6, v1, v2, v3, v4, v5, and v6 are independently 1 or 2.

Embodiment P15. The compound of embodiment P14, wherein the targeted autophagy protein binder has the formula:

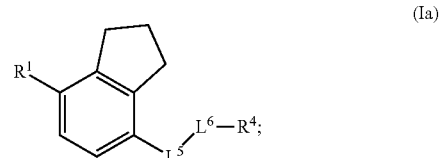

(Ia)

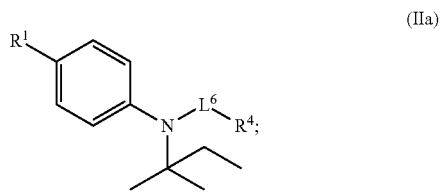

(IIa)

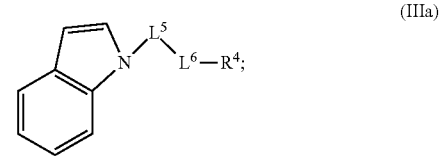

(IIIa)

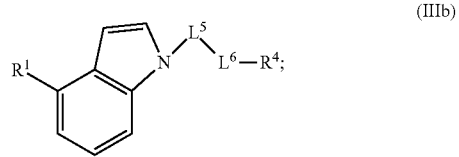

(IIIb)

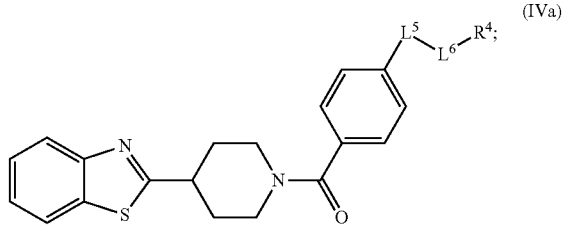

(IVa)

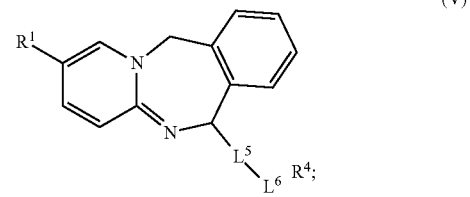

(V)

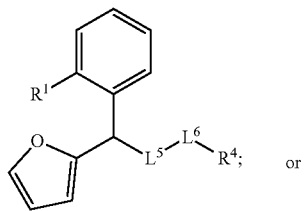
(VIa)

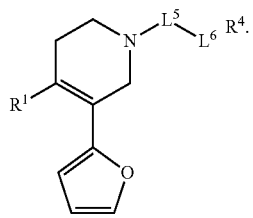
(VIIa)

Embodiment P16. The compound of embodiment P14, wherein the targeted autophagy protein binder has the formula:

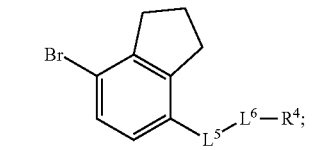
(Ib)

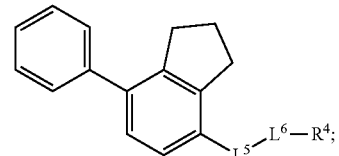
(Ic)

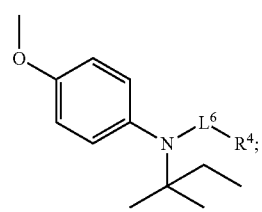
(IIb)

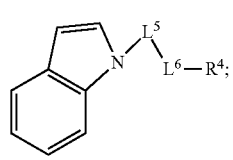
(IIIa)

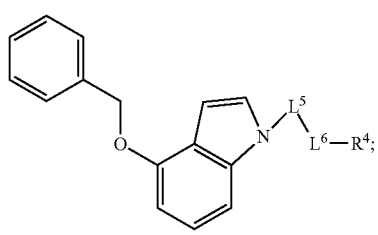
(IIIc)

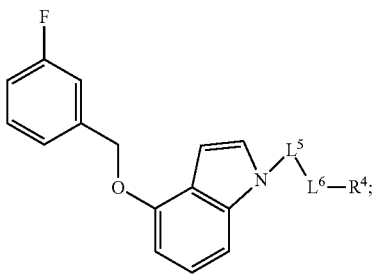
(IIId)

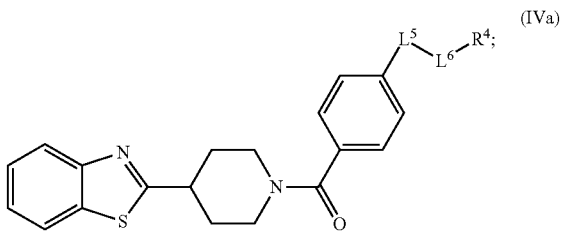
(IVa)

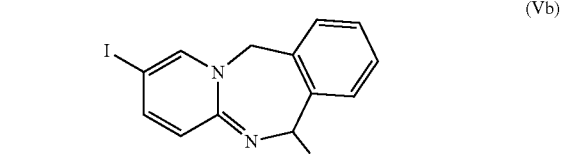
(Vb)

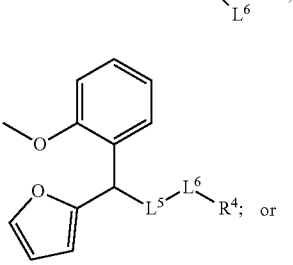
(VIb)

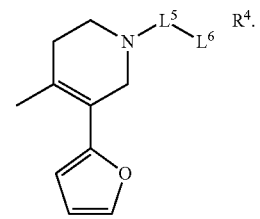
(VIIb)

Embodiment P17. The compound of one of embodiments P14 to P15, wherein $R^4$ is E.

Embodiment P18. The compound of one of embodiments P14 to P17, wherein E is a covalent cysteine modifier, covalent lysine modifier, covalent serine modifier, or covalent methionine modifier.

Embodiment P19. The compound of one of embodiments P14 to P17, wherein E is

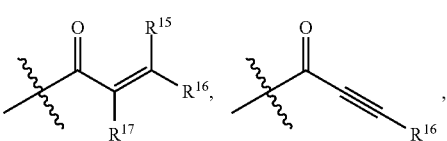

-continued

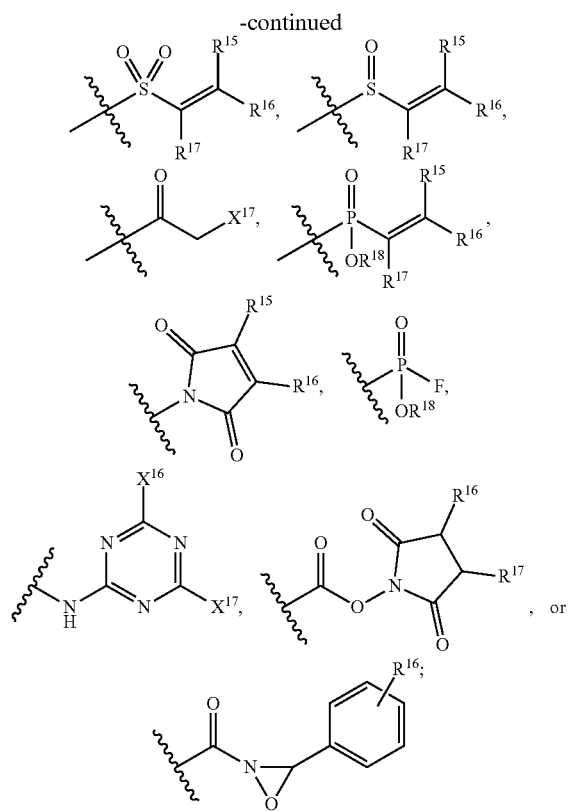

R$^{15}$ is independently hydrogen, halogen, —CX$^{15}_3$, —CHX$^{15}_2$, —CH$_2$X$^{15}$, —CN, —SO$_{n15}$R$^{15D}$, —SO$_{v15}$NR$^{15A}$R$^{15B}$, —NHNR$^{15A}$R$^{15B}$, —ONR$^{15A}$R$^{15B}$, —NHC=(O)NHNR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, —OCX$^{15}_3$, —OCHX$^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{16}$ is independently hydrogen, halogen, —CX$^{16}_3$, —CHX$^{16}_2$, —CH$_2$X$^{16}$, —CN, —SO$_{n16}$R$^{16D}$, —SO$_{v16}$NR$^{16A}$R$^{16B}$, —NHNR$^{16A}$R$^{16B}$, —ONR$^{16A}$R$^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}_3$, —OCHX$^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{17}$ is independently hydrogen, halogen, —CX$^{17}_3$, —CHX$^{17}_2$, —CH$_2$X$^{17}$, —CN, —SO$_{n17}$R$^{17D}$, —SO$_{v17}$NR$^{17A}$R$^{17B}$, —NHNR$^{17A}$R$^{17B}$, —ONR$^{17A}$R$^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, —OCX$^{17}_3$, —OCHX$^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{18}$ is independently hydrogen, —CX$^{18}_3$, —CHX$^{18}_2$, —CH$_2$X$^{18}$, —C(O)R$^{18C}$, —C(O)OR$^{18C}$, —C(O)NR$^{18A}$R$^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18C}$, R$^{18D}$, are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15A}$ and R$^{15B}$ substituents bonded to the same nitrogen atom may optionally be joined to form a substituted or unsubstituted heterocycloalkyl or substituted or unsubstituted heteroaryl; R$^{16A}$ and R$^{16B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl;

each X, X$^{15}$, X$^{16}$, X$^{17}$ and X$^{18}$ is independently —F, —Cl, —Br, or —I;

n15, n16, and n17 are independently an integer from 0 to 4; and m15, m16, m17, v15, v16, and v17 are independently and integer from 1 to 2.

Embodiment P20. The compound of one of embodiments P14 to P17, wherein E is

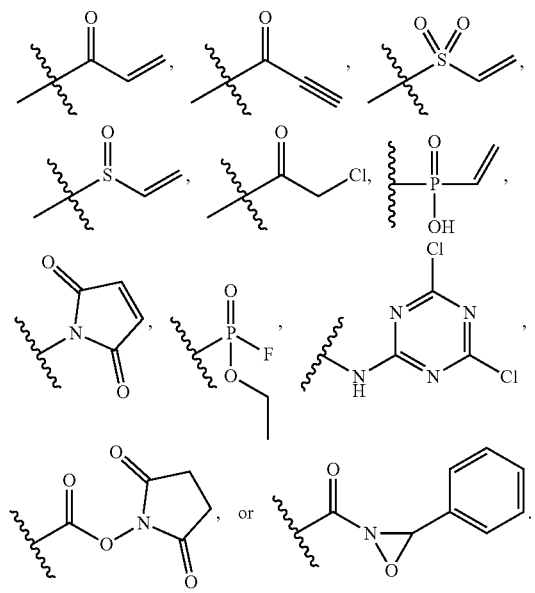

Embodiment P21. The compound of one of embodiments P14 to P17, wherein E is

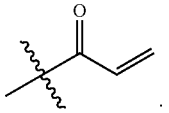 [SMILES: *C(=O)C=C]

Embodiment P22. The compound of one of embodiments P14 to P17, wherein the targeted autophagy protein binder has the formula:

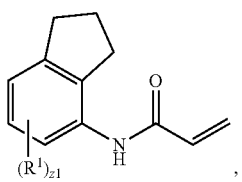
(Id)

wherein z1 is an integer from 0 to 9;

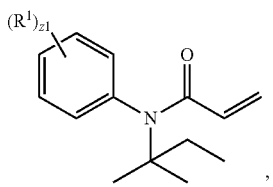
(IIc)

wherein z1 is an integer from 0 to 5;

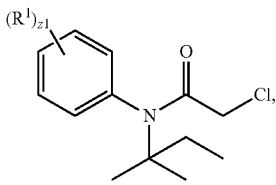
(IId)

wherein z1 is an integer from 0 to 5;

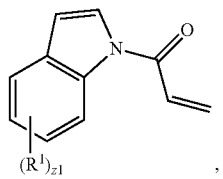
(IIIe)

wherein z1 is an integer from 0 to 6;

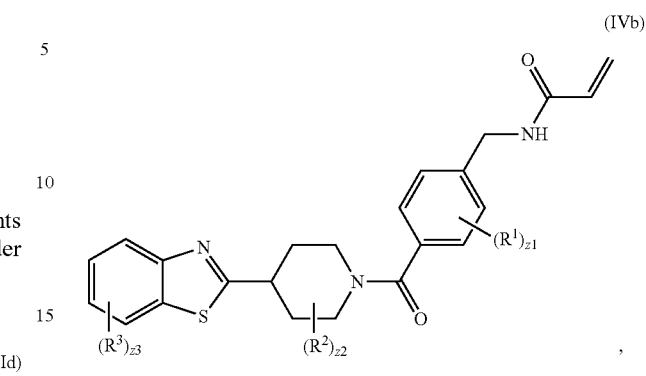
(IVb)

wherein z1 is an integer from 0 to 4, z2 is an integer from 0 to 8, and z3 is an integer from 0 to 4;

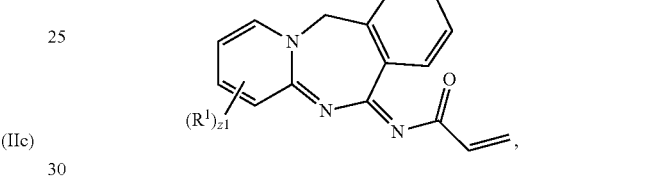
(Vc)

wherein z1 is an integer from 0 to 11;

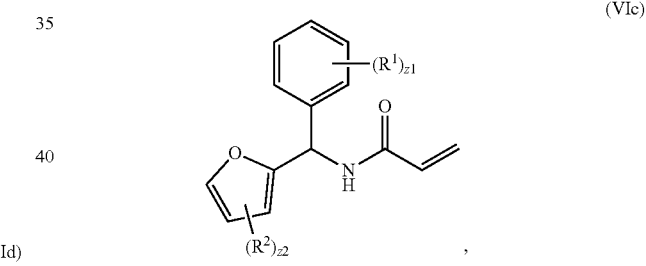
(VIc)

wherein z1 is an integer from 0 to 5 and z2 is an integer from 0 to 3; or

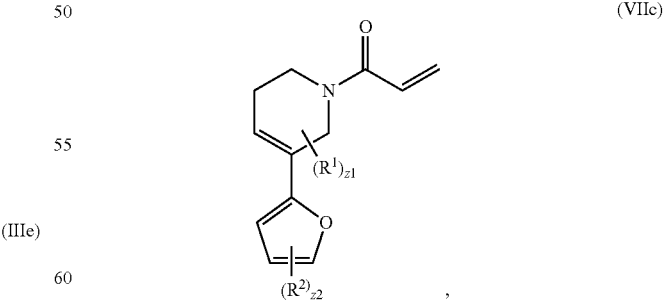
(VIIc)

wherein z1 is an integer from 0 to 5 and z2 is an integer from 0 to 3.

Embodiment P23. The compound of one of embodiments P14 to P20, wherein the targeted autophagy protein binder has the formula:

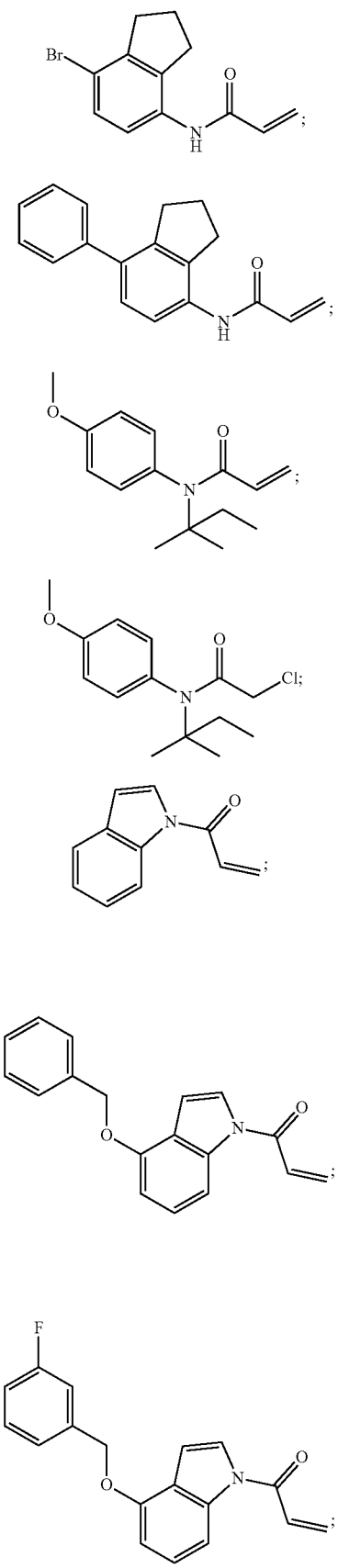
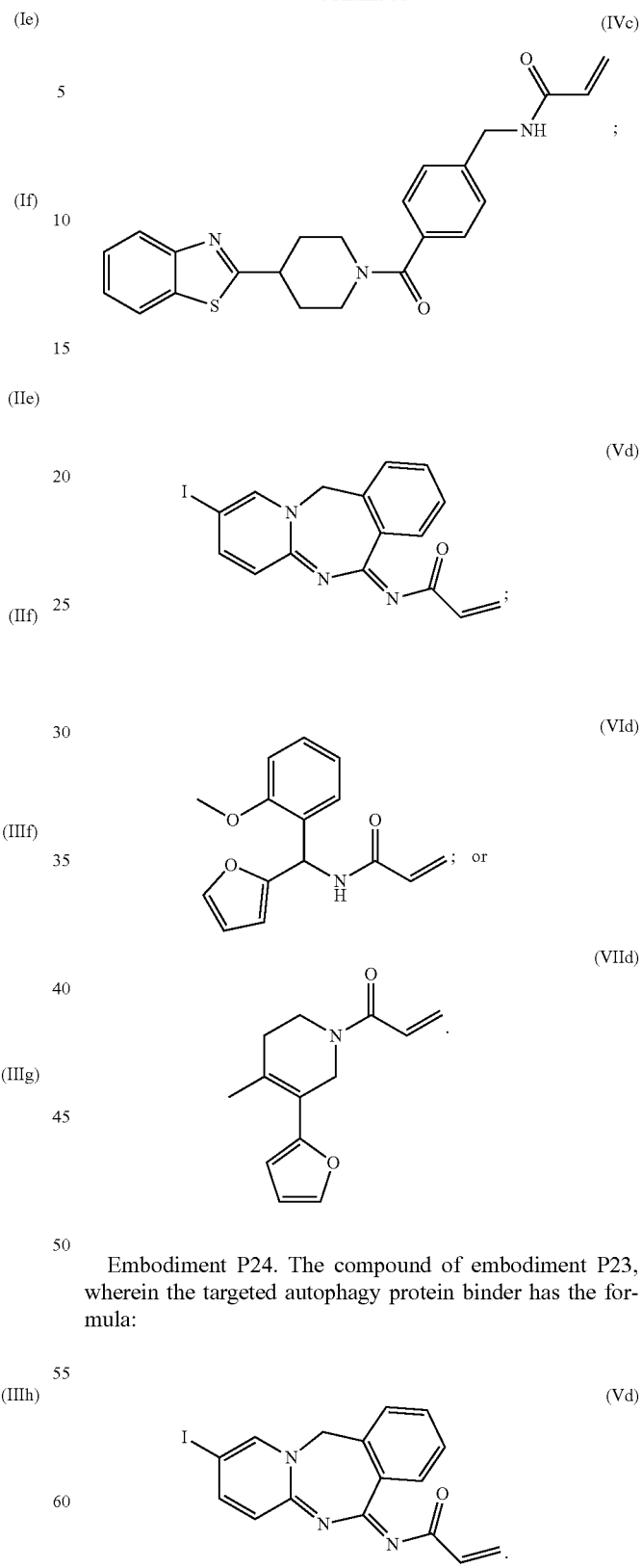
Embodiment P24. The compound of embodiment P23, wherein the targeted autophagy protein binder has the formula:
Embodiment P25. The compound of embodiment P23, wherein the monovalent targeted autophagy protein binder has the formula:

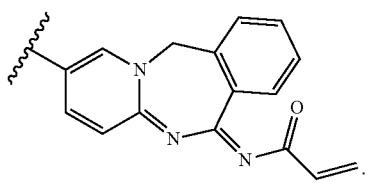

(Ve)

Embodiment P26. The compound of one of embodiments P1 to P25, wherein the cellular component binder is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P27. The compound of one of embodiments P1 to P25, wherein the monovalent cellular component binder is capable of binding BRD4.

Embodiment P28. The compound of embodiment P27, wherein the monovalent cellular component binder has the formula:

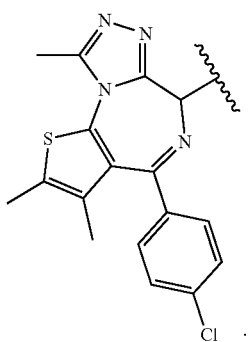 [SMILES: *C1N=C(c2ccc(Cl)cc2)c2c(sc(C)c2C)-n2c(C)nnc21]

Embodiment P29. The compound of one of embodiments P1 to P25, wherein the monovalent cellular component binder is capable of binding a protein aggregate.

Embodiment P30. The compound of embodiment P29, wherein the monovalent cellular component binder has the formula:

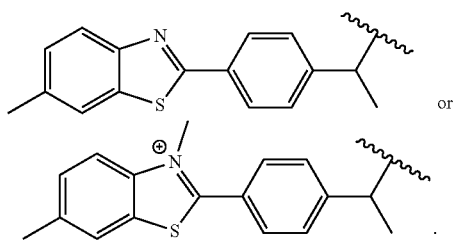

Embodiment P31. A pharmaceutical composition comprising a compound of one of embodiments P1 to P30 and a pharmaceutically acceptable excipient.

Embodiment P32. A method of reducing the level of a cellular component, said method comprising contacting the cellular component with a targeted autophagy degrader.

Embodiment P33. The method of embodiment P32, wherein the targeted autophagy degrader comprises a monovalent cellular component binder and a monovalent autophagy adapter protein binder.

Embodiment P34. The method of embodiment P33, wherein the monovalent cellular component binder and monovalent autophagy adapter protein binder are covalently bonded by a linker.

Embodiment P35. The method of one of embodiments P32 to P34, wherein the cellular component is a protein.

Embodiment P36. The method of one of embodiments P32 to P34, wherein the cellular component is an organelle.

Embodiment P37. The method of one of embodiments P32 to P34, wherein the cellular component is a complex of a plurality of optionally different proteins.

Embodiment P38. The method of one of embodiments P32 to P34, wherein the cellular component is a protein aggregate.

Embodiment P39. The method of one of embodiments P32 to P34, wherein the cellular component is a macromolecule.

Embodiment P40. The method of one of embodiments P32 to P34, wherein the cellular component is an ion, lipid, nucleic acid, nucleotide, amino acid, protein, particle, organelle, cellular compartment, microorganism, vesicle, or small molecule.

Embodiment P41. The method of one of embodiments P33 to P40, wherein the monovalent autophagy adapter protein binder is a monovalent autophagy adapter protein binder.

Embodiment P42. The method of embodiment P41, wherein the autophagy adapter protein is LC3, p62, NBR1, NDP52, Optineurin, or a derivative, fragment, or homolog thereof.

Embodiment P43. A method of reducing the level of a cellular component, said method comprising contacting the cellular component with a targeted autophagy degrader, wherein the targeted autophagy degrader is a compound of one of embodiments P1 to P30.

Embodiment P44. The method of one of embodiments P32 to P43, further comprising the steps:
  A) Allowing formation of an autophagosome including the cellular component-targeted autophagy degrader-autophagy adapter protein complex;
  B) Allowing the autophagosome to acidify; and
  C) Allowing degradation of the cellular component.

Embodiment P45. A method of treating cancer, said method comprising contacting a cellular component associated with cancer with a targeted autophagy degrader.

Embodiment P46. A method of treating cancer, said method comprising administering to a subject in need thereof a therapeutically effective amount of a compound of one of embodiments P1 to P30.

Embodiment P47. A method of treating neurodegenerative disease, said method comprising contacting a cellular component associated with the neurodegenerative disease with a targeted autophagy degrader.

Embodiment P48. A method of treating a neurodegenerative disease, said method comprising administering to a subject in need thereof a therapeutically effective amount of a compound of one of embodiments P1 to P30.

Embodiment P49. The method of embodiment P48, wherein said neurodegenerative disease is Huntington Disease, Alzheimer Disease, or Parkinson's Disease.

Embodiment P50. A method of treating a metabolic disease, said method comprising contacting a cellular component associated with the metabolic disease with a targeted autophagy degrader.

Embodiment P51. A method of treating a metabolic disease, said method comprising administering to a subject in need thereof a therapeutically effective amount of a compound of one of embodiments P1 to P30.

Embodiment P52. A method of treating an infectious disease, said method comprising contacting a cellular component associated with the infectious disease with a targeted autophagy degrader.

Embodiment P53. A method of treating an infectious disease, said method comprising administering to a subject in need thereof a therapeutically effective amount of a compound of one of embodiments P1 to P30.

Embodiment P54. A method of treating an autoimmune disease, said method comprising contacting a cellular component associated with the autoimmune disease with a targeted autophagy degrader.

Embodiment P55. A method of treating an autoimmune disease, said method comprising administering to a subject in need thereof a therapeutically effective amount of a compound of one of embodiments P1 to P30.

Embodiment P56. A method of treating an inflammatory disease, said method comprising contacting a cellular component associated with the inflammatory disease with a targeted autophagy degrader.

Embodiment P57. A method of treating an inflammatory disease, said method comprising administering to a subject in need thereof a therapeutically effective amount of a compound of one of embodiments P1 to P30.

Embodiment P58. A method of reducing the level of a cellular component, said method comprising contacting a cellular component with a targeted autophagy degrader; wherein the targeted autophagy degrader comprises:
  i) a monovalent autophagy associated protein binder;
  ii) a monovalent cellular component binder; and
  iii) a covalent linker directly bonded to the monovalent autophagy associated protein binder and the monovalent cellular component binder.

Embodiment P59. The method of embodiment P58, wherein the autophagy associated protein is an autophagy adapter protein.

Embodiment P60. The method of one of embodiments P58 to P59, wherein the cellular component is a protein, ion, lipid, nucleic acid, nucleotide, amino acid, particle, organelle, cellular compartment, microorganism, virus, vesicle, small molecule, protein complex, protein aggregate, or macromolecule.

Embodiment P61. The method of one of embodiments P58 to P60, wherein prior to the contacting, the targeted autophagy degrader is synthesized by covalently reacting a cellular component binder, a linker, and an autophagy associated protein binder to produce the targeted autophagy degrader.

Embodiment P62. The method of embodiment P61, wherein prior to the synthesizing, the autophagy associated protein binder is identified.

Embodiment P63. The method of embodiment P62, wherein the autophagy associated protein binder is identified by a method comprising the steps:
  i) mixing an autophagy associated protein with a library of candidate autophagy associated protein binders; and
  ii) identifying the candidate autophagy associated protein binders that bind to the autophagy associated protein.

Embodiment P64. The method of embodiment P63, wherein the candidate autophagy associated protein binders comprise a covalent cysteine modifier moiety and a candidate autophagy associated protein binder is identified as an autophagy associated protein binder by detection of covalent binding of the autophagy associated protein binder to the autophagy associated protein.

Embodiment P65. The method of embodiment P64, wherein the detection of covalent binding of the candidate autophagy associated protein binder to the autophagy associated protein comprises use of a detectable label or mass spectroscopic detection of the covalent binding.

Embodiment P66. The method of embodiment P64, wherein prior to the synthesizing, the cellular component binder is identified.

Embodiment P67. The method of embodiment P66, wherein the cellular component binder is identified by a method comprising the steps:
  i) mixing a cellular component protein with a library of candidate cellular component binders; and
  ii) identifying the candidate cellular component binders that bind to the cellular component.

Embodiment P68. The method of embodiment P67, wherein the candidate cellular component binders comprise a covalent cysteine modifier moiety and a candidate cellular component binder is identified as a cellular component binder by detection of covalent binding of the cellular component binder to the cellular component.

Embodiment P69. The method of embodiment P68, wherein the detection of covalent binding of the candidate cellular component binder to the cellular component comprises use of a detectable label or mass spectroscopic detection of the covalent binding.

Embodiment P70. The method of embodiment P61, wherein prior to the synthesizing, the autophagy associated protein binder is modified to remove a covalent cysteine modifier moiety.

Embodiment P71. The method of one of embodiments P1 to P70, wherein targeted autophagy degrader is a compound of any one of embodiments P1 to P30.

VIII. Additional Embodiments

Embodiment 1. A compound comprising a monovalent cellular component binder covalently bound to a monovalent targeted autophagy protein binder.

Embodiment 2. The compound of embodiment 1, wherein a divalent linker binds said monovalent cellular component binder to said monovalent targeted autophagy protein binder.

Embodiment 3. The compound of one of embodiments 1 to 2, wherein the cellular component is a protein, ion, lipid, nucleic acid, nucleotide, amino acid, particle, organelle, cellular compartment, microorganism, virus, lipid droplet, vesicle, small molecule, protein complex, protein aggregate, or macromolecule.

Embodiment 4. The compound of one of embodiments 1 to 3, wherein the cellular component is associated with a disease.

Embodiment 5. The compound of embodiment 4, wherein the disease is cancer, a neurodegenerative disease, a metabolic disease, an infectious disease, an autoimmune disease, or an inflammatory disease.

Embodiment 6. The compound of one of embodiments 1 to 5, wherein the monovalent targeted autophagy protein binder is a monovalent form of an oligonucleotide or a monovalent form of a protein.

Embodiment 7. The compound of embodiment 6, wherein the monovalent form of the oligonucleotide is a monovalent form of DNA, RNA, or siRNA.

Embodiment 8. The compound of embodiment 6, wherein the monovalent form of the protein is a monovalent form of: an antibody, an anti-LC3 antibody, an anti-p62 antibody, an anti-NBR1 antibody, an anti-NDP52 antibody, an anti-Optineurin antibody, an anti-NUFIP1 antibody, an anti-WDFY3 antibody, an anti-RETREG1 antibody, an anti-Nix antibody, an anti-TOLLIP antibody, an anti-TAX1BP1 antibody, an anti-LC3 binding antibody fragment, an anti-p62 binding antibody fragment, an anti-NBR1 binding antibody fragment, an anti-NDP52 binding antibody fragment, an anti-Optineurin binding antibody fragment, an anti-NUFIP1 binding antibody fragment, an anti-WDFY3 binding antibody fragment, an anti-RETREG1 binding antibody fragment, an anti-Nix binding antibody fragment, an anti-TOLLIP binding antibody fragment, or an anti-TAX1BP1 binding antibody fragment.

Embodiment 9. The compound of one of embodiments 1 to 8, wherein the monovalent targeted autophagy protein binder is a monovalent autophagy adapter protein binder.

Embodiment 10. The compound of embodiment 9, wherein the monovalent autophagy adapter protein binder binds LC3, p62, NBR1, NDP52, Optineurin, NUFIP1, WDFY3, RETREG1, Nix, TOLLIP, TAX1BP1, or a derivative, fragment, or homolog thereof.

Embodiment 11. The compound of one of embodiments 2 to 10, wherein the divalent linker has the formula:

-L$^1$-L$^2$-L$^3$-L$^4$-;

L$^1$ is connected directly to said monovalent targeted autophagy protein binder;
L$^1$ is —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
L$^2$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
L$^3$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
L$^4$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 12. The compound of one of embodiments 1 to 11, wherein the targeted autophagy protein binder is capable of contacting an amino acid corresponding to C17 of human LC3A protein.

Embodiment 13. The compound of one of embodiments 1 to 11, wherein the targeted autophagy protein binder is capable of contacting an amino acid corresponding to C26 of human p62/SQSTM1 protein.

Embodiment 14. The compound of one of embodiments 1 to 11, wherein the targeted autophagy protein binder is capable of contacting an amino acid corresponding to C27 of human p62/SQSTM1 protein.

Embodiment 15. The compound of one of embodiments 1 to 11, wherein the targeted autophagy protein binder is capable of contacting an amino acid corresponding to C113 of human p62/SQSTM1 protein.

Embodiment 16. The compound of one of embodiments 1 to 11, wherein the targeted autophagy protein binder is capable of contacting an amino acid corresponding to C120 of human NBR1 protein.

Embodiment 17. The compound of one of embodiments 1 to 11, wherein the targeted autophagy protein binder is capable of contacting an amino acid corresponding to C321 of human NDP52/CALCOCO2 protein.

Embodiment 18. The compound of one of embodiments 1 to 11, wherein the targeted autophagy protein binder is capable of contacting an amino acid corresponding to C558 of human OPTN protein.

Embodiment 19. The compound of one of embodiments 12 to 18, wherein the targeted autophagy protein binder is capable of forming a covalent bond to the cysteine.

Embodiment 20. The compound of one of embodiments 1 to 12, wherein the monovalent targeted autophagy protein binder is a monovalent form of the formula:

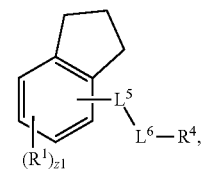

(I)

wherein z1 is an integer from 0 to 9;

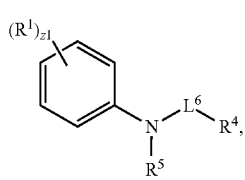

(II)

wherein z1 is an integer from 0 to 5;

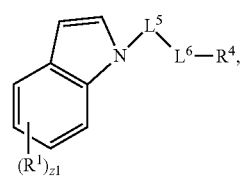

(III)

wherein z1 is an integer from 0 to 6;

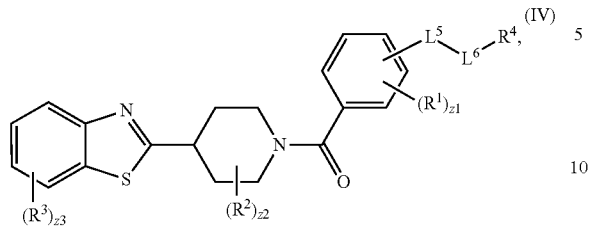
(IV)

wherein z1 is an integer from 0 to 4, z2 is an integer from 0 to 8, and z3 is an integer from 0 to 4;

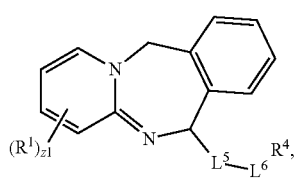
(V)

wherein z1 is an integer from 0 to 11;

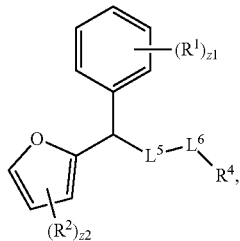
(VI)

wherein z1 is an integer from 0 to 5 and z2 is an integer from 0 to 3;

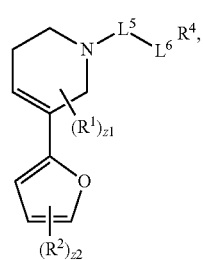
(VII)

wherein z1 is an integer from 0 to 7 and z2 is an integer from 0 to 3;

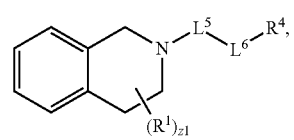
(VIII)

wherein z1 is an integer from 0 to 10;

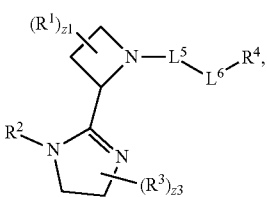
(IX)

wherein z1 is an integer from 0 to 5 and z3 is an integer from 0 to 4;

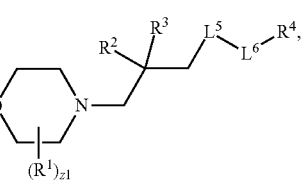
(X)

wherein z1 is an integer from 0 to 8;

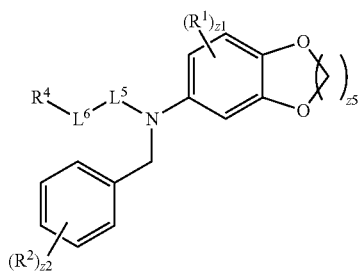
(XI)

wherein z1 is an integer from 0 to 7, z2 is an integer from 0 to 5, and z5 is 1 or 2;

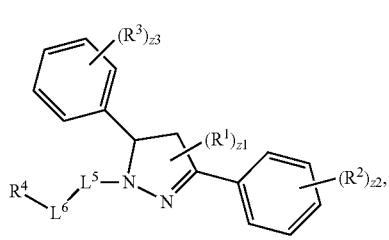
(XII)

wherein z1 is an integer from 0 to 2, z2 is an integer from 0 to 5, and z3 is an integer from 0 to 5;

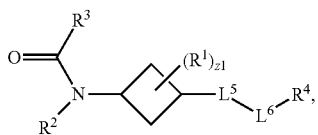
(XIII)

wherein z1 is an integer from 0 to 6;

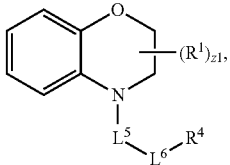
(XIV)

wherein z1 is an integer from 0 to 6;

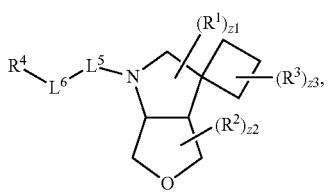
(XV)

wherein z1 is an integer from 0 to 4, z2 is an integer from 0 to 6, and z3 is an integer from 0 to 6;

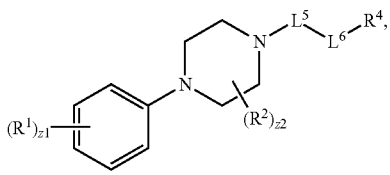
(XVI)

wherein z1 is an integer from 0 to 5 and z2 is an integer from 0 to 8;

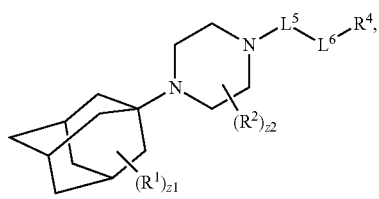
(XVII)

wherein z1 is an integer from 0 to 15 and z2 is an integer from 0 to 8;

$R^1$ is independently oxo, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{15A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently oxo, halogen, $-CX^2_3$, $-CHX^2_2$, $-CH_2X^2$, $-OCX^2_3$, $-OCH_2^2$, $-OCHX^2_2$, $-CN$, $-SO_{n2}R^{1D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{1C}$, $-C(O)NR^{1A}R^{1B}$, $-OR^{1D}$, $-NR^{15A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^3$ is independently oxo, halogen, $-CX^3_3$, $-CHX^3_2$, $-CH_2X^3$, $-OCX^3_3$, $-OCH_2^3$, $-OCHX^3_2$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{13A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-CX^4_3$, $-CHX^4_2$, $-CH_2X^4$, $-OCX^4_3$, $-OCH_2^4$, $-OCHX^4_2$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{15A}SO_2R^{4D}$, $-NR^{4A}C(O)R^{4C}$, $-NR^{4A}C(O)OR^{4C}$, $-NR^{4A}OR^{4C}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

$L^5$ is a bond, $-S(O)_2-$, $-S(O)-$, $-NR^5-$, $=N-$, $-O-$, $-S-$, $-C(O)-$, $-C(O)NR^5-$, $-NR^5C(O)-$, $-NR^5C(O)NH-$, $-NHC(O)NR^5-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^5$ is hydrogen, $-CX^5_3$, $-CHX^5_2$, $-CH_2X^5$, $-OCX^5_3$, $-OCH_2X^5$, $-OCHX^5_2$, $-CN$, $-C(O)R^{5C}$, $-C(O)-OR^{5C}$, $-C(O)NR^{5A}R^{5B}$, $-OR^{5D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^6$ is a bond, $-S(O)_2-$, $-S(O)-$, $-NR^6-$, $=N-$, $-O-$, $-S-$, $-C(O)-$, $-C(O)NR^6-$, $-NR^6C(O)-$, $-NR^6C(O)NH-$, $-NHC(O)NR^6-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^6$ is hydrogen, —CX$^6_3$, —CHX$^6_2$, —CH$_2$X$^6$, —OCX$^6_3$, —OCH$_2$X$^6$, —OCHX$^6_2$, —CN, —C(O)R$^{6C}$, —C(O)OR$^{6C}$, —C(O)NR$^{6A}$R$^{6B}$, —OR$^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, and R$^{6D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl;

X, X$^1$, X$^2$, X$^3$, X$^4$, X$^5$, and X$^6$ are independently —F, —Cl, —Br, or —I;

n1, n2, n3, n4, n5, and n6 are independently an integer from 0 to 4; and m1, m2, m3, m4, m5, m6, v1, v2, v3, v4, v5, and v6 are independently 1 or 2.

Embodiment 21. The compound of embodiment 20, wherein the monovalent targeted autophagy protein binder is a monovalent form of the formula:

(Ia)

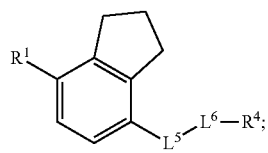

(IIa)

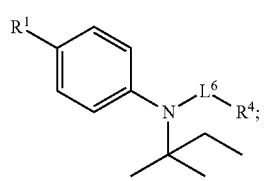

(IIIa)

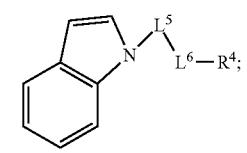

-continued (IIIb)

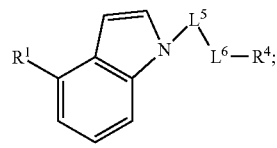

(IVa)

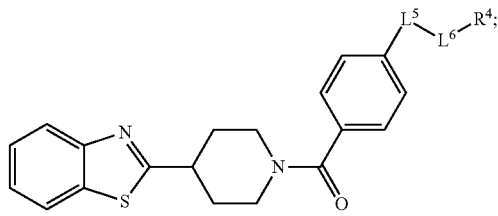

(Va)

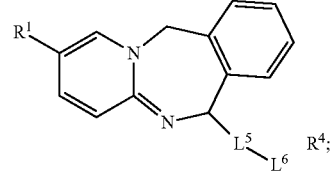

(VIa)

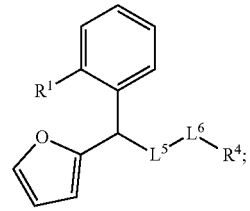

(VIIa)

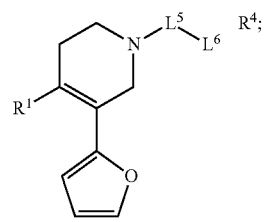

(VIIIa)

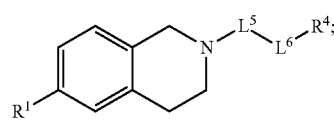

(IXa)

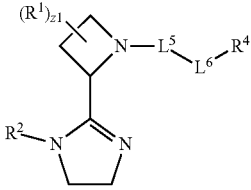

wherein z1 is an integer from 0 to 5;

(Xa)

-continued
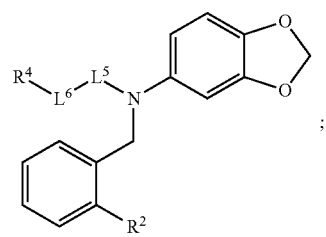
(XIa)
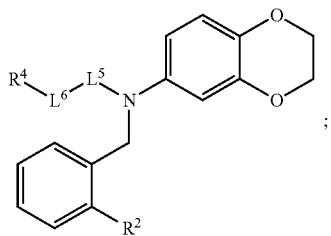
(XIb)
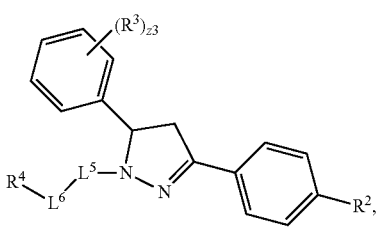
(XIIa)
wherein z3 is 2;
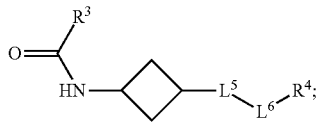
(XIIIa)
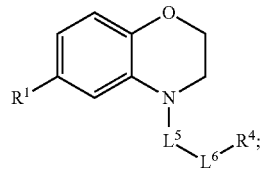
(XIVa)
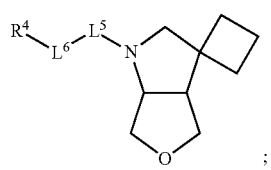
(XVa)
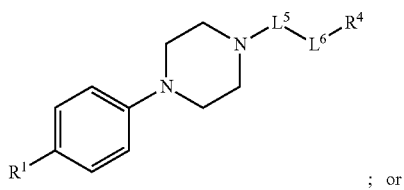
(XVIa)
; or
-continued
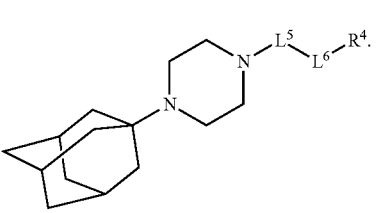
(XVIIa)
Embodiment 22. The compound of embodiment 20, wherein the monovalent targeted autophagy protein binder is a monovalent form of the formula:
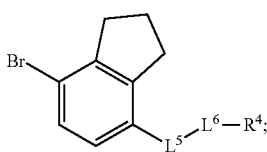
(Ib)
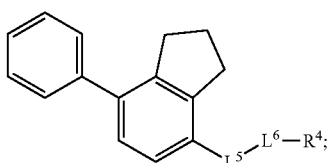
(Ic)
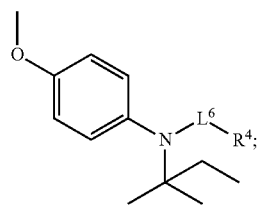
(IIb)
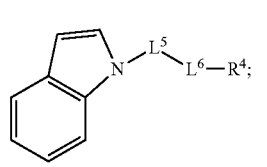
(IIIa)
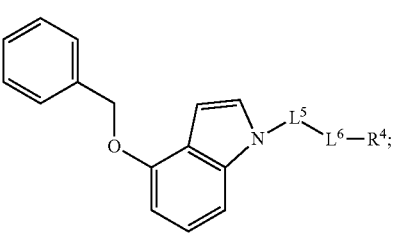
(IIIc)
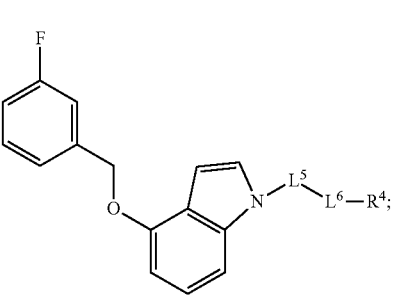
(IIId)

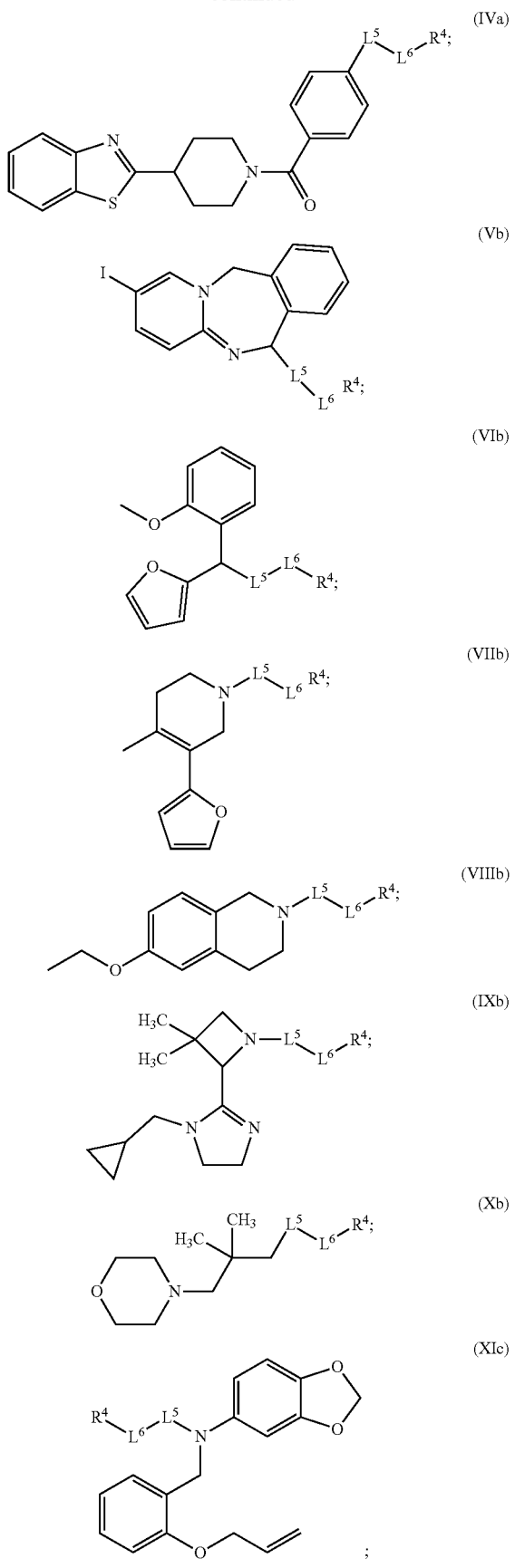
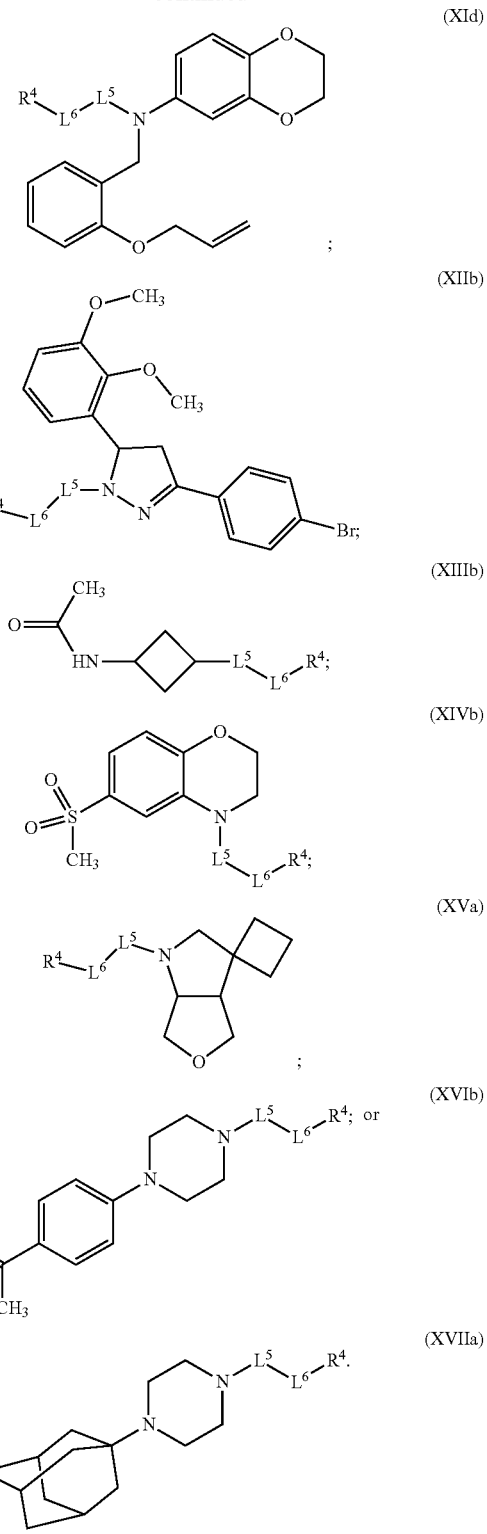
Embodiment 23. The compound of one of embodiments 20 to 22, wherein $R^4$ is E.
Embodiment 24. The compound of one of embodiments 20 to 23, wherein E is a covalent cysteine modifier, covalent lysine modifier, covalent serine modifier, or covalent methionine modifier.

Embodiment 25. The compound of one of embodiments 20 to 23, wherein E is

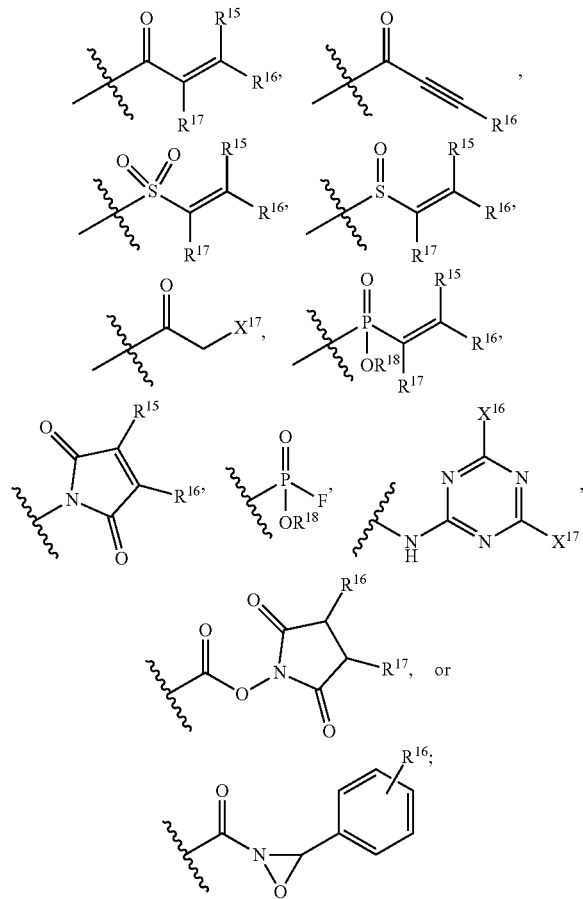

$R^{15}$ is independently hydrogen, halogen, $-CX^{15}_3$, $-CHX^{15}_2$, $-CH_2X^{15}$, $-CN$, $-SO_{n15}R^{15D}$, $-SO_{v15}NR^{15A}R^{15B}$, $-NHNR^{15A}R^{15B}$, $-ONR^{15A}R^{15B}$, $-NHC=(O)NHNR^{15A}R^{15B}$, $-NHC(O)NR^{15A}R^{15B}$, $-N(O)_{m15}$, $-NR^{15A}R^{15B}$, $-C(O)R^{15C}$, $-C(O)OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)OR^{15C}$, $-NR^{15A}OR^{15C}$, $-OCX^{15}_3$, $-OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is independently hydrogen, halogen, $-CX^{16}_3$, $-CHX^{16}_2$, $-CH_2X^{16}$, $-CN$, $-SO_{n16}R^{16D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, $-OCX^{16}_3$, $-OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, $-CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, $-OCX^{17}_3$, $-OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{18}$ is independently hydrogen, $-CX^{18}_3$, $-CHX^{18}_2$, $-CH_2X^{18}$, $-C(O)R^{18C}$, $-C(O)OR^{18C}$, $-C(O)NR^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18C}$, $R^{18D}$, are idenpendently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl;

each X, $X^{15}$, $X^{16}$, $X^{17}$ and $X^{18}$ is independently $-F$, $-Cl$, $-Br$, or $-I$;

n15, n16, and n17 are independently an integer from 0 to 4; and m15, m16, m17, v15, v16, and v17 are independently and integer from 1 to 2.

Embodiment 26. The compound of one of embodiments 20 to 23, wherein E is

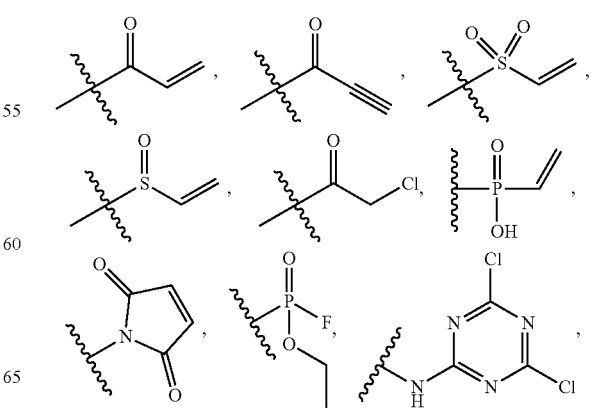

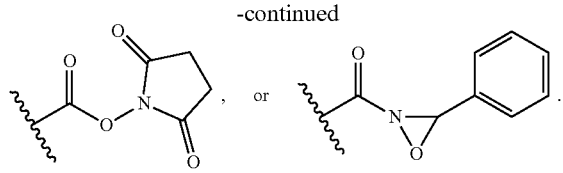 or 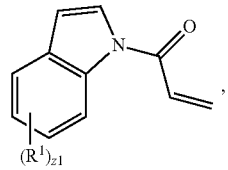

Embodiment 27. The compound of one of embodiments 20 to 23, wherein E is

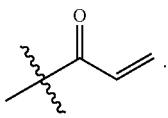 [SMILES: *C(=O)C=C]

Embodiment 28. The compound of one of embodiments 20 to 23, wherein E is

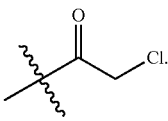

Embodiment 29. The compound of one of embodiments 20 to 23, wherein the monovalent targeted autophagy protein binder is a monovalent form of the formula:

(Id)

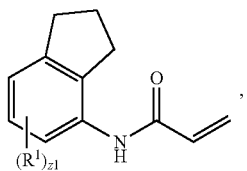

wherein z1 is an integer from 0 to 9;

(IIc)

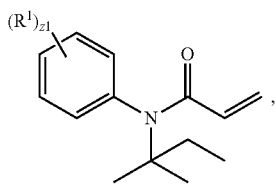

wherein z1 is an integer from 0 to 5;

(IId)

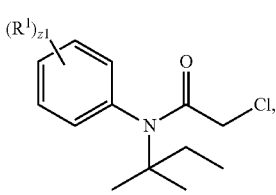

wherein z1 is an integer from 0 to 5;

(IIIe)

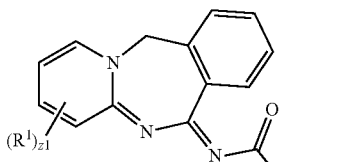

wherein z1 is an integer from 0 to 6;

(IVb)

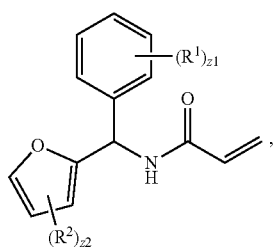

wherein z1 is an integer from 0 to 4, z2 is an integer from 0 to 8, and z3 is an integer from 0 to 4;

(Vc)

wherein z1 is an integer from 0 to 11;

(VIc)

wherein z1 is an integer from 0 to 5 and z2 is an integer from 0 to 3;

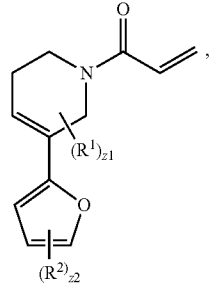
(VIIc)

wherein z1 is an integer from 0 to 5 and z2 is an integer from 0 to 3;

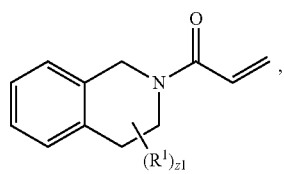
(VIIIc)

wherein z1 is an integer from 0 to 10;

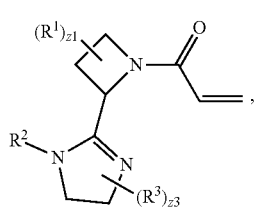
(IXc)

wherein z1 is an integer from 0 to 5 and z3 is an integer from 0 to 4;

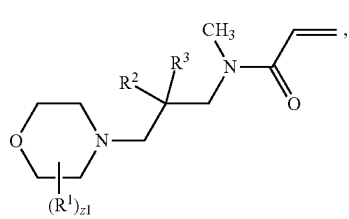
(Xc)

wherein z1 is an integer from 0 to 8;

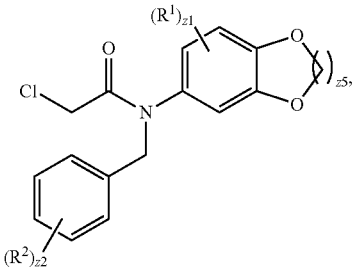
(XIe)

wherein z1 is an integer from 0 to 7, z2 is an integer from 0 to 5, and z5 is 1 or 2;

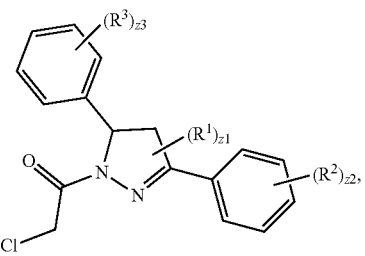
(XIIc)

wherein z1 is an integer from 0 to 2, z2 is an integer from 0 to 5, and z3 is an integer from 0 to 5;

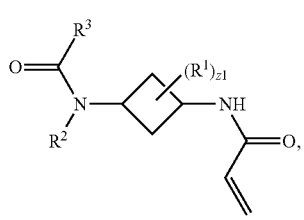
(XIIIc)

wherein z1 is an integer from 0 to 6,

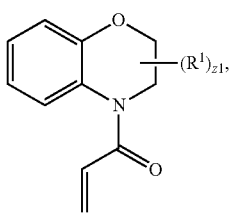
(XIVc)

wherein z1 is an integer from 0 to 6;

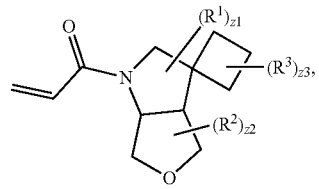
(XVb)

wherein z1 is an integer from 0 to 4, z2 is an integer from 0 to 6, and z3 is an integer from 0 to 6;

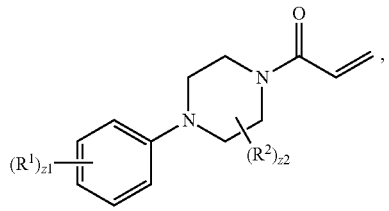
(XVIc)

wherein z1 is an integer from 0 to 5 and z2 is an integer from 0 to 8; or

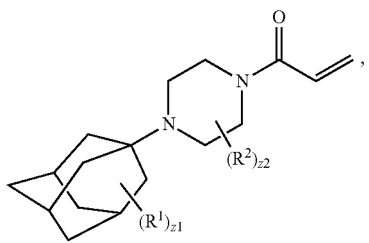
(XVIIb)

wherein z1 is an integer from 0 to 15 and z2 is an integer from 0 to 8.

Embodiment 30. The compound of one of embodiments 20 to 26, wherein the monovalent targeted autophagy protein binder is a monovalent form of the formula:

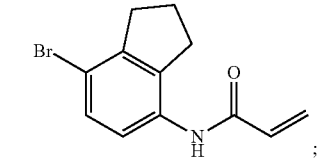
(Ie)

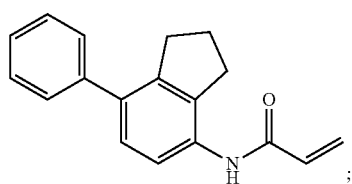
(If)

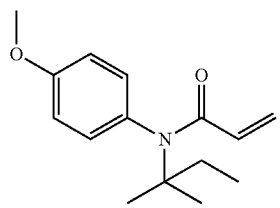
(IIe)

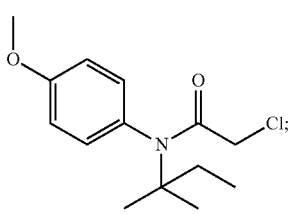
(IIf)

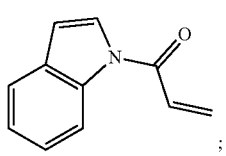
(IIIf)

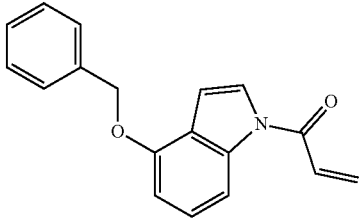
(IIIg)

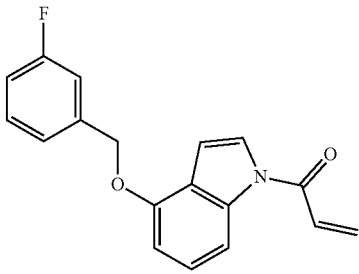
(IIIh)

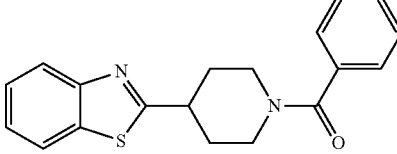
(IVc)

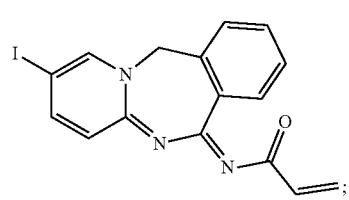
(Vd)

-continued
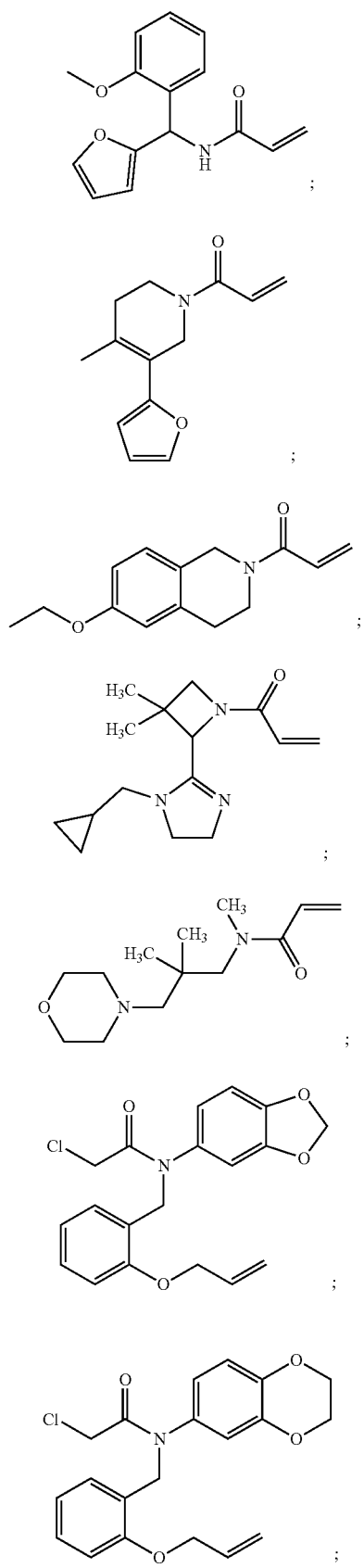
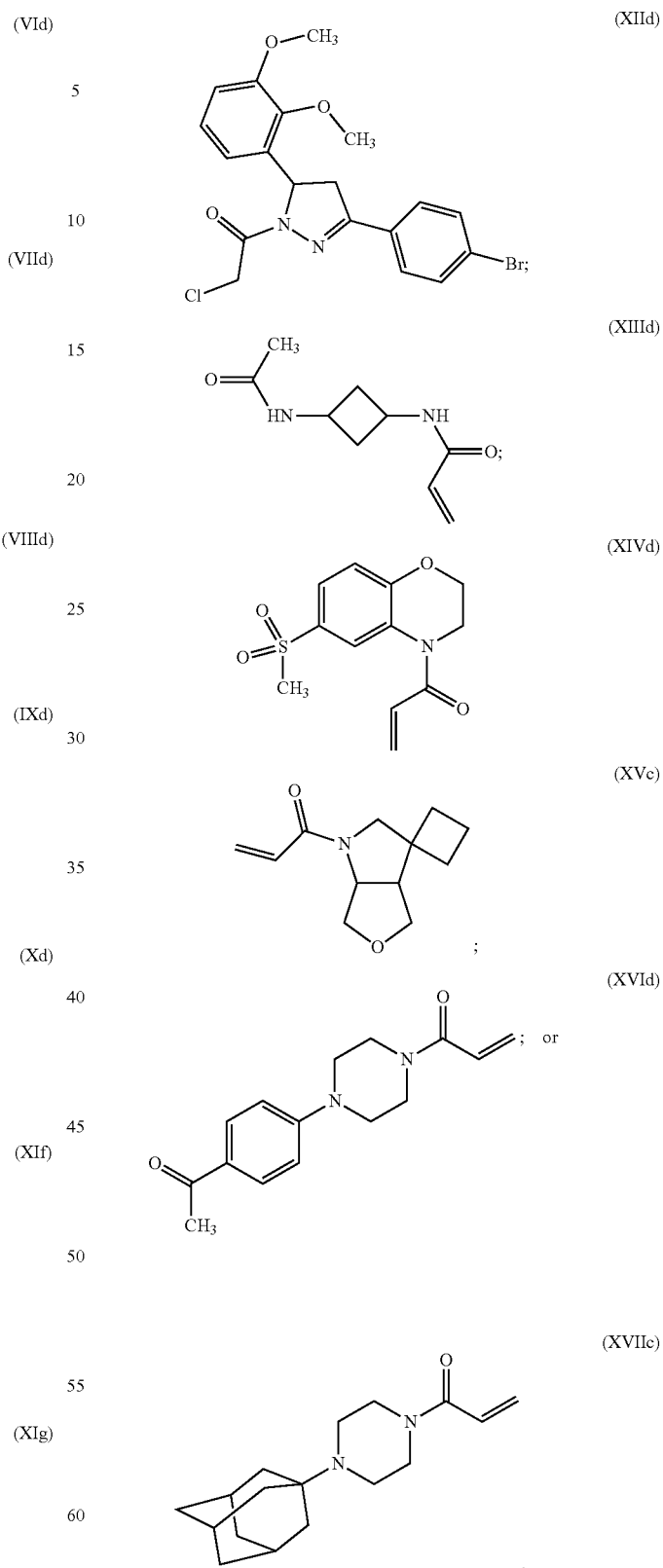
Embodiment 31. The compound of embodiment 30, wherein the monovalent targeted autophagy protein binder is a monovalent form of the formula:

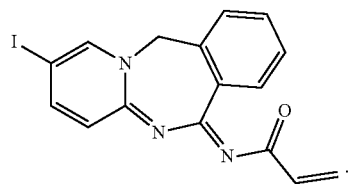

(Vd)

Embodiment 32. The compound of embodiment 30, wherein the monovalent targeted autophagy protein binder has the formula:

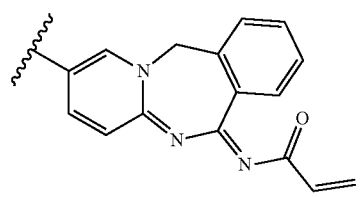

(mVe)

Embodiment 33. The compound of embodiment 30, wherein the monovalent targeted autophagy protein binder is a monovalent form of the formula:

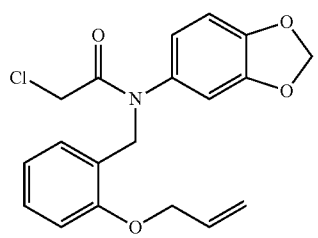

(XIf)

Embodiment 34. The compound of embodiment 30, wherein the monovalent targeted autophagy protein binder has the formula:

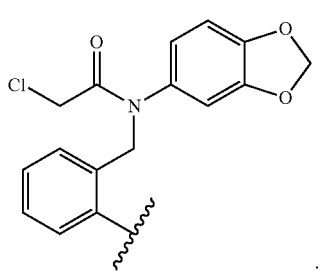

(mXIf)

Embodiment 35. The compound of one of embodiments 1 to 32, wherein the monovalent cellular component binder is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 36. The compound of one of embodiments 1 to 32, wherein the monovalent cellular component binder is capable of binding BRD4.

Embodiment 37. The compound of embodiment 36, wherein the monovalent cellular component binder has the formula:

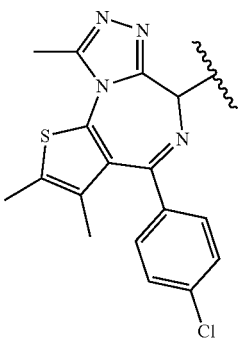

Embodiment 38. The compound of one of embodiments 1 to 37, having the formula

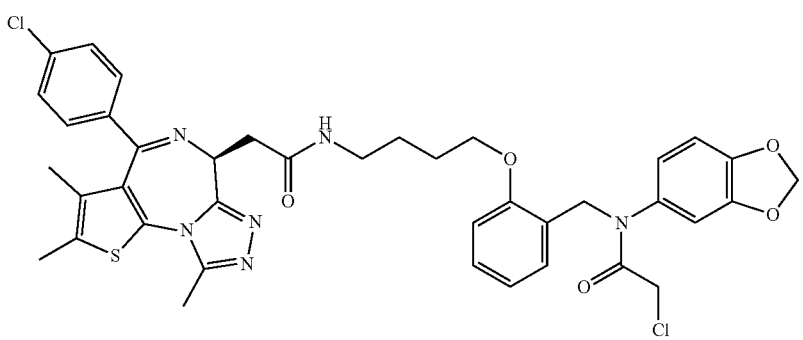 [SMILES: Cc1sc2c(c1C)C(c1ccc(Cl)cc1)=N[C@@H](CC(=O)NCCCCOc1ccccc1CN(C(=O)CCl)c1ccc3c(c1)OCO3)c1nnc(C)n1-2]

Embodiment 39. The compound of one of embodiments 1 to 38, wherein the monovalent cellular component binder is capable of binding a protein aggregate.

Embodiment 40. The compound of embodiment 39, wherein the monovalent cellular component binder is capable of binding a huntingtin aggregate.

Embodiment 41. The compound of embodiment 39, wherein the monovalent cellular component binder is capable of binding a PolyQ huntingtin aggregate.

Embodiment 42. The compound of embodiment 39, wherein the monovalent cellular component binder is capable of binding an amyloid protein aggregate.

Embodiment 43. The compound of embodiment 39, wherein the monovalent cellular component binder is capable of binding a protein aggregate comprising a protein selected from amyloid precursor protein, beta amyloid, 1APP, alpha-synuclein, PrP, prion protein Sc, Huntingtin, calcitonin, atrial natriuretic factor, apolipoprotein A1, Serum amyloid A, medin, prolactin, transthyretin, lysozyme, beta-2 microglobulin, gelsolin, keratoepithelin, cystatin, immunoglobulin light chain AL, and S-IBM.

Embodiment 44. The compound of embodiment 39, wherein the monovalent cellular component binder is a monovalent form of thioflavin or a derivative thereof.

Embodiment 45. The compound of embodiment 39, wherein the monovalent cellular component binder is a monovalent form of the formula:

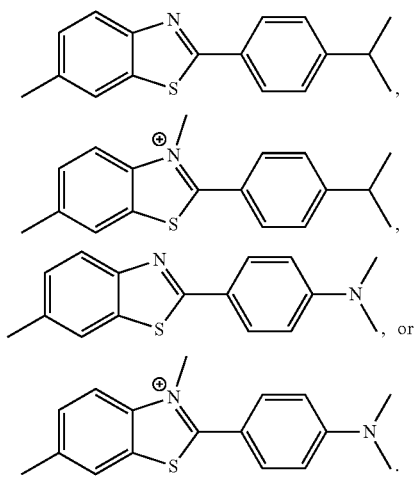

Embodiment 46. The compound of embodiment 39, wherein the monovalent cellular component binder is a monovalent form of the formula:

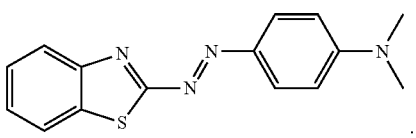 [SMILES: CN(C)c1ccc(/N=N/c2nc3ccccc3s2)cc1]

Embodiment 47. The compound of embodiment 39, wherein the monovalent cellular component binder has the formula:

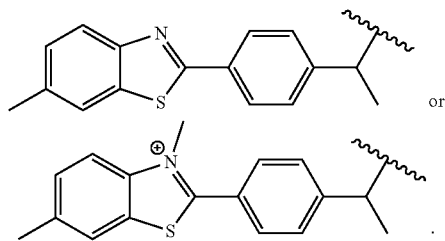

Embodiment 48. The compound of embodiment 39, wherein the monovalent cellular component binder has the formula:

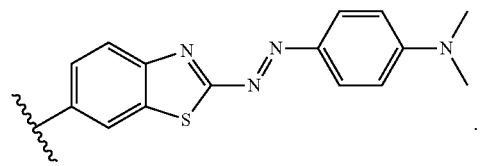 [SMILES: *c1ccc2nc(/N=N/c3ccc(N(C)C)cc3)sc2c1]

Embodiment 49. A compound comprising a monovalent cellular component binder covalently bound to a monovalent targeted autophagy protein binder, wherein the monovalent targeted autophagy protein binder is a monovalent form of the formula:

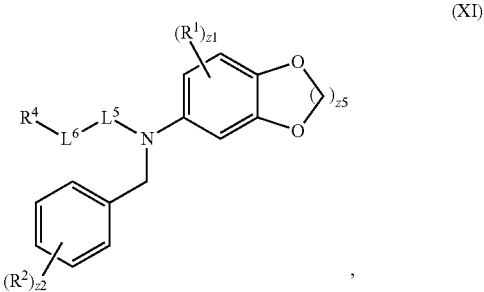

(XI)

wherein z1 is an integer from 0 to 7, z2 is an integer from 0 to 5, and z5 is 1 or 2;

$R^1$ is independently oxo, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{15A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —N(O)$_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

$L^5$ is a bond, —$S(O)_2$—, —$S(O)$—, —$NR^5$—, =N—, —O—, —S—, —$C(O)$—, —$C(O)NR^5$—, —$NR^5C(O)$—, —$NR^5C(O)NH$—, —$NHC(O)NR^5$—, —$C(O)O$—, —$OC(O)$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^5$ is hydrogen, —$CX^5_3$, —$CHX^5_2$, —$CH_2X^5$, —$OCX^5_3$, —$OCH_2X^5$, —$OCHX^5_2$, —CN, —$C(O)R^{5C}$, —$C(O)$—$OR^{5C}$, —$C(O)NR^{5A}R^{5B}$, —$OR^{5D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^6$ is a bond, —$S(O)_2$—, —$S(O)$—, —$NR^6$—, =N—, —O—, —S—, —$C(O)$—, —$C(O)NR^6$—, —$NR^6C(O)$—, —$NR^6C(O)NH$—, —$NHC(O)NR^6$—, —$C(O)O$—, —$OC(O)$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^6$ is hydrogen, —$CX^6_3$, —$CHX^6_2$, —$CH_2X^6$, —$OCX^6_3$, —$OCH_2X^6$, —$OCHX^6_2$, —CN, —$C(O)R^{6C}$, —$C(O)$—$OR^{6C}$, —$C(O)NR^{6A}R^{6B}$, —$OR^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, and $R^{6D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl;

X, $X^1$, $X^2$, $X^4$, $X^5$, and $X^6$ are independently —F, —Cl, —Br, or —I;

n1, n2, n4, n5, and n6 are independently an integer from 0 to 4; and m1, m2, m4, m5, m6, v1, v2, v4, v5, and v6 are independently 1 or 2.

Embodiment 50. The compound of embodiment 49, wherein the monovalent targeted autophagy protein binder is a monovalent form of the formula:

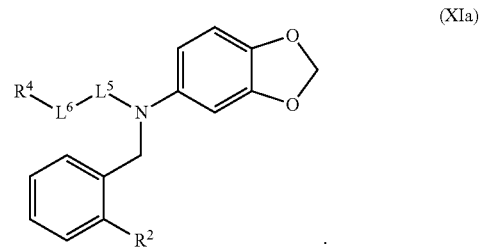

(XIa)

Embodiment 51. The compound of embodiment 49, wherein the monovalent targeted autophagy protein binder is a monovalent form of the formula:

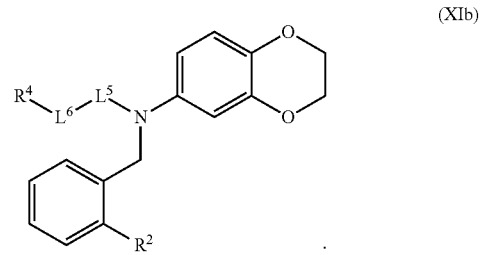

(XIb)

Embodiment 52. The compound of embodiment 49, wherein the monovalent targeted autophagy protein binder is a monovalent form of the formula:

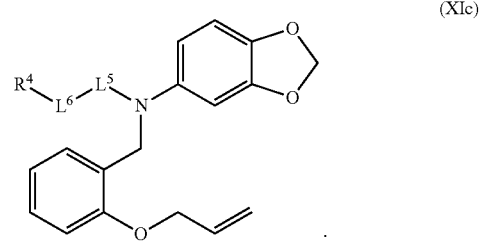

(XIc)

Embodiment 53. The compound of embodiment 49, wherein the monovalent targeted autophagy protein binder is a monovalent form of the formula:

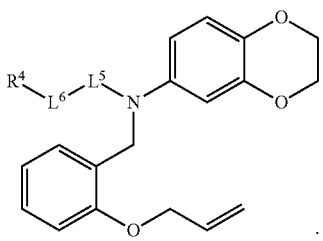

(XId)

Embodiment 54. The compound of one of embodiments 49 to 53, wherein $R^4$ is E.

Embodiment 55. The compound of one of embodiments 49 to 53, wherein E is a covalent cysteine modifier, covalent lysine modifier, covalent serine modifier, or covalent methionine modifier.

Embodiment 56. The compound of one of embodiments 49 to 55, wherein E is

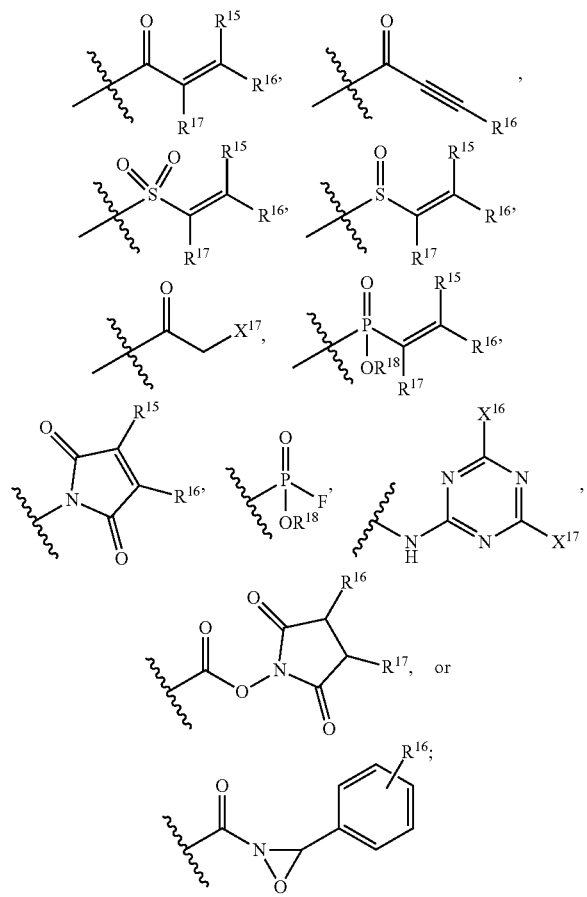

$R^{15}$ is independently hydrogen, halogen, —$CX^{15}{}_3$, —$CHX^{15}{}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —NHC=(O)NHNR$^{15A}R^{15B}$, —NHC(O)NR$^{15A}R^{15B}$, —N(O)$_{m15}$, —$NR^{15A}R^{15B}$, —C(O)R$^{15C}$, —C(O)OR$^{15C}$, —C(O)NR$^{15A}R^{15B}$, —OR$^{15D}$, —NR$^{15A}SO_2R^{15D}$, —NR$^{15A}C(O)R^{15C}$, —NR$^{15A}C(O)OR^{15C}$, —NR$^{15A}OR^{15C}$, —$OCX^{15}{}_3$, —$OCHX^{15}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is independently hydrogen, halogen, —$CX^{16}{}_3$, —$CHX^{16}{}_2$, —$CH_2X^{16}$, —CN, —$SO_{n16}R^{16D}$, —$SO_{v16}NR^{16A}R^{16B}$, —$NHNR^{16A}R^{16B}$, —$ONR^{16A}R^{16B}$, —NHC=(O)NHNR$^{16A}R^{16B}$, —NHC(O)NR$^{16A}R^{16B}$, —N(O)$_{m16}$, —$NR^{16A}R^{16B}$, —C(O)R$^{16C}$, —C(O)OR$^{16C}$, —C(O)NR$^{16A}R^{16B}$, —OR$^{16D}$, —NR$^{16A}SO_2R^{16D}$, —NR$^{16A}C(O)R^{16C}$, —NR$^{16A}C(O)OR^{16C}$, —NR$^{16A}OR^{16C}$, —$OCX^{16}{}_3$, —$OCHX^{16}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is independently hydrogen, halogen, —$CX^{17}{}_3$, —$CHX^{17}{}_2$, —$CH_2X^{17}$, —CN, —$SO_{n17}R^{17D}$, —$SO_{v17}NR^{17A}R^{17B}$, —$NHNR^{17A}R^{17B}$, —$ONR^{17A}R^{17B}$, —NHC=(O)NHNR$^{17A}R^{17B}$, —NHC(O)NR$^{17A}R^{17B}$, —N(O)$_{m17}$, —$NR^{17A}R^{17B}$, —C(O)R$^{17C}$, —C(O)OR$^{17C}$, —C(O)NR$^{17A}R^{17B}$, —OR$^{17D}$, —NR$^{17A}SO_2R^{17D}$, —NR$^{17A}C(O)R^{17C}$, —NR$^{17A}C(O)OR^{17C}$, —NR$^{17A}OR^{17C}$, —$OCX^{17}{}_3$, —$OCHX^{15}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{18}$ is independently hydrogen, —$CX^{18}{}_3$, —$CHX^{18}{}_2$, —$CH_2X^{18}$, —C(O)R$^{18C}$, —C(O)OR$^{18C}$, —C(O)NR$^{18A}R^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18C}$, $R^{18D}$, are idenpendently hydrogen, —$CX_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl;

each X, $X^{15}$, $X^{16}$, $X^{17}$ and $X^{18}$ is independently —F, —Cl, —Br, or —I;

n15, n16, and n17 are independently an integer from 0 to 4; and m15, m16, m17, v15, v16, and v17 are independently and integer from 1 to 2.

Embodiment 57. The compound of one of embodiments 49 to 55, wherein E is

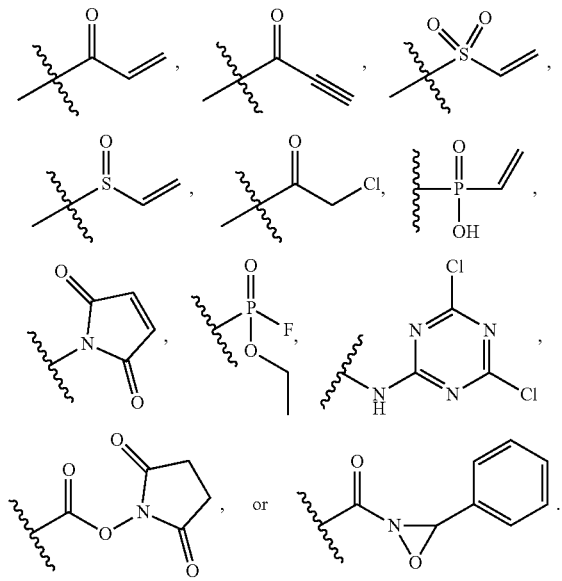

Embodiment 58. The compound of one of embodiments 49 to 55, wherein E is

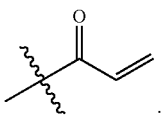 [SMILES: *C(=O)C=C]

Embodiment 59. The compound of one of embodiments 49 to 53, wherein -$L^5$-$L^6$-$R^4$ is —C(O)CH$_2$-(halogen).

Embodiment 60. The compound of one of embodiments 49 to 53, wherein -$L^5$-$L^6$-$R^4$ is C(O)CH$_2$—Cl.

Embodiment 61. The compound of one of embodiments 49 to 53, wherein -$L^5$-$L^6$-$R^4$ is C(O)CH$_2$—Br.

Embodiment 62. The compound of embodiment 49, wherein the monovalent targeted autophagy protein binder is a monovalent form of the formula:

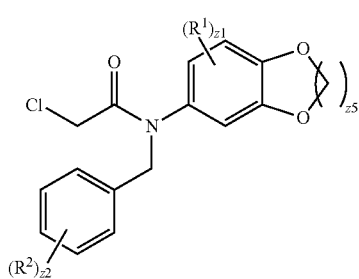

(XIe)

Embodiment 63. The compound of embodiment 49, wherein the monovalent targeted autophagy protein binder is a monovalent form of the formula:

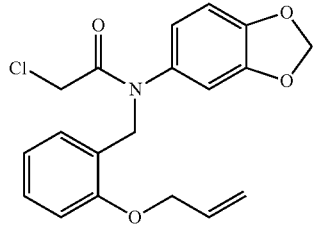

(XIf)

Embodiment 64. The compound of embodiment 49, wherein the monovalent targeted autophagy protein binder is a monovalent form of the formula:

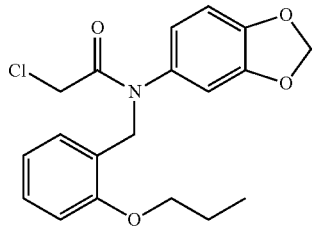

(XIh)

Embodiment 65. The compound of embodiment 49, wherein the monovalent targeted autophagy protein binder is a monovalent form of the formula:

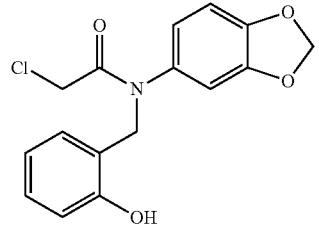

(XIi)

Embodiment 66. The compound of embodiment 49, wherein the monovalent targeted autophagy protein binder has the formula:

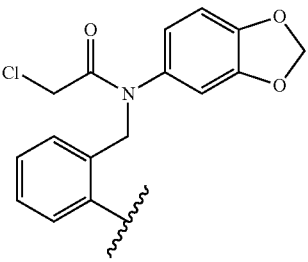

(mXIf)

Embodiment 67. The compound of one of embodiments 49 to 66, wherein the monovalent targeted autophagy protein binder is capable of contacting an amino acid corresponding to C113 of human p62/SQSTM1 protein.

Embodiment 68. The compound of one of embodiments 49 to 66, wherein the monovalent targeted autophagy protein binder is capable of forming a covalent bond to the amino acid corresponding to C113 of human p62/SQSTM1 protein.

Embodiment 69. The compound of one of embodiments, 49 to 68, wherein the monovalent cellular component binder is capable of binding a protein aggregate.

Embodiment 70. The compound of one of embodiments 49 to 68, wherein the monovalent cellular component binder is capable of binding a huntingtin aggregate.

Embodiment 71. The compound of one of embodiments 49 to 68, wherein the monovalent cellular component binder is capable of binding a PolyQ huntingtin aggregate.

Embodiment 72. The compound of one of embodiments 49 to 68, wherein the monovalent cellular component binder is capable of binding an amyloid protein aggregate.

Embodiment 73. The compound of one of embodiments 49 to 68, wherein the monovalent cellular component binder is capable of binding a protein aggregate comprising a protein selected from amyloid precursor protein, beta amyloid, IAPP, alpha-synuclein, PrP, prion protein Sc, Huntingtin, calcitonin, atrial natriuretic factor, apolipoprotein A1, Serum amyloid A, medin, prolactin, transthyretin, lysozyme, beta-2 microglobulin, gelsolin, keratoepithelin, cystatin, immunoglobulin light chain AL, and S-IBM.

Embodiment 74. The compound of one of embodiments wherein the monovalent cellular component binder is a monovalent form of thioflavin or a derivative thereof.

Embodiment 75. The compound of one of embodiments 49 to 68, wherein the monovalent cellular component binder is a monovalent form of the formula:

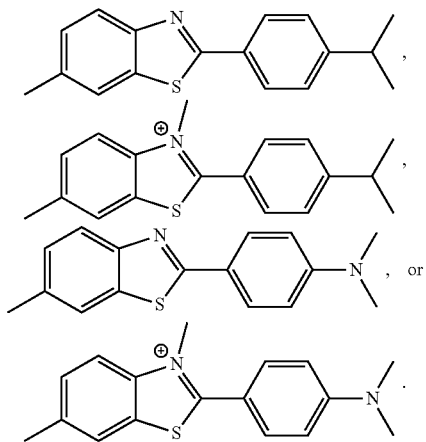

Embodiment 76. The compound of one of embodiments 49 to 68, wherein the monovalent cellular component binder is a monovalent form of the formula:

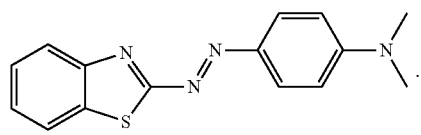 [SMILES: CN(C)c1ccc(/N=N/c2nc3ccccc3s2)cc1]

Embodiment 77. The compound of one of embodiments 49 to 68, wherein the monovalent cellular component binder has the formula:

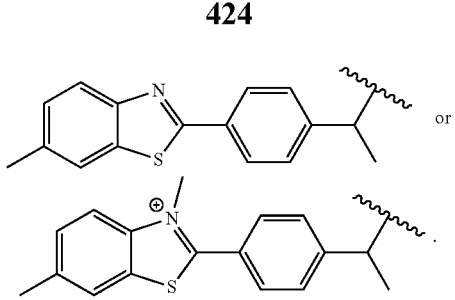

Embodiment 78. The compound of one of embodiments 49 to 68, wherein the monovalent cellular component binder has the formula:

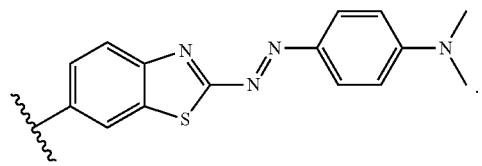 [SMILES: *c1ccc2nc(/N=N/c3ccc(N(C)C)cc3)sc2c1]

Embodiment 79. The compound of one of embodiments 49 to 78, wherein a divalent linker covalently binds said monovalent cellular component binder to said monovalent targeted autophagy protein binder.

Embodiment 80. The compound of embodiment 79, wherein the divalent linker has the formula:

$-L^1-L^2-L^3-L^4-$.

$L^1$ is connected directly to said monovalent targeted autophagy protein binder;

$L^1$ is —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^2$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^4$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 81. The compound of embodiment 49, having the formula:

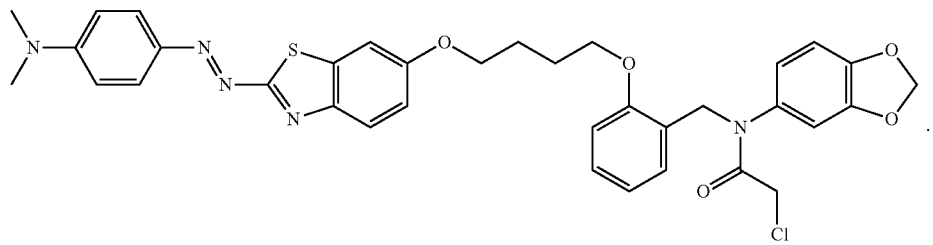 [SMILES: CN(C)c1ccc(/N=N/c2nc3ccc(OCCCCOc4ccccc4CN(C(=O)CCl)c4ccc5c(c4)OCO5)cc3s2)cc1]

Embodiment 82. An autophagy adapter protein covalently bonded to a fragment of a compound of one of embodiments 1 to 81.

Embodiment 83. The autophagy adapter protein of embodiment 82, wherein the autophagy adapter protein is LC3, p62, NBR1, NDP52, Optineurin, NUFIP1, WDFY3, RETREG1, Nix, TOLLIP, TAX1BP1, or a derivative, fragment, or homolog thereof.

Embodiment 84. A pharmaceutical composition comprising a compound of one of embodiments 1 to 81 and a pharmaceutically acceptable excipient.

Embodiment 85. A method of reducing the level of a cellular component, said method comprising contacting the cellular component with a targeted autophagy degrader.

Embodiment 86. The method of embodiment 85, wherein the targeted autophagy degrader comprises a monovalent cellular component binder and a monovalent targeted autophagy protein binder.

Embodiment 87. The method of embodiment 86, wherein the monovalent cellular component binder and monovalent targeted autophagy protein binder are covalently bonded by a linker.

Embodiment 88. The method of one of embodiments 85 to 87, wherein the cellular component is a protein.

Embodiment 89. The method of one of embodiments 85 to 87, wherein the cellular component is an organelle.

Embodiment 90. The method of one of embodiments 85 to 87, wherein the cellular component is a complex of a plurality of optionally different proteins.

Embodiment 91. The method of one of embodiments 85 to 87, wherein the cellular component is a protein aggregate.

Embodiment 92. The method of one of embodiments 85 to 87, wherein the cellular component is a macromolecule.

Embodiment 93. The method of one of embodiments 85 to 87, wherein the cellular component is an ion, lipid, nucleic acid, nucleotide, amino acid, protein, particle, organelle, cellular compartment, microorganism, vesicle, or small molecule.

Embodiment 94. The method of one of embodiments 86 to 93, wherein the monovalent targeted autophagy protein binder is a monovalent autophagy adapter protein binder.

Embodiment 95. The method of embodiment 94, wherein the monovalent autophagy adapter protein binder is capable of binding an autophagy adapter protein and the autophagy adapter protein is LC3, p62, NBR1, NDP52, Optineurin, NUFIP1, WDFY3, RETREG1, Nix, TOLLIP, TAX1BP1, or a derivative, fragment, or homolog thereof.

Embodiment 96. A method of reducing the level of a cellular component, said method comprising contacting the cellular component with a targeted autophagy degrader, wherein the targeted autophagy degrader is a compound of one of embodiments 1 to 81.

Embodiment 97. The method of one of embodiments 85 to 96, further comprising the steps:

A) Allowing formation of an autophagosome comprising a cellular component-targeted autophagy degrader-autophagy adapter protein complex;
B) Allowing the autophagosome to acidify; and
C) Allowing degradation of the cellular component.

Embodiment 98. A method of treating cancer, said method comprising contacting a cellular component associated with cancer with a targeted autophagy degrader.

Embodiment 99. A method of treating cancer, said method comprising contacting a cellular component associated with cancer with a compound of one of embodiments 1 to 81.

Embodiment 100. A method of treating cancer, said method comprising administering to a subject in need thereof a therapeutically effective amount of a compound of one of embodiments 1 to 81.

Embodiment 101. A method of treating neurodegenerative disease, said method comprising contacting a cellular component associated with the neurodegenerative disease with a targeted autophagy degrader.

Embodiment 102. A method of treating a neurodegenerative disease, said method comprising administering to a subject in need thereof a therapeutically effective amount of a compound of one of embodiments 1 to 81.

Embodiment 103. A method of treating a neurodegenerative disease, said method comprising administering to a subject in need thereof a therapeutically effective amount of a compound of one of embodiments 1 to 81.

Embodiment 104. The method of embodiment 101, wherein said neurodegenerative disease is Huntington Disease, Alzheimer Disease, or Parkinson's Disease.

Embodiment 105. A method of treating a metabolic disease, said method comprising contacting a cellular component associated with the metabolic disease with a targeted autophagy degrader.

Embodiment 106. A method of treating a metabolic disease, said method comprising contacting a cellular component associated with the metabolic disease with a compound of one of embodiments 1 to 81.

Embodiment 107. A method of treating a metabolic disease, said method comprising administering to a subject in need thereof a therapeutically effective amount of a compound of one of embodiments 1 to 81.

Embodiment 108. A method of treating an infectious disease, said method comprising contacting a cellular component associated with the infectious disease with a targeted autophagy degrader.

Embodiment 109. A method of treating an infectious disease, said method comprising contacting a cellular component associated with the infectious disease with a compound of one of embodiments 1 to 81.

Embodiment 110. A method of treating an infectious disease, said method comprising administering to a subject in need thereof a therapeutically effective amount of a compound of one of embodiments 1 to 81.

Embodiment 111. A method of treating an autoimmune disease, said method comprising contacting a cellular component associated with the autoimmune disease with a targeted autophagy degrader.

Embodiment 112. A method of treating an autoimmune disease, said method comprising contacting a cellular component associated with the autoimmune disease with a compound of one of embodiments 1 to 81.

Embodiment 113. A method of treating an autoimmune disease, said method comprising administering to a subject in need thereof a therapeutically effective amount of a compound of one of embodiments 1 to 81.

Embodiment 114. A method of treating an inflammatory disease, said method comprising contacting a cellular component associated with the inflammatory disease with a targeted autophagy degrader.

Embodiment 115. A method of treating an inflammatory disease, said method comprising contacting a cellular component associated with the inflammatory disease with a compound of one of embodiments 1 to 81.

Embodiment 116. A method of treating an inflammatory disease, said method comprising administering to a subject in need thereof a therapeutically effective amount of a compound of one of embodiments 1 to 81.

Embodiment 117. A method of reducing the level of a cellular component, said method comprising contacting a cellular component with a targeted autophagy degrader; wherein the targeted autophagy degrader comprises:
  i) a monovalent autophagy associated protein binder;
  ii) a monovalent cellular component binder; and
  iii) a covalent linker directly bonded to the monovalent autophagy associated protein binder and the monovalent cellular component binder.

Embodiment 118. The method of embodiment 117, wherein the cellular component binder is associated with a disease.

Embodiment 119. The method of embodiment 118, wherein the disease is cancer, a neurodegenerative disease, a metabolic disease, an infectious disease, an autoimmune disease, or an inflammatory disease.

Embodiment 120. The method of one of embodiments 117 to 119, wherein the monovalent autophagy associated protein binder is capable of binding an autophagy associated protein and the autophagy associated protein is an autophagy adapter protein.

Embodiment 121. The method of one of embodiments 117 to 120, wherein the cellular component is a protein, ion, lipid, nucleic acid, nucleotide, amino acid, particle, organelle, cellular compartment, microorganism, virus, vesicle, small molecule, protein complex, protein aggregate, or macromolecule.

Embodiment 122. The method of one of embodiments 117 to 121, wherein prior to the contacting, the targeted autophagy degrader is synthesized by covalently reacting a cellular component binder, a linker, and an autophagy associated protein binder to produce the targeted autophagy degrader.

Embodiment 123. The method of embodiment 122, wherein prior to the synthesizing, the autophagy associated protein binder is identified.

Embodiment 124. The method of embodiment 123, wherein the autophagy associated protein binder is identified by a method comprising the steps:
  i) mixing an autophagy associated protein with a library of candidate autophagy associated protein binders; and
  ii) identifying the candidate autophagy associated protein binders that bind to the autophagy associated protein.

Embodiment 125. The method of embodiment 124, wherein the candidate autophagy associated protein binders comprise a covalent cysteine modifier moiety and a candidate autophagy associated protein binder is identified as an autophagy associated protein binder by detection of covalent binding of the autophagy associated protein binder to the autophagy associated protein.

Embodiment 126. The method of embodiment 125, wherein the detection of covalent binding of the candidate autophagy associated protein binder to the autophagy associated protein comprises use of a detectable label or mass spectroscopic detection of the covalent binding.

Embodiment 127. The method of embodiment 122, wherein prior to the synthesizing, the cellular component binder is identified.

Embodiment 128. The method of embodiment 127, wherein the cellular component binder is identified by a method comprising the steps:
  i) mixing a cellular component protein with a library of candidate cellular component binders; and
  ii) identifying the candidate cellular component binders that bind to the cellular component.

Embodiment 129. The method of embodiment 128, wherein the candidate cellular component binders comprise a covalent cysteine modifier moiety and a candidate cellular component binder is identified as a cellular component binder by detection of covalent binding of the cellular component binder to the cellular component.

Embodiment 130. The method of embodiment 129, wherein the detection of covalent binding of the candidate cellular component binder to the cellular component comprises use of a detectable label or mass spectroscopic detection of the covalent binding.

Embodiment 131. The method of embodiment 122, wherein prior to the synthesizing, the autophagy associated protein binder is modified to remove a covalent cysteine modifier moiety.

Embodiment 132. The method of one of embodiments 85 to 131 wherein the targeted autophagy degrader is a compound of any one of embodiments 1 to 81.

IX. Examples

Example 1. Targeting Protein Autophagy

We disclose here a platform for Targeted Protein Autophagy (TPA) of specific proteins, protein aggregates or misfolded proteins, organelles, cellular compartments, or microorganisms in cells for drug discovery applications. TPA uses bifunctional small-molecule degraders that consist of one end that targets a protein of interest, a linker, and another end that recruits an autophagy adapter protein (e.g., LC3, p62, NBR1, NDP52, Optineurin, or any other protein adapter involved in autophagy) to engulf the protein cargo into an autophagosome for lysosomal degradation. This strategy can be applied for therapeutically degrading any specific protein target, protein complex, or aggregated or misfolded proteins within the cell. Furthermore, we can potentially also use this platform for targeting and lysosomally degrading organelles, such as mitochondria, lipid droplets, endoplasmic reticulum) and ribosomes through mitophagy, lipophagy, ERophagy or ribophagy, respectively. We can also use this platform for targeting proteins on microorganisms that may infect cells to target these pathogens for lysosomal degradation.

Even with the identification of many novel protein targets to treat human diseases, these potential therapy targets have remained largely untranslated, because the majority of the proteome is "undruggable" or difficult to target with small-molecules. These undruggable proteins do not possess known functional binding pockets or "druggable hotspots" that conventional small-molecules may bind to affect their function. This represents a major challenge in developing next-generation disease cures. We describe two core technologies that allow us to overcome the challenges faced by drug discovery in tackling the undruggable proteome: 1) chemoproteomics-enabled covalent ligand discovery platforms using activity-based protein profiling (ABPP); and 2) targeted protein autophagy (TAP).

Figure 1A:
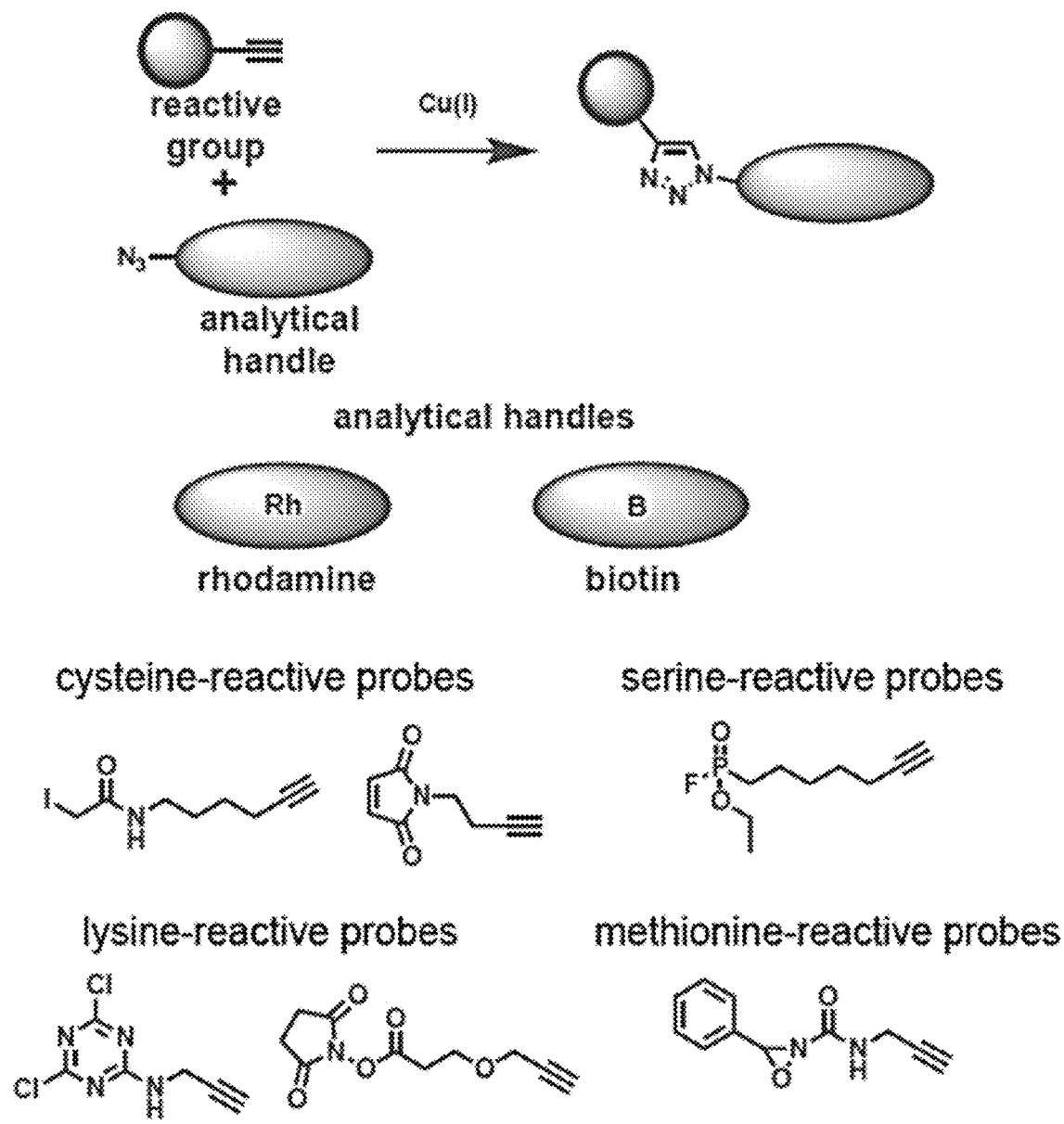
FIGS. 1A-1B. Activity-based protein profiling (ABPP) to map druggable hotspots in complex proteomes.
Figure 1B:
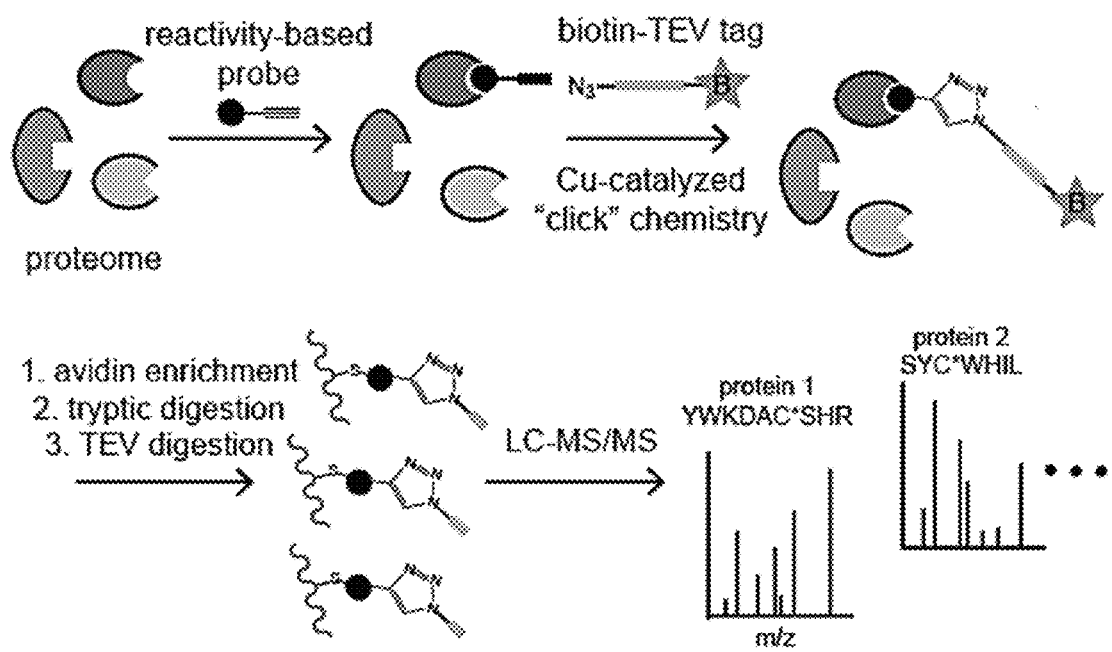
Figure 2A:
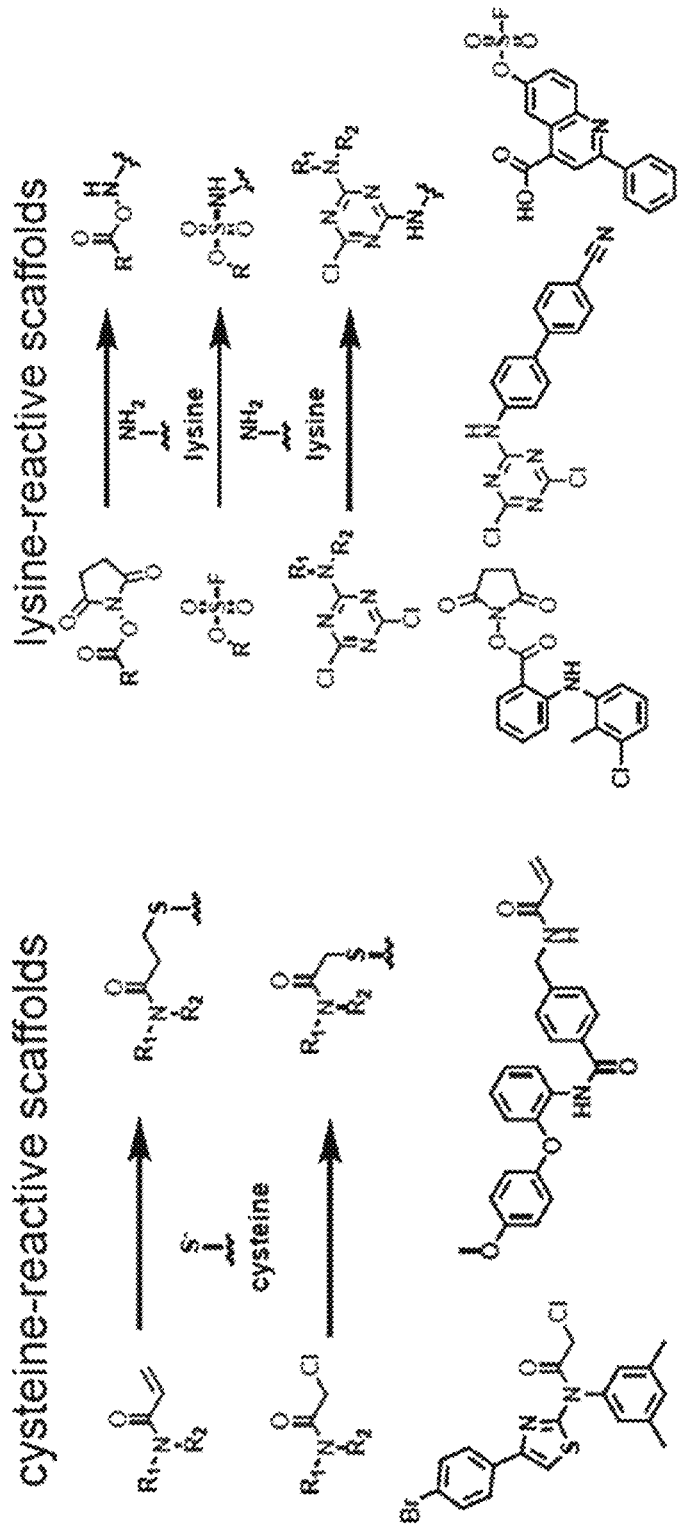
FIGS. 2A-2C. Covalent ligand screening to pharmacologically target undruggable proteins.
Figure 2B:
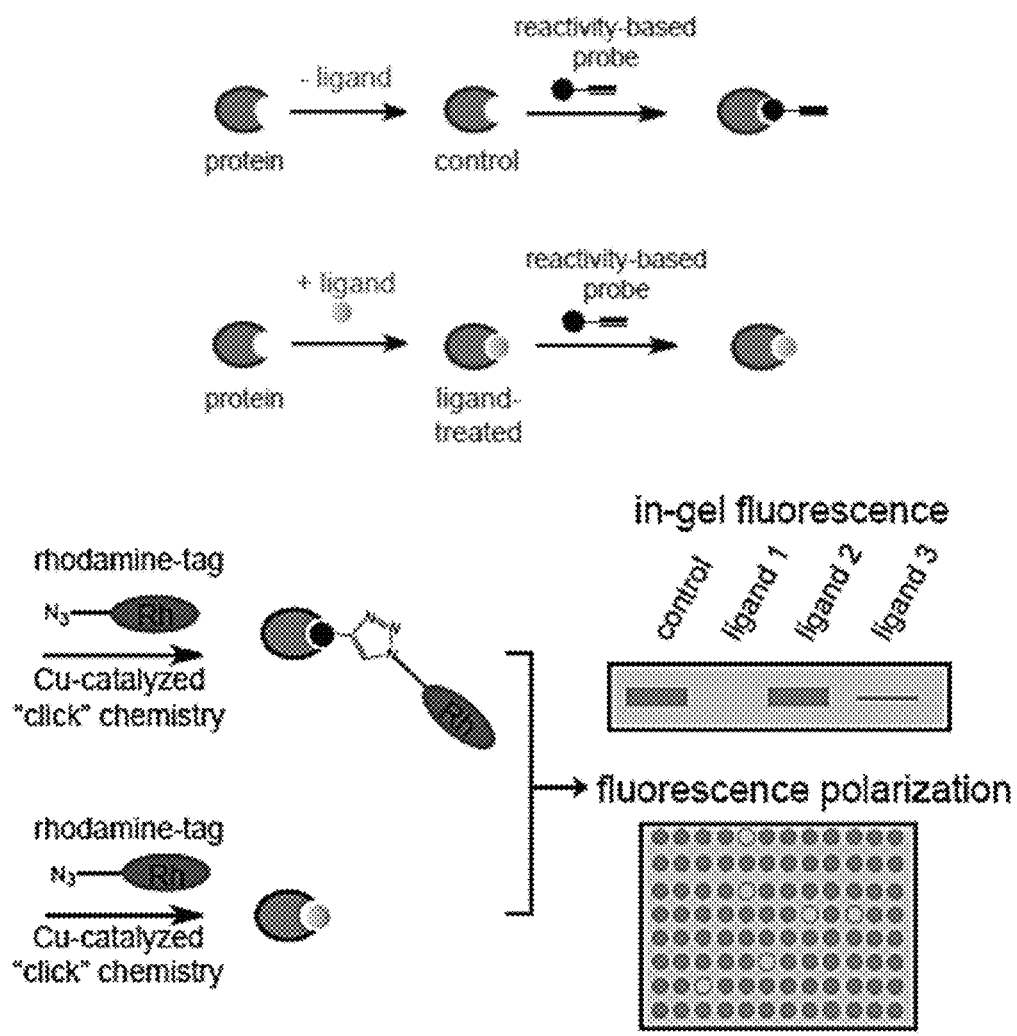
Figure 2C:
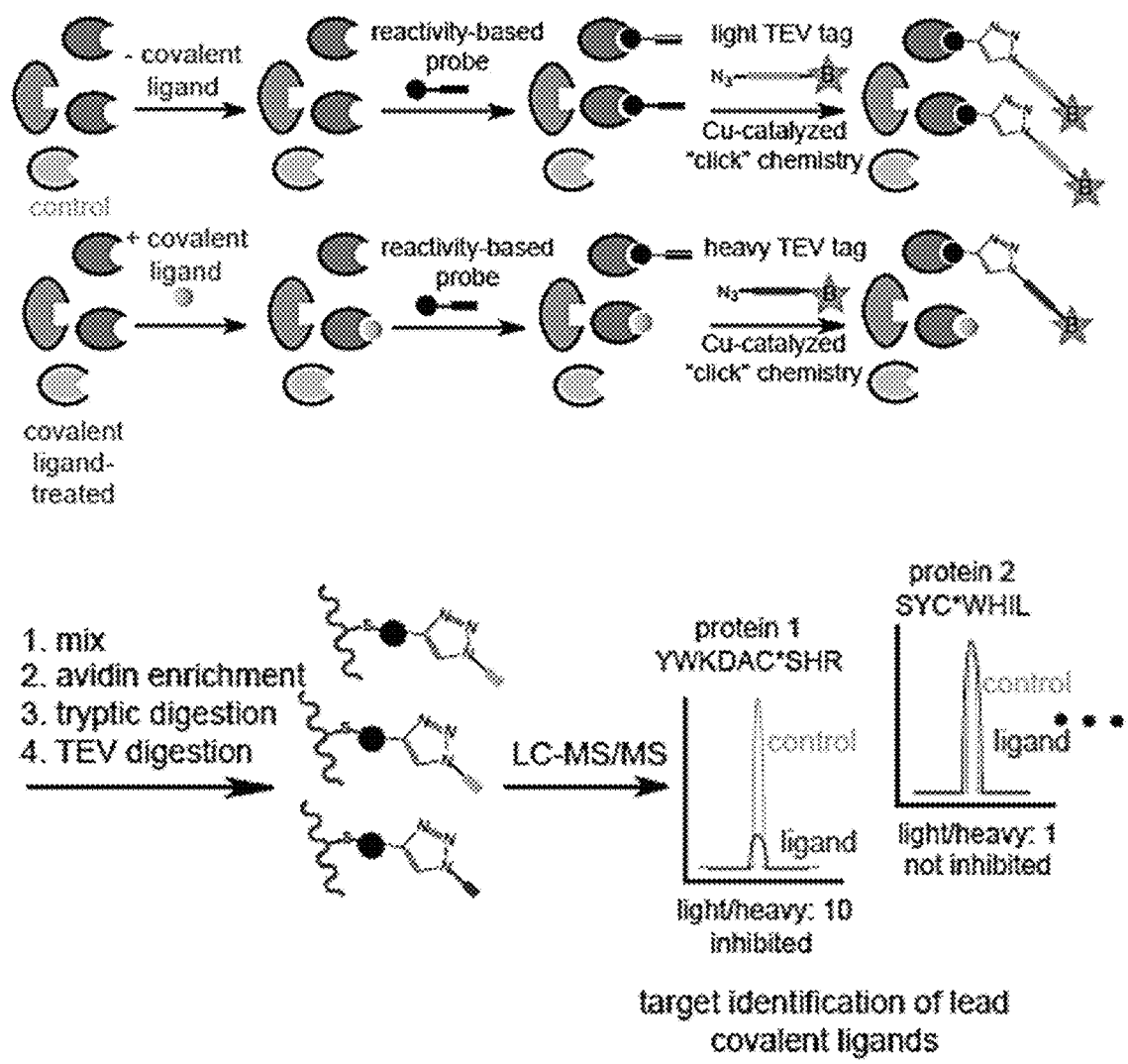
Figure 3:
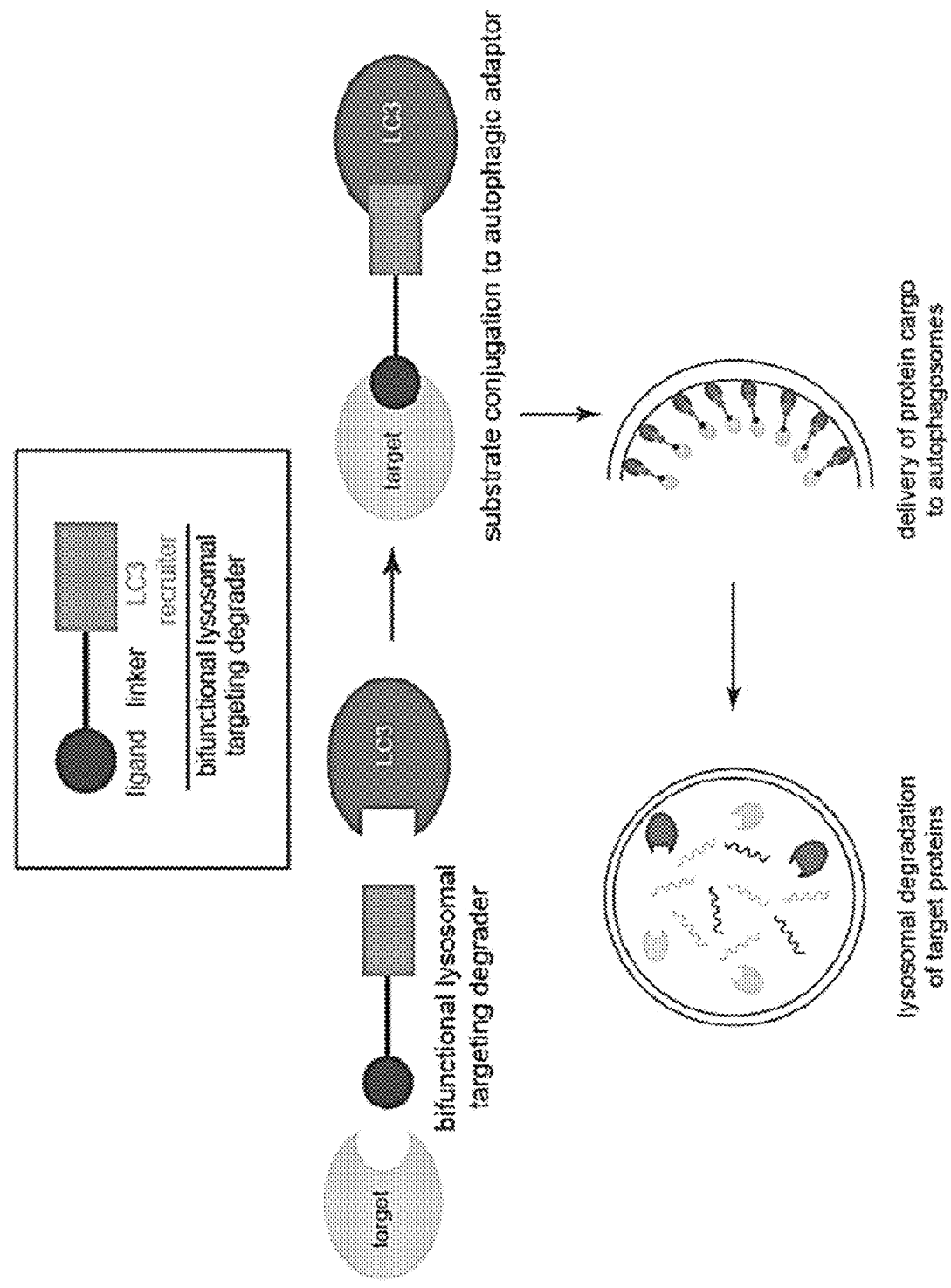
FIG. 3. Targeted Protein Autophagy. Targeted protein autophagy utilizes bifunctional targeted protein autophagy degraders that consist of a protein-targeting ligand, a linker, and a autophagy adapter recruiter to recruit autophagy adapter proteins to a target of interest to degrade the protein through autophagy and lysosomal degradation.

Activity-Based Protein Profiling (ABPP) and Covalent Ligand Discovery. A chemoproteomic technology termed isotopic tandem orthogonal proteolysis-enabled activity-based protein profiling (isoTOP-ABPP) has arisen as a powerful approach for targeting the undruggable proteome (FIGS. 1A-1B)[2-6]. The main reason "undruggable" proteins are intractable to pharmacological interrogation is because these proteins do not possess obvious small-molecule binding pockets. The isoTOP-ABPP chemoproteomic platform enables proteome-wide discovery of unique and novel small-molecule binding pockets or druggable hotspots. When coupled with interrogation of these hotspots with covalent ligands, this chemoproteomic approach enables rapid pharmacological targeting of these novel druggable hotspots. IsoTOP-ABPP uses reactivity-based chemical probes to map proteome-wide reactive, functional, and druggable hotspots directly in complex proteomes (FIGS. 1A-1B). When used in a competitive manner, covalent ligands can be competed against reactivity-based probe binding to druggable hotspots to discover pharmacological modulators against disease-relevant targets (FIGS. 2A-2C). We have developed two major assets: 1) reactivity-based probes for targeting multiple classes of amino acid reactivities and mapping proteome-wide druggable hotspots using the ABPP chemoproteomic platform; and 2) fragment-based covalent ligand libraries that can be used to pharmacologically interrogate druggable hotspots for drug discovery applications.

A frequently overlooked parameter that defines functional "hotspots" in the proteome is amino acid side-chain reactivity, which can vary by orders of magnitude for given residues depending on local protein microenvironment. Such hotspot amino acids, including Cys, Lys, Ser, are highly enriched in functional residues that are involved in catalysis, protein-protein interactions, metal binding, post-translational modification, or allosteric regulation. These druggable hotspots can be labeled with our covalently-acting cysteine-, lysine-, and serine-reactive biorthogonal probes directly in complex proteomes and coupled with cleavable enrichment handles to enrich probe-modified peptides for high-resolution quantitative proteomic analysis. There are three features to probe design and the isoTOP-ABPP technology that enable deep and broad mining of proteome-wide druggable hotspots in complex proteomes. Reactivity-based probes consist of: 1) covalently-acting chemical warheads that react with functional amino acid hotspots on proteins; 2) an alkyne for "click chemistry" conjugation of an enrichment handle to detect probe-labeled proteins and peptides; and 3) an azide functionalized TEV protease recognition peptide linker bearing an isotopically light or heavy valine and a biotin group which can be appended onto probe-labeled proteins for subsequent avidin enrichment of probe-labeled proteins, and digestion, isolation, and TEV release of probe-labeled peptides for subsequent quantitative proteomic analyses comparing isotopically light to heavy ratios of probe-modified peptides (FIGS. 1A-1B). This technology enables us to enrich tens of thousands of probe-modified tryptic peptides from complex proteomes in a quantitative manner on a proteome-wide scale. Collectively, across our reactivity-based probes targeting cysteines and lysines, we have discovered >100,000 probe-modified sites across 20,000 distinct proteins. These sites each represent ligandable hotspots that can potentially be interrogated with covalent ligands, and as such, we now have a strategy for potentially liganding nearly the entire proteome through isoTOP-ABPP and covalent ligand discovery approaches.

When used in a competitive manner, covalently-acting small-molecules can be competed against reactivity-based probe binding to reactive hotspots in complex proteomes to enable inhibitor and target discovery. To facilitate drug discovery against druggable hotspots identified by isoTOP-ABPP platforms, we have developed libraries of covalent ligands, currently targeting cysteines and lysines (FIG. 2A). These covalent ligand libraries employ the following scaffolds: 1) chloroacetamides, acrylamides, and enones for cysteines; 2) dichlotriazines, NEIS-esters, and benzoylfluorides for lysines.

We have coupled the biochemical, target-based, or phenotypic screening of fragment-based covalent ligand libraries with isoTOP-ABPP platforms to rapidly discover both new therapeutic compounds and novel druggable hotspots within undruggable proteins that can be targeted for disease therapy.

Targeted Protein Autophagy. Autophagy is central to the maintenance of organismal homeostasis in both physiological and pathological situations. It is an essential, conserved lysosomal degradation pathway that controls the quality of the cytoplasm by eliminating aggregated proteins and damaged organelles. Accordingly, alterations in autophagy have been linked to a wide range of diseases and conditions, including aging, cancer, metabolic disorders, and neurodegenerative diseases. We have developed a platform targeted protein autophagy which uses bifunctional small-molecule degraders that consist of a protein-targeting ligand, a linker, and a recruiter for autophagy adapter proteins to target specific proteins, misfolded proteins, protein aggregates, organelles, or microorganisms to autophagasomes for lysosomal degradation.

Autophagy begins with double-membraned autophagosomes which engulf portions of the cytoplasm, which is followed by fusion of these vesicles with lysososomes and degradation of the autophagic contents. This pathway is dysregulated across many human disorders, including metabolic conditions, neurodegenerative diseases, cancers, and infectious diseases. Autophagosome formation is a multistep process that includes the biogenesis of the phagophore, followed by its elongation and closure. More than 15 autophagy-related ATG proteins, as well as class III PI3 kinases, are required to construct the autophagosome, including the only transmembrane ATG protein ATG9, along with membranes from multiple sources cellular sources. The proteins ATG8 and microtubule-associated protein 1 light-chain 3 (LC3) are involved in expansion and fusion of phagophore edges, and recruit adapter proteins such as ubiquitin-binding protein p62 and NBR1 to autophagosomes via their LC3-interacting region (LIR) domains. In turn, autophagic adapters enable the selective degradation of aged or damaged cellular structures, protein aggregates, and microorganisms.

Most neurodegenerative disease are associated with intracytoplasmic deposition of aggregate-prone proteins in neurons and with mitochondrial dysfunction. Autophagy is a powerful process for removing such proteins and for maintaining mitochondrial homeostasis. Over recent years, evidence has accumulated to demonstrate that upregulation of autophagy is protective against neurodegeneration. Numerous studies have demonstrated that aggregate-prone proteins at the heart of neurodegenerative disease toxicity are autophagy substrates and that pharmacological upregulators of autophagy can be beneficial in both cell and animal models of these diseases, in which they are able to reduce both intracytoplasmic aggregates and associated cell death. Developing a strategy to specifically target aggregated proteins to autophagy and lysosomal degradation would enable clearing of toxic protein aggregates and prevent neurodegeneration.

Towards this goal, we developed a strategy to target specific proteins for degradation through the autophagy-lysosomal degradation pathway through a platform termed targeted protein autophagy. To achieve, we sought to create a bifunctional targeted protein autophagy degrader that consists of: 1) a small-molecule targeting a protein of interest; 2) a linker; and 3) a small-molecule recruiter of an autophagy adapter such as LC3, p62, NBR1, NDP52, Optineurin, or any other protein adapter involved in autophagy. Our approach harnesses the autophagy mechanism when the pathway is not necessarily dysregulated as well. That is, it is a general mechanism for addressing the elimination of any construct in the human body—biological, chemical, and other, self and foreign, naturally occurring and man-made. For example, cells infected by viruses or virus particles (infections), overproduction of cytokines (autoimmune), adipose cells (weight/fat loss), environment pollutants (endocrine, immune, nervous and reproductive system diseases), etc. Additional examples include asbestos (relevant to mesothelioma; could remove by binding directly, the fibers that they form, or alveolar macrophages) and iron (relevant to hemochromatosis; could remove directly by binding iron, hemoglobin, or red blood cells).

Figure 6:
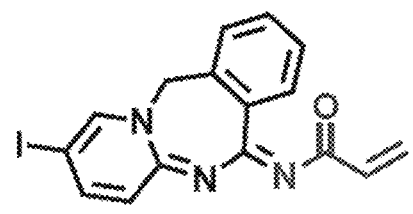
FIG. 6. Gel-based ABPP analysis of EN7 against LC3A shows EN7 targeting of C17 down to 1 microM.
Figure 6:
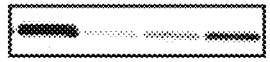
Figure 7A:
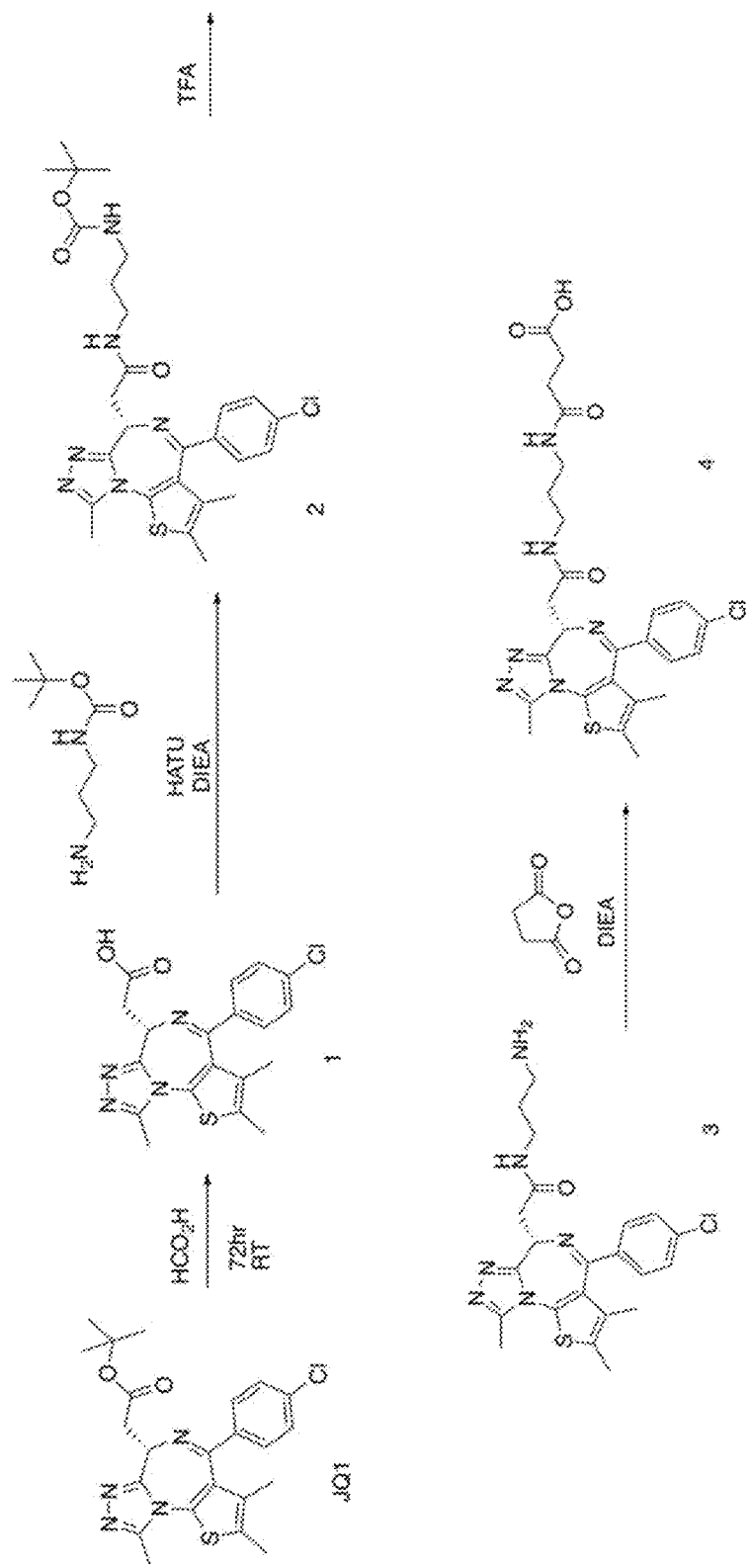
FIGS. 7A-7C. Synthesis of JQ1 targeted protein autophagy degrader for BRD4.
Figure 7B:
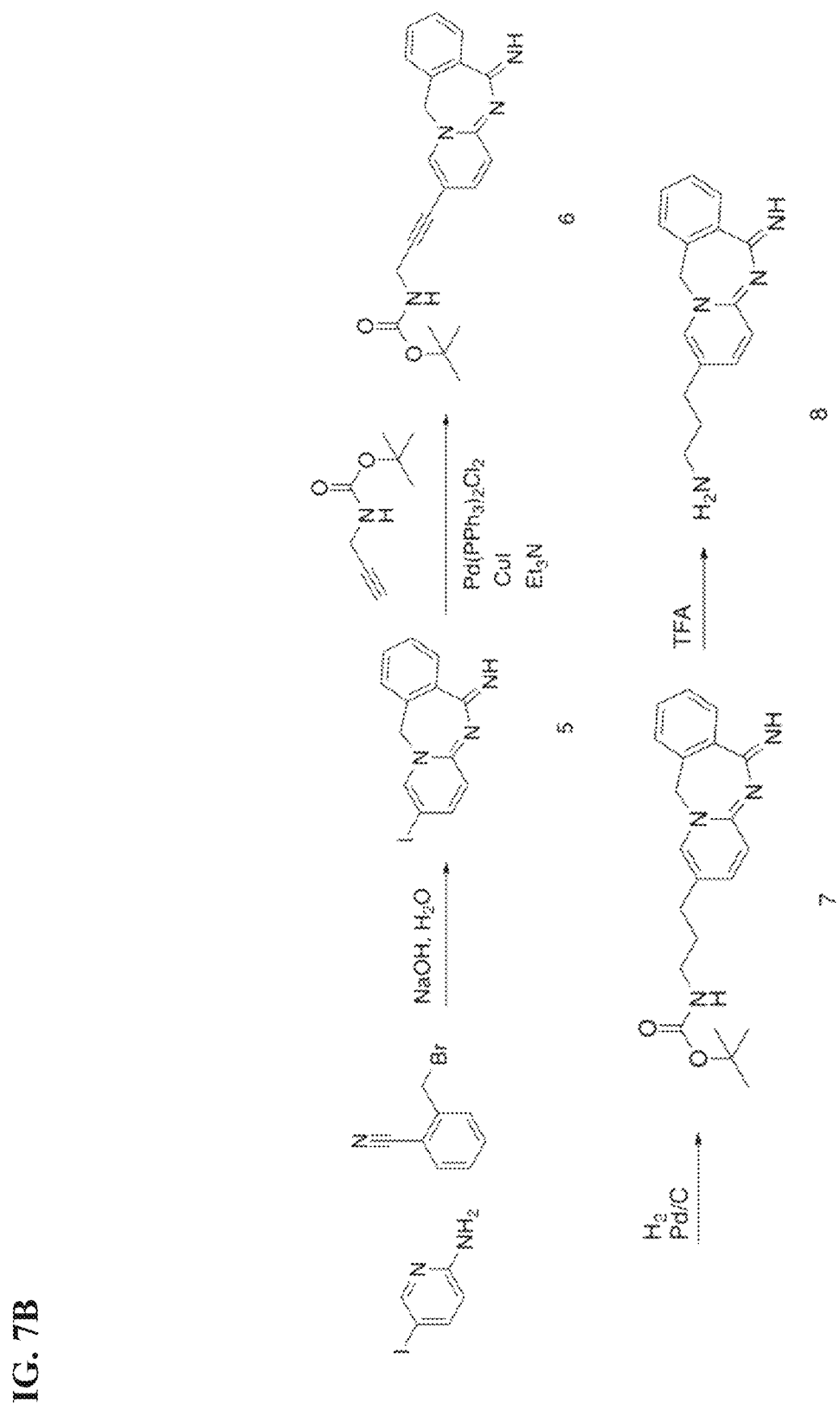
Figure 7C:
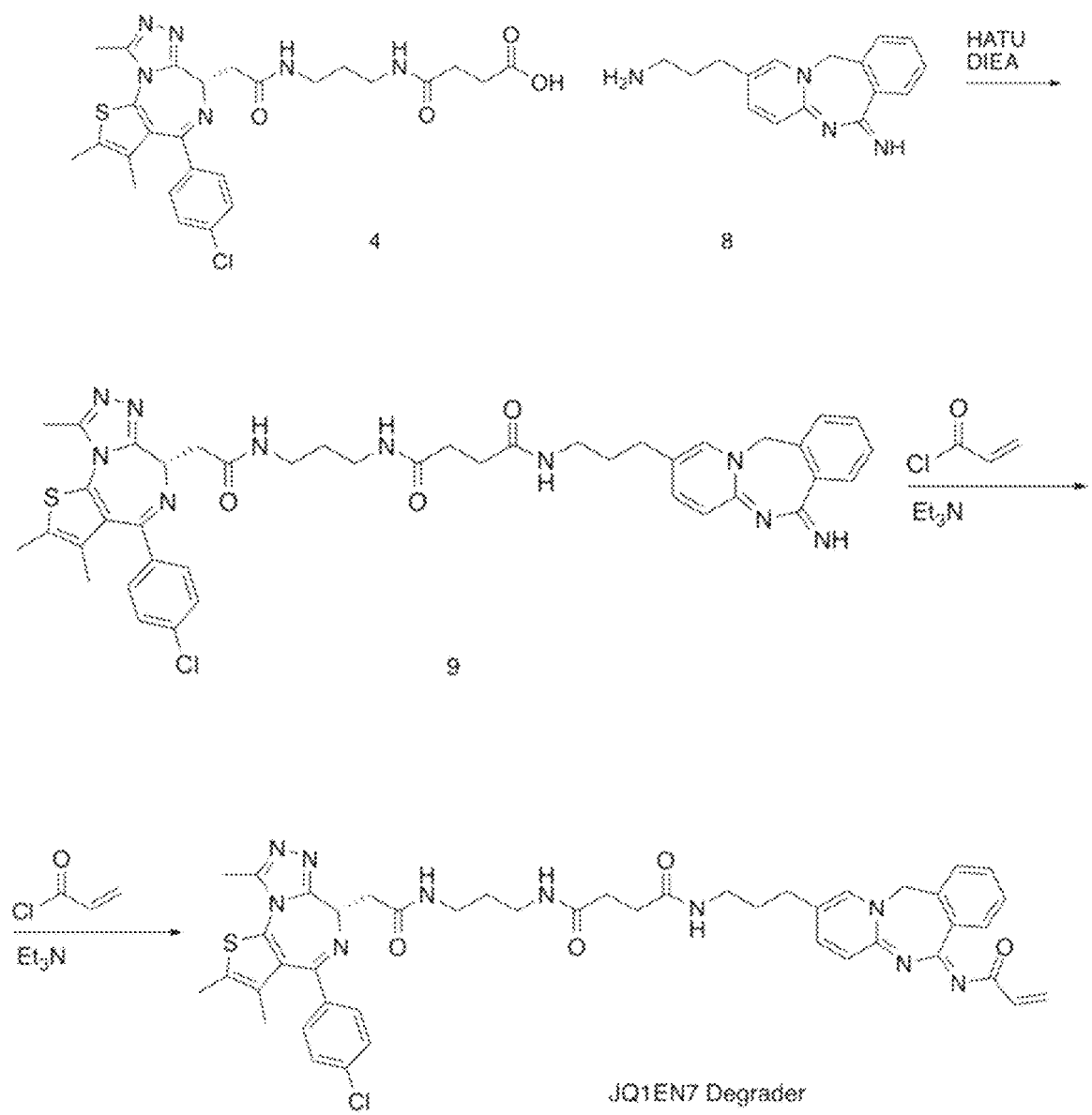
Figure 8:
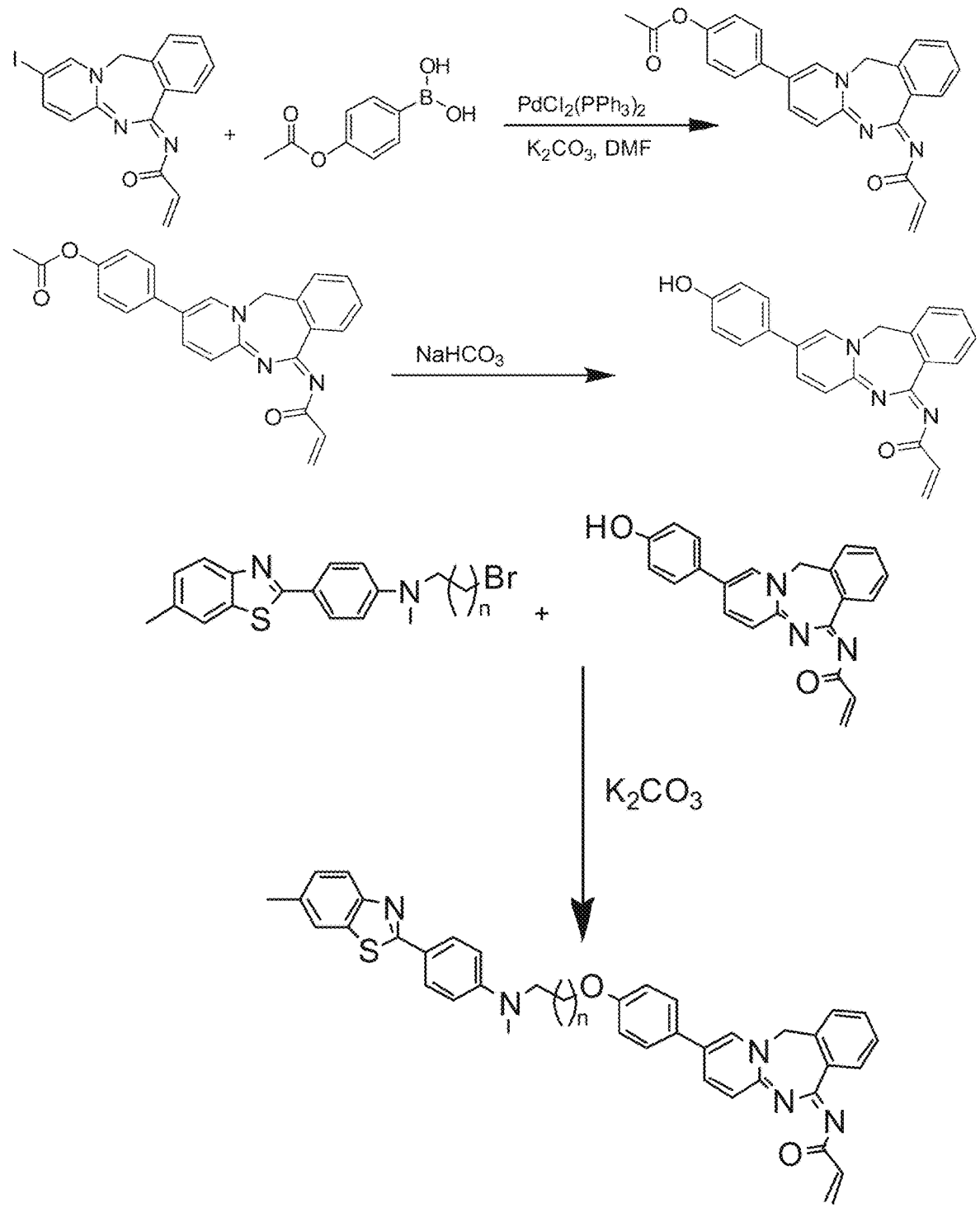
FIG. 8. Synthesis of Thioflavin T targeted protein autophagy degrader for targeted protein autophagy-mediated lysosomal degradation of neurodegenerative disease protein aggregates.
Figure 9A:
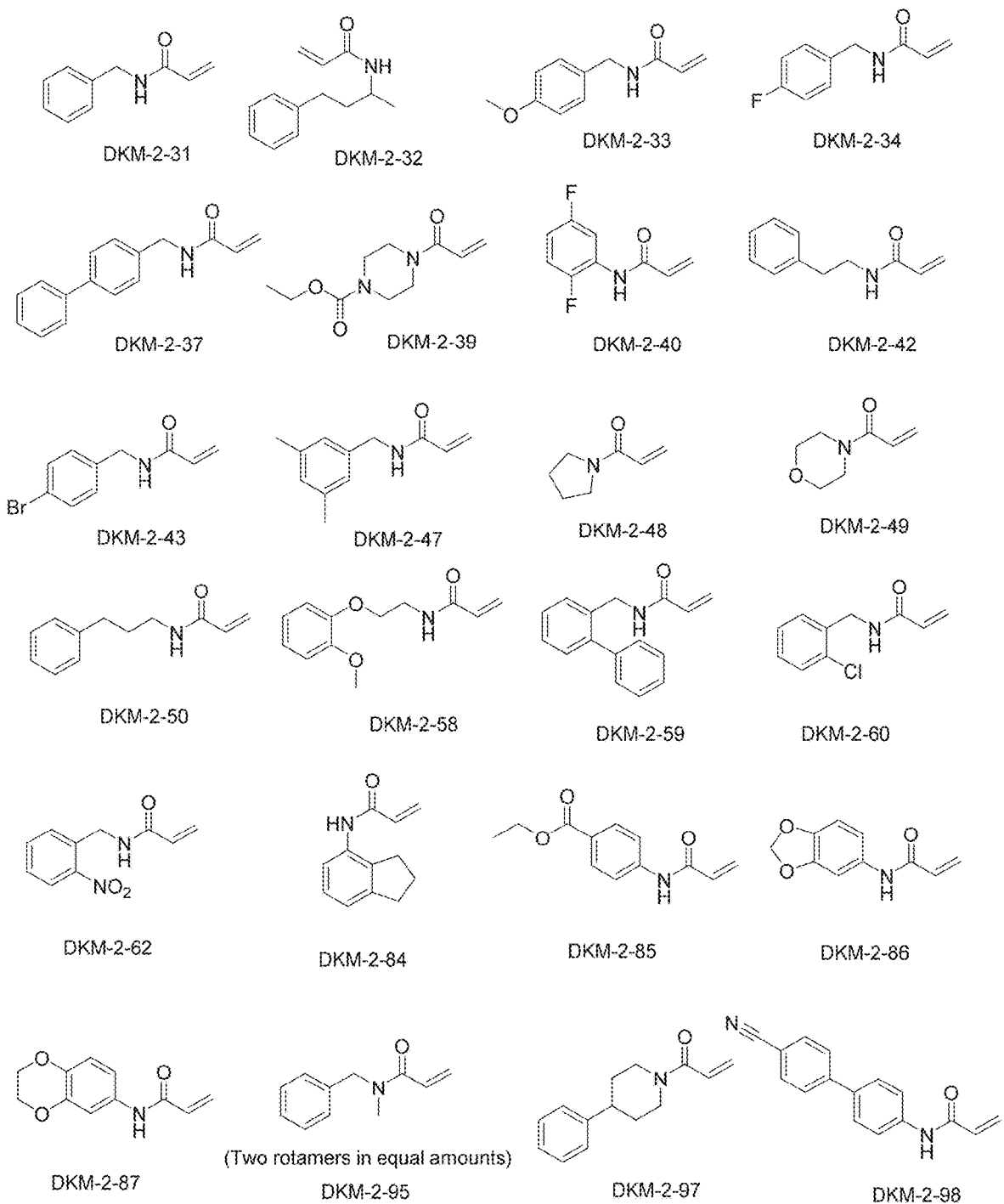
Figure 9B:
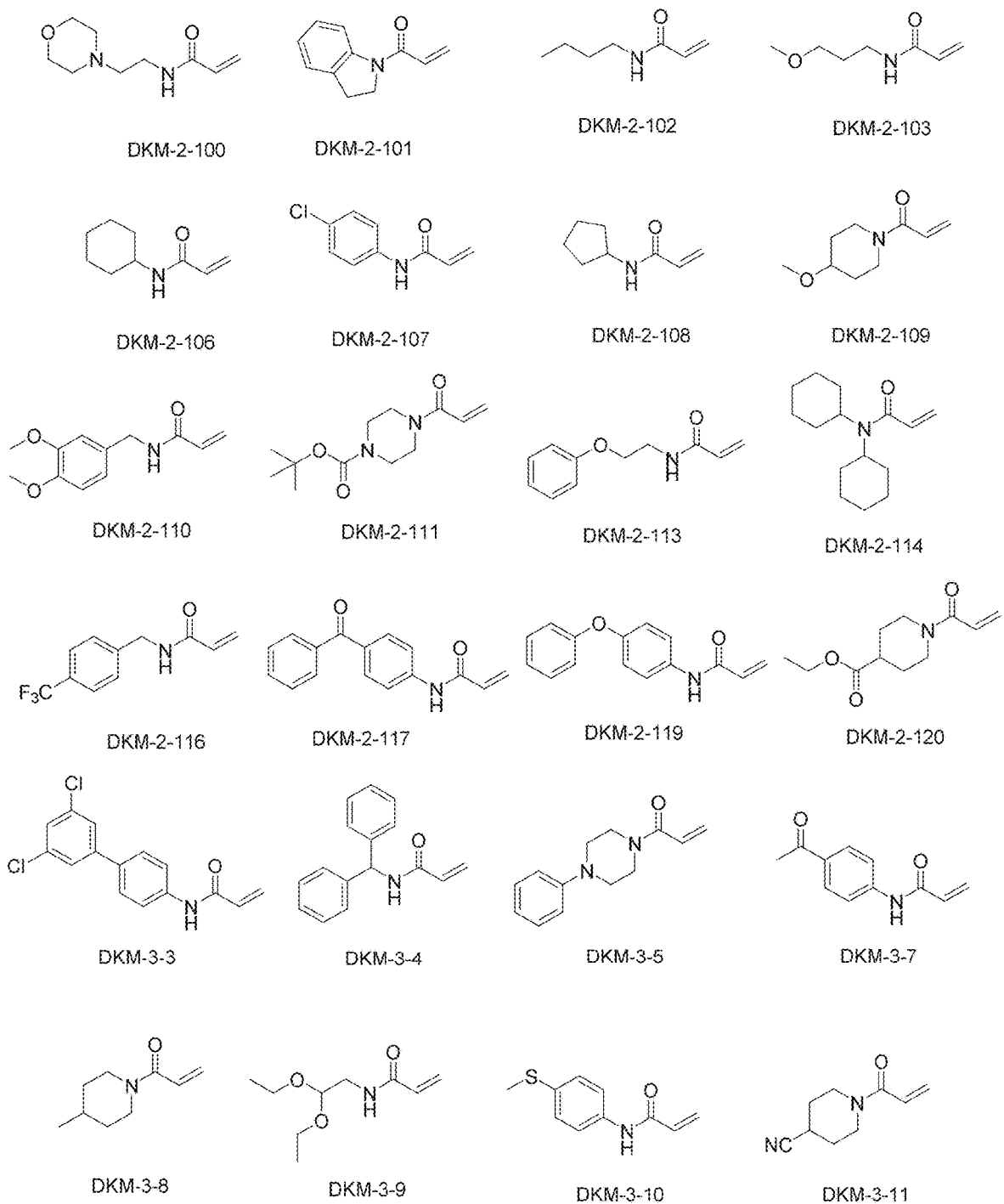
Figure 9C:
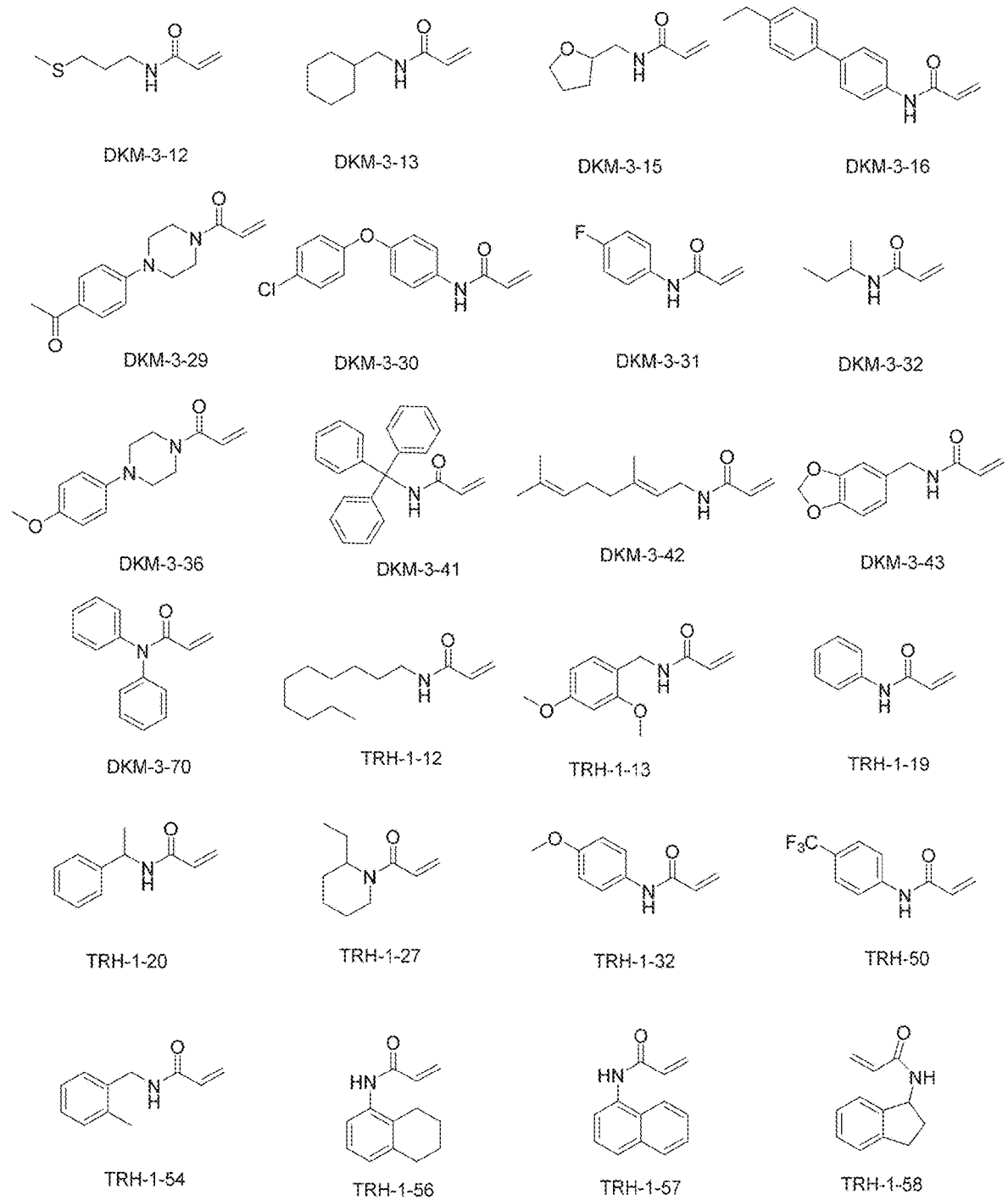
Figure 9D:
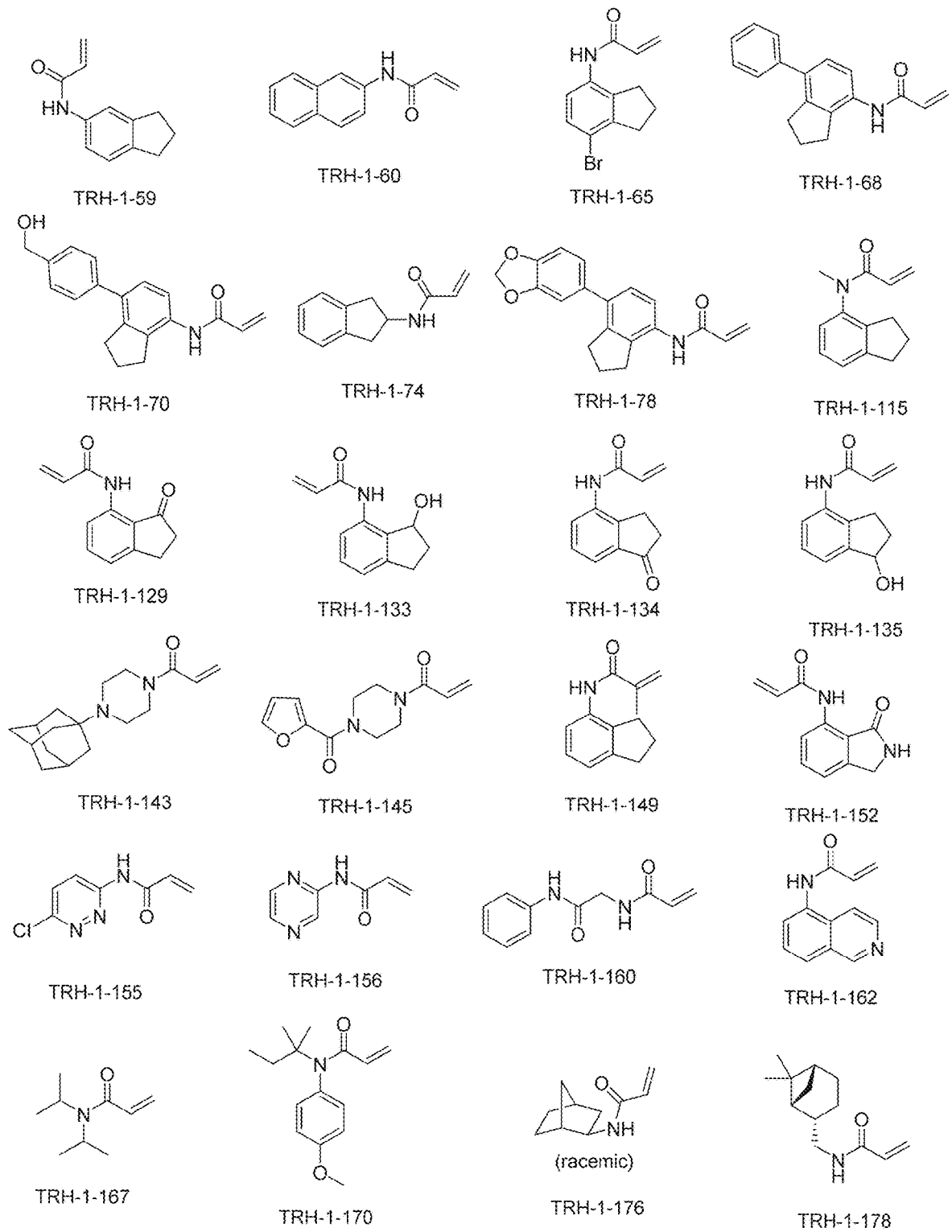
Figure 9E:
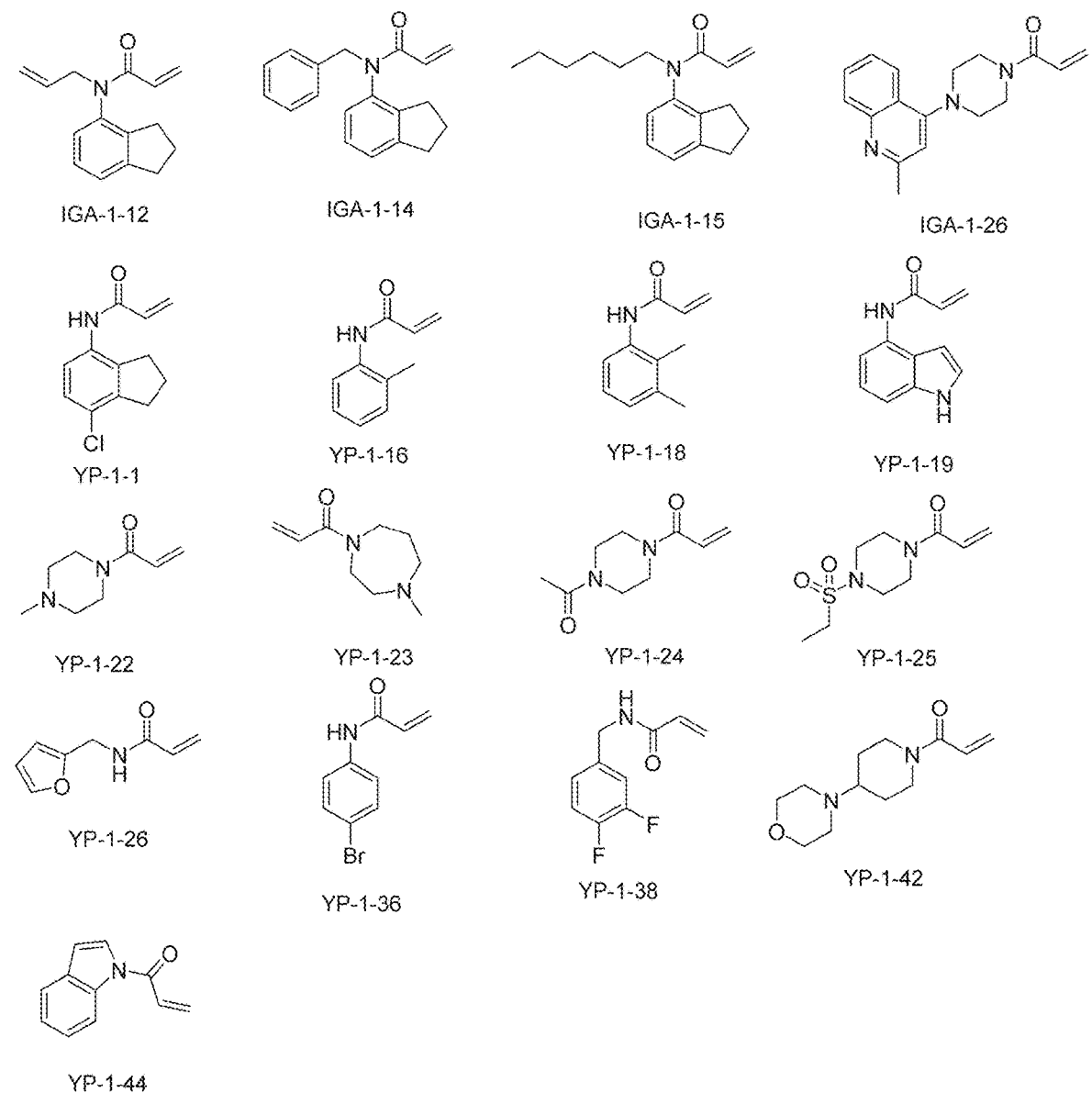
Figure 9F:
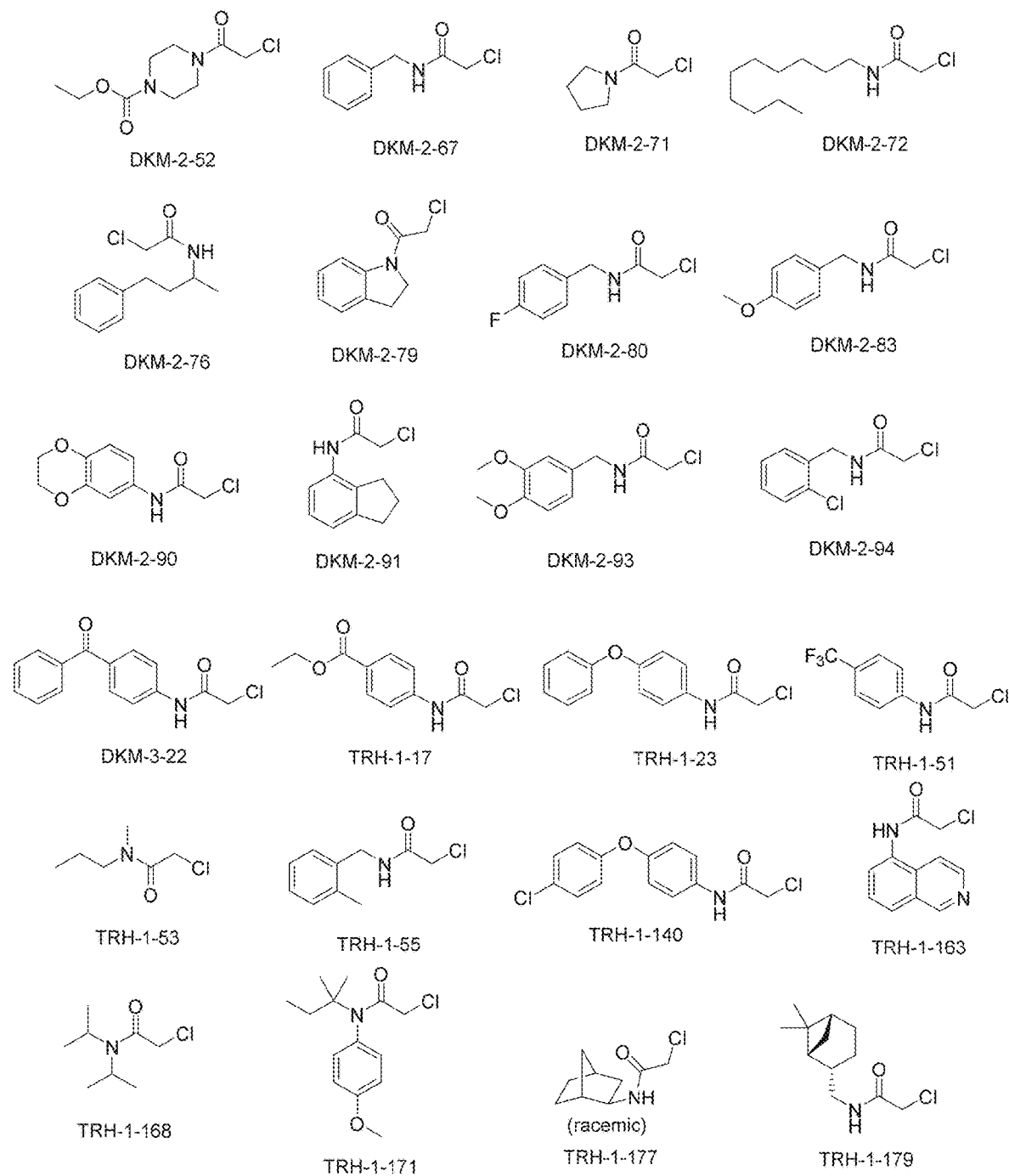
Figure 9G:
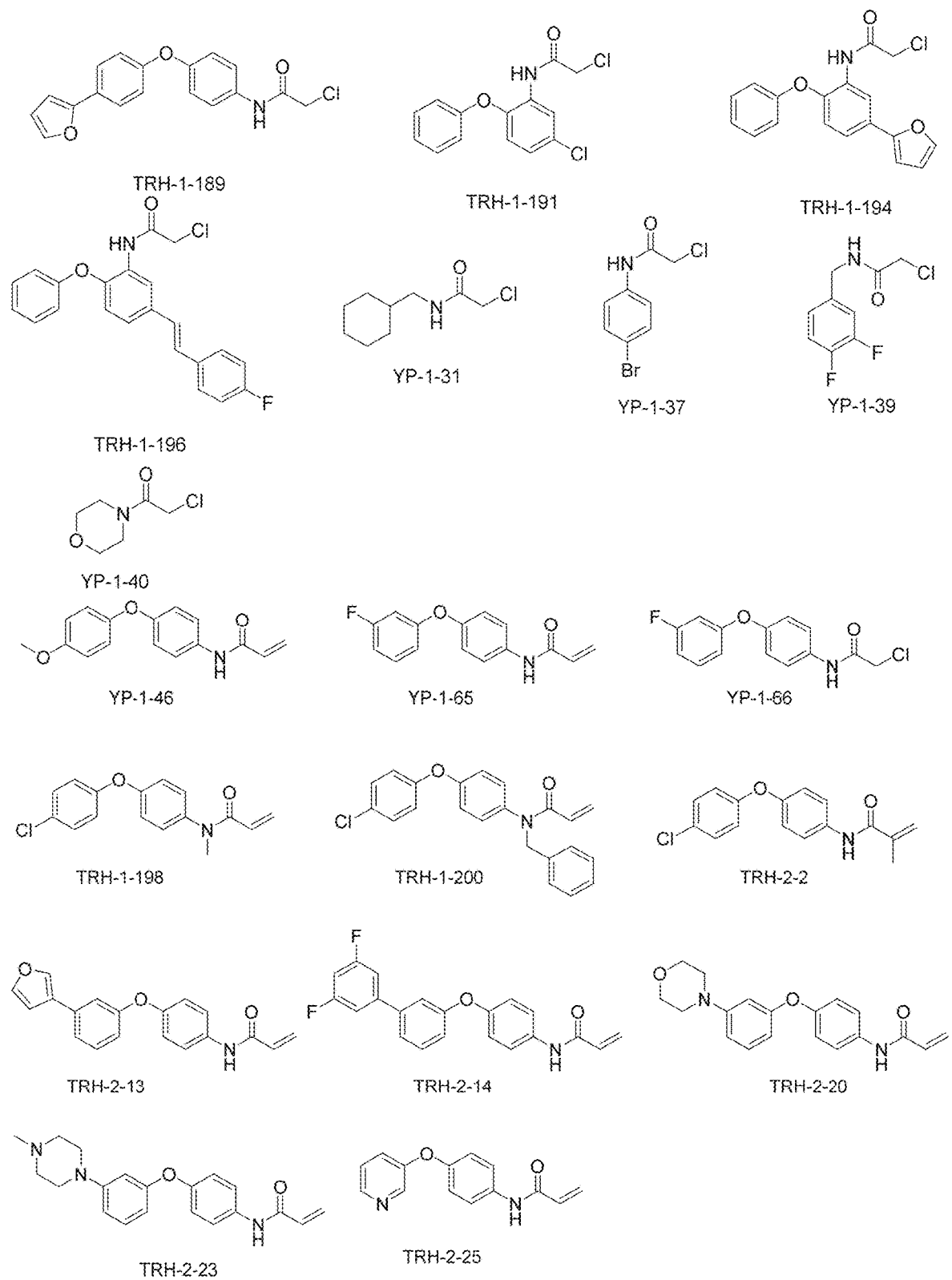

The critical part of this platform was to first develop a small-molecule recruiter for an autophagy adapter. We performed chemoproteomics-enabled covalent ligand discovery against the autophagy adapter LC3A, an important autophagy protein involved in substrate recognition, to discover an LC3A-recruiter, which can be combined with a protein targeting ligand via a linker to enable targeted protein autophagy of undruggable targets. We first showed that both our cysteine-reactive IA-alkyne as well as our lysine-reactive NHS-ester-alkyne probes labeled LC3A using gel-based ABPP methods where we incubated pure LC3A protein with our probes, followed by appending on rhodamide-azide onto the probe-labeled protein by copper-catalyzed click chemistry, SDS/PAGE, and analysis of in-gel fluorescence. While the NETS-ester probe appeared to label multiple sites on LC3A, the IA-alkyne probe apparently labeled one site, consistent with only one cysteine within LC3A-C17. Across the LC3 proteins, LC3A is the only protein that bears one cysteine. We next screened our cysteine-reactive covalent ligand library against iodoacetamide-alkyne (IA-alkyne) labeling of C17 on LC3A, and looked for hits that displaced probe-labeling resulting in loss of fluorescence by gel. Through this effort, we identified several cysteine-reactive acrylamide hits, including TRH 1-65, TRH 1-68, TRH 1-170, TRH 1-171, YP 1-44, CC 1-42, CC 1-48, EN2, EN7, EN35, and EN40 (FIGS. 5A-5D). These small-molecule recruiters or analogs of these chemical scaffolds that also bind to LC3A C17 can now be appended to linkers and protein targeting ligands to send specific protein cargo, and associated cellular contents, compartments, cells, or organelles off for targeted protein autophagy and lysososomal degradation. Among these LC3A recruiters, we have further validated and tested the potency of one of these compounds EN7 and show that this compound binds to EN7 down to 1 microM (FIG. 6). Examples of compounds that can be appended onto an autophagy adapter recruiter is JQ1, an inhibitor of bromodomain-containing BRD4 protein (an epigenetic regulator implicated in numerous human cancers). JQ1 can be appended to a linker, and an LC3A recruiter EN7 to degrade BRD4 in cells (FIGS. 7A-7C). Protein autophagy degrader can also be used to broadly recognize misfolded proteins and protein aggregates by conjugating thioflavin T, a general aggregate-protein recognizing compound, to a linker and EN7 to send these toxic protein aggregates and misfolded proteins to the autophagosome for lysosomal degradation (FIG. 8).

Furthermore, mining our pre-existing chemoproteomic data, we have identified multiple potential druggable hotspots for recruiter development for the other autophagy adapters as well. For p62/SQSTM1 (uniprot C9J6J8), C26 and C27 are sites of labeling with our IA-alkyne probe and represents potentially ligandable sites, wherein the * indicates the amino acid of interest:

```
                                          (SEQ ID NO: 5)
         RFSFC*CSPEPEAEAEAAAGPGPCERL

RFSFCC*SPEPEAEAEAAAGPGPCERL
```

For NBR1, C120 (uniprot ID B7Z5R6) is a site of labeling with our IA-alkyne probe and represents a ligandable site, wherein the * indicates the amino acid of interest:

```
                                          (SEQ ID NO: 7)
         KTPEDPAVQSFPLVPC*DTDQPQDKPPDWFTSYLETFRE
```

For NDP52 (or CALCOCO2), C321 (uniprot ID Q13137) is a site of labeling with our IA-alkyne probe and represents a ligandable site, wherein the * indicates the amino acid of interest:

```
                                          (SEQ ID NO: 9)
                  RLSENEIIC*NALQRQ
```

For OPTN, C558 in OPTN (uniprot ID Q96CV9) is a site of labeling with our IA-alkyne probe and represents a ligandable site, wherein the * indicates the amino acid of interest:

```
                                         (SEQ ID NO: 11)
               KC*GEVLPDIDTLQIHVMDCII.
```

To test the efficacy of the targeted protein autophagy degrader, we will treat cells or animal models with targeted protein autophagy degrader and then test by Western blotting or proteomics studies whether the protein expression is reduced. The dependence on autophagy can be tested by showing attenuation of the reduction in protein expression by pre-treatment of cells or an autophagy inhibitor (e.g., bafilomycin).

Example 2. Targeted Autophagy Degrader Technology (TADT)

We have performed a cysteine-reactive covalent ligand screen against the autophagy adapter protein SQSTM1 (p62) using gel-based activity-based protein profiling (ABPP) approaches. We have identified several hit compounds that targeted a cysteine on SQSTM1 (FIGS. 10A-10B). Among these hits, we found that EN96 was the most potent covalent ligand against SQSTM1. To test whether we can use this potential SQSTM1 recruiter EN96 in a TADT platform, we synthesized BMF-1-64, which links EN96 to a BRD4 inhibitor JQ1, to determine whether we could degrade BRD4 in a proteasome-independent manner (FIG. 11). We confirm that BMF-1-64 still interacts with SQSTM1 and shows even better potency against SQSTM1 with an $IC_{50}$ of 0.42 microM (FIG. 12). We show that treatment of U2OS cells with BMF-1-64 leads to the degradation of BRD4 and that this treatment is not prevented with pre-treatment of these cells with a proteasome inhibitor bortezomib (BTZ) (FIG. 13). We also show that this BMF-1-64-mediated degradation of BRD4 is dose- and time-dependent (FIG. 13). We believe that the lesser degradation observed at the higher 5 microM concentration of BMF-1-64 is likely due to the "hook effect" observed with other types of E3 ligase-dependent degraders, or non-productive interactions of the bifunctional degrader with either SQSTM1 bound but not BRD4 or vice versa.

Thus, we show initial proof-of-concept that a SQSTM1-targeting covalent ligand EN96 can be linked to a protein-targeting ligand to degrade a protein target in a proteasome-independent and likely autophagy-dependent manner.

Example 3. Thioflavin T-Derivative Linked to EN96 p62/SQSTM1 Ligand

To determine whether the targeted autophagy degradation technology (TADT) could also be used to degrade protein aggregates, we synthesized a degrader BMF-1-141 linking the p62/SQSTM1 recruiter EN96 to a thioflavin T derivative that recognizes protein aggregates such as amyloid and polyQ-Huntingtin (HTT) (FIG. 15). We then treated this degrader in a U2OS cell line model in which we could induce the expression of HTT fused to a polyQ-HTT protein, which leads to the generation of HTT protein aggregates (Bersuker et al 2016). We show significant reduction in polyQ-HTT protein levels from treatment of these cells with BMF-1-141 (FIG. 16). These results show potential proof-of-concept that the TADT technology could be used to degrade protein aggregates.

BMF-1-141: $^{1}$H NMR (400 MHz, $CDCl_3$) δ 7.96 (d, J=16.7 Hz, 2H), 7.94 (d, J=8.7 Hz, 1H), 7.30 (d, J=7.7 Hz, 1H), 7.23 (d, J=7.7 Hz, 1H), 7.05 (dd, J=8.9, 2.5 Hz, 1H), 6.88 (t, J=7.4 Hz, 2H), 6.78 (t, J=8.8 Hz, 3H),), 6.69 (d, J=8.0 Hz, 1H), 6.54-6.45 (m, 2H), 5.94 (s, 2H), 4.94 (s, 2H), 4.13-4.02 (m, 2H), 3.90 (q, J=4.1, 2.7 Hz, 4H), 3.16 (s, 6H), 1.94-1.79 (m, 4H).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

1. Tomoshige, S., Nomura, S., Ohgane, K., Hashimoto, Y., Ishikawa, M. (2017) Discovery of Small Molecules that Induce the Degradation of Huntingtin. Angew. Chem. Int. Ed. 56, 11530-11533. 2. Tomoshige, S., Nomura, S., Ohgane, K., Hashimoto, Y., Ishikawa, M. (2018) Degradation of huntingtin mediated by a hybrid molecule composed of IAP antagonist linked to phenyldiazenyl benzothioazole derivative. Bioorg. Med. Chem. Lett. 28, 707-710. 3. Bersuker K, Brandeis M, Kopito R R (2016) Protein misfolding specifies recruitment to cytoplasmic inclusion bodies. The Journal of Cell Biology 213, 229-241.

---

What is claimed is:

1. A compound comprising a monovalent cellular component binder covalently bound to a monovalent targeted autophagy adapter protein binder,
wherein the monovalent targeted autophagy adapter protein binder binds LC3, p62, NBR1, NDP52, Optineurin, NUFIP1, WDFY3, RETREG1, Nix, TOLLIP, TAX1BP1, or a homolog, isoform, or functional fragment thereof; and
wherein the monovalent targeted autophagy adapter protein binder is a small molecule of molecular weight equal to or less than 900 Daltons.

2. The compound of claim 1, wherein a divalent linker binds said monovalent cellular component binder to said monovalent targeted autophagy adapter protein binder.

3. The compound of claim 1, wherein the cellular component is a protein, ion, lipid, nucleic acid, nucleotide, amino acid, particle, organelle, cellular compartment, microorganism, virus, lipid droplet, vesicle, small molecule, protein complex, protein aggregate, or macromolecule.

4. The compound of claim 1, wherein the cellular component is associated with a disease.

5. The compound of claim 4, wherein the disease is cancer, a neurodegenerative disease, a metabolic disease, an infectious disease, an autoimmune disease, or an inflammatory disease.

6. The compound of claim 2, wherein the divalent linker has the formula:

-L$^1$-L$^2$-L$^3$-L$^4$-;

L$^1$ is connected directly to said monovalent targeted autophagy adapter protein binder;
L$^1$ is —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
L$^2$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
L$^3$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and
L$^4$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

7. The compound of claim 1, wherein the targeted autophagy adapter protein binder is capable of contacting an amino acid corresponding to C17 of human LC3A protein.

8. The compound of claim 1, wherein the targeted autophagy adapter protein binder is capable of contacting an amino acid corresponding to C26 of human p62/SQSTM1 protein.

9. The compound of claim 1, wherein the targeted autophagy adapter protein binder is capable of contacting an amino acid corresponding to C27 of human p62/SQSTM1protein.

10. The compound of claim 1, wherein the targeted autophagy adapter protein binder is capable of contacting an amino acid corresponding to C113 of human p62/SQSTM1protein.

11. The compound of claim 1, wherein the targeted autophagy adapter protein binder is capable of contacting an amino acid corresponding to C120 of human NBR1 protein.

12. The compound of claim 1, wherein the targeted autophagy adapter protein binder is capable of contacting an amino acid corresponding to C321 of human NDP52/CALCOCO2 protein.

13. The compound of claim 1, wherein the targeted autophagy adapter protein binder is capable of contacting an amino acid corresponding to C558 of human OPTN protein.

14. The compound of claim 10, wherein the targeted autophagy adapter protein binder is capable of forming a covalent bond to the cysteine.

15. A compound comprising a monovalent cellular component binder covalently bound to a monovalent targeted autophagy protein binder, wherein the monovalent targeted autophagy protein binder is a monovalent form of the formula:

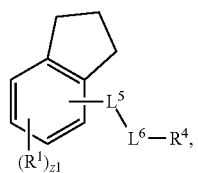

(I)

wherein z1 is an integer from 0 to 9;

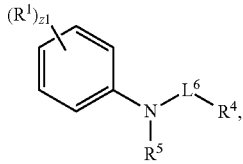
(II)

wherein z1 is an integer from 0 to 5;

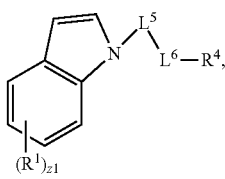
(III)

wherein z1 is an integer from 0 to 6;

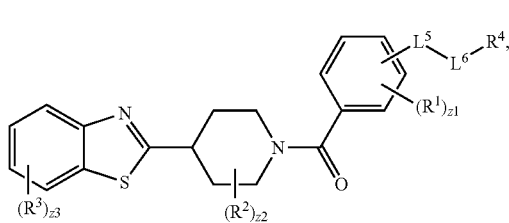
(IV)

wherein z1 is an integer from 0 to 4, z2 is an integer from 0 to 8, and z3 is an integer from 0 to 4;

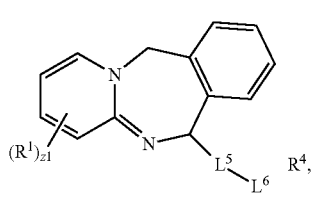
(V)

wherein z1 is an integer from 0 to 11;

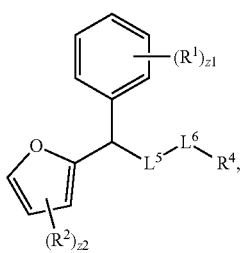
(VI)

wherein z1 is an integer from 0 to 5 and z2 is an integer from 0 to 3;

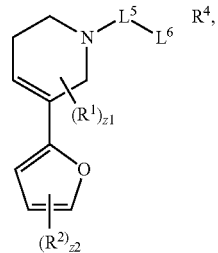
(VII)

wherein z1 is an integer from 0 to 7 and z2 is an integer from 0 to 3;

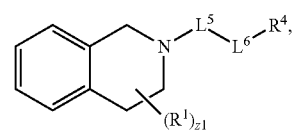
(VIII)

wherein z1 is an integer from 0 to 10;

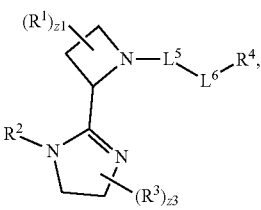
(IX)

wherein z1 is an integer from 0 to 5 and z3 is an integer from 0 to 4;

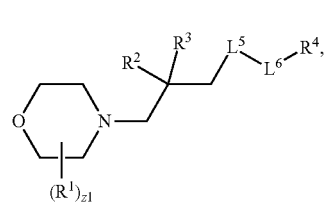
(X)

wherein z1 is an integer from 0 to 8;

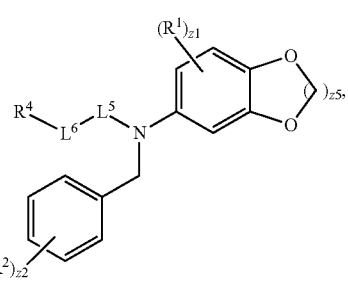
(XI)

wherein z1 is an integer from 0 to 7, z2 is an integer from 0 to 5, and z5 is 1 or 2;

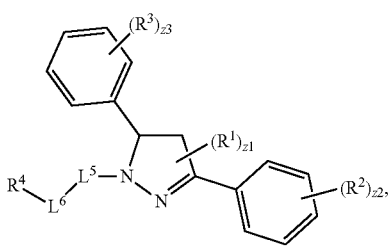
(XII)

wherein z1 is an integer from 0 to 2, z2 is an integer from 0 to 5, and z3 is an integer from 0 to 5;

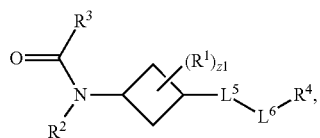
(XIII)

wherein z1 is an integer from 0 to 6;

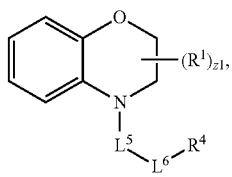
(XIV)

wherein z1 is an integer from 0 to 6;

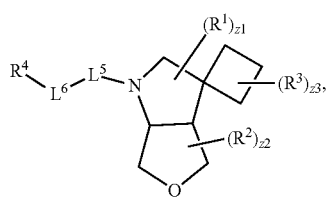
(XV)

wherein z1 is an integer from 0 to 4, z2 is an integer from 0 to 6, and z3 is an integer from 0 to 6;

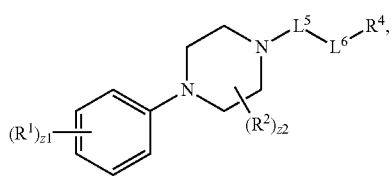
(XVI)

wherein z1 is an integer from 0 to 5 and z2 is an integer from 0 to 8; or

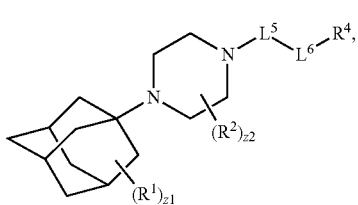
(XVII)

wherein z1 is an integer from 0 to 15 and z2 is an integer from 0 to 8;

$R^1$ is independently oxo, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, $SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, $SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^3$ is independently oxo, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, $SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^3D$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^3$ substituents may optionally be joined to form a substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, $SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

$L^5$ is a bond, —S(O)$_2$—, —S(O)—, —NR$^5$—, =N—, —O—, —S—, —C(O)—, —C(O)NR$^5$—, —NR$^5$C(O)—, —NR$^5$C(O)NH—, —NHC(O)NR$^5$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^5$ is hydrogen, —CX$^5_3$, —CHX$^5_2$, —CH$_2$X$^5$, —OCX$^5_3$, —OCH$_2$X$^5$, —OCHX$^5_2$, —CN, —C(O)R$^{5C}$, —C(O)—OR$^{5C}$, —C(O)NR$^{5A}$R$^{5B}$, —OR$^{5D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^6$ is a bond, —S(O)$_2$—, —S(O)—, —NR$^6$—, =N—, —O—, —S—, —C(O)—, —C(O)NR$^6$—, —NR$^6$C(O)—, —NR$^6$C(O)NH—, —NHC(O)NR$^6$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^6$ is hydrogen, —CX$^6_3$, —CHX$^6_2$, —CH$_2$X$^6$, —OCX$^6_3$, —OCH$_2$X$^6$, —OCHX$^6_2$, —CN, —C(O)R$^{6C}$, —C(O)—OR$^{6C}$, —C(O)NR$^{6A}$R$^{6B}$, —OR$^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, and $R^{6D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl;

X, $X^1$, $X^2$, $X^3$, $X^4$, $X^5$, and $X^6$ are independently —F, —Cl, —Br, or —I;

n1, n2, n3, n4, n5, and n6 are independently an integer from 0 to 4; and m1, m2, m3, m4, m5, m6, v1, v2, v3, v4, v5, and v6 are independently 1 or 2.

16. The compound of claim 15, wherein the monovalent targeted autophagy protein binder is a monovalent form of the formula:

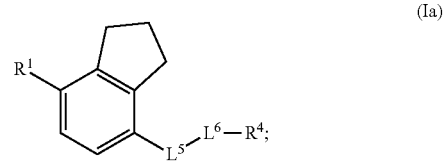

(Ia)

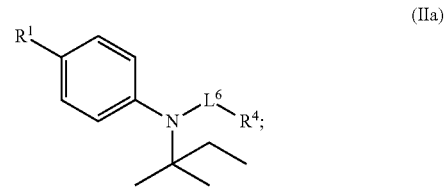

(IIa)

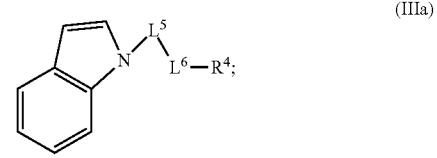

(IIIa)

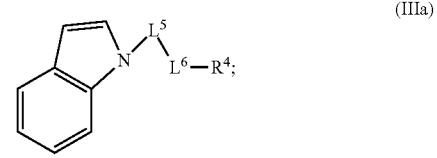

(IIIb)

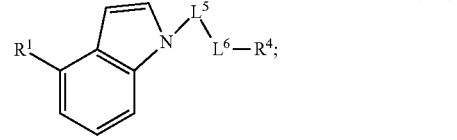

(IVa)

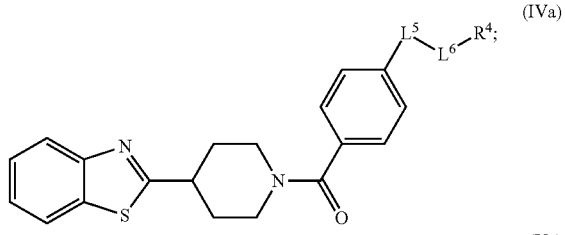

(Va)

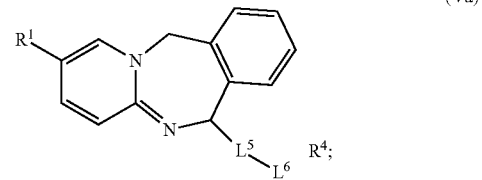

(VIa)

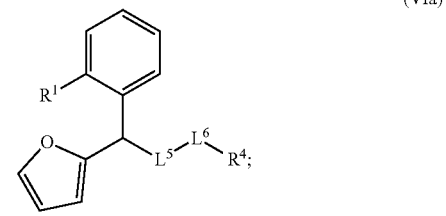

-continued
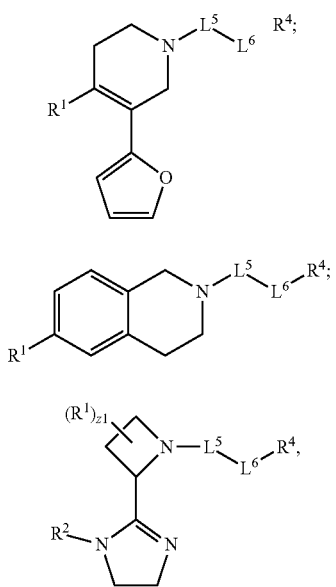
(VIIa)
(VIIIa)
(IXa)
wherein z1 is an integer from 0 to 5;
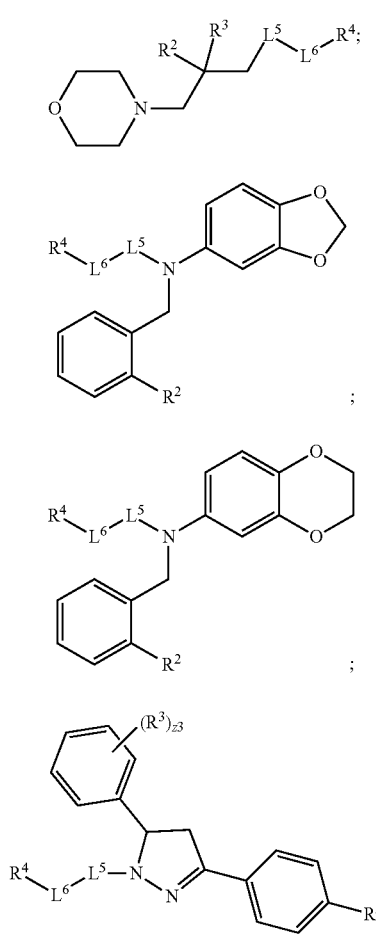
(Xa)
(XIa)
(XIb)
(XIIa)
(XIIa), wherein z3 is 2;
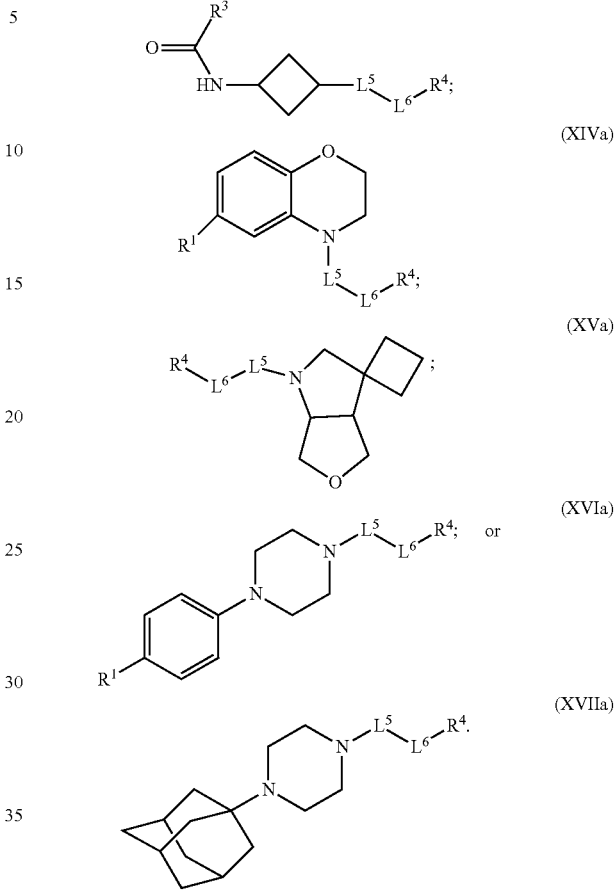
(XIIIa)
(XIVa)
(XVa)
(XVIa)
(XVIIa)
17. The compound of claim 15, wherein the monovalent targeted autophagy protein binder is a monovalent form of the formula:
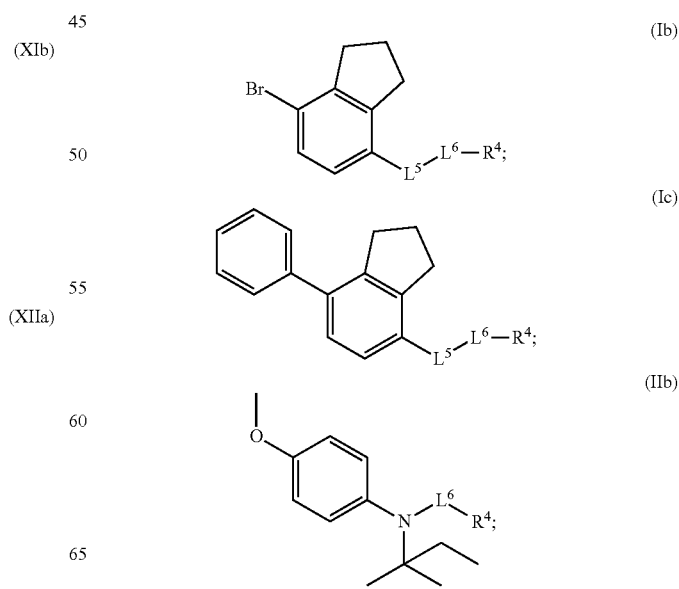
(Ib)
(Ic)
(IIb)

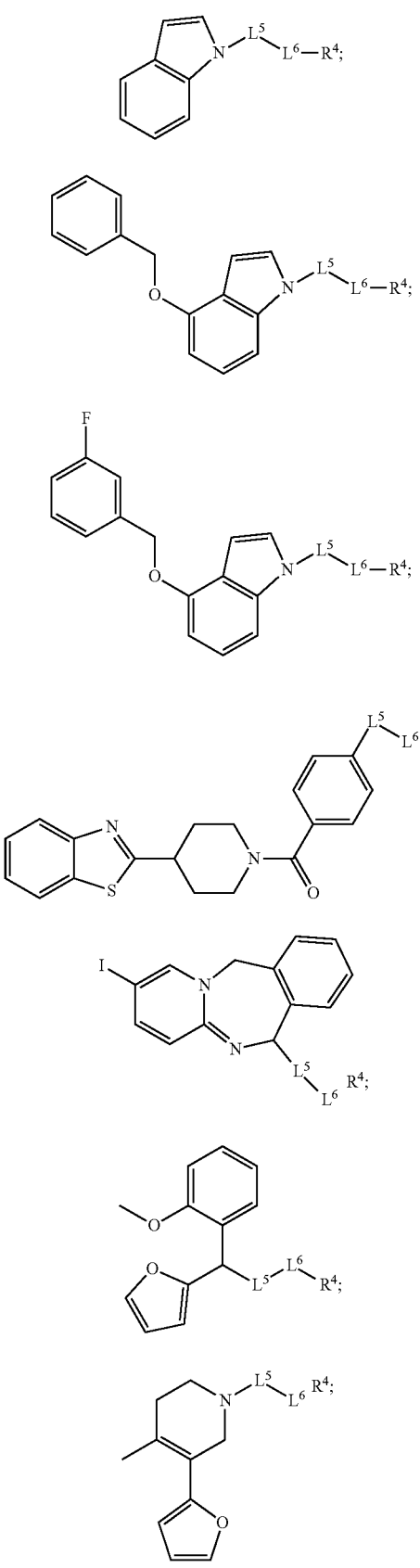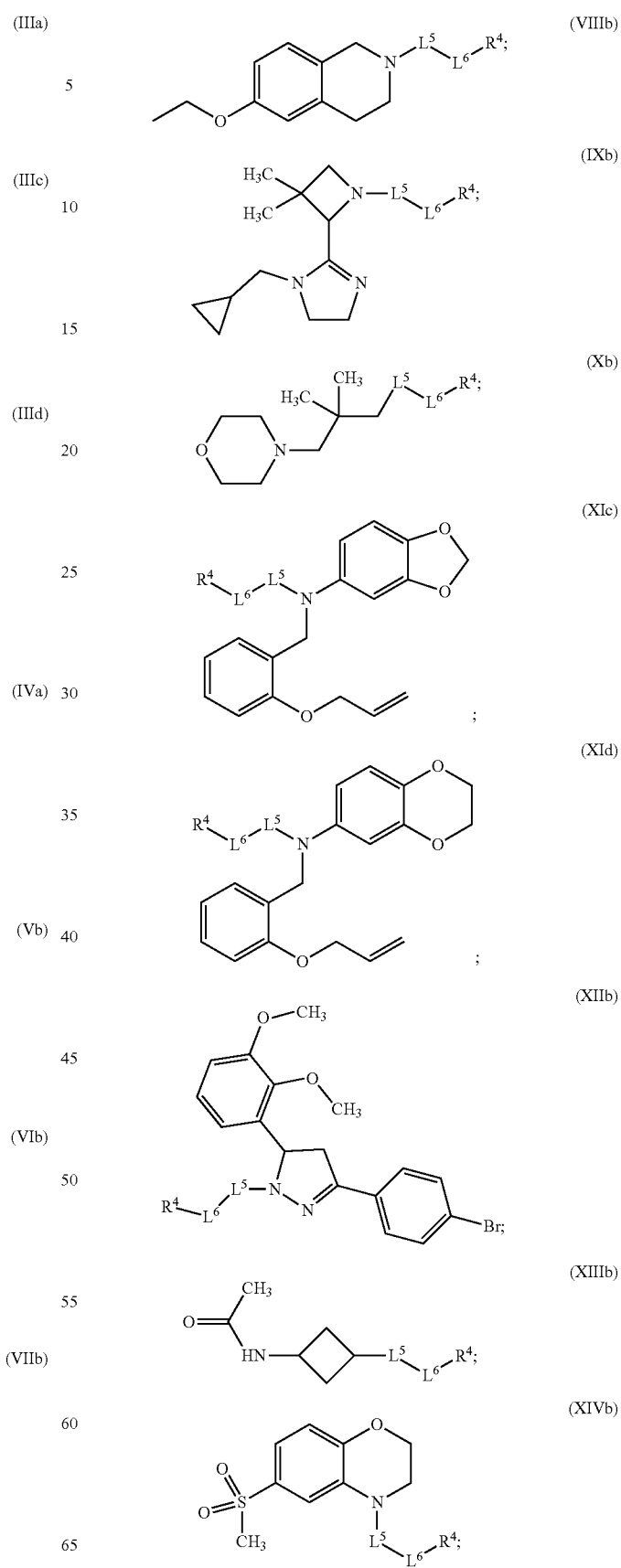

491

-continued

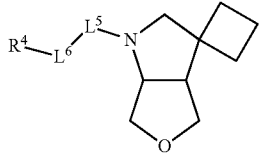
(XVa)

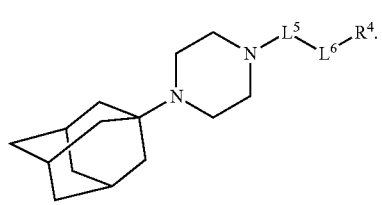
(XVIb)

(XVIIa)

18. The compound of claim 15, wherein $R^4$ is E.

19. The compound of claim 15, wherein E is a covalent cysteine modifier, covalent lysine modifier, covalent serine modifier, or covalent methionine modifier.

20. The compound of claim 15, wherein E is

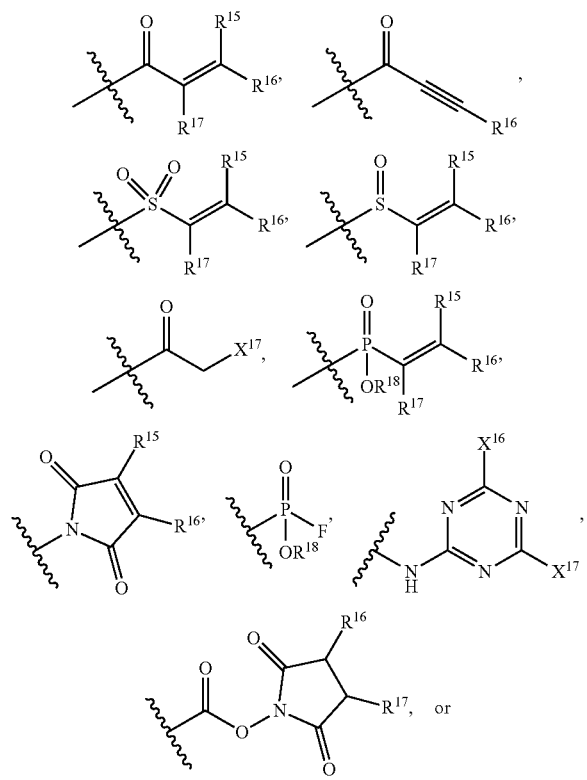

492

-continued

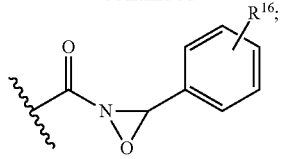

$R^{15}$ is hydrogen, halogen, —$CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —NHC=(O)NHNR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, —OCX$^{15}_3$, —OCHX$^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is hydrogen, halogen, —$CX^{16}_3$, —$CHX^{16}_2$, —$CH_2X^{16}$, —CN, —$SO_{n16}R^{16D}$, —$SO_{v16}NR^{16A}R^{16B}$, —$NHNR^{16A}R^{16B}$, —$ONR^{16A}R^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}_3$, —OCHX$^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is hydrogen, halogen, —$CX^{17}_3$, —$CHX^{17}_2$, —$CH_2X^{17}$, —CN, —$SO_{n17}R^{17D}$, —$SO_{v17}NR^{17A}R^{17B}$, —$NHNR^{17A}R^{17B}$, —$ONR^{17A}R^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, —OCX$^{17}_3$, —OCHX$^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{18}$ is hydrogen, —$CX^{18}_3$, —$CHX^{18}_2$, —$CH_2X^{18}$, —C(O)R$^{18C}$, —C(O)OR$^{18C}$, —C(O)NR$^{18A}$R$^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, and $R^{18C}$ are independently hydrogen, —$CX_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl;

each X, $X^{15}$, $X^{16}$, $X^{17}$ and $X^{18}$ is independently —F, —Cl, —Br, or —I;

n15, n16, and n17 are independently an integer from 0 to 4; and m15, m16, m17, v15, v16, and v17 are independently and integer from 1 to 2.

21. The compound of claim 15, wherein E is

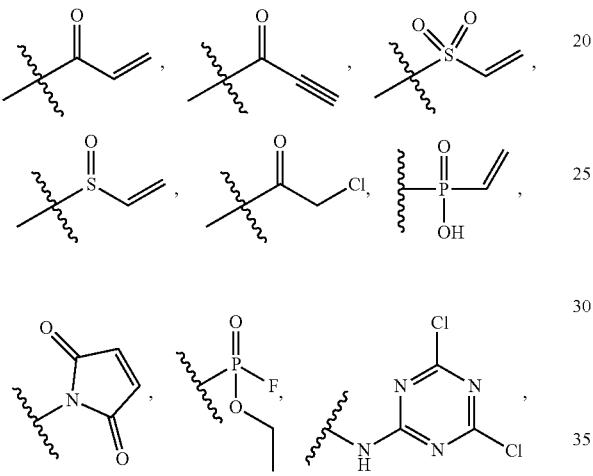

22. The compound of claim 15, wherein E is

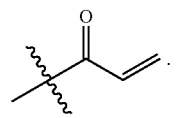

23. The compound of claim 15, wherein E is

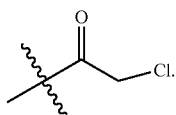 [SMILES: *C(=O)CCl]

24. The compound of claim 15, wherein the monovalent targeted autophagy protein binder is a monovalent form of the formula:

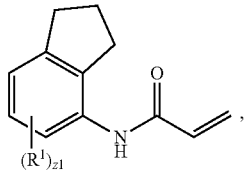 (Id)

wherein z1 is an integer from 0 to 9;

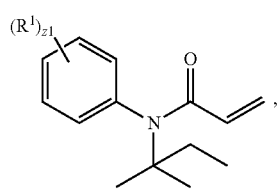 (IIc)

wherein z1 is an integer from 0 to 5;

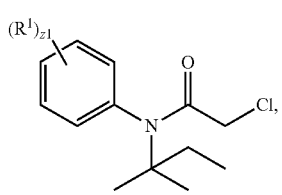 (IId)

wherein z1 is an integer from 0 to 5;

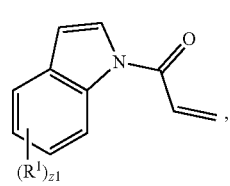 (IIIe)

wherein z1 is an integer from 0 to 6;

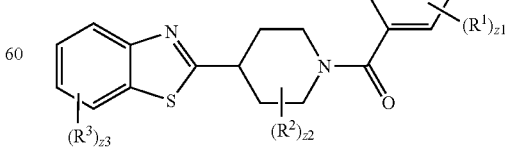 (IVb)

wherein z1 is an integer from 0 to 4, z2 is an integer from 0 to 8, and z3 is an integer from 0 to 4;

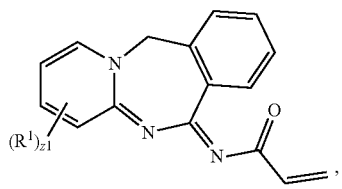

(Vc)

wherein z1 is an integer from 0 to 11;

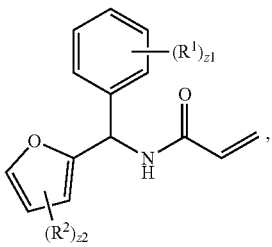

(VIc)

wherein z1 is an integer from 0 to 5 and z2 is an integer from 0 to 3;

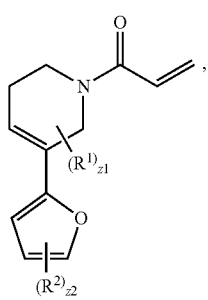

(VIIc)

wherein z1 is an integer from 0 to 5 and z2 is an integer from 0 to 3;

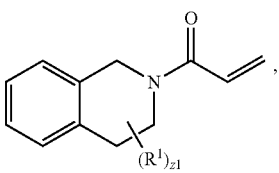

(VIIIc)

wherein z1 is an integer from 0 to 10;

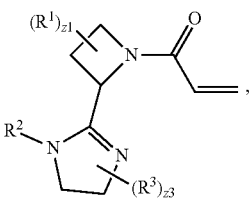

(IXc)

wherein z1 is an integer from 0 to 5 and z3 is an integer from 0 to 4;

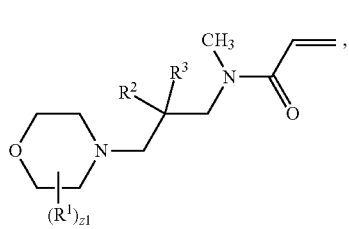

(Xc)

wherein z1 is an integer from 0 to 8;

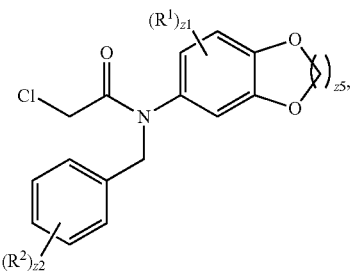

(XIc)

wherein z1 is an integer from 0 to 7, z2 is an integer from 0 to 5, and z5 is 1 or 2;

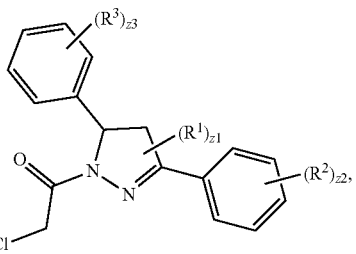

(XIIc)

wherein z1 is an integer from 0 to 2, z2 is an integer from 0 to 5, and z3 is an integer from 0 to 5;

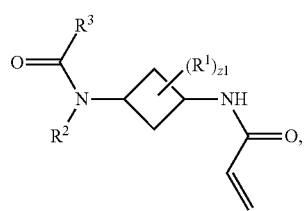

wherein z1 is an integer from 0 to 6,

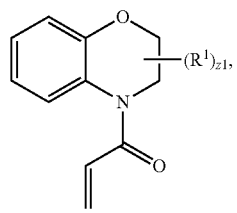

wherein z1 is an integer from 0 to 6;

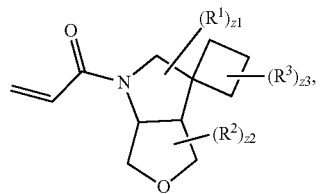

wherein z1 is an integer from 0 to 4, z2 is an integer from 0 to 6, and z3 is an integer from 0 to 6;

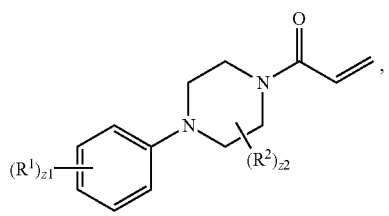

wherein z1 is an integer from 0 to 5 and z2 is an integer from 0 to 8; or

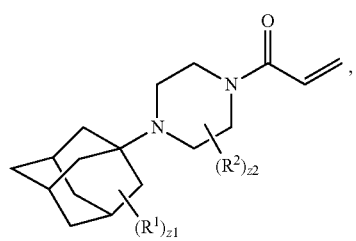

wherein z1 is an integer from 0 to 15 and z2 is an integer from 0 to 8.

25. The compound of claim 15, wherein the monovalent targeted autophagy protein binder is a monovalent form of the formula:

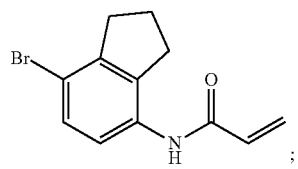

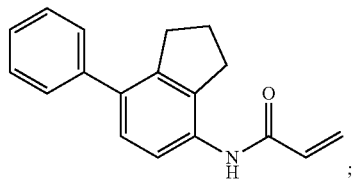

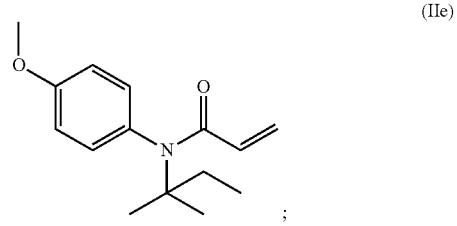

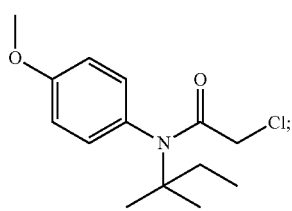

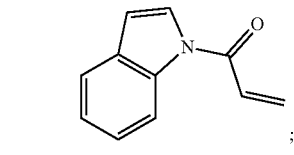

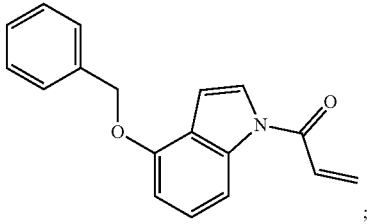

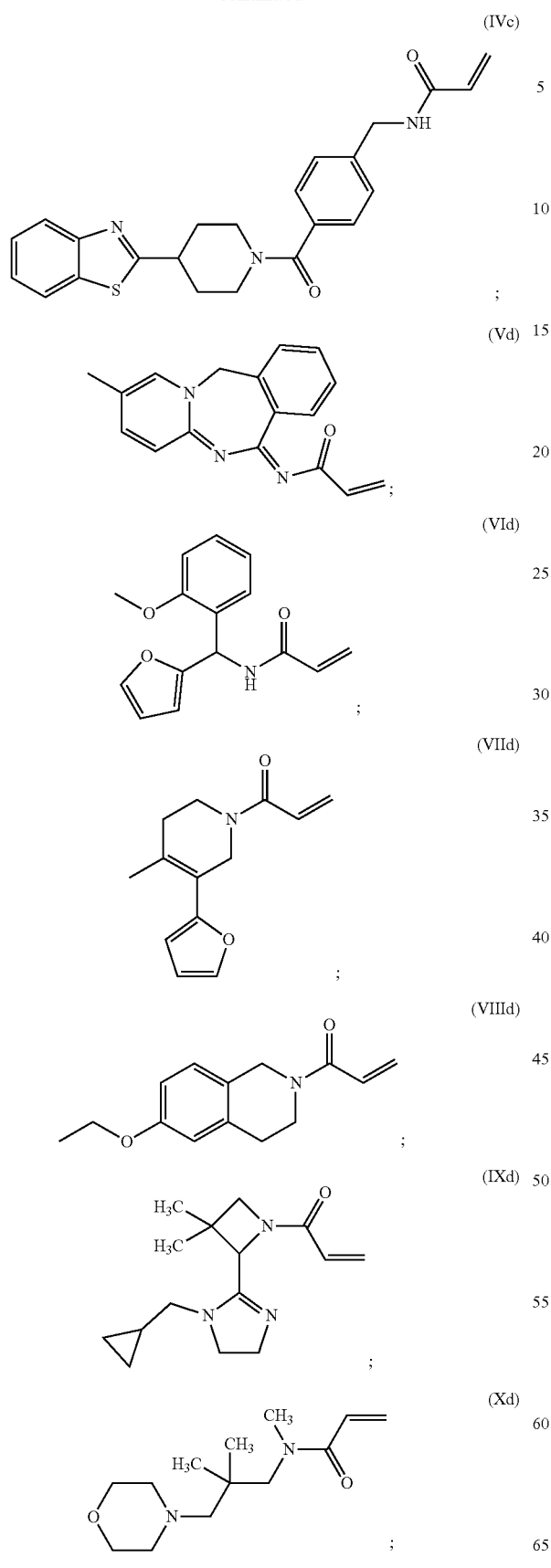
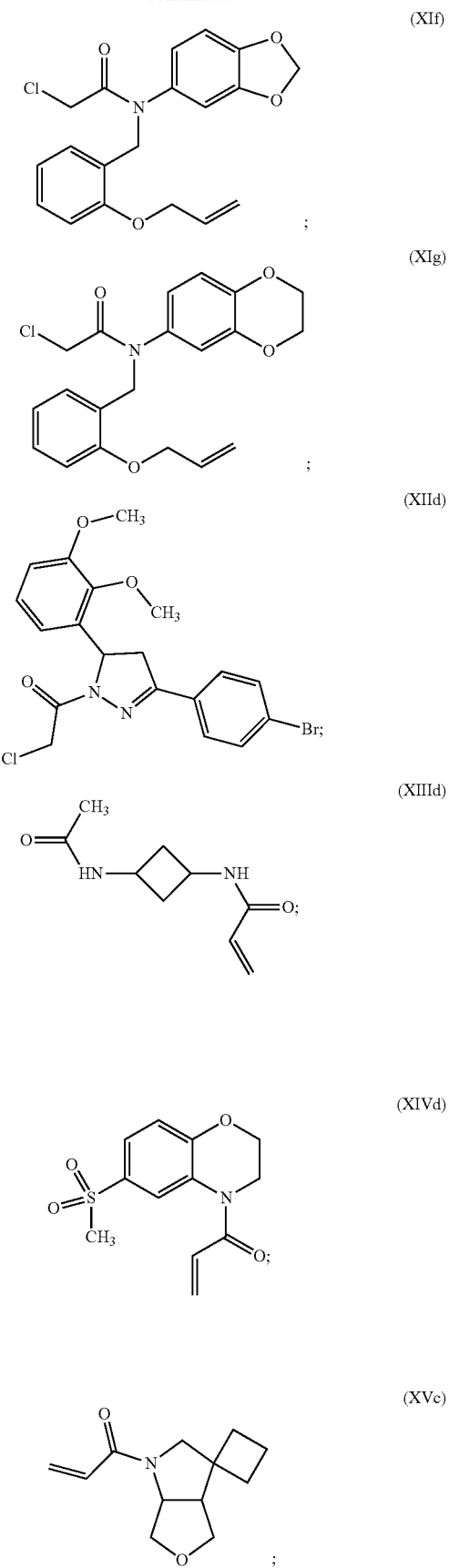

-continued

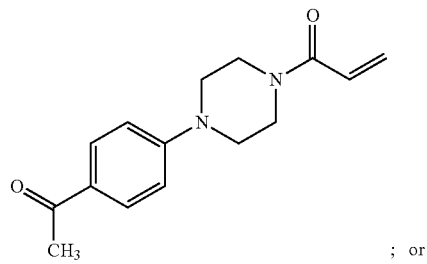
(XVId)

; or

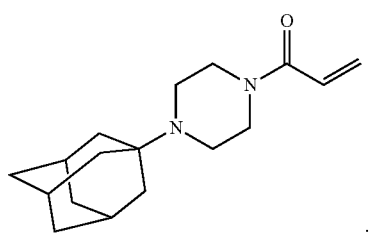
(XVIIc)

26. The compound of claim 25, wherein the monovalent targeted autophagy protein binder is a monovalent form of the formula:

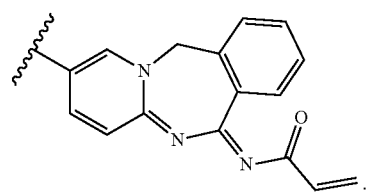
(Vd)

27. The compound of claim 25, wherein the monovalent targeted autophagy protein binder has the formula:

(mVe)

28. The compound of claim 25, wherein the monovalent targeted autophagy protein binder is a monovalent form of the formula:

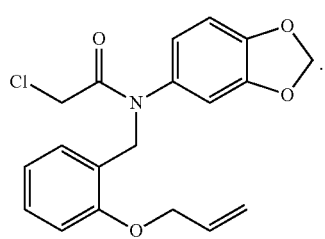
(XIf)

29. The compound of claim 15, wherein the monovalent targeted autophagy protein binder has the formula:

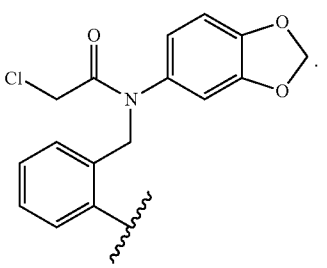
(mXIf)

30. The compound of claim 1, wherein the monovalent cellular component binder is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

31. The compound of claim 1, wherein the monovalent cellular component binder is capable of binding BRD4.

32. The compound of claim 31, wherein the monovalent cellular component binder has the formula:

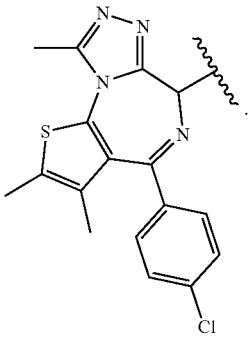 [SMILES: *C1N=C(c2ccc(Cl)cc2)c2c(sc(C)c2C)-n2c(C)nnc21]

33. The compound of claim 15, having the formula

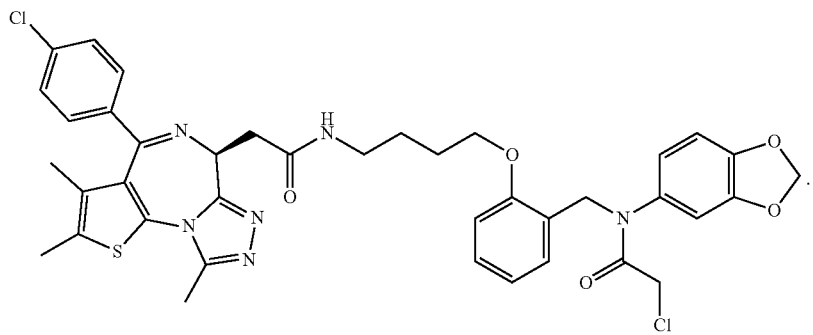 [SMILES: Cc1sc2c(c1C)C(c1ccc(Cl)cc1)=N[C@@H](CC(=O)NCCCCOc1ccccc1CN(C(=O)CCl)c1ccc3c(c1)OCO3)c1nnc(C)n1-2]

34. The compound of claim 1, wherein the monovalent cellular component binder is capable of binding a protein aggregate.

35. The compound of claim 34, wherein the monovalent cellular component binder is capable of binding a huntingtin aggregate.

36. The compound of claim 34, wherein the monovalent cellular component binder is capable of binding a PolyQ huntingtin aggregate.

37. The compound of claim 34, wherein the monovalent cellular component binder is capable of binding an amyloid protein aggregate.

38. The compound of claim 34, wherein the monovalent cellular component binder is capable of binding a protein aggregate comprising a protein selected from amyloid precursor protein, beta amyloid, IAPP, alpha-synuclein, PrP, prion protein Sc, Huntingtin, calcitonin, atrial natriuretic factor, apolipoprotein A1, Serum amyloid A, medin, prolactin, transthyretin, lysozyme, beta-2 microglobulin, gelsolin, keratoepithelin, cystatin, immunoglobulin light chain AL, and S-IBM.

39. The compound of claim 34, wherein the monovalent cellular component binder is a monovalent form of thioflavin or a derivative thereof.

40. The compound of claim 34, wherein the monovalent cellular component binder is a monovalent form of the formula:

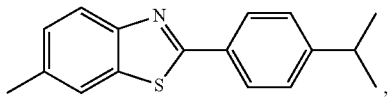

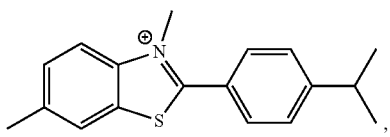

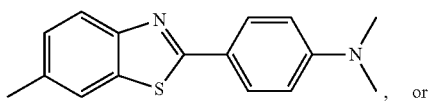

-continued

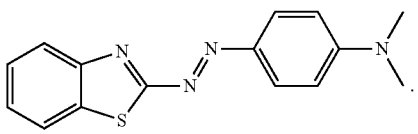 [SMILES: CN(C)c1ccc(/N=N/c2nc3ccccc3s2)cc1]

41. The compound of claim 34, wherein the monovalent cellular component binder is a monovalent form of the formula:

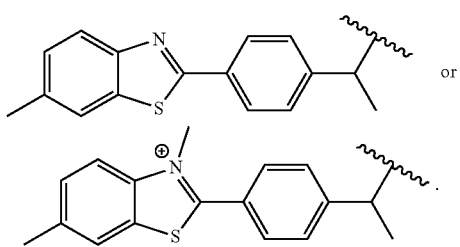

42. The compound of claim 34, wherein the monovalent cellular component binder has the formula:

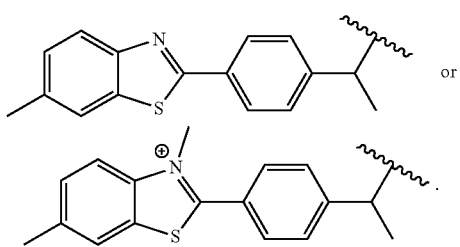

43. The compound of claim 34, wherein the monovalent cellular component binder has the formula:

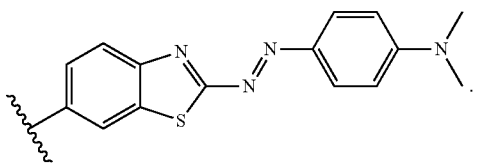 [SMILES: *c1ccc2nc(/N=N/c3ccc(N(C)C)cc3)sc2c1]

44. A compound comprising a monovalent cellular component binder covalently bound to a monovalent targeted autophagy protein binder, wherein the monovalent targeted autophagy protein binder is a monovalent form of the formula:

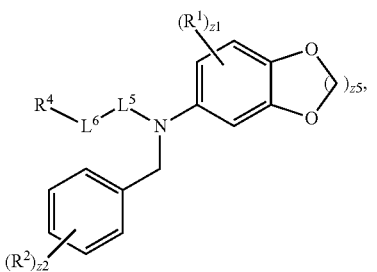

(XI)

wherein z1 is an integer from 0 to 7, z2 is an integer from 0 to 5, and z5 is 1 or 2;

$R^1$ is independently oxo, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, $SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, $SO_{v2}NR^{2A}R^{2B}$, —$NHC(O)NR^{2A}R^{2B}$, —$N(O)_{m2}$, —$NR^{2A}R^{2B}$, $C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, $SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, E, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

E is an electrophilic moiety;

$L^5$ is a bond, —$S(O)_2$—, —$S(O)$—, —$NR^5$—, =N—, —O—, —S—, —C(O)—, —$C(O)NR^5$—, —$NR^5C(O)$—, —$NR^5C(O)NH$—, —$NHC(O)NR^5$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^5$ is hydrogen, —$CX^5_3$, —$CHX^5_2$, —$CH_2X^5$, —$OCX^5_3$, —$OCH_2X^5$, —$OCHX^5_2$, —CN, —$C(O)R^{5C}$, —$C(O)$—$OR^{5C}$, —$C(O)NR^{5A}R^{5B}$, —$OR^{5D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^6$ is a bond, —$S(O)_2$—, —$S(O)$—, —$NR^6$—, =N—, —O—, —S—, —C(O)—, —$C(O)NR^6$—, —$NR^6C(O)$—, —$NR^6C(O)NH$—, —$NHC(O)NR^6$—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^6$ is hydrogen, —$CX^6_3$, —$CHX^6_2$, —$CH_2X^6$, —$OCX^6_3$, —$OCH_2X^6$, —$OCHX^6_2$, —CN, —$C(O)R^{6C}$, —$C(O)$—$OR^{6C}$, —$C(O)NR^{6A}R^{6B}$, —$OR^{6D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, and $R^{6D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl;

X, $X^1$, $X^2$, $X^4$, $X^5$, and $X^6$ are independently —F, —Cl, —Br, or —I;

n1, n2, n4, n5, and n6 are independently an integer from 0 to 4; and m1, m2, m4, m5, m6, v1, v2, v4, v5, and v6 are independently 1 or 2.

45. The compound of claim 44, wherein the monovalent targeted autophagy protein binder is a monovalent form of the formula:

(XIa)

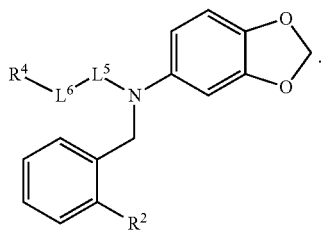

46. The compound of claim 44, wherein the monovalent targeted autophagy protein binder is a monovalent form of the formula:

(XIb)

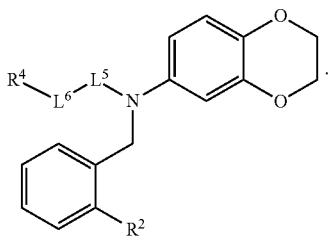

47. The compound of claim 44, wherein the monovalent targeted autophagy protein binder is a monovalent form of the formula:

(XIc)

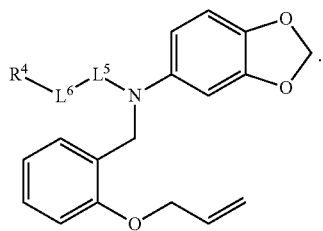

48. The compound of claim 44, wherein the monovalent targeted autophagy protein binder is a monovalent form of the formula:

(XId)

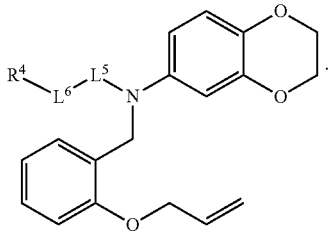

49. The compound of claim 44, wherein $R^4$ is E.

50. The compound of claim 44, wherein E is a covalent cysteine modifier, covalent lysine modifier, covalent serine modifier, or covalent methionine modifier.

51. The compound of claim 44, wherein E is

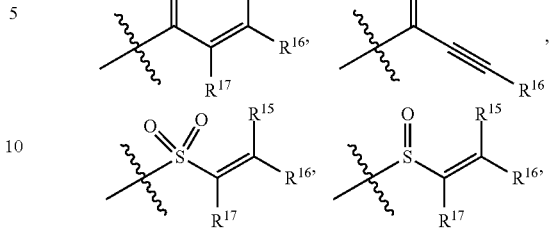

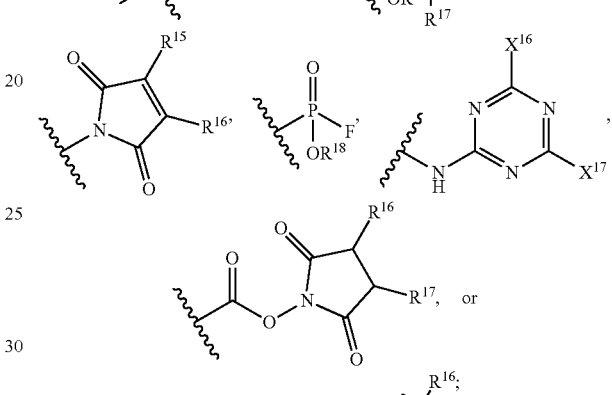

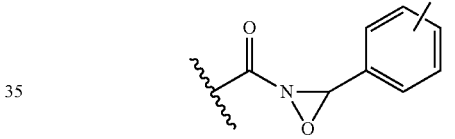

$R^{15}$ is hydrogen, halogen, —$CX^{15}_3$, —$CHX^{15}_2$, —$CH_2X^{15}$, —CN, —$SO_{n15}R^{15D}$, —$SO_{v15}NR^{15A}R^{15B}$, —$NHNR^{15A}R^{15B}$, —$ONR^{15A}R^{15B}$, —NHC=(O)$NHNR^{15A}R^{15B}$, —NHC(O)$NR^{15A}R^{15B}$, —N(O)$_{m15}$, —$NR^{15A}R^{15B}$, —C(O)$R^{15C}$, —C(O)—$OR^{15C}$, —C(O)$NR^{15A}R^{15B}$, —$OR^{15D}$, $NR^{15A}SO_2R^{15D}$, —$NR^{15A}C(O)R^{15C}$, —$NR^{15A}C(O)OR^{15C}$, —$NR^{15A}OR^{15C}$, —$OCX^{15}_3$, —$OCHX^{15}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is hydrogen, halogen, —$CX^{16}_3$, —$CHX^{16}_2$, —$CH_2X^{16}$, —CN, —$SO_{n16}R^{16D}$, —$SO_{v16}NR^{16A}R^{16B}$, —$NHNR^{16A}R^{16B}$, —$ONR^{16A}R^{16B}$, —NHC=(O)$NHNR^{16A}R^{16B}$, —NHC(O)$NR^{16A}R^{16B}$, —N(O)$_{m16}$, —$NR^{16A}R^{16B}$, —C(O)$R^{16C}$, —C(O)—$OR^{16C}$, —C(O)$NR^{16A}R^{16B}$, —$OR^{16D}$, $NR^{16A}SO_2R^{16D}$, —$NR^{16A}C(O)R^{16C}$, —$NR^{16A}C(O)OR^{16C}$, —$NR^{16A}OR^{16C}$, —$OCX^{16}_3$, —$OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{17}$ is hydrogen, halogen, —$CX^{17}_3$, —$CHX^{17}_2$, —$CH_2X^{17}$, —CN, —$SO_{n17}R^{17D}$, —$SO_{v17}NR^{17A}R^{17B}$, —$NHNR^{17A}R^{17B}$, —$ONR^{17A}R^{17B}$, —NHC=(O)$NHNR^{17A}R^{17B}$, —NHC(O)$NR^{17A}R^{17B}$, —N(O)$_{m17}$, —$NR^{17A}R^{17B}$, —C(O)$R^{17C}$, —C(O)—$OR^{17C}$, —C(O)

NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, —OCX$^{17}_3$, —OCHX$^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{18}$ is hydrogen, —CX$^{18}_3$, —CHX$^{18}_2$, —CH$_2$X$^{18}$, —C(O)R$^{18C}$, —C(O)OR$^{18C}$, —C(O)NR$^{18A}$R$^{18B}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, and R$^{18C}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15A}$ and R$^{15B}$ substituents bonded to the same nitrogen atom may optionally be joined to form a substituted or unsubstituted heterocycloalkyl or substituted or unsubstituted heteroaryl; R$^{16A}$ and R$^{16B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl;

each X, X$^{15}$, X$^{16}$, X$^{17}$ and X$^{18}$ is independently —F, —Cl, —Br, or —I;

n15, n16, and n17 are independently an integer from 0 to 4; and m15, m16, m17, v15, v16, and v17 are independently and integer from 1 to 2.

52. The compound of claim 44, wherein E is

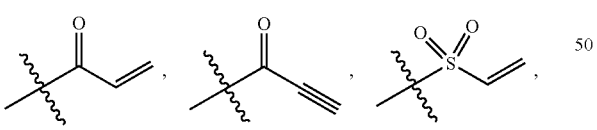

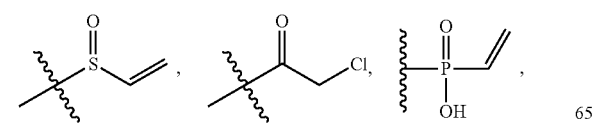

53. The compound of claim 44, wherein E is

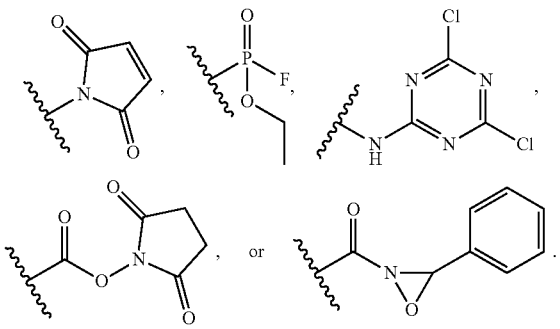

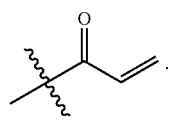 [SMILES: *C(=O)C=C]

54. The compound of claim 44, wherein -L$^5$-L$^6$-R$^4$ is —C(O)CH$_2$-(halogen).

55. The compound of claim 44, wherein -L$^5$-L$^6$-R$^4$ is —C(O)CH$_2$—Cl.

56. The compound of claim 44, wherein -L$^5$-L$^6$-R$^4$ is —C(O)CH$_2$—Br.

57. The compound of claim 44, wherein the monovalent targeted autophagy protein binder is a monovalent form of the formula:

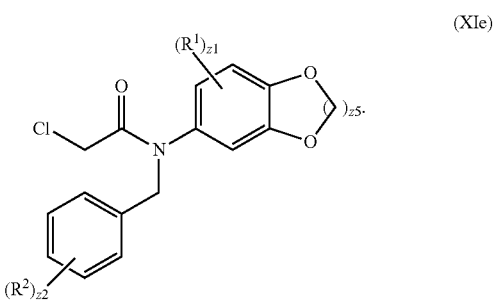

(XIe)

58. The compound of claim 44, wherein the monovalent targeted autophagy protein binder is a monovalent form of the formula:

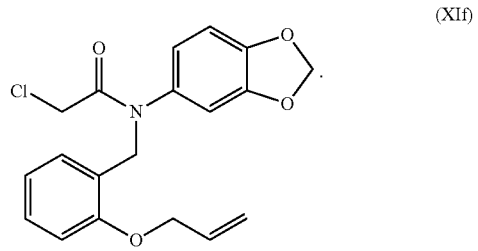 [SMILES: C=CCOc1ccccc1CN(C(=O)CCl)c1ccc2c(c1)OCO2]

(XIf)

59. The compound of claim 44, wherein the monovalent targeted autophagy protein binder is a monovalent form of the formula:

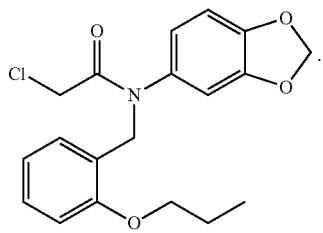

(XIh)

60. The compound of claim 44, wherein the monovalent targeted autophagy protein binder is a monovalent form of the formula:

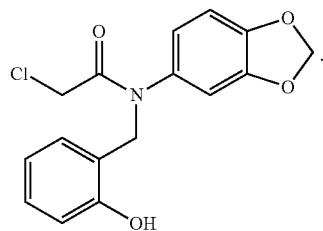

(XIi)

61. The compound of claim 44, wherein the monovalent targeted autophagy protein binder has the formula:

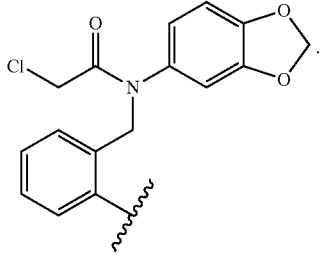

(mXIf)

62. The compound of claim 44, wherein the monovalent targeted autophagy protein binder is capable of contacting an amino acid corresponding to C113 of human p62/SQSTM1 protein.

63. The compound of claim 44, wherein the monovalent targeted autophagy protein binder is capable of forming a covalent bond to the amino acid corresponding to C113 of human p62/SQSTM1protein.

64. The compound of claim 44, wherein the monovalent cellular component binder is capable of binding a protein aggregate.

65. The compound of claim 44, wherein the monovalent cellular component binder is capable of binding a huntingtin aggregate.

66. The compound of claim 44, wherein the monovalent cellular component binder is capable of binding a PolyQ huntingtin aggregate.

67. The compound of claim 44, wherein the monovalent cellular component binder is capable of binding an amyloid protein aggregate.

68. The compound of claim 44, wherein the monovalent cellular component binder is capable of binding a protein aggregate comprising a protein selected from amyloid precursor protein, beta amyloid, IAPP, alpha-synuclein, PrP, prion protein Sc, Huntingtin, calcitonin, atrial natriuretic factor, apolipoprotein A1, Serum amyloid A, medin, prolactin, transthyretin, lysozyme, beta-2 microglobulin, gelsolin, keratoepithelin, cystatin, immunoglobulin light chain AL, and S-IBM.

69. The compound of claim 44, wherein the monovalent cellular component binder is a monovalent form of thioflavin or a derivative thereof.

70. The compound of claim 44, wherein the monovalent cellular component binder is a monovalent form of the formula.

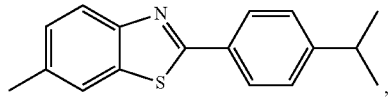,

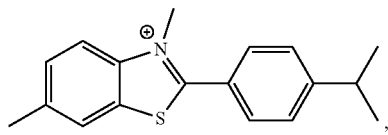,

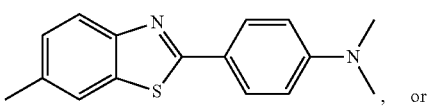, or

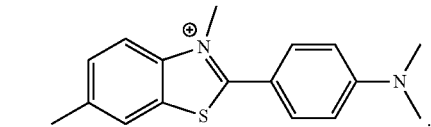.

71. The compound of claim 44, wherein the monovalent cellular component binder is a monovalent form of the formula:

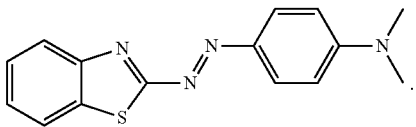 [SMILES: CN(C)c1ccc(/N=N/c2nc3ccccc3s2)cc1]

72. The compound of claim 44, wherein the monovalent cellular component binder has the formula:

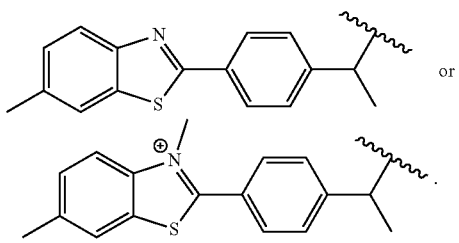

or

73. The compound of claim 44, wherein the monovalent cellular component binder has the formula:

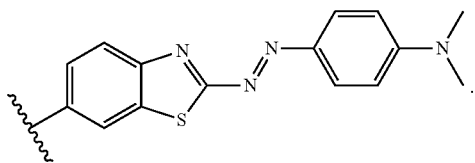 [SMILES: *c1ccc2nc(/N=N/c3ccc(N(C)C)cc3)sc2c1]

74. The compound of claim 44, wherein a divalent linker covalently binds said monovalent cellular component binder to said monovalent targeted autophagy protein binder.

75. The compound of claim 74, wherein the divalent linker has the formula:

-$L^1$-$L^2$-$L^3$-$L^4$-;

$L^1$ is connected directly to said monovalent targeted autophagy protein binder;

$L^1$ is —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^2$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^3$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^4$ is a bond, —S(O)$_2$—, —S(O)—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

76. The compound of claim 44, having the formula:

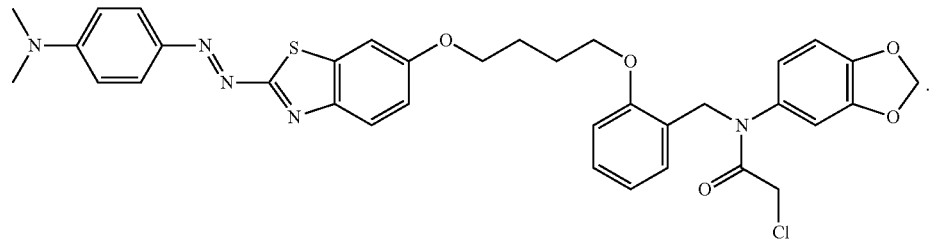 [SMILES: CN(C)c1ccc(/N=N/c2nc3ccc(OCCCCOc4ccccc4CN(C(=O)CCl)c4ccc5c(c4)OCO5)cc3s2)cc1]

77. An autophagy adapter protein covalently bonded to a fragment of a compound of claim 1.

78. The autophagy adapter protein of claim 77, wherein the autophagy adapter protein is LC3, p62, NBR1, NDP52, Optineurin, NUFIP1, WDFY3, RETREG1, Nix, TOLLIP, TAX1BP1, or a derivative, fragment, or homolog thereof.

79. A pharmaceutical composition comprising a compound of claim 1 and a pharmaceutically acceptable excipient.

* * * * *

SEQUENCE LISTING

```
<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 1

Tyr Trp Lys Asp Ala Cys Ser His Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Ser Tyr Cys Trp His Ile Leu
1               5

<210> SEQ ID NO 3
<211> LENGTH: 73
```

```
<212> TYPE: PRT
<213> ORGANISM: Artificial Sequence
<220> FEATURE:
<223> OTHER INFORMATION: Synthetic polypeptide

<400> SEQUENCE: 3

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Gly Gly Gly Phe Arg
65                  70

<210> SEQ ID NO 4
<211> LENGTH: 440
<212> TYPE: PRT
<213> ORGANISM: Artificial Sequence
<220> FEATURE:
<223> OTHER INFORMATION: Synthetic polypeptide

<400> SEQUENCE: 4

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
    130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Glu Ala Arg Pro Gly Pro Thr Ala Glu Ser
    210                 215                 220

Ala Ser Gly Pro Ser Glu Asp Pro Ser Val Asn Phe Leu Lys Asn Val
225                 230                 235                 240

Gly Glu Ser Val Ala Ala Ala Leu Ser Pro Leu Gly Ile Glu Val Asp
                245                 250                 255
```

```
Ile Asp Val Glu His Gly Gly Lys Arg Ser Arg Leu Thr Pro Val Ser
            260                 265                 270

Pro Glu Ser Ser Ser Thr Glu Lys Ser Ser Ser Gln Pro Ser Ser
        275                 280                 285

Cys Cys Ser Asp Pro Ser Lys Pro Gly Gly Asn Val Glu Gly Ala Thr
    290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
                325                 330                 335

Asp Trp Thr His Leu Ser Ser Lys Glu Val Asp Pro Ser Thr Gly Glu
            340                 345                 350

Leu Gln Ser Leu Gln Met Pro Glu Ser Glu Gly Pro Ser Ser Leu Asp
        355                 360                 365

Pro Ser Gln Glu Gly Pro Thr Gly Leu Lys Glu Ala Ala Leu Tyr Pro
    370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
            420                 425                 430

Tyr Ser Lys His Pro Pro Leu
            435                 440

<210> SEQ ID NO 5
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 5

Arg Phe Ser Phe Cys Cys Ser Pro Glu Pro Glu Ala Glu Ala Glu Ala
1               5                   10                  15

Ala Ala Gly Pro Gly Pro Cys Glu Arg Leu
            20                  25

<210> SEQ ID NO 6
<211> LENGTH: 837
<212> TYPE: PRT
<213> ORGANISM: Artificial Sequence
<220> FEATURE:
<223> OTHER INFORMATION: Synthetic polypeptide

<400> SEQUENCE: 6

Met Glu Pro Gln Val Thr Leu Asn Val Thr Phe Lys Asn Glu Ile Gln
1               5                   10                  15

Ser Phe Leu Val Ser Asp Pro Glu Asn Thr Thr Trp Ala Asp Ile Glu
            20                  25                  30

Ala Met Val Ser Ile Asn Ser Gln Gly Glu Tyr Glu Glu Ala Leu Lys
        35                  40                  45

Met Ala Val Lys Gln Gly Asn Gln Leu Gln Met Gln Val His Glu Gly
    50                  55                  60

His His Val Val Asp Glu Ala Pro Pro Val Val Gly Ala Lys Arg
65                  70                  75                  80

Leu Ala Ala Arg Ala Gly Lys Lys Pro Leu Ala His Tyr Ser Ser Leu
```

```
                 85                  90                  95
Val Arg Val Leu Gly Ser Asp Met Lys Thr Pro Glu Asp Pro Ala Val
            100                 105                 110
Gln Ser Phe Pro Leu Val Pro Cys Asp Thr Asp Gln Pro Gln Asp Lys
            115                 120                 125
Pro Pro Asp Trp Phe Thr Ser Tyr Leu Glu Thr Phe Arg Glu Gln Val
            130                 135                 140
Val Asn Glu Thr Val Glu Lys Leu Glu Gln Lys Leu His Glu Lys Leu
145                 150                 155                 160
Val Leu Gln Asn Pro Ser Leu Gly Ser Cys Pro Ser Glu Val Ser Met
            165                 170                 175
Pro Thr Ser Glu Glu Thr Leu Phe Leu Pro Glu Asn Gln Phe Ser Trp
            180                 185                 190
His Ile Ala Cys Asn Asn Cys Gln Arg Arg Ile Val Gly Val Arg Tyr
            195                 200                 205
Gln Cys Ser Leu Cys Pro Ser Tyr Asn Ile Cys Glu Asp Cys Glu Ala
            210                 215                 220
Gly Pro Tyr Gly His Asp Thr Asn His Val Leu Leu Lys Leu Arg Arg
225                 230                 235                 240
Pro Val Val Gly Ser Ser Glu Pro Phe Cys His Ser Lys Tyr Ser Thr
            245                 250                 255
Pro Arg Leu Pro Ala Ala Leu Glu Gln Val Arg Leu Gln Lys Gln Val
            260                 265                 270
Asp Lys Asn Phe Leu Lys Ala Glu Lys Gln Arg Leu Arg Ala Glu Lys
            275                 280                 285
Lys Gln Arg Lys Ala Glu Val Lys Glu Leu Lys Lys Gln Leu Lys Leu
            290                 295                 300
His Arg Lys Ile His Leu Trp Asn Ser Ile His Gly Leu Gln Ser Pro
305                 310                 315                 320
Lys Ser Pro Leu Gly Arg Pro Glu Ser Leu Leu Gln Ser Asn Thr Leu
            325                 330                 335
Met Leu Pro Leu Gln Pro Cys Thr Ser Val Met Pro Met Leu Ser Ala
            340                 345                 350
Ala Phe Val Asp Glu Asn Leu Pro Asp Gly Thr His Leu Gln Pro Gly
            355                 360                 365
Thr Lys Phe Ile Lys His Trp Arg Met Lys Asn Thr Gly Asn Val Lys
            370                 375                 380
Trp Ser Ala Asp Thr Lys Leu Lys Phe Met Trp Gly Asn Leu Thr Leu
385                 390                 395                 400
Ala Ser Thr Glu Lys Lys Asp Val Leu Val Pro Cys Leu Lys Ala Gly
            405                 410                 415
His Val Gly Val Val Ser Val Glu Phe Ile Ala Pro Ala Leu Glu Gly
            420                 425                 430
Thr Tyr Thr Ser His Trp Arg Leu Ser His Lys Gly Gln Gln Phe Gly
            435                 440                 445
Pro Arg Val Trp Cys Ser Ile Ile Val Asp Pro Phe Pro Ser Glu Glu
            450                 455                 460
Ser Pro Asp Asn Ile Glu Lys Gly Met Ile Ser Ser Lys Thr Asp
465                 470                 475                 480
Asp Leu Thr Cys Gln Gln Glu Glu Thr Phe Leu Leu Ala Lys Glu Glu
            485                 490                 495
Arg Gln Leu Gly Glu Val Thr Glu Gln Thr Glu Gly Thr Ala Ala Cys
            500                 505                 510
```

-continued

```
Ile Pro Gln Lys Ala Lys Asn Val Ala Ser Glu Arg Glu Leu Tyr Ile
        515                 520                 525
Pro Ser Val Asp Leu Leu Thr Ala Gln Asp Leu Leu Ser Phe Glu Leu
    530                 535                 540
Leu Asp Ile Asn Ile Val Gln Glu Leu Glu Arg Val Pro His Asn Thr
545                 550                 555                 560
Pro Val Asp Val Thr Pro Cys Met Ser Pro Leu Pro His Asp Ser Pro
                565                 570                 575
Leu Ile Glu Lys Pro Gly Leu Gly Gln Ile Glu Glu Asn Glu Gly
            580                 585                 590
Ala Gly Phe Lys Ala Leu Pro Asp Ser Met Val Ser Val Lys Arg Lys
        595                 600                 605
Ala Glu Asn Ile Ala Ser Val Glu Glu Ala Glu Asp Leu Ser Gly
    610                 615                 620
Thr Gln Phe Val Cys Glu Thr Val Ile Arg Ser Leu Thr Leu Asp Ala
625                 630                 635                 640
Ala Pro Asp His Asn Pro Pro Cys Arg Gln Lys Ser Leu Gln Met Thr
                645                 650                 655
Phe Ala Leu Pro Glu Gly Pro Leu Gly Asn Lys Glu Glu Ile Ile
            660                 665                 670
His Ile Ala Glu Glu Ala Val Met Glu Glu Glu Asp Glu Glu
        675                 680                 685
Asp Glu Glu Glu Glu Asp Glu Leu Lys Asp Glu Val Gln Ser Gln Ser
    690                 695                 700
Ser Ala Ser Ser Glu Asp Tyr Ile Ile Ile Leu Pro Glu Cys Phe Asp
705                 710                 715                 720
Thr Ser Arg Pro Leu Gly Asp Ser Met Tyr Ser Ser Ala Leu Ser Gln
                725                 730                 735
Pro Gly Leu Glu Arg Gly Ala Glu Gly Lys Pro Gly Val Glu Ala Gly
            740                 745                 750
Gln Glu Pro Ala Glu Ala Gly Glu Arg Leu Pro Gly Gly Glu Asn Gln
        755                 760                 765
Pro Gln Glu His Ser Ile Ser Asp Ile Leu Thr Thr Ser Gln Thr Leu
    770                 775                 780
Glu Thr Val Pro Leu Ile Pro Glu Val Val Glu Leu Pro Pro Ser Leu
785                 790                 795                 800
Pro Arg Ser Ser Pro Cys Val His His His Gly Ser Pro Gly Val Asp
                805                 810                 815
Leu Pro Val Thr Ile Pro Glu Val Ser Ser Val Pro Asp Gln Ile Arg
            820                 825                 830
Gly Ala Asn Asn Phe
        835

<210> SEQ ID NO 7
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 7

Lys Thr Pro Glu Asp Pro Ala Val Gln Ser Phe Pro Leu Val Pro Cys
1               5                   10                  15
Asp Thr Asp Gln Pro Gln Asp Lys Pro Pro Asp Trp Phe Thr Ser Tyr
            20                  25                  30
```

Leu Glu Thr Phe Arg Glu
        35

<210> SEQ ID NO 8
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 8

Met Glu Glu Thr Ile Lys Asp Pro Pro Thr Ser Ala Val Leu Leu Asp
1               5                   10                  15

His Cys His Phe Ser Gln Val Ile Phe Asn Ser Val Glu Lys Phe Tyr
            20                  25                  30

Ile Pro Gly Gly Asp Val Thr Cys His Tyr Thr Phe Thr Gln His Phe
        35                  40                  45

Ile Pro Arg Arg Lys Asp Trp Ile Gly Ile Phe Arg Val Gly Trp Lys
    50                  55                  60

Thr Thr Arg Glu Tyr Tyr Thr Phe Met Trp Val Thr Leu Pro Ile Asp
65                  70                  75                  80

Leu Asn Asn Lys Ser Ala Lys Gln Gln Glu Val Gln Phe Lys Ala Tyr
                85                  90                  95

Tyr Leu Pro Lys Asp Asp Glu Tyr Tyr Gln Phe Cys Tyr Val Asp Glu
            100                 105                 110

Asp Gly Val Val Arg Gly Ala Ser Ile Pro Phe Gln Phe Arg Pro Glu
        115                 120                 125

Asn Glu Glu Asp Ile Leu Val Val Thr Thr Gln Gly Glu Val Glu Glu
    130                 135                 140

Ile Glu Gln His Asn Lys Glu Leu Cys Lys Glu Asn Gln Glu Leu Lys
145                 150                 155                 160

Asp Ser Cys Ile Ser Leu Gln Lys Gln Asn Ser Asp Met Gln Ala Glu
                165                 170                 175

Leu Gln Lys Lys Gln Glu Glu Leu Glu Thr Leu Gln Ser Ile Asn Lys
            180                 185                 190

Lys Leu Glu Leu Lys Val Lys Glu Gln Lys Asp Tyr Trp Glu Thr Glu
        195                 200                 205

Leu Leu Gln Leu Lys Glu Gln Asn Gln Lys Met Ser Ser Glu Asn Glu
    210                 215                 220

Lys Met Gly Ile Arg Val Asp Gln Leu Gln Ala Gln Leu Ser Thr Gln
225                 230                 235                 240

Glu Lys Glu Met Glu Lys Leu Val Gln Gly Asp Gln Asp Lys Thr Glu
                245                 250                 255

Gln Leu Glu Gln Leu Lys Lys Glu Asn Asp His Leu Phe Leu Ser Leu
            260                 265                 270

Thr Glu Gln Arg Lys Asp Gln Lys Lys Leu Glu Gln Thr Val Glu Gln
        275                 280                 285

Met Lys Gln Asn Glu Thr Thr Ala Met Lys Lys Gln Gln Glu Leu Met
    290                 295                 300

Asp Glu Asn Phe Asp Leu Ser Lys Arg Leu Ser Glu Asn Glu Ile Ile
305                 310                 315                 320

Cys Asn Ala Leu Gln Arg Gln Lys Glu Arg Leu Glu Gly Glu Asn Asp
                325                 330                 335

Leu Leu Lys Arg Glu Asn Ser Arg Leu Leu Ser Tyr Met Gly Leu Asp
            340                 345                 350

```
Phe Asn Ser Leu Pro Tyr Gln Val Pro Thr Ser Asp Glu Gly Gly Ala
            355                 360                 365

Arg Gln Asn Pro Gly Leu Ala Tyr Gly Asn Pro Tyr Ser Gly Ile Gln
    370                 375                 380

Glu Ser Ser Ser Pro Ser Pro Leu Ser Ile Lys Lys Cys Pro Ile Cys
385                 390                 395                 400

Lys Ala Asp Asp Ile Cys Asp His Thr Leu Glu Gln Gln Gln Met Gln
                405                 410                 415

Pro Leu Cys Phe Asn Cys Pro Ile Cys Asp Lys Ile Phe Pro Ala Thr
            420                 425                 430

Glu Lys Gln Ile Phe Glu Asp His Val Phe Cys His Ser Leu
    435                 440                 445

<210> SEQ ID NO 9
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 9

Arg Leu Ser Glu Asn Glu Ile Ile Cys Asn Ala Leu Gln Arg Gln
1               5                   10                  15

<210> SEQ ID NO 10
<211> LENGTH: 577
<212> TYPE: PRT
<213> ORGANISM: Artificial Sequence
<220> FEATURE:
<223> OTHER INFORMATION: Synthetic polypeptide

<400> SEQUENCE: 10

Met Ser His Gln Pro Leu Ser Cys Leu Thr Glu Lys Glu Asp Ser Pro
1               5                   10                  15

Ser Glu Ser Thr Gly Asn Gly Pro Pro His Leu Ala His Pro Asn Leu
            20                  25                  30

Asp Thr Phe Thr Pro Glu Glu Leu Leu Gln Gln Met Lys Glu Leu Leu
        35                  40                  45

Thr Glu Asn His Gln Leu Lys Glu Ala Met Lys Leu Asn Asn Gln Ala
    50                  55                  60

Met Lys Gly Arg Phe Glu Glu Leu Ser Ala Trp Thr Glu Lys Gln Lys
65                  70                  75                  80

Glu Glu Arg Gln Phe Phe Glu Ile Gln Ser Lys Glu Ala Lys Glu Arg
                85                  90                  95

Leu Met Ala Leu Ser His Glu Asn Glu Lys Leu Lys Glu Glu Leu Gly
            100                 105                 110

Lys Leu Lys Gly Lys Ser Glu Arg Ser Ser Glu Asp Pro Thr Asp Asp
        115                 120                 125

Ser Arg Leu Pro Arg Ala Glu Ala Glu Gln Lys Asp Gln Leu Arg
    130                 135                 140

Thr Gln Val Val Arg Leu Gln Ala Glu Lys Ala Asp Leu Leu Gly Ile
145                 150                 155                 160

Val Ser Glu Leu Gln Leu Lys Leu Asn Ser Ser Gly Ser Ser Glu Asp
                165                 170                 175

Ser Phe Val Glu Ile Arg Met Ala Glu Gly Glu Ala Glu Gly Ser Val
            180                 185                 190

Lys Glu Ile Lys His Ser Pro Gly Pro Thr Arg Thr Val Ser Thr Gly
```

-continued

```
                195                 200                 205
Thr Ala Leu Ser Lys Tyr Arg Ser Arg Ser Ala Asp Gly Ala Lys Asn
210                 215                 220

Tyr Phe Glu His Glu Glu Leu Thr Val Ser Gln Leu Leu Cys Leu
225                 230                 235                 240

Arg Glu Gly Asn Gln Lys Val Glu Arg Leu Glu Val Ala Leu Lys Glu
                245                 250                 255

Ala Lys Glu Arg Val Ser Asp Phe Glu Lys Lys Thr Ser Asn Arg Ser
                260                 265                 270

Glu Ile Glu Thr Gln Thr Glu Gly Ser Thr Glu Lys Glu Asn Asp Glu
                275                 280                 285

Glu Lys Gly Pro Glu Thr Val Gly Ser Glu Val Glu Ala Leu Asn Leu
                290                 295                 300

Gln Val Thr Ser Leu Phe Lys Glu Leu Gln Glu Ala His Thr Lys Leu
305                 310                 315                 320

Ser Lys Ala Glu Leu Met Lys Lys Arg Leu Gln Glu Lys Cys Gln Ala
                325                 330                 335

Leu Glu Arg Lys Asn Ser Ala Ile Pro Ser Glu Leu Asn Glu Lys Gln
                340                 345                 350

Glu Leu Val Tyr Thr Asn Lys Lys Leu Glu Leu Gln Val Glu Ser Met
                355                 360                 365

Leu Ser Glu Ile Lys Met Glu Gln Ala Lys Thr Glu Asp Glu Lys Ser
370                 375                 380

Lys Leu Thr Val Leu Gln Met Thr His Asn Lys Leu Leu Gln Glu His
385                 390                 395                 400

Asn Asn Ala Leu Lys Thr Ile Glu Glu Leu Thr Arg Lys Glu Ser Glu
                405                 410                 415

Lys Val Asp Arg Ala Val Leu Lys Glu Leu Ser Glu Lys Leu Glu Leu
                420                 425                 430

Ala Glu Lys Ala Leu Ala Ser Lys Gln Leu Gln Met Asp Glu Met Lys
                435                 440                 445

Gln Thr Ile Ala Lys Gln Glu Glu Asp Leu Glu Thr Met Thr Ile Leu
450                 455                 460

Arg Ala Gln Met Glu Val Tyr Cys Ser Asp Phe His Ala Glu Arg Ala
465                 470                 475                 480

Ala Arg Glu Lys Ile His Glu Glu Lys Glu Gln Leu Ala Leu Gln Leu
                485                 490                 495

Ala Val Leu Leu Lys Glu Asn Asp Ala Phe Glu Asp Gly Gly Arg Gln
                500                 505                 510

Ser Leu Met Glu Met Gln Ser Arg His Gly Ala Arg Thr Ser Asp Ser
                515                 520                 525

Asp Gln Gln Ala Tyr Leu Val Gln Arg Gly Ala Glu Asp Arg Asp Trp
530                 535                 540

Arg Gln Gln Arg Asn Ile Pro Ile His Ser Cys Pro Lys Cys Gly Glu
545                 550                 555                 560

Val Leu Pro Asp Ile Asp Thr Leu Gln Ile His Val Met Asp Cys Ile
                565                 570                 575

Ile

<210> SEQ ID NO 11
<211> LENGTH: 21
<212> TYPE: PRT
<213> ORGANISM: Artificial Sequence
<220> FEATURE:
```

<223> OTHER INFORMATION: Synthetic polypeptide

<400> SEQUENCE: 11

Lys Cys Gly Glu Val Leu Pro Asp Ile Asp Thr Leu Gln Ile His Val
1               5                   10                  15

Met Asp Cys Ile Ile
            20

<210> SEQ ID NO 12
<211> LENGTH: 495
<212> TYPE: PRT
<213> ORGANISM: Artificial Sequence
<220> FEATURE:
<223> OTHER INFORMATION: Synthetic polypeptide

<400> SEQUENCE: 12

Met Ala Glu Pro Thr Ser Asp Phe Glu Thr Pro Ile Gly Trp His Ala
1               5                   10                  15

Ser Pro Glu Leu Thr Pro Thr Leu Gly Pro Leu Ser Asp Thr Ala Pro
                20                  25                  30

Pro Arg Asp Ser Trp Met Phe Trp Ala Met Leu Pro Pro Pro Pro Pro
            35                  40                  45

Pro Leu Thr Ser Ser Leu Pro Ala Ala Gly Ser Lys Pro Ser Ser Glu
        50                  55                  60

Ser Gln Pro Pro Met Glu Ala Gln Ser Leu Pro Gly Ala Pro Pro Pro
65                  70                  75                  80

Phe Asp Ala Gln Ile Leu Pro Gly Ala Gln Pro Phe Asp Ala Gln
                85                  90                  95

Ser Pro Leu Asp Ser Gln Pro Gln Pro Ser Gly Gln Pro Trp Asn Phe
                100                 105                 110

His Ala Ser Thr Ser Trp Tyr Trp Arg Gln Ser Ser Asp Arg Phe Pro
            115                 120                 125

Arg His Gln Lys Ser Phe Asn Pro Ala Val Lys Asn Ser Tyr Tyr Pro
        130                 135                 140

Arg Lys Tyr Asp Ala Lys Phe Thr Asp Phe Ser Leu Pro Pro Ser Arg
145                 150                 155                 160

Lys Gln Lys Lys Lys Lys Arg Lys Glu Pro Val Phe His Phe Phe Cys
                165                 170                 175

Asp Thr Cys Asp Arg Gly Phe Lys Asn Gln Glu Lys Tyr Asp Lys His
            180                 185                 190

Met Ser Glu His Thr Lys Cys Pro Glu Leu Asp Cys Ser Phe Thr Ala
        195                 200                 205

His Glu Lys Ile Val Gln Phe His Trp Arg Asn Met His Ala Pro Gly
210                 215                 220

Met Lys Lys Ile Lys Leu Asp Thr Pro Glu Ile Ala Arg Trp Arg
225                 230                 235                 240

Glu Glu Arg Arg Lys Asn Tyr Pro Thr Leu Ala Asn Ile Glu Arg Lys
                245                 250                 255

Lys Lys Leu Lys Leu Glu Lys Glu Lys Arg Gly Ala Val Leu Thr Thr
            260                 265                 270

Thr Gln Tyr Gly Lys Met Lys Gly Met Ser Arg His Ser Gln Met Ala
        275                 280                 285

Lys Ile Arg Ser Pro Gly Lys Asn His Lys Trp Lys Asn Asp Asn Ser
    290                 295                 300

Arg Gln Arg Ala Val Thr Gly Ser Gly Ser His Leu Cys Asp Leu Lys
305                 310                 315                 320

-continued

```
Leu Glu Gly Pro Pro Glu Ala Asn Ala Asp Pro Leu Gly Val Leu Ile
            325                 330                 335

Asn Ser Asp Ser Glu Ser Asp Lys Glu Lys Pro Gln His Ser Val
        340                 345                 350

Ile Pro Lys Glu Val Thr Pro Ala Leu Cys Ser Leu Met Ser Ser Tyr
    355                 360                 365

Gly Ser Leu Ser Gly Ser Glu Ser Glu Pro Glu Glu Thr Pro Ile Lys
    370                 375                 380

Thr Glu Ala Asp Val Leu Ala Glu Asn Gln Val Leu Asp Ser Ser Ala
385                 390                 395                 400

Pro Lys Ser Pro Ser Gln Asp Val Lys Ala Thr Val Arg Asn Phe Ser
                405                 410                 415

Glu Ala Lys Ser Glu Asn Arg Lys Lys Ser Phe Glu Lys Thr Asn Pro
            420                 425                 430

Lys Arg Lys Lys Asp Tyr His Asn Tyr Gln Thr Leu Phe Glu Pro Arg
        435                 440                 445

Thr His His Pro Tyr Leu Leu Glu Met Leu Leu Ala Pro Asp Ile Arg
    450                 455                 460

His Glu Arg Asn Val Ile Leu Gln Cys Val Arg Tyr Ile Ile Lys Lys
465                 470                 475                 480

Asp Phe Phe Gly Leu Asp Thr Asn Ser Ala Lys Ser Lys Asp Val
                485                 490                 495
```

<210> SEQ ID NO 13
<211> LENGTH: 3526
<212> TYPE: PRT
<213> ORGANISM: Artificial Sequence
<220> FEATURE:
<223> OTHER INFORMATION: Synthetic polypeptide

<400> SEQUENCE: 13

```
Met Asn Met Val Lys Arg Ile Met Gly Arg Pro Arg Gln Glu Glu Cys
1               5                   10                  15

Ser Pro Gln Asp Asn Ala Leu Gly Leu Met His Leu Arg Arg Leu Phe
                20                  25                  30

Thr Glu Leu Cys His Pro Pro Arg His Met Thr Gln Lys Glu Gln Glu
            35                  40                  45

Glu Lys Leu Tyr Met Met Leu Pro Val Phe Asn Arg Val Phe Gly Asn
        50                  55                  60

Ala Pro Pro Asn Thr Met Thr Glu Lys Phe Ser Asp Leu Leu Gln Phe
65                  70                  75                  80

Thr Thr Gln Val Ser Arg Leu Met Val Thr Glu Ile Arg Arg Arg Ala
                85                  90                  95

Ser Asn Lys Ser Thr Glu Ala Ala Ser Arg Ala Ile Val Gln Phe Leu
            100                 105                 110

Glu Ile Asn Gln Ser Glu Glu Ala Ser Arg Gly Trp Met Leu Leu Thr
        115                 120                 125

Thr Ile Asn Leu Leu Ala Ser Ser Gly Gln Lys Thr Val Asp Cys Met
    130                 135                 140

Thr Thr Met Ser Val Pro Ser Thr Leu Val Lys Cys Leu Tyr Leu Phe
145                 150                 155                 160

Phe Asp Leu Pro His Val Pro Glu Ala Val Gly Gly Ala Gln Asn Glu
                165                 170                 175

Leu Pro Leu Ala Glu Arg Arg Gly Leu Leu Gln Lys Val Phe Val Gln
            180                 185                 190
```

-continued

```
Ile Leu Val Lys Leu Cys Ser Phe Val Ser Ala Glu Leu Ala
            195                 200             205

Gln Lys Asp Asp Leu Gln Leu Leu Phe Ser Ala Ile Thr Ser Trp Cys
    210                 215                 220

Pro Pro Tyr Asn Leu Pro Trp Arg Lys Ser Ala Gly Glu Val Leu Met
225                 230                 235                 240

Thr Ile Ser Arg His Gly Leu Ser Val Asn Val Val Lys Tyr Ile His
                245                 250                 255

Glu Lys Glu Cys Leu Ser Thr Cys Val Gln Asn Met Gln Gln Ser Asp
                260                 265                 270

Asp Leu Ser Pro Leu Glu Ile Val Glu Met Phe Ala Gly Leu Ser Cys
                275                 280                 285

Phe Leu Lys Asp Ser Ser Asp Val Ser Gln Thr Leu Leu Asp Asp Phe
    290                 295                 300

Arg Ile Trp Gln Gly Tyr Asn Phe Leu Cys Asp Leu Leu Arg Leu
305                 310                 315                 320

Glu Gln Ala Lys Glu Ala Glu Ser Lys Asp Ala Leu Lys Asp Leu Val
                325                 330                 335

Asn Leu Ile Thr Ser Leu Thr Thr Tyr Gly Val Ser Glu Leu Lys Pro
                340                 345                 350

Ala Gly Ile Thr Thr Gly Ala Pro Phe Leu Leu Pro Gly Phe Ala Val
                355                 360                 365

Pro Gln Pro Ala Gly Lys Gly His Ser Val Arg Asn Val Gln Ala Phe
370                 375                 380

Ala Val Leu Gln Asn Ala Phe Leu Lys Ala Lys Thr Ser Phe Leu Ala
385                 390                 395                 400

Gln Ile Ile Leu Asp Ala Ile Thr Asn Ile Tyr Met Ala Asp Asn Ala
                405                 410                 415

Asn Tyr Phe Ile Leu Glu Ser Gln His Thr Leu Ser Gln Phe Ala Glu
                420                 425                 430

Lys Ile Ser Lys Leu Pro Glu Val Gln Asn Lys Tyr Phe Glu Met Leu
                435                 440                 445

Glu Phe Val Val Phe Ser Leu Asn Tyr Ile Pro Cys Lys Glu Leu Ile
    450                 455                 460

Ser Val Ser Ile Leu Leu Lys Ser Ser Ser Tyr His Cys Ser Ile
465                 470                 475                 480

Ile Ala Met Lys Thr Leu Leu Lys Phe Thr Arg His Asp Tyr Ile Phe
                485                 490                 495

Lys Asp Val Phe Arg Glu Val Gly Leu Leu Glu Val Met Val Asn Leu
                500                 505                 510

Leu His Lys Tyr Ala Ala Leu Leu Lys Asp Pro Thr Gln Ala Leu Asn
    515                 520                 525

Glu Gln Gly Asp Ser Arg Asn Asn Ser Ser Val Glu Asp Gln Lys His
    530                 535                 540

Leu Ala Leu Leu Val Met Glu Thr Leu Thr Val Leu Leu Gln Gly Ser
545                 550                 555                 560

Asn Thr Asn Ala Gly Ile Phe Arg Glu Phe Gly Gly Ala Arg Cys Ala
                565                 570                 575

His Asn Ile Val Lys Tyr Pro Gln Cys Arg Gln His Ala Leu Met Thr
                580                 585                 590

Ile Gln Gln Leu Val Leu Ser Pro Asn Gly Asp Asp Met Gly Thr
    595                 600                 605
```

```
Leu Leu Gly Leu Met His Ser Ala Pro Pro Thr Glu Leu Gln Leu Lys
            610             615                 620

Thr Asp Ile Leu Arg Ala Leu Leu Ser Val Leu Arg Glu Ser His Arg
625             630                 635                 640

Ser Arg Thr Val Phe Arg Lys Val Gly Gly Phe Val Tyr Ile Thr Ser
                645                 650                 655

Leu Leu Val Ala Met Glu Arg Ser Leu Ser Cys Pro Pro Lys Asn Gly
            660                 665                 670

Trp Glu Lys Val Asn Gln Asn Gln Val Phe Glu Leu Leu His Thr Val
            675                 680                 685

Phe Cys Thr Leu Thr Ala Ala Met Arg Tyr Glu Pro Ala Asn Ser His
690                 695                 700

Phe Phe Lys Thr Glu Ile Gln Tyr Glu Lys Leu Ala Asp Ala Val Arg
705                 710                 715                 720

Phe Leu Gly Cys Phe Ser Asp Leu Arg Lys Ile Ser Ala Met Asn Val
                725                 730                 735

Phe Pro Ser Asn Thr Gln Pro Phe Gln Arg Leu Leu Glu Glu Asp Val
            740                 745                 750

Ile Ser Ile Glu Ser Val Ser Pro Thr Leu Arg His Cys Ser Lys Leu
            755                 760                 765

Phe Ile Tyr Leu Tyr Lys Val Ala Thr Asp Ser Phe Asp Ser Arg Ala
770                 775                 780

Glu Gln Ile Pro Pro Cys Leu Thr Ser Glu Ser Ser Leu Pro Ser Pro
785                 790                 795                 800

Trp Gly Thr Pro Ala Leu Ser Arg Lys Arg His Ala Tyr His Ser Val
                805                 810                 815

Ser Thr Pro Pro Val Tyr Pro Pro Lys Asn Val Ala Asp Leu Lys Leu
            820                 825                 830

His Val Thr Thr Ser Ser Leu Gln Ser Ser Asp Ala Val Ile Ile His
            835                 840                 845

Pro Gly Ala Met Leu Ala Met Leu Asp Leu Leu Ala Ser Val Gly Ser
850                 855                 860

Val Thr Gln Pro Glu His Ala Leu Asp Leu Gln Leu Ala Val Ala Asn
865                 870                 875                 880

Ile Leu Gln Ser Leu Val His Thr Glu Arg Asn Gln Gln Val Met Cys
                885                 890                 895

Glu Ala Gly Leu His Ala Arg Leu Leu Gln Arg Cys Ser Ala Ala Leu
            900                 905                 910

Ala Asp Glu Asp His Ser Leu His Pro Pro Leu Gln Arg Met Phe Glu
            915                 920                 925

Arg Leu Ala Ser Gln Ala Leu Glu Pro Met Val Leu Arg Glu Phe Leu
930                 935                 940

Arg Leu Ala Ser Pro Leu Asn Cys Gly Ala Trp Asp Lys Lys Leu Leu
945                 950                 955                 960

Lys Gln Tyr Arg Val His Lys Pro Ser Ser Leu Ser Tyr Glu Pro Glu
                965                 970                 975

Met Arg Ser Ser Met Ile Thr Ser Leu Glu Gly Leu Gly Thr Asp Asn
            980                 985                 990

Val Phe Ser Leu His Glu Asp Asn His Tyr Arg Ile Ser Lys Ser Leu
            995                 1000                1005

Val Lys Ser Ala Glu Gly Ser Thr Val Pro Leu Thr Arg Val Lys
    1010            1015                1020

Cys Leu Val Ser Met Thr Thr Pro His Asp Ile Arg Leu His Gly
```

-continued

```
                1025                1030                1035
Ser Ser Val Thr Pro Ala Phe Val Glu Phe Asp Thr Ser Leu Glu
    1040                1045                1050
Gly Phe Gly Cys Leu Phe Leu Pro Ser Leu Ala Pro His Asn Ala
    1055                1060                1065
Pro Thr Asn Asn Thr Val Thr Thr Gly Leu Ile Asp Gly Ala Val
    1070                1075                1080
Val Ser Gly Ile Gly Ser Gly Glu Arg Phe Phe Pro Pro Pro Ser
    1085                1090                1095
Gly Leu Ser Tyr Ser Ser Trp Phe Cys Ile Glu His Phe Ser Ser
    1100                1105                1110
Pro Pro Asn Asn His Pro Val Arg Leu Leu Thr Val Val Arg Arg
    1115                1120                1125
Ala Asn Ser Ser Glu Gln His Tyr Val Cys Leu Ala Ile Val Leu
    1130                1135                1140
Ser Ala Lys Asp Arg Ser Leu Ile Val Ser Thr Lys Glu Glu Leu
    1145                1150                1155
Leu Gln Asn Tyr Val Asp Asp Phe Ser Glu Glu Ser Ser Phe Tyr
    1160                1165                1170
Glu Ile Leu Pro Cys Cys Ala Arg Phe Arg Cys Gly Glu Leu Ile
    1175                1180                1185
Ile Glu Gly Gln Trp His His Leu Val Leu Val Met Ser Lys Gly
    1190                1195                1200
Met Leu Lys Asn Ser Thr Ala Ala Leu Tyr Ile Asp Gly Gln Leu
    1205                1210                1215
Val Asn Thr Val Lys Leu His Tyr Val His Ser Thr Pro Gly Gly
    1220                1225                1230
Ser Gly Ser Ala Asn Pro Pro Val Val Ser Thr Val Tyr Ala Tyr
    1235                1240                1245
Ile Gly Thr Pro Pro Ala Gln Arg Gln Ile Ala Ser Leu Val Trp
    1250                1255                1260
Arg Leu Gly Pro Thr His Phe Leu Glu Glu Val Leu Pro Ser Ser
    1265                1270                1275
Asn Val Thr Thr Ile Tyr Glu Leu Gly Pro Asn Tyr Val Gly Ser
    1280                1285                1290
Phe Gln Ala Val Cys Met Pro Cys Lys Asp Ala Lys Ser Glu Gly
    1295                1300                1305
Val Val Pro Ser Pro Val Ser Leu Val Pro Glu Glu Lys Val Ser
    1310                1315                1320
Phe Gly Leu Tyr Ala Leu Ser Val Ser Ser Leu Thr Val Ala Arg
    1325                1330                1335
Ile Arg Lys Val Tyr Asn Lys Leu Asp Ser Lys Ala Ile Ala Lys
    1340                1345                1350
Gln Leu Gly Ile Ser Ser His Glu Asn Ala Thr Pro Val Lys Leu
    1355                1360                1365
Ile His Asn Ser Ala Gly His Leu Asn Gly Ser Ala Arg Thr Ile
    1370                1375                1380
Gly Ala Ala Leu Ile Gly Tyr Leu Gly Val Arg Thr Phe Val Pro
    1385                1390                1395
Lys Pro Val Ala Thr Thr Leu Gln Tyr Val Gly Gly Ala Ala Ala
    1400                1405                1410
Ile Leu Gly Leu Val Ala Met Ala Ser Asp Val Glu Gly Leu Tyr
    1415                1420                1425
```

```
Ala Ala Val Lys Ala Leu Val Cys Val Val Lys Ser Asn Pro Leu
1430              1435                  1440

Ala Ser Lys Glu Met Glu Arg Ile Lys Gly Tyr Gln Leu Leu Ala
1445              1450                  1455

Met Leu Leu Lys Lys Arg Ser Leu Leu Asn Ser His Ile Leu
1460              1465                  1470

His Leu Thr Phe Ser Leu Val Gly Thr Val Asp Ser Gly His Glu
1475              1480                  1485

Thr Ser Ile Ile Pro Asn Ser Thr Ala Phe Gln Asp Leu Leu Cys
1490              1495                  1500

Asp Phe Glu Val Trp Leu His Ala Pro Tyr Glu Leu His Leu Ser
1505              1510                  1515

Leu Phe Glu His Phe Ile Glu Leu Leu Thr Glu Ser Ser Glu Ala
1520              1525                  1530

Ser Lys Asn Ala Lys Leu Met Arg Glu Phe Gln Leu Ile Pro Lys
1535              1540                  1545

Leu Leu Leu Thr Leu Arg Asp Met Ser Leu Ser Gln Pro Thr Ile
1550              1555                  1560

Ala Ala Ile Ser Asn Val Leu Ser Phe Leu Leu Gln Gly Phe Pro
1565              1570                  1575

Ser Ser Asn Asp Leu Leu Arg Phe Gly Gln Phe Ile Ser Ser Thr
1580              1585                  1590

Leu Pro Thr Phe Ala Val Cys Glu Lys Phe Val Val Met Glu Ile
1595              1600                  1605

Asn Asn Glu Glu Lys Leu Asp Thr Gly Thr Glu Glu Glu Phe Gly
1610              1615                  1620

Gly Leu Val Ser Ala Asn Leu Ile Leu Leu Arg Asn Arg Leu Leu
1625              1630                  1635

Asp Ile Leu Leu Lys Leu Ile Tyr Thr Ser Lys Glu Lys Thr Ser
1640              1645                  1650

Ile Asn Leu Gln Ala Cys Glu Glu Leu Val Lys Thr Leu Gly Phe
1655              1660                  1665

Asp Trp Ile Met Met Phe Met Glu Glu His Leu His Ser Thr Thr
1670              1675                  1680

Val Thr Ala Ala Met Arg Ile Leu Val Val Leu Leu Ser Asn Gln
1685              1690                  1695

Ser Ile Leu Ile Lys Phe Lys Glu Gly Leu Ser Gly Gly Gly Trp
1700              1705                  1710

Leu Glu Gln Thr Asp Ser Val Leu Thr Asn Lys Ile Gly Thr Val
1715              1720                  1725

Leu Gly Phe Asn Val Gly Arg Ser Ala Gly Gly Arg Ser Thr Val
1730              1735                  1740

Arg Glu Ile Asn Arg Asp Ala Cys His Phe Pro Gly Phe Pro Val
1745              1750                  1755

Leu Gln Ser Phe Leu Pro Lys His Thr Asn Val Pro Ala Leu Tyr
1760              1765                  1770

Phe Leu Leu Met Ala Leu Phe Leu Gln Gln Pro Val Ser Glu Leu
1775              1780                  1785

Pro Glu Asn Leu Gln Val Ser Val Pro Val Ile Ser Cys Arg Ser
1790              1795                  1800

Lys Gln Gly Cys Gln Phe Asp Leu Asp Ser Ile Trp Thr Phe Ile
1805              1810                  1815
```

```
Phe Gly Val Pro Ala Ser Ser Gly Thr Val Val Ser Ser Ile His
    1820            1825                1830

Asn Val Cys Thr Glu Ala Val Phe Leu Leu Leu Gly Met Leu Arg
    1835            1840                1845

Ser Met Leu Thr Ser Pro Trp Gln Ser Glu Glu Gly Ser Trp
    1850            1855                1860

Leu Arg Glu Tyr Pro Val Thr Leu Met Gln Phe Phe Arg Tyr Leu
    1865            1870                1875

Tyr His Asn Val Pro Asp Leu Ala Ser Met Trp Met Ser Pro Asp
    1880            1885                1890

Phe Leu Cys Ala Leu Ala Ala Thr Val Phe Pro Phe Asn Ile Arg
    1895            1900                1905

Pro Tyr Ser Glu Met Val Thr Asp Leu Asp Asp Glu Val Gly Ser
    1910            1915                1920

Pro Ala Glu Glu Phe Lys Ala Phe Ala Ala Asp Thr Gly Met Asn
    1925            1930                1935

Arg Ser Gln Ser Glu Tyr Cys Asn Val Gly Thr Lys Thr Tyr Leu
    1940            1945                1950

Thr Asn His Pro Ala Lys Lys Phe Val Phe Asp Phe Met Arg Val
    1955            1960                1965

Leu Ile Ile Asp Asn Leu Cys Leu Thr Pro Ala Ser Lys Gln Thr
    1970            1975                1980

Pro Leu Ile Asp Leu Leu Leu Glu Ala Ser Pro Glu Arg Ser Thr
    1985            1990                1995

Arg Thr Gln Gln Lys Glu Phe Gln Thr Tyr Ile Leu Asp Ser Val
    2000            2005                2010

Met Asp His Leu Leu Ala Ala Asp Val Leu Leu Gly Glu Asp Ala
    2015            2020                2025

Ser Leu Pro Ile Thr Ser Gly Gly Ser Tyr Gln Val Leu Val Asn
    2030            2035                2040

Asn Val Phe Tyr Phe Thr Gln Arg Val Val Asp Lys Leu Trp Gln
    2045            2050                2055

Gly Met Phe Asn Lys Glu Ser Lys Leu Leu Ile Asp Phe Ile Ile
    2060            2065                2070

Gln Leu Ile Ala Gln Ser Lys Arg Arg Ser Gln Gly Leu Ser Leu
    2075            2080                2085

Asp Ala Val Tyr His Cys Leu Asn Arg Thr Ile Leu Tyr Gln Phe
    2090            2095                2100

Ser Arg Ala His Lys Thr Val Pro Gln Gln Val Ala Leu Leu Asp
    2105            2110                2115

Ser Leu Arg Val Leu Thr Val Asn Arg Asn Leu Ile Leu Gly Pro
    2120            2125                2130

Gly Asn His Asp Gln Glu Phe Ile Ser Cys Leu Ala His Cys Leu
    2135            2140                2145

Ile Asn Leu His Val Gly Ser Asn Val Asp Gly Phe Gly Leu Glu
    2150            2155                2160

Ala Glu Ala Arg Met Thr Thr Trp His Ile Met Ile Pro Ser Asp
    2165            2170                2175

Ile Glu Pro Asp Gly Ser Tyr Ser Gln Asp Ile Ser Glu Gly Arg
    2180            2185                2190

Gln Leu Leu Ile Lys Ala Val Asn Arg Val Trp Thr Glu Leu Ile
    2195            2200                2205

His Ser Lys Lys Gln Val Leu Glu Glu Leu Phe Lys Val Thr Leu
```

-continued

```
              2210                2215                2220

Pro Val Asn Glu Arg Gly His Val Asp Ile Ala Thr Ala Arg Pro
        2225                2230                2235

Leu Ile Glu Glu Ala Ala Leu Lys Cys Trp Gln Asn His Leu Ala
        2240                2245                2250

His Glu Lys Lys Cys Ile Ser Arg Gly Glu Ala Leu Ala Pro Thr
        2255                2260                2265

Thr Gln Ser Lys Leu Ser Arg Val Ser Ser Gly Phe Gly Leu Ser
        2270                2275                2280

Lys Leu Thr Gly Ser Arg Arg Asn Arg Lys Glu Ser Gly Leu Asn
        2285                2290                2295

Lys His Ser Leu Ser Thr Gln Glu Ile Ser Gln Trp Met Phe Thr
        2300                2305                2310

His Ile Ala Val Val Arg Asp Leu Val Asp Thr Gln Tyr Lys Glu
        2315                2320                2325

Tyr Gln Glu Arg Gln Gln Asn Ala Leu Lys Tyr Val Thr Glu Glu
        2330                2335                2340

Trp Cys Gln Ile Glu Cys Glu Leu Leu Arg Glu Arg Gly Leu Trp
        2345                2350                2355

Gly Pro Pro Ile Gly Ser His Leu Asp Lys Trp Met Leu Glu Met
        2360                2365                2370

Thr Glu Gly Pro Cys Arg Met Arg Lys Lys Met Val Arg Asn Asp
        2375                2380                2385

Met Phe Tyr Asn His Tyr Pro Tyr Val Pro Glu Thr Glu Gln Glu
        2390                2395                2400

Thr Asn Val Ala Ser Glu Ile Pro Ser Lys Gln Pro Glu Thr Pro
        2405                2410                2415

Asp Asp Ile Pro Gln Lys Lys Pro Ala Arg Tyr Arg Arg Ala Val
        2420                2425                2430

Ser Tyr Asp Ser Lys Glu Tyr Tyr Met Arg Leu Ala Ser Gly Asn
        2435                2440                2445

Pro Ala Ile Val Gln Asp Ala Ile Val Glu Ser Ser Glu Gly Glu
        2450                2455                2460

Ala Ala Gln Gln Glu Pro Glu His Gly Glu Asp Thr Ile Ala Lys
        2465                2470                2475

Val Lys Gly Leu Val Lys Pro Pro Leu Lys Arg Ser Arg Ser Ala
        2480                2485                2490

Pro Asp Gly Gly Asp Glu Glu Asn Gln Glu Gln Leu Gln Asp Gln
        2495                2500                2505

Ile Ala Glu Gly Ser Ser Ile Glu Glu Glu Glu Lys Thr Asp Asn
        2510                2515                2520

Ala Thr Leu Leu Arg Leu Leu Glu Glu Gly Glu Lys Ile Gln His
        2525                2530                2535

Met Tyr Arg Cys Ala Arg Val Gln Gly Leu Asp Thr Ser Glu Gly
        2540                2545                2550

Leu Leu Leu Phe Gly Lys Glu His Phe Tyr Val Ile Asp Gly Phe
        2555                2560                2565

Thr Met Thr Ala Thr Arg Glu Ile Arg Asp Ile Glu Thr Leu Pro
        2570                2575                2580

Pro Asn Met His Glu Pro Ile Ile Pro Arg Gly Ala Arg Gln Gly
        2585                2590                2595

Pro Ser Gln Leu Lys Arg Thr Cys Ser Ile Phe Ala Tyr Glu Asp
        2600                2605                2610
```

-continued

```
Ile Lys Glu Val His Lys Arg Arg Tyr Leu Leu Gln Pro Ile Ala
2615                2620                2625

Val Glu Val Phe Ser Gly Asp Gly Arg Asn Tyr Leu Leu Ala Phe
2630                2635                2640

Gln Lys Gly Ile Arg Asn Lys Val Tyr Gln Arg Phe Leu Ala Val
2645                2650                2655

Val Pro Ser Leu Thr Asp Ser Ser Glu Ser Val Ser Gly Gln Arg
2660                2665                2670

Pro Asn Thr Ser Val Glu Gln Gly Ser Gly Leu Leu Ser Thr Leu
2675                2680                2685

Val Gly Glu Lys Ser Val Thr Gln Arg Trp Glu Arg Gly Glu Ile
2690                2695                2700

Ser Asn Phe Gln Tyr Leu Met His Leu Asn Thr Leu Ala Gly Arg
2705                2710                2715

Ser Tyr Asn Asp Leu Met Gln Tyr Pro Val Phe Pro Trp Ile Leu
2720                2725                2730

Ala Asp Tyr Asp Ser Glu Glu Val Asp Leu Thr Asn Pro Lys Thr
2735                2740                2745

Phe Arg Asn Leu Ala Lys Pro Met Gly Ala Gln Thr Asp Glu Arg
2750                2755                2760

Leu Ala Gln Tyr Lys Lys Arg Tyr Lys Asp Trp Glu Asp Pro Asn
2765                2770                2775

Gly Glu Thr Pro Ala Tyr His Tyr Gly Thr His Tyr Ser Ser Ala
2780                2785                2790

Met Ile Val Ala Ser Tyr Leu Val Arg Met Glu Pro Phe Thr Gln
2795                2800                2805

Ile Phe Leu Arg Leu Gln Gly Gly His Phe Asp Leu Ala Asp Arg
2810                2815                2820

Met Phe His Ser Val Arg Glu Ala Trp Tyr Ser Ala Ser Lys His
2825                2830                2835

Asn Met Ala Asp Val Lys Glu Leu Ile Pro Glu Phe Phe Tyr Leu
2840                2845                2850

Pro Glu Phe Leu Phe Asn Ser Asn Asn Phe Asp Leu Gly Cys Lys
2855                2860                2865

Gln Asn Gly Thr Lys Leu Gly Asp Val Ile Leu Pro Pro Trp Ala
2870                2875                2880

Lys Gly Asp Pro Arg Glu Phe Ile Arg Val His Arg Glu Ala Leu
2885                2890                2895

Glu Cys Asp Tyr Val Ser Ala His Leu His Glu Trp Ile Asp Leu
2900                2905                2910

Ile Phe Gly Tyr Lys Gln Gln Gly Pro Ala Ala Val Glu Ala Val
2915                2920                2925

Asn Val Phe His His Leu Phe Tyr Glu Gly Gln Val Asp Ile Tyr
2930                2935                2940

Asn Ile Asn Asp Pro Leu Lys Glu Thr Ala Thr Ile Gly Phe Ile
2945                2950                2955

Asn Asn Phe Gly Gln Ile Pro Lys Gln Leu Phe Lys Lys Pro His
2960                2965                2970

Pro Pro Lys Arg Val Arg Ser Arg Leu Asn Gly Asp Asn Ala Gly
2975                2980                2985

Ile Ser Val Leu Pro Gly Ser Thr Ser Asp Lys Ile Phe Phe His
2990                2995                3000
```

-continued

His Leu Asp Asn Leu Arg Pro Ser Leu Thr Pro Val Lys Glu Leu
3005                      3010                3015

Lys Glu Pro Val Gly Gln Ile Val Cys Thr Asp Lys Gly Ile Leu
3020                      3025                3030

Ala Val Glu Gln Asn Lys Val Leu Ile Pro Pro Thr Trp Asn Lys
3035                      3040                3045

Thr Phe Ala Trp Gly Tyr Ala Asp Leu Ser Cys Arg Leu Gly Thr
3050                      3055                3060

Tyr Glu Ser Asp Lys Ala Met Thr Val Tyr Glu Cys Leu Ser Glu
3065                      3070                3075

Trp Gly Gln Ile Leu Cys Ala Ile Cys Pro Asn Pro Lys Leu Val
3080                      3085                3090

Ile Thr Gly Gly Thr Ser Thr Val Val Cys Val Trp Glu Met Gly
3095                      3100                3105

Thr Ser Lys Glu Lys Ala Lys Thr Val Thr Leu Lys Gln Ala Leu
3110                      3115                3120

Leu Gly His Thr Asp Thr Val Thr Cys Ala Thr Ala Ser Leu Ala
3125                      3130                3135

Tyr His Ile Ile Val Ser Gly Ser Arg Asp Arg Thr Cys Ile Ile
3140                      3145                3150

Trp Asp Leu Asn Lys Leu Ser Phe Leu Thr Gln Leu Arg Gly His
3155                      3160                3165

Arg Ala Pro Val Ser Ala Leu Cys Ile Asn Glu Leu Thr Gly Asp
3170                      3175                3180

Ile Val Ser Cys Ala Gly Thr Tyr Ile His Val Trp Ser Ile Asn
3185                      3190                3195

Gly Asn Pro Ile Val Ser Val Asn Thr Phe Thr Gly Arg Ser Gln
3200                      3205                3210

Gln Ile Ile Cys Cys Cys Met Ser Glu Met Asn Glu Trp Asp Thr
3215                      3220                3225

Gln Asn Val Ile Val Thr Gly His Ser Asp Gly Val Val Arg Phe
3230                      3235                3240

Trp Arg Met Glu Phe Leu Gln Val Pro Glu Thr Pro Ala Pro Glu
3245                      3250                3255

Pro Ala Glu Val Leu Glu Met Gln Glu Asp Cys Pro Glu Ala Gln
3260                      3265                3270

Ile Gly Gln Glu Ala Gln Asp Glu Asp Ser Ser Asp Ser Glu Ala
3275                      3280                3285

Asp Glu Gln Ser Ile Ser Gln Asp Pro Lys Asp Thr Pro Ser Gln
3290                      3295                3300

Pro Ser Ser Thr Ser His Arg Pro Arg Ala Ala Ser Cys Arg Ala
3305                      3310                3315

Thr Ala Ala Trp Cys Thr Asp Ser Gly Ser Asp Asp Ser Arg Arg
3320                      3325                3330

Trp Ser Asp Gln Leu Ser Leu Asp Glu Lys Asp Gly Phe Ile Phe
3335                      3340                3345

Val Asn Tyr Ser Glu Gly Gln Thr Arg Ala His Leu Gln Gly Pro
3350                      3355                3360

Leu Ser His Pro His Pro Asn Pro Ile Glu Val Arg Asn Tyr Ser
3365                      3370                3375

Arg Leu Lys Pro Gly Tyr Arg Trp Glu Arg Gln Leu Val Phe Arg
3380                      3385                3390

Ser Lys Leu Thr Met His Thr Ala Phe Asp Arg Lys Asp Asn Ala

```
              3395                3400                3405
His Pro Ala Glu Val Thr Ala Leu Gly Ile Ser Lys Asp His Ser
    3410                3415                3420

Arg Ile Leu Val Gly Asp Ser Arg Gly Arg Val Phe Ser Trp Ser
    3425                3430                3435

Val Ser Asp Gln Pro Gly Arg Ser Ala Ala Asp His Trp Val Lys
    3440                3445                3450

Asp Glu Gly Gly Asp Ser Cys Ser Gly Cys Ser Val Arg Phe Ser
    3455                3460                3465

Leu Thr Glu Arg Arg His His Cys Arg Asn Cys Gly Gln Leu Phe
    3470                3475                3480

Cys Gln Lys Cys Ser Arg Phe Gln Ser Glu Ile Lys Arg Leu Lys
    3485                3490                3495

Ile Ser Ser Pro Val Arg Val Cys Gln Asn Cys Tyr Tyr Asn Leu
    3500                3505                3510

Gln His Glu Arg Gly Ser Glu Asp Gly Pro Arg Asn Cys
    3515                3520                3525

<210> SEQ ID NO 14
<211> LENGTH: 497
<212> TYPE: PRT
<213> ORGANISM: Artificial Sequence
<220> FEATURE:
<223> OTHER INFORMATION: Synthetic polypeptide

<400> SEQUENCE: 14

Met Ala Ser Pro Ala Pro Pro Glu His Ala Glu Glu Gly Cys Pro Ala
1               5                   10                  15

Pro Ala Ala Glu Glu Gln Ala Pro Pro Ser Pro Pro Pro Pro Gln Ala
            20                  25                  30

Ser Pro Ala Glu Arg Gln Gln Glu Glu Glu Ala Gln Glu Ala Gly
        35                  40                  45

Ala Ala Glu Gly Ala Gly Leu Gln Val Glu Glu Ala Ala Gly Arg Ala
    50                  55                  60

Ala Ala Ala Val Thr Trp Leu Gly Glu Pro Val Leu Trp Leu Gly
65                  70                  75                  80

Cys Arg Ala Asp Glu Leu Leu Ser Trp Lys Arg Pro Leu Arg Ser Leu
                85                  90                  95

Leu Gly Phe Val Ala Ala Asn Leu Leu Phe Trp Phe Leu Ala Leu Thr
            100                 105                 110

Pro Trp Arg Val Tyr His Leu Ile Ser Val Met Ile Leu Gly Arg Val
        115                 120                 125

Ile Met Gln Ile Ile Lys Asp Met Val Leu Ser Arg Thr Arg Gly Ala
    130                 135                 140

Gln Leu Trp Arg Ser Leu Ser Glu Ser Trp Glu Val Ile Asn Ser Lys
145                 150                 155                 160

Pro Asp Glu Arg Pro Arg Leu Ser His Cys Ile Ala Glu Ser Trp Met
                165                 170                 175

Asn Phe Ser Ile Phe Leu Gln Glu Met Ser Leu Phe Lys Gln Gln Ser
            180                 185                 190

Pro Gly Lys Phe Cys Leu Leu Val Cys Ser Val Cys Thr Phe Thr
        195                 200                 205

Ile Leu Gly Ser Tyr Ile Pro Gly Val Ile Leu Ser Tyr Leu Leu Leu
    210                 215                 220

Leu Cys Ala Phe Leu Cys Pro Leu Phe Lys Cys Asn Asp Ile Gly Gln
```

```
                    225                 230                 235                 240

Lys Ile Tyr Ser Lys Ile Lys Ser Val Leu Leu Lys Leu Asp Phe Gly
                245                 250                 255

Ile Gly Glu Tyr Ile Asn Gln Lys Lys Arg Glu Arg Ser Glu Ala Asp
                260                 265                 270

Lys Glu Lys Ser His Lys Asp Asp Ser Glu Leu Asp Phe Ser Ala Leu
            275                 280                 285

Cys Pro Lys Ile Ser Leu Thr Val Ala Ala Lys Glu Leu Ser Val Ser
        290                 295                 300

Asp Thr Asp Val Ser Glu Val Ser Trp Thr Asp Asn Gly Thr Phe Asn
305                 310                 315                 320

Leu Ser Glu Gly Tyr Thr Pro Gln Thr Asp Thr Ser Asp Asp Leu Asp
                325                 330                 335

Arg Pro Ser Glu Glu Val Phe Ser Arg Asp Leu Ser Asp Phe Pro Ser
                340                 345                 350

Leu Glu Asn Gly Met Gly Thr Asn Asp Glu Asp Glu Leu Ser Leu Gly
            355                 360                 365

Leu Pro Thr Glu Leu Lys Arg Lys Lys Glu Gln Leu Asp Ser Gly His
        370                 375                 380

Arg Pro Ser Lys Glu Thr Gln Ser Ala Ala Gly Leu Thr Leu Pro Leu
385                 390                 395                 400

Asn Ser Asp Gln Thr Phe His Leu Met Ser Asn Leu Ala Gly Asp Val
                405                 410                 415

Ile Thr Ala Ala Val Thr Ala Ala Ile Lys Asp Gln Leu Glu Gly Val
                420                 425                 430

Gln Gln Ala Leu Ser Gln Ala Ala Pro Ile Pro Glu Glu Asp Thr Asp
            435                 440                 445

Thr Glu Glu Gly Asp Asp Phe Glu Leu Leu Asp Gln Ser Glu Leu Asp
        450                 455                 460

Gln Ile Glu Ser Glu Leu Gly Leu Thr Gln Asp Gln Glu Ala Glu Ala
465                 470                 475                 480

Gln Gln Asn Lys Lys Ser Ser Gly Phe Leu Ser Asn Leu Leu Gly Gly
                485                 490                 495

His

<210> SEQ ID NO 15
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 15

Met Ser Ser His Leu Val Glu Pro Pro Pro Leu His Asn Asn Asn
1               5                   10                  15

Asn Asn Cys Glu Glu Asn Glu Gln Ser Leu Pro Pro Ala Gly Leu
            20                  25                  30

Asn Ser Ser Trp Val Glu Leu Pro Met Asn Ser Ser Asn Gly Asn Asp
        35                  40                  45

Asn Gly Asn Gly Lys Asn Gly Gly Leu Glu His Val Pro Ser Ser Ser
    50                  55                  60

Ser Ile His Asn Gly Asp Met Glu Lys Ile Leu Leu Asp Ala Gln His
65                  70                  75                  80

Glu Ser Gly Gln Ser Ser Ser Arg Gly Ser Ser His Cys Asp Ser Pro
                85                  90                  95
```

```
Ser Pro Gln Glu Asp Gly Gln Ile Met Phe Asp Val Glu Met His Thr
            100                 105                 110

Ser Arg Asp His Ser Ser Gln Ser Glu Glu Val Glu Gly Glu
        115                 120                 125

Lys Glu Val Glu Ala Leu Lys Lys Ser Ala Asp Trp Val Ser Asp Trp
130                 135                 140

Ser Ser Arg Pro Glu Asn Ile Pro Pro Lys Glu Phe His Phe Arg His
145                 150                 155                 160

Pro Lys Arg Ser Val Ser Leu Ser Met Arg Lys Ser Gly Ala Met Lys
                165                 170                 175

Lys Gly Gly Ile Phe Ser Ala Glu Phe Leu Lys Val Phe Ile Pro Ser
            180                 185                 190

Leu Phe Leu Ser His Val Leu Ala Leu Gly Leu Gly Ile Tyr Ile Gly
            195                 200                 205

Lys Arg Leu Ser Thr Pro Ser Ala Ser Thr Tyr
            210                 215

<210> SEQ ID NO 16
<211> LENGTH: 274
<212> TYPE: PRT
<213> ORGANISM: Artificial Sequence
<220> FEATURE:
<223> OTHER INFORMATION: Synthetic polypeptide

<400> SEQUENCE: 16

Met Ala Thr Thr Val Ser Thr Gln Arg Gly Pro Val Tyr Ile Gly Glu
1               5                   10                  15

Leu Pro Gln Asp Phe Leu Arg Ile Thr Pro Thr Gln Gln Arg Gln
            20                  25                  30

Val Gln Leu Asp Ala Gln Ala Ala Gln Gln Leu Gln Tyr Gly Gly Ala
        35                  40                  45

Val Gly Thr Val Gly Arg Leu Asn Ile Thr Val Val Gln Ala Lys Leu
    50                  55                  60

Ala Lys Asn Tyr Gly Met Thr Arg Met Asp Pro Tyr Cys Arg Leu Arg
65                  70                  75                  80

Leu Gly Tyr Ala Val Tyr Glu Thr Pro Thr Ala His Asn Gly Ala Lys
                85                  90                  95

Asn Pro Arg Trp Asn Lys Val Ile His Cys Thr Val Pro Pro Gly Val
            100                 105                 110

Asp Ser Phe Tyr Leu Glu Ile Phe Asp Glu Arg Ala Phe Ser Met Asp
        115                 120                 125

Asp Arg Ile Ala Trp Thr His Ile Thr Ile Pro Glu Ser Leu Arg Gln
130                 135                 140

Gly Lys Val Glu Asp Lys Trp Tyr Ser Leu Ser Gly Arg Gln Gly Asp
145                 150                 155                 160

Asp Lys Glu Gly Met Ile Asn Leu Val Met Ser Tyr Ala Leu Leu Pro
                165                 170                 175

Ala Ala Met Val Met Pro Pro Gln Pro Val Val Leu Met Pro Thr Val
            180                 185                 190

Tyr Gln Gln Gly Val Gly Tyr Val Pro Ile Thr Gly Met Pro Ala Val
        195                 200                 205

Cys Ser Pro Gly Met Val Pro Val Ala Leu Pro Pro Ala Ala Val Asn
    210                 215                 220

Ala Gln Pro Arg Cys Ser Glu Glu Asp Leu Lys Ala Ile Gln Asp Met
225                 230                 235                 240
```

-continued

Phe Pro Asn Met Asp Gln Glu Val Ile Arg Ser Val Leu Glu Ala Gln
                245                 250                 255

Arg Gly Asn Lys Asp Ala Ala Ile Asn Ser Leu Leu Gln Met Gly Glu
            260                 265                 270

Glu Pro

<210> SEQ ID NO 17
<211> LENGTH: 789
<212> TYPE: PRT
<213> ORGANISM: Artificial Sequence
<220> FEATURE:
<223> OTHER INFORMATION: Synthetic polypeptide

<400> SEQUENCE: 17

Met Thr Ser Phe Gln Glu Val Pro Leu Gln Thr Ser Asn Phe Ala His
1               5                   10                  15

Val Ile Phe Gln Asn Val Ala Lys Ser Tyr Leu Pro Asn Ala His Leu
            20                  25                  30

Glu Cys His Tyr Thr Leu Thr Pro Tyr Ile His Pro His Pro Lys Asp
        35                  40                  45

Trp Val Gly Ile Phe Lys Val Gly Trp Ser Thr Ala Arg Asp Tyr Tyr
    50                  55                  60

Thr Phe Leu Trp Ser Pro Met Pro Glu His Tyr Val Glu Gly Ser Thr
65                  70                  75                  80

Val Asn Cys Val Leu Ala Phe Gln Gly Tyr Tyr Leu Pro Asn Asp Asp
                85                  90                  95

Gly Glu Phe Tyr Gln Phe Cys Tyr Val Thr His Lys Gly Glu Ile Arg
            100                 105                 110

Gly Ala Ser Thr Pro Phe Gln Phe Arg Ala Ser Ser Pro Val Glu Glu
        115                 120                 125

Leu Leu Thr Met Glu Asp Glu Gly Asn Ser Asp Met Leu Val Val Thr
    130                 135                 140

Thr Lys Ala Gly Leu Leu Glu Leu Lys Ile Glu Lys Thr Met Lys Glu
145                 150                 155                 160

Lys Glu Glu Leu Leu Lys Leu Ile Ala Val Leu Glu Lys Glu Thr Ala
                165                 170                 175

Gln Leu Arg Glu Gln Val Gly Arg Met Glu Arg Glu Leu Asn His Glu
            180                 185                 190

Lys Glu Arg Cys Asp Gln Leu Gln Ala Glu Gln Lys Gly Leu Thr Glu
        195                 200                 205

Val Thr Gln Ser Leu Lys Met Glu Asn Glu Glu Phe Lys Lys Arg Phe
    210                 215                 220

Ser Asp Ala Thr Ser Lys Ala His Gln Leu Glu Glu Asp Ile Val Ser
225                 230                 235                 240

Val Thr His Lys Ala Ile Glu Lys Glu Thr Glu Leu Asp Ser Leu Lys
                245                 250                 255

Asp Lys Leu Lys Lys Ala Gln His Glu Arg Glu Gln Leu Glu Cys Gln
            260                 265                 270

Leu Lys Thr Glu Lys Asp Glu Lys Glu Leu Tyr Lys Val His Leu Lys
        275                 280                 285

Asn Thr Glu Ile Glu Asn Thr Lys Leu Met Ser Glu Val Gln Thr Leu
    290                 295                 300

Lys Asn Leu Asp Gly Asn Lys Glu Ser Val Ile Thr His Phe Lys Glu
305                 310                 315                 320

-continued

Glu Ile Gly Arg Leu Gln Leu Cys Leu Ala Gly Lys Glu Asn Leu Gln
            325                 330                 335

Arg Thr Phe Leu Leu Thr Thr Ser Ser Lys Glu Asp Thr Cys Phe Leu
        340                 345                 350

Lys Glu Gln Leu Arg Lys Ala Glu Glu Gln Val Gln Ala Thr Arg Gln
        355                 360                 365

Glu Val Val Phe Leu Ala Lys Glu Leu Ser Asp Ala Val Asn Val Arg
370                 375                 380

Asp Arg Thr Met Ala Asp Leu His Thr Ala Arg Leu Glu Asn Glu Lys
385                 390                 395                 400

Val Lys Lys Gln Leu Ala Asp Ala Val Ala Glu Leu Lys Leu Asn Ala
                405                 410                 415

Met Lys Lys Asp Gln Asp Lys Thr Asp Thr Leu Glu His Glu Leu Arg
            420                 425                 430

Arg Glu Val Glu Asp Leu Lys Leu Arg Leu Gln Met Ala Ala Asp His
        435                 440                 445

Tyr Lys Glu Lys Phe Lys Glu Cys Gln Arg Leu Gln Lys Gln Ile Asn
    450                 455                 460

Lys Leu Ser Asp Gln Ser Ala Asn Asn Asn Val Phe Thr Lys Lys
465                 470                 475                 480

Thr Gly Asn Gln Gln Lys Val Asn Asp Ala Ser Val Asn Thr Asp Pro
                485                 490                 495

Ala Thr Ser Ala Ser Thr Val Asp Val Lys Pro Ser Pro Ser Ala Ala
            500                 505                 510

Glu Ala Asp Phe Asp Ile Val Thr Lys Gly Gln Val Cys Glu Met Thr
        515                 520                 525

Lys Glu Ile Ala Asp Lys Thr Glu Lys Tyr Asn Lys Cys Lys Gln Leu
    530                 535                 540

Leu Gln Asp Glu Lys Ala Lys Cys Asn Lys Tyr Ala Asp Glu Leu Ala
545                 550                 555                 560

Lys Met Glu Leu Lys Trp Lys Glu Gln Val Lys Ile Ala Glu Asn Val
                565                 570                 575

Lys Leu Glu Leu Ala Glu Val Gln Asp Asn Tyr Lys Glu Leu Lys Arg
            580                 585                 590

Ser Leu Glu Asn Pro Ala Glu Arg Lys Met Glu Gly Gln Asn Ser Gln
        595                 600                 605

Ser Pro Gln Cys Phe Lys Thr Cys Ser Glu Gln Asn Gly Tyr Val Leu
    610                 615                 620

Thr Leu Ser Asn Ala Gln Pro Val Leu Gln Tyr Gly Asn Pro Tyr Ala
625                 630                 635                 640

Ser Gln Glu Thr Arg Asp Gly Ala Asp Gly Ala Phe Tyr Pro Asp Glu
                645                 650                 655

Ile Gln Arg Pro Pro Val Arg Val Pro Ser Trp Gly Leu Glu Asp Asn
            660                 665                 670

Val Val Cys Ser Gln Pro Ala Arg Asn Phe Ser Arg Pro Asp Gly Leu
        675                 680                 685

Glu Asp Ser Glu Asp Ser Lys Glu Asp Glu Asn Val Pro Thr Ala Pro
    690                 695                 700

Asp Pro Pro Ser Gln His Leu Arg Gly His Gly Thr Gly Phe Cys Phe
705                 710                 715                 720

Asp Ser Ser Phe Asp Val His Lys Lys Cys Pro Leu Cys Glu Leu Met
                725                 730                 735

Phe Pro Pro Asn Tyr Asp Gln Ser Lys Phe Glu Glu His Val Glu Ser

```
                    740                 745                 750
His Trp Lys Val Cys Pro Met Cys Ser Glu Gln Phe Pro Pro Asp Tyr
        755                 760                 765

Asp Gln Gln Val Phe Glu Arg His Val Gln Thr His Phe Asp Gln Asn
    770                 775                 780

Val Leu Asn Phe Asp
785
```